United States Patent
Zhang et al.

(10) Patent No.: US 11,910,709 B2
(45) Date of Patent: Feb. 20, 2024

(54) ORGANIC COMPOUND, AND ELECTRONIC ELEMENT AND ELECTRONIC DEVICE USING SAME

(71) Applicant: Shaanxi Lighte Optoelectronics Material Co., Ltd., Xi'an (CN)

(72) Inventors: Kongyan Zhang, Xi'an (CN); Tiantian Ma, Xi'an (CN); Jiamei Cao, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 102 days.

(21) Appl. No.: 17/913,193

(22) PCT Filed: May 11, 2021

(86) PCT No.: PCT/CN2021/093160
§ 371 (c)(1),
(2) Date: Sep. 21, 2022

(87) PCT Pub. No.: WO2021/228111
PCT Pub. Date: Nov. 18, 2021

(65) Prior Publication Data
US 2023/0301182 A1    Sep. 21, 2023

(30) Foreign Application Priority Data

May 12, 2020  (CN) .......................... 202010398845.6
Aug. 28, 2020 (CN) .......................... 202010889735.X

(51) Int. Cl.
*C07D 251/24*     (2006.01)
*C07D 403/04*     (2006.01)
(Continued)

(52) U.S. Cl.
CPC ......... *H10K 85/654* (2023.02); *C07D 251/24* (2013.01); *C07D 403/04* (2013.01);
(Continued)

(58) Field of Classification Search
CPC .. C07D 251/24; C07D 405/04; C07D 405/10; C07D 405/14; C07D 409/04;
(Continued)

(56) References Cited

U.S. PATENT DOCUMENTS

2016/0260908 A1    9/2016    Zeng

FOREIGN PATENT DOCUMENTS

CN    110183333 A    8/2019
CN    110240546 A    9/2019
(Continued)

OTHER PUBLICATIONS

Machine-generated English-language translation of KR-20210048334-A.*

(Continued)

*Primary Examiner* — Vu A Nguyen
(74) *Attorney, Agent, or Firm* — TUCKER ELLIS LLP

(57) ABSTRACT

The present disclosure belongs to the technical field of organic materials and relates to an organic compound, and an electronic element and electronic device using the same.

(Continued)

The organic compound has the structure represented by the following Formula I. The organic compound of the present disclosure can improve the performance of the electronic element.

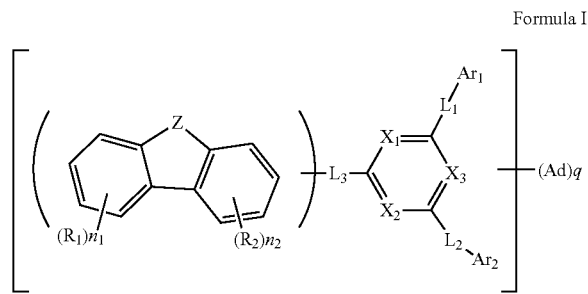

Formula I

15 Claims, 1 Drawing Sheet

(51) Int. Cl.
C07D 405/04 (2006.01)
C07D 405/10 (2006.01)
C07D 405/14 (2006.01)
C07D 409/14 (2006.01)
H01L 51/00 (2006.01)
H01L 51/50 (2006.01)
H10K 85/60 (2023.01)
H10K 50/11 (2023.01)

(52) U.S. Cl.
CPC ......... *C07D 405/04* (2013.01); *C07D 405/10* (2013.01); *C07D 405/14* (2013.01); *C07D 409/14* (2013.01); *H10K 85/615* (2023.02); *H10K 85/626* (2023.02); *H10K 85/6572* (2023.02); *H10K 85/6574* (2023.02); *H10K 85/6576* (2023.02); *H10K 50/11* (2023.02)

(58) Field of Classification Search
CPC .. C07D 409/10; C07D 409/14; C07D 403/04; C07D 403/10; C07D 403/14; H10K 85/615; H10K 85/626; H10K 85/654; H10K 85/6572; H10K 85/6574; H10K 85/6576
See application file for complete search history.

(56) References Cited

FOREIGN PATENT DOCUMENTS

| | | | | |
|---|---|---|---|---|
| CN | 110563647 A | | 12/2019 | |
| CN | 110662750 A | | 1/2020 | |
| CN | 110746429 A | | 2/2020 | |
| CN | 111018843 A | | 4/2020 | |
| CN | 112159348 A | * | 1/2021 | ........... C07D 213/57 |
| CN | 110746429 B | * | 11/2022 | ........... C07D 209/86 |
| EP | 3636641 A1 | | 4/2020 | |
| KR | 20210048334 A | * | 5/2021 | ........... C07D 471/04 |
| WO | WO-2021029598 A1 | * | 2/2021 | ........... C07D 405/14 |
| WO | WO-2021080253 A1 | * | 4/2021 | ........... C07D 405/04 |

OTHER PUBLICATIONS

International Search Report from corresponding International Application No. PCT/CN2021/093160, dated Jul. 27, 2021, 4 pages with translation.

* cited by examiner

ORGANIC COMPOUND, AND ELECTRONIC ELEMENT AND ELECTRONIC DEVICE USING SAME

CROSS REFERENCE TO RELATED APPLICATIONS

The present application claims priorities to Chinese Patent Application No. 202010398845.6 filed on May 12, 2020, and Chinese Patent Application No. 202010889735.X filed on Aug. 28, 2020, the contents of which are hereby incorporated by reference in their entirety as part of this application.

TECHNICAL FIELD

The present disclosure relates to the technical field of organic materials, and in particular, provides an organic compound, and an electronic element and electronic device using the same.

BACKGROUND

With the development of electronic technology and the advancement of material science, electronic elements for achieving electroluminescence or photoelectric conversion are used in an increasingly wide range of uses. Such electronic element usually includes a cathode, an anode which are arranged oppositely to the anode, and a functional layer between the cathode and the anode. The functional layer consists of a plurality of organic or inorganic film layers and generally includes an energy conversion layer, a hole transport layer located between the energy conversion layer and the anode, and an electron transport layer located between the energy conversion layer and the cathode.

An organic electroluminescent device, for example, generally includes an anode, a hole transport layer, an electroluminescent layer as an energy conversion layer, an electron transport layer and a cathode that are sequentially stacked. When voltages are applied to the cathode and the anode, respectively, the two electrodes generate an electric field. Under the effect of the electric field, electrons at the cathode move to the electroluminescent layer, and holes at the anode also move to the electroluminescent layer, so that excitons are formed by combining the electrons and the holes in the electroluminescent layer. The excitons are in an excited state to release energy outward, which makes the electroluminescent layer emit light outward.

At present, the use of organic electroluminescent devices has the problems such as reduced luminous efficiency and shortened lifetime, resulting in the degradation of the performance of organic electroluminescent devices.

SUMMARY

In response to the above-mentioned problems of the prior art, the aims of the present disclosure are to provide an organic compound and an electronic element and electronic device using the same, and the organic compound is used in an organic electroluminescent device to improve the performance of the organic electroluminescent device.

In order to achieve the above purpose, the present disclosure provides an organic compound having a structure represented by the following Formula I:

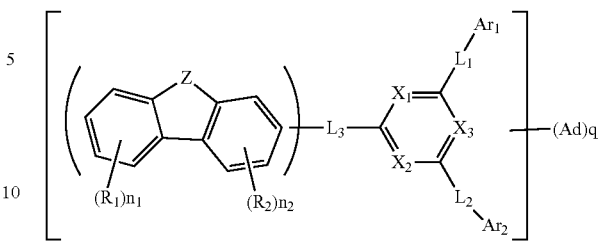

Formula I where Z is selected from O, S, $C(R_3R_4)$ or $N(R_5)$, $Si(R_3R_4)$, and Se, where $R_3$, $R_4$ and $R_5$ are the same or different, and are each independently selected from alkyl with 1 to 10 carbon atoms, substituted or unsubstituted aryl with 6 to 30 carbon atoms, or substituted or unsubstituted heteroaryl with 2 to 30 carbon atoms, or the $R_3$ and $R_4$ can form a ring together with the atoms to which they are jointly connected;

$X_1$, $X_2$ and $X_3$ are the same or different, and are each independently selected from CH or N, and at least one of $X_1$, $X_2$ and $X_3$ is N;

$R_1$ and $R_2$ are the same or different, and are each independently selected from deuterium, halogen group, alkyl with 1 to 10 carbon atoms, cycloalkyl with 3 to 10 carbon atoms, trialkylsilyl with 3 to 12 carbon atoms, substituted or unsubstituted aryl with 6 to 30 carbon atoms, substituted or unsubstituted heteroaryl with 3 to 30 carbon atoms, and alkoxy with 1 to 10 carbon atoms; $n_1$ represents the number of $R_1$ and $n_2$ represents the number of $R_2$; $R_1$ and $R_2$ are represented by $R_i$, and $n_1$ to $n_2$ are represented by $n_i$, i is a variable expressing 1 or 2; $n_i$ is each independently selected from 0, 1, 2, 3 or 4; and any two $n_i$s are the same or different when $n_i$ is greater than one; optionally, any two adjacent $R_i$s form a ring;

$Ar_1$ and $Ar_2$ are the same or different, and are each independently selected from substituted or unsubstituted aryl with 6 to 40 carbon atoms, or substituted or unsubstituted heteroaryl with 2 to 30 carbon atoms;

$L_1$, $L_2$ and $L_3$ are the same or different, and are each independently selected from a single bond, substituted or unsubstituted arylene with 6 to 35 carbon atoms, and substituted or unsubstituted heteroarylene with 3 to 30 carbon atoms;

substituents in $R_1$ to $R_5$, $L_1$ to $L_3$ and $Ar_1$ to $Ar_2$ are the same or different, and are each independently selected from deuterium, halogen group, a group A, trialkylsilyl with 3 to 12 carbon atoms, triarylsilyl with 18 to 24 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, and alkenyl with 2 to 6 carbon atoms; the group A is selected from substituted or unsubstituted heteroaryl with 3 to 20 carbon atoms or substituted or unsubstituted aryl with 6 to 20 carbon atoms, and substituents in the group A are selected from deuterium, halogen group, and alkyl with 1 to 4 carbon atoms; optionally, any two adjacent substituents form a ring;

Ad represents an adamantyl, and q is selected from 1, 2 or 3.

A second aspect of the present disclosure provides an electronic element comprising an anode, a cathode which is arranged oppositely to the anode, and a functional layer disposed between the anode and the cathode. The functional layer comprises the organic compound as described in the first aspect of the present disclosure.

A third aspect of the present disclosure provides an electronic device comprising the electronic element as described in the second aspect of the present disclosure.

The organic compound of the present disclosure uses N-heterobenzene as the parent core which is connected with aromatic heterocyclic groups around it, thereby destroying the crystallinity of the molecule and avoiding intermolecular aggregation. Adamantane is introduced into the molecular structure by connecting with an aromatic group and then connecting with the parent core. The resulting non-conjugated rigid structure effectively interrupts the conjugation and electron transfer of different functional groups, and the access of large groups with steric hindrance avoids the aggregation of compounds and the formation of π aggregates or excimer due to the direct stacking of conjugated planes. The use of the organic compound in organic electroluminescent devices can improve the luminescence efficiency, while ensuring relatively low drive voltage of the devices. In addition, this structure can improve the film-forming property of materials, while enhancing the overall molecular weight and asymmetry and improving the thermal stability of the molecule. The compound of the present disclosure has good film-forming property and fluorescence quantum efficiency. The electron donor and electron acceptor contained within the molecule can increase the orbital overlap and improve the luminescence efficiency, and the aromatic heterocyclic groups connected within the molecule help to obtain charge-transfer materials with spatially separated HOMO and LUMO. Accordingly, the organic compound of the present disclosure can effectively enhance the device efficiency and extend the lifetime of organic electroluminescent devices when used in the light-emitting layer of organic electroluminescent devices.

EXPLANATION OF REFERENCE NUMBERS

Figure 1:
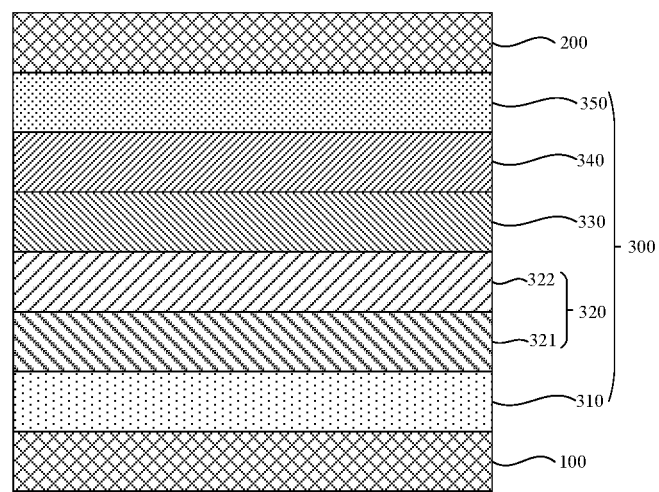
FIG. 1 is a schematic structural view of an organic electroluminescent device according to an embodiment of the present disclosure.

100: anode; 200: cathode; 300: functional layer; 310: hole injection layer; 320: hole transport layer; 321: first hole transport layer; 322: second hole transport layer; 330: organic light-emitting layer; 340: electron transport layer; 350: electron injection layer; 400: electronic device.

DETAILED DESCRIPTION

Specific embodiments of the present disclosure are described in detail below with reference to accompanying drawings. It is to be understood that the specific embodiments described herein are intended only to illustrate and explain the present disclosure and are not intended to limit the present disclosure.

In a first aspect, the present disclosure provides an organic compound having a structure represented by the following Formula I:

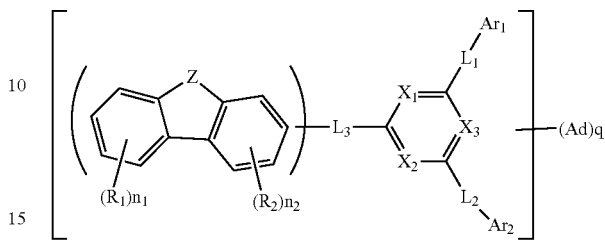

Formula I where Z is selected from O, S, $C(R_3R_4)$, $N(R_5)$, $Si(R_3R_4)$, and Se, where $R_3$, $R_4$ and $R_5$ are the same or different, and are each independently selected from alkyl with 1 to 10 carbon atoms, substituted or unsubstituted aryl with 6 to 30 carbon atoms or substituted or unsubstituted heteroaryl with 2 to 30 carbon atoms, or the $R_3$ and $R_4$ can form a ring together with the atoms to which they are jointly connected;

$X_1$, $X_2$ and $X_3$ are the same or different, and are each independently selected from CH or N, and at least one of $X_1$, $X_2$ and $X_3$ is N;

$R_1$ and $R_2$ are the same or different, and are each independently selected from deuterium, halogen group, alkyl with 1 to 10 carbon atoms, cycloalkyl with 3 to 10 carbon atoms, trialkylsilyl with 3 to 12 carbon atoms, substituted or unsubstituted aryl with 6 to 30 carbon atoms, substituted or unsubstituted heteroaryl with 3 to 30 carbon atoms, and alkoxy with 1 to 10 carbon atoms; $n_1$ represents the number $R_1$ and $n_2$ represents the number of $R_2$; $R_1$ and $R_2$ are represented by $R_i$, and $n_1$ to $n_2$ are represented by $n_i$, i is a variable expressing 1 or 2, $n_i$ is each independently selected from 0, 1, 2, 3 or 4; and any two $n_i$s are the same or different when $n_i$ is greater than one; optionally, any two adjacent $R_i$s form a ring, such as any two adjacent $R_i$s forming a benzene ring;

$Ar_1$ and $Ar_2$ are the same or different, and are each independently selected from substituted or unsubstituted aryl with 6 to 40 carbon atoms, or substituted or unsubstituted heteroaryl with 2 to 30 carbon atoms;

$L_1$, $L_2$ and $L_3$ are the same or different, and are each independently selected from a single bond, substituted or unsubstituted arylene with 6 to 35 carbon atoms, and substituted or unsubstituted heteroarylene with 3 to 30 carbon atoms;

$R_1$ to $R_5$, $L_1$ to $L_3$ and $Ar_1$ to $Ar_2$ have same or different substituents which are each independently selected from deuterium, halogen group, a group A, trialkylsilyl with 3 to 12 carbon atoms, triarylsilyl with 18 to 24 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, and alkenyl with 2 to 6 carbon atoms; the group A is selected from substituted or unsubstituted heteroaryl with 3 to 20 carbon atoms or substituted or unsubstituted aryl with 6 to 20 carbon atoms, and substituents in the group A are selected from deuterium, halogen group, and alkyl with 1 to 4 carbon atoms; optionally, any two adjacent substituents form a ring;

Ad represents adamantyl, and q is selected from 1, 2 or 3.

In the present disclosure, in formula I,

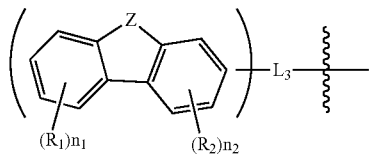

means that the group $L_3$ may be connected to any of benzene rings in the structure

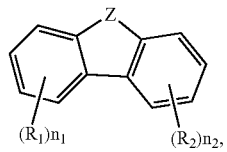

i.e., $L_3$ may be connected to any of the positions represented by 1, 2, 3, 4, a, b, c, d in

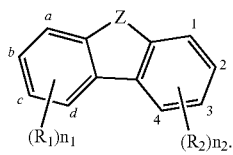

For example, when $L_3$ is connected to the benzene ring corresponding to $R_2$, the structure

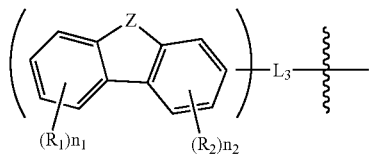

may include:

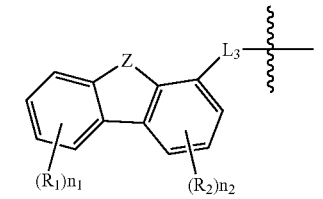

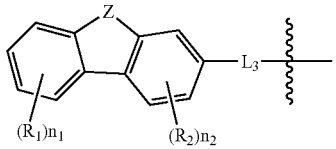

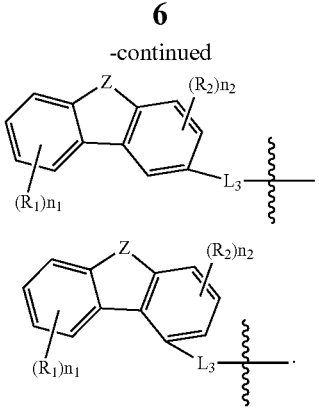

It is to be understood that when $L_3$ is connected to the benzene ring corresponding to $R_1$, $n_1$ is selected from 1, 2, or 3, and when $L_3$ is connected to the benzene ring corresponding to $R_2$, $n_2$ is selected from 1, 2, or 3. In addition, when the benzene ring of

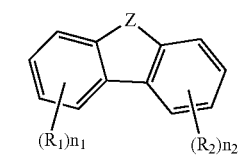

further include a fused ring formed, the group $L_3$ is optionally connected to the fused ring. For example, when

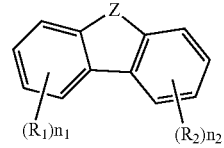

is

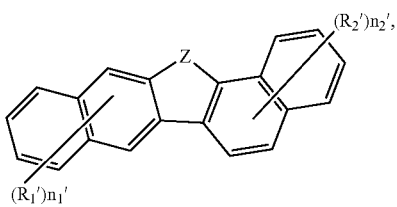

the group $L_3$ may be connected to any of positions on two naphthalene rings.

In the present disclosure, in formula I, "-(Ad)$_q$" means that a total of q Ad are connected to the structures

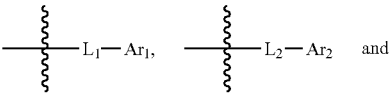

-continued

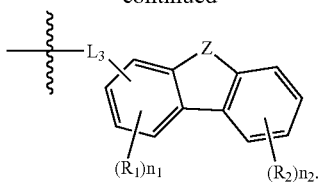

Ad may be connected to L₁, L₂ or L₃ (L₁, L₂ and L₃ are not a single bond), also may be connected to Ar₁ and Ar₂, or may be connected to the benzene ring structures shown in

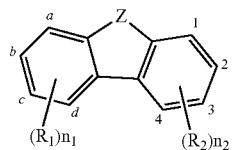

(i.e., to any of the positions represented by 1, 2, 3, 4, a, b, c, or d), and R₁, R₂ and Z thereon. In addition, in individual groups above, when a substituted group is present, Ad may be connected to the body of the group or to the substituents. For example, when Ar₁ is an aryl group substituted by a heteroaryl group, Ad may be connected to the aryl group, or connected to the heteroaryl group which is a substituent.

In the present disclosure, the descriptions of "each . . . independently is" and "independently respectively" and "independently selected from" may be interchanged, and will be understood in a broad sense as either meaning that specific options expressed by the same symbols in different groups do not affect each other, or that specific options expressed by the same symbols in the same groups do not affect each other. For example, in

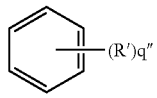
formula Q-1

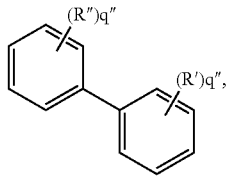
formula Q-2 each q" is independently 0, 1, 2 or 3, and each R" is independently selected from hydrogen, deuterium, fluorine, chlorine. This means that, formula Q-1 represents that there are substituents R" in amount of q" on the benzene ring, the R" may be the same or different, and the options of each R" do not affect each other; formula Q-2 represents that there are substituents R" in amount of q" on each of benzene rings in biphenyl, the numbers of the substituents R" on two benzene rings are the same or different, the R" may be the same or different, and the options of each R" do not affect each other.

In the present disclosure, the term "optional" or "optionally" means that the event or circumstance described subsequently may, but need not, occur, and that the description includes instances where the event or circumstance occurs or does not occur. For example, "optionally, two adjacent substituents xx form a ring" means that the two substituents may form a ring but do not have to form a ring, including scenarios in which two adjacent substituents form a ring and scenarios in which two adjacent substituents do not form a ring.

In the present disclosure, the term "substituted or unsubstituted" means that the functional group recited after the term may or may not have a substituent (hereinafter, the substituent is collectively referred to as Rc, for ease of description). For example, "substituted or unsubstituted aryl" refers to an aryl group having a substituent Rc or a non-substituted aryl group. The above-mentioned substituent Rc may be, for example, deuterium, halogen group, substituted or unsubstituted heteroaryl, substituted or un substituted aryl, tri alkyl silyl, tri aryl silyl, alkyl, haloalkyl, etc. When the substituent Rc itself is selected from substituted or unsubstituted heteroaryl, and substituted or unsubstituted aryl, it means that the substituent Rc is selected from heteroaryl, substituted heteroaryl, aryl, and substituted aryl.

In the present disclosure, the number of carbon atoms of a substituted or unsubstituted functional group refers to the number of all carbon atoms. For example, if L₁ is selected from a substituted arylene group with 12 carbon atoms, the number of all carbon atoms of the arylene group and the substituents thereon is 12.

In the present disclosure, aryl refers to an optional functional group or substituent derived from an aromatic carbon ring. The aryl group may be a monocyclic aryl group (e.g., phenyl) or a polycyclic aryl group. In other words, the aryl group may be a monocyclic aryl group, a fused aryl group, two or more monocyclic aryl groups connected by carbon-carbon bond conjugation, a monocyclic aryl group and a fused aryl group connected by carbon-carbon bond conjugation, and two or more fused aryl groups connected by carbon-carbon bond conjugation. That is, unless otherwise stated, two or more aromatic groups connected by carbon-carbon bond conjugation may also be considered as an aryl group of this disclosure. Among them, the fused aryl group may include, for example, a fused bicyclic aryl group (e.g., naphthyl), a fused tricyclic aryl group (e.g., phenanthryl, fluorenyl, anthracenyl), etc. The aryl groups do not contain heteroatoms such as B, N, O, S, P, Se and Si. For example, in the present disclosure, all of a biphenyl group, a terphenyl group, etc. are aryl groups. Examples of aryl groups may include, but are not limited to, a phenyl group, a naphthyl group, a fluorenyl group, an anthracenyl group, a phenanthryl group, a biphenyl group, a terphenyl group, a quaterphenyl group, a quinquephenyl group, a benzo[9,10] phenanthryl group, a pyrenyl group, a benzofluorathenyl group, a chrysenyl group, and the like. In the present disclosure, the arylene group involved is a divalent group formed by the further loss of a hydrogen atom from an aryl group.

In the present disclosure, the substituted aryl group may be an aryl in which one or more hydrogen atoms are substituted by, for example, a deuterium atom, halogen group, cyano, aryl, heteroaryl, trialkylsilyl, alkyl, cycloalkyl, alkoxy, alkylthio. It is to be understood that the number of carbon atoms of the substituted aryl group refers to the total number of carbon atoms of the aryl group and the substituents thereon. For example, a substituted aryl with 18 carbon atoms means that the total number of carbon atoms of the aryl group and the substituents is 18.

In the present disclosure, the heteroaryl is a monovalent aromatic ring or a derivative thereof that contains at least one heteroatom in the ring, and the heteroatom may be at least one of B, O, N, P, Si, Se and S. The heteroaryl may be a monocyclic heteroaryl or a polycyclic heteroaryl. In other words, the heteroaryl may be a single aromatic ring system, or a plurality of aromatic ring systems formed by conjugate connection of carbon-carbon bonds, and any of aromatic ring systems is a monocyclic aromatic ring or a fused aromatic ring. Examples of the heteroaryl group may include a thienyl group, a furanyl group, a pyrrolyl group, an imidazolyl group, a thiazolyl group, an oxazolyl group, an oxadiazolyl group, a triazolyl group, a pyridinyl group, a bipyridinyl group, a pyrimidinyl group, a triazinyl group, an acridinyl group, a pyridazinyl group, a pyrazinyl group, a quinolinyl group, a quinazolinyl group, a quinoxalinyl group, a phenoxazinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothienyl group, a dibenzothienyl group, a thienothienyl group, a benzofuranyl group, a phenanthrolinyl group, an isoxazolyl group, a thiadiazolyl group, a benzothiazolyl group, a phenothiazinyl group, a silylfluorenyl group, a dibenzofuranyl group, an N-phenylcarbazolyl group, an N-pyridylcarbazolyl group, an N-methylcarbazolyl group, and the like, without being limited thereto. Among them, the thienyl group, the furanyl group, the phenanthrolinyl group and the like are heteroaryl groups each with a single aromatic ring system, and the N-phenylcarbazolyl group and the N-pyridylcarbazolyl group are heteroaryl groups each with polycyclic ring systems connected by carbon-carbon bond conjugation. In the present disclosure, the heteroaryl group involved is a divalent group formed by further loss of a hydrogen atom of the heteroaryl group.

In the present disclosure, the substituted heteroaryl may be a heteroaryl in which one or more hydrogen atoms are substituted by, for example, a deuterium atom, halogen group, aryl, heteroaryl, trialkylsilyl, alkyl, cycloalkyl, alkoxy, alkylthio. Specific examples of aryl-substituted heteroaryl groups include, but are not limited to, a phenyl-substituted dibenzofuranyl group, a phenyl-substituted dibenzothienyl group, and a phenyl-substituted pyridyl group. It is to be understood that the number of carbon atoms of the substituted heteroaryl group refers to the total number of carbon atoms of the heteroaryl group and the substituents on the heteroaryl group.

In the present disclosure, in "any two adjacent substituents form a ring", the "any two adjacent" means that two substituents are located on the same atom, or one substituent is located on each of the two adjacent atoms. When two substituents are located on the same atom, the two substituents may form a saturated or unsaturated ring together with the atoms to which they are jointly connected; and when one substituent is located on each of the two adjacent atoms, the two substituents may be fused into a ring.

In the present disclosure, a nonlocalized linkage bond is a single bond that extends from the ring system, which means that one end of the linkage bond may be connected to any position in the ring system through which the bond runs, and the other end to the rest of the compound molecule.

For example, as shown in formula (f) below, the naphthyl group represented by formula (f) is connected to the rest of the molecule by two nonlocalized linkage bonds through the bicyclic ring, including any of the possible ways of connection shown in formulae (f-1) to (f-10):

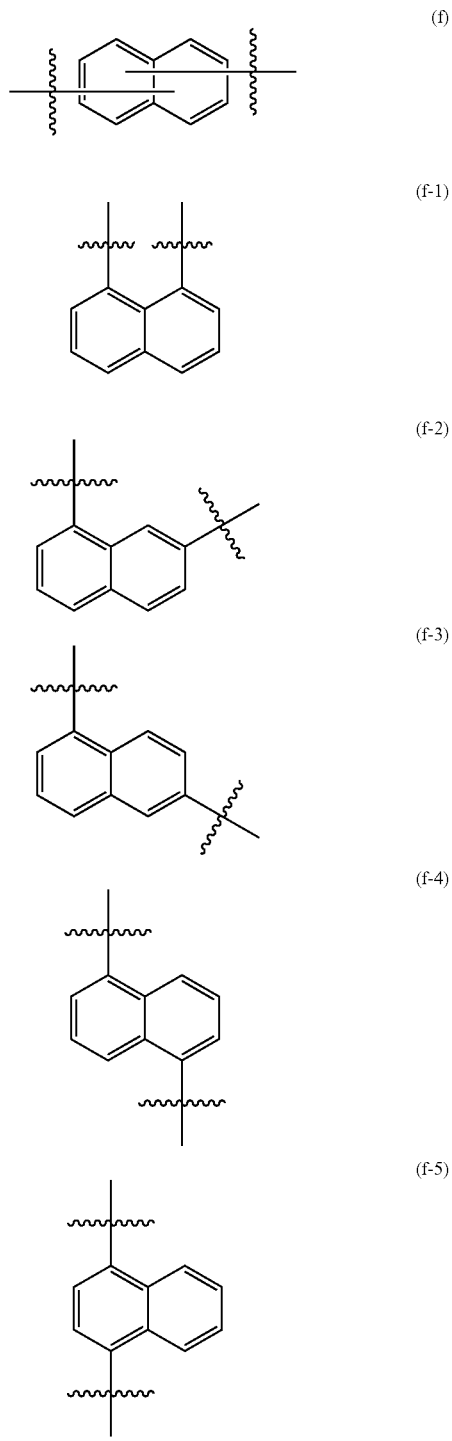

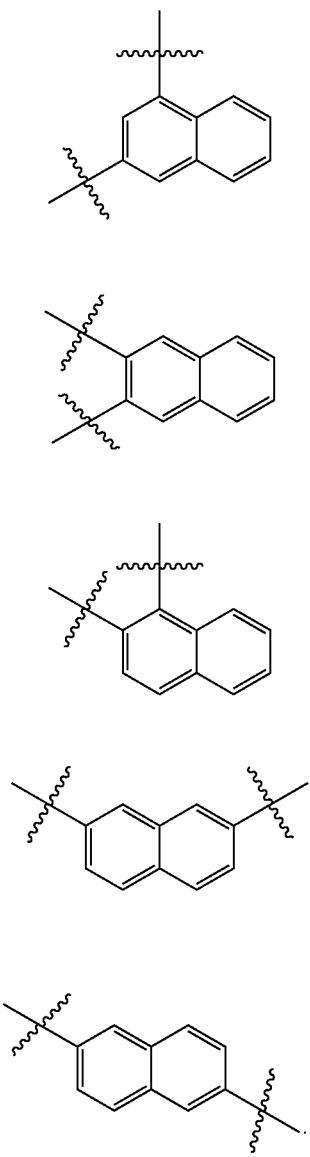

(f-6)
(f-7)
(f-8)
(f-9)
(f-10)

For another example, as shown in formula (X') below, the phenanthryl group represented by equation (X') is connected to the rest of the molecule by a nonlocalized linkage bond extending from the middle of the benzene ring on one side, including any of the possible ways of connection shown in formulae (X'-1) to (X'-4):

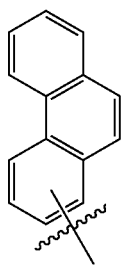

(X')

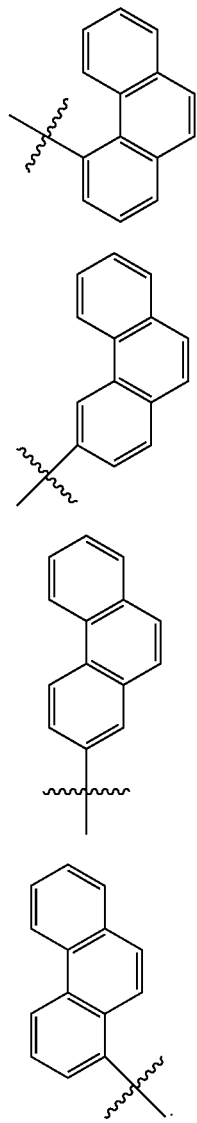

(X'-1)
(X'-2)
(X'-3)
(X'-4)

A nonlocalized substituent in the present disclosure refers to a substituent connected by a single bond extending from the center of a ring system, which means that the substituent may be connected at any possible position in the ring system. For example, as shown in formula (Y) below, the substituent R' represented by formula (Y) is connected to the quinoline ring by a nonlocalized linkage bond, including any of the possible ways of connection shown in formulae (Y-1) to (Y-7):

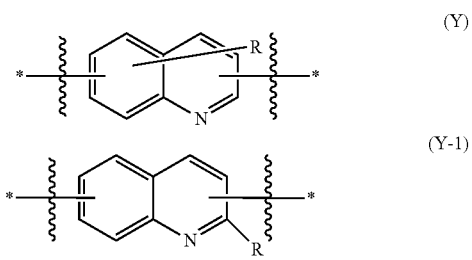

(Y)
(Y-1)

-continued

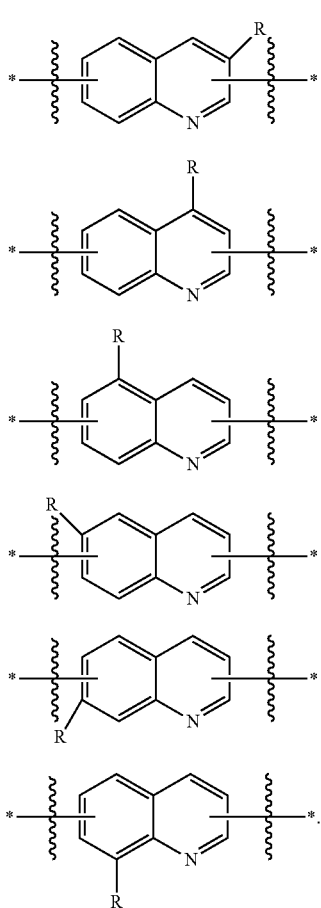

(Y-2)
(Y-3)
(Y-4)
(Y-5)
(Y-6)
(Y-7)

In the present disclosure, the alkyl group with 1 to 10 carbon atoms may include a linear alkyl group with 1 to 10 carbon atoms and a branched alkyl group with 3 to 10 carbon atoms, and the number of carbon atoms may be, for example, 1, 2, 3, 4, 5, 6, 7, 8, 9, or 10. Specific examples of alkyl groups with 1 to 10 carbon atoms include, but are not limited to, a methyl group, an ethyl group, an n-propyl group, an isopropyl group, an n-butyl group, an isobutyl group, a tert-butyl group, an n-pentyl group, an iso-pentyl group, a neopentyl group, a cyclopentyl group, an n-hexyl group, a heptyl group, an n-octyl group, a 2-ethylhexyl group, a nonyl group, a decyl group, and a 3,7-dimethyl octyl group.

In the present disclosure, the halogen group may include fluorine, iodine, bromine and chlorine, and the like.

In the present disclosure, the aryl group with 6 to 20 carbon atoms may have the number of carbon atoms of, for example, 6 (phenyl), 10 (naphthyl), 12 (e.g., biphenyl), 14, 15, and 16, etc. The heteroaryl group with 3 to 20 carbon atoms may have the number of carbon atoms of, for example, 5, 8, 12, 15, and 18, and the like.

In the present disclosure, specific examples of trialkylsilyl groups with 3 to 12 carbon atoms include, but are not limited to, a trimethylsilyl group, a triethylsilyl group, and the like.

In the present disclosure, specific examples of cycloalkyl groups with 3 to 10 carbon atoms include, but are not limited to, a cyclopentyl group, a cyclohexyl group, an adamantyl group, and the like. A cycloalkyl with 5 to 10 carbon atoms may be, for example, a cyclopentyl group, or a cyclohexyl group.

In some embodiments, the organic compound has a structure represented by any one of formulae 2-1 to 2-12:

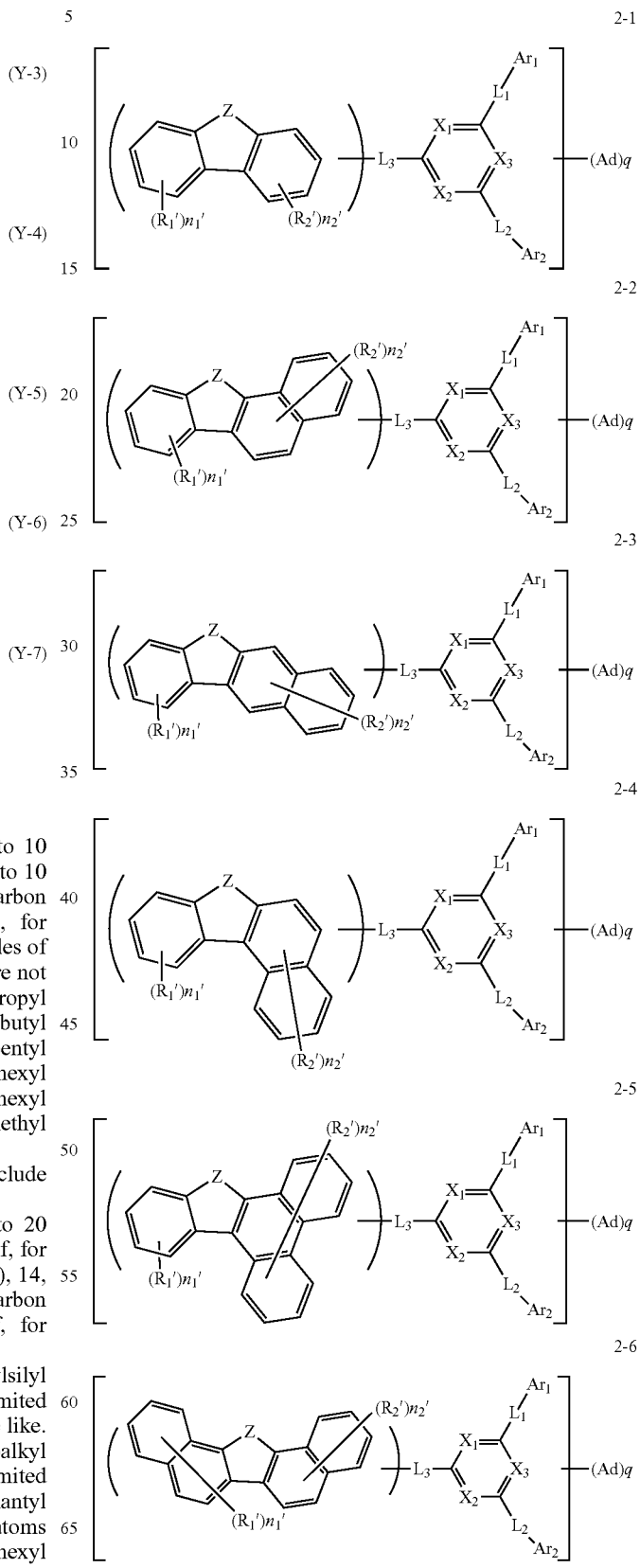

2-1
2-2
2-3
2-4
2-5
2-6

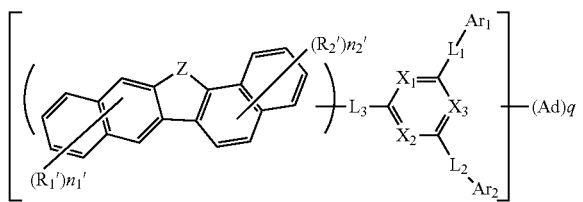

2-7

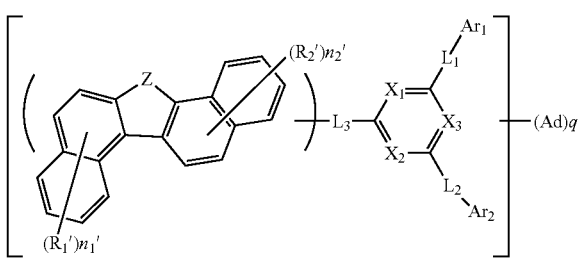

2-8

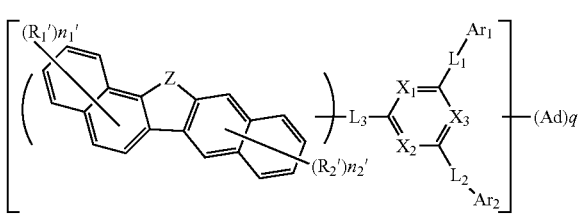

2-9

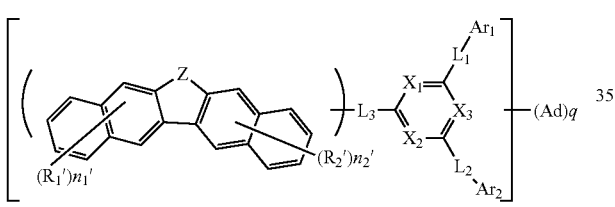

2-10

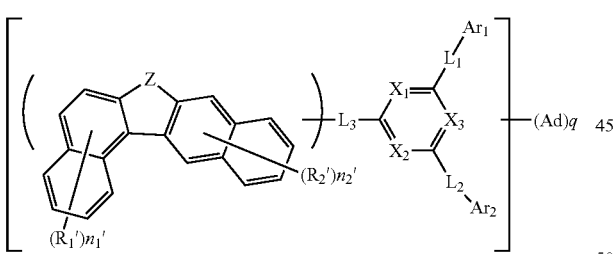

2-11

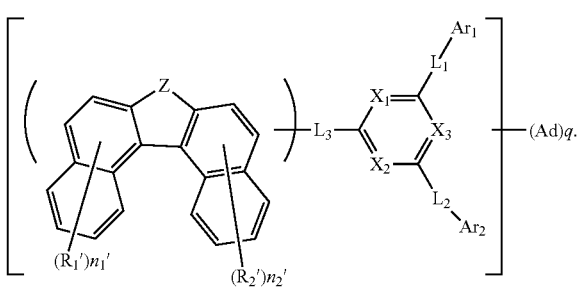

2-12

$R_1'$ and $R_2'$ are the same or different, and are each independently selected from deuterium, halogen group, alkyl with 1 to 10 carbon atoms, haloalkyl with 1 to 10 carbon atoms, trialkylsilyl with 3 to 12 carbon atoms, substituted or unsubstituted aryl with 6 to 12 carbon atoms, and substituted or unsubstituted heteroaryl with 3 to 20 carbon atoms; the substituents in $R_1'$ and $R_2'$ are each independently selected from deuterium, fluorine, trialkylsilyl with 3 to 7 carbon atoms, cycloalkyl with 5 to 10 carbon atoms, haloalkyl with 1 to 4 carbon atoms, alkoxy with 1 to 4 carbon atoms, and alkylthio with 1 to 4 carbon atoms, $n_1'$ represents the number of $R_1'$ and $n_2'$ represents the number of $R_2'$; and $n_1'$ and $n_2'$ are each independently 0, 1 or 2.

Optionally, the entire structure shown in Formula I includes up to 3 Ad.

In some embodiments, the organic compound has the structure represented by any one of formula 3-1 to formula 3-8:

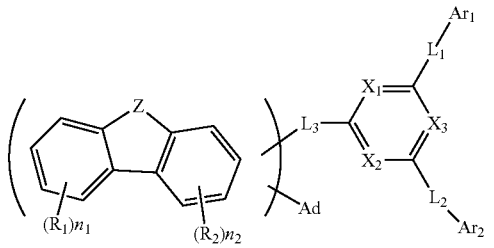

3-1

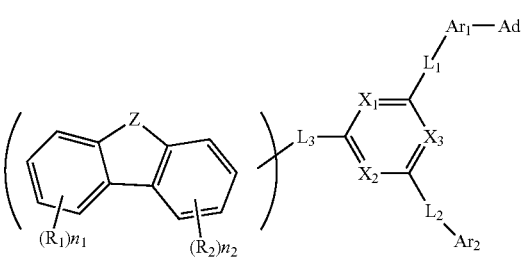

3-2

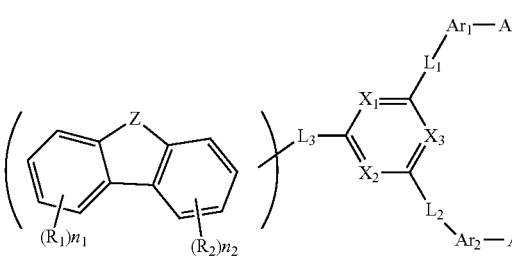

3-3

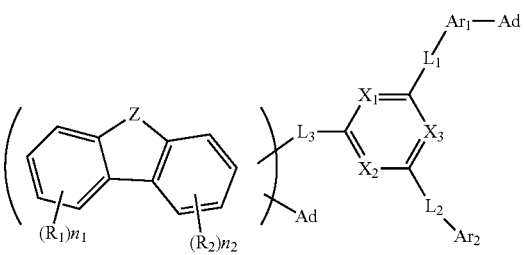

3-4

3-5

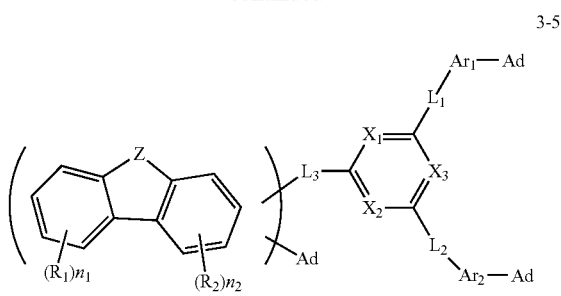

3-6

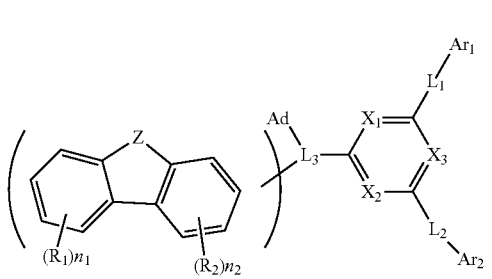

3-7

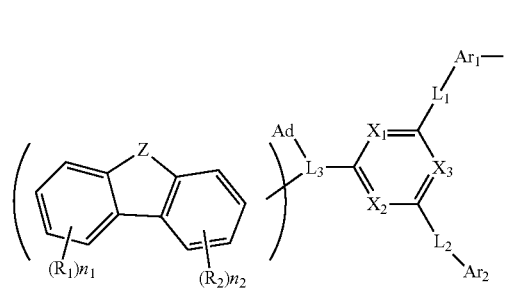

3-8

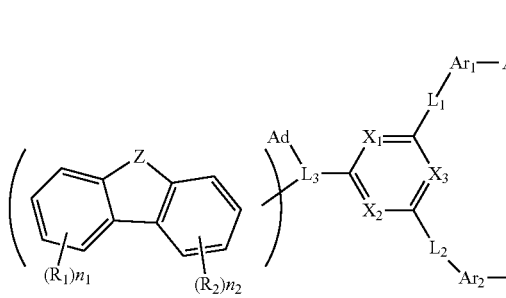

in formulae 3-1, 3-2 and 3-6, just only one Ad is present. In formulae 3-3, 3-4, and 3-7, just only two Ads are present. In formulae 3-5 and 3-8, just only three Ads are present.

In the present disclosure, Ad may be 1-adamantyl

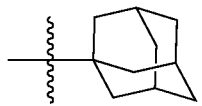

or 2-adamantyl

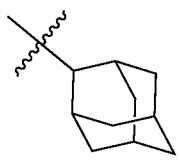 [SMILES: *C1C2CC3CC(C2)CC1C3]

Optionally, Ad is 1-adamantyl.

In the present disclosure, in some embodiments, $X_1$, $X_2$, and $X_3$ are not N at the same time, for example, two of $X_1$, $X_2$, and $X_3$ are N, or one of $X_1$, $X_2$, and $X_3$ is N. In other embodiments, all of $X_1$, $X_2$, and $X_3$ are N.

In the present disclosure, in some embodiments, $Ar_1$ and $Ar_2$ are the same or different, and are each independently selected from the group consisting of groups represented by the following formulae i-1 to i-15:

i-1

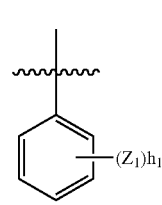

i-2

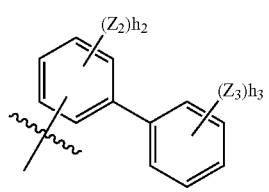

i-3

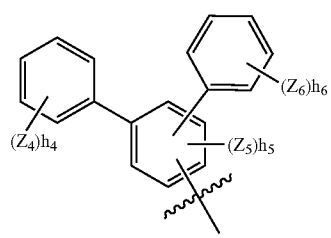

i-4

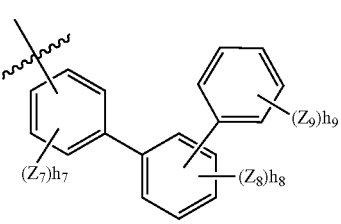

i-5

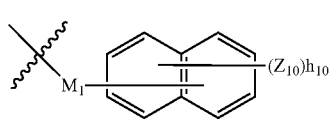

i-6

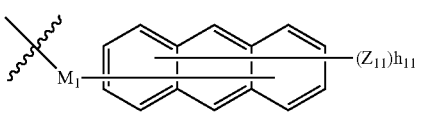

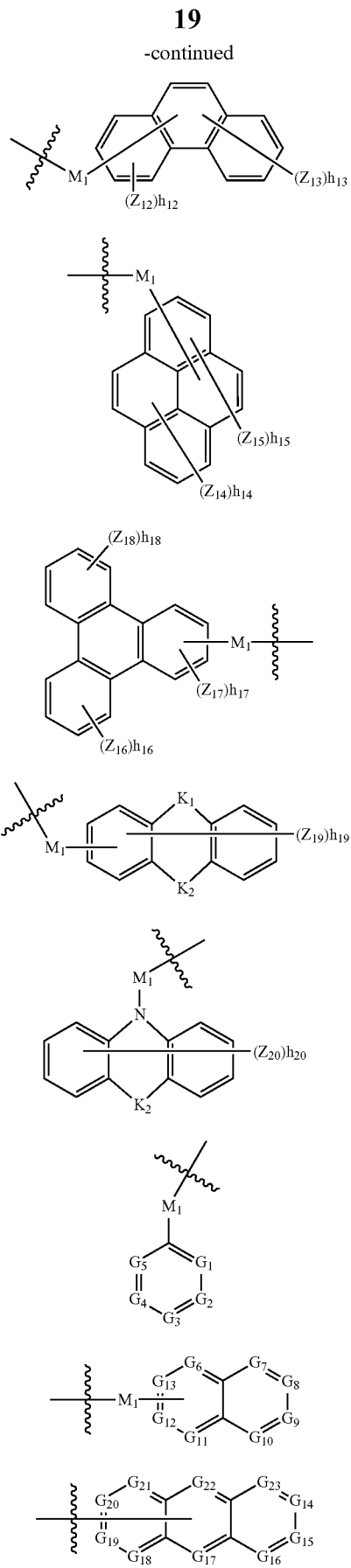

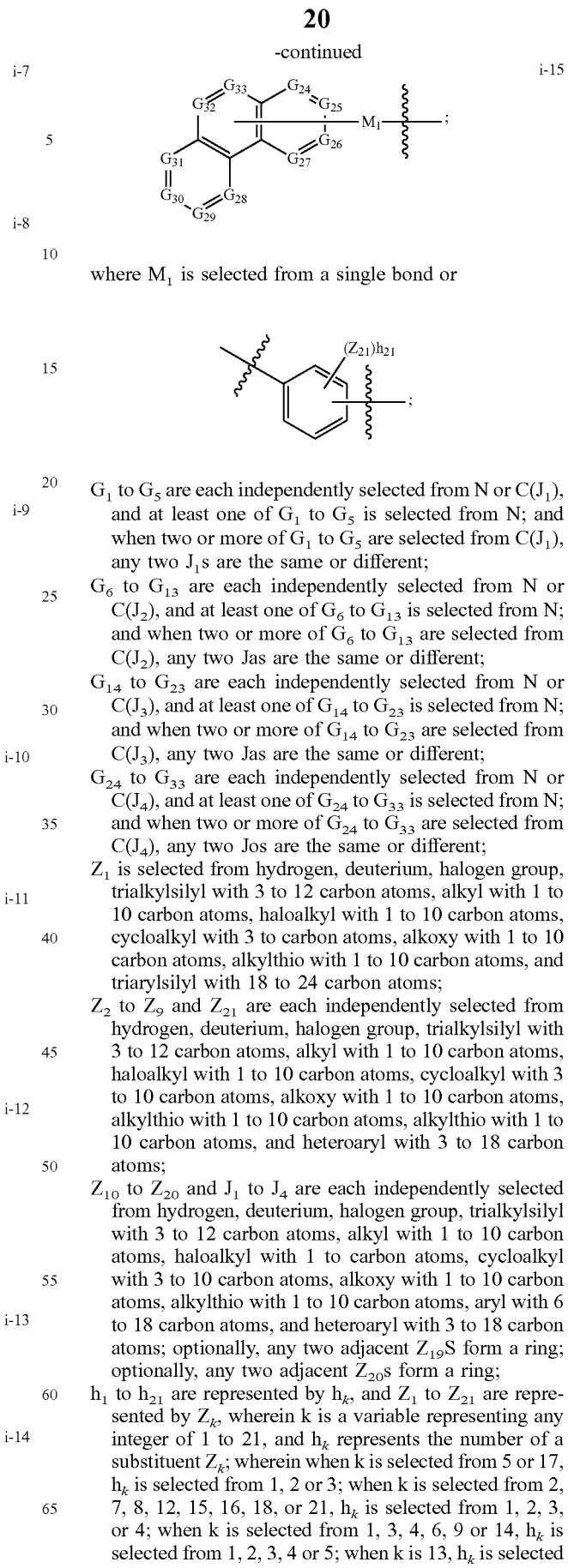

where $M_1$ is selected from a single bond or $G_1$ to $G_5$ are each independently selected from N or $C(J_1)$, and at least one of $G_1$ to $G_5$ is selected from N; and when two or more of $G_1$ to $G_5$ are selected from $C(J_1)$, any two $J_1$s are the same or different;

$G_6$ to $G_{13}$ are each independently selected from N or $C(J_2)$, and at least one of $G_6$ to $G_{13}$ is selected from N; and when two or more of $G_6$ to $G_{13}$ are selected from $C(J_2)$, any two Jas are the same or different;

$G_{14}$ to $G_{23}$ are each independently selected from N or $C(J_3)$, and at least one of $G_{14}$ to $G_{23}$ is selected from N; and when two or more of $G_{14}$ to $G_{23}$ are selected from $C(J_3)$, any two Jas are the same or different;

$G_{24}$ to $G_{33}$ are each independently selected from N or $C(J_4)$, and at least one of $G_{24}$ to $G_{33}$ is selected from N; and when two or more of $G_{24}$ to $G_{33}$ are selected from $C(J_4)$, any two Jos are the same or different;

$Z_1$ is selected from hydrogen, deuterium, halogen group, trialkylsilyl with 3 to 12 carbon atoms, alkyl with 1 to 10 carbon atoms, haloalkyl with 1 to 10 carbon atoms, cycloalkyl with 3 to carbon atoms, alkoxy with 1 to 10 carbon atoms, alkylthio with 1 to 10 carbon atoms, and triarylsilyl with 18 to 24 carbon atoms;

$Z_2$ to $Z_9$ and $Z_{21}$ are each independently selected from hydrogen, deuterium, halogen group, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, alkylthio with 1 to 10 carbon atoms, and heteroaryl with 3 to 18 carbon atoms;

$Z_{10}$ to $Z_{20}$ and $J_1$ to $J_4$ are each independently selected from hydrogen, deuterium, halogen group, trialkylsilyl with 3 to 12 carbon atoms, alkyl with 1 to 10 carbon atoms, haloalkyl with 1 to carbon atoms, cycloalkyl with 3 to 10 carbon atoms, alkoxy with 1 to 10 carbon atoms, alkylthio with 1 to 10 carbon atoms, aryl with 6 to 18 carbon atoms, and heteroaryl with 3 to 18 carbon atoms; optionally, any two adjacent $Z_{19}$s form a ring; optionally, any two adjacent $Z_{20}$s form a ring;

$h_1$ to $h_{21}$ are represented by $h_k$, and $Z_1$ to $Z_{21}$ are represented by $Z_k$, wherein k is a variable representing any integer of 1 to 21, and $h_k$ represents the number of a substituent $Z_k$; wherein when k is selected from 5 or 17, $h_k$ is selected from 1, 2 or 3; when k is selected from 2, 7, 8, 12, 15, 16, 18, or 21, $h_k$ is selected from 1, 2, 3, or 4; when k is selected from 1, 3, 4, 6, 9 or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is 20, $h_k$ is selected from 1, 2, 3, 4, 5, 6, 7 or 8; when k is 11, $h_k$ is selected from 1, 2, 3, 4, 5, 6, 7, 8 or 9; and when $h_k$ is greater than one, any two $Z_k$s are the same or different;

$K_1$ is selected from O, S, $N(Z_{22})$, $C(Z_{23}Z_{24})$, and $Si(Z_{23}Z_{24})$, where $Z_{22}$, $Z_{23}$ and $Z_{24}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{23}$ and the $Z_{24}$ are connected to each other to form a saturated or unsaturated ring with 3 to 15 carbon atoms together with the atoms to which they are jointly connected;

$K_2$ is selected from a single bond, O, S, $N(Z_{25})$, $C(Z_{26}Z_{27})$, and $Si(Z_{26}Z_{27})$, where $Z_{25}$, $Z_{26}$, and $Z_{27}$ are each independently selected from aryl with 6 to 18 carbon atoms, heteroaryl with 3 to 18 carbon atoms, alkyl with 1 to 10 carbon atoms, or cycloalkyl with 3 to 10 carbon atoms, or the $Z_{26}$ and the $Z_{27}$ are connected to each other to form a saturated or unsaturated ring with 3 to 15 carbon atoms together with the atoms to which they are jointly connected.

In formulae i-13 to i-15, $j_2$ to $J_4$ may be represented by $J_j$, where j is a variable representing 2, 3 or 4. For example, when j is 2, $J_j$ refers to $J_2$. It is to be understood that, when a nonlocalized linkage bond is connected to $C(J_j)$, the $J_j$ of $C(J_j)$ is not present. For example, in formula i-13, when

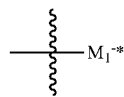

is connected to $G_{12}$, $G_{12}$ may just only represent C atoms, that is, the specific structure of formula i-13 is

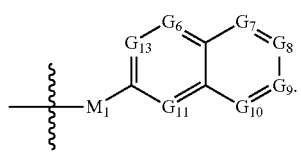

Similarly, in formulae j-10 to j-12, which relate hereinafter to $L_1$ to $L_3$, Q represents a C atom when

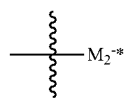

is connected to Q (e.g., $Q_1$) of each C-containing group (e.g., $C(J_5)$).

In the present disclosure, the ring formed by the interconnection between the groups $Z_{23}$ and $Z_{24}$ or between the groups $Z_{26}$ and $Z_{27}$ may be a saturated or unsaturated ring with 3 to 15 carbon atoms. For example, in formula i-10, when both of $K_2$ and $M_1$ are a single bond, $Z_{19}$ is hydrogen, and when $K_1$ is $C(Z_{23}Z_{24})$ and the $Z_{23}$ and the $Z_{24}$ are connected to each other to form a ring together with the atoms to which they are jointly connected, formula i-10 is

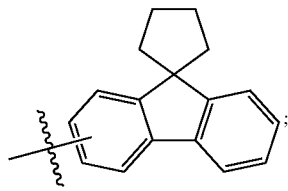

similarly, formula i-10 may also represent

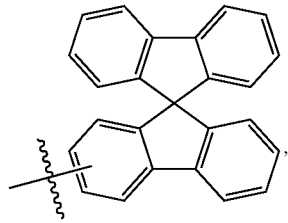

that is, the $Z_{23}$ and the $Z_{24}$ are connected to each other to form a partially unsaturated 13-membered ring together with the atoms to which they are jointly connected. Similarly, in the following formulae j-8 to j-9, which relate hereafter to $L_1$ to $L_3$, the rings formed by the interconnection between the groups $E_{16}$ and $E_{17}$ or between the groups $E_{19}$ and $E_{20}$ have a similar explanation, and are not described herein again.

Optionally, $Ar_1$ and $Ar_2$ are the same or different, and are each independently selected from substituted or unsubstituted aryl with 6 to 25 carbon atoms, or substituted or unsubstituted heteroaryl with 5 to 20 carbon atoms.

In some embodiments, $Ar_1$ and $Ar_2$ are the same or different, and are each independently selected from a substituted or unsubstituted group $V_1$, where the unsubstituted group $V_1$ is selected from the group consisting of the following groups:

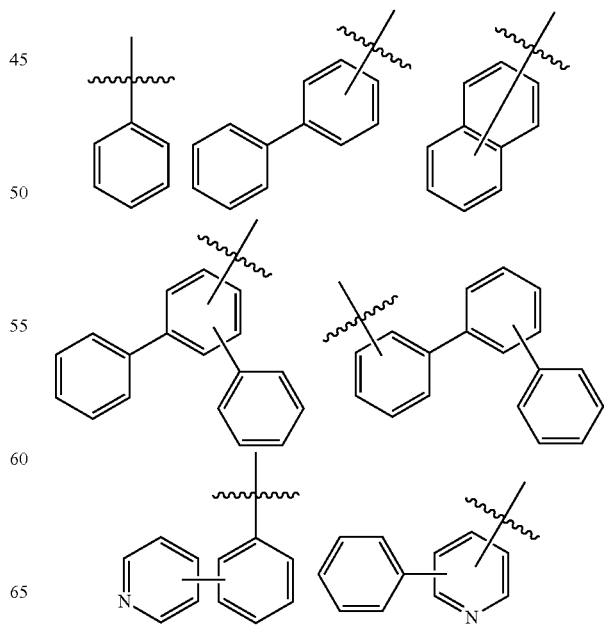

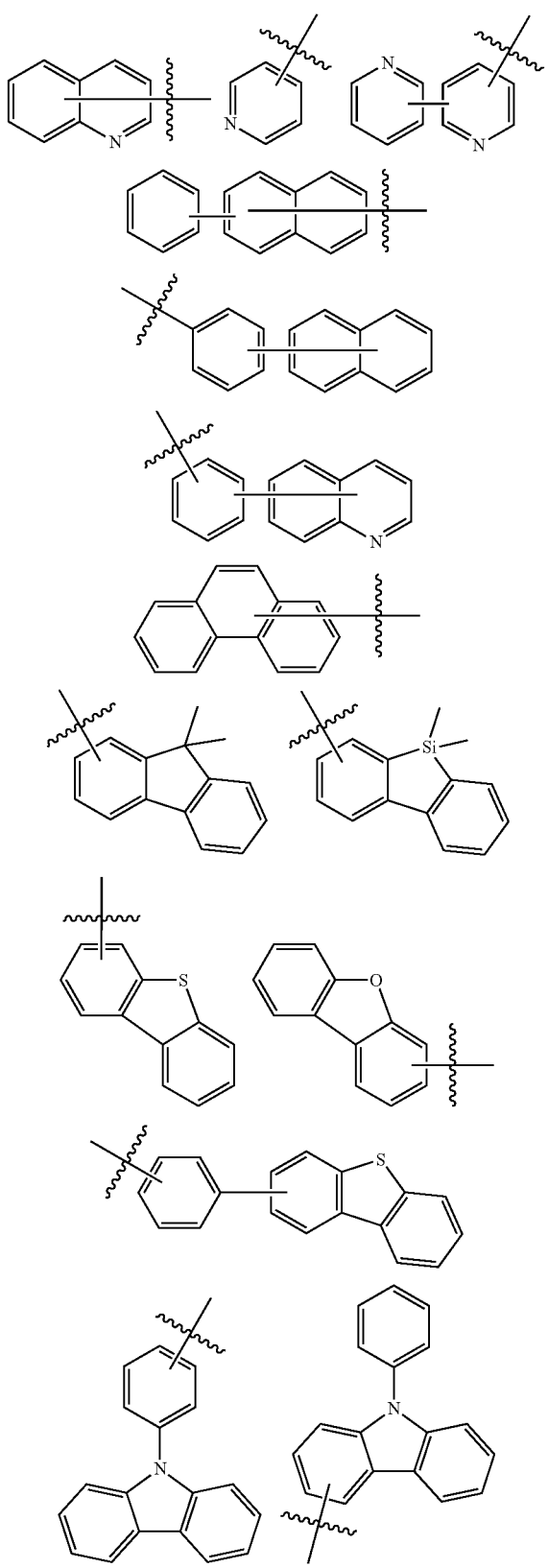
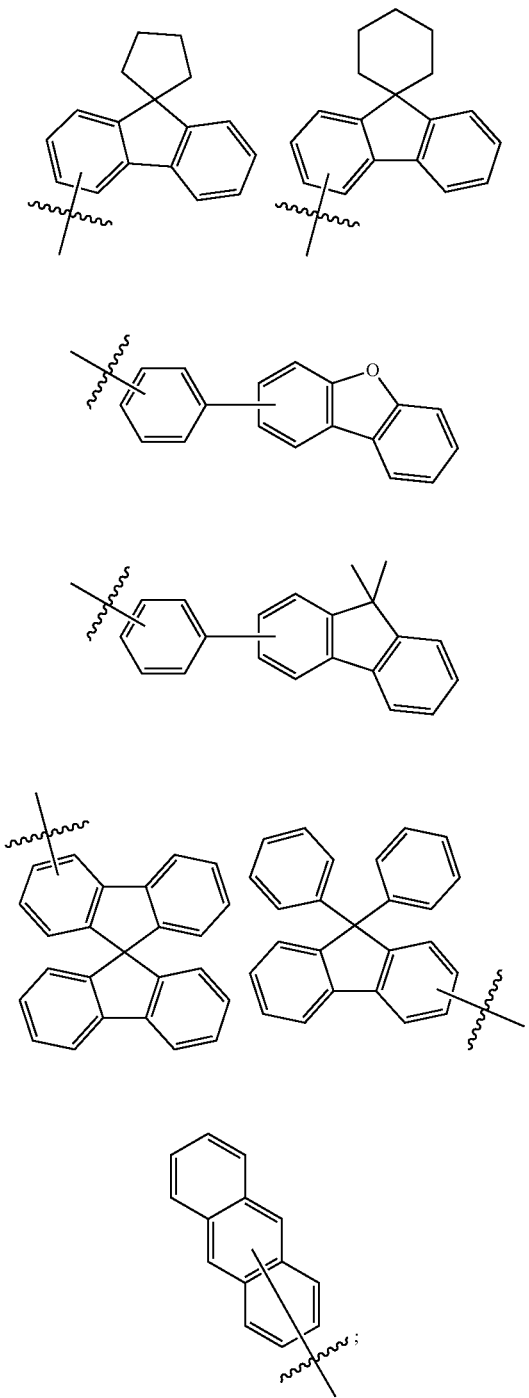

the substituted group $V_1$ has one or more substituents, where the substituents are each independently selected from deuterium, fluorine, alkyl with 1 to 4 carbon atoms, fluoroalkyl with 1 to 4 carbon atoms (e.g., trifluoromethyl), trialkylsilyl with 3 to 7 carbon atoms, alkoxy with 1 to 4 carbon atoms, alkylthio with 1 to 4 carbon atoms, cyclopentyl, cyclohexyl, pyridyl, and phenyl. When the number of substituents is greater than one, the substituents are the same or different, and optionally two adjacent substituents may be fused into a ring.

Further optionally, at least one of $Ar_1$ and $Ar_2$ is selected from substituted or unsubstituted
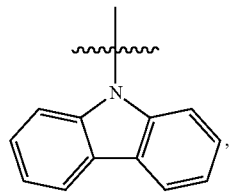 [SMILES: *n1c2ccccc2c2ccccc21]
with the substituent being phenyl.
Optionally, $Ar_1$ and $Ar_2$ are the same or different, and are each independently selected from the group consisting of the following groups:
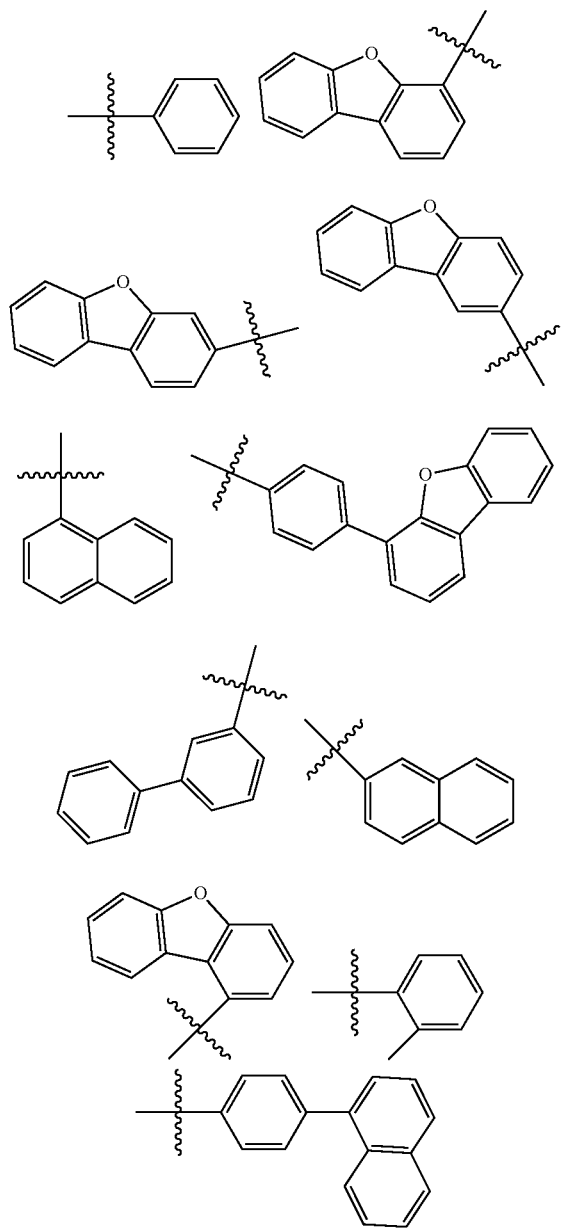
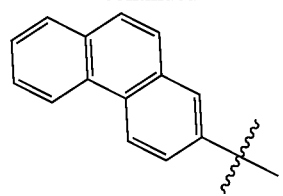
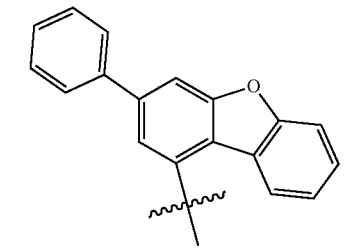
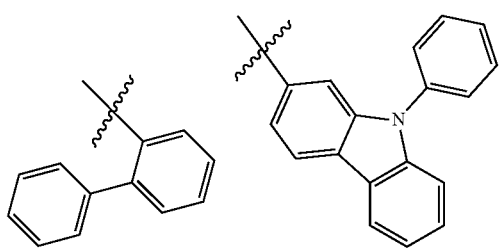
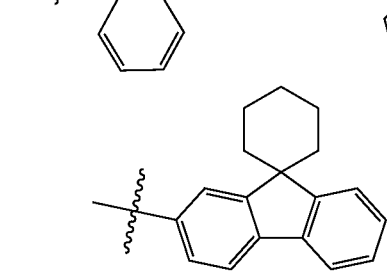
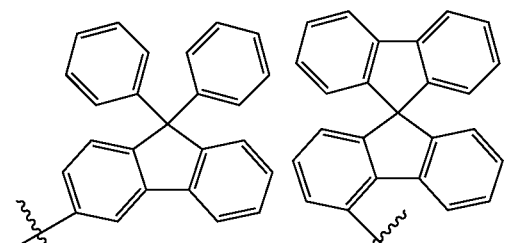
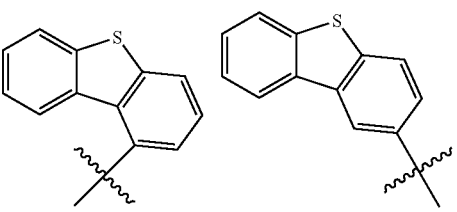

-continued
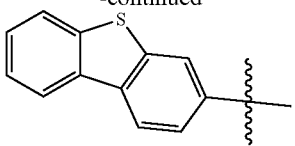
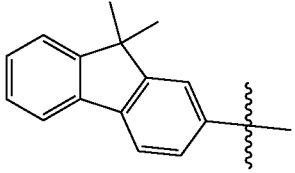
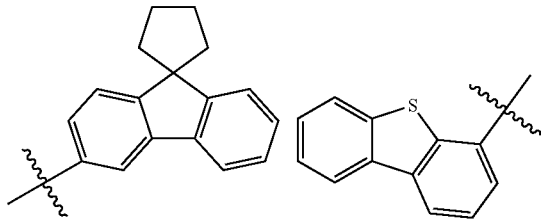
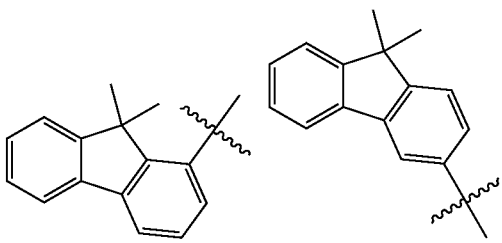
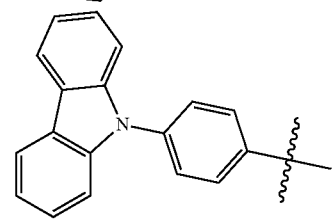
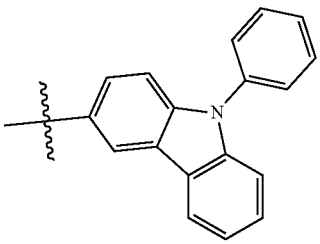

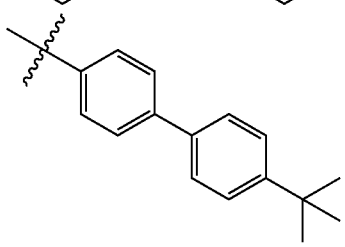
-continued
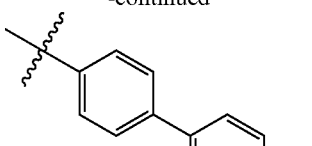
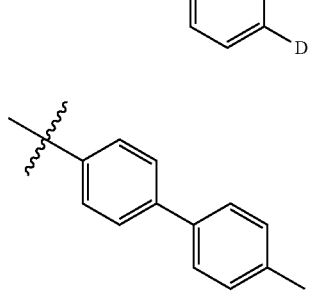
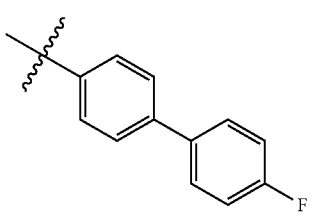
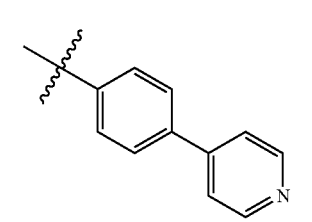
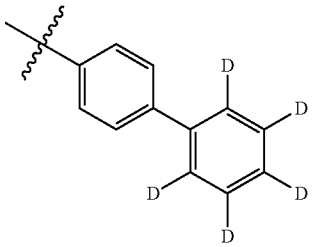
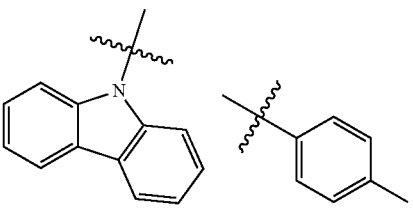
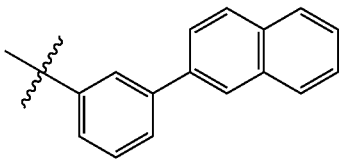
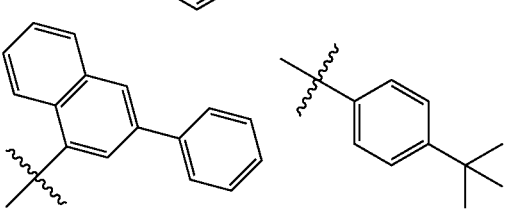

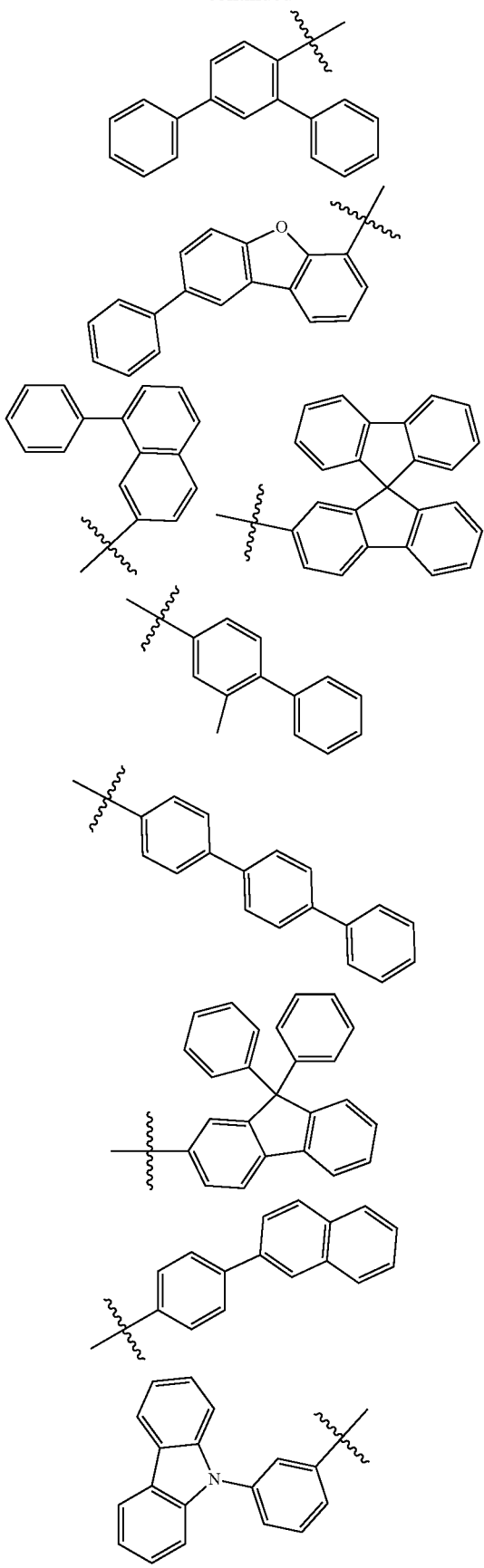
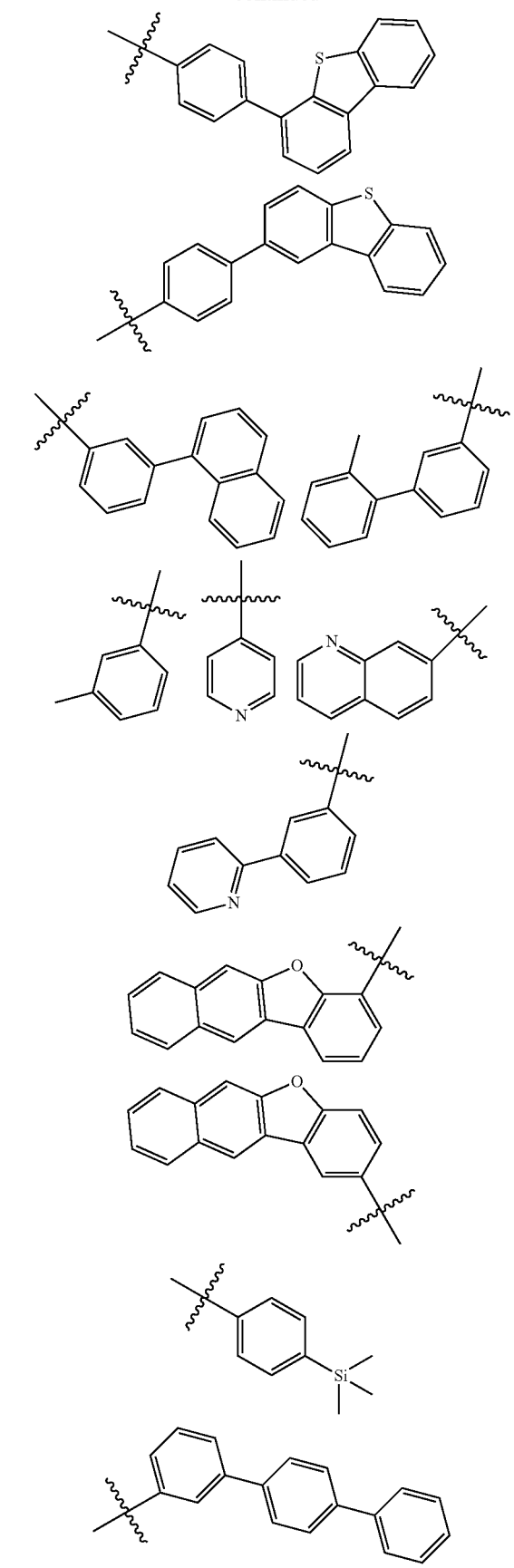

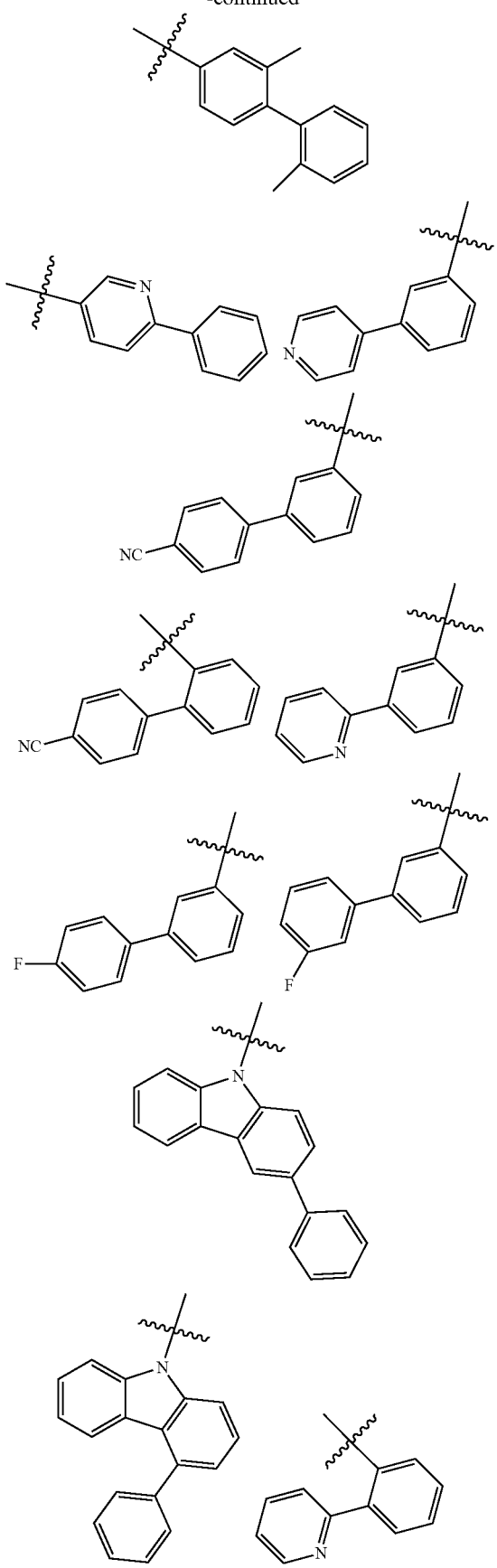
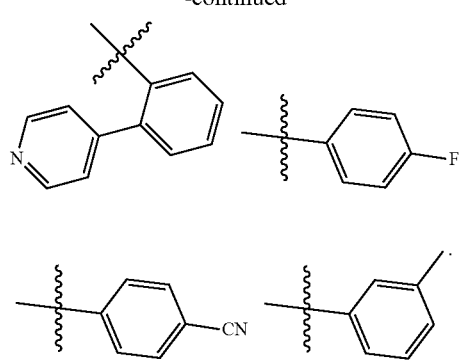
In some examples, $L_1$, $L_2$, and $L_3$ are the same or different, and are each independently a single bond, or are selected from the group consisting of groups represented by formulae j-1 to j-12:
j-1
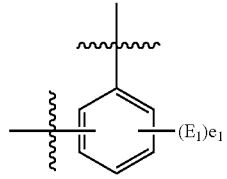
j-2
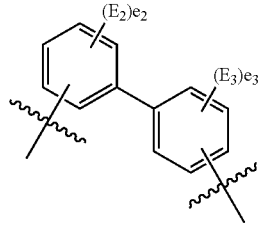
j-3
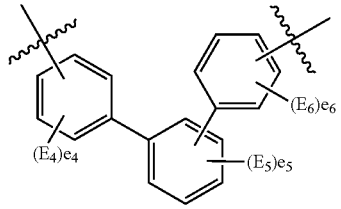
j-4
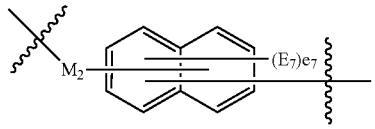
j-5
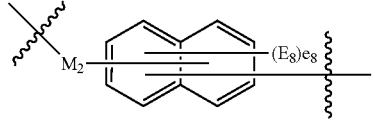

-continued

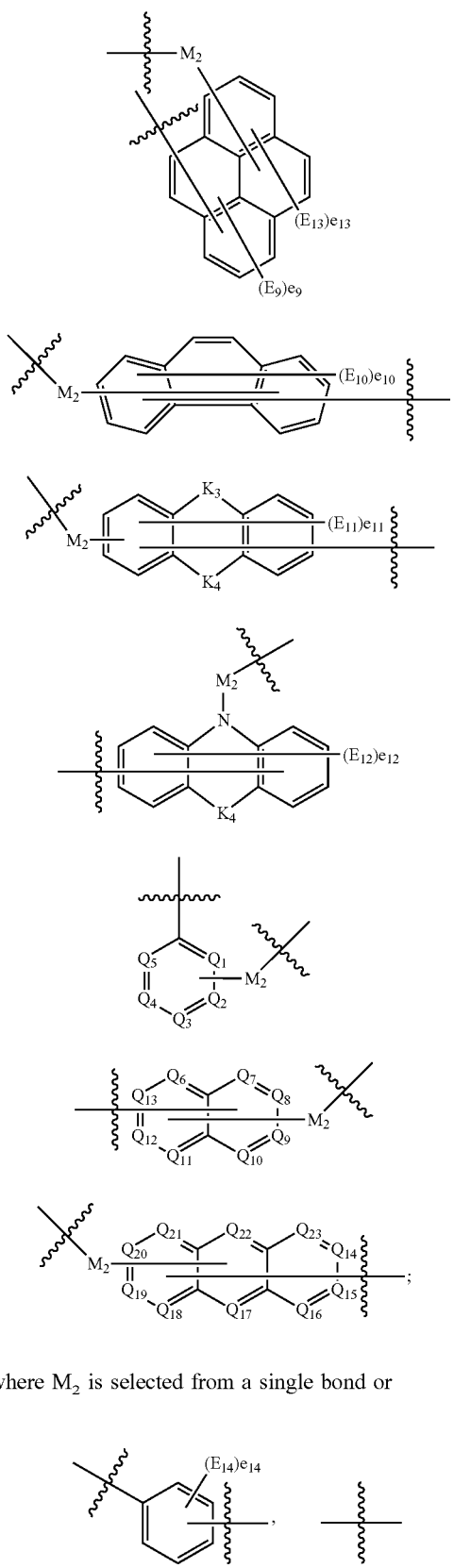

where M₂ is selected from a single bond or represents a chemical bond;

Q₁ to Q₅ are each independently selected from N or C(J₅), and at least one of Q₁ to Q₅ is selected from N; and when two or more of Q₁ to Q₅ are selected from C(J₅), any two J₅s are the same or different;

Q₆ to Q₁₃ are each independently selected from N or C(J₆), and at least one of Q₆ to Q₁₃ is selected from N; and when two or more of Q₆ to Q₁₃ are selected from C(J₆), any two J₆s are the same or different;

Q₁₄ to Q₂₃ are each independently selected from N or C(J₇), and at least one of Q₁₄ to Q₂₃ is selected from N; and when two or more of Q₁₄ to Q₂₃ are selected from C(J₇), any two J₇s are the same or different;

E₁ to E₁₄ and J₅ to J₇ are each independently selected from hydrogen, deuterium, halogen group, a group B, trialkylsilyl with 3 to 12 carbon atoms, alkyl with 1 to 10 carbon atoms, haloalkyl with 1 to 10 carbon atoms, alkenyl with 2 to 6 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, and triarylsilyl with 18 to 24 carbon atoms. The group B is selected from substituted or unsubstituted aryl with 6 to 20 carbon atoms and substituted or unsubstituted heteroaryl with 3 to 20 carbon atoms, and substituents in the group B are selected from alkyl with 1 to 4 carbon atoms, fluorine, and deuterium; optionally, any two adjacent E₁₁ s form a ring; optionally, any two adjacent E₁₂ s form a ring;

e₁ to e₁₄ are represented by $e_r$, and E₁ to E₁₄ are represented by $E_r$, wherein r is a variable representing any integer of 1 to 14, and $e_r$ represents the number of a substituent $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6 or 7; when r is selected from 8 or 10, $e_r$ is selected from 1, 2, 3, 4, 5, 6, 7 or 8; and when $e_r$ is greater than one, any two $E_r$s are the same or different;

K₃ is selected from O, S, Se, N(E₁₅), C(E₁₆E₁₇), and Si(E₁₆E₁₇), where E₁₅, E₁₆, and E₁₇ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or the E₁₆ and the E₁₇ are connected to each other to form a saturated or unsaturated ring with 3 to 15 carbon atoms together with the atoms to which they are jointly connected;

K₄ is selected from a single bond, O, S, Se, N(E₁₈), C(E₁₉E₂₀), Si(E₁₉E₂₀), where E₁₈ to E₂₀ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or the E₁₉ and the E₂₀ are connected to each other to form a saturated or unsaturated ring with 3 to 15 carbon atoms together with the atoms to which they are jointly connected.

In the present disclosure, optionally, L₁, L₂, and L₃ are the same or different, and are each independently a single bond, substituted or unsubstituted arylene with 6 to 30 carbon atoms, or substituted or unsubstituted heteroarylene with 3-30 carbon atoms.

In some embodiments, L₁ is selected from a single bond, substituted or unsubstituted arylene with 6 to 30 carbon atoms, and substituted or unsubstituted heteroarylene with 5 to 30 carbon atoms; and L₂ and L₃ are the same or different, and are each independently selected from a single bond, substituted or unsubstituted arylene with 6 to 25 carbon atoms, or substituted or unsubstituted heteroarylene with 3 to 20 carbon atoms.

In some specific embodiments, $L_1$ is selected from a single bond, substituted or unsubstituted phenylene, substituted or unsubstituted naphthylene, substituted or unsubstituted biphenylene, substituted or unsubstituted terphenylene, substituted or unsubstituted fluorenylene, substituted or unsubstituted anthrylene, substituted or unsubstituted phenanthrylene, substituted or unsubstituted carb azolylene, substituted or unsubstituted dibenzofuranylene, substituted or unsubstituted dibenzothiophenylene, and substituted or unsubstituted pyridylene. Substituents in the $L_1$ are each independently selected from a group C, deuterium, fluorine, alkyl with 1 to 4 carbon atoms, trialkylsilyl with 3 to 7 carbon atoms, and cycloalkyl with 5 to 10 carbon atoms. The group C is selected from substituted or unsubstituted aryl with 6 to 15 carbon atoms, and substituted or unsubstituted heteroaryl with 5 to 15 carbon atoms. Substituent in the group C are selected from deuterium, fluorine, and alkyl with 1 to 4 carbon atoms. Optionally, any two adjacent substituents form a ring.

In other specific embodiments, $L_1$ is substituted or unsubstituted phenylene, and the substituent of phenylene is selected from arylene with 6 to 15 carbon atoms and heteroarylene with 5-18 carbon atoms. Specific examples of substituents include, but are not limited to, phenyl, naphthyl, biphenyl, pyridyl, 9,9-dimethylfluorenyl, dibenzofuryl, dibenzothienyl, N-phenylcarbazolyl, and the like.

In some specific embodiments, $L_2$ and $L_3$ are the same or different, and are each independently selected from a single bond, substituted or unsubstituted phenylene, substituted or unsubstituted naphthylene, substituted or unsubstituted biphenylene, substituted or unsubstituted fluorenylene, substituted or unsubstituted anthrylene, substituted or unsubstituted phenanthrylene, substituted or unsubstituted carbazolylene, substituted or unsubstituted dibenzofuranylene, substituted or unsubstituted dibenzothiophenylene, and substituted or unsubstituted pyridylene. Substituents in $L_2$ and $L_3$ are each independently selected from deuterium, fluorine, alkyl with 1 to 4 carbon atoms, trialkylsilyl with 3 to 7 carbon atoms, cycloalkyl with 5 to 10 carbon atoms, aryl with 6 to 12 carbon atoms, and heteroaryl with 5 to 12 carbon atoms. Optionally, any two adjacent substituents form a ring.

According to an embodiment, $L_1$ is a single bond or a substituted or unsubstituted group $T_1$, where the unsubstituted group $T_1$ is selected from the group consisting of the following groups:

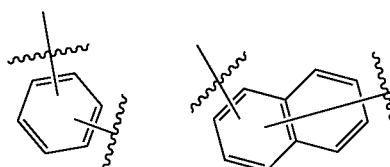

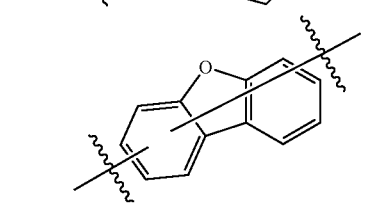

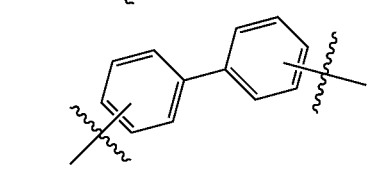

-continued

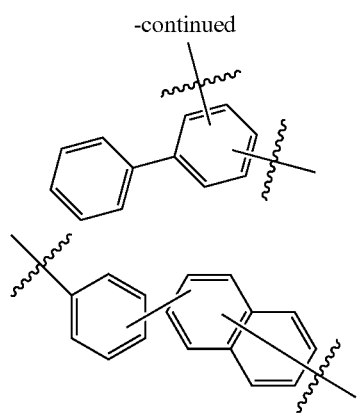

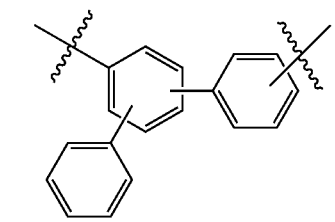

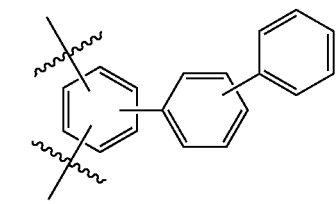

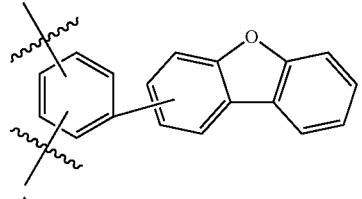

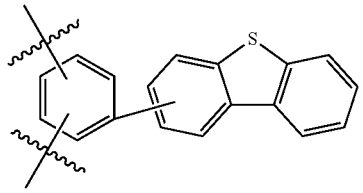

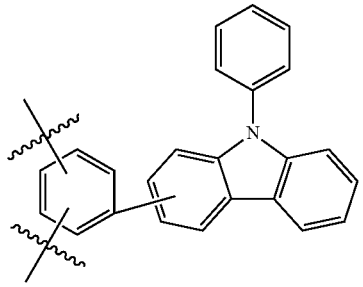

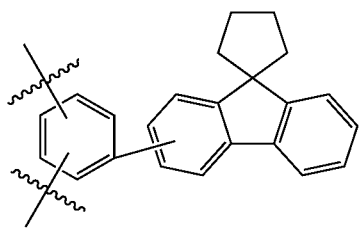

-continued

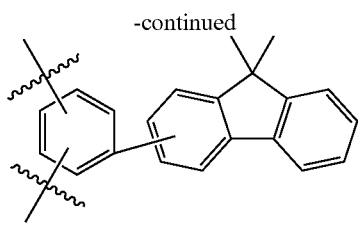

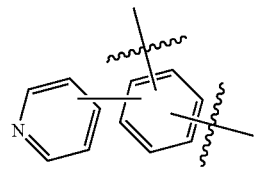

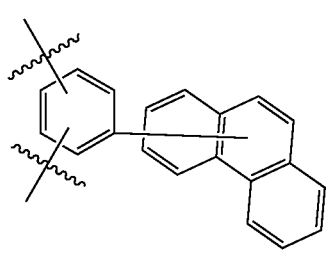

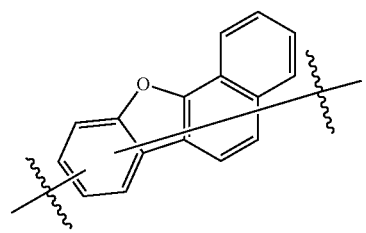

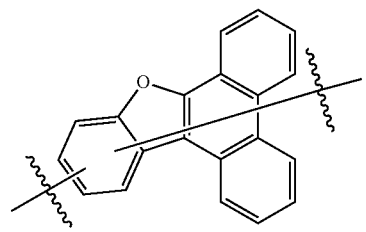

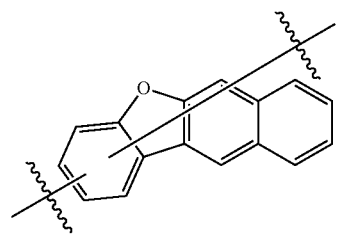

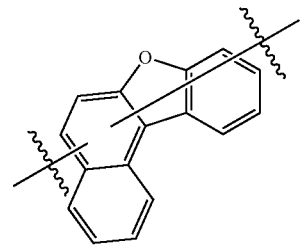

-continued

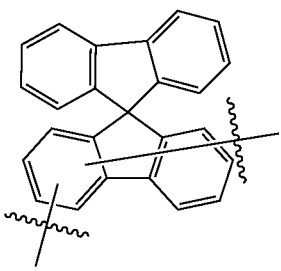

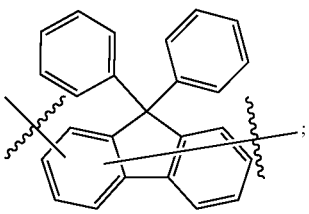

where the substituted group $T_1$ has one or more substituents, where the substituents are each independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, trialkylsilyl with 3 to 7 carbon atoms, and naphthyl. When the number of substituents is greater than one, the substituents are the same or different.

Further optionally, $L_1$ is selected from a single bond or the group consisting of the following groups:

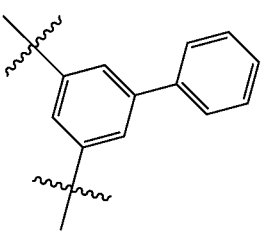

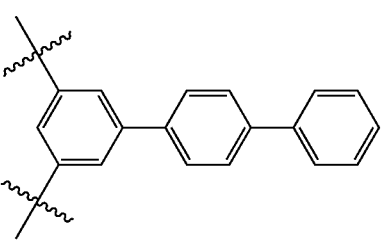

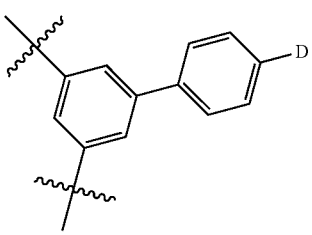

-continued
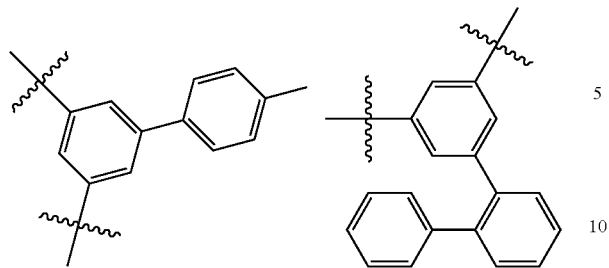
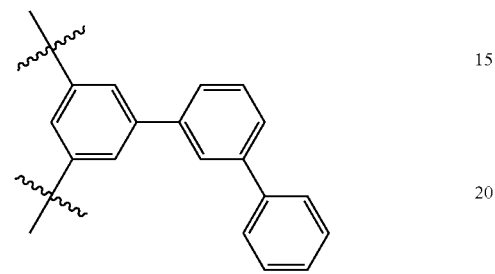
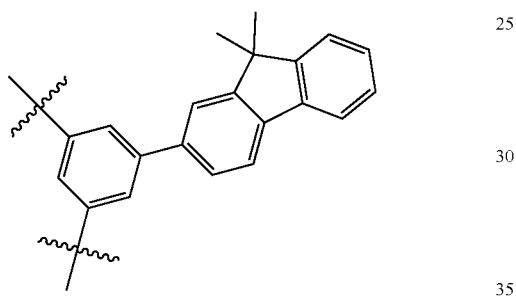
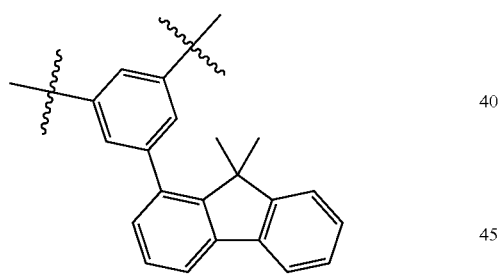
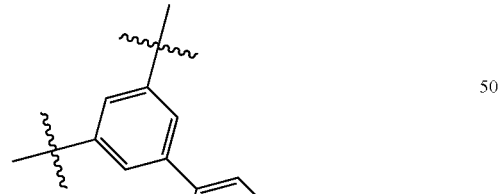
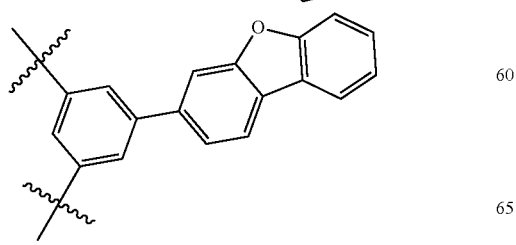
-continued
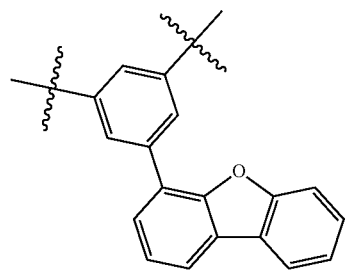
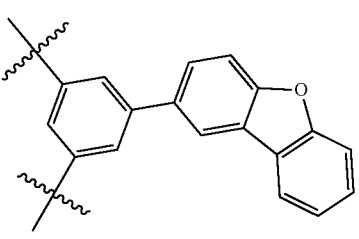
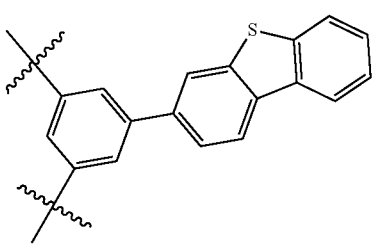
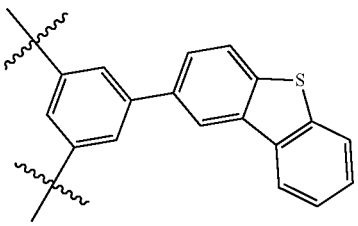
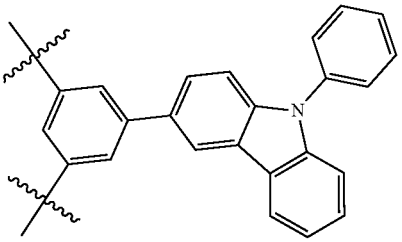
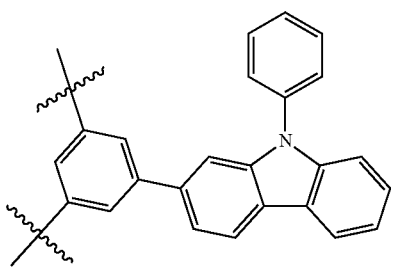

-continued
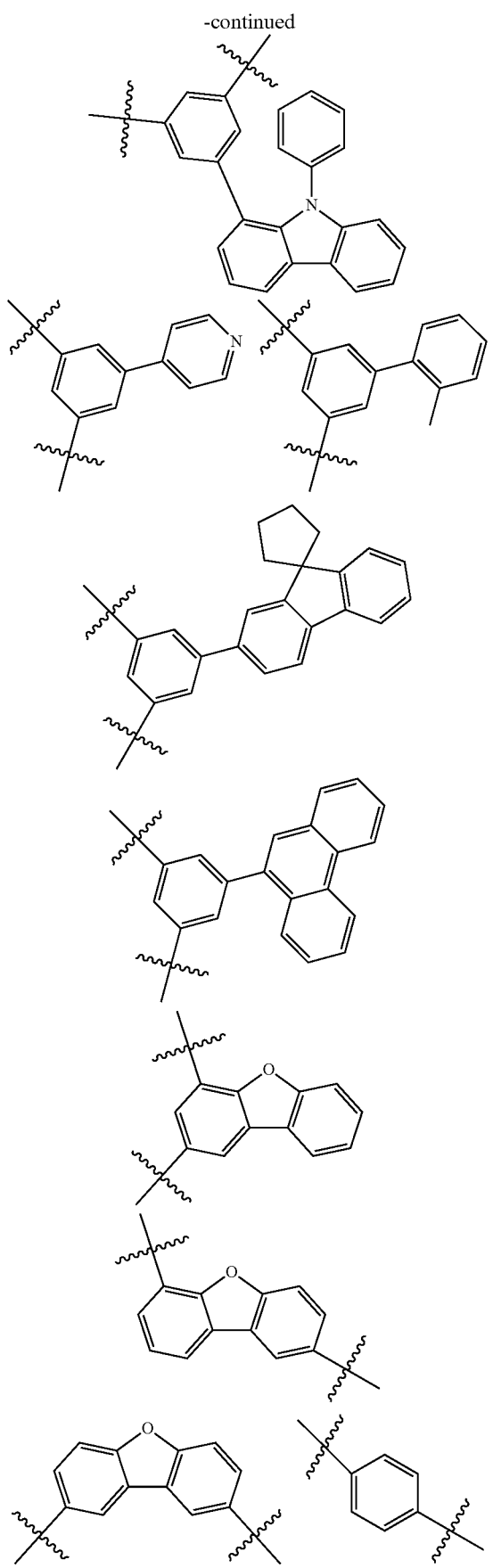
-continued
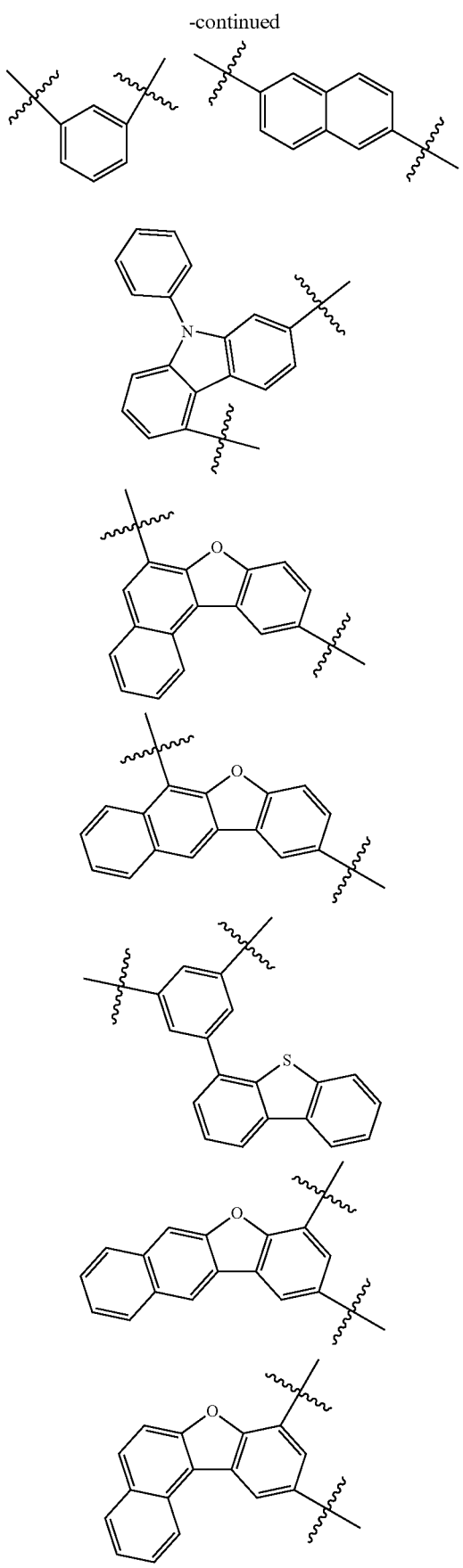

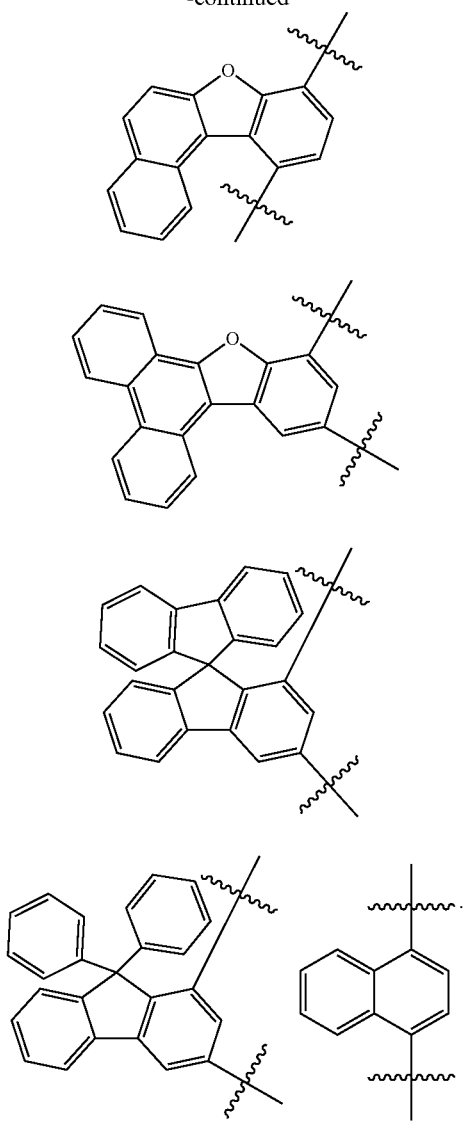
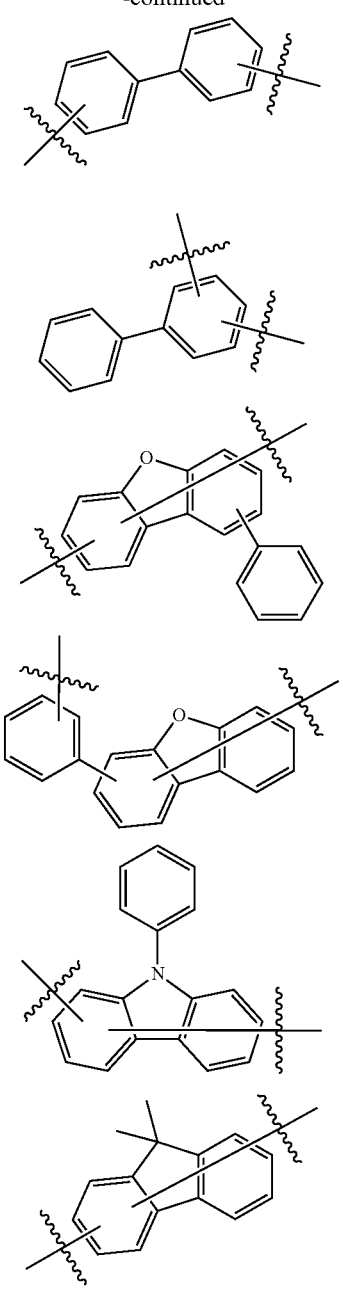
According to an embodiment, $L_2$ is selected from a single bond, and a substituted or unsubstituted group $T_2$, where the unsubstituted group $T_2$ is selected from the group consisting of the following groups:
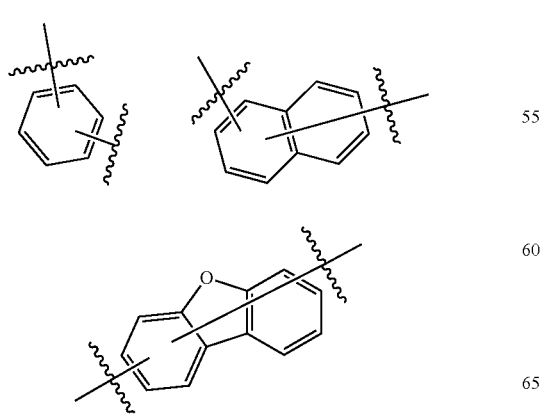
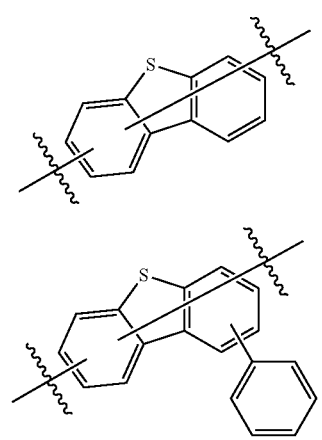

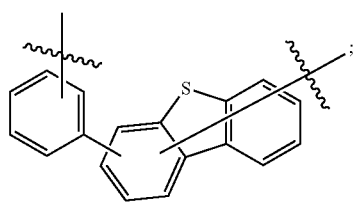

where the substituted group $T_2$ has one or more substituents, where the substituents are each independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, trialkylsilyl with 3 to 7 carbon atoms, and phenyl. When the number of substituents is greater than one, the substituents are the same or different.

Optionally, $L_2$ is selected from a single bond or the group consisting of the following groups:

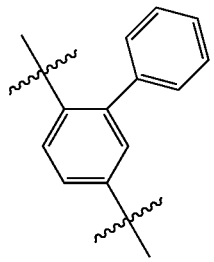

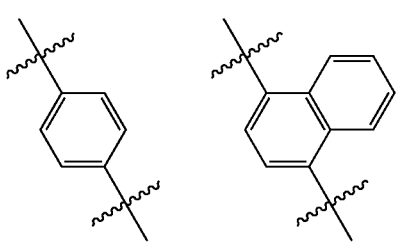

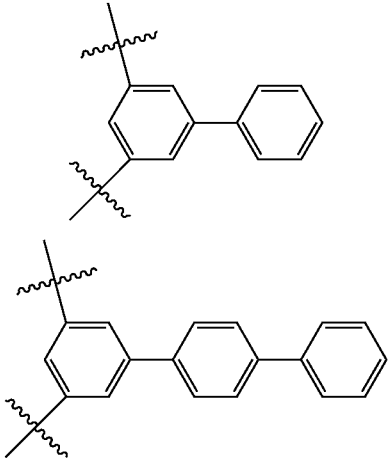

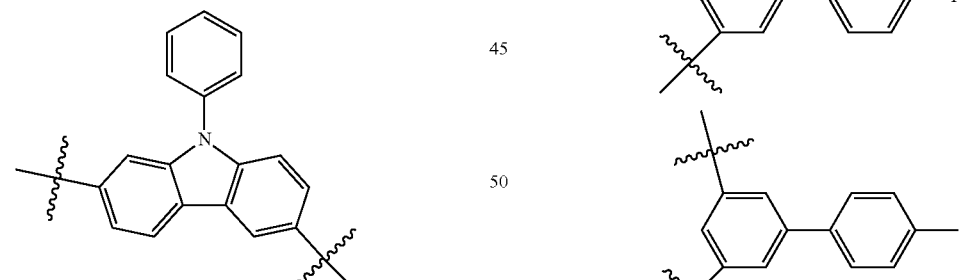

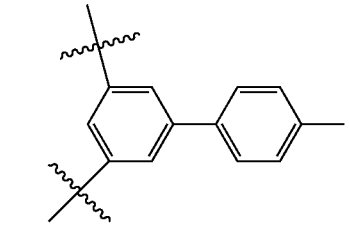

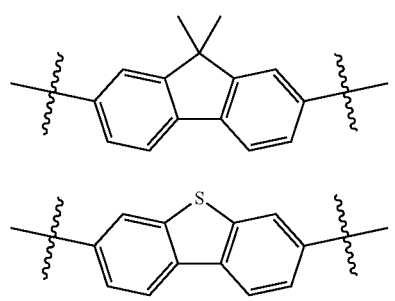

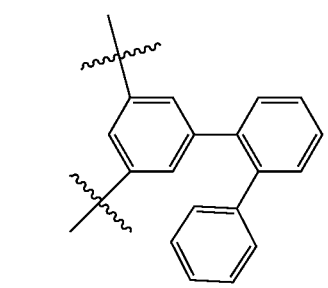

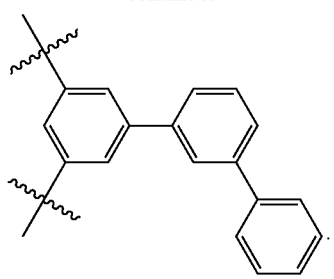

According to an embodiment, L₃ is a single bond, or a substituted or unsubstituted group $T_3$, where the unsubstituted group $T_3$ is selected from the group consisting of the following groups:

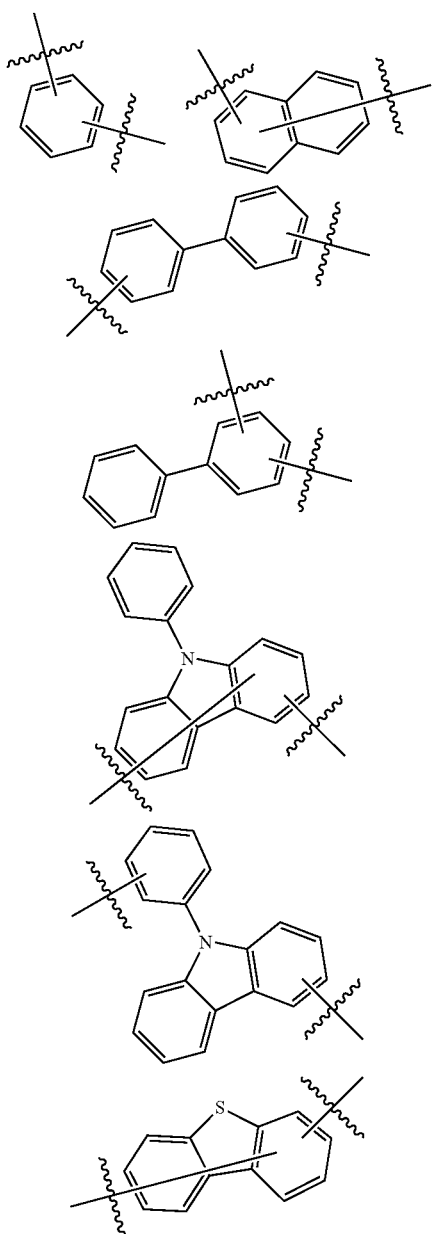

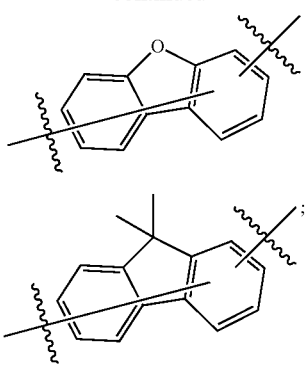

where the substituted group $T_3$ has one or more substituents, where the substituents are each independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, and trialkylsilyl with 3 to 7 carbon atoms. When the number of substituents is greater than one the substituents are the same or different.

Optionally, L₃ is selected from a single bond or the group consisting of the following groups:

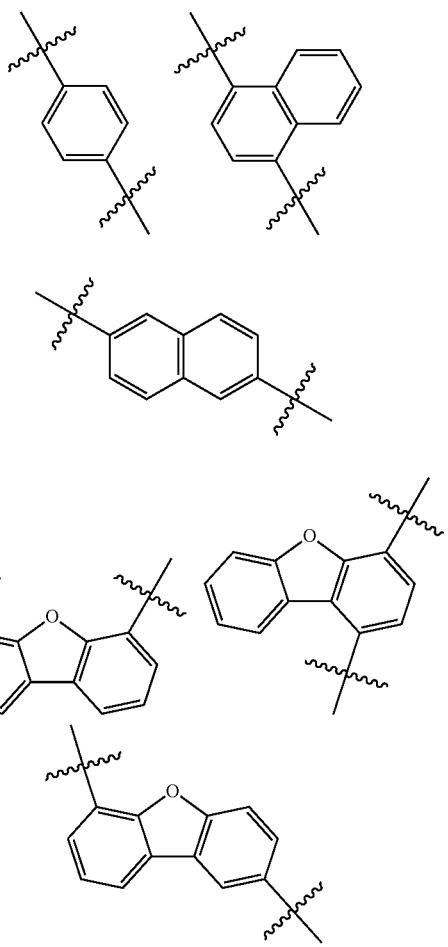

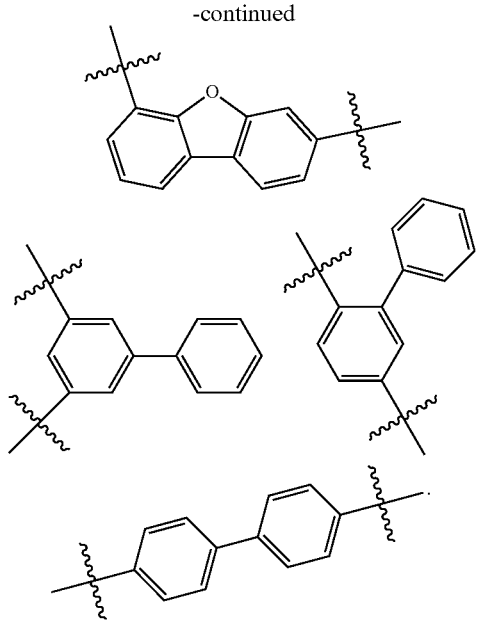

In some embodiments, $R_1$ and $R_2$ are the same or different, and are each independently selected from deuterium, fluorine, alkyl with 1 to 4 carbon atoms, cycloalkyl with 5 to 10 carbon atoms, alkoxy with 1 to 4 carbon atoms, trialkylsilyl with 3 to 7 carbon atoms, and a group D, the group D is selected from substituted or unsubstituted aryl with 6 to 20 carbon atoms, and substituted or unsubstituted heteroaryl with 3 to 20 carbon atoms, the substituents in the group D are selected from deuterium, fluorine, alkyl with 1 to 4 carbon atoms, cycloalkyl with 5 to 10 carbon atoms, and trialkylsilyl with 3 to 7 carbon atoms. Optionally, when the number of $n_1$ is greater than one, any adjacent two $R_1$s may be fused into a ring, and when the number of $n_2$ is greater than one, any adjacent two $R_2$s may be fused into a ring.

Specific embodiments of $R_1$ and $R_2$ in the present disclosure include, but are not limited to, deuterium, fluorine, cyano, methyl, tert-butyl, cyclopentyl, cyclohexyl, trimethylsilyl, trifluoromethyl, phenyl, naphthyl, biphenyl, pyridyl, dibenzofuranyl, substituted phenyl, substituted naphthyl, and substituted biphenyl. In the substituted phenyl group, the substituted naphthyl group, and the substituted biphenyl group, the substituents thereof may be deuterium, fluorine, cyano, methyl, tert-butyl, trimethylsilyl, trifluoromethyl, and the like.

In some embodiments, $R_3$ and $R_4$ are the same or different, and are each independently selected from alkyl with 1 to 4 carbon atoms, aryl with 6 to 12 carbon atoms, or heteroaryl with 3 to 12 carbon atoms, or $R_3$ and $R_4$ can form a saturated or unsaturated ring with 5 to 15 carbon atoms together with the atoms to which they are jointly connected. Specific examples of $R_3$ and $R_4$ include, but are not limited to, methyl, ethyl, n-propyl, phenyl, and the like.

In some embodiments, $R_5$ is selected from substituted or unsubstituted aryl with 6 to 20 carbon atoms, and substituted or unsubstituted heteroaryl with 3 to 20 carbon atoms, and the substituents in $R_5$ are selected from deuterium, fluorine, alkyl with 1 to 4 carbon atoms, cycloalkyl with 5 to 10 carbon atoms, and trialkylsilyl with 3 to 7 carbon atoms. Specific examples of $R_5$ include, but are not limited to, phenyl, naphthyl, biphenyl, dibenzofuryl, dibenzothienyl, carbazolyl, substituted phenyl, substituted naphthyl, and substituted biphenyl. In the substituted phenyl group, the substituted naphthyl group, and the substituted biphenyl group, the substituents thereof may be deuterium, fluorine, cyano, methyl, tert-butyl, trimethylsilyl, trifluoromethyl, and the like.

Optionally, one Ad is connected to $R_5$.

Optionally, in formulae 3-2, 3-3, 3-4, 3-5, 3-7 and 3-8,

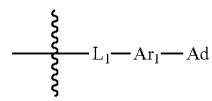

is each independently selected from the group consisting of the following structures:

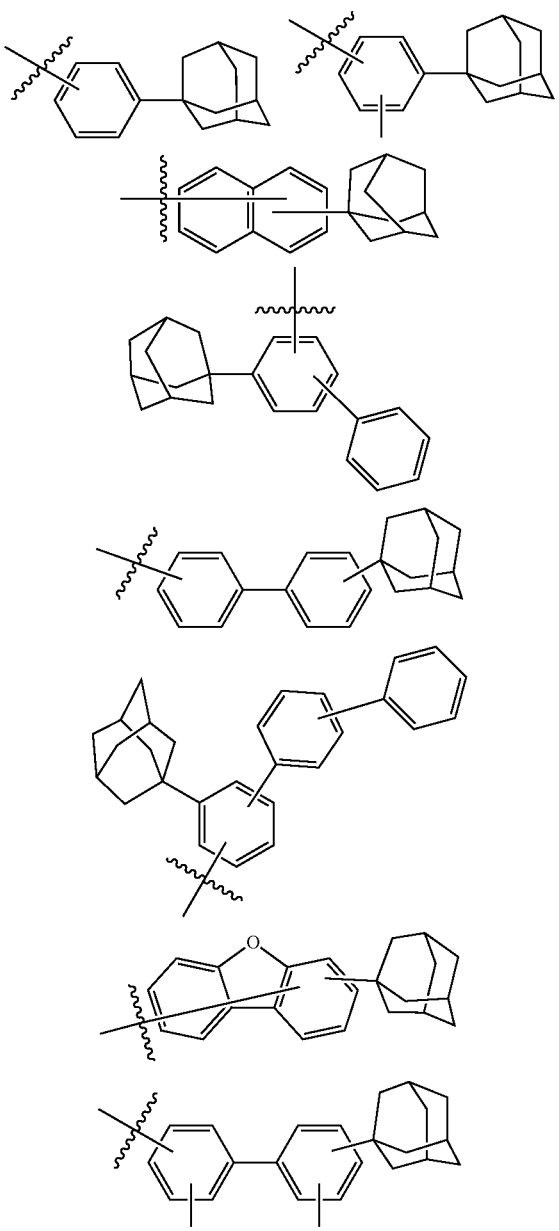

-continued
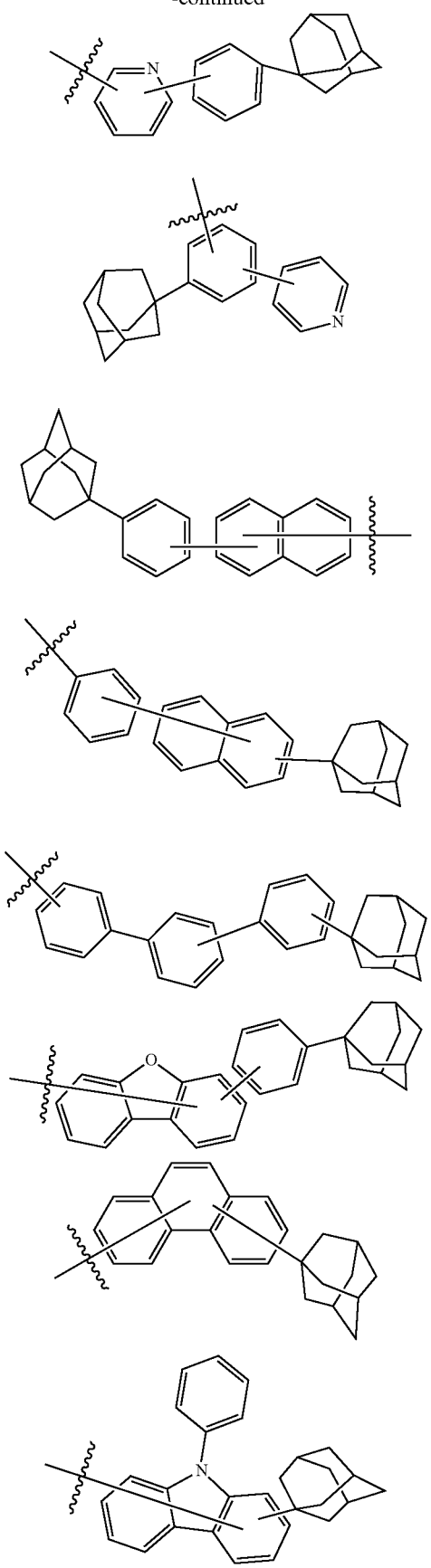
-continued
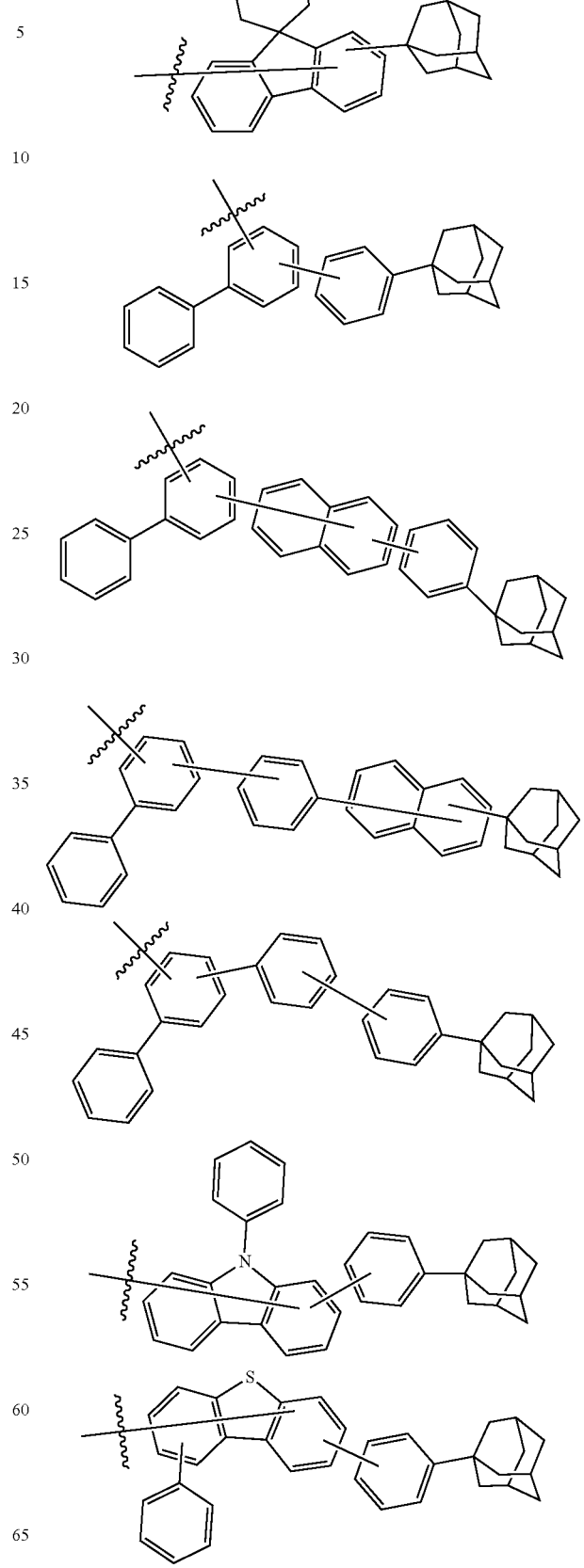

53
-continued
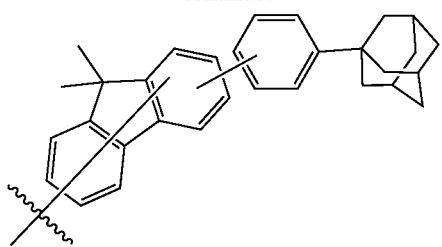
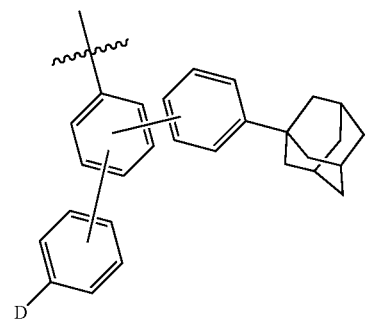
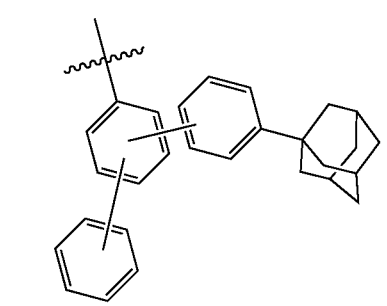
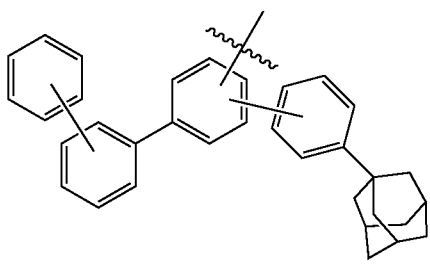
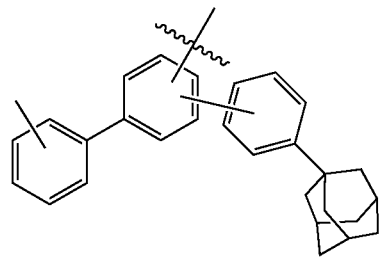
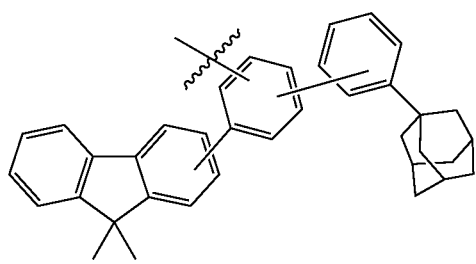
54
-continued
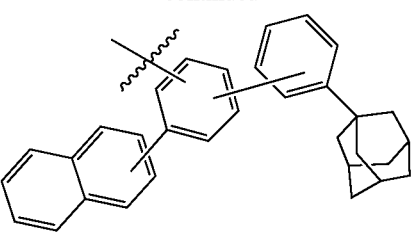
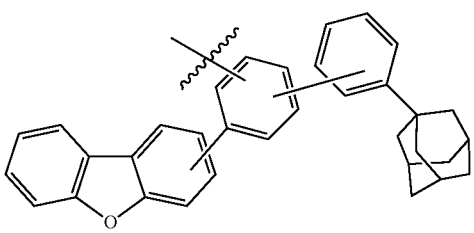
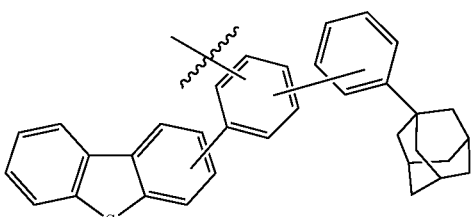
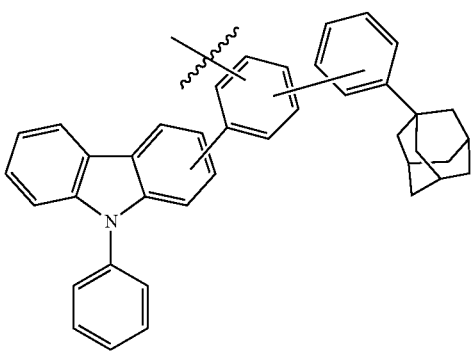
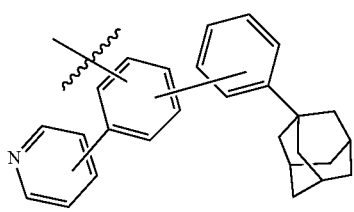
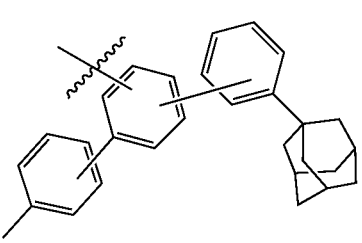

-continued
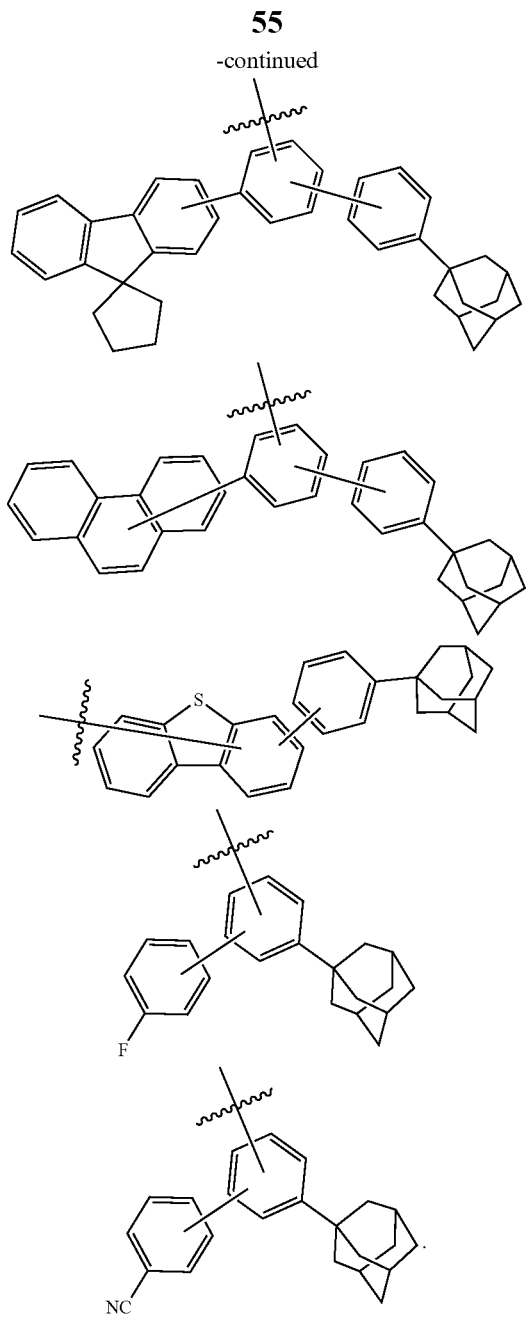
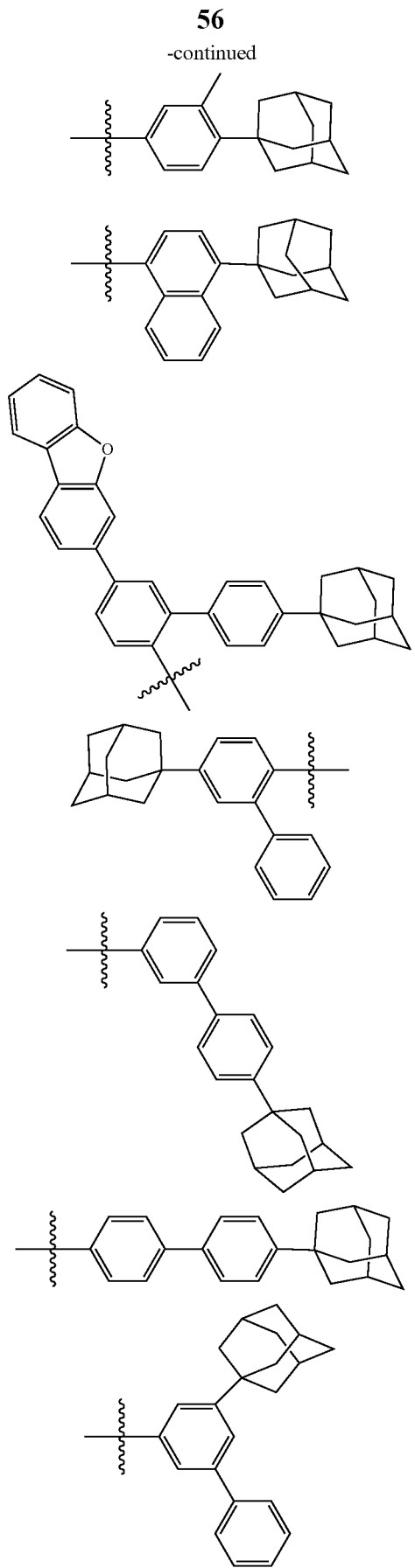
Further optionally,
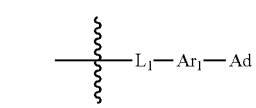
is each independently selected from-the following structures:
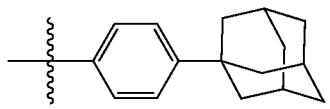

57
-continued
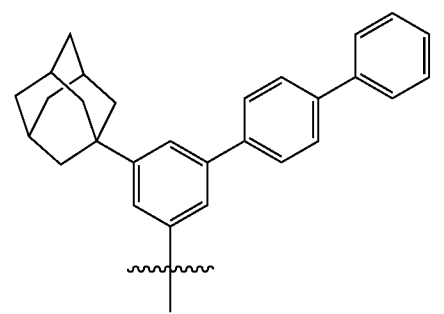
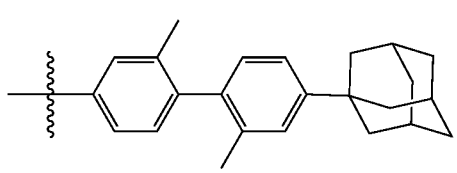
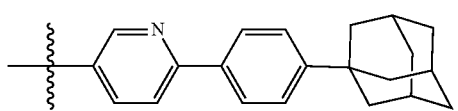
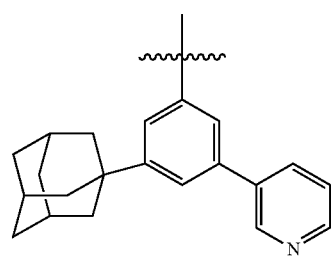
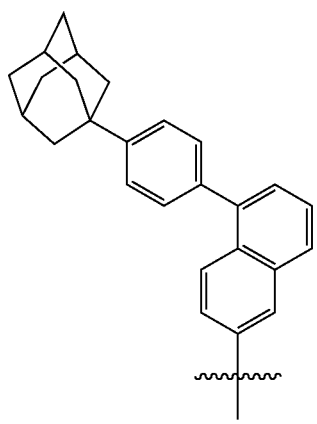
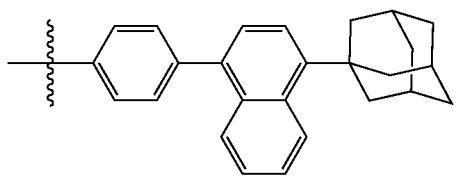
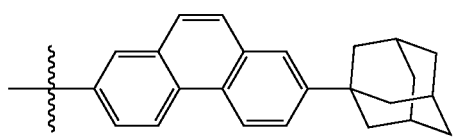
58
-continued
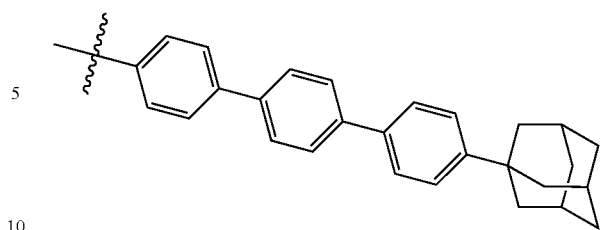
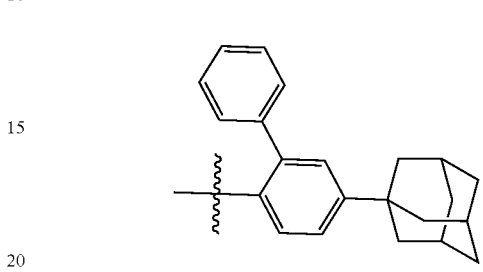
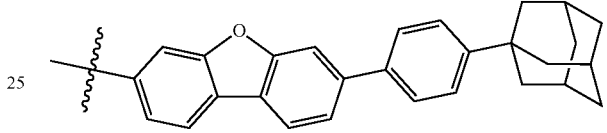
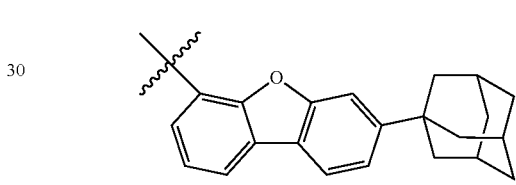
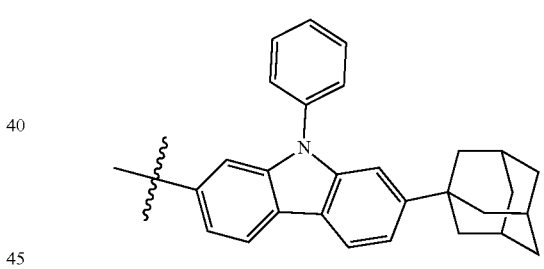
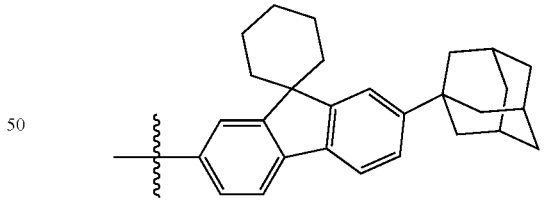
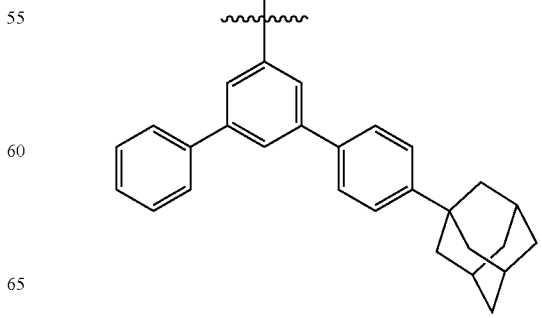

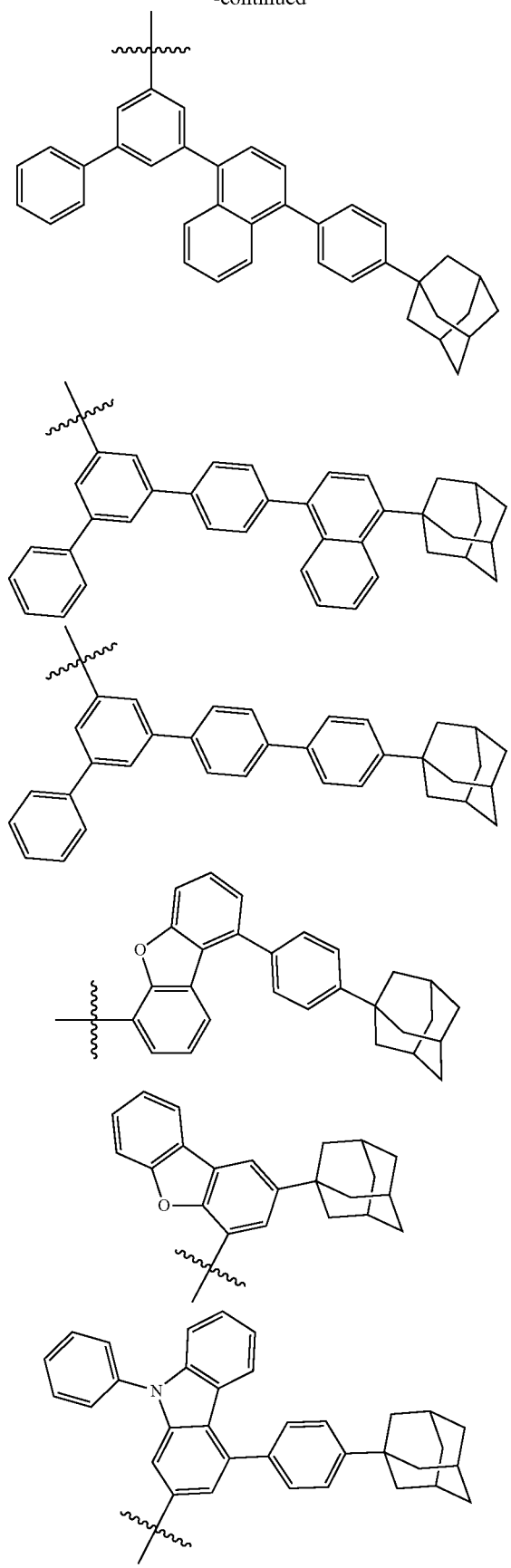
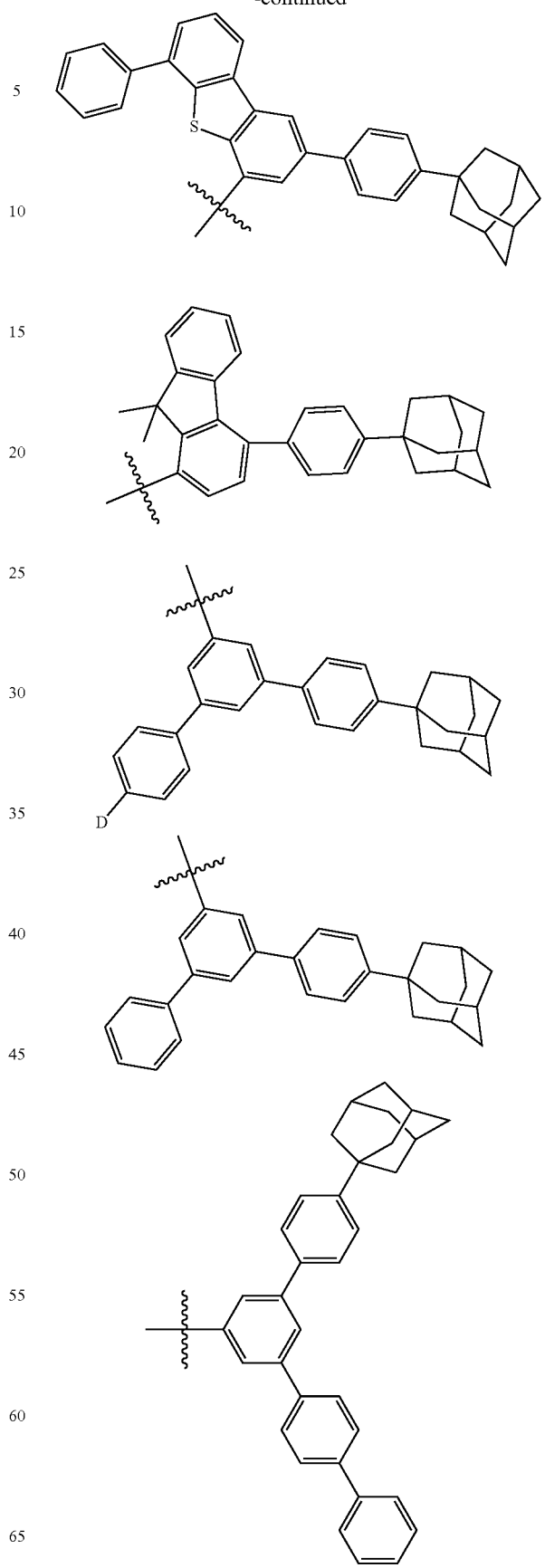

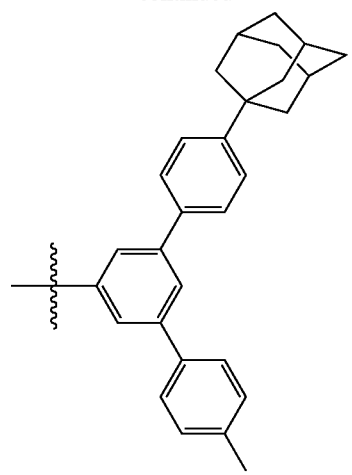
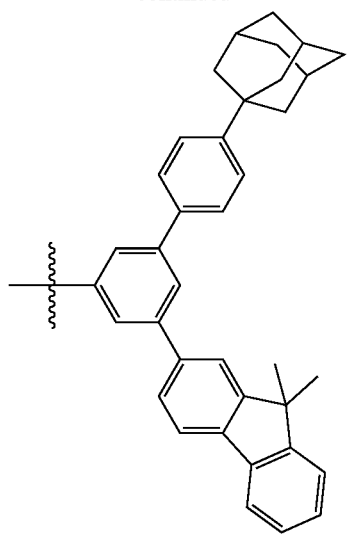
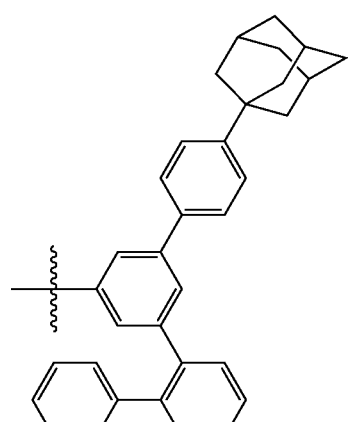
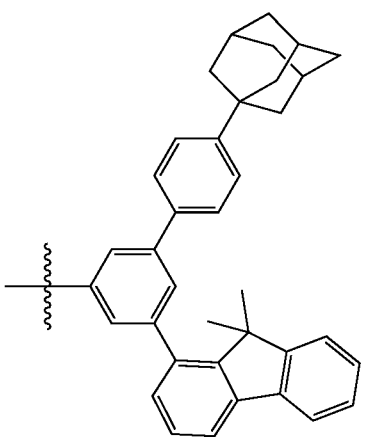
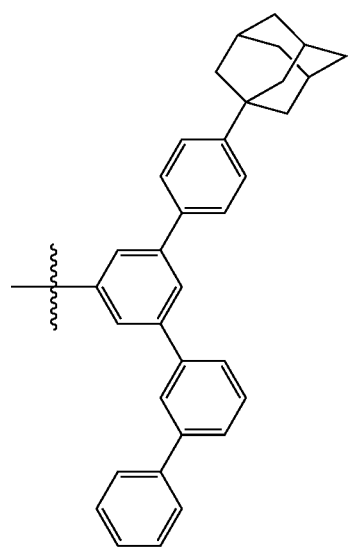
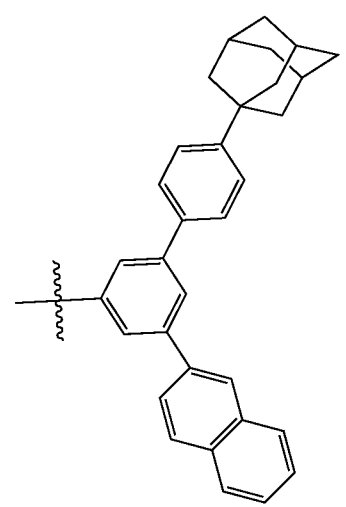

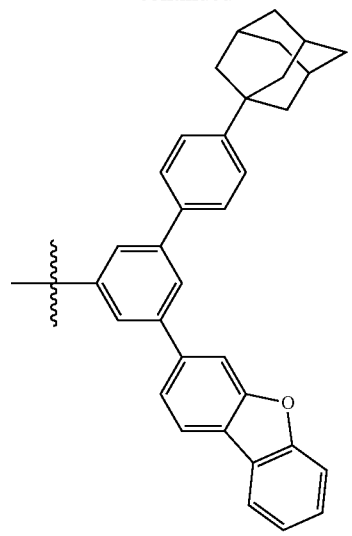
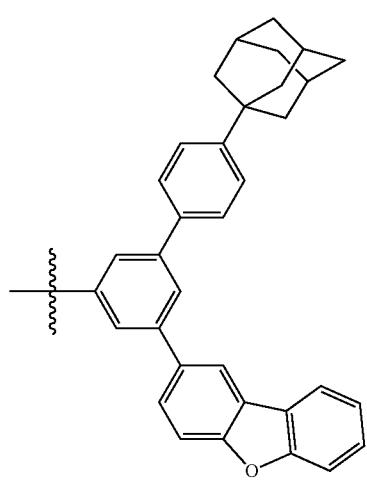
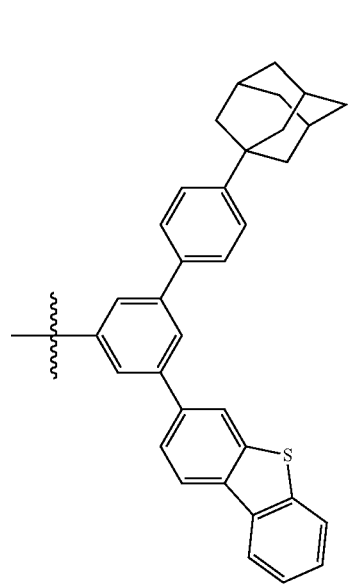
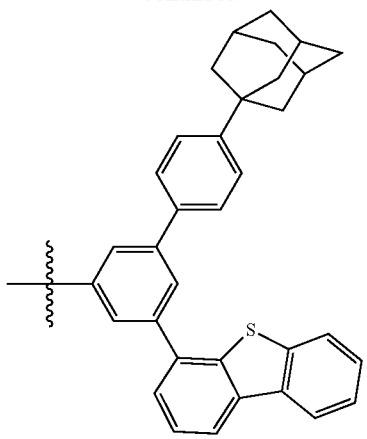
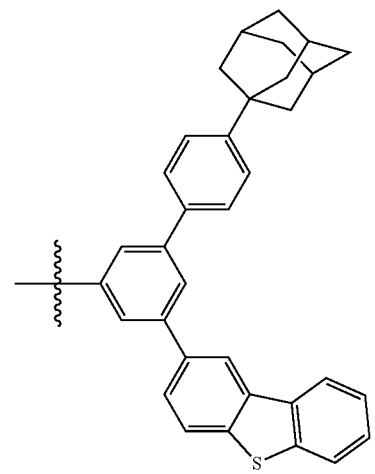
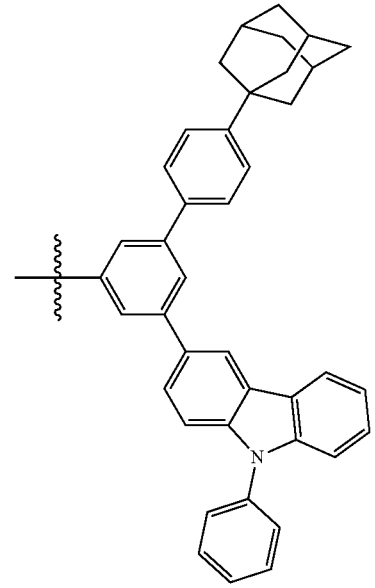

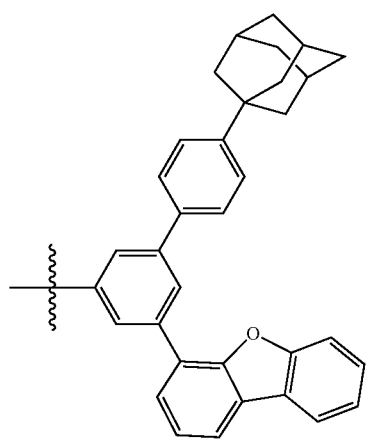
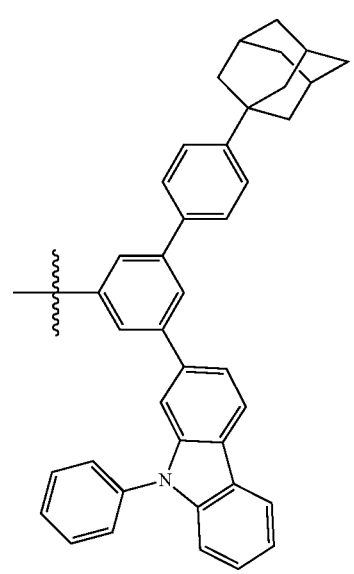
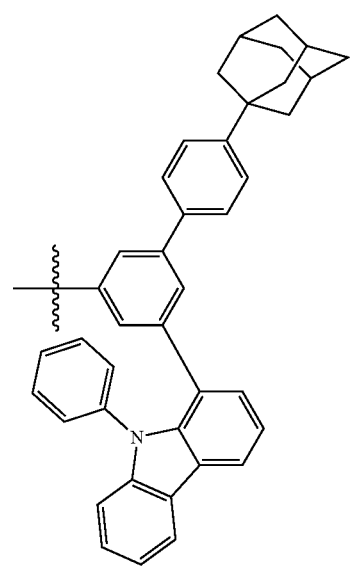
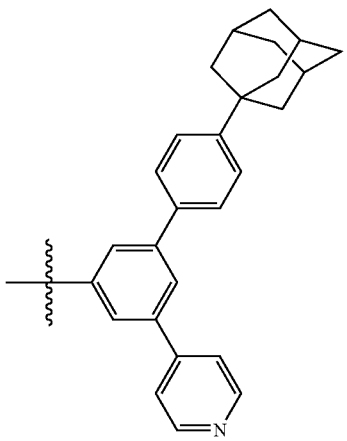
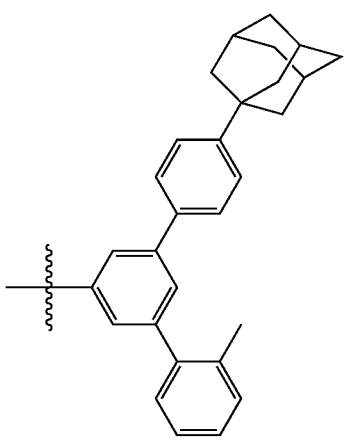
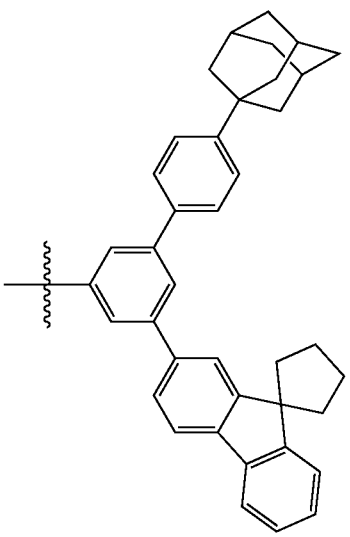

67
-continued
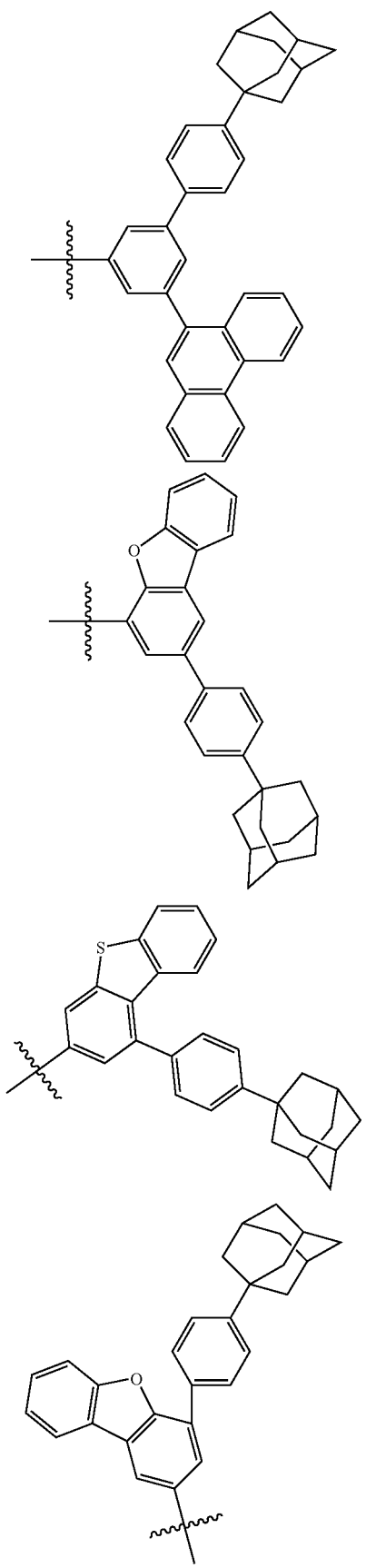
68
-continued
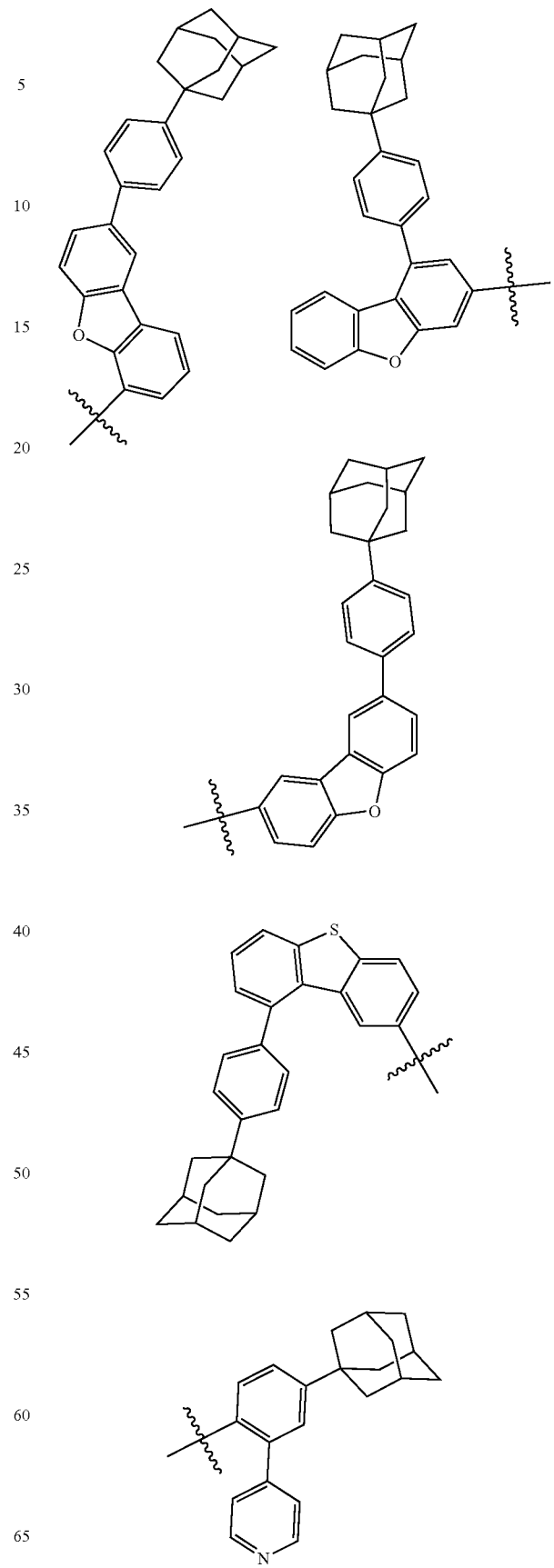

-continued
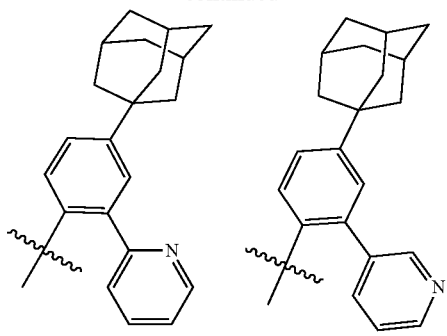
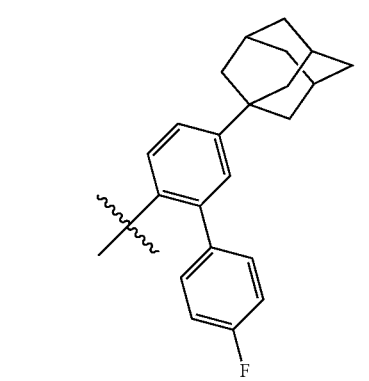
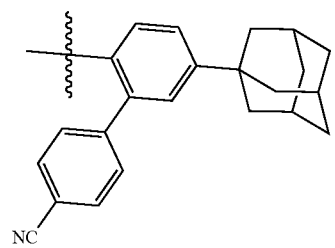
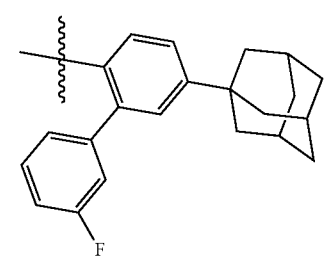
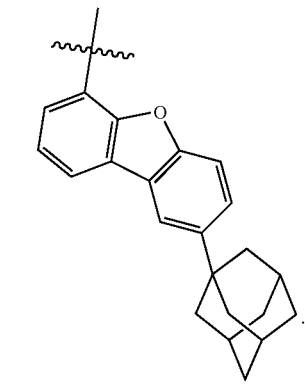
In one embodiment, one Ad is connected to
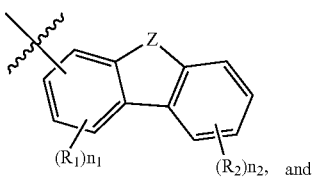
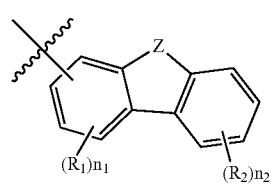
connected with one Ad is selected from the group consisting of the following groups:
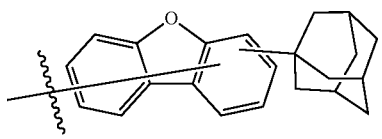
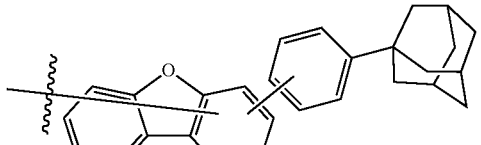
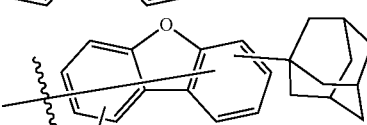
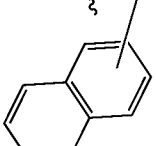
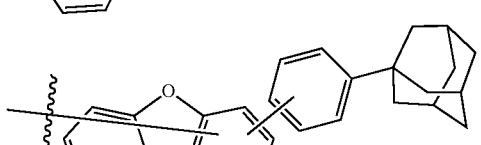
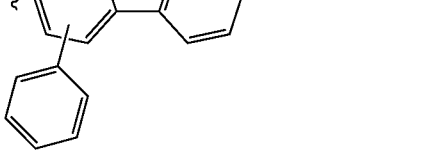
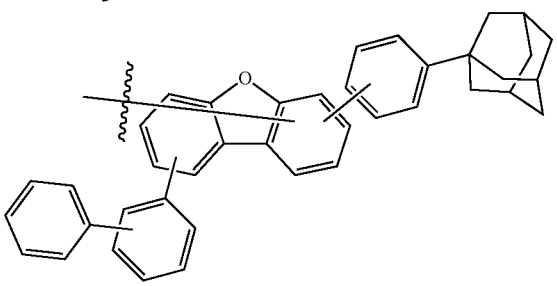

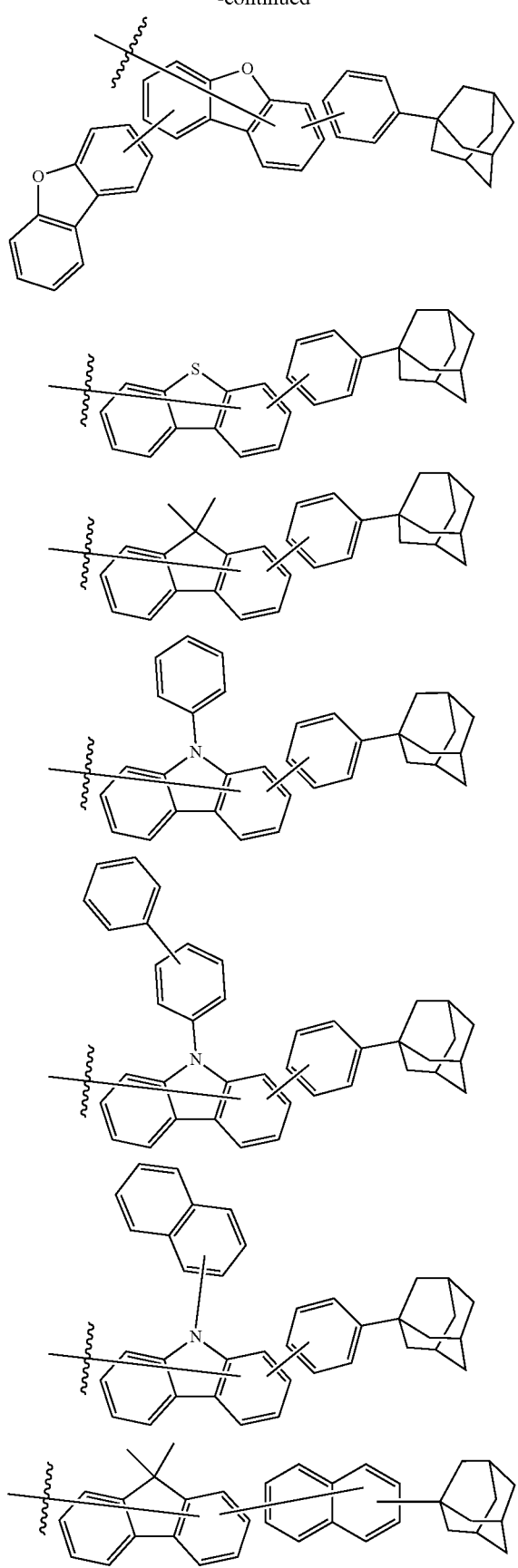
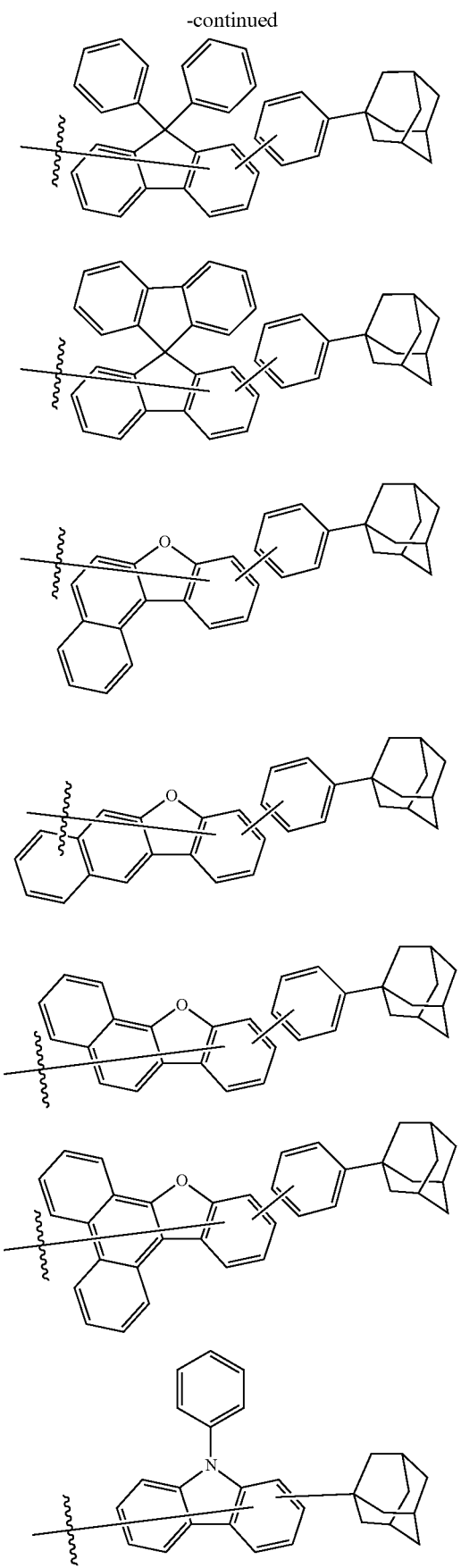

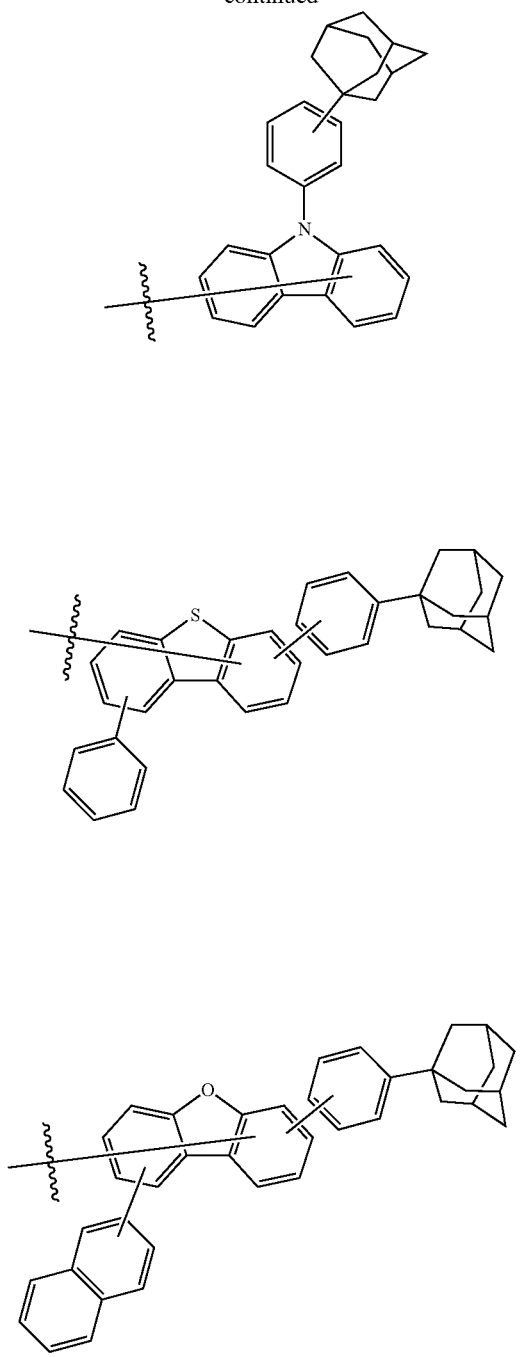
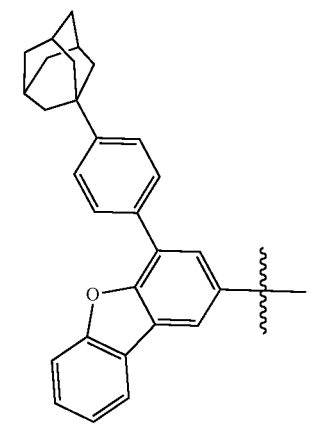
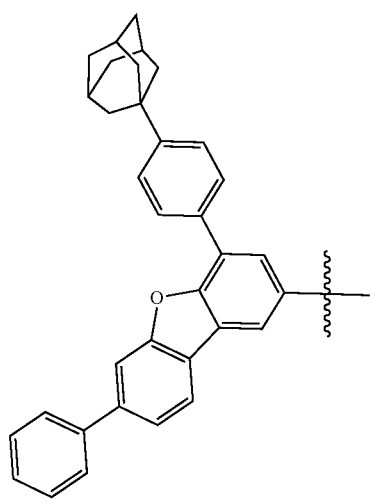
Optionally,
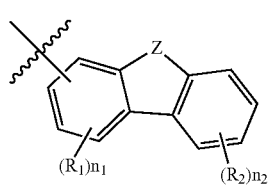
connected with the Ad is selected from the group consisting of the following groups:

75
-continued
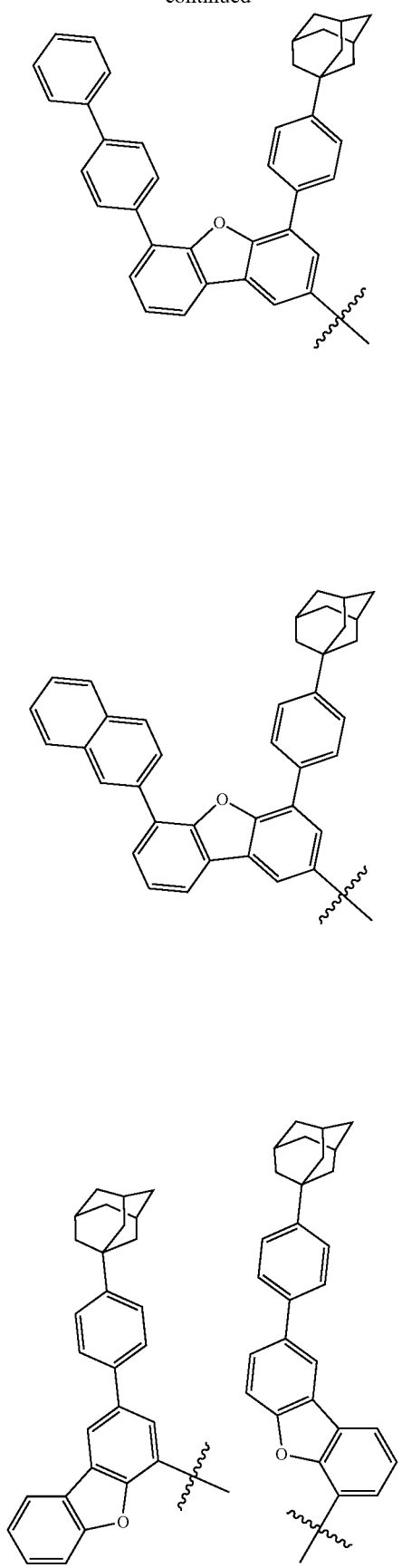
76
-continued
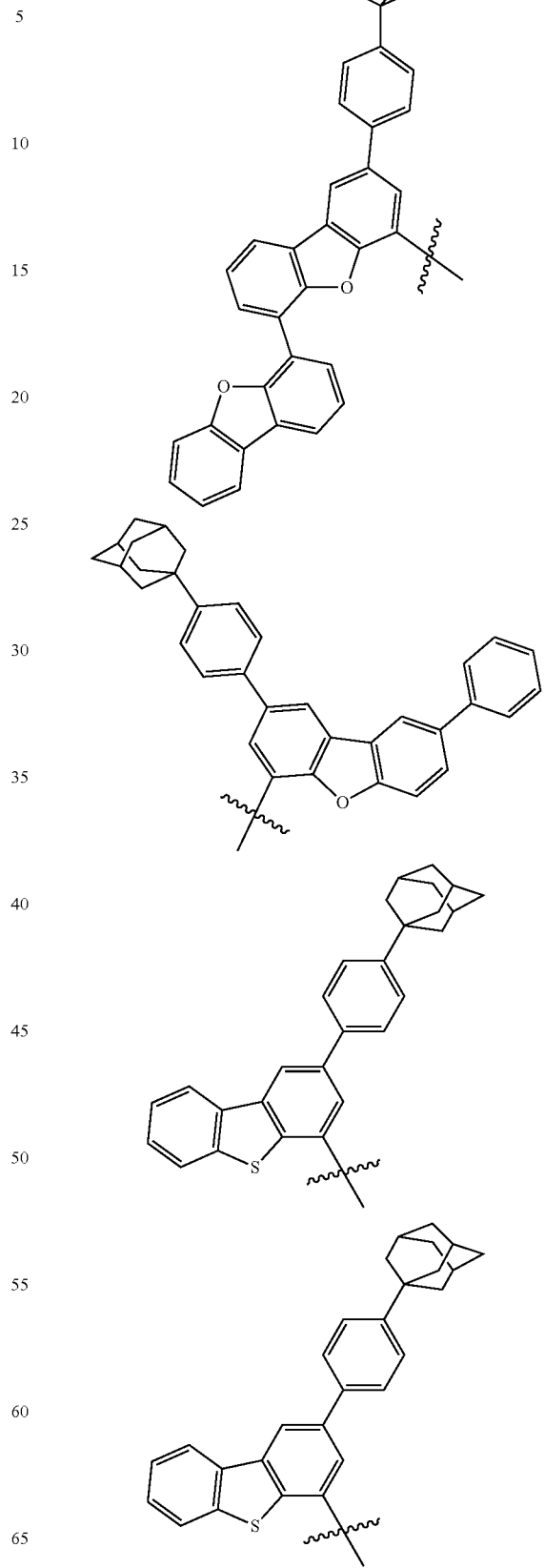

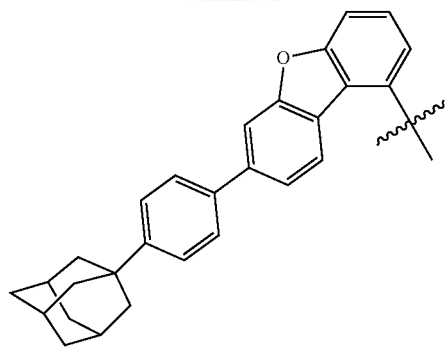
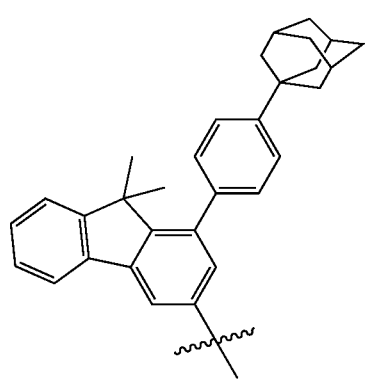
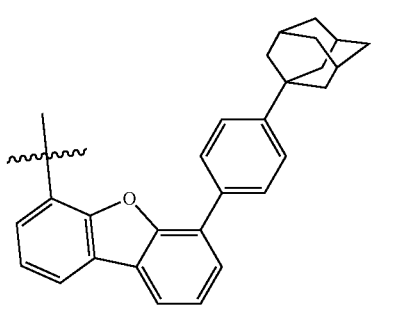
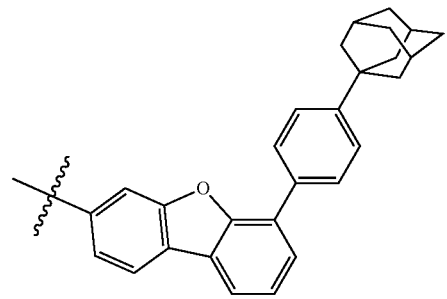
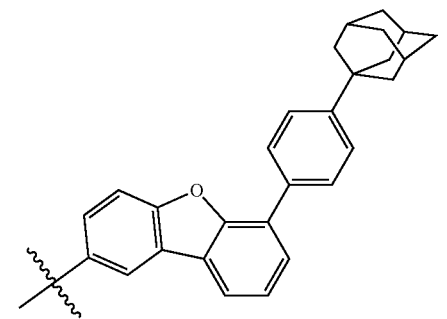
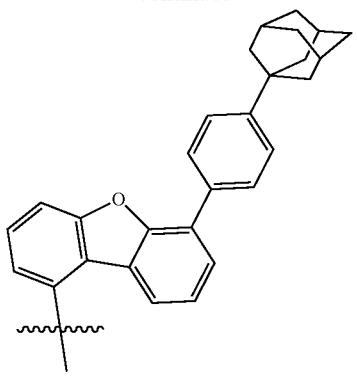
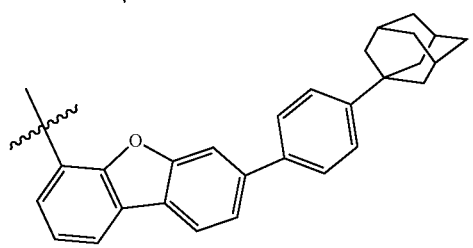
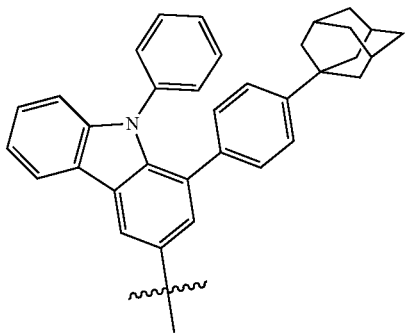
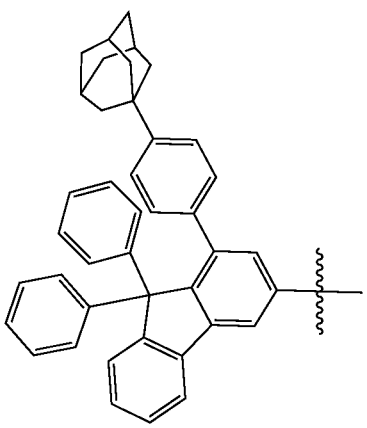

79
-continued
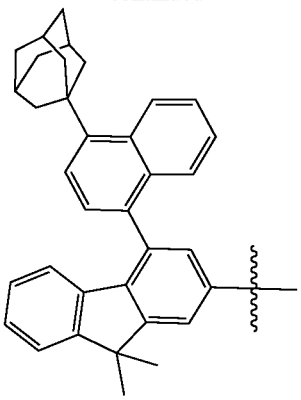
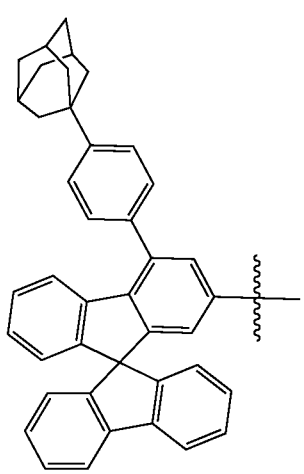
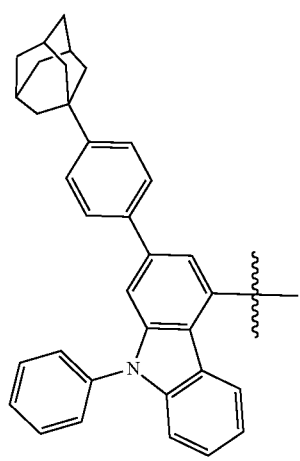
80
-continued
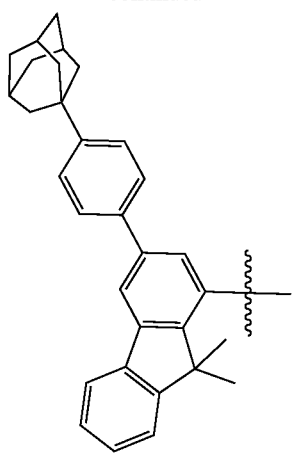
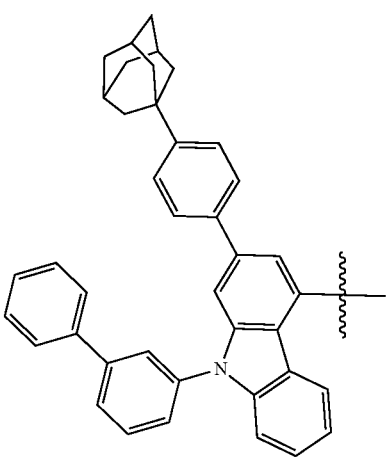
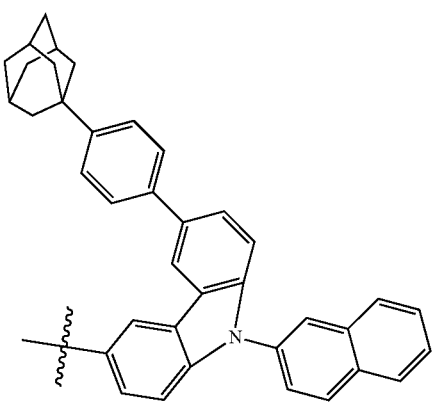

-continued
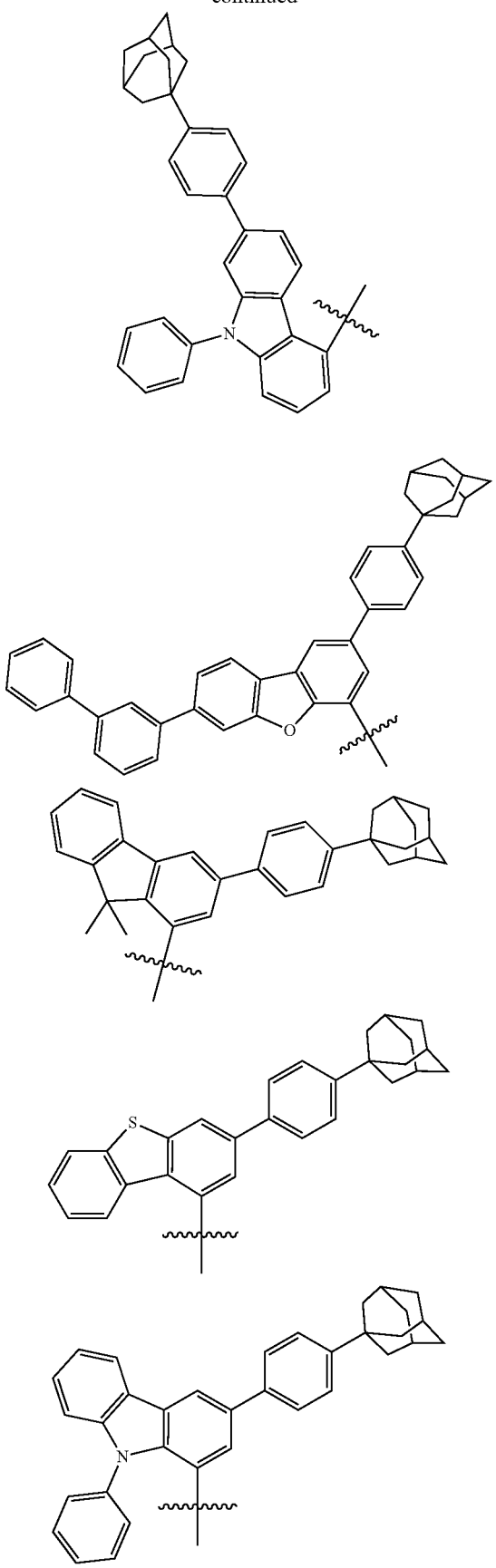
-continued
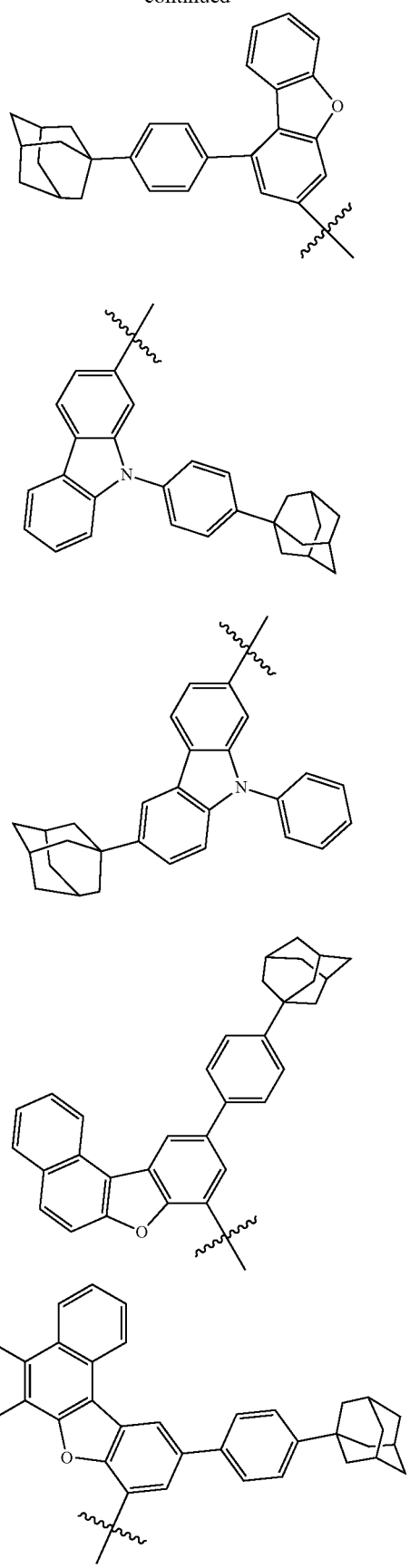

83
-continued
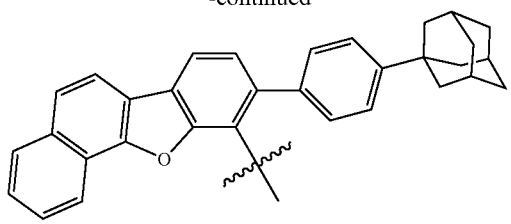
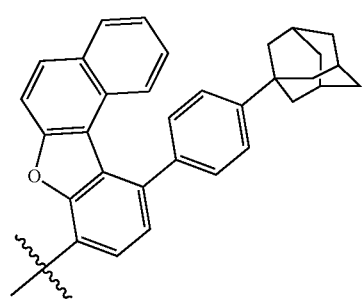
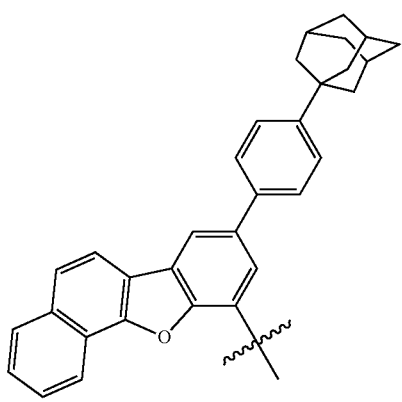
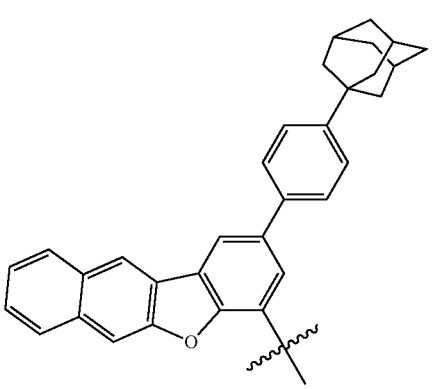
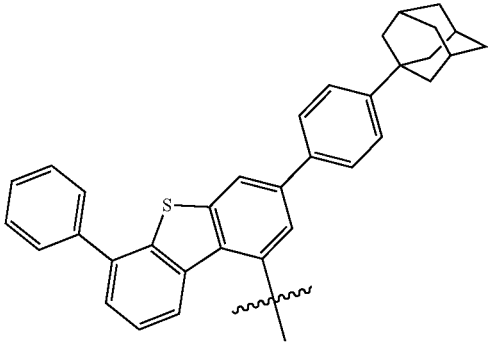
84
-continued
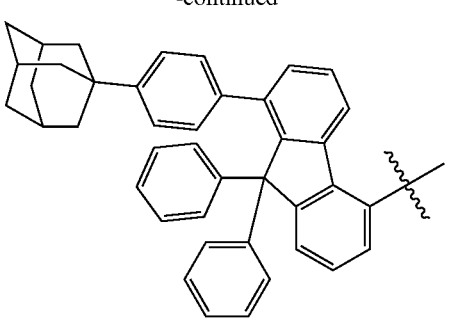
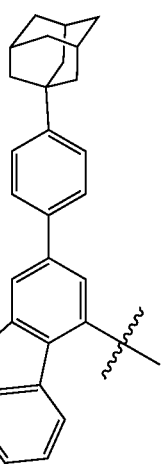
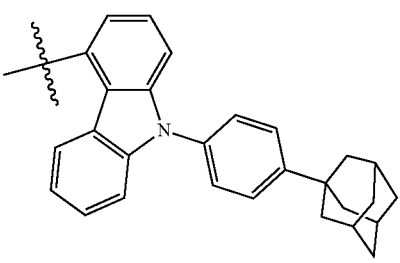
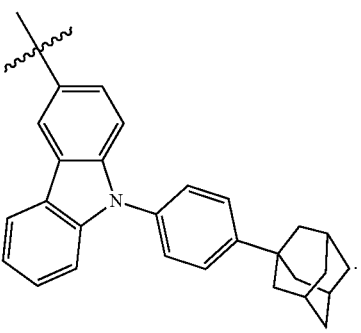

In this embodiment, the structures of $L_1$, $L_2$, $Ar_1$ and $Ar_a$ optionally do not include

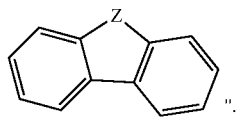

".

Optionally, in formulae 3-6 to 3-8, $L_3$ may be phenylene.

In a preferred embodiment, at least one of $L_1$, $L_2$ and $L_3$ of the organic compound is

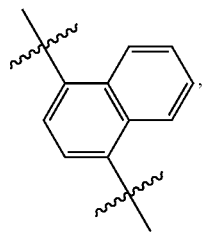 [SMILES: *c1ccc(*)c2ccccc12]

and all of $X_1$, $X_2$ and $X_3$ are N. In this case, the organic compound may improve the performance of a red light device when applied to the device.

In the present disclosure, the organic compound is optionally selected from the group consisting of the following compounds:

1

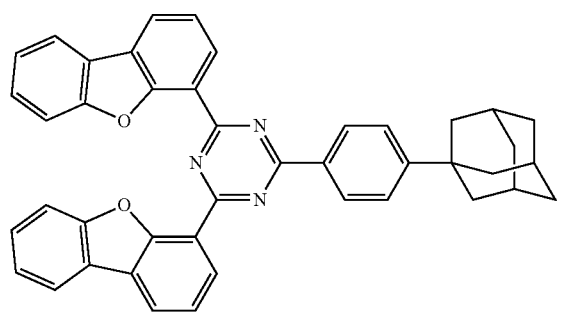

2

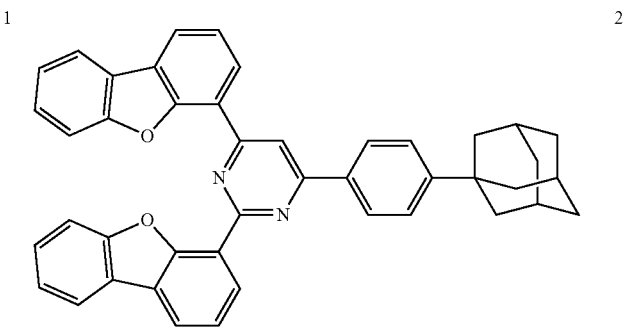

3

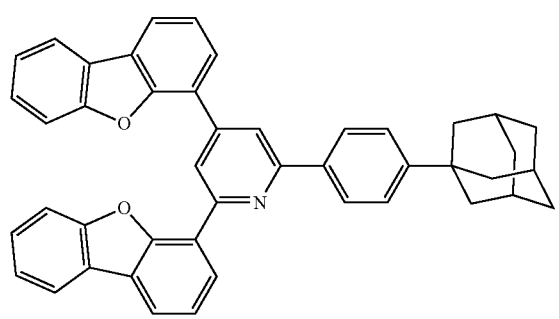

4

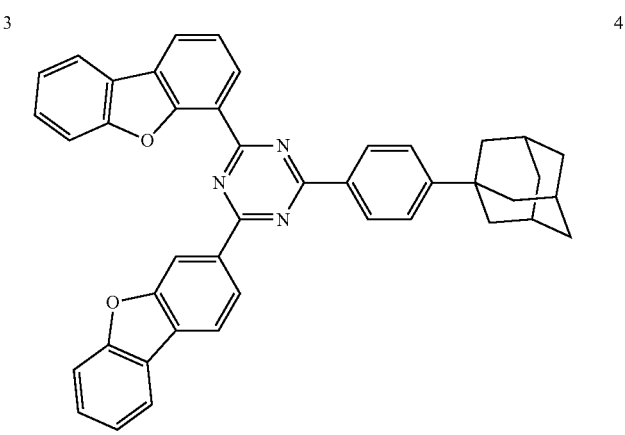

-continued
5
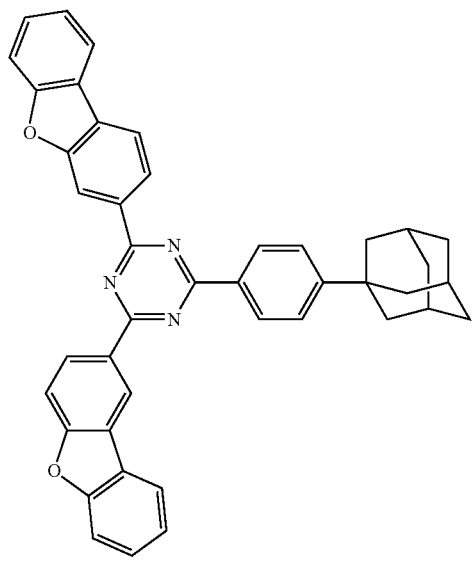
6
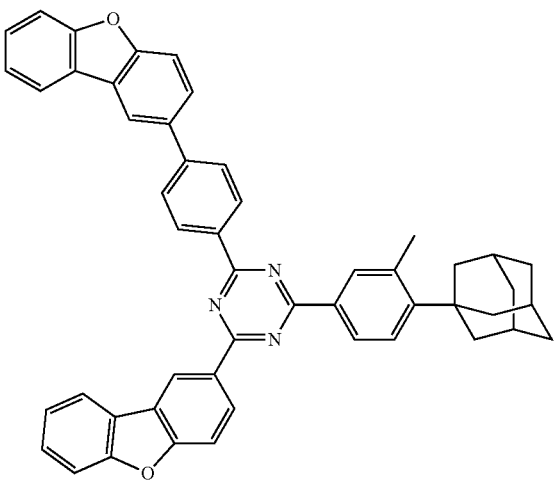
7
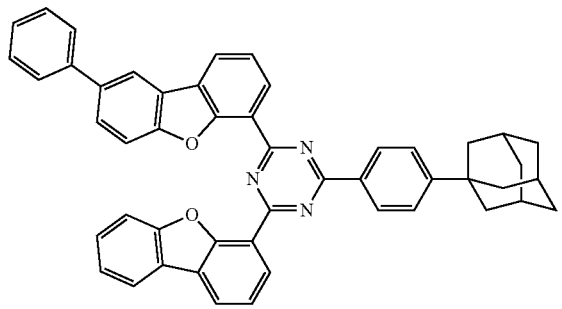
8
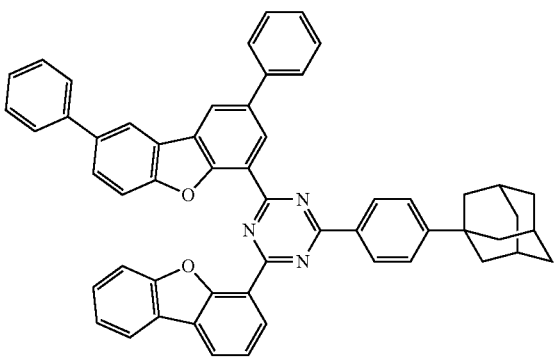
9
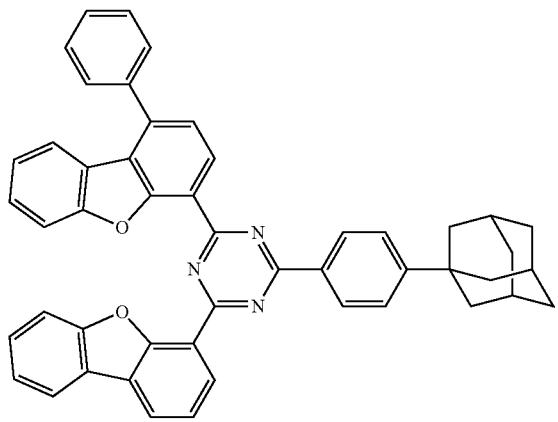
10
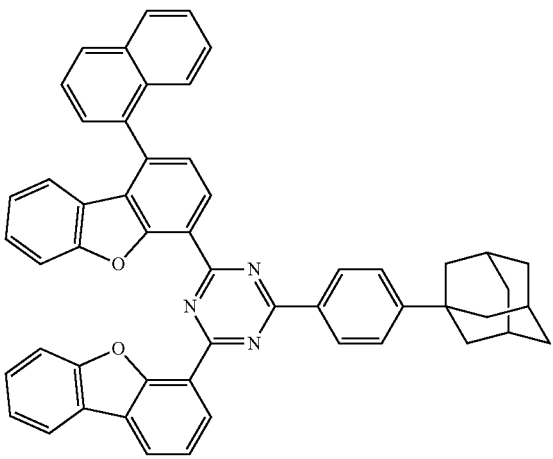

11
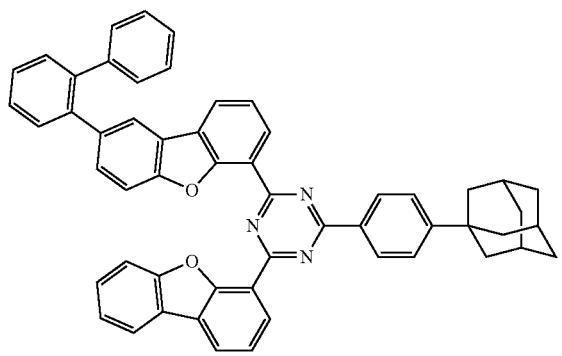
12
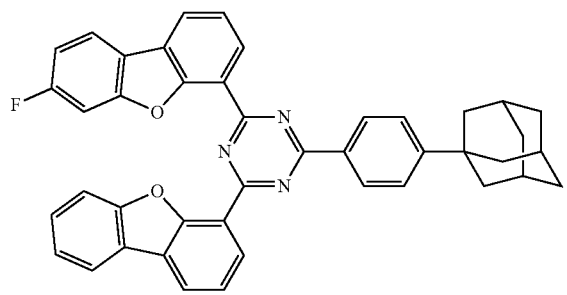
13
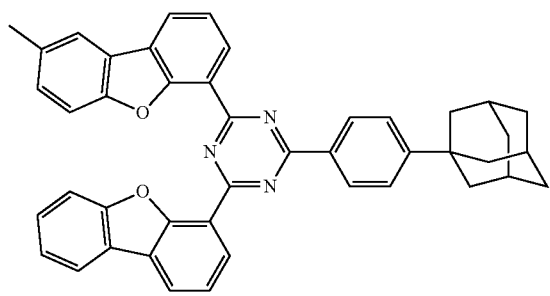
14
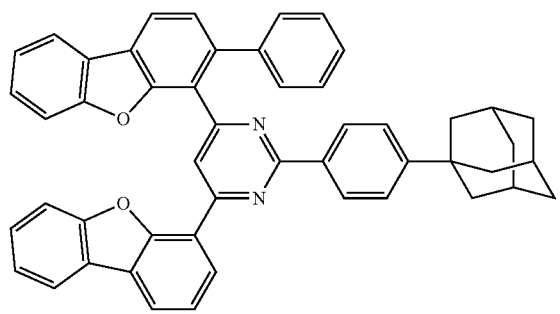
15
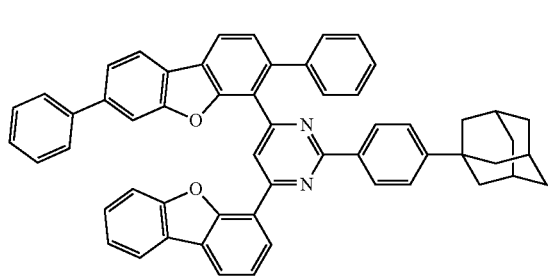
16
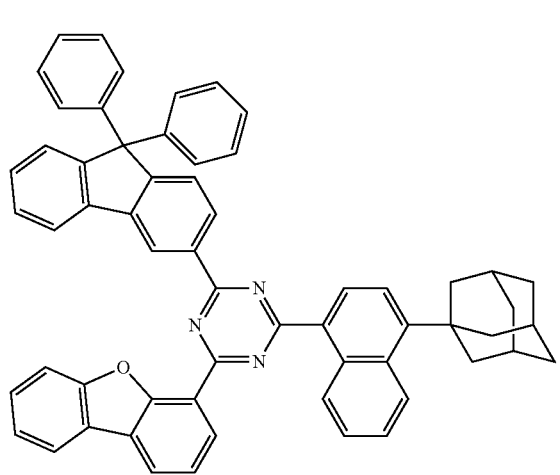

-continued
17
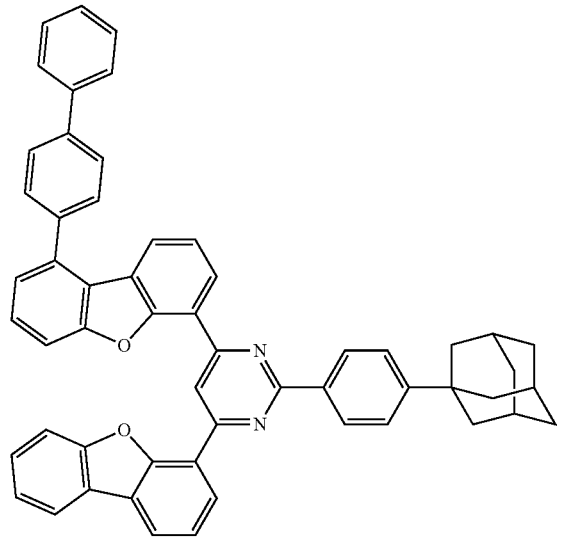
18
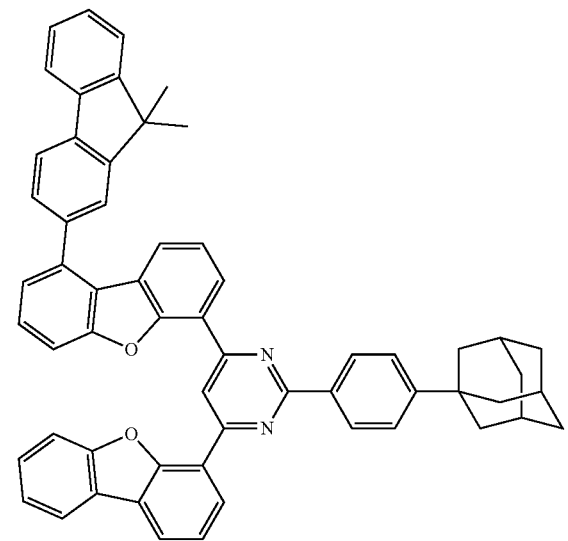
19
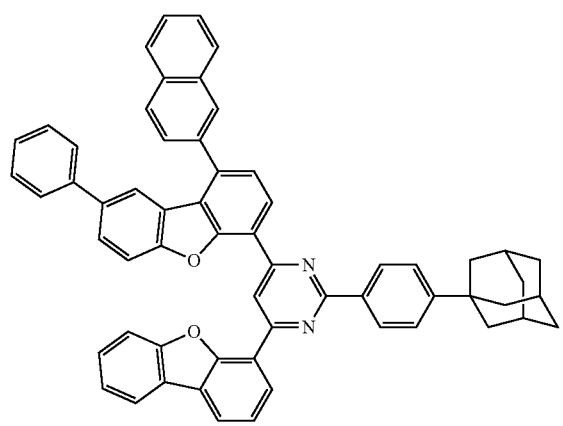
20
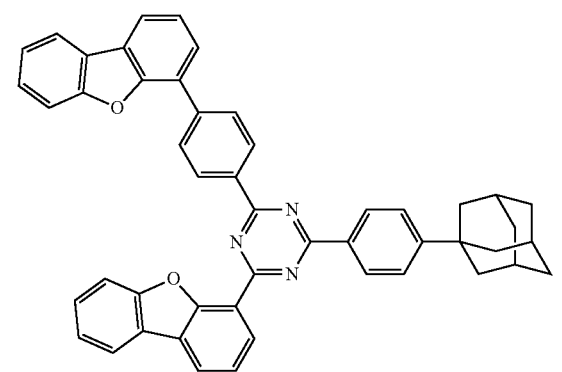
21
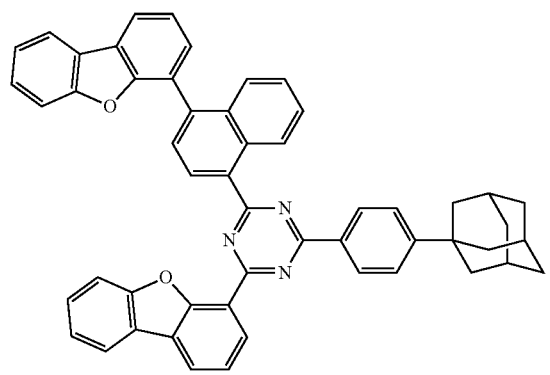
22
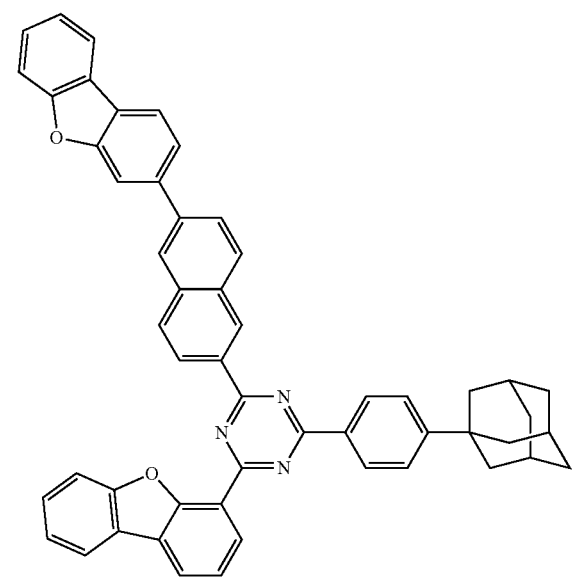

23
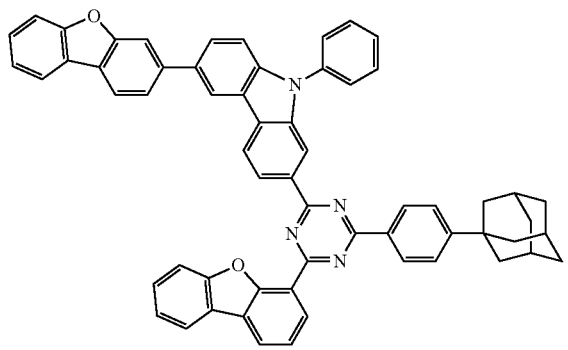
24
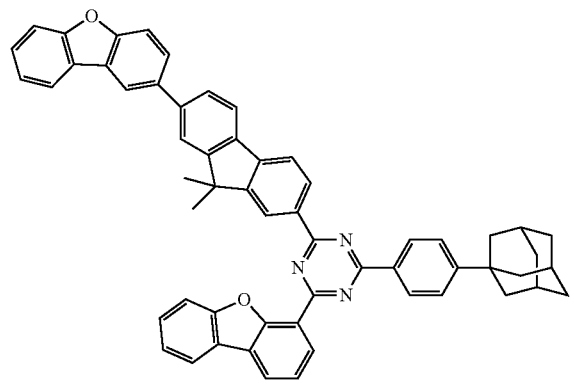
25
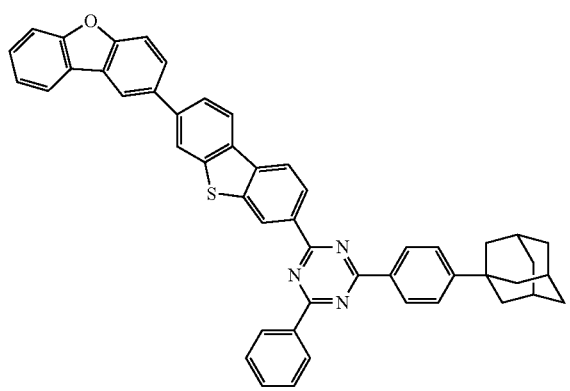
26
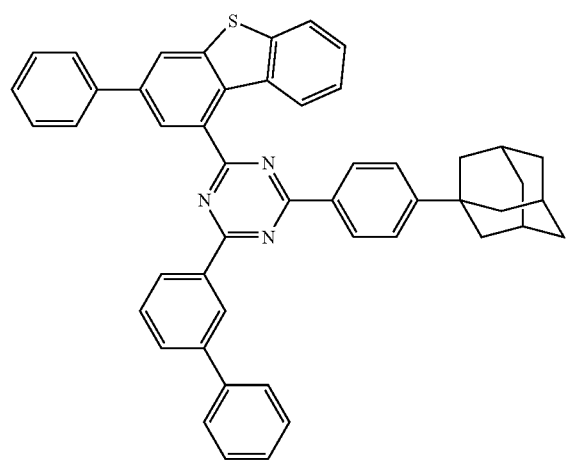
27
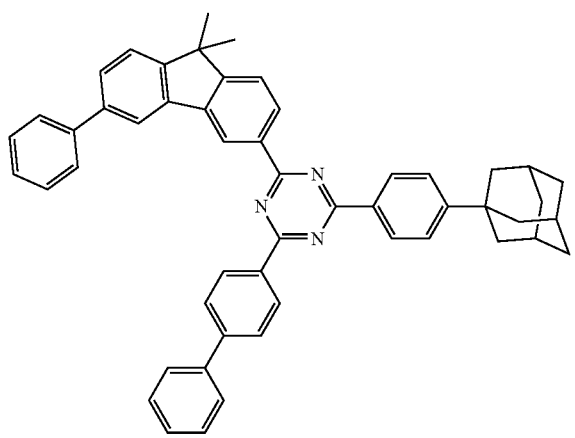
28
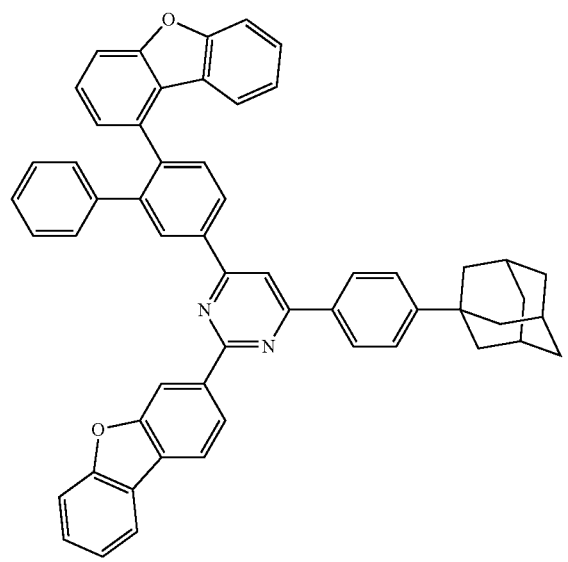

29
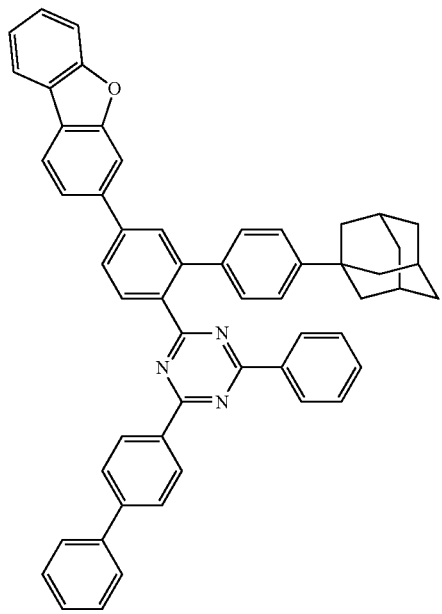
30
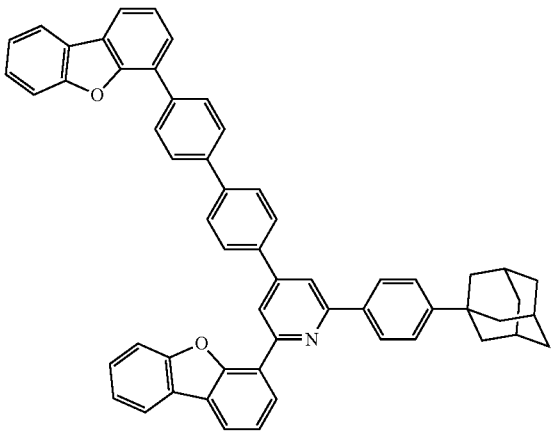
31
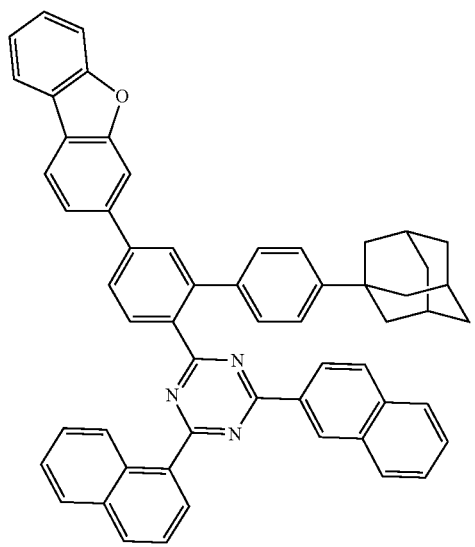
32
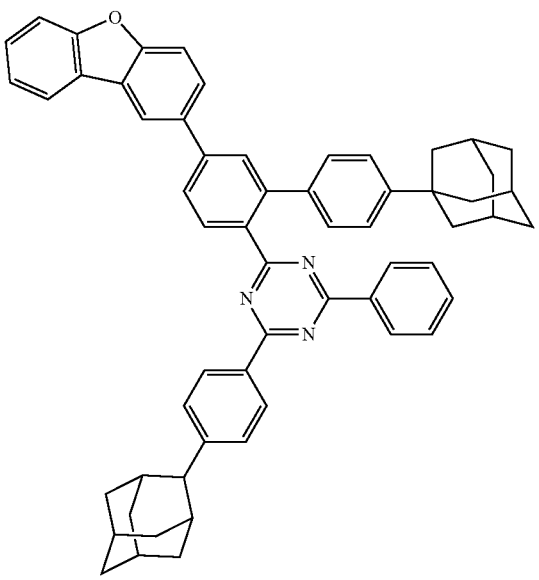
33
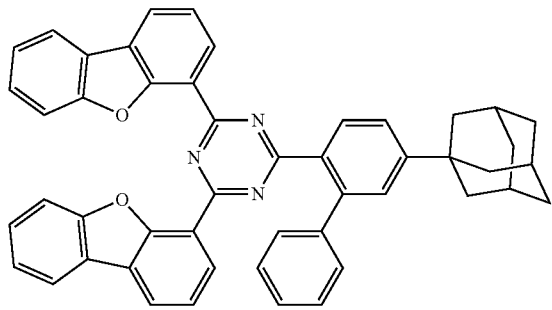
34
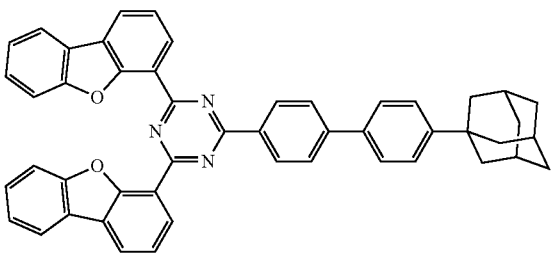

-continued
35
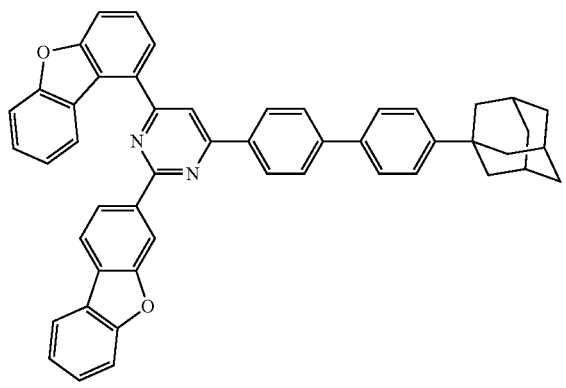
36
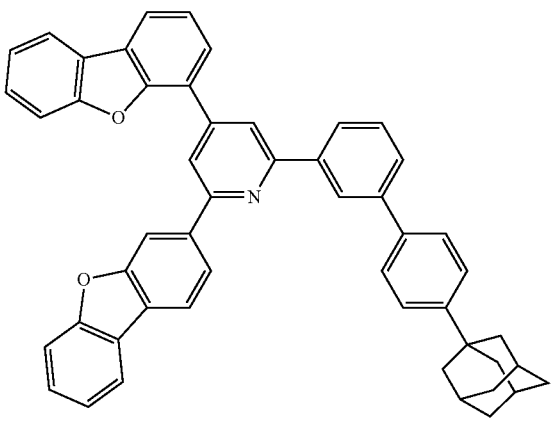
37
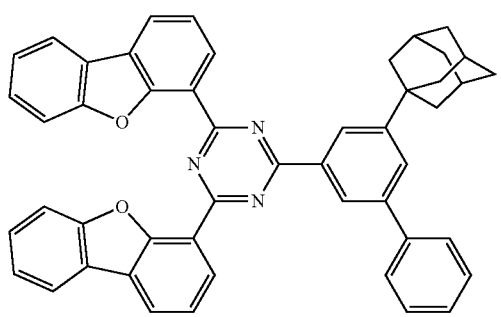
38
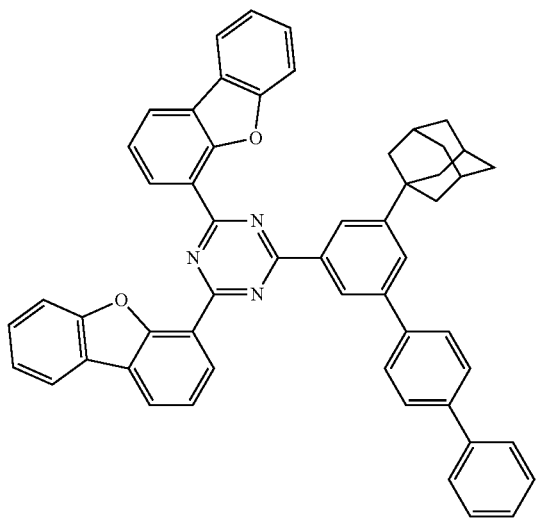
39
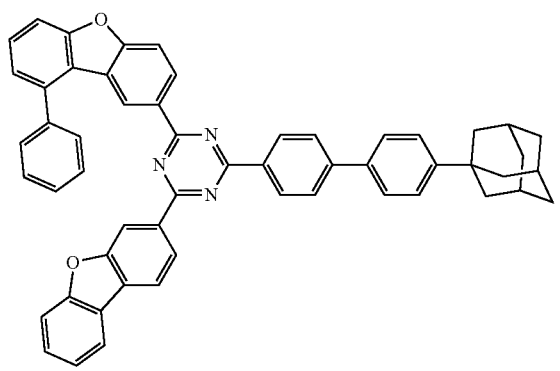
40
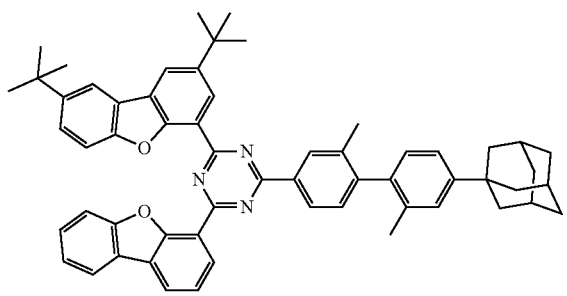

-continued
41
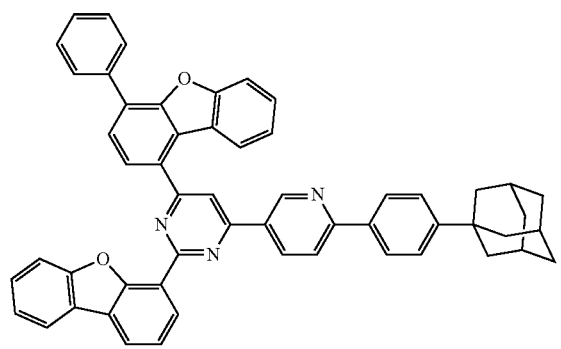
42
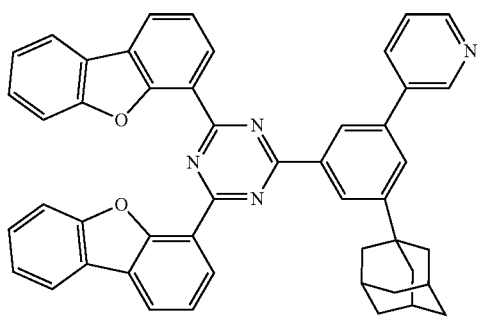
43
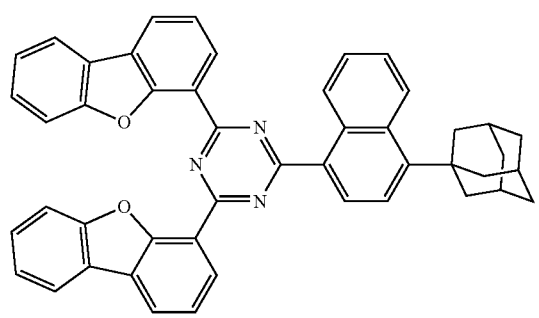
44
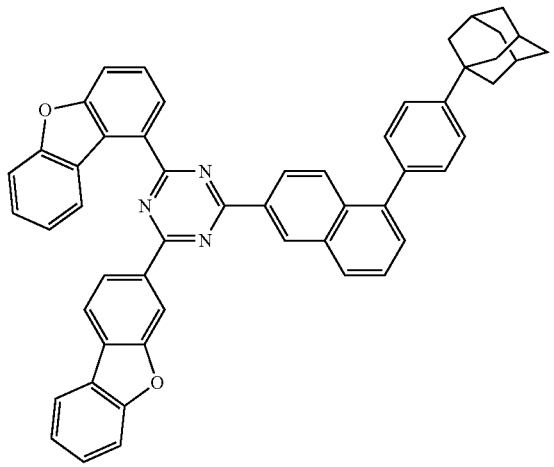
45
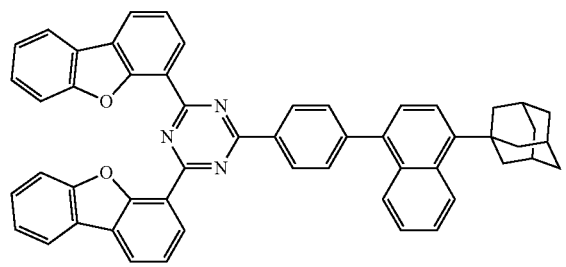
46
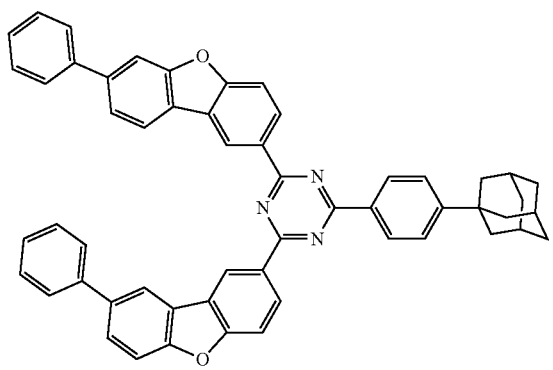

-continued
47
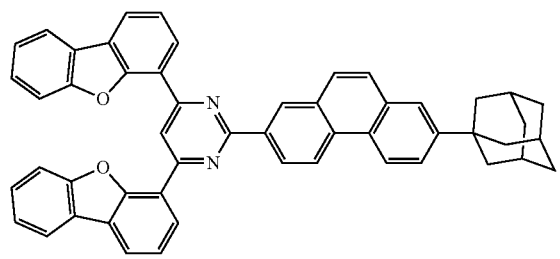
48
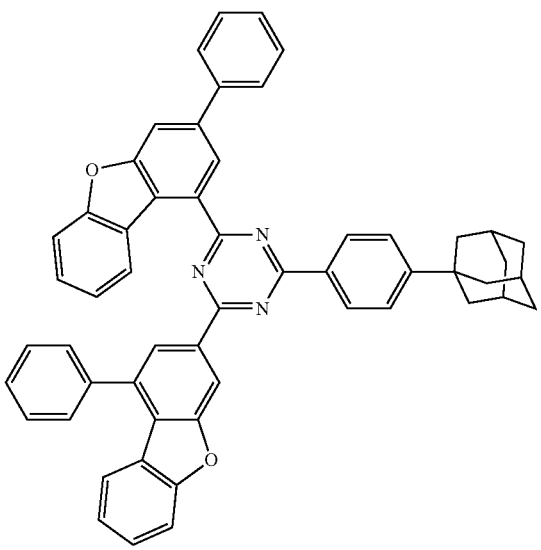
49
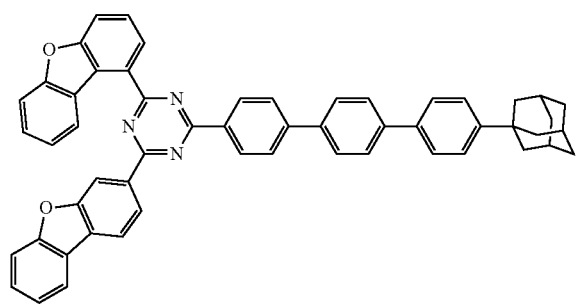
50
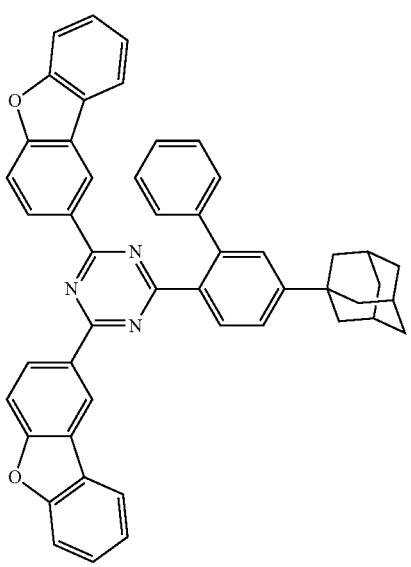
51
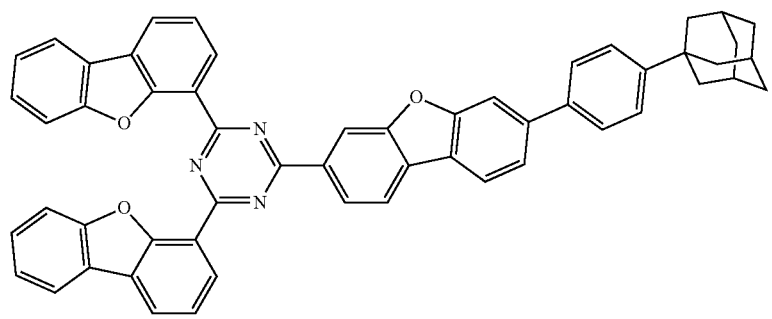

52
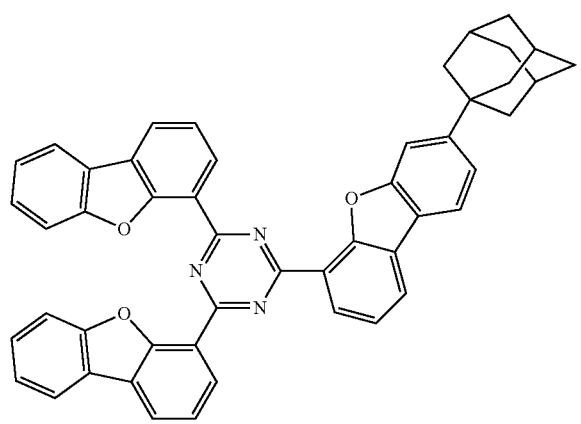
53
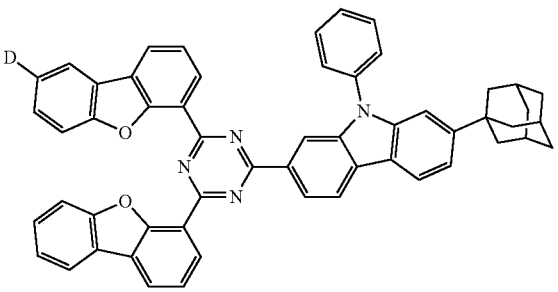
54
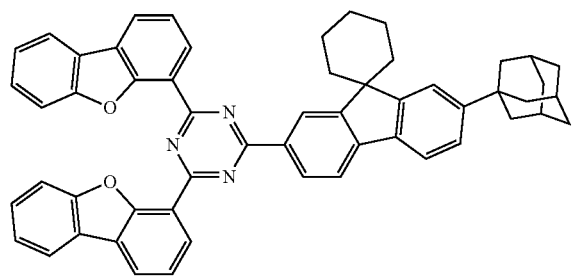
55
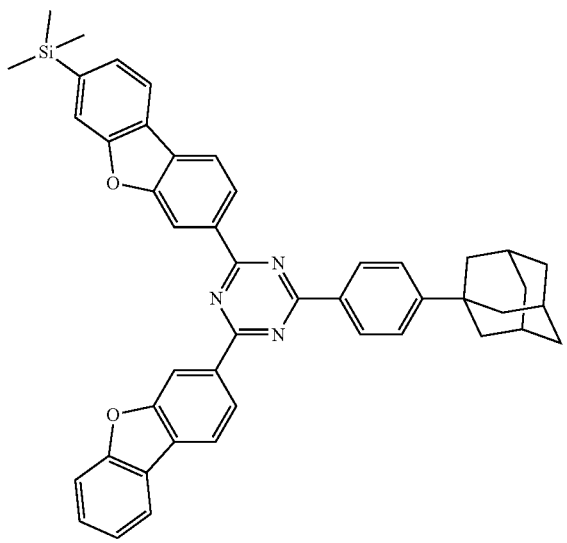
56
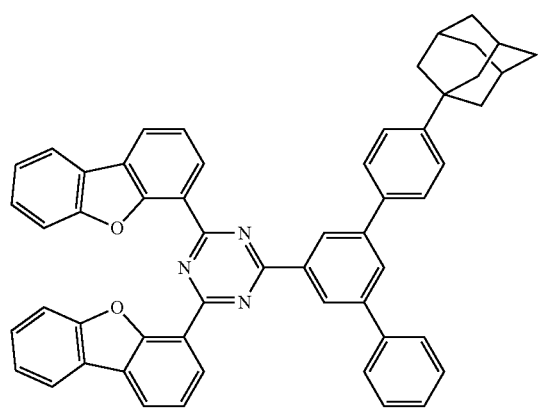
57
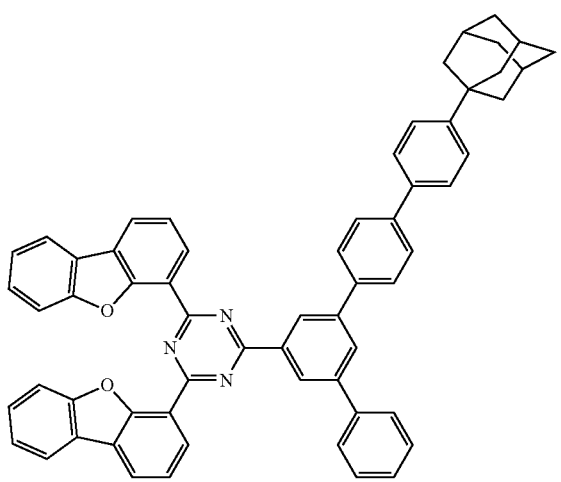

-continued
58
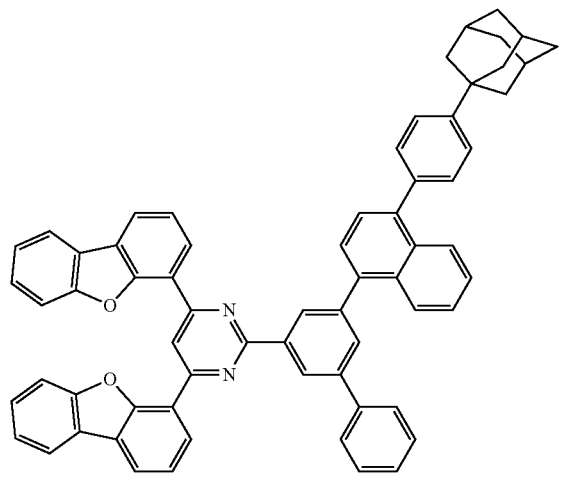
59
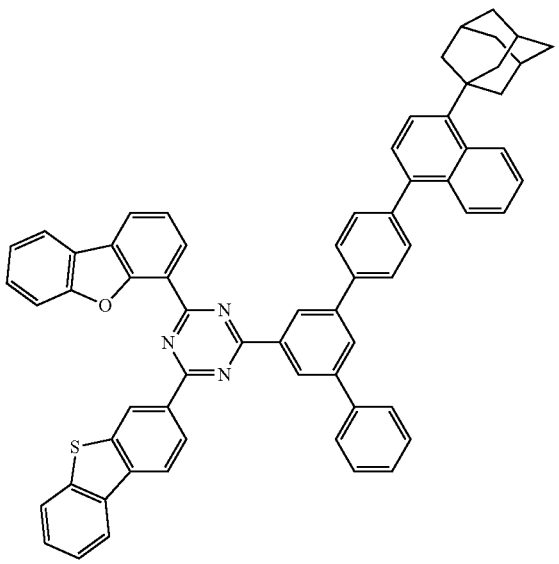
60
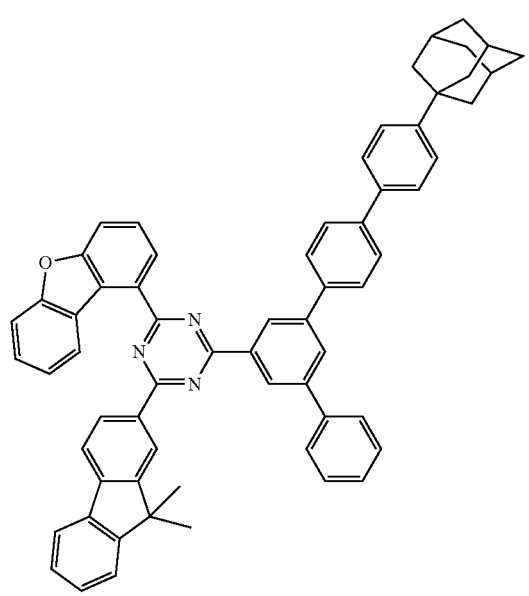
61
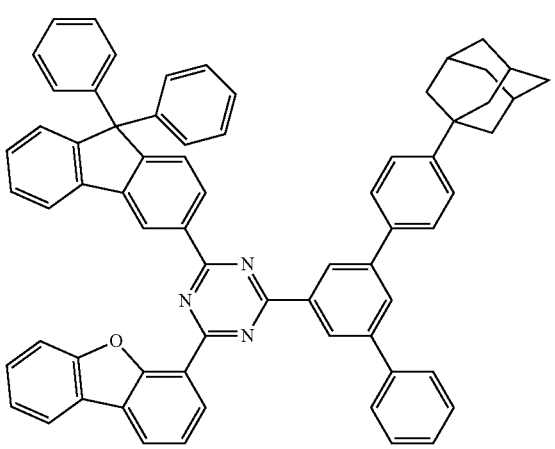
62
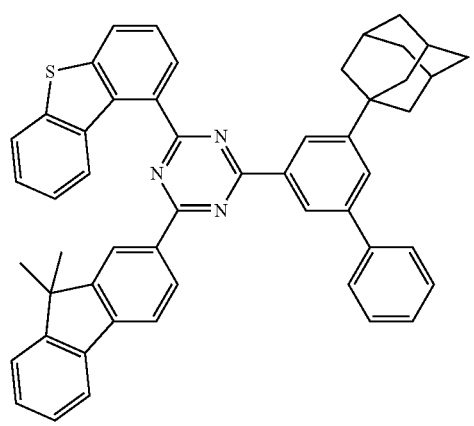
63
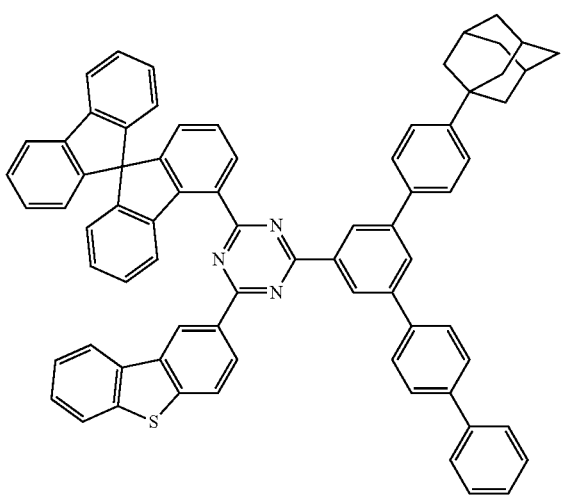

64
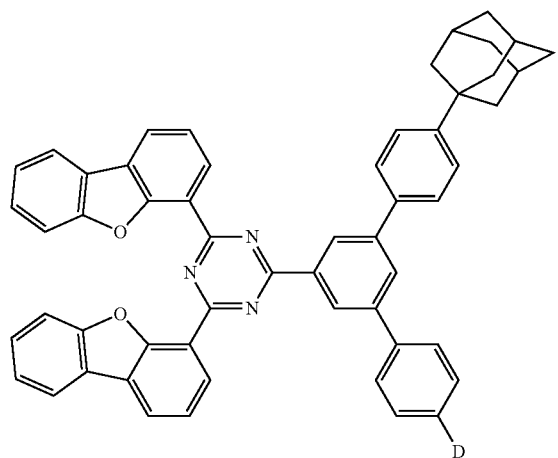
65
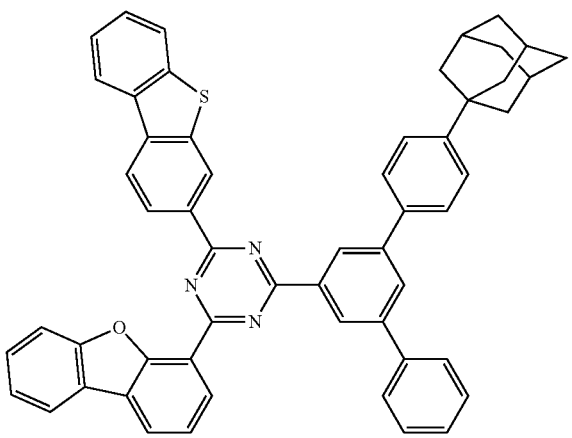
66
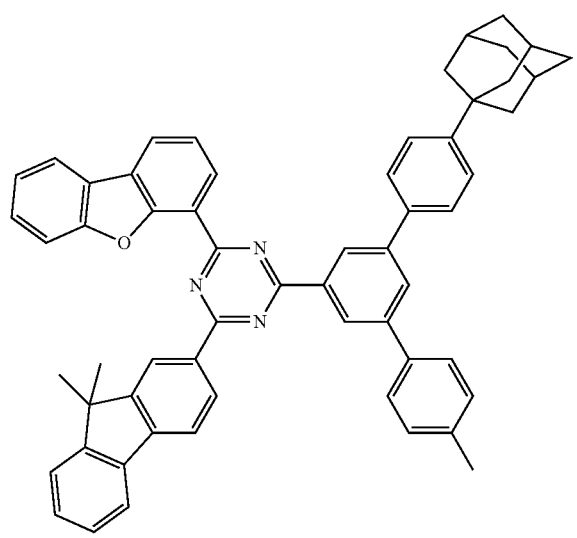
67
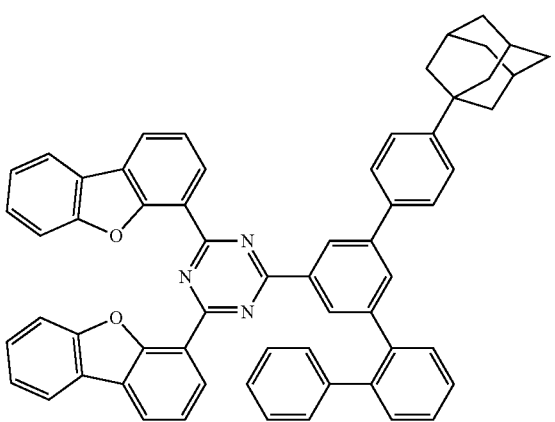
68
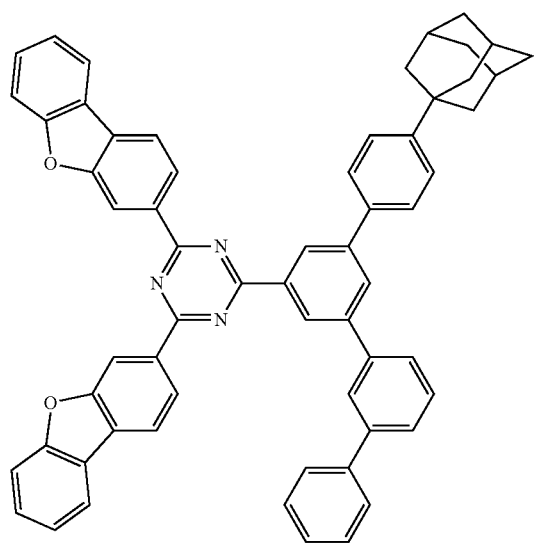
69
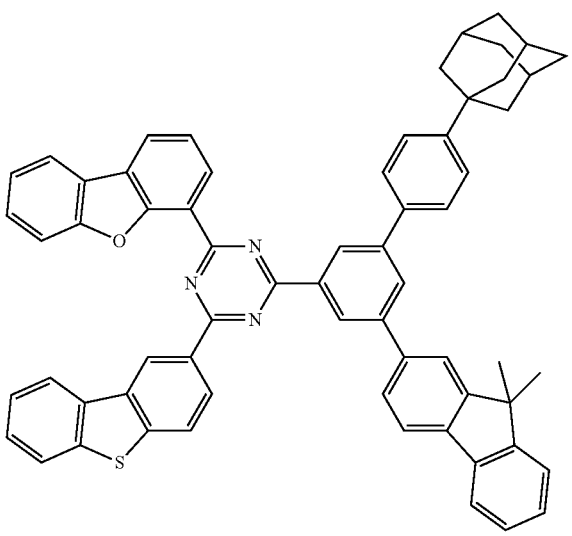

-continued
70
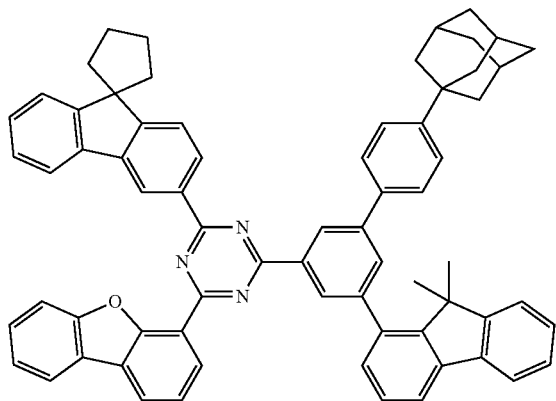
71
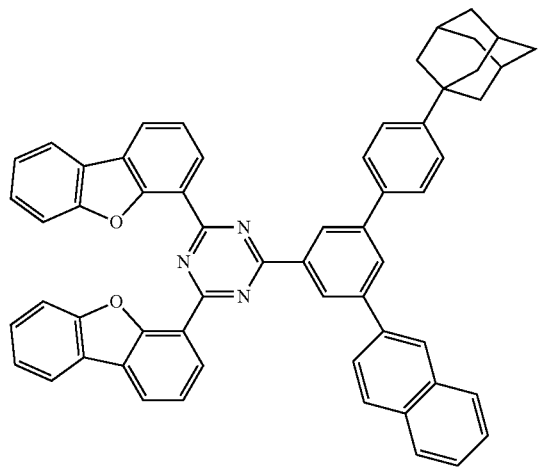
72
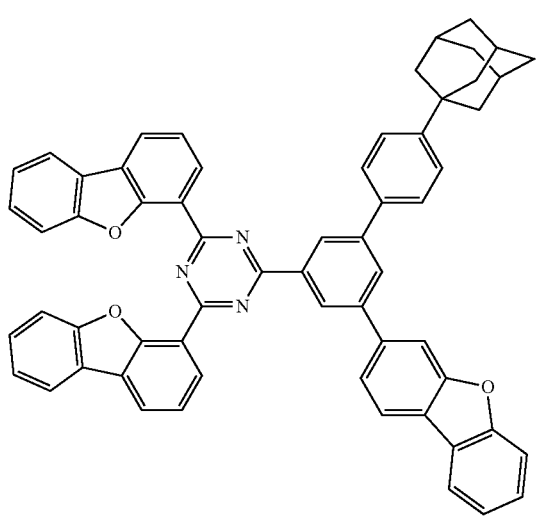
73
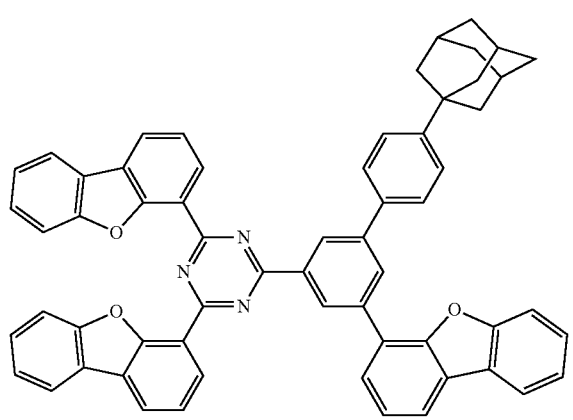
74
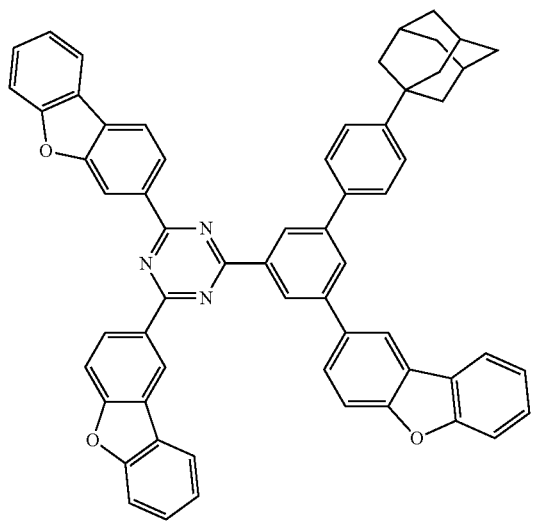
75
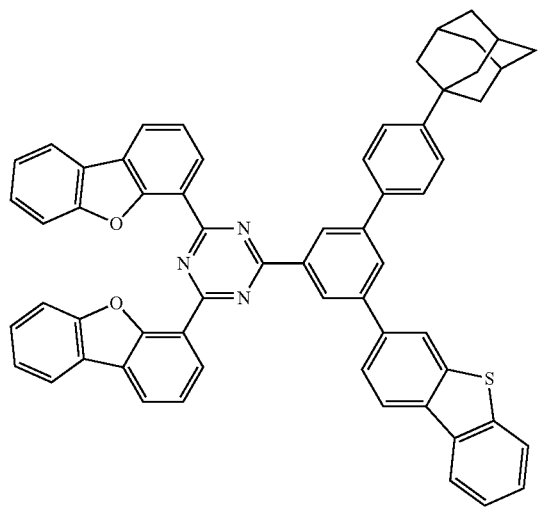

76
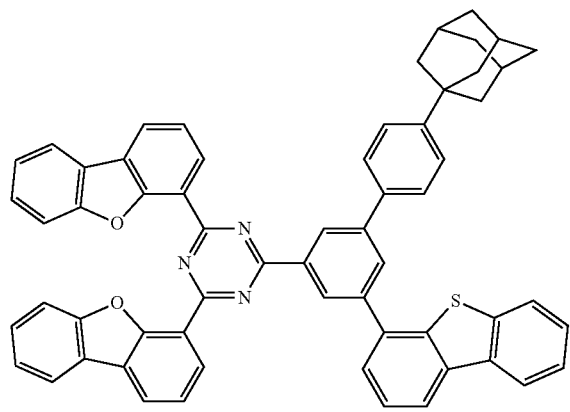
77
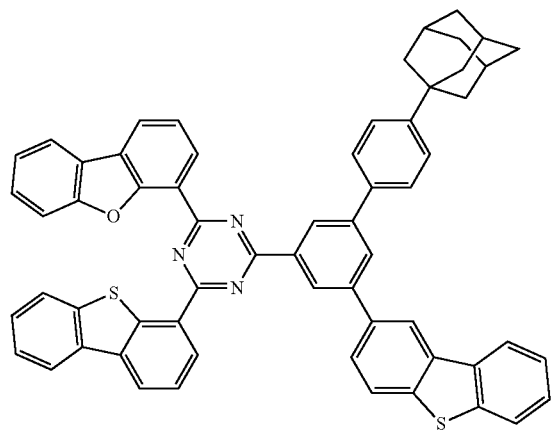
78
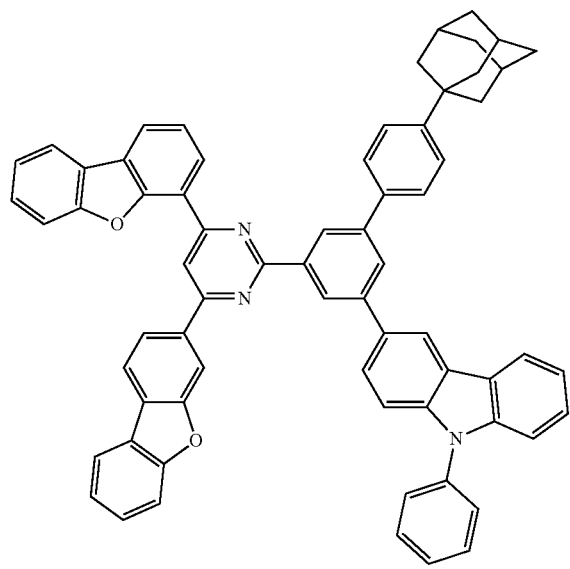
79
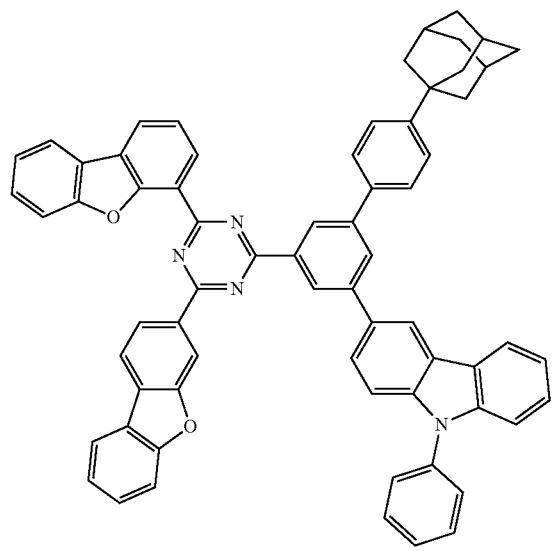
80
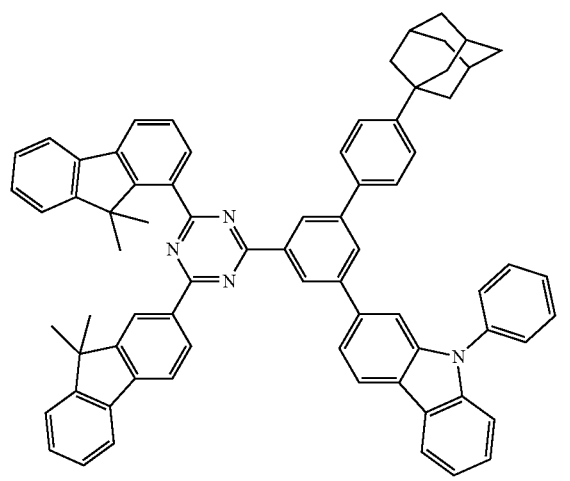
81
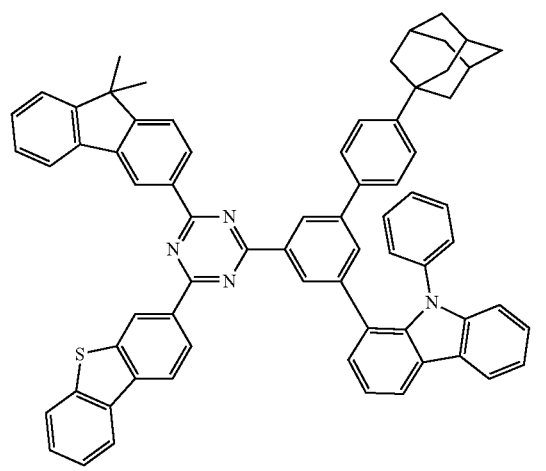

-continued
82
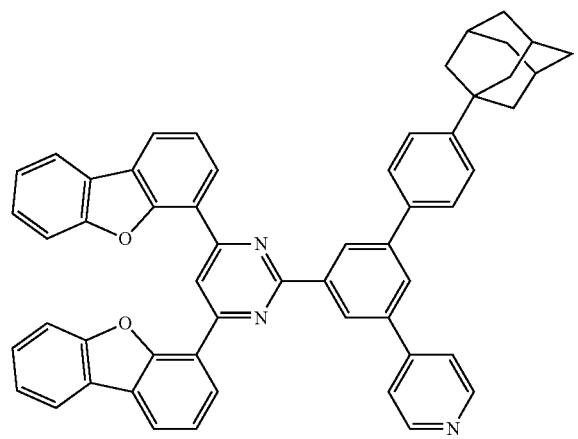
83
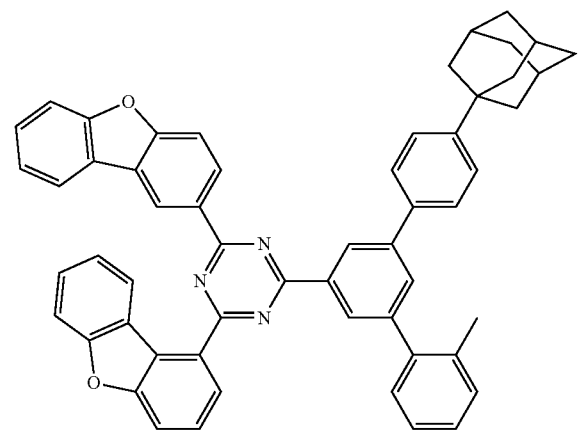
84
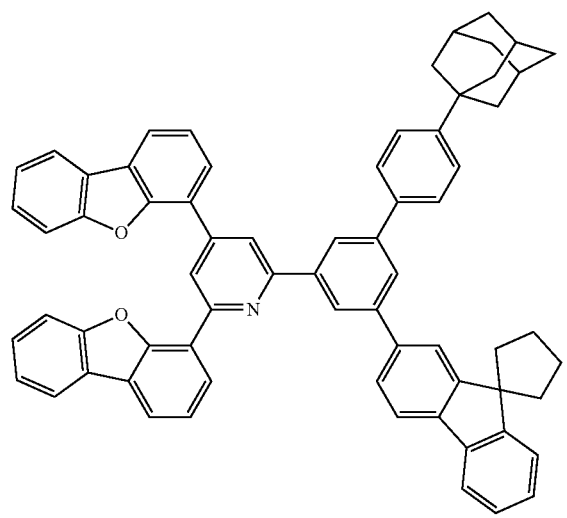
85
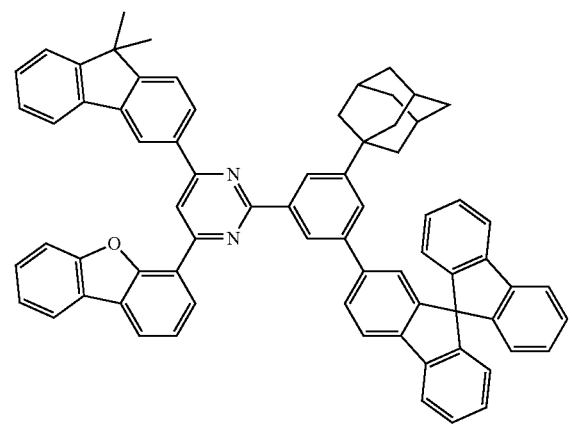
86
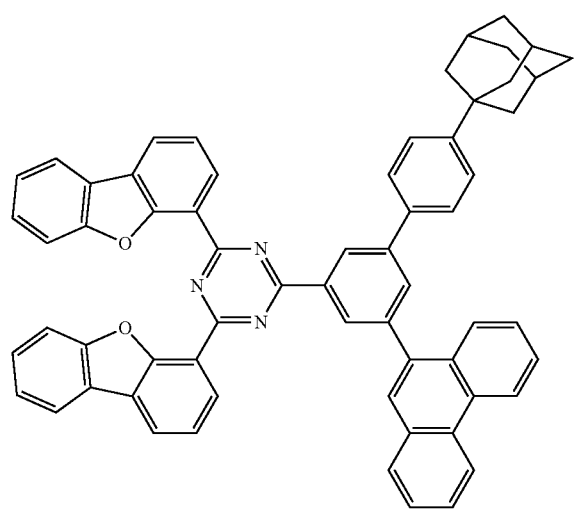
87
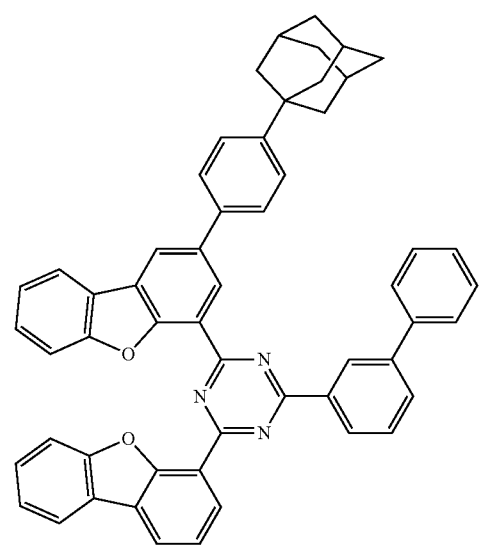

-continued
88
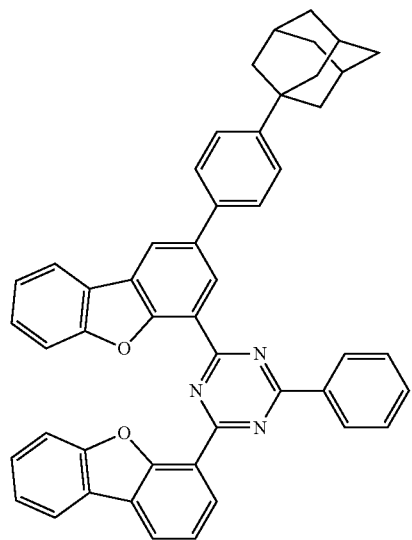
89
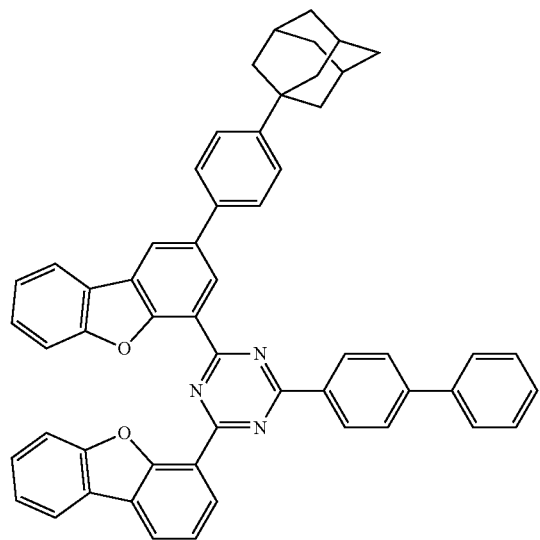
90
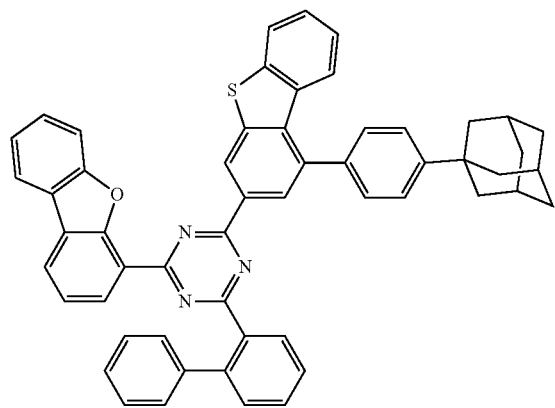
91
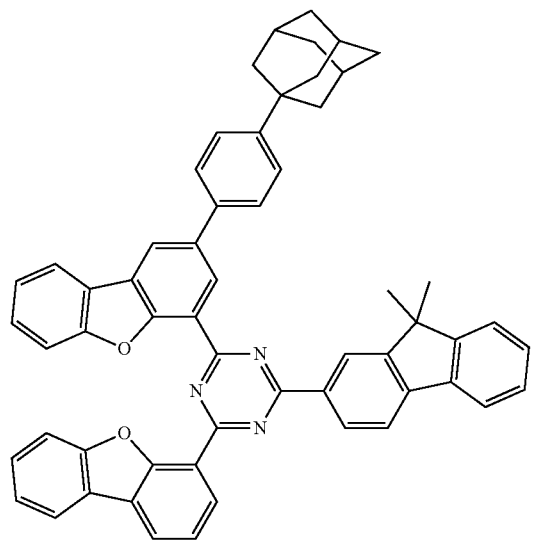
92
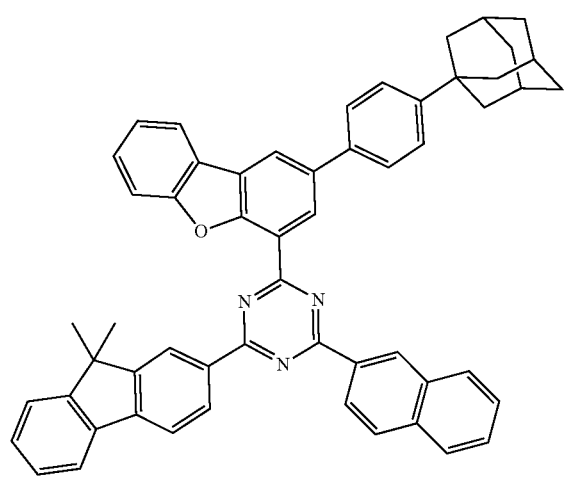
93
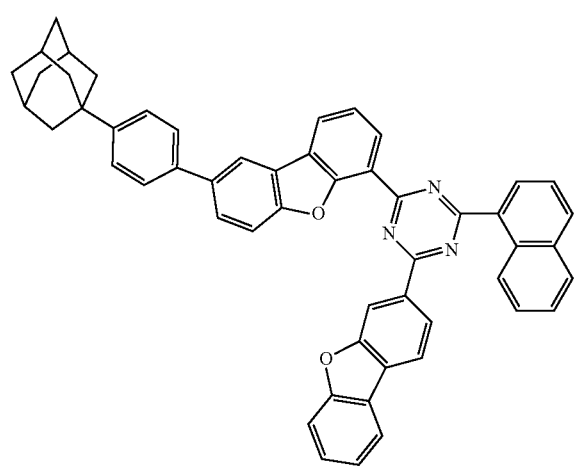

-continued
94
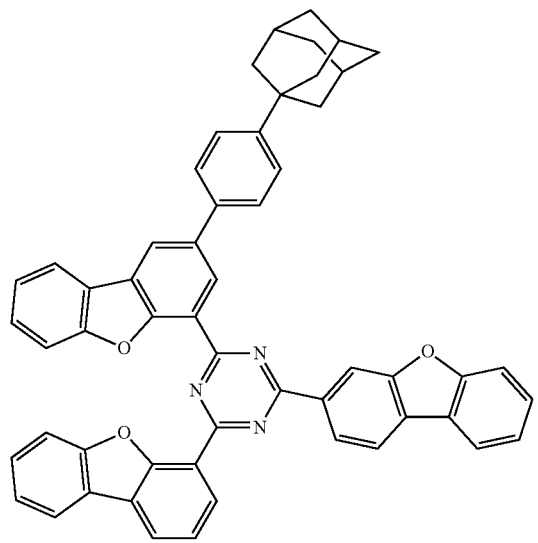
95
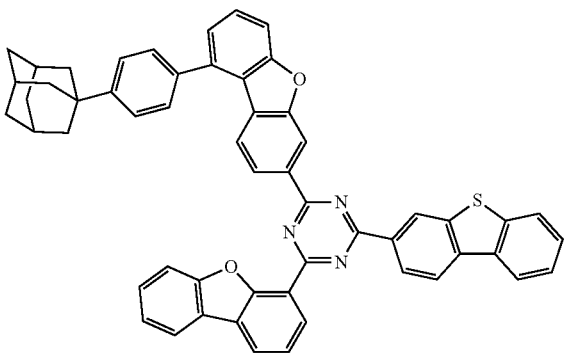
96
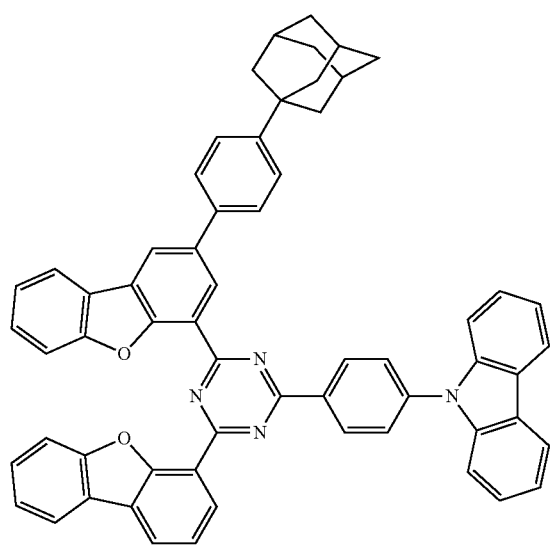
97
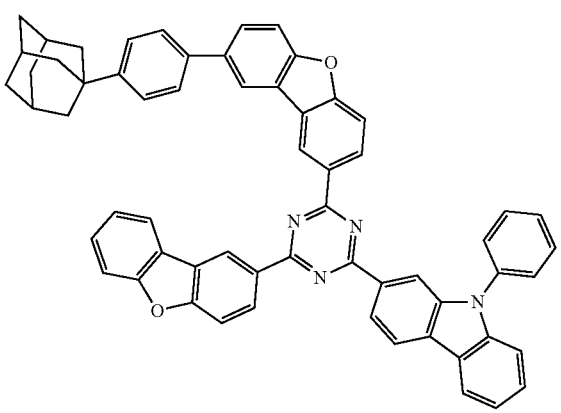
98
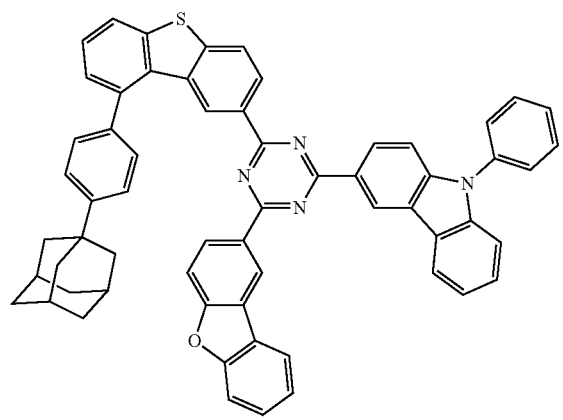
99
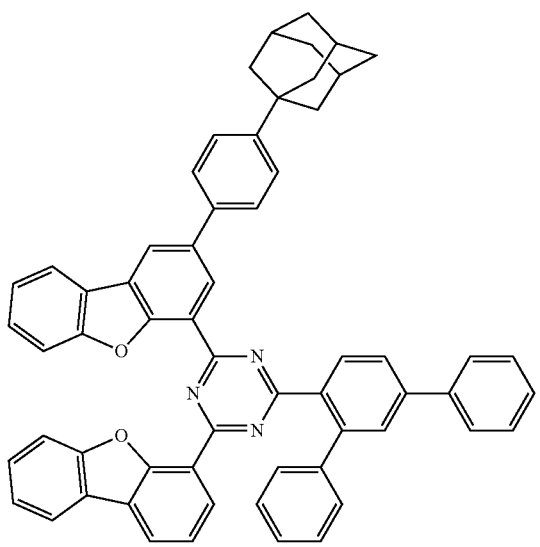

-continued
100
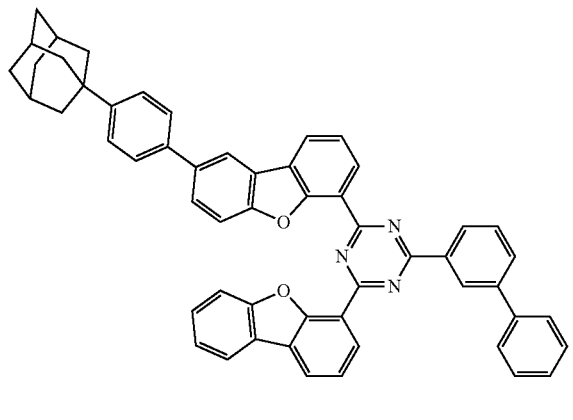
101
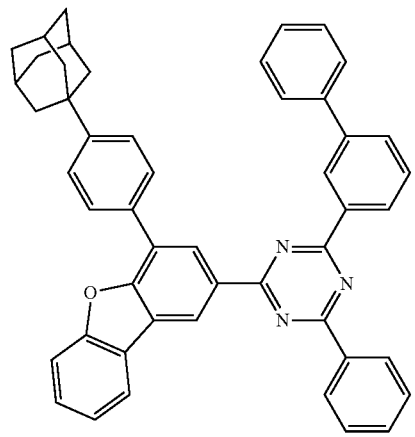
102
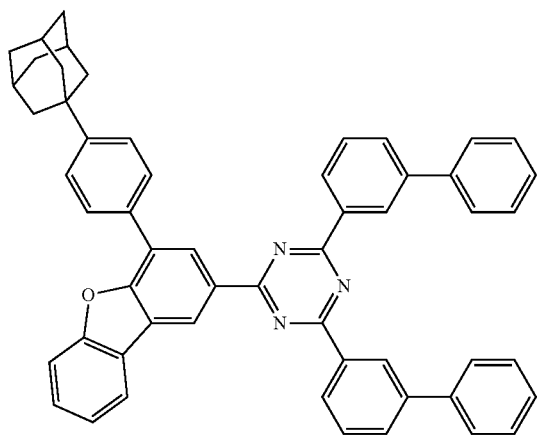
103
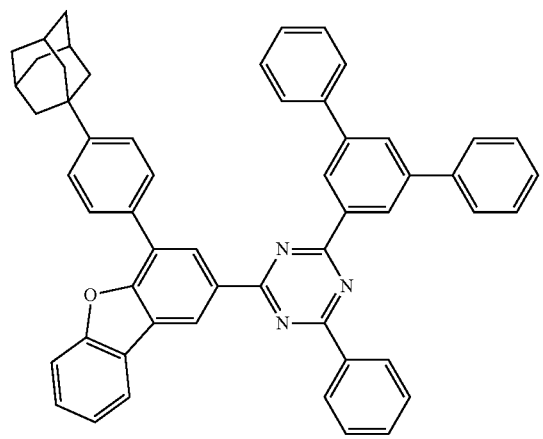
104
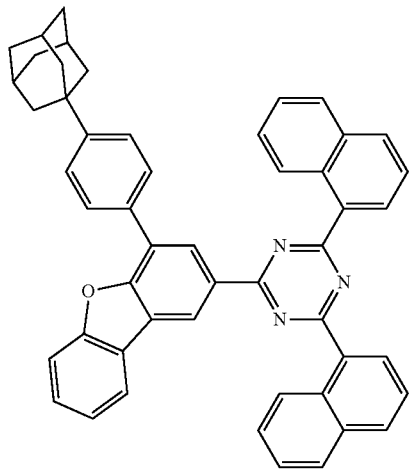
105
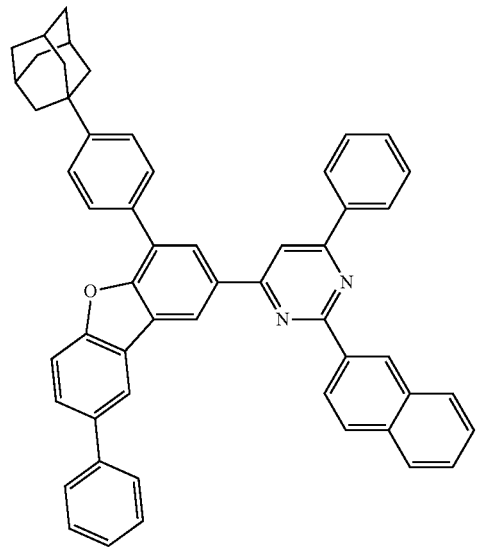

-continued
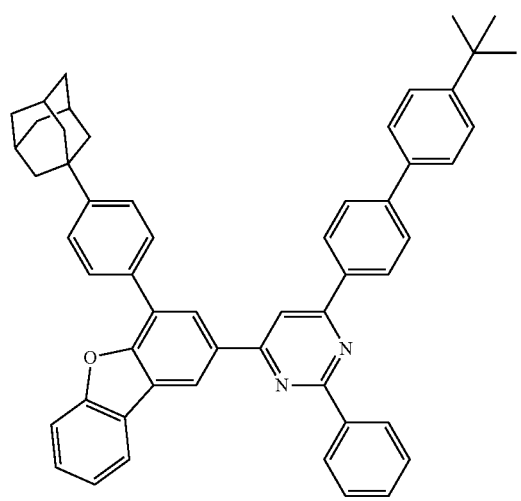
106
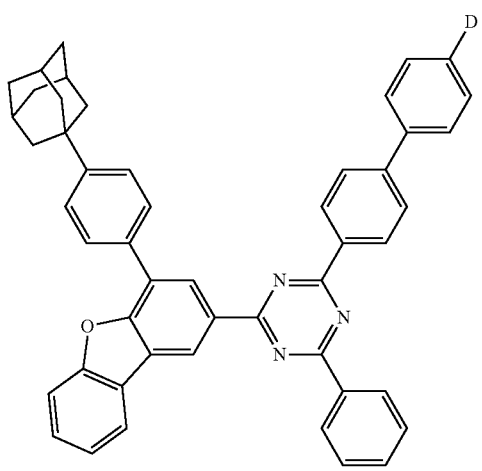
107
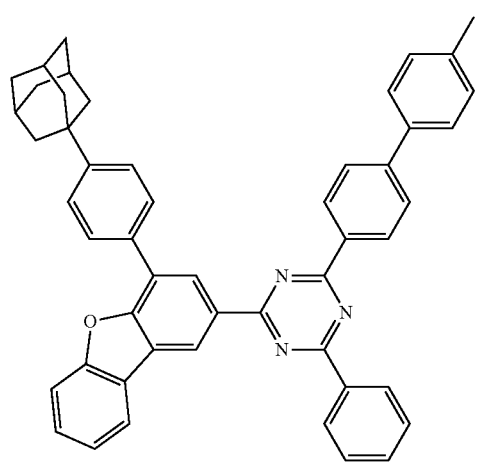
108
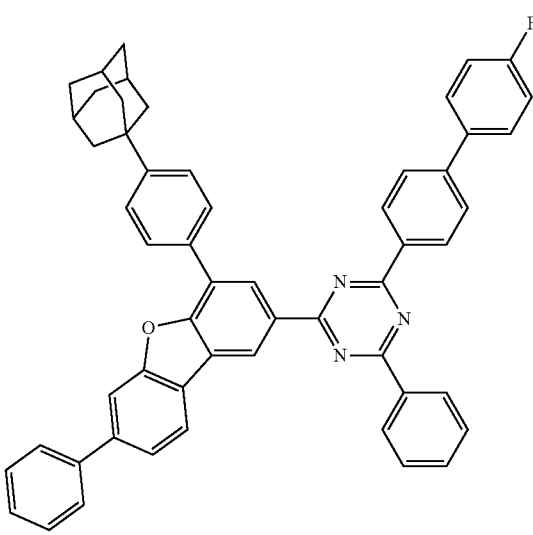
109
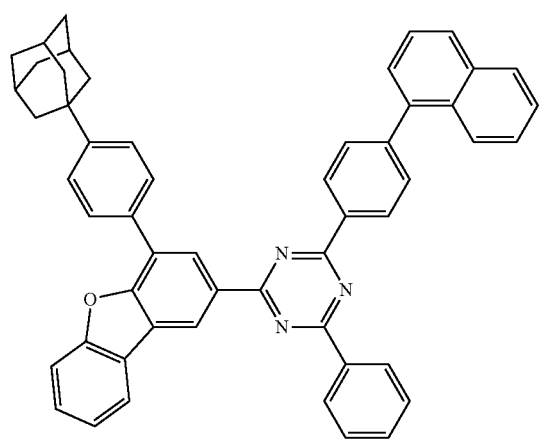
110
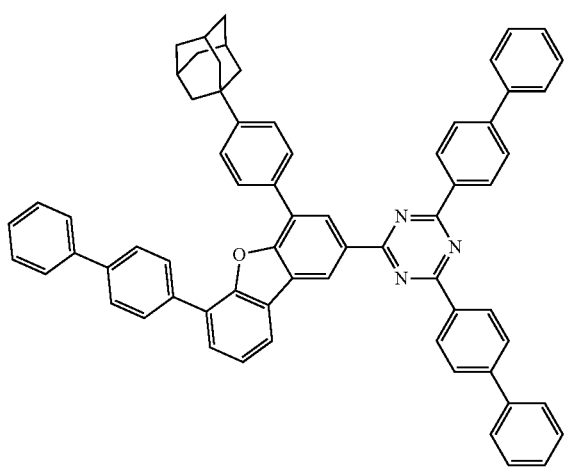
111

-continued
112
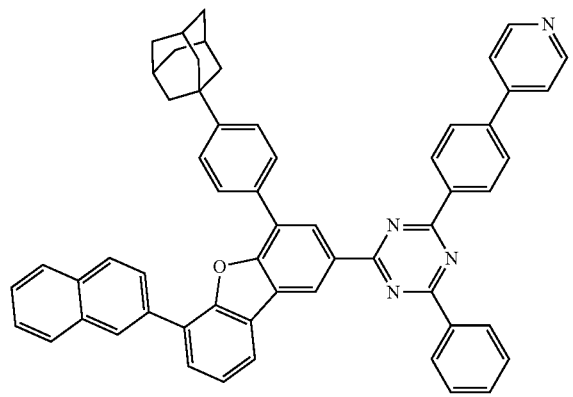
113
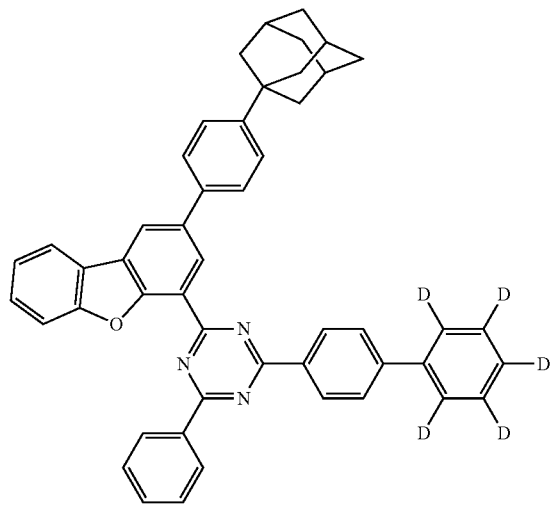
114
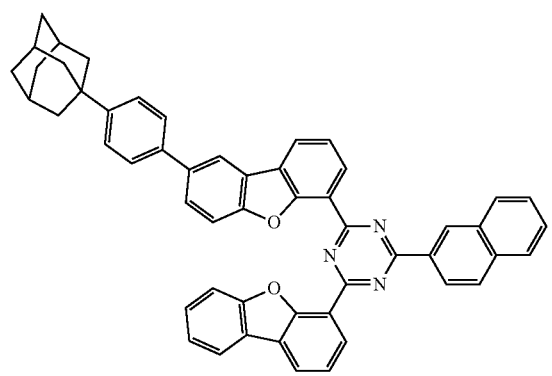
115
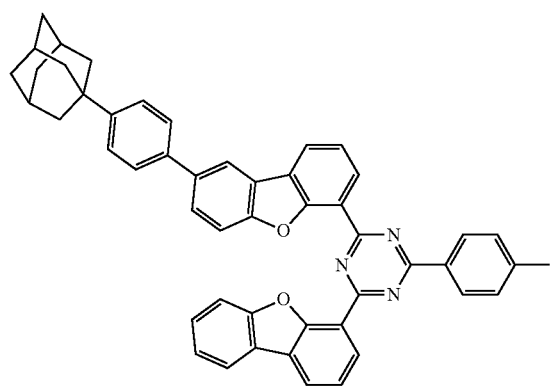
116
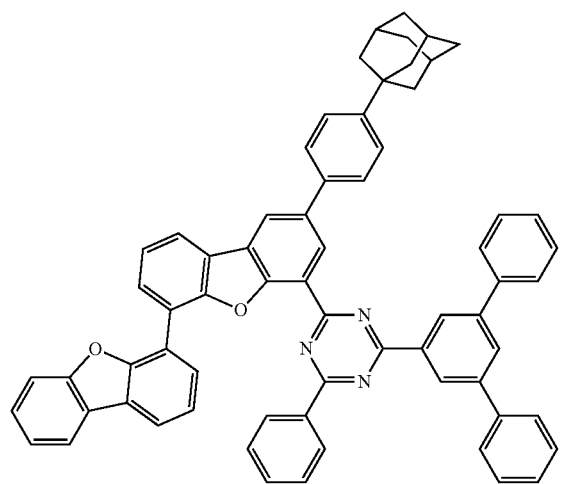
117
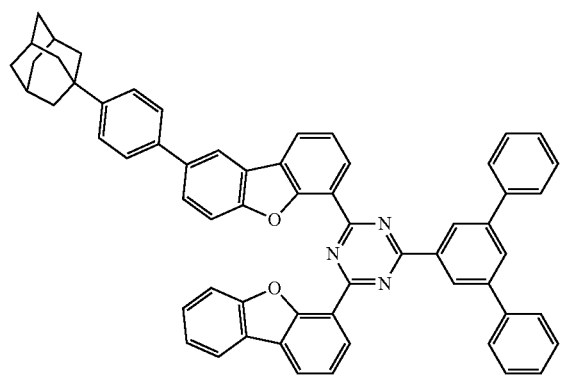

-continued
118
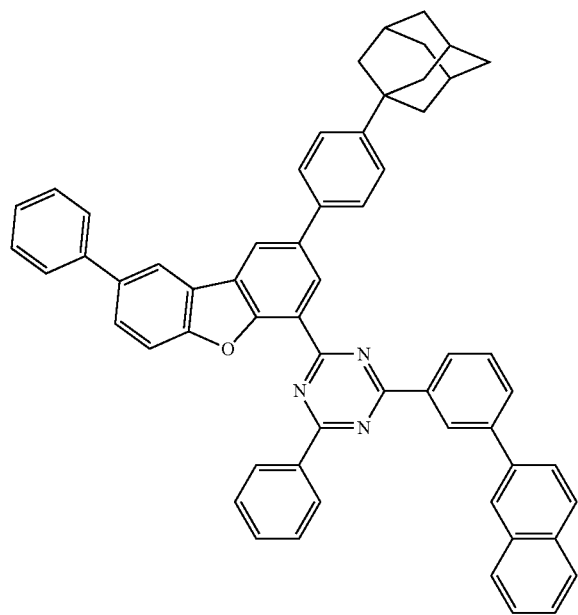
119
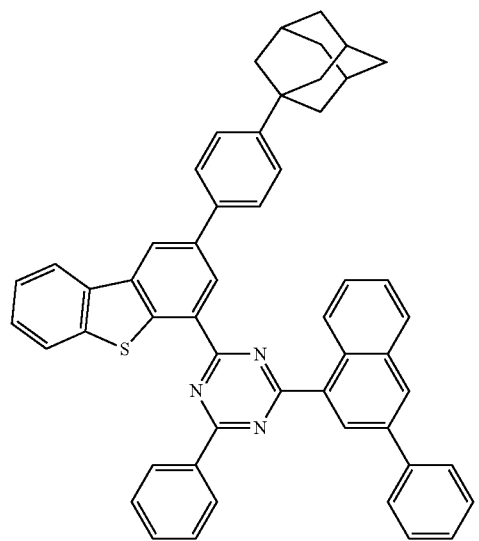
120
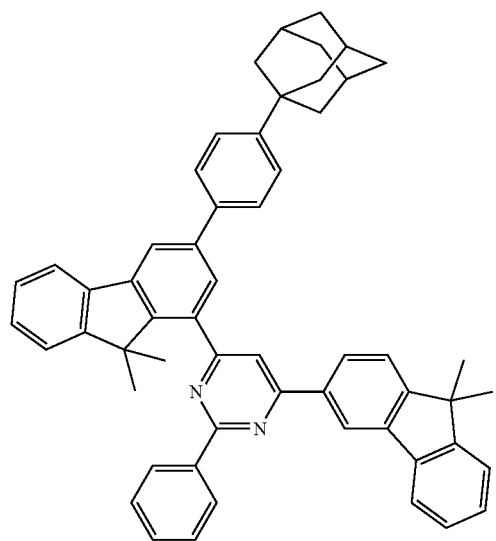
121
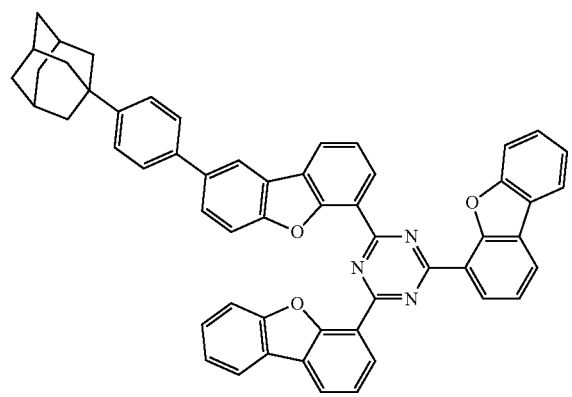

-continued
122
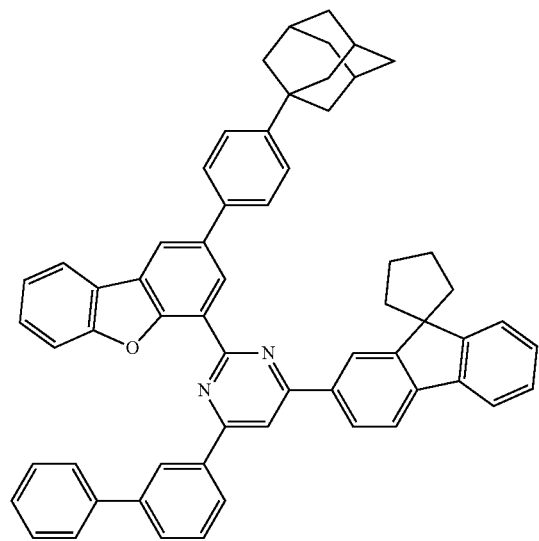
123
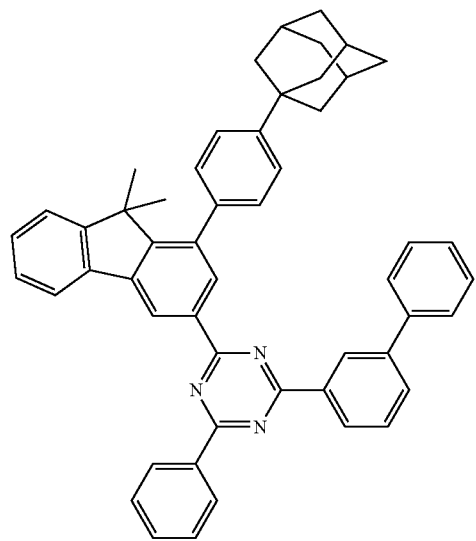
124
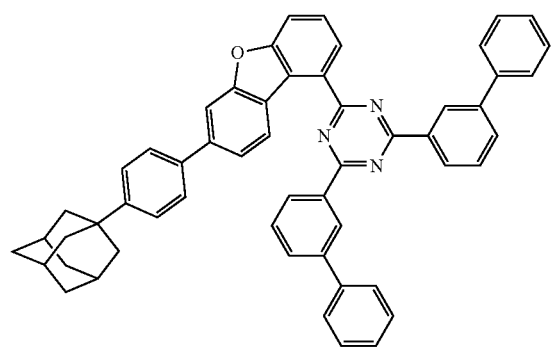
125
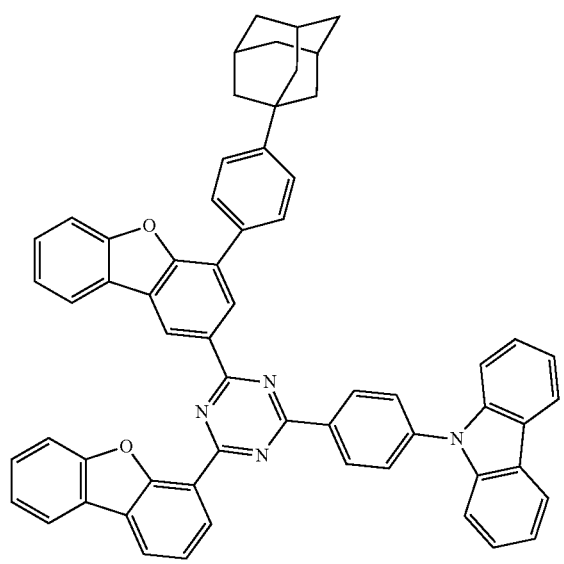
126
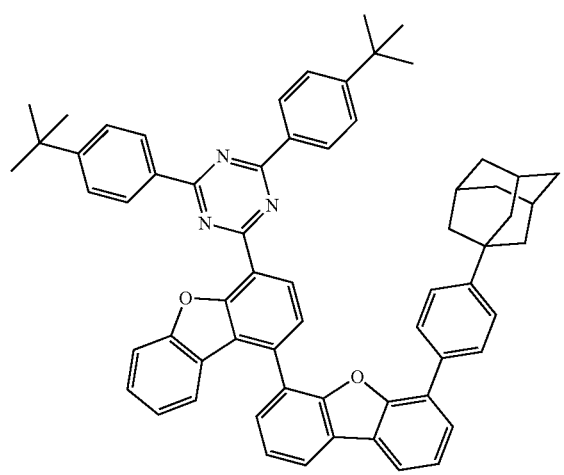

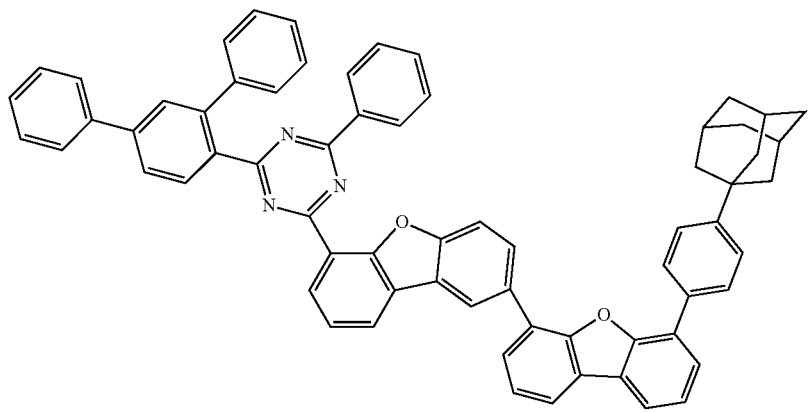
127
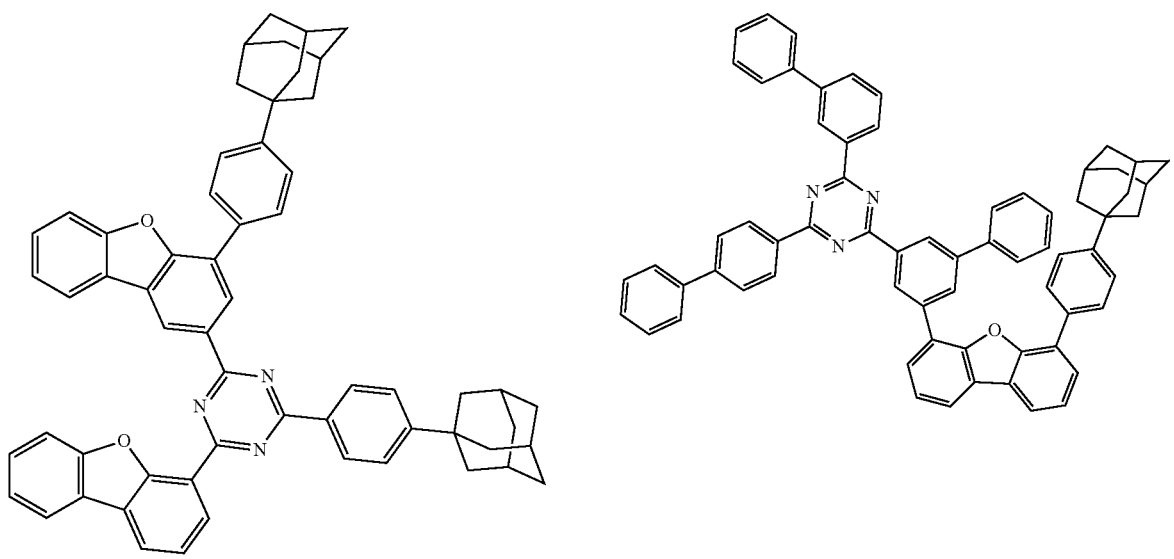
128
129
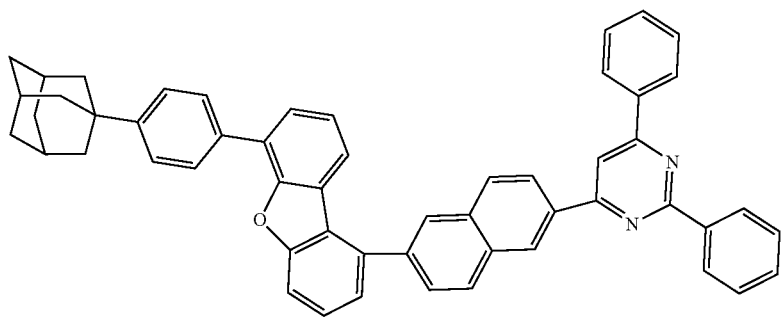
130

-continued
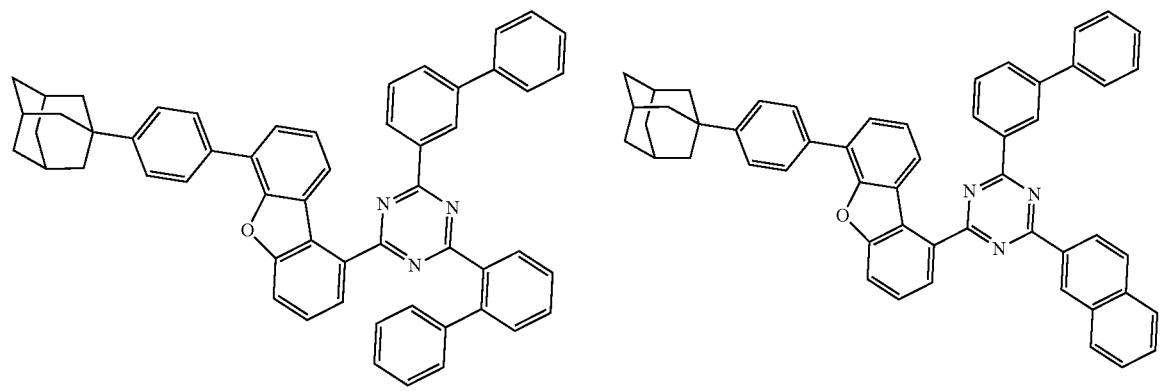
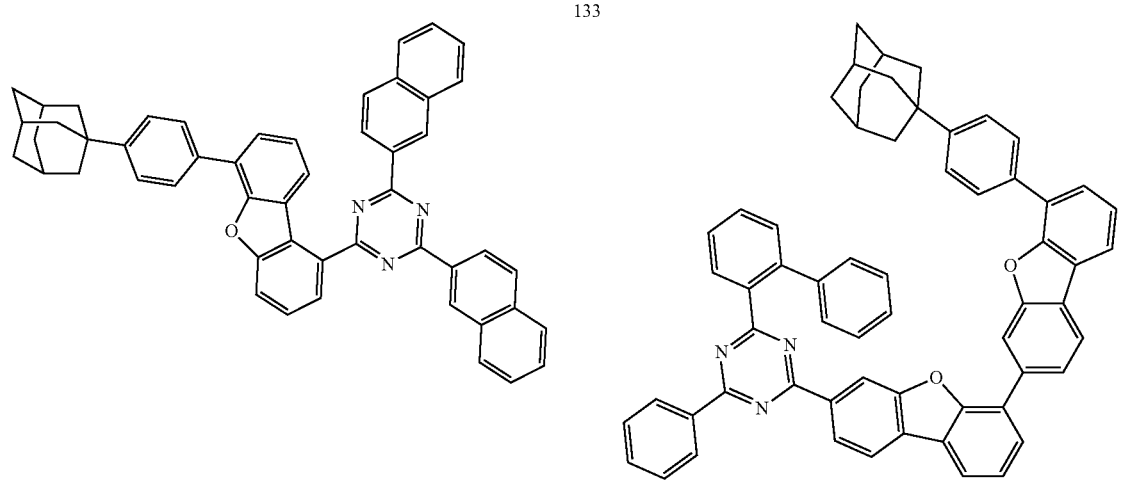
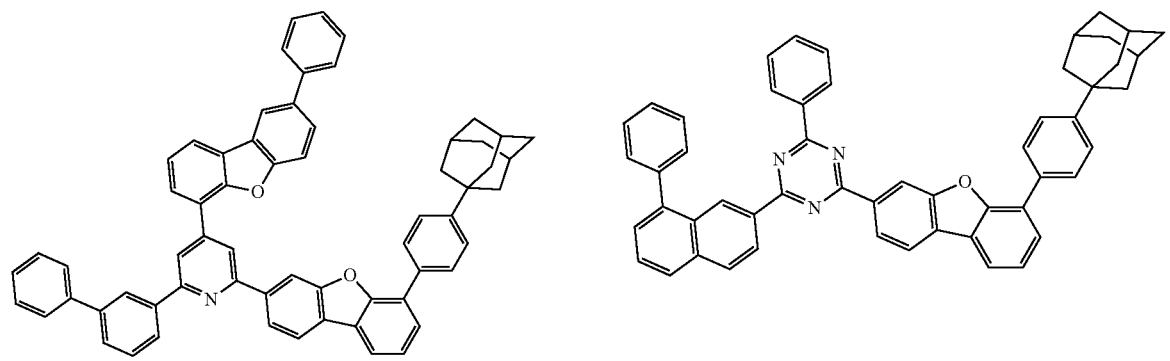

137
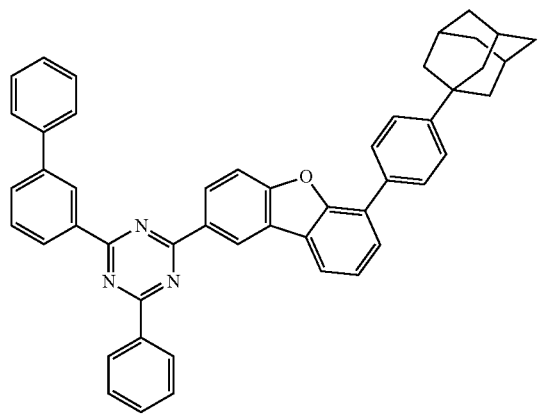
138
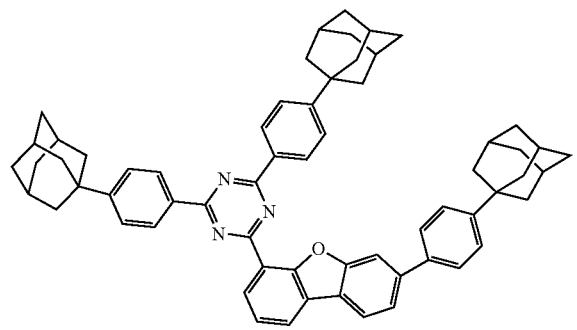
139
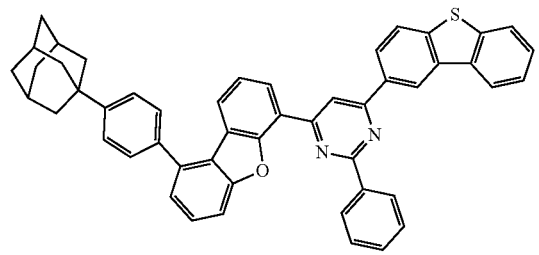
140
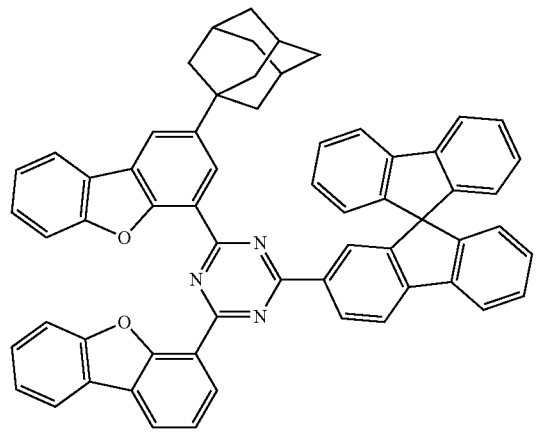
141
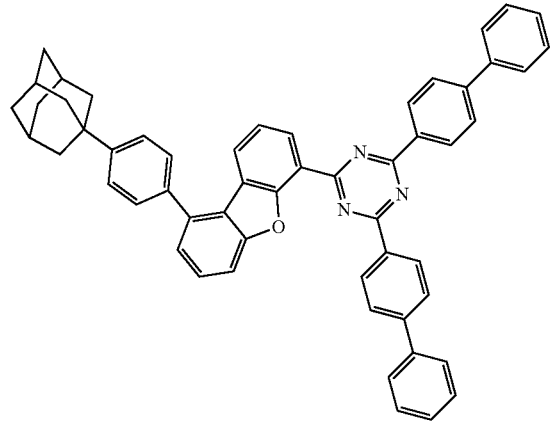
142
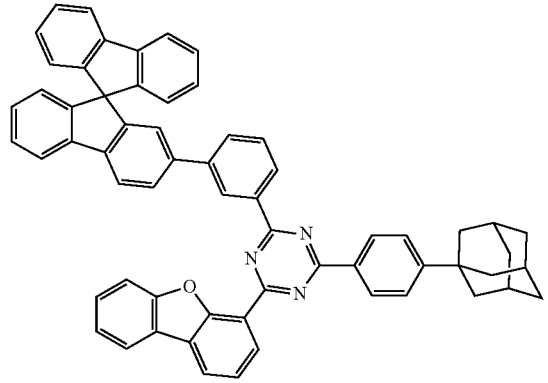

-continued
143
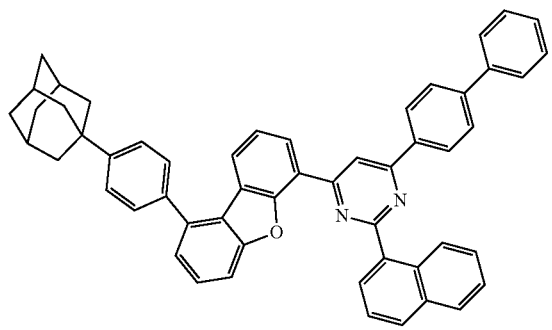
144
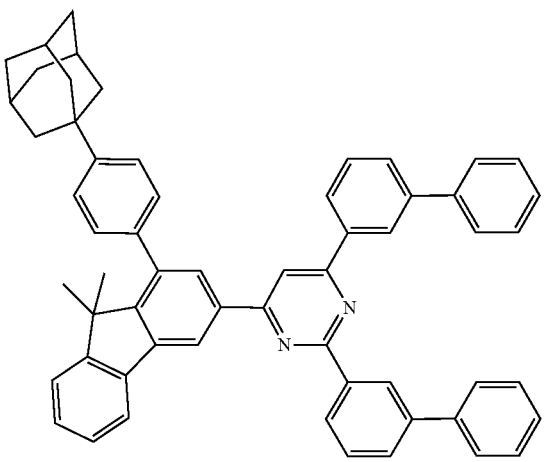
145
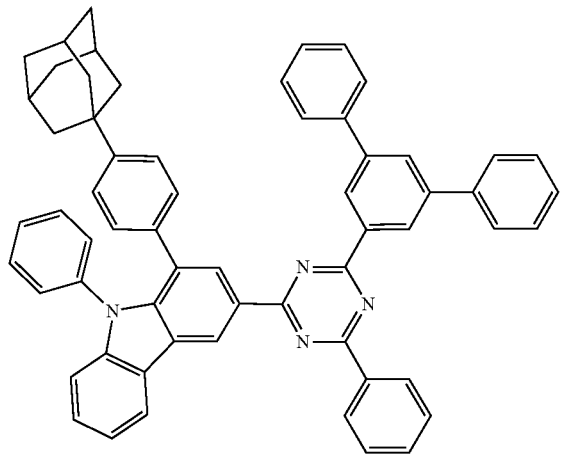
146
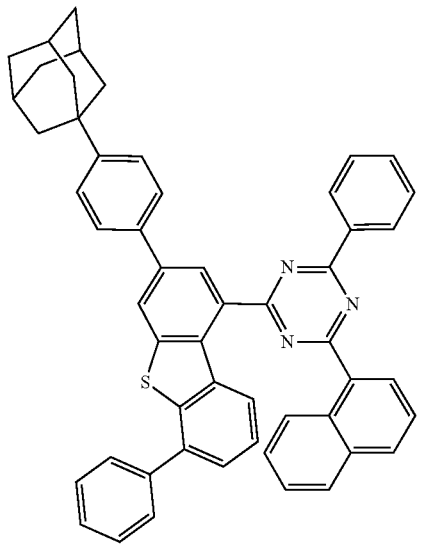
147
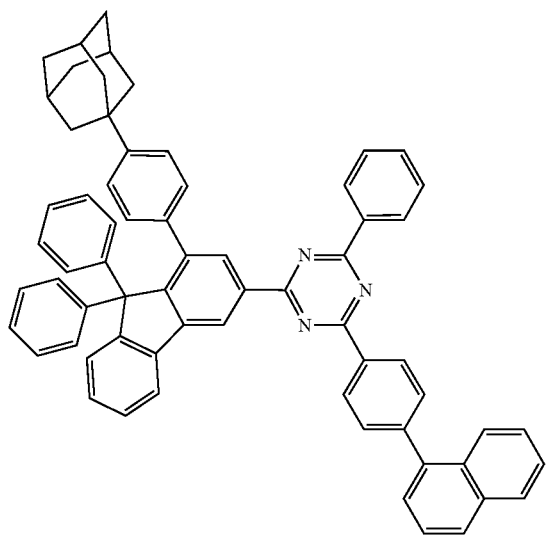
148
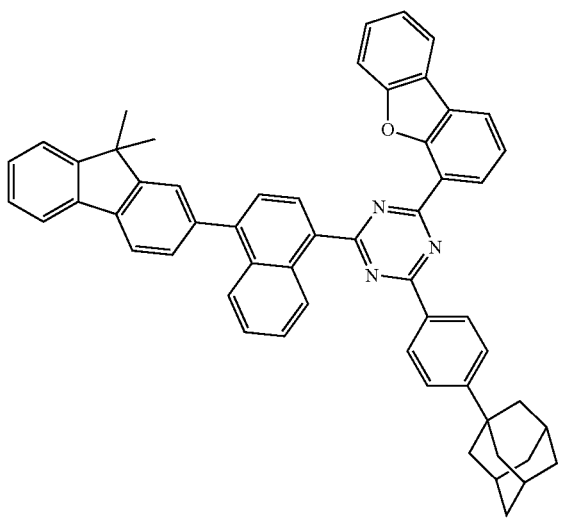

149
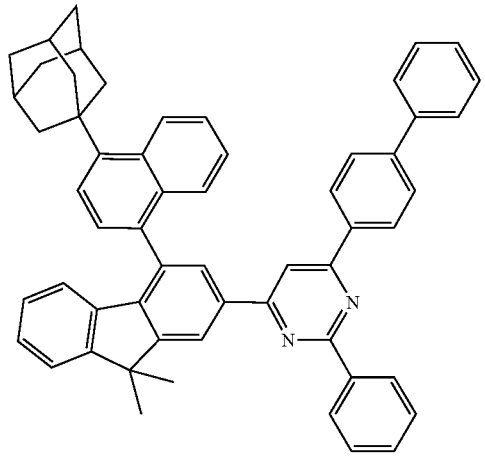
150
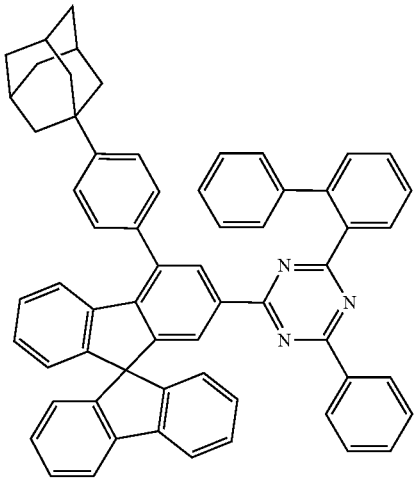
151
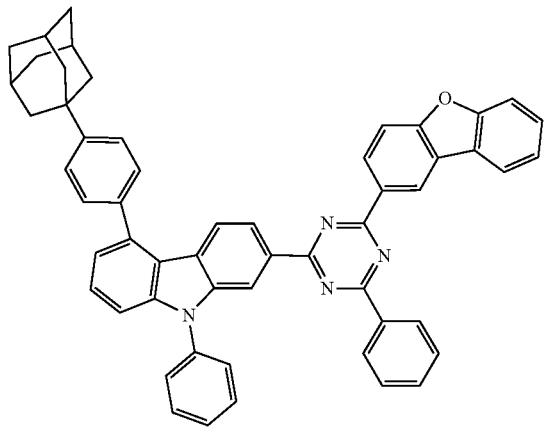
152
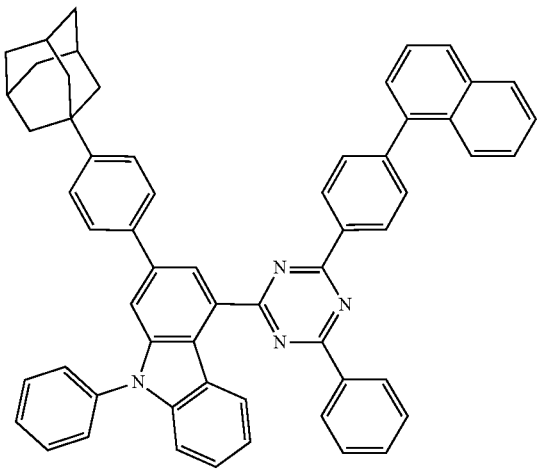
153
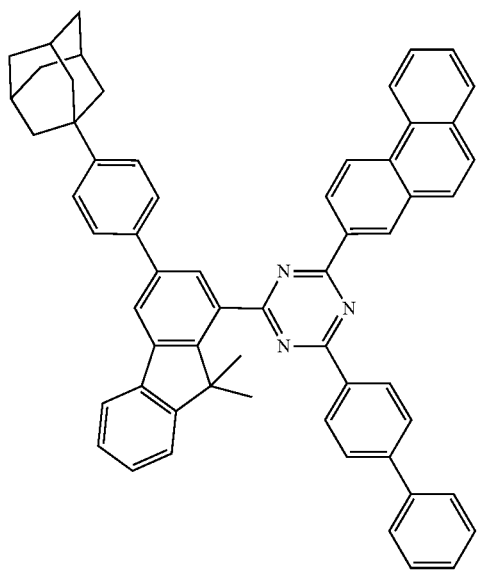
154
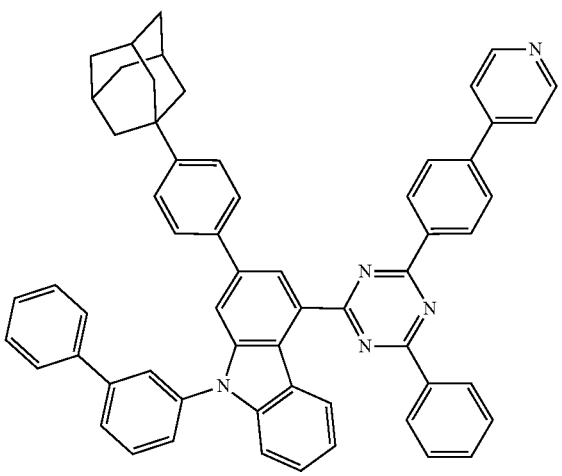

-continued
155
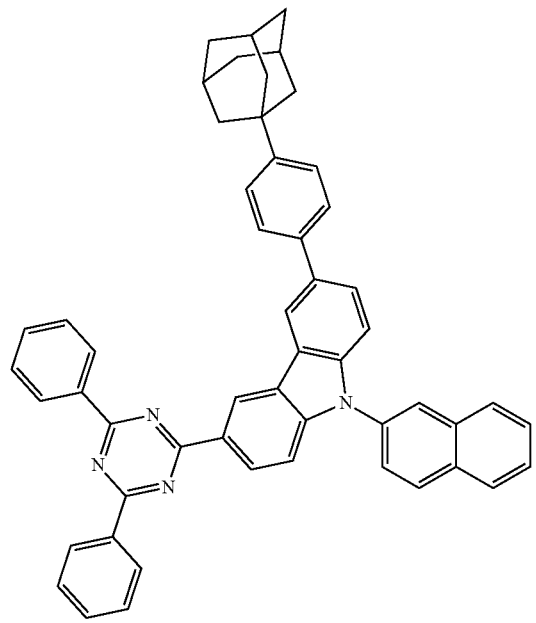
156
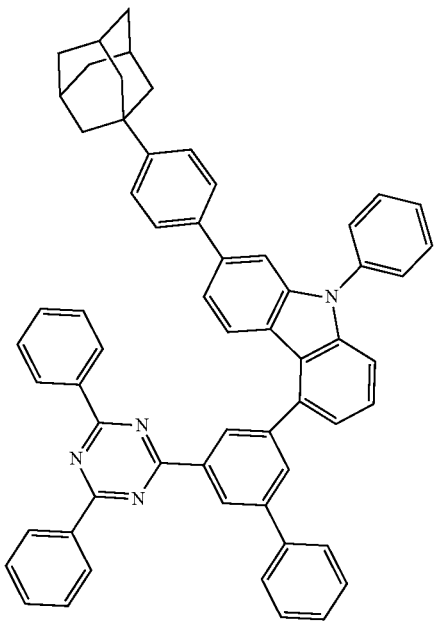
157
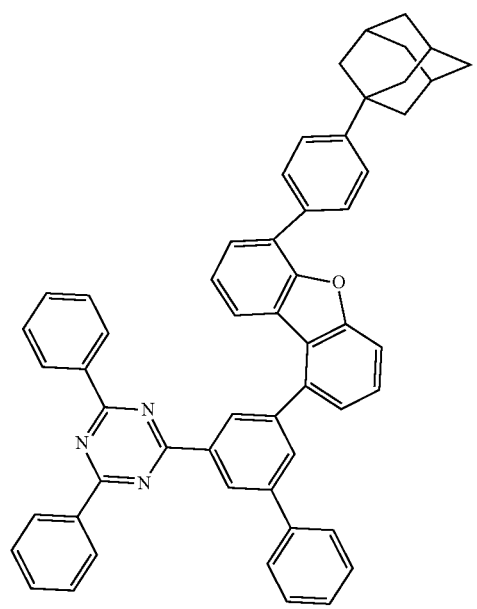
158
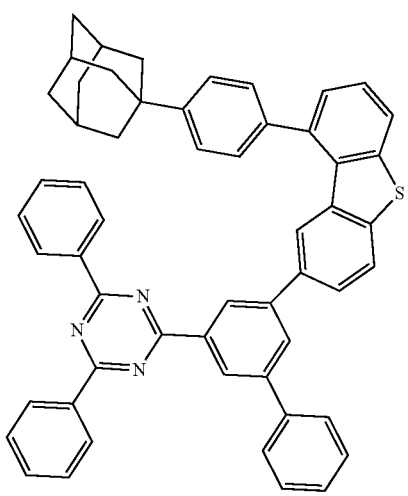
159
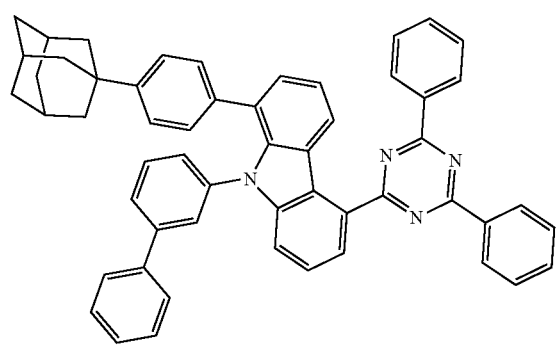
160
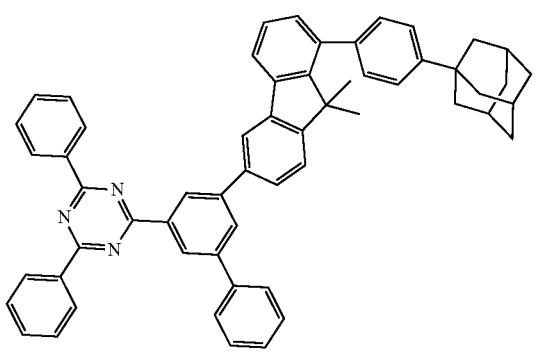

-continued
161
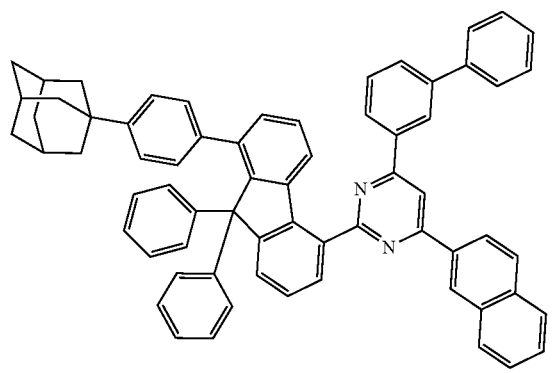
162
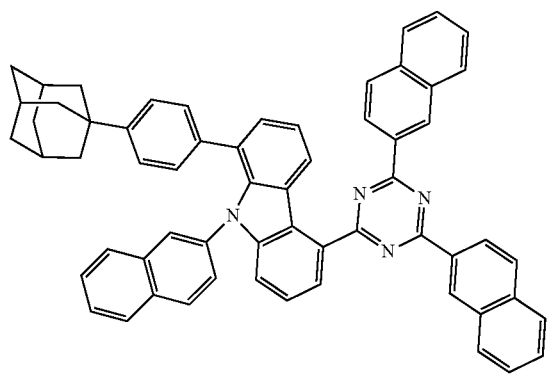
163
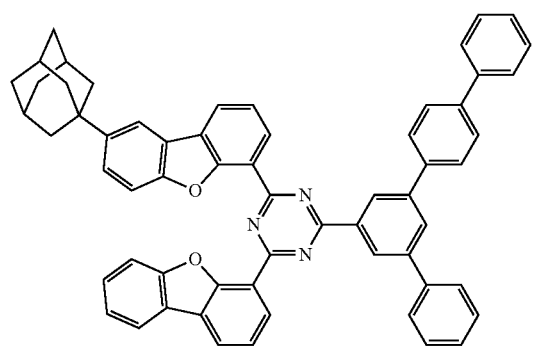
164
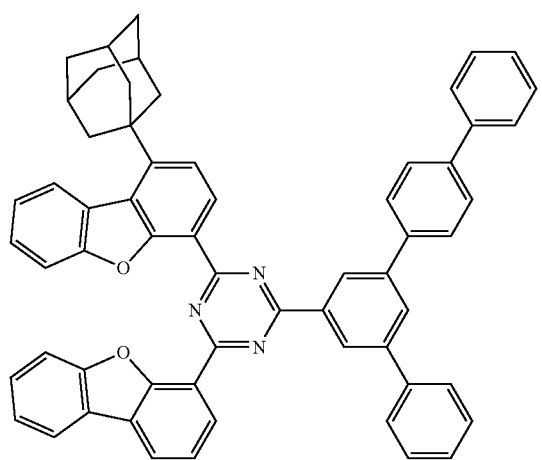
165
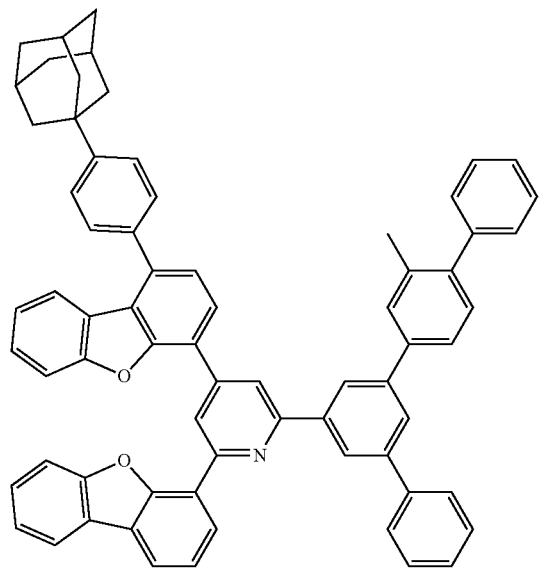
166
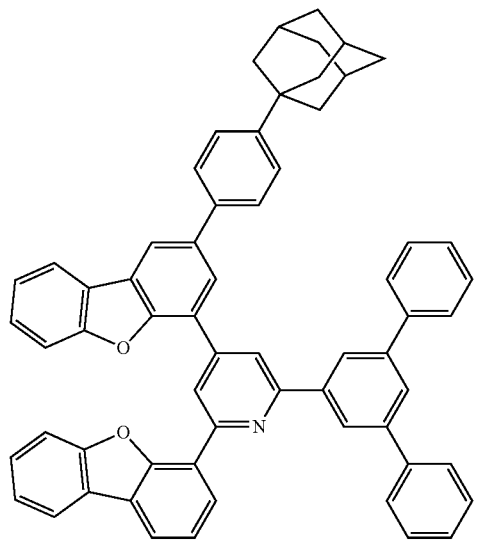

143
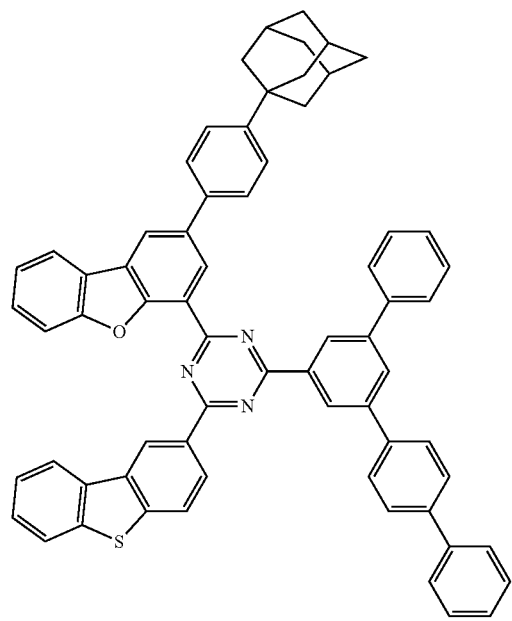
144
-continued
167
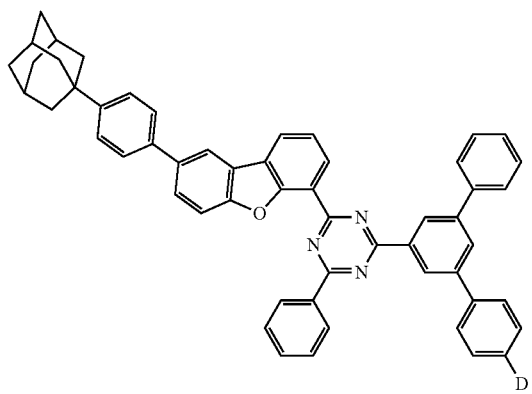
168
169
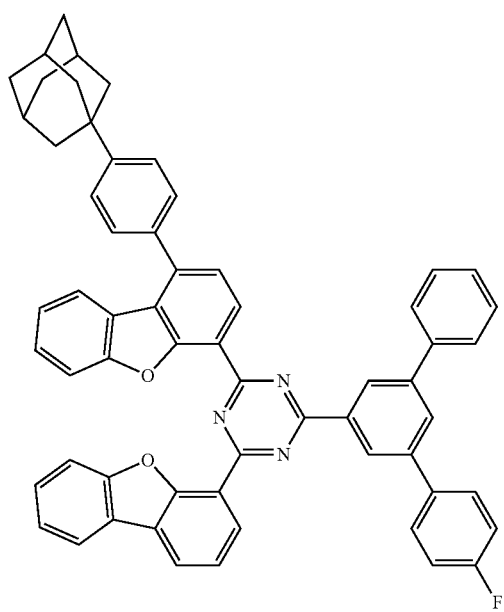
170
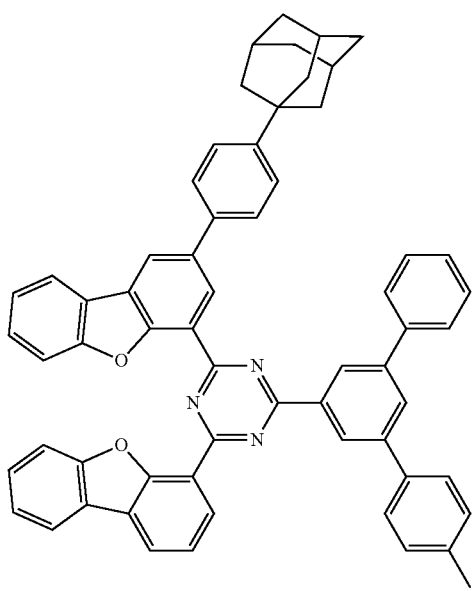

-continued
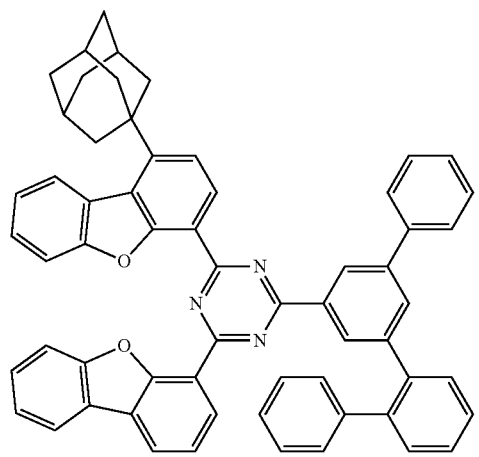
171
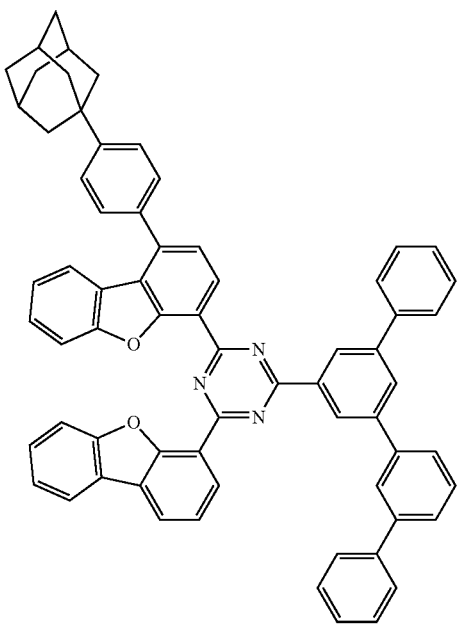
172
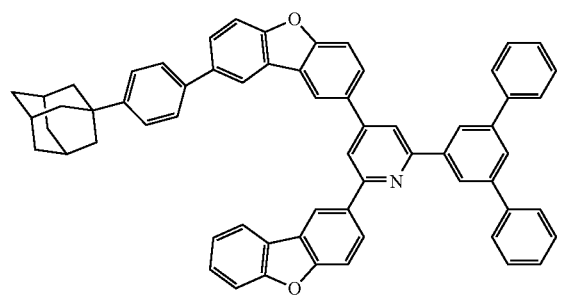
173
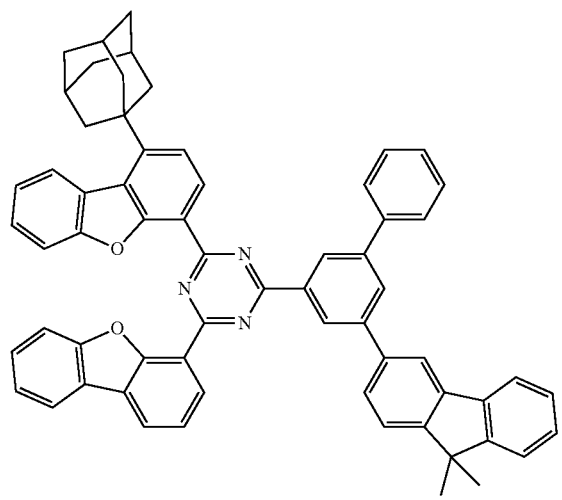
174
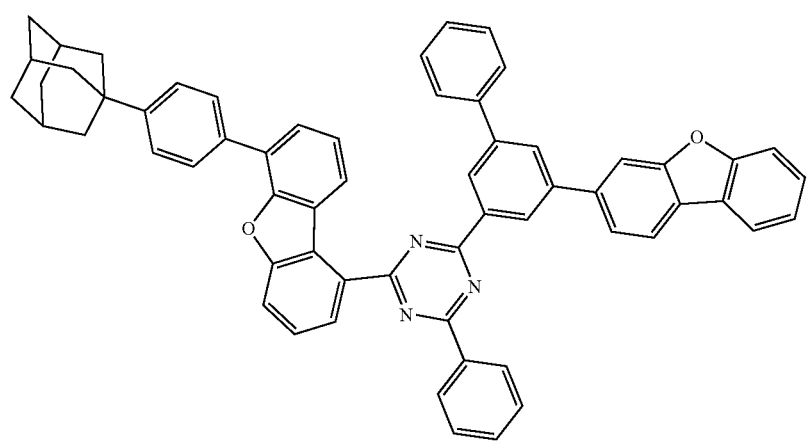
175

-continued
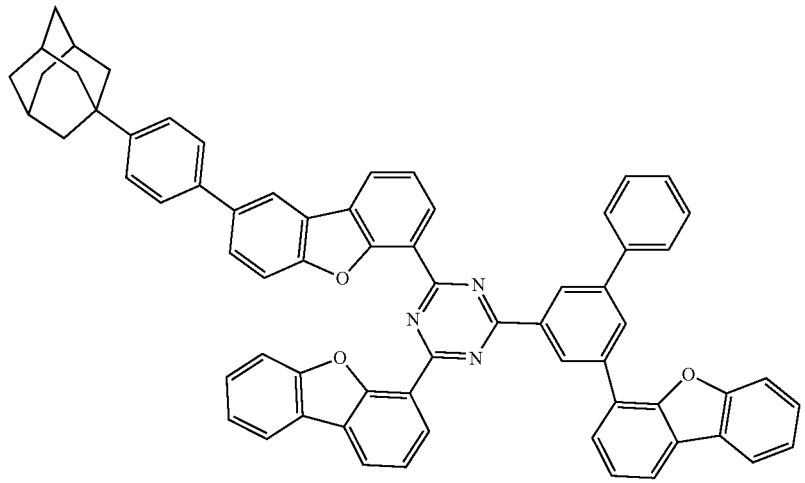
176
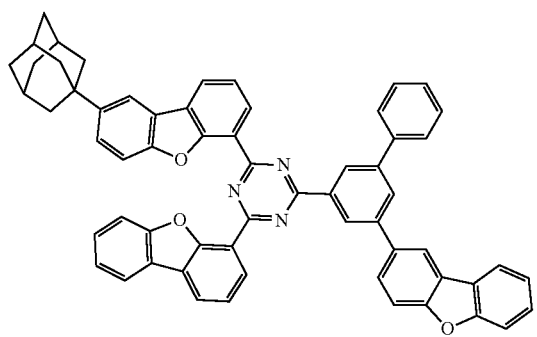
177
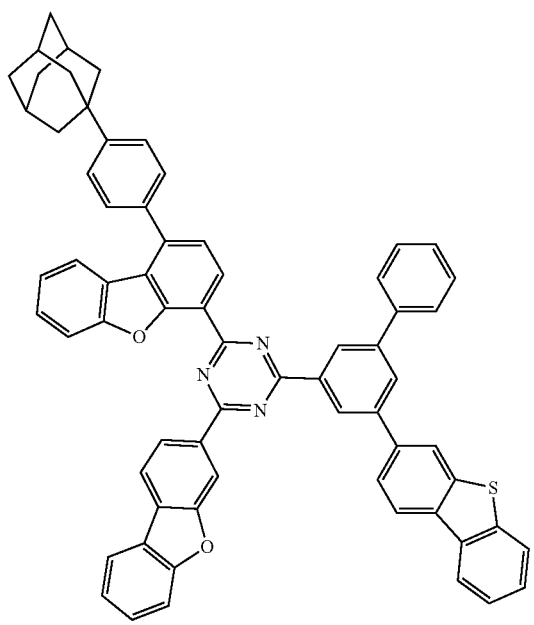
178

-continued
179
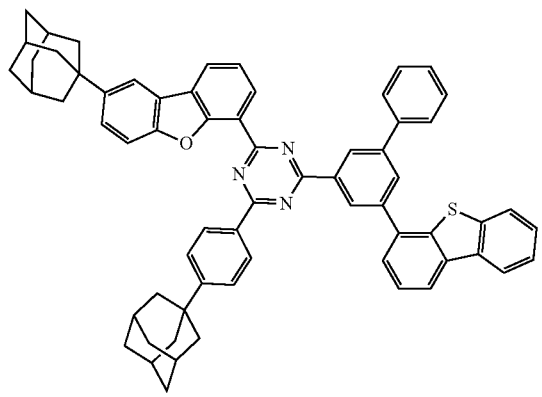
180
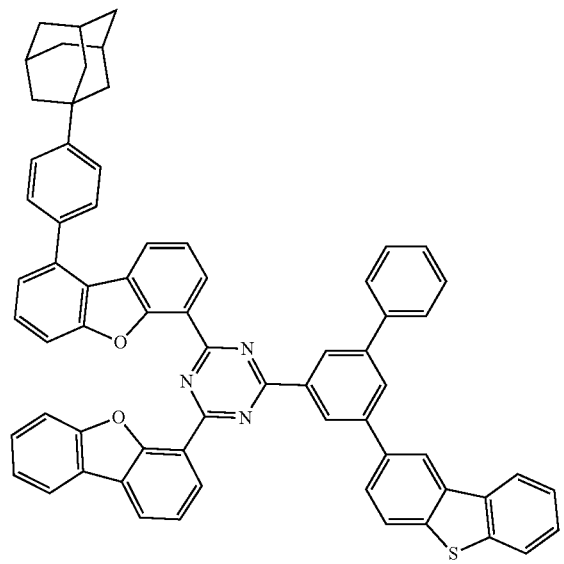
181
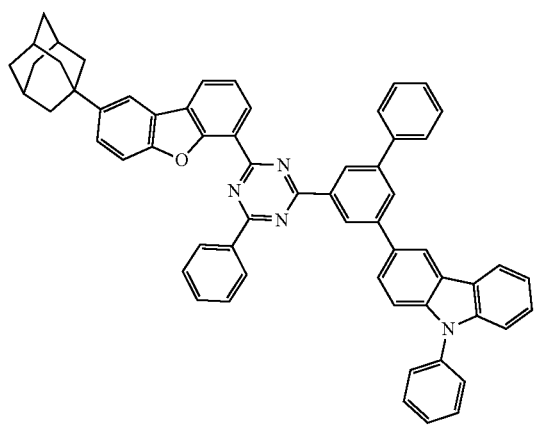
182
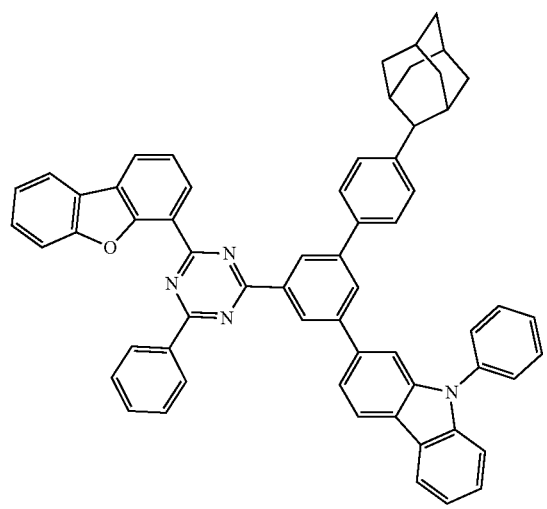
183
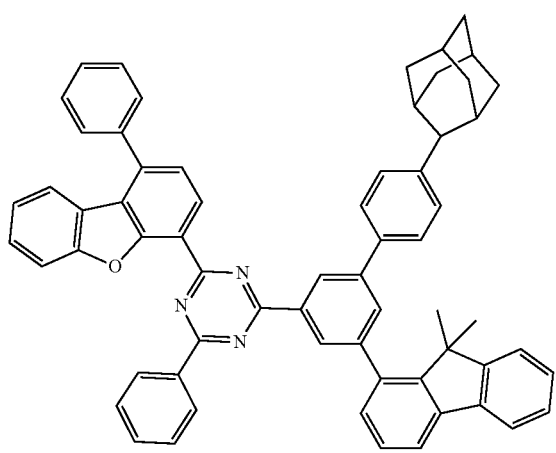
184
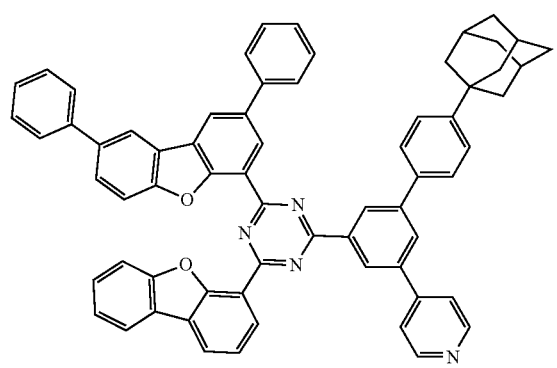

-continued
151 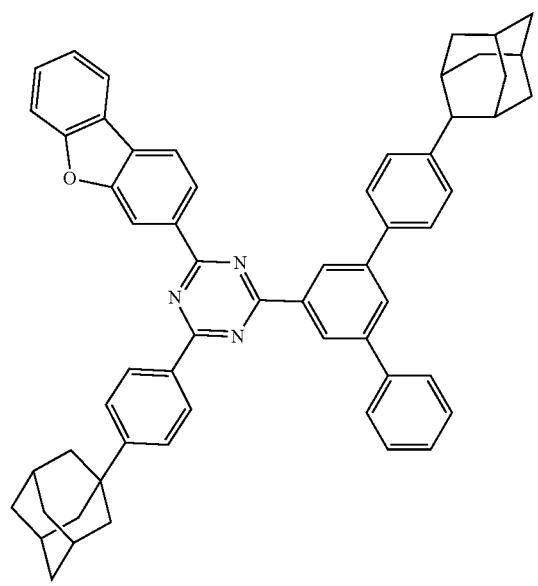 152 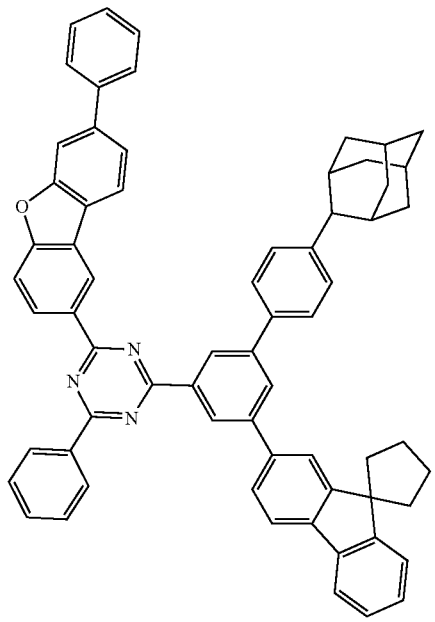
187 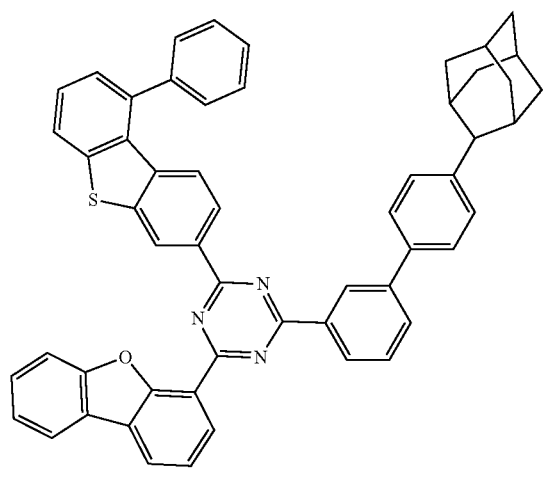 188 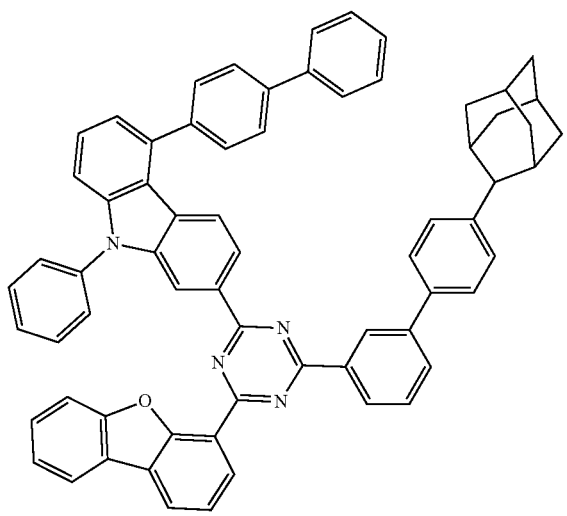

-continued
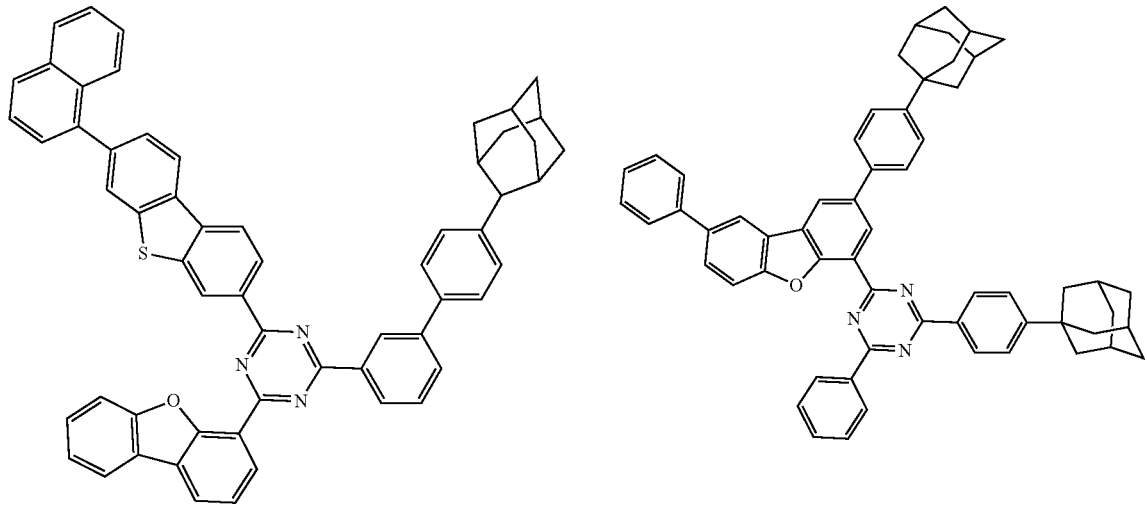
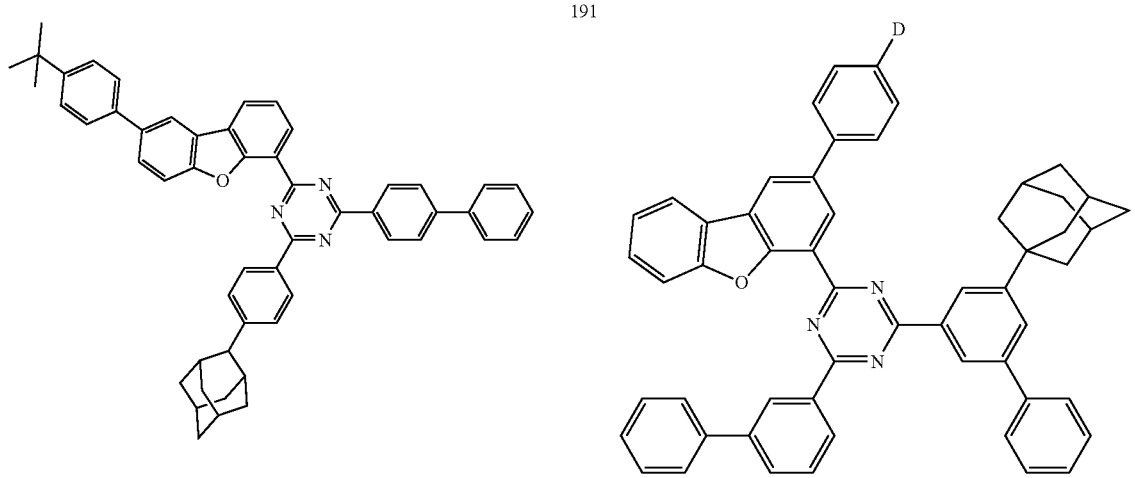
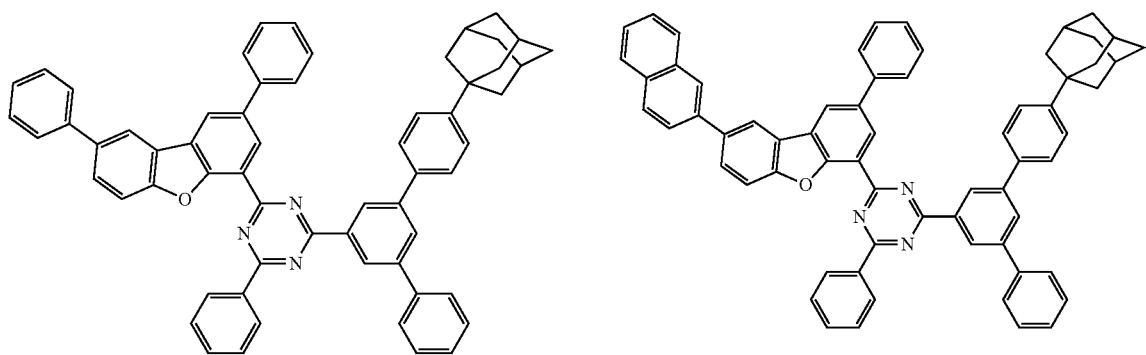

-continued
155
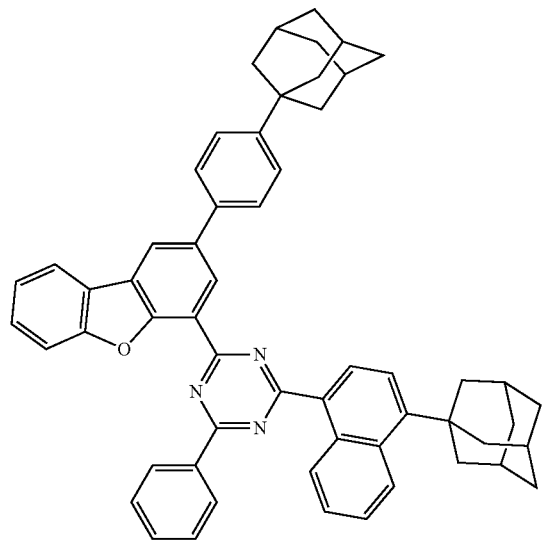
195
156
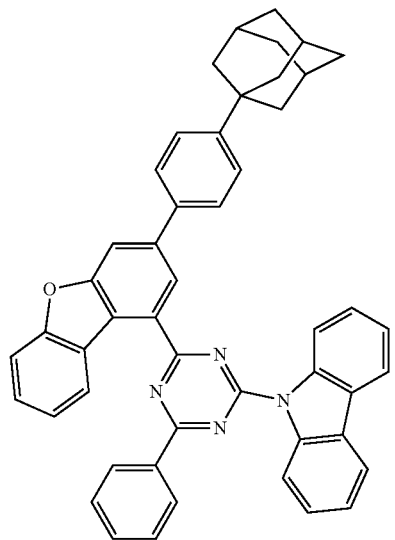
196
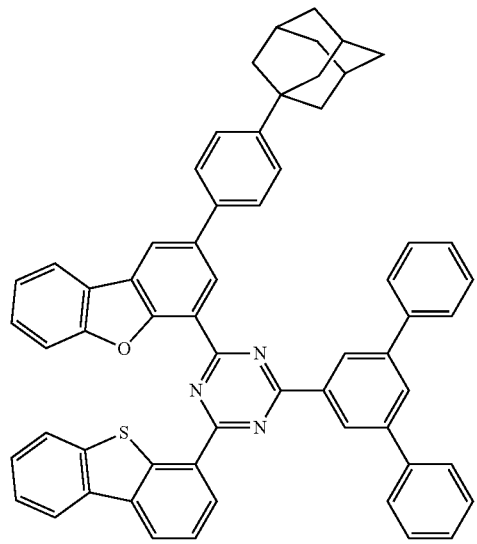
197
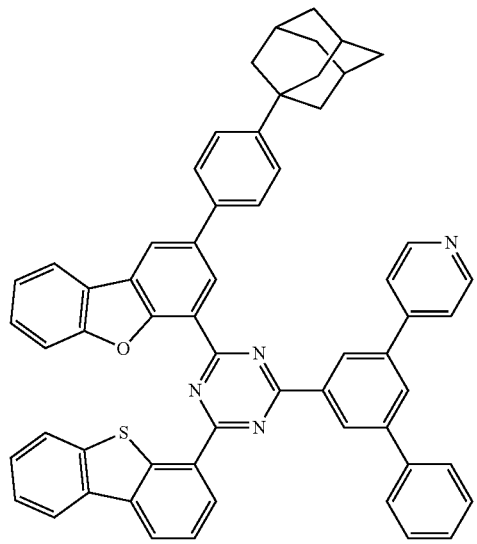
198
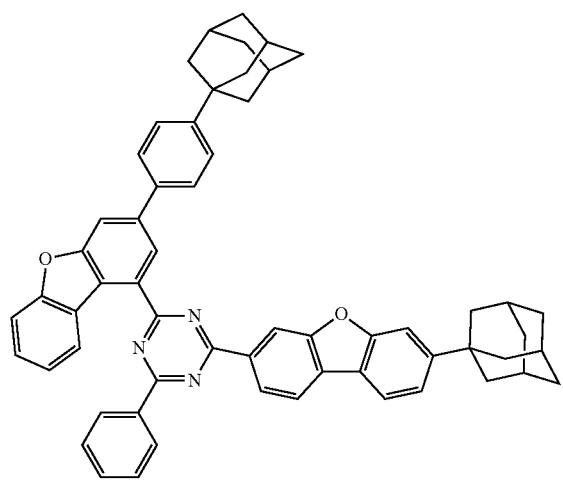
199
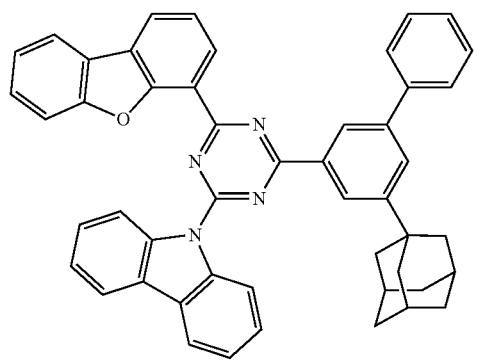
248

-continued
200 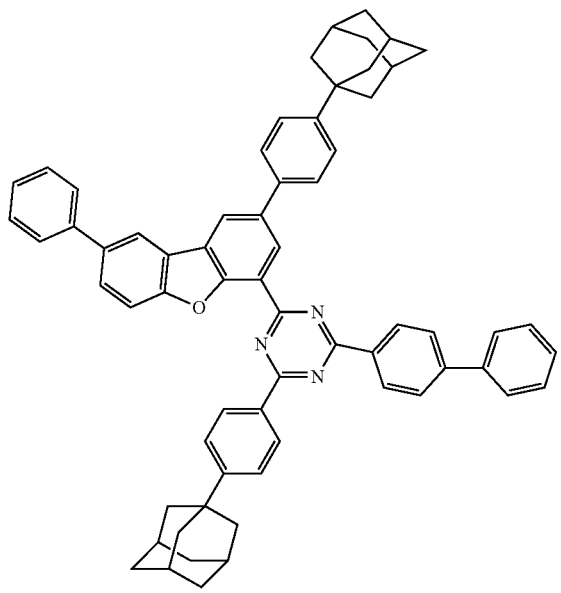
201 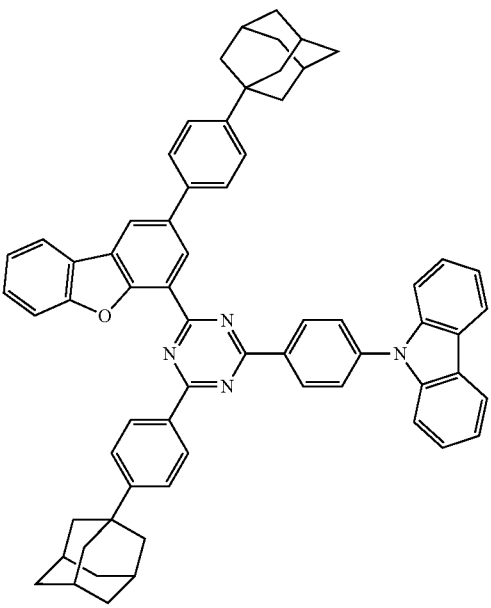
202 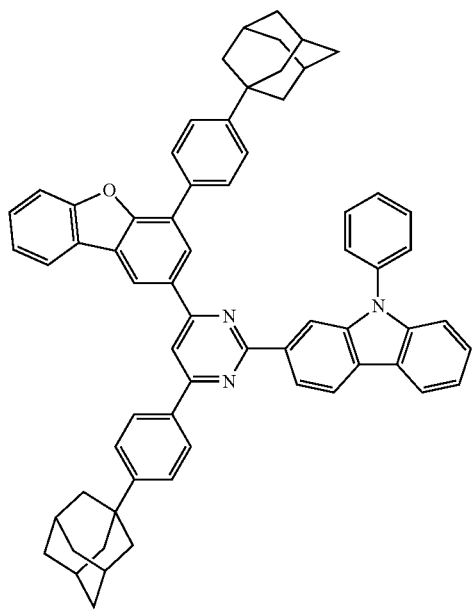
203 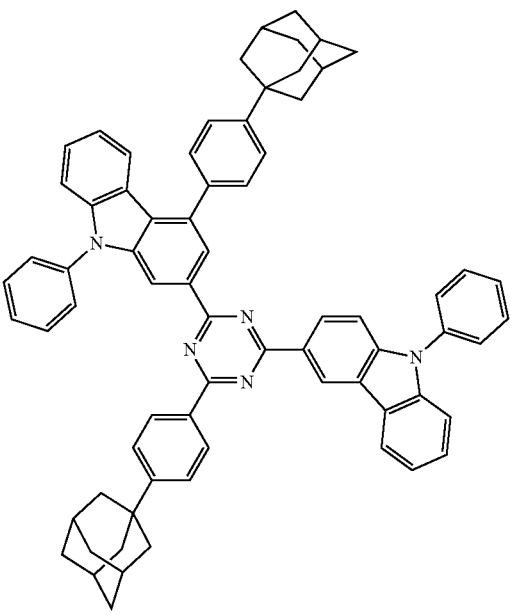

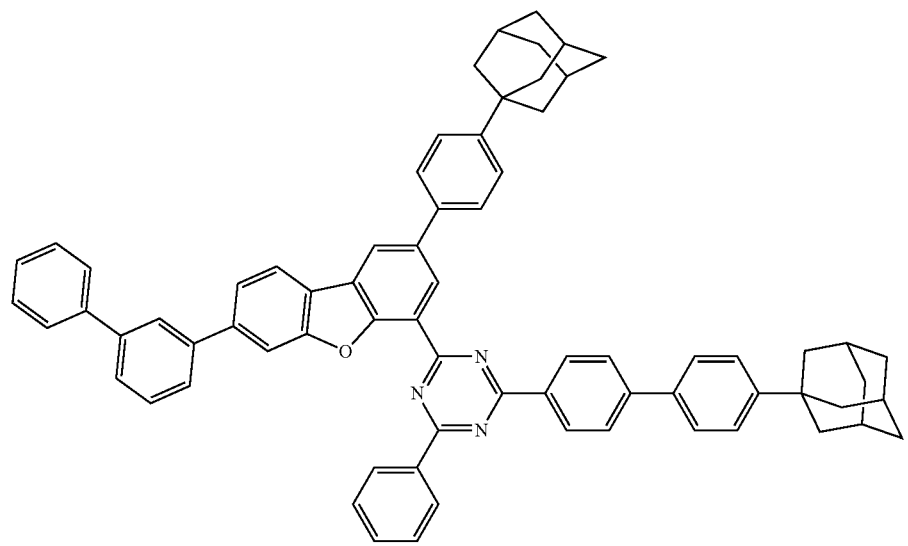
204
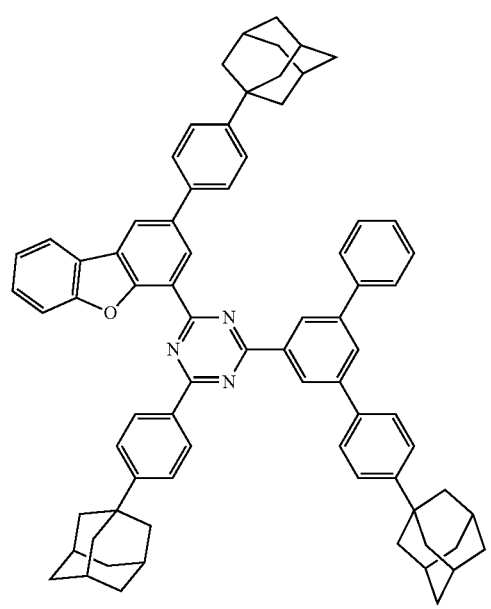
205
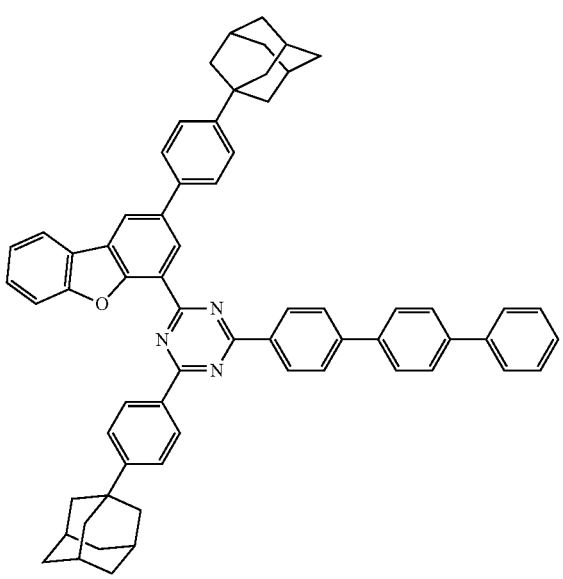
206

207
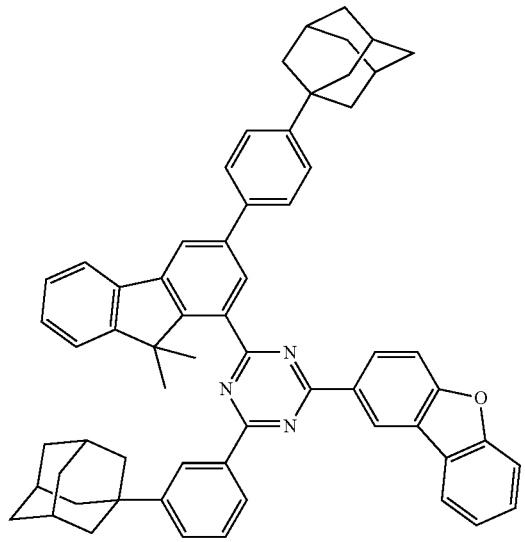
208
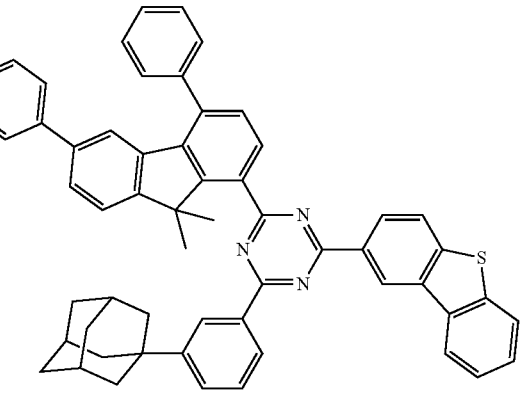
209
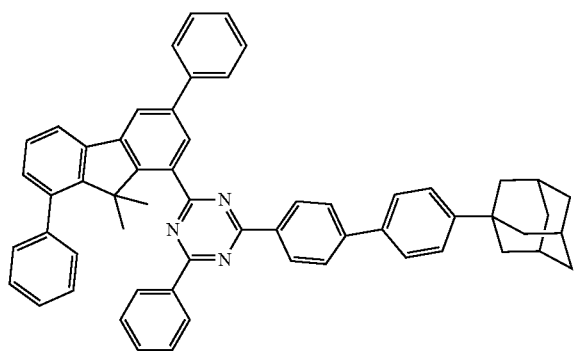
210
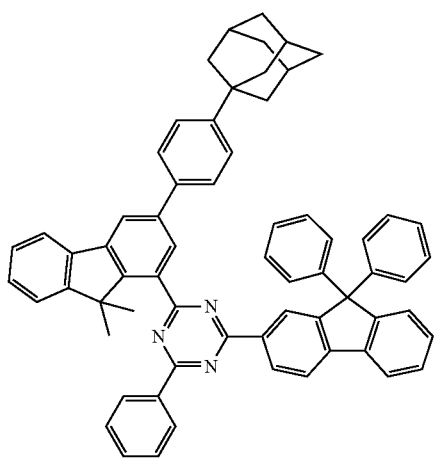
211
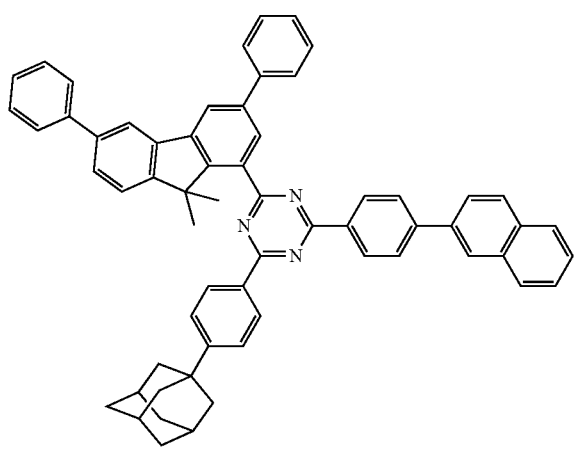
212
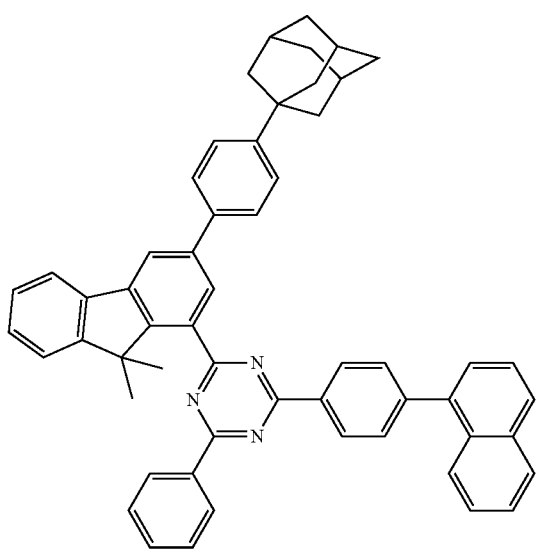

-continued
213
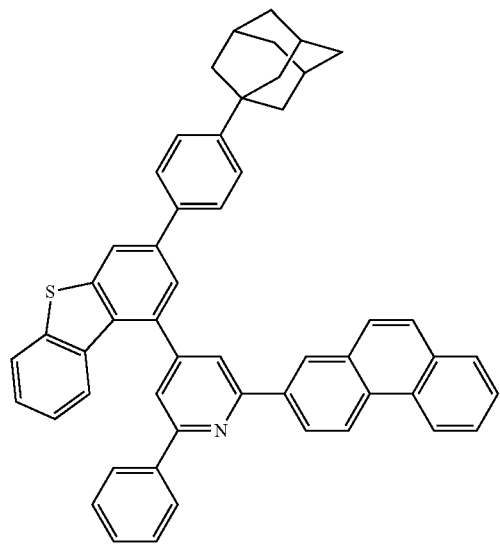
214
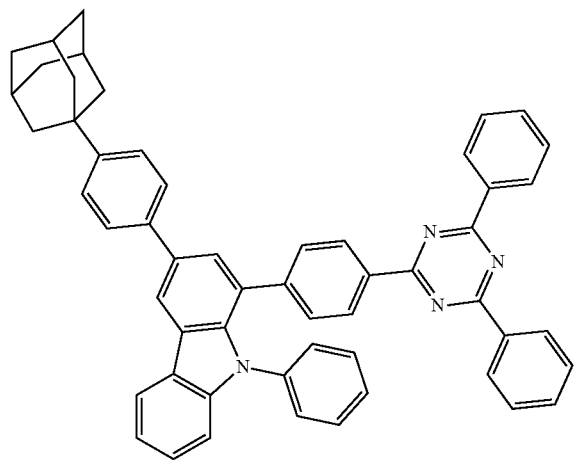
215
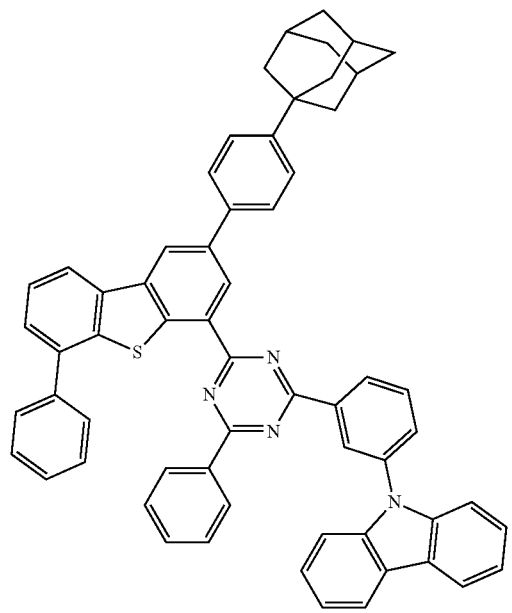
216
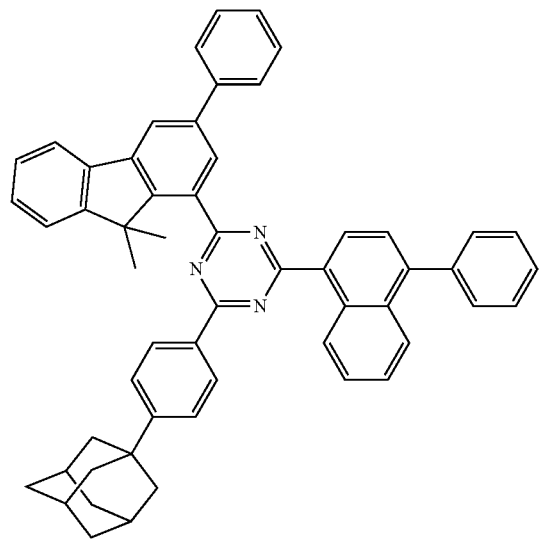

217
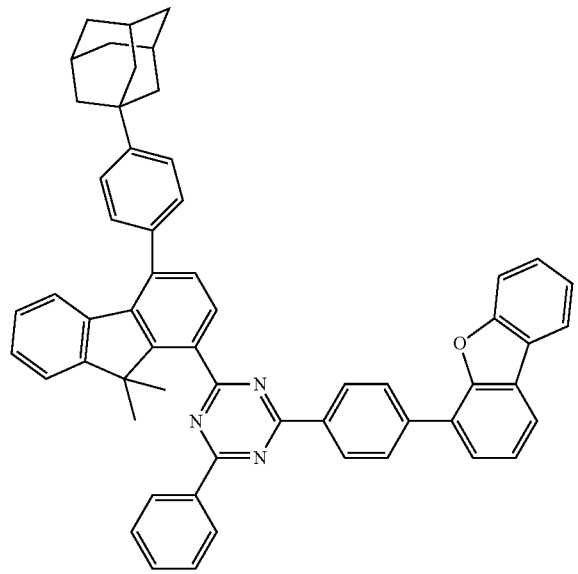
218
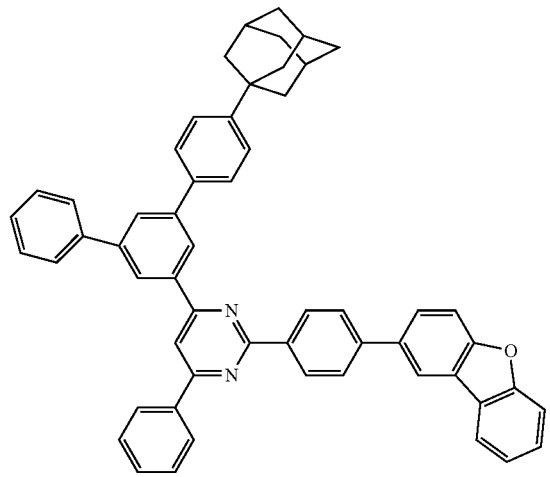
219
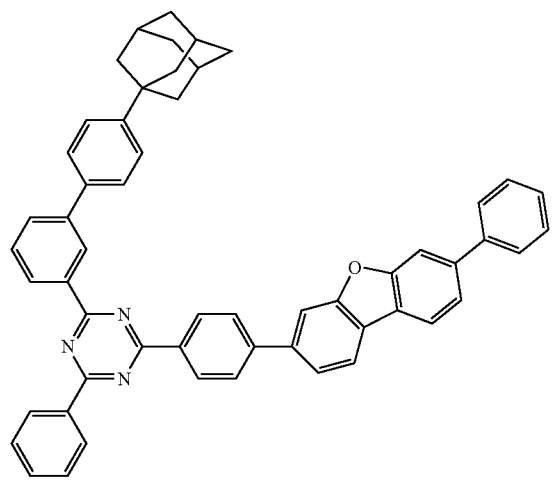
220
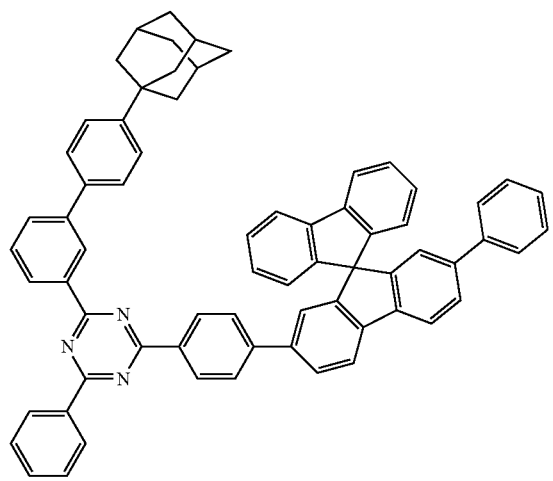

-continued
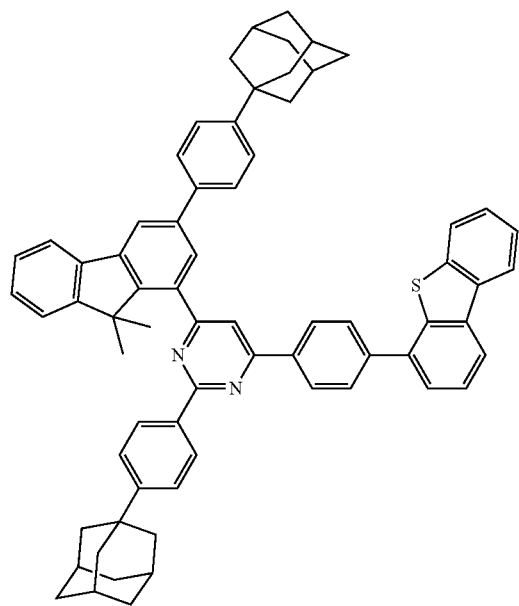

-continued
225
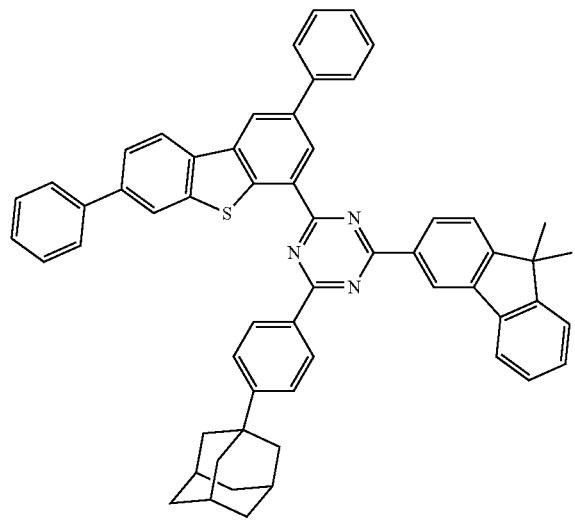
226
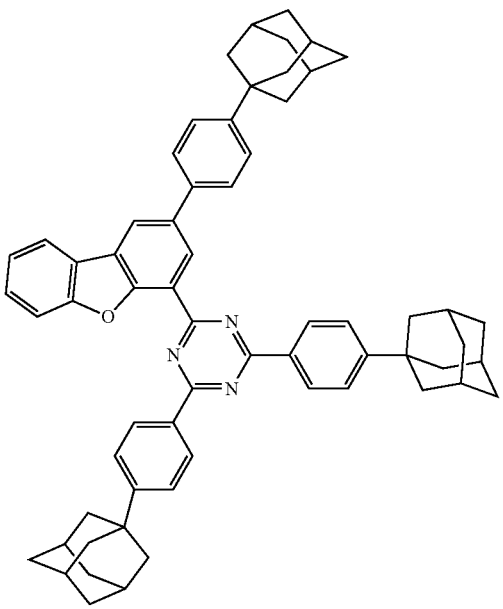
227
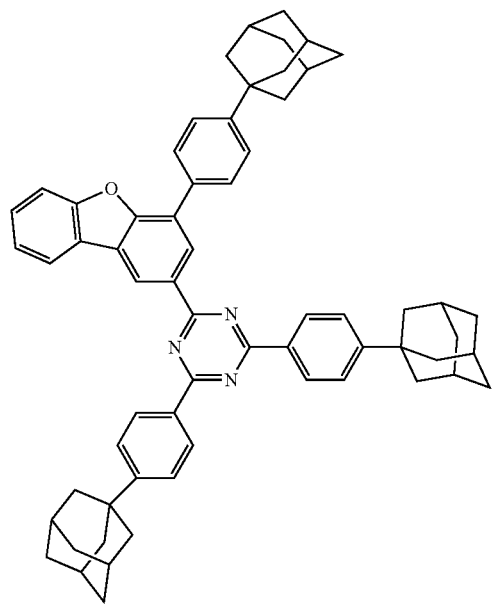
228
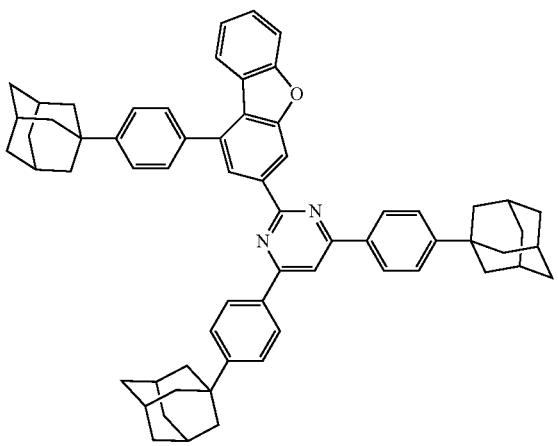

-continued
229
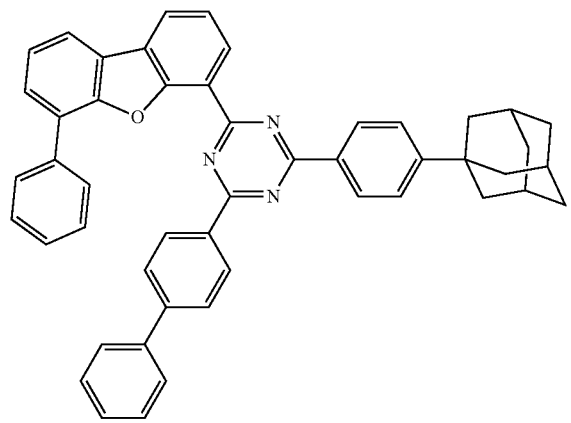
230
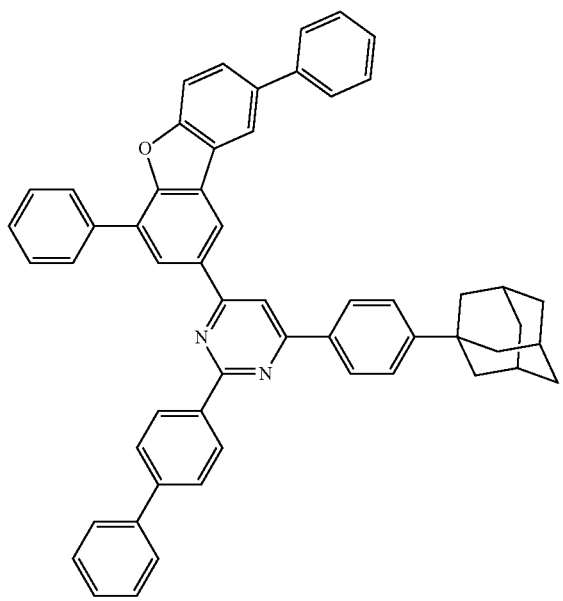
231
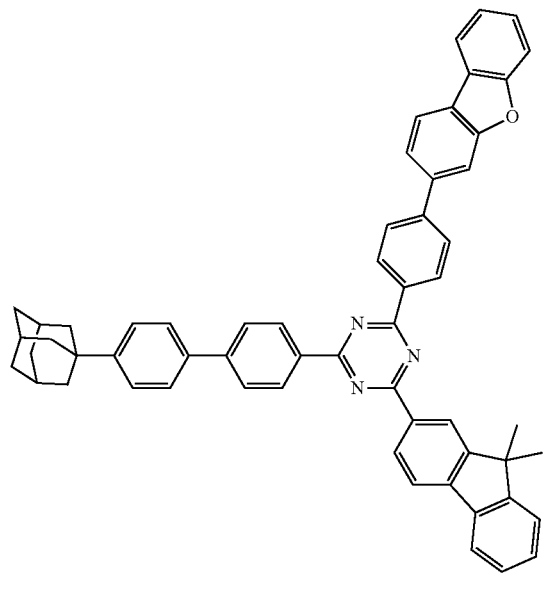
232
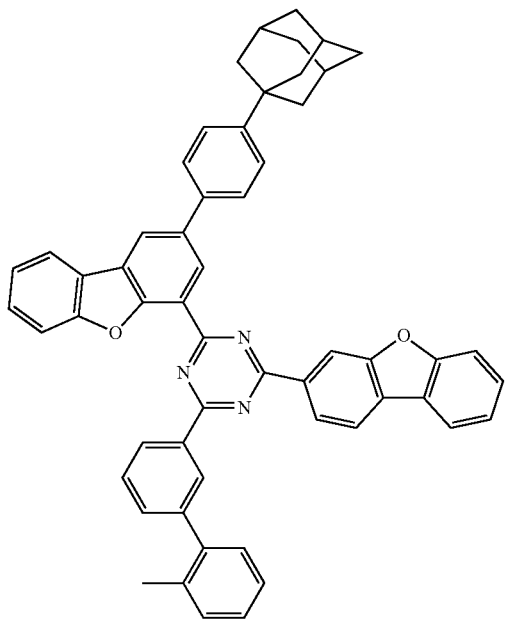

-continued
233
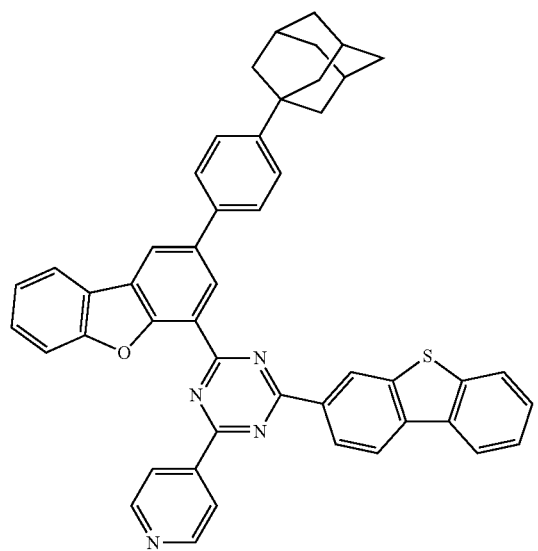
234
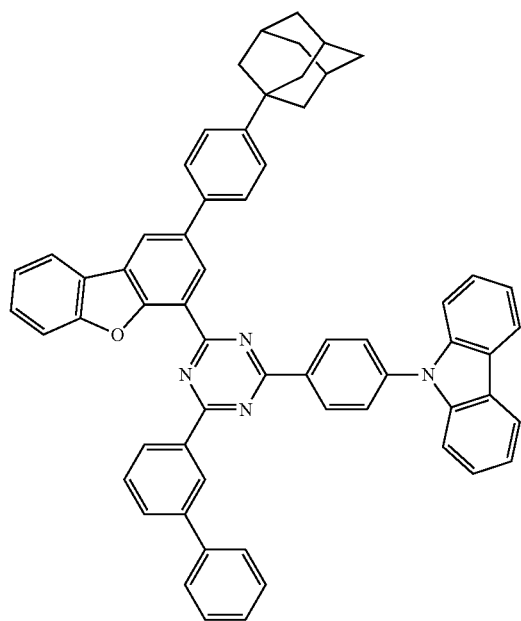
235
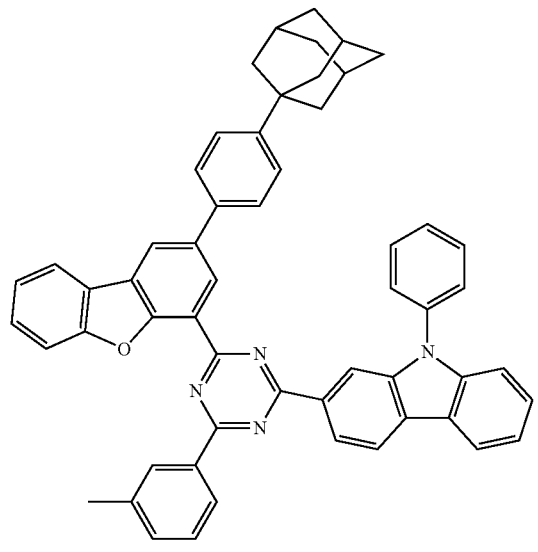
236
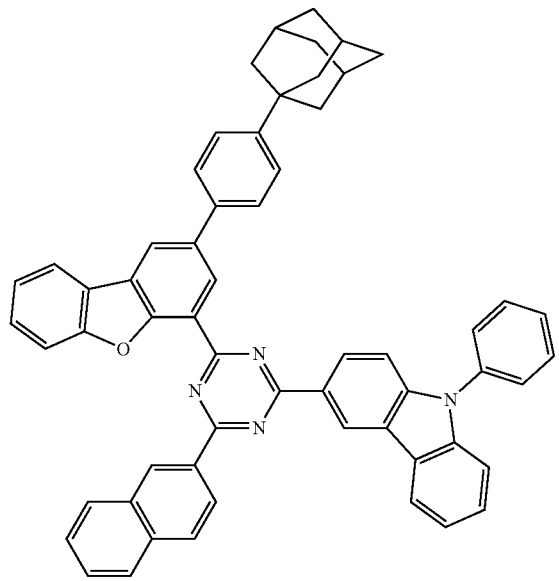

-continued
237
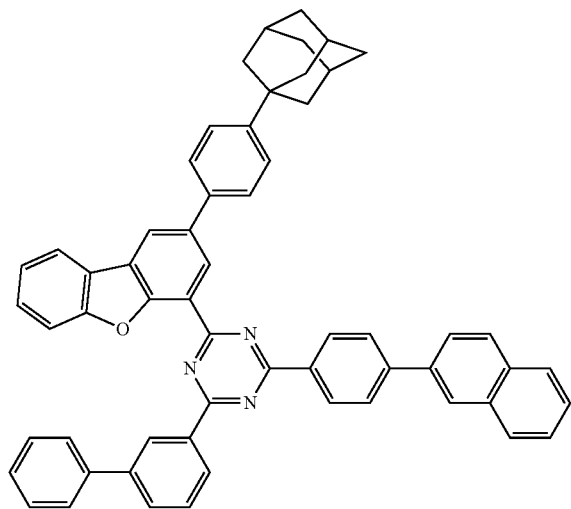
238
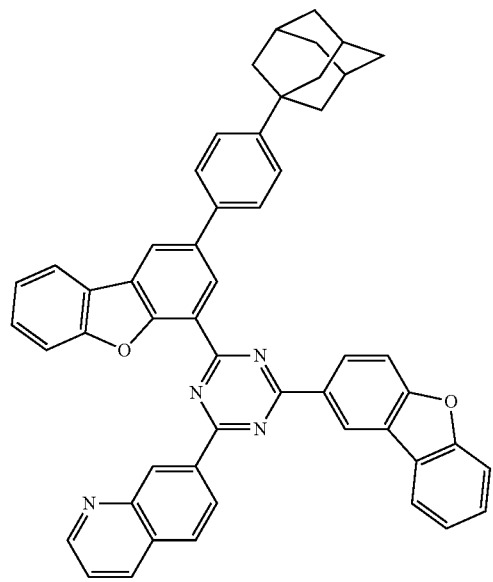
239
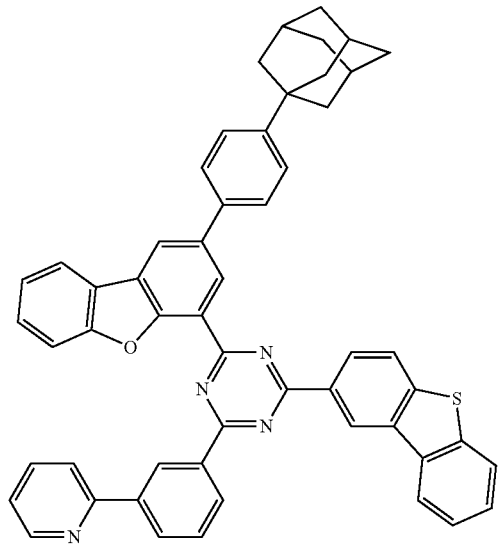
240
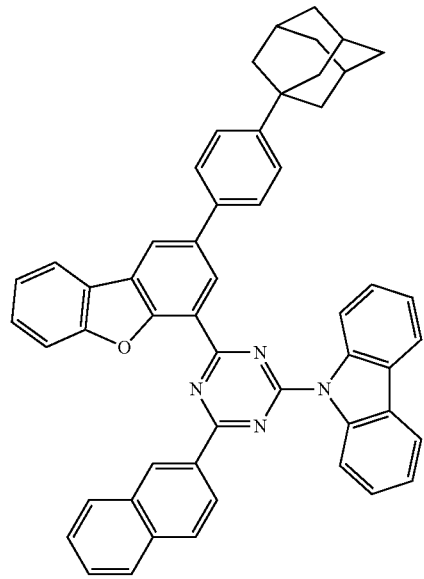

-continued
177
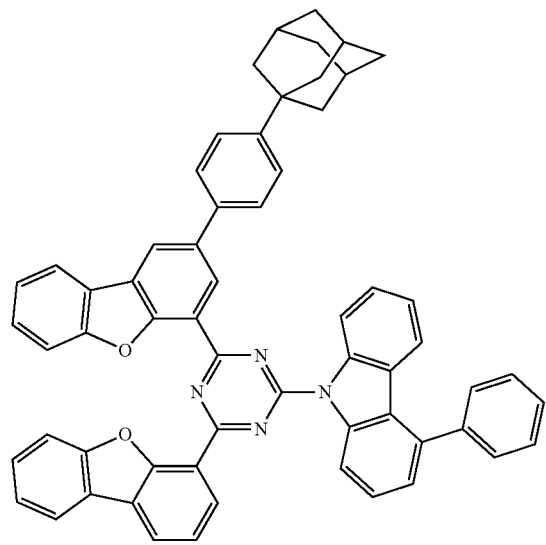
241
178
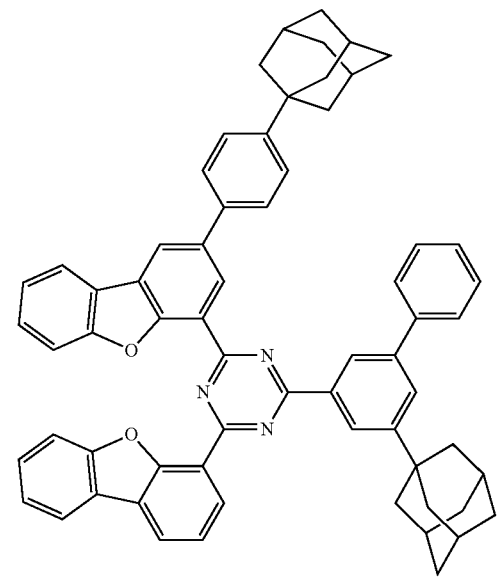
242
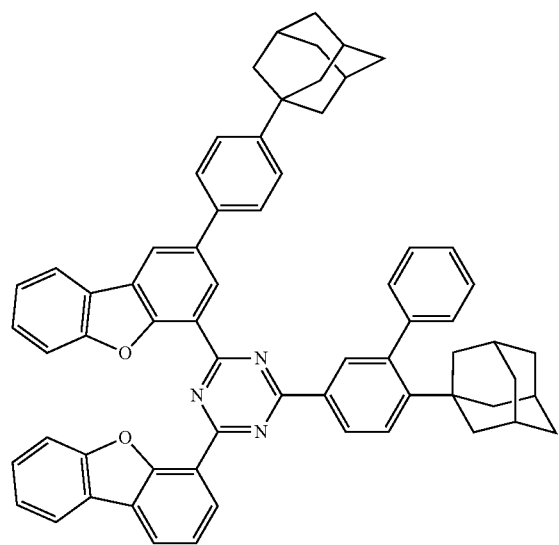
243
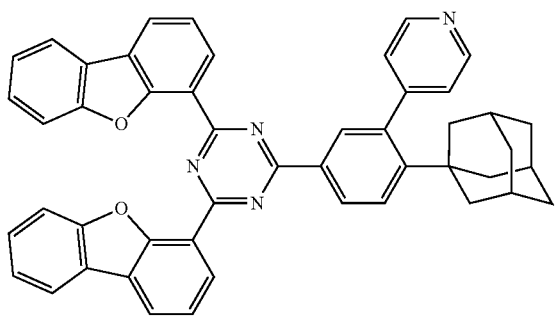
244

-continued
245
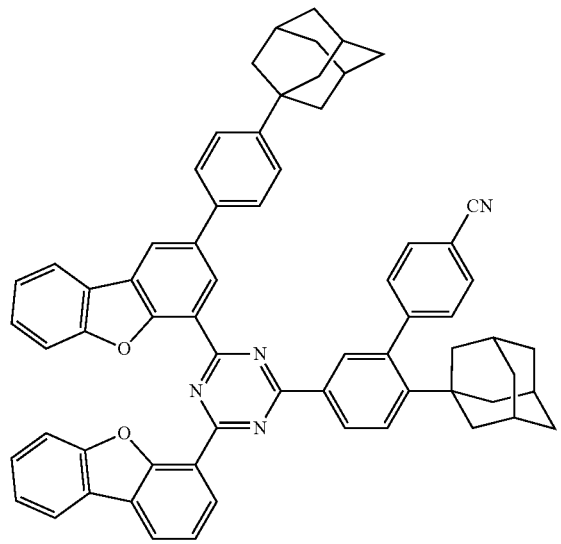
246
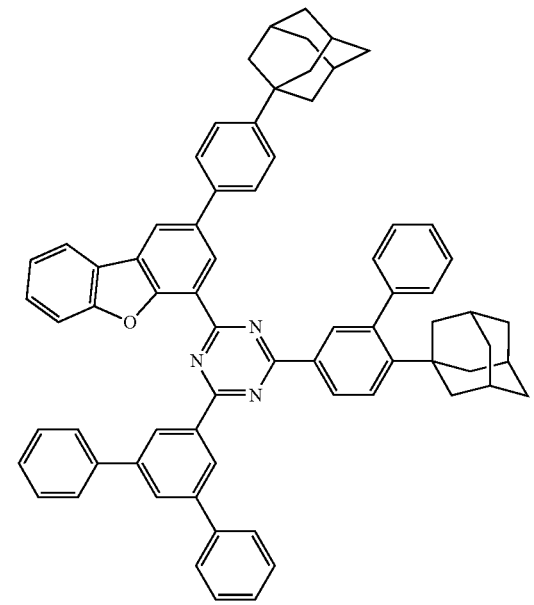
247
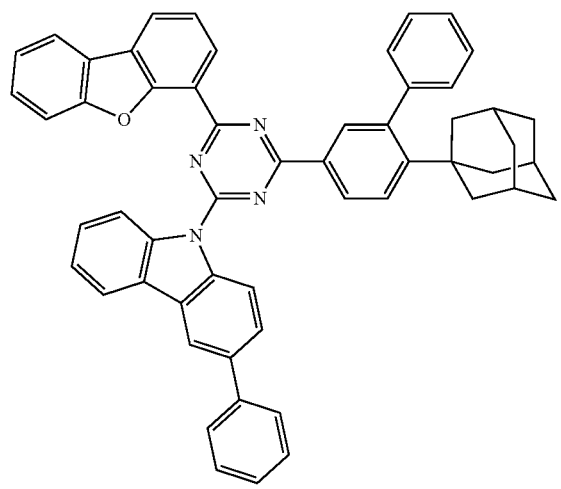
249
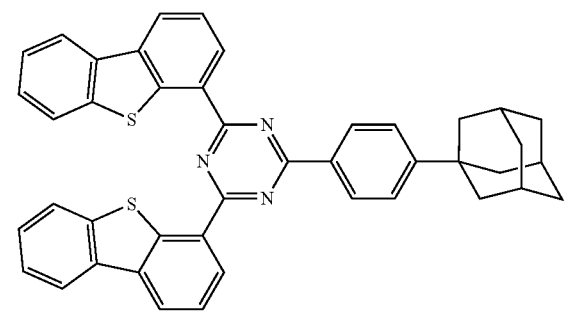
250
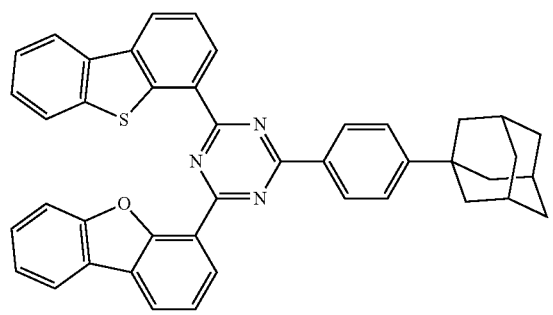
251
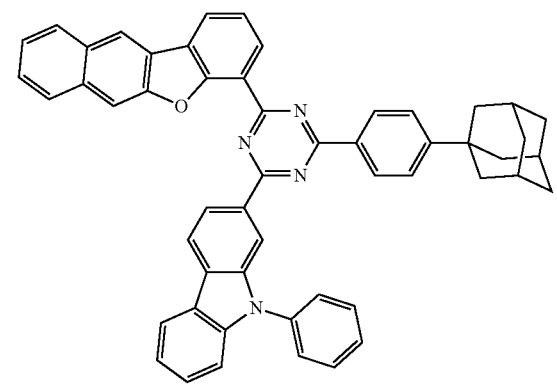

-continued
252
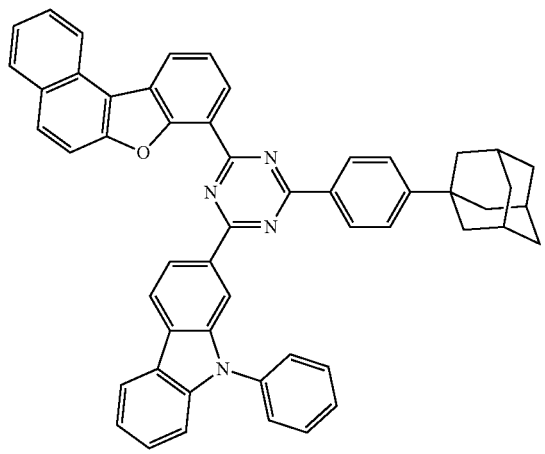
253
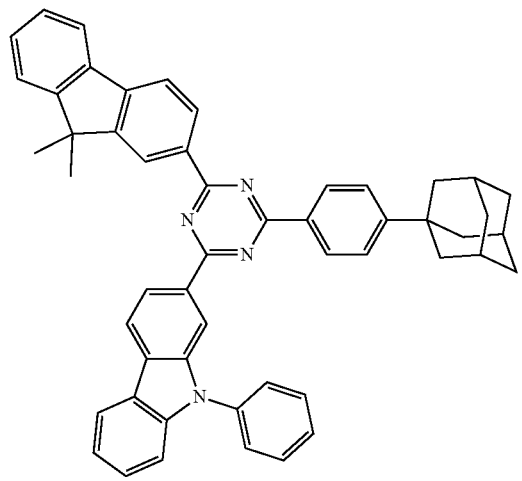
254
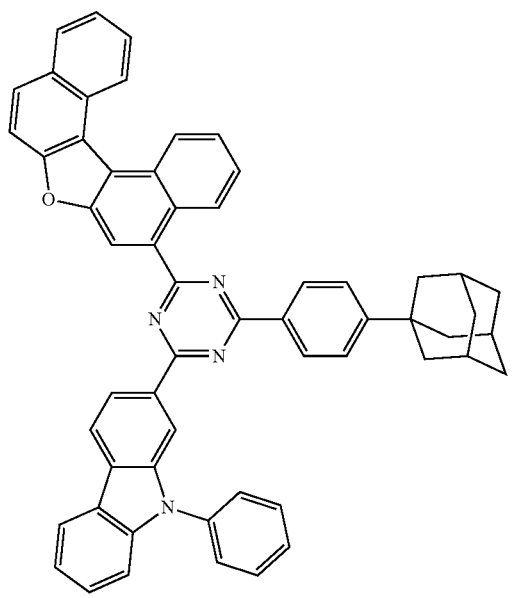
255
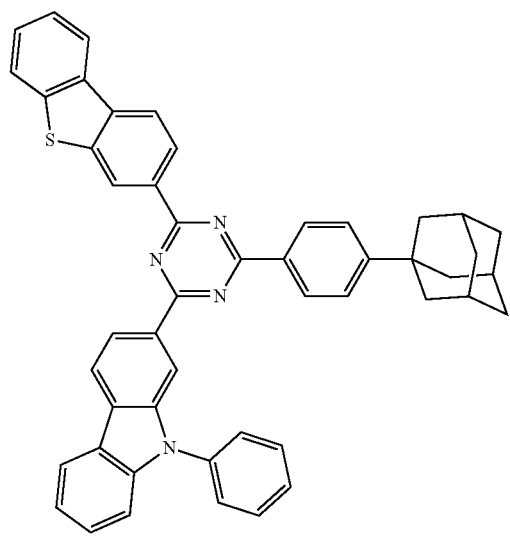
256
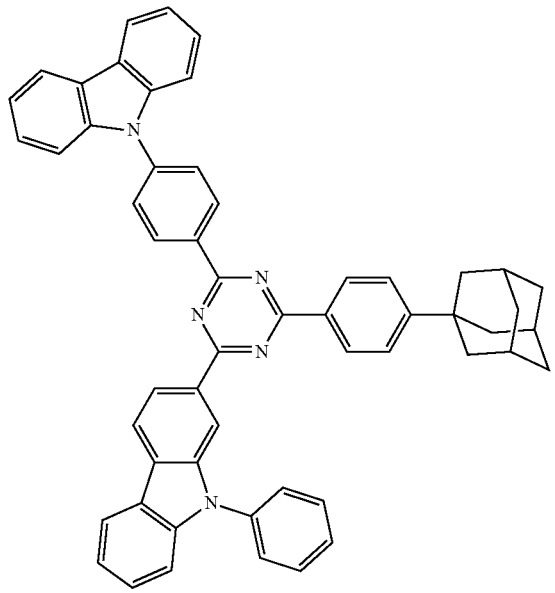
257
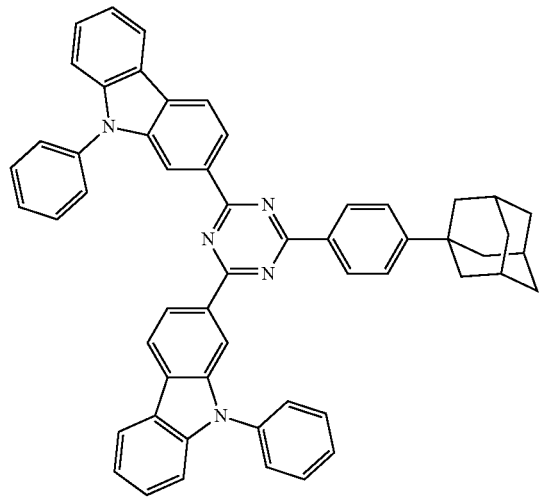

-continued
258
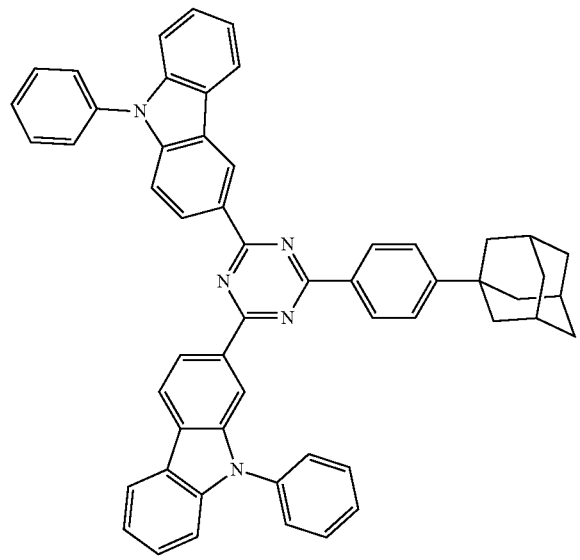
259
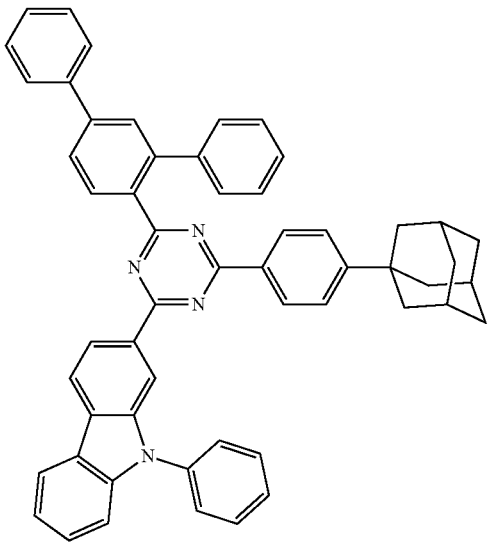
260
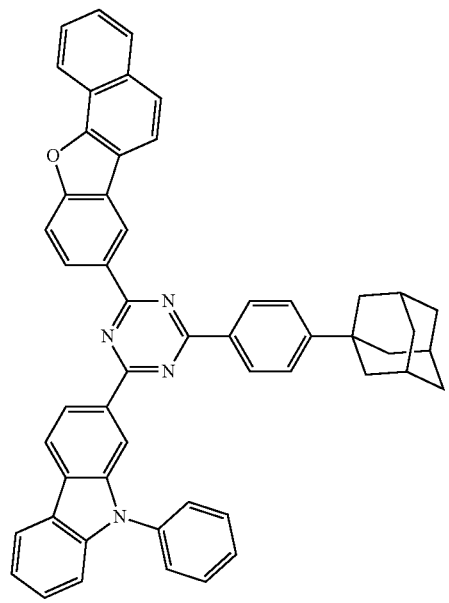
261
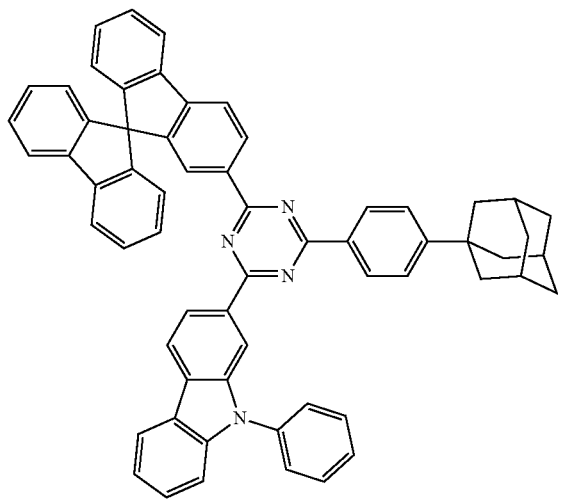
262
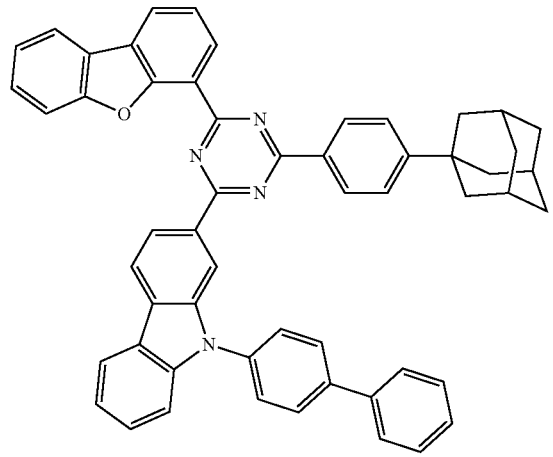
263
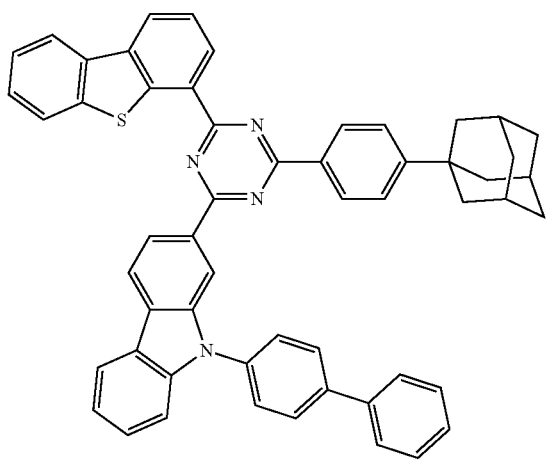

-continued
264
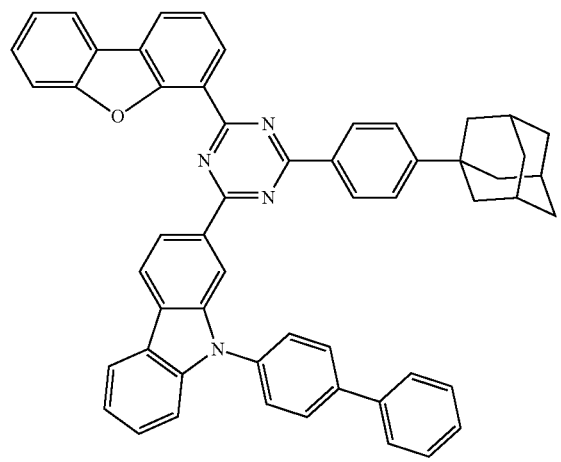
265
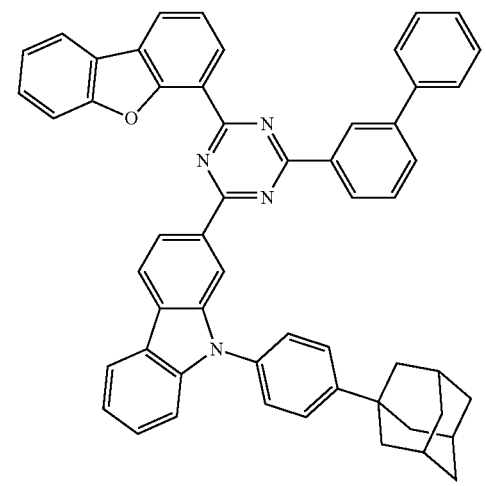
266
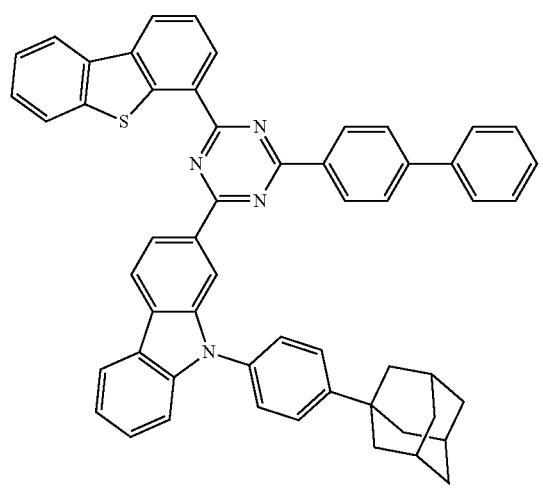
267
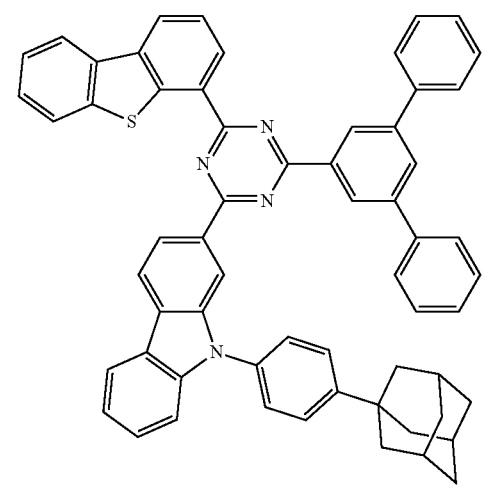
268
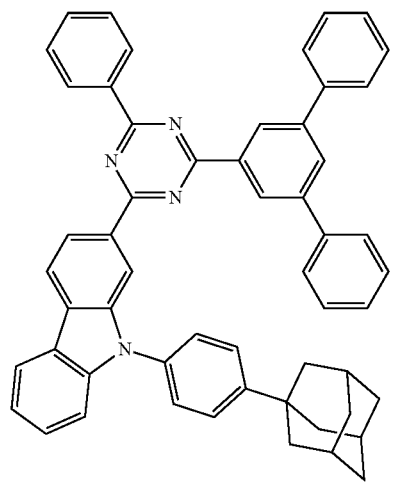
269
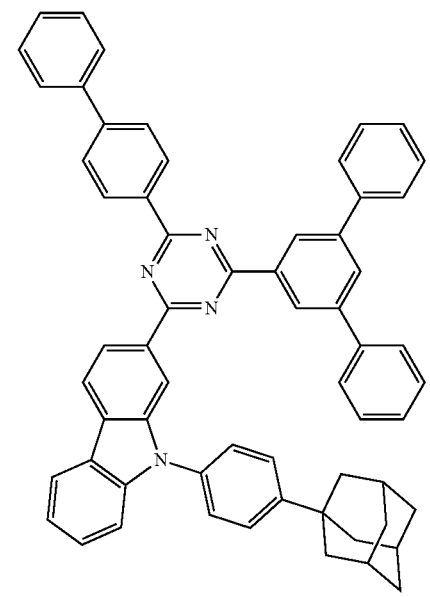

-continued
270
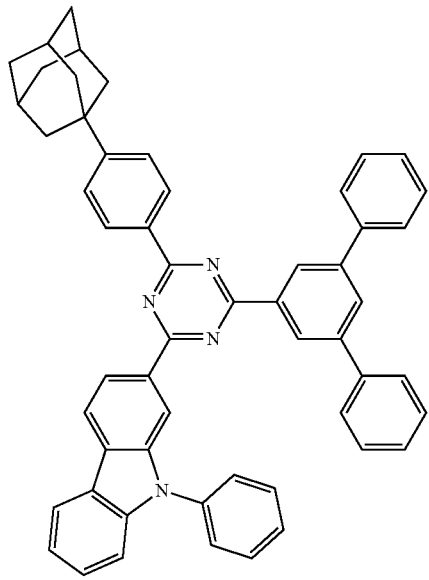
271
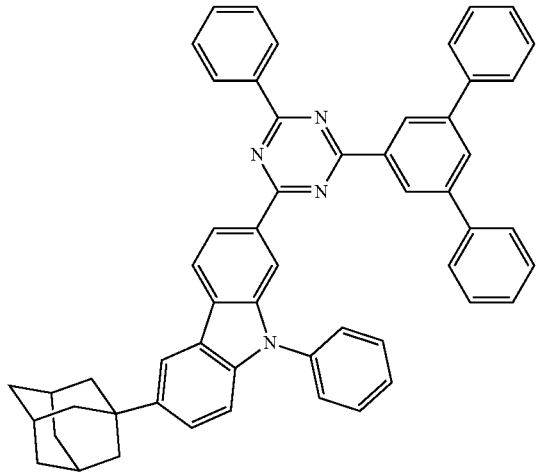
272
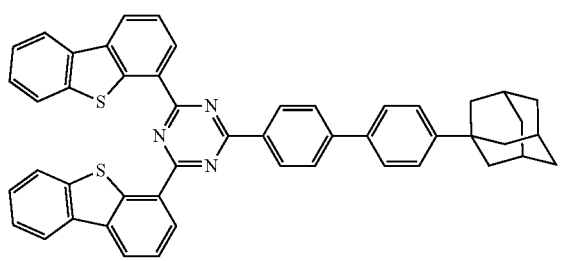
273
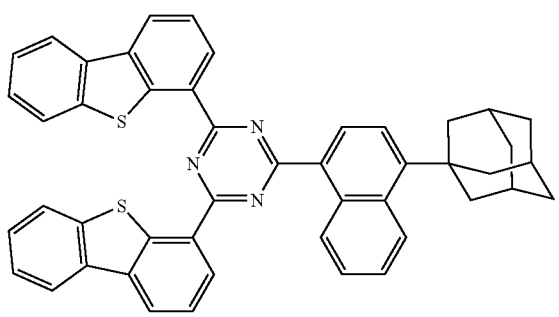
274
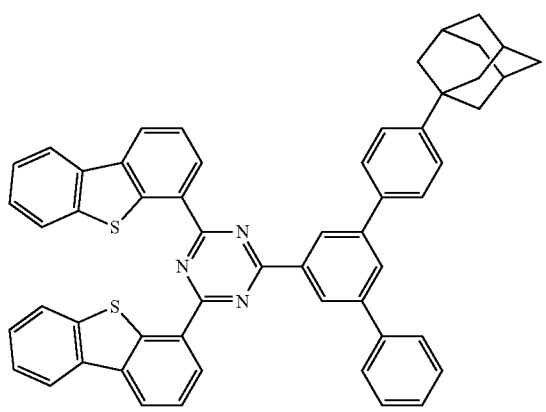
275
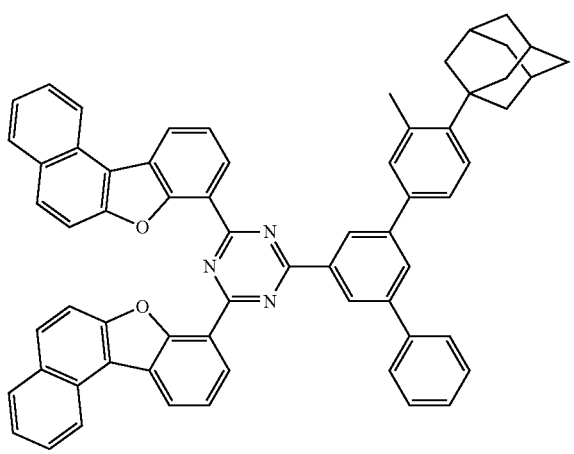

-continued
276
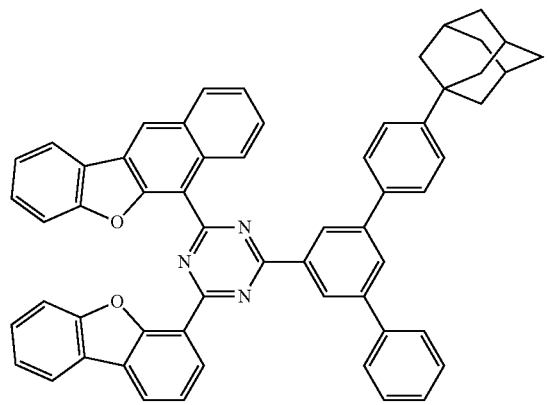
277
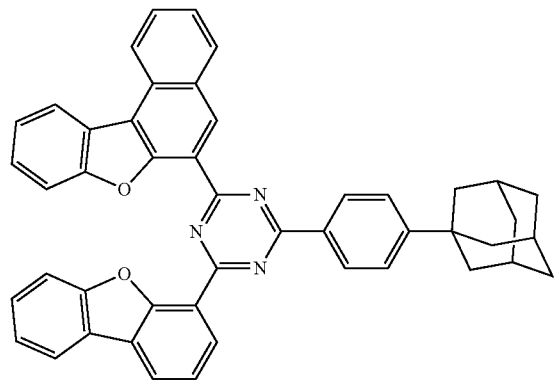
278
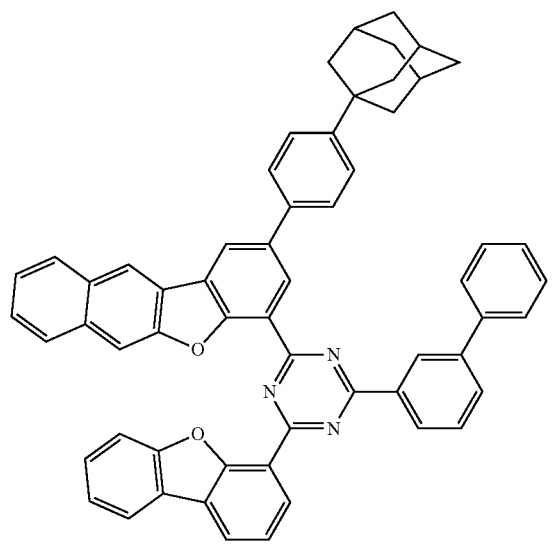
279
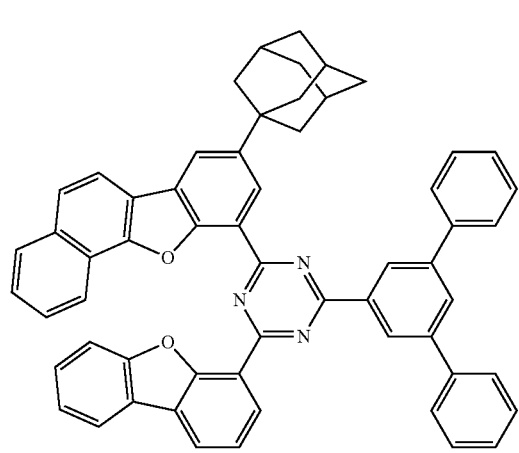
280
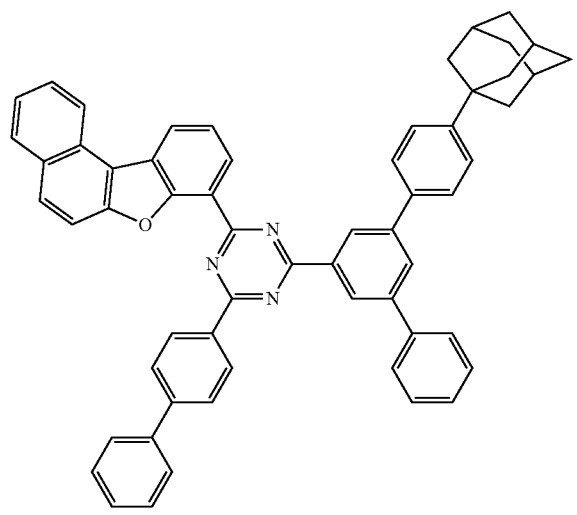
281
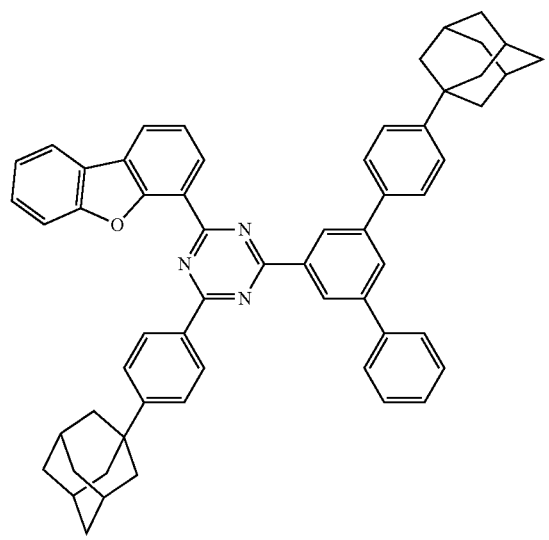

282
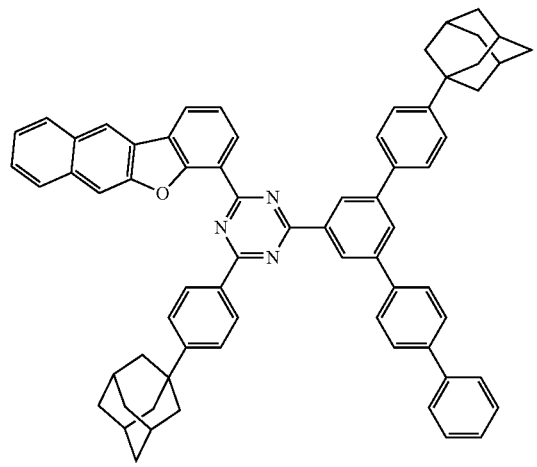
283
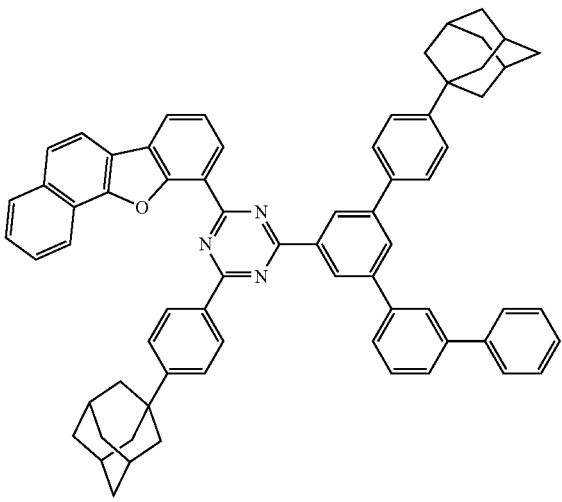
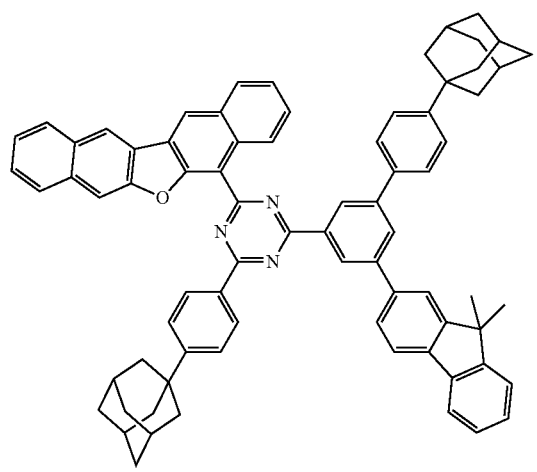
284
285
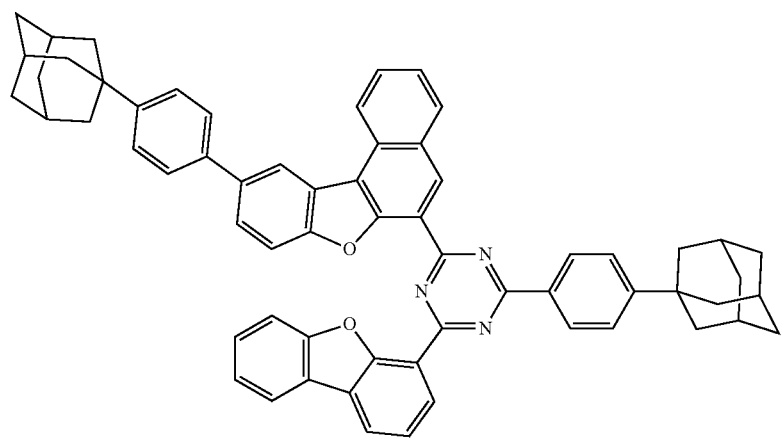

286
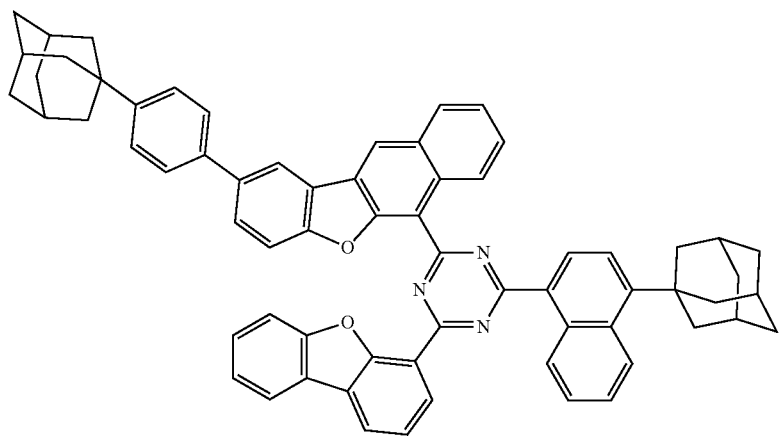
287
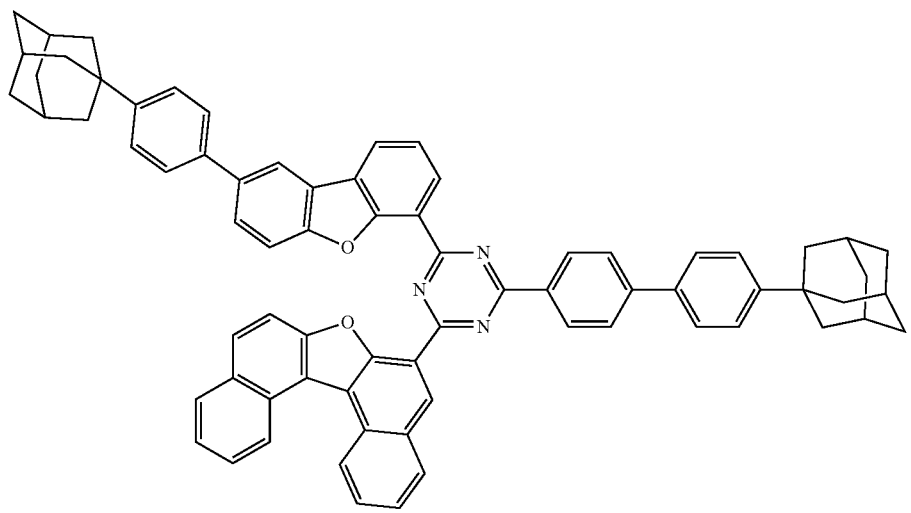
288
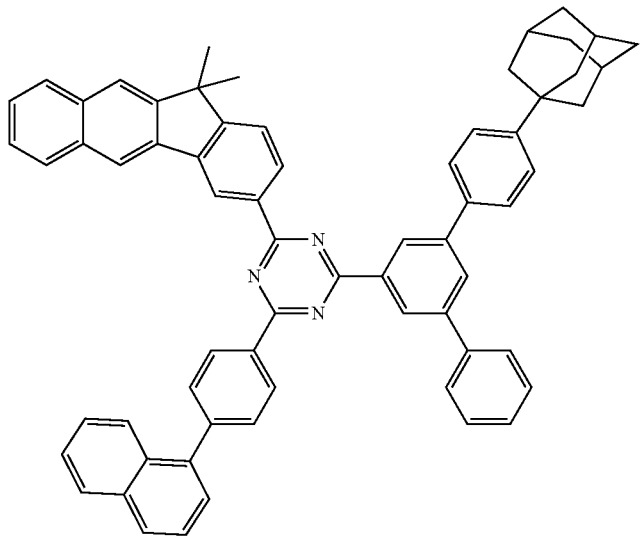

289
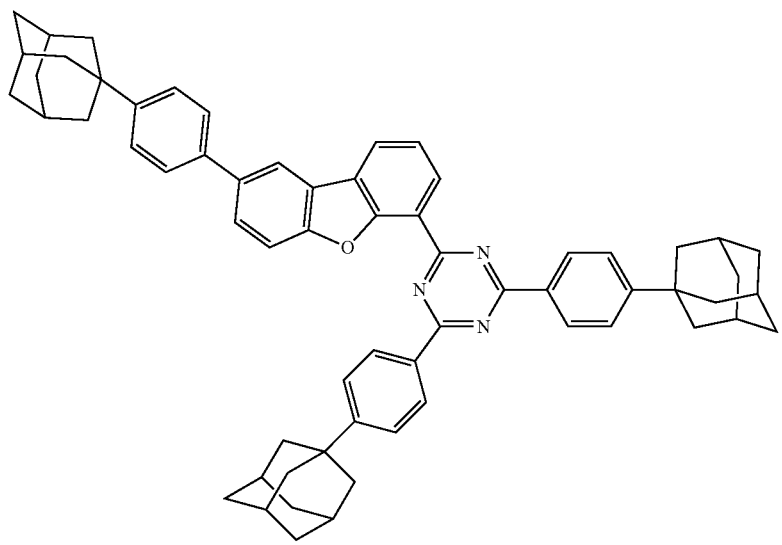
290
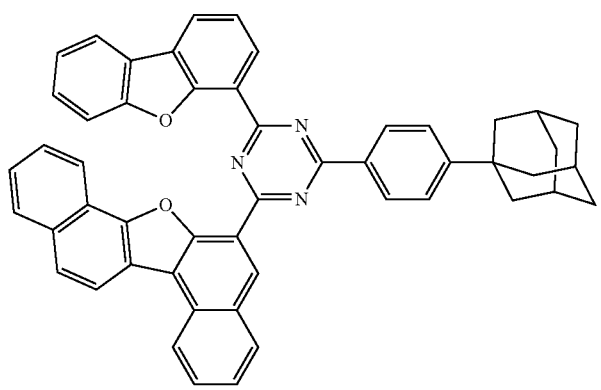
291
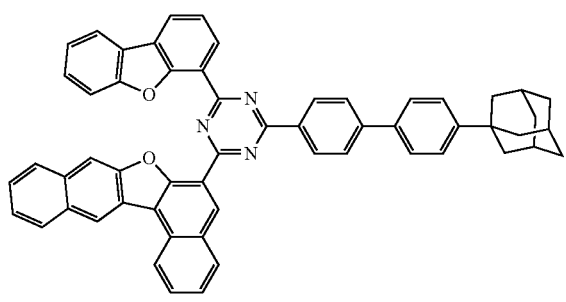
292
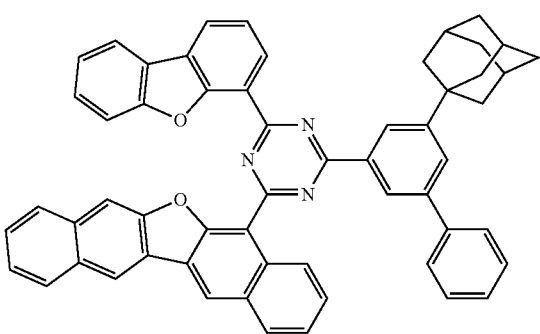

-continued
293
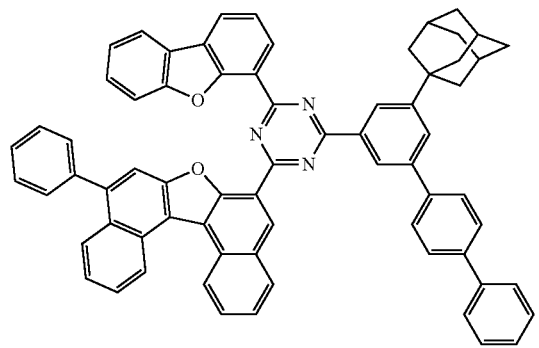
294
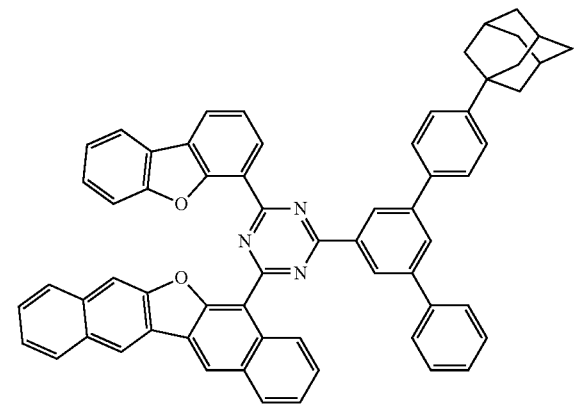
295
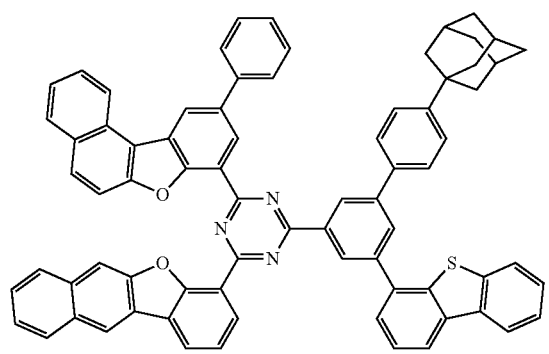
296
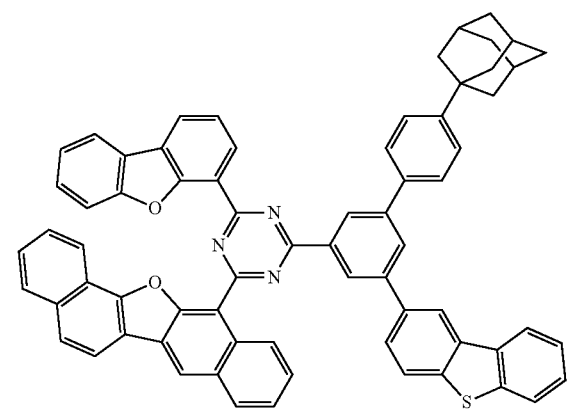
297
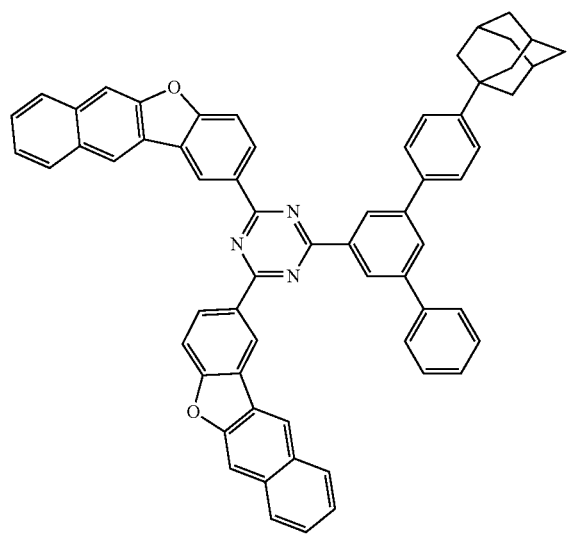
298
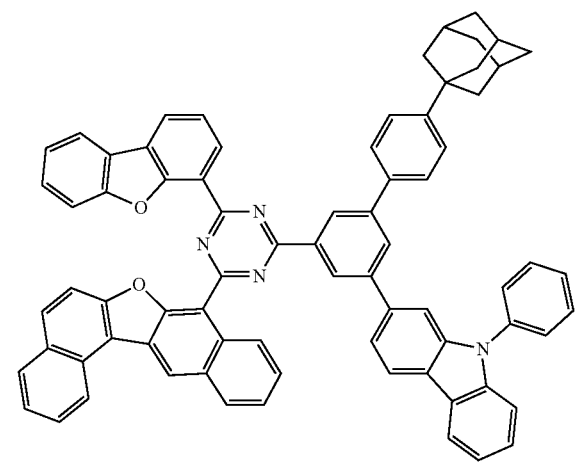

-continued
299
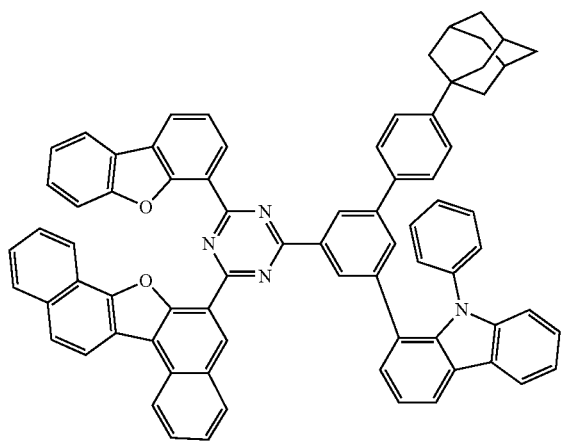
300
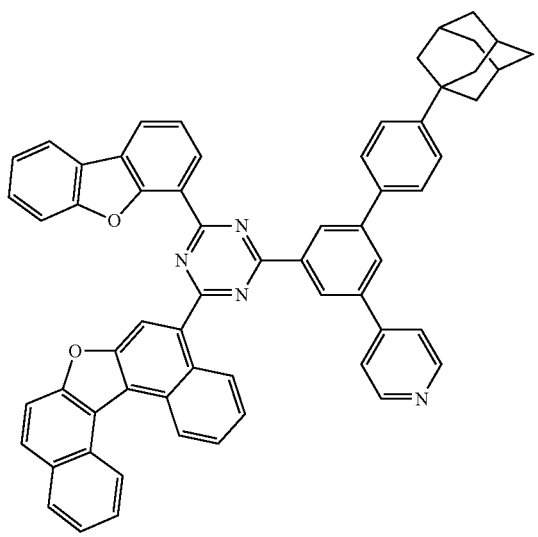
301
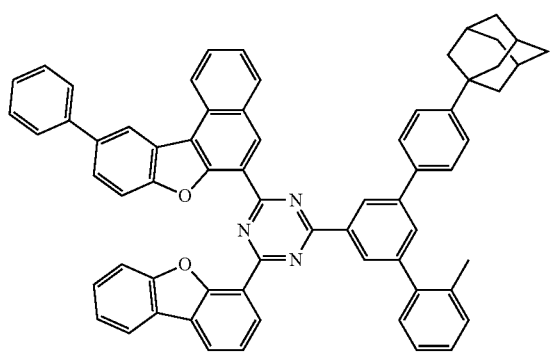
302
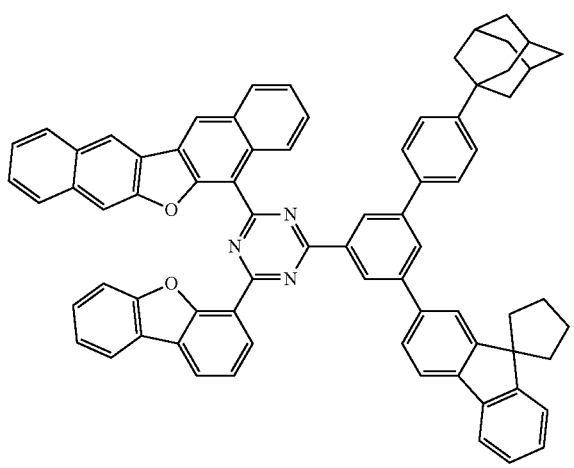
303
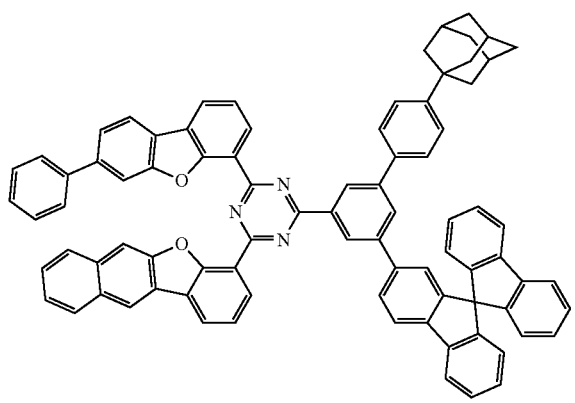
304
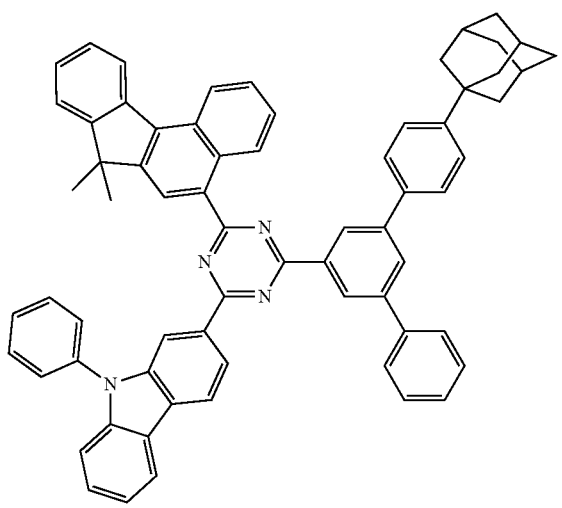

-continued
305
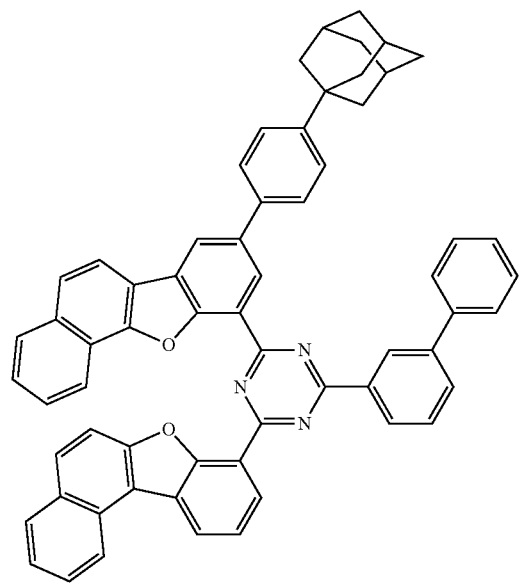
306
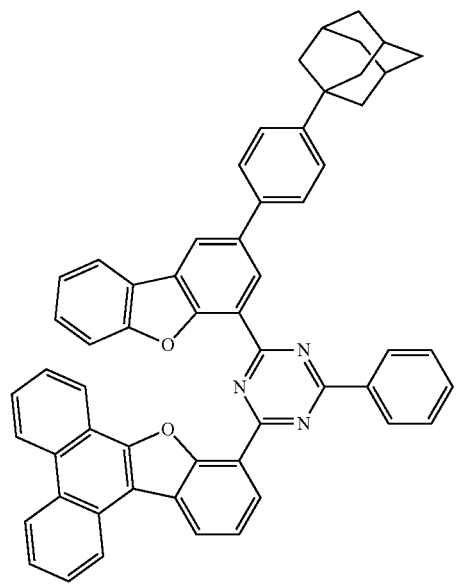
307
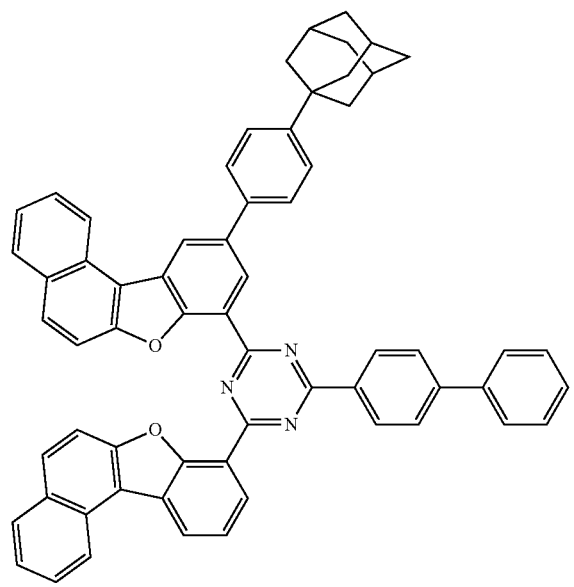
308
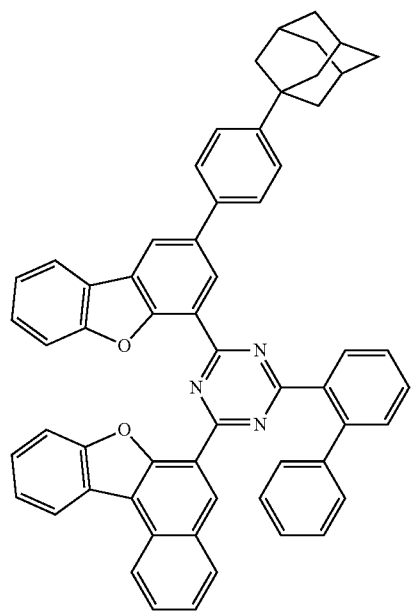

-continued
309
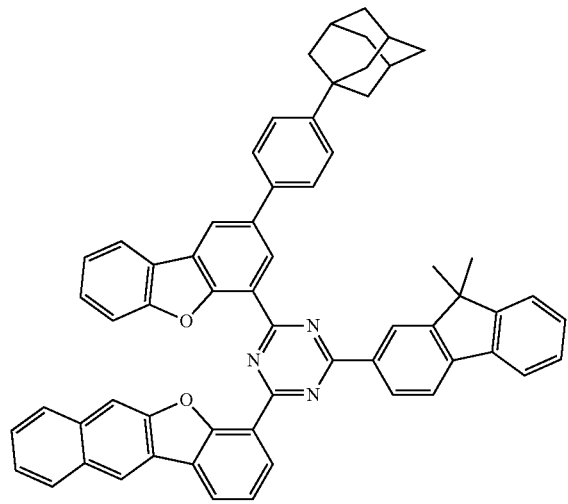
310
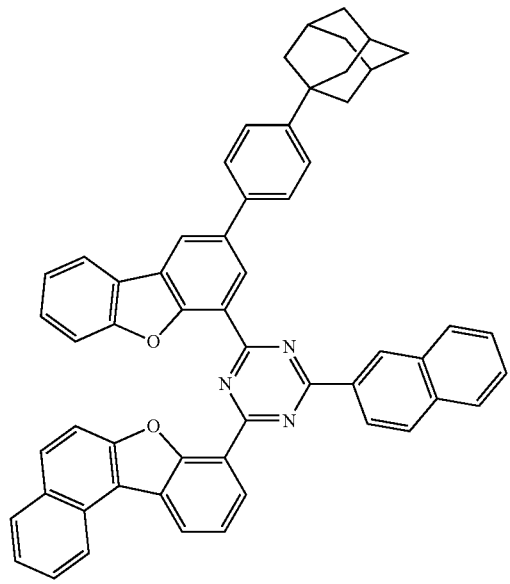
311
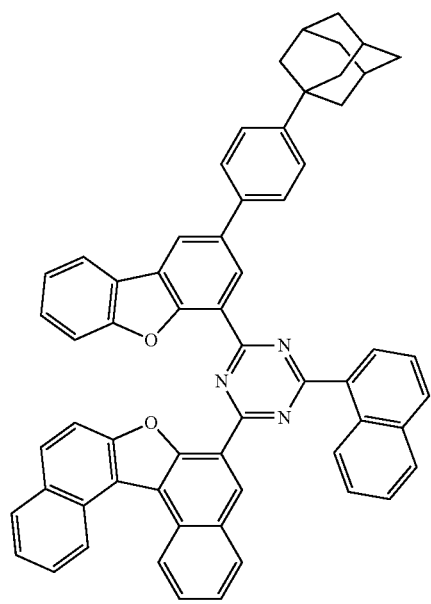
312
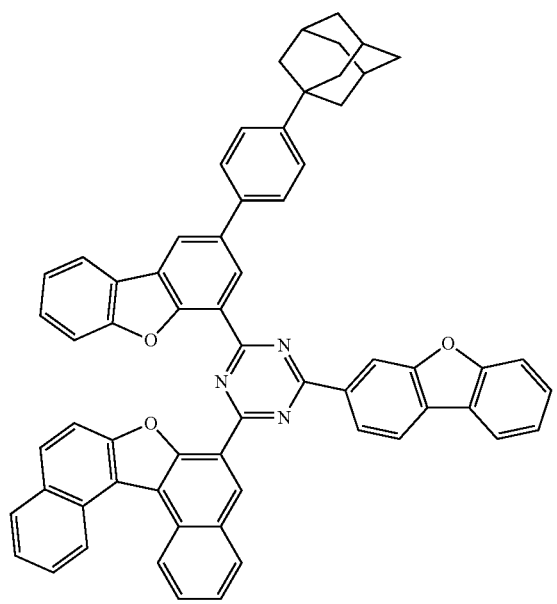

-continued
313
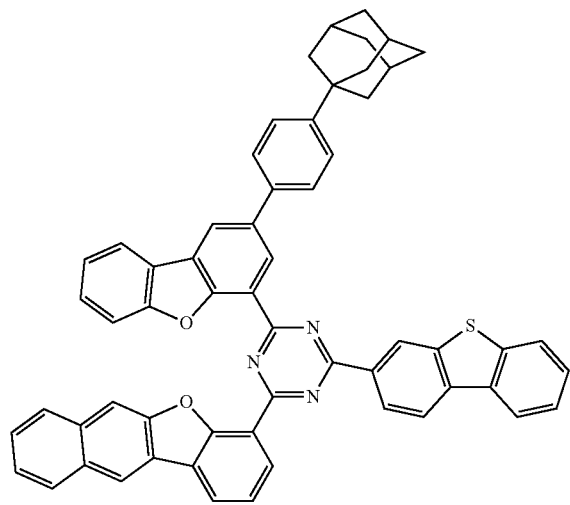
314
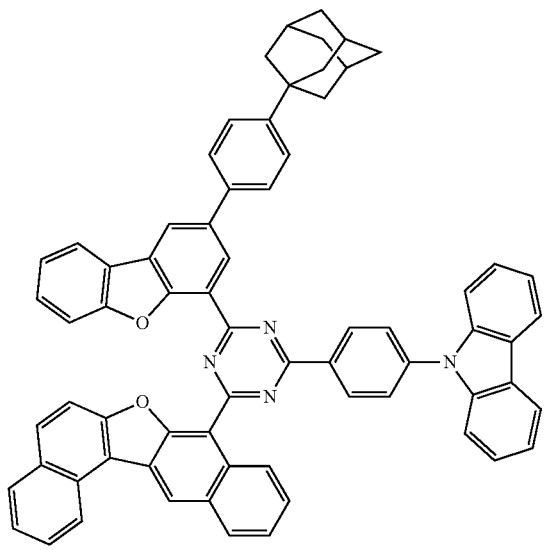
315
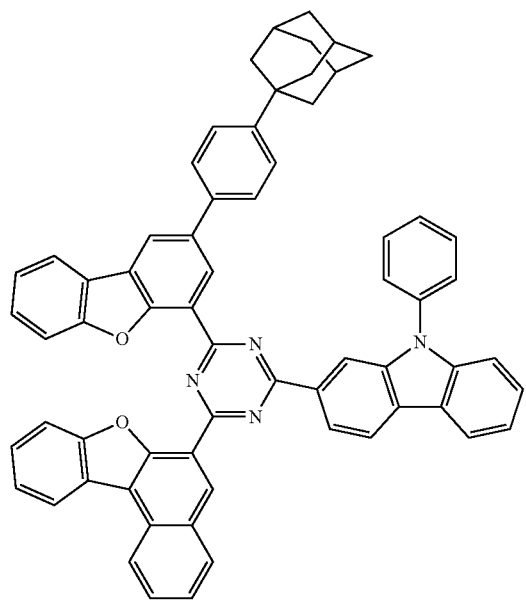
316
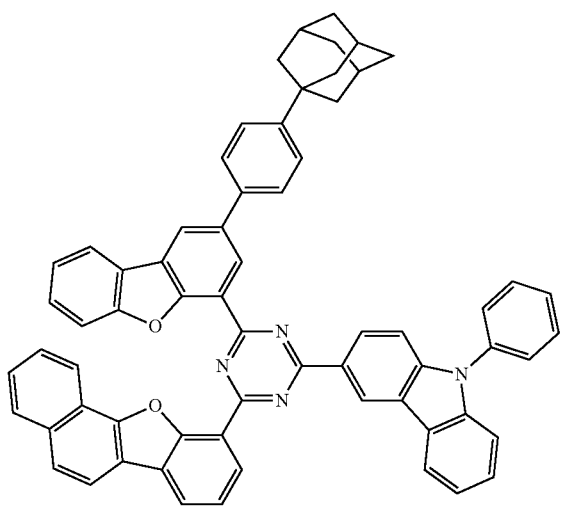

-continued
317 207
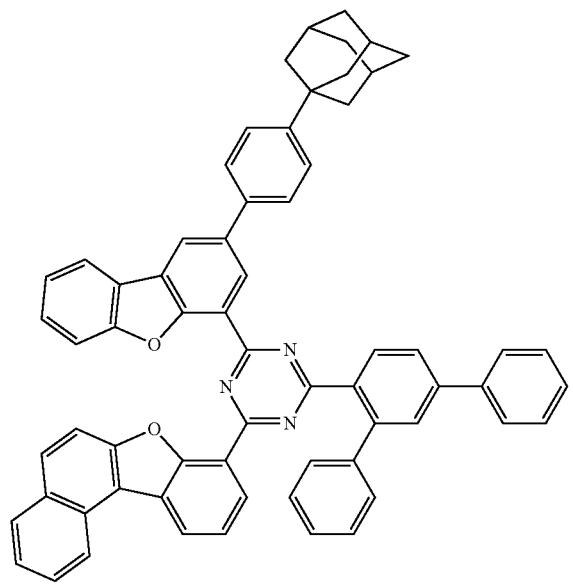
318 208
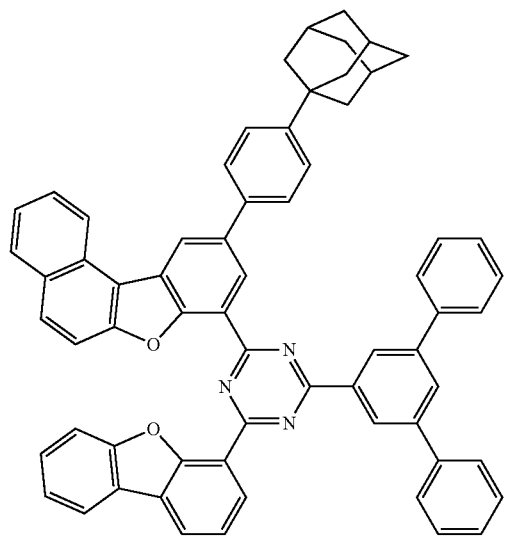
319
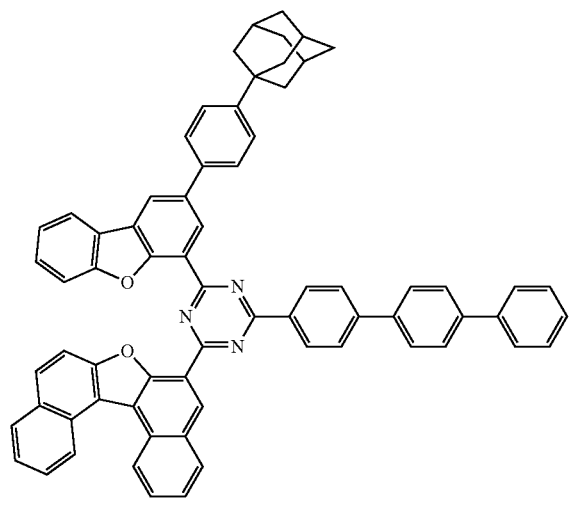
320
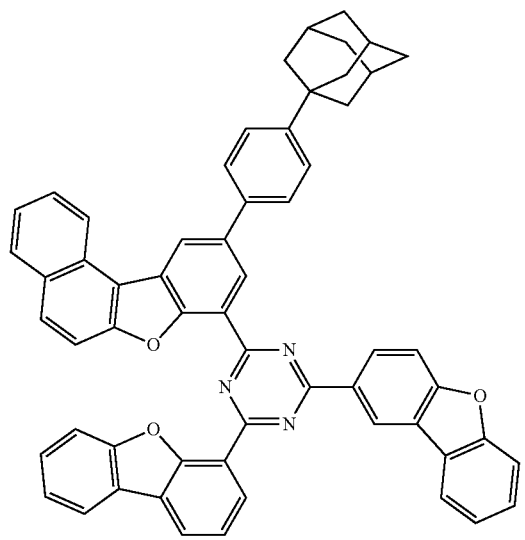

-continued
209
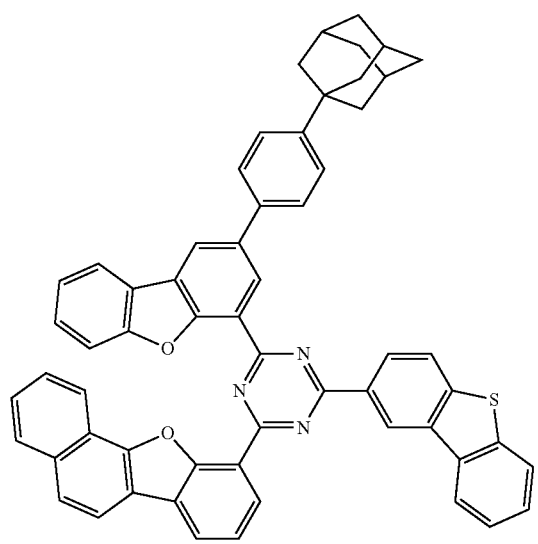
321
210
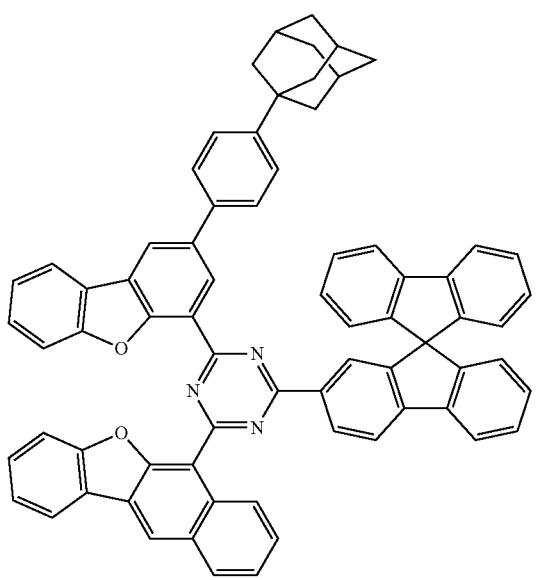
322
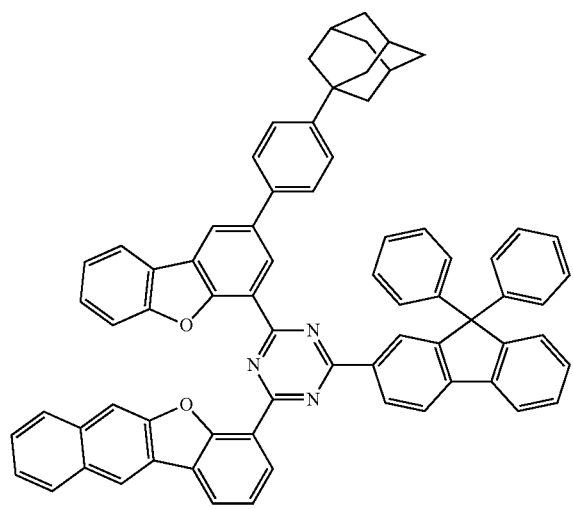
323
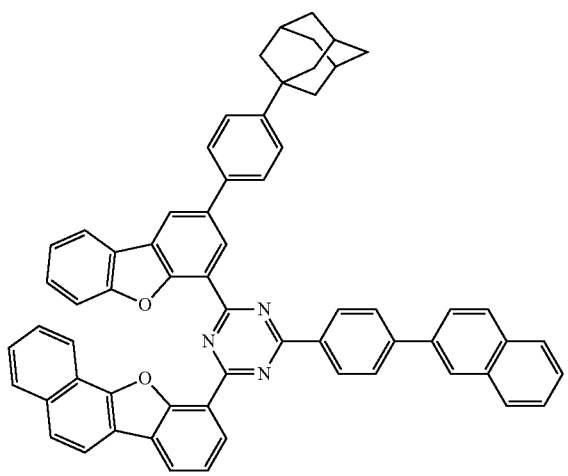
324

-continued
211    325    212    326
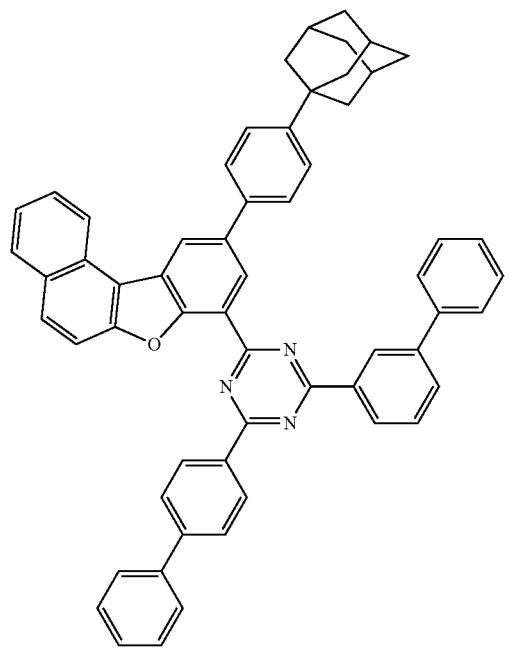
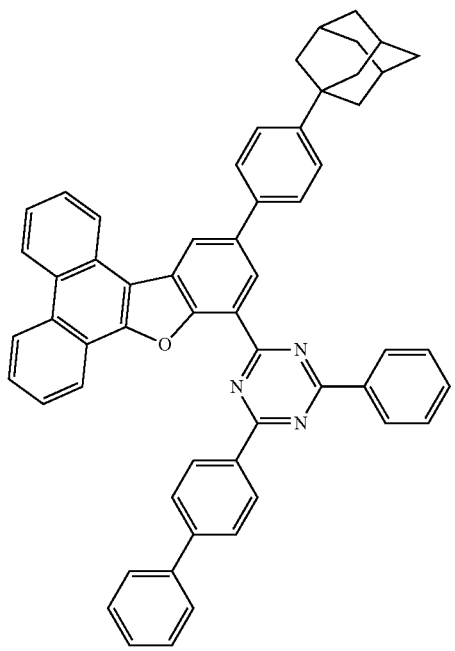
327    328
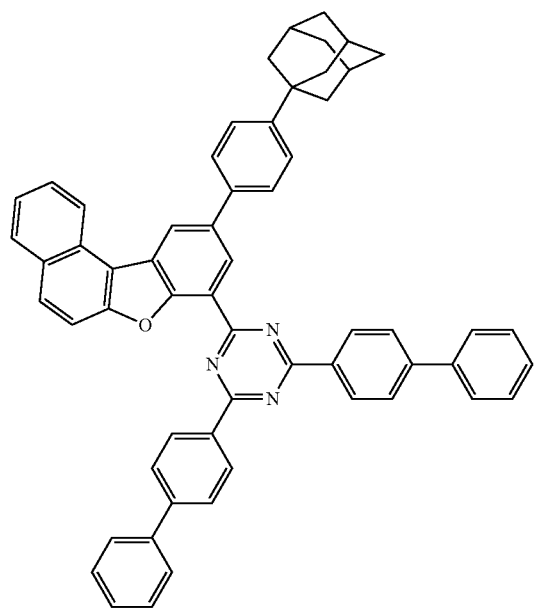
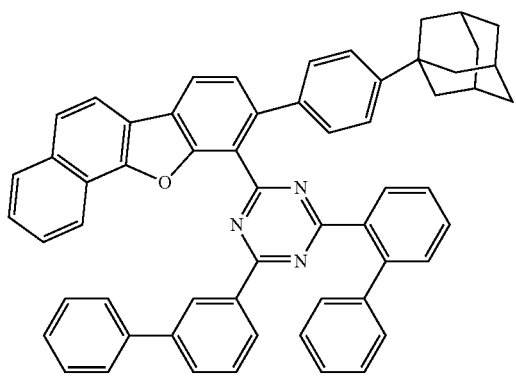

-continued
213 329
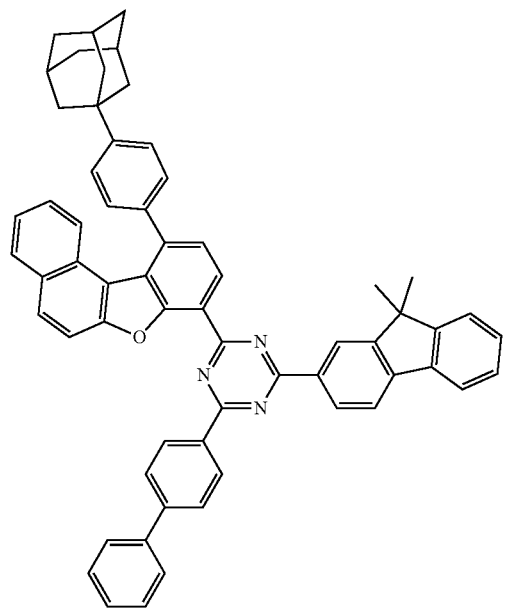
214 330
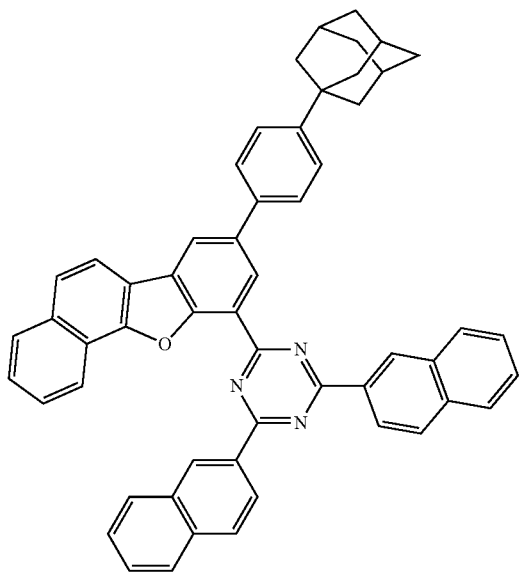
331
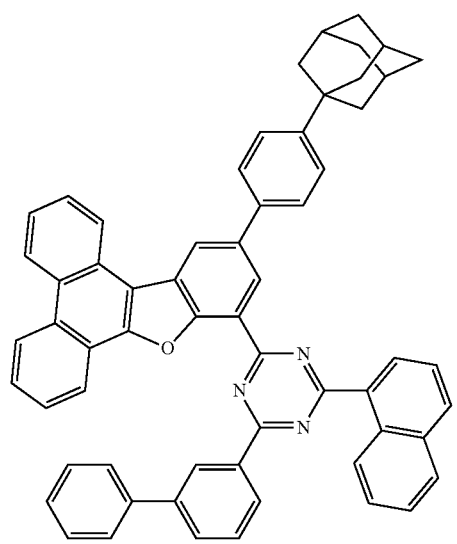
332
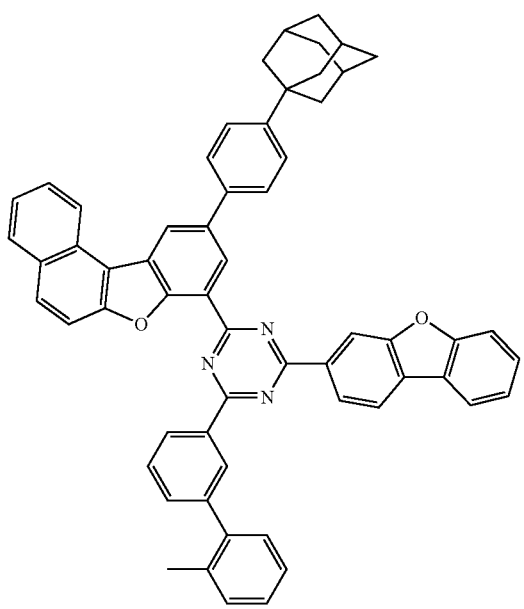

333
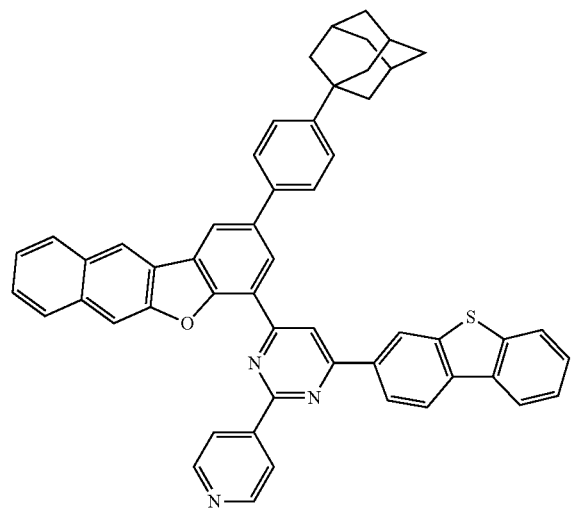
334
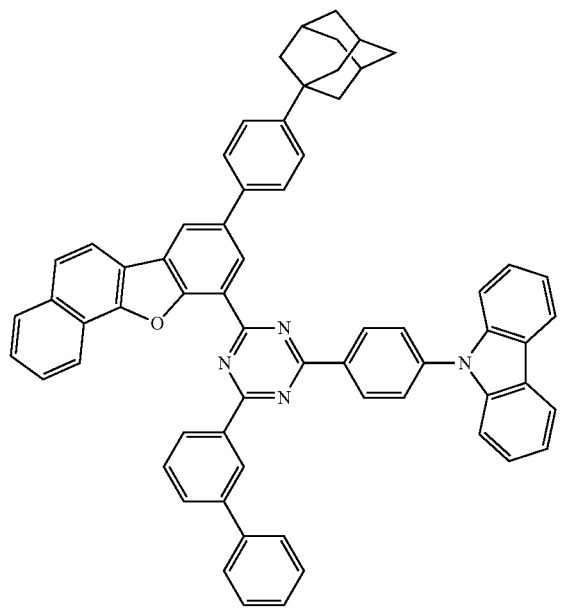
335
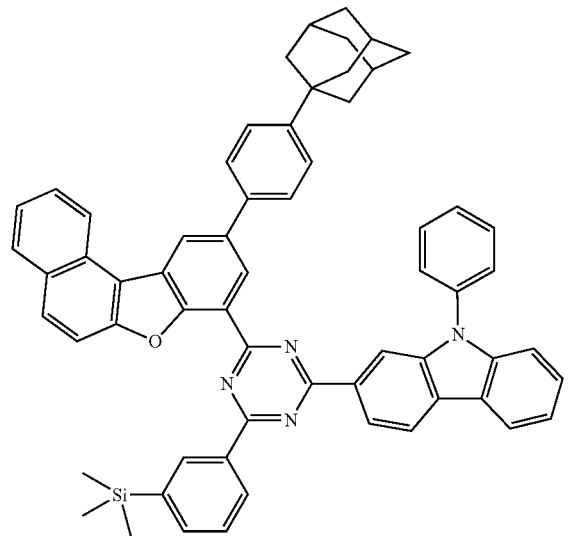
336
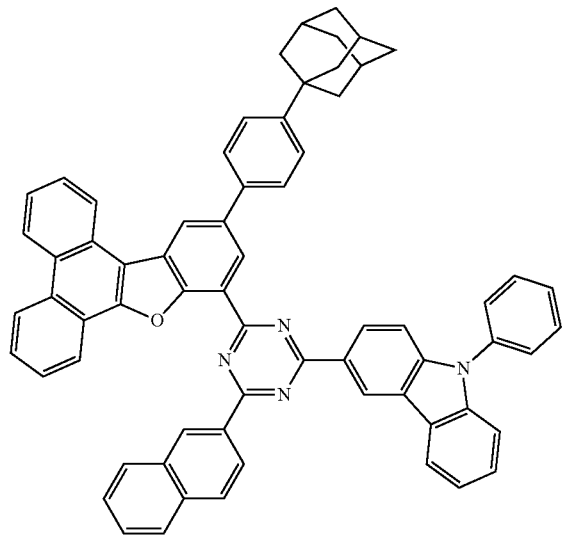

-continued
337
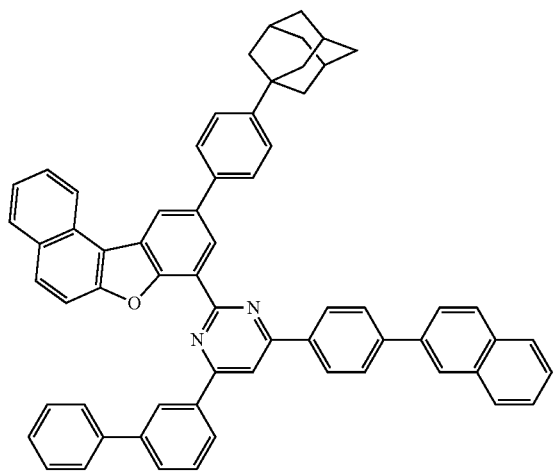
338
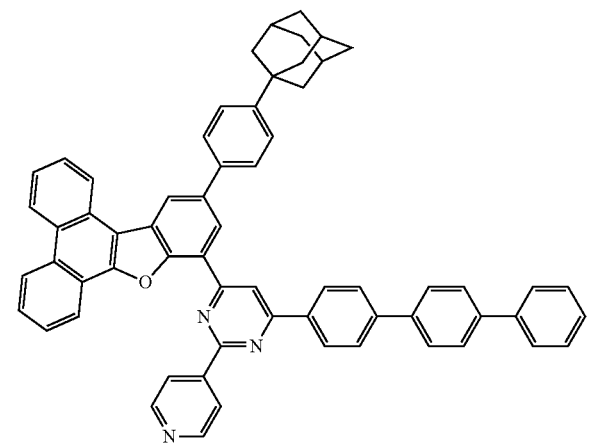
339
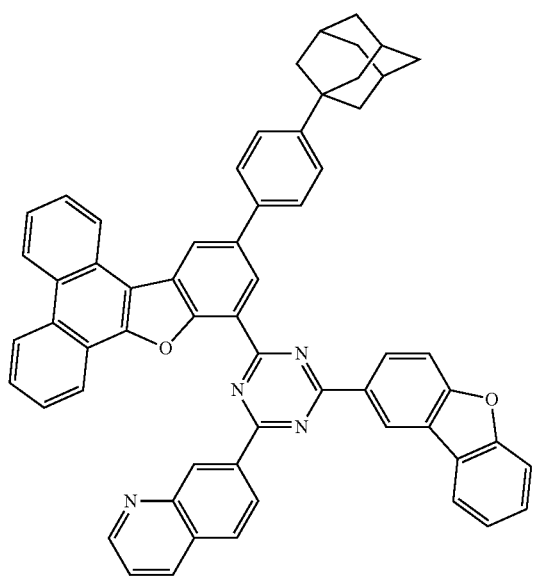
340
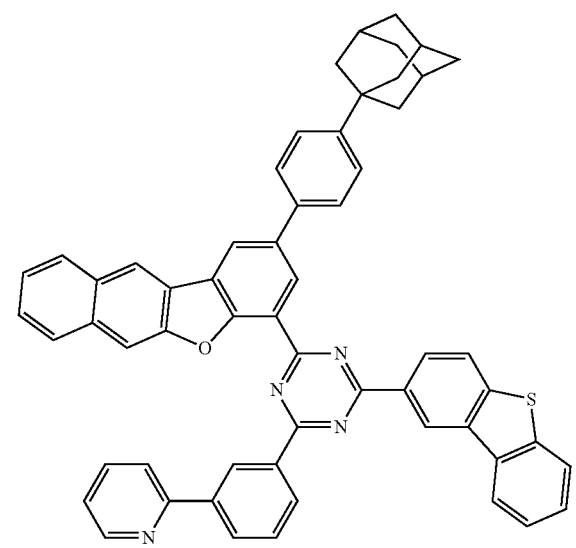
341
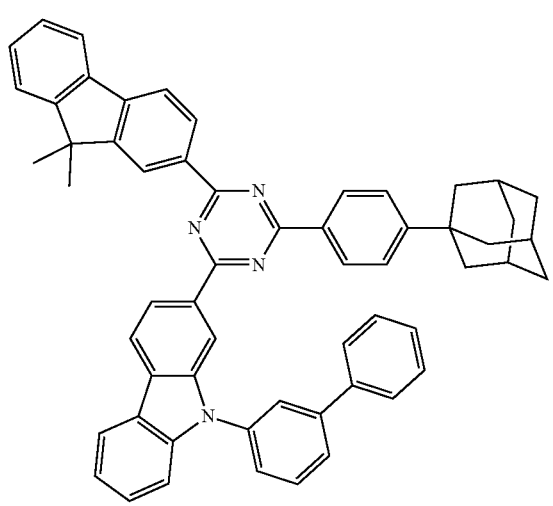
342
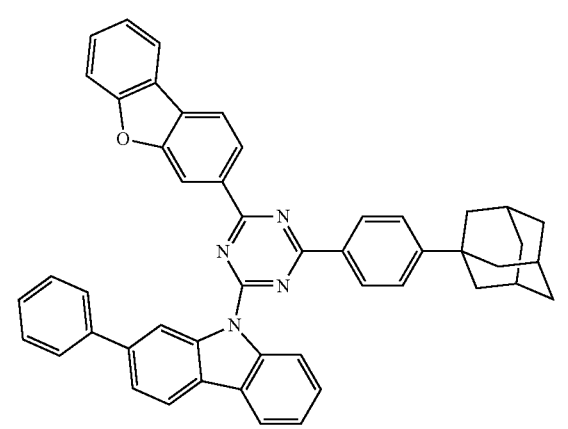

-continued
219
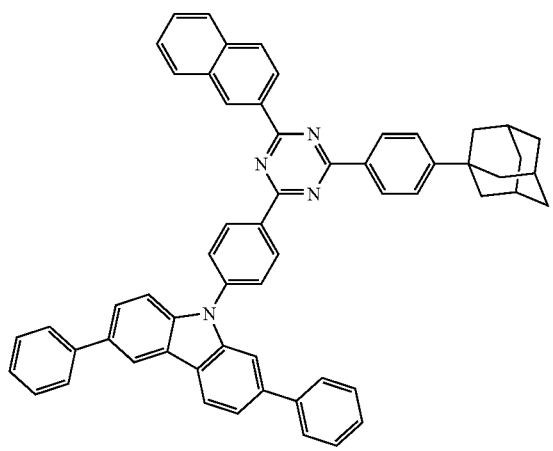
220
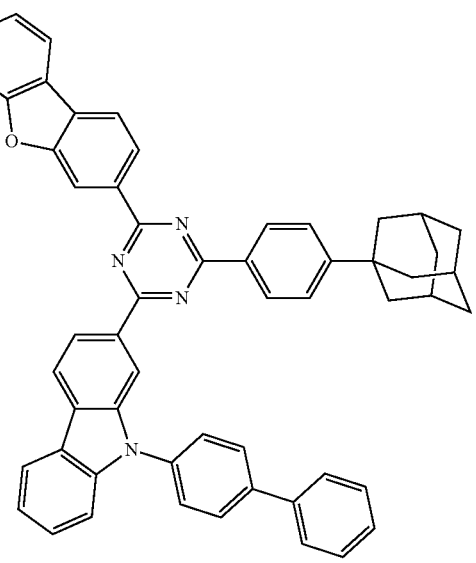
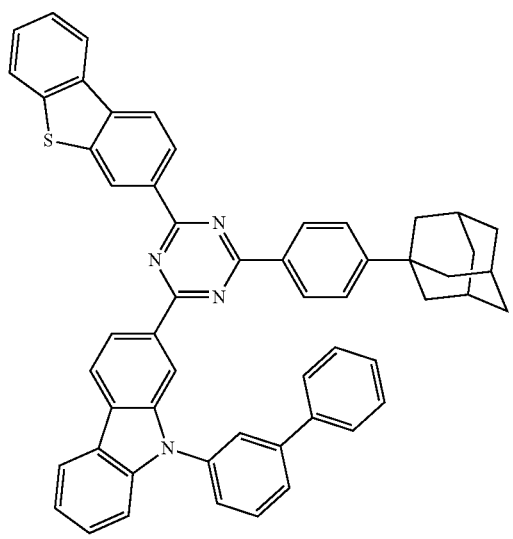
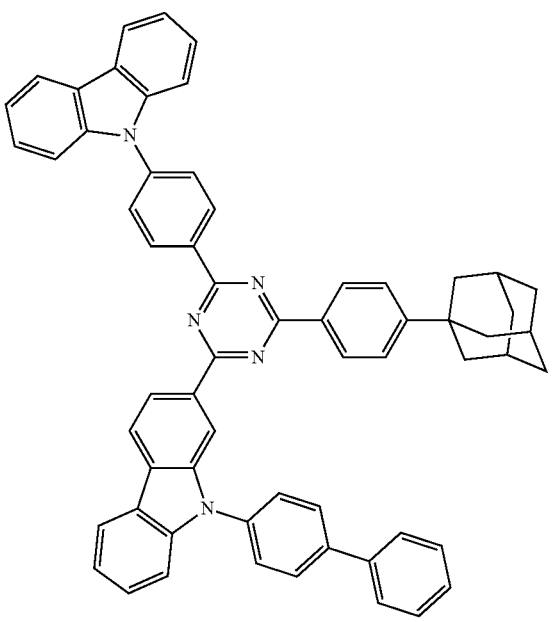

-continued
347
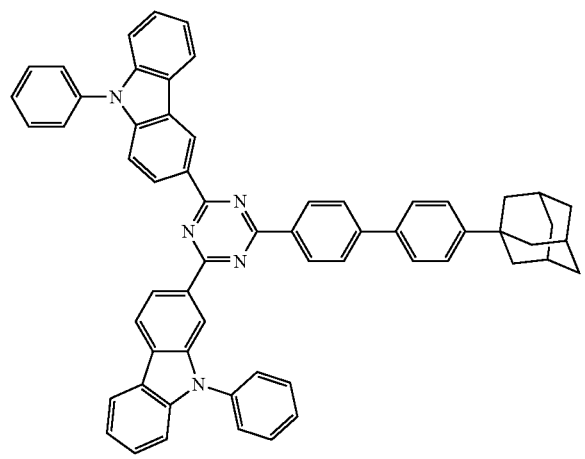
348
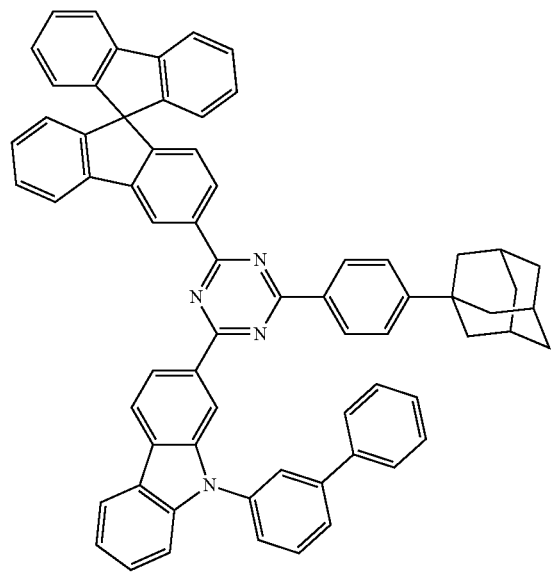
349
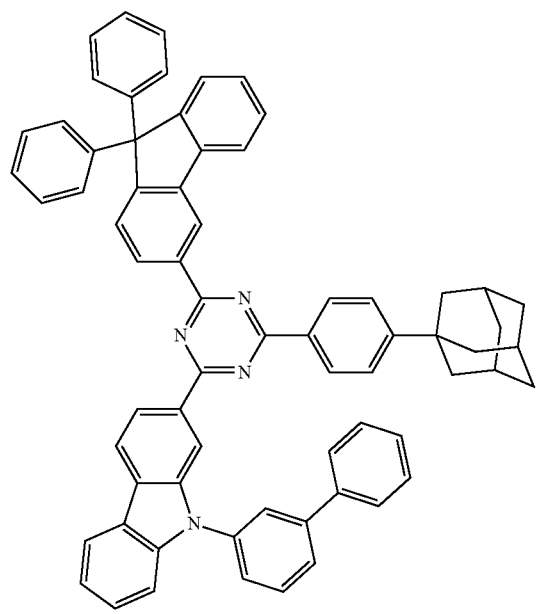
350
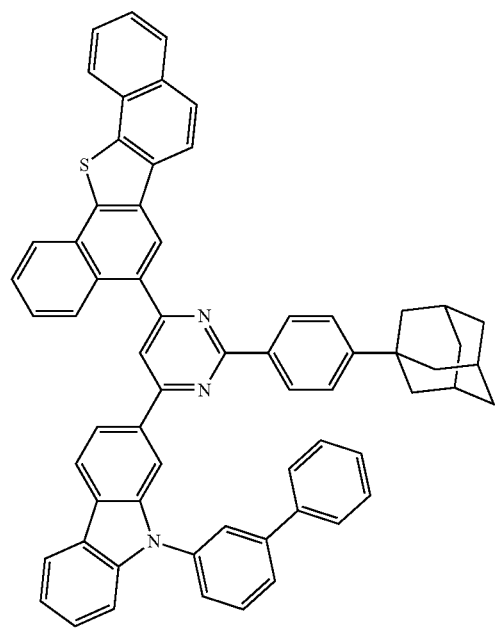

-continued
351
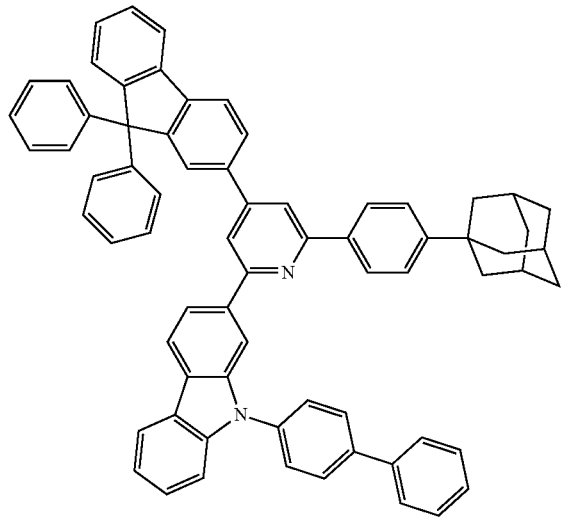
352
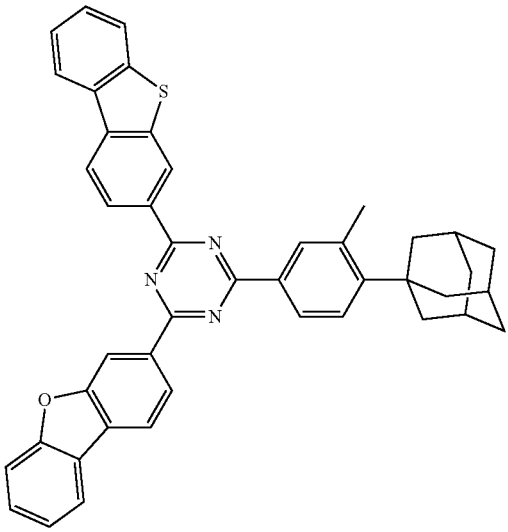
353
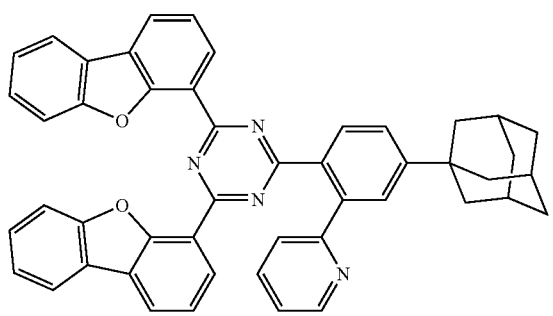
354
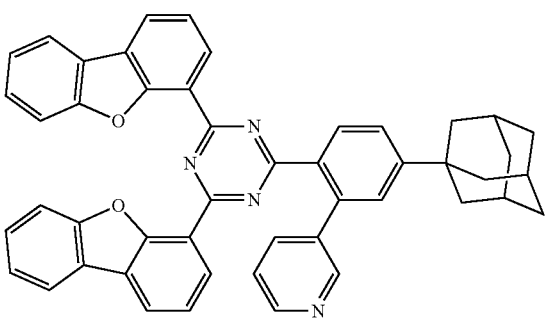
355
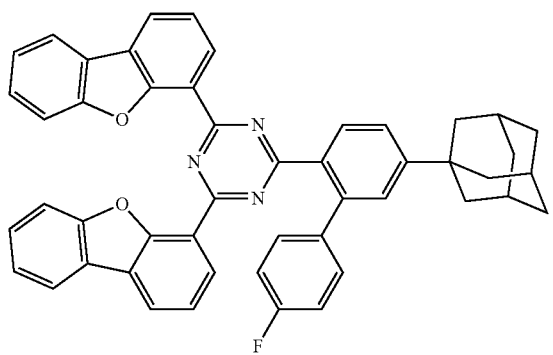
356
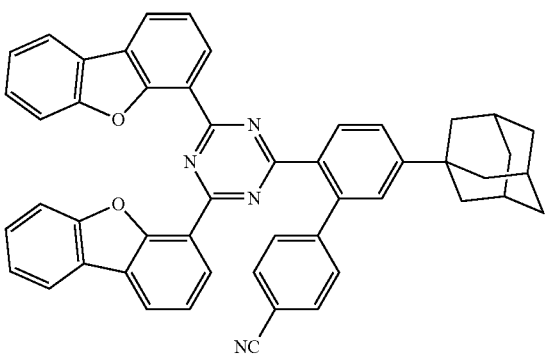
357
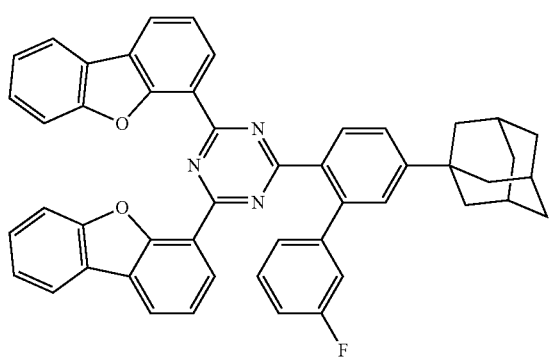
358
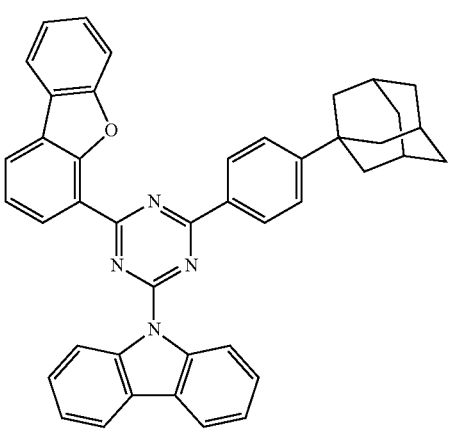

-continued
359
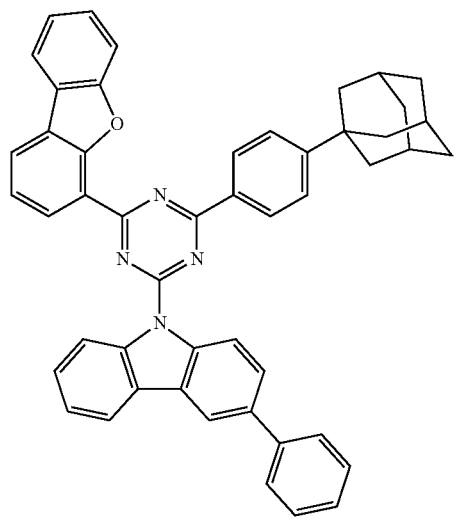
360
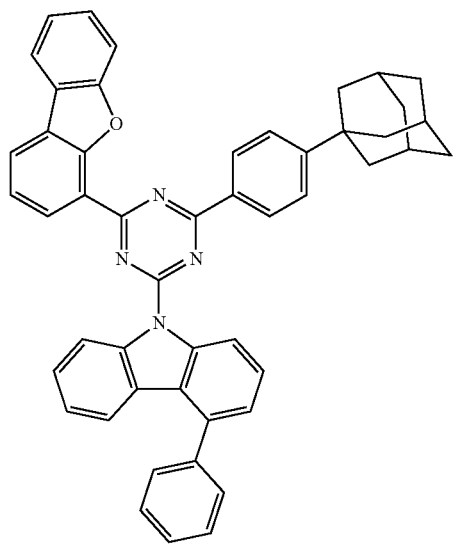
361
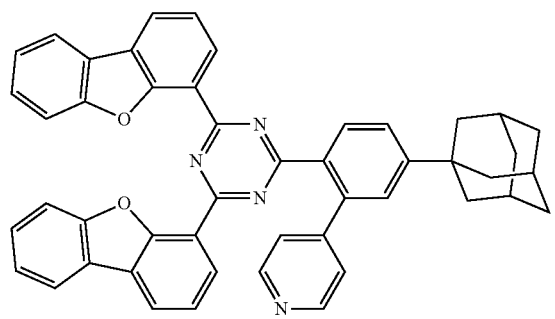
362
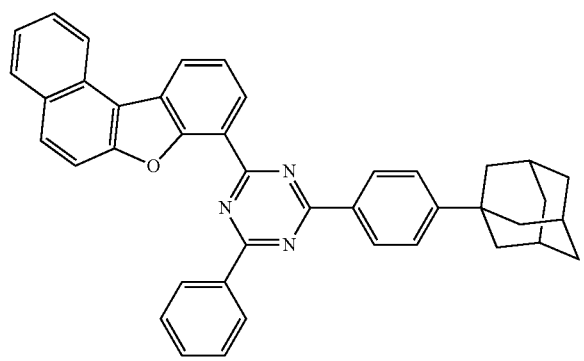
363
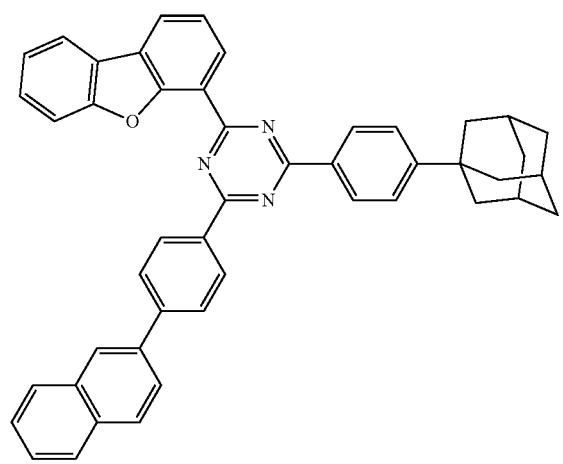
364
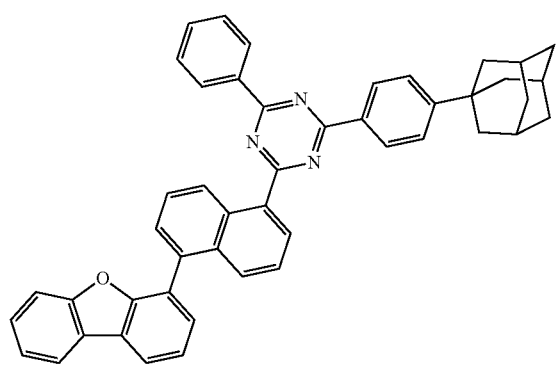

227
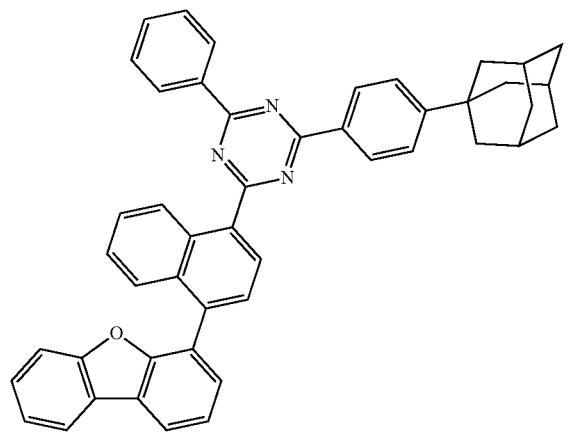
228
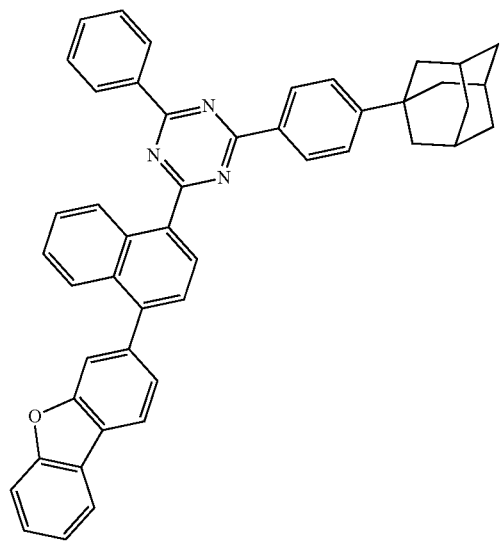
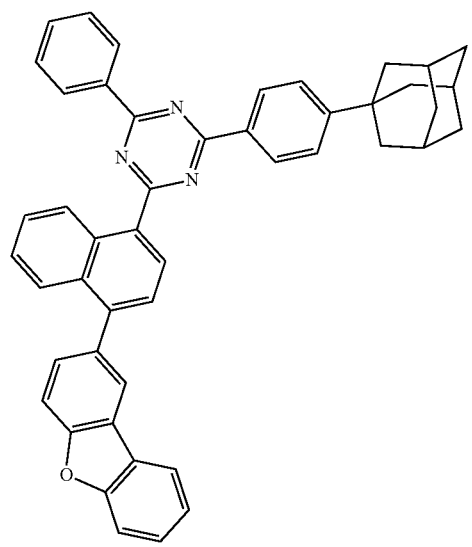
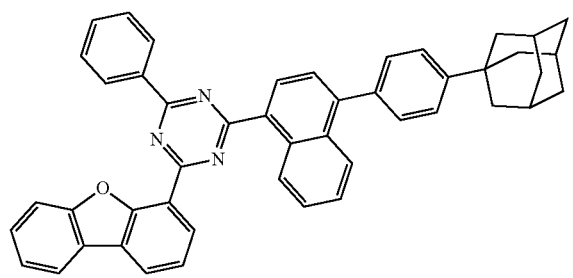

-continued
369
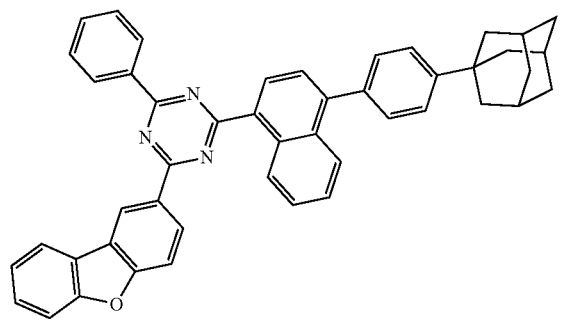
370
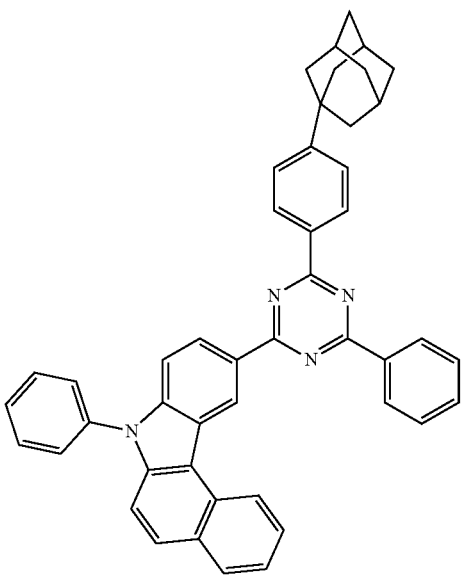
371
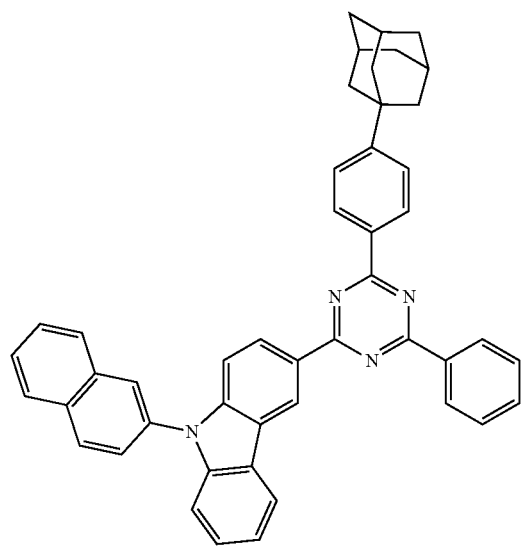
372
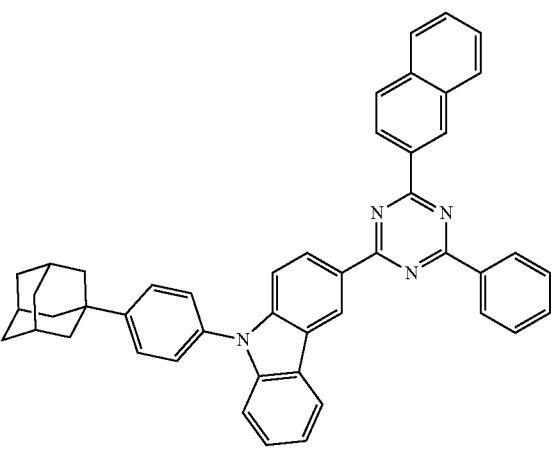
373
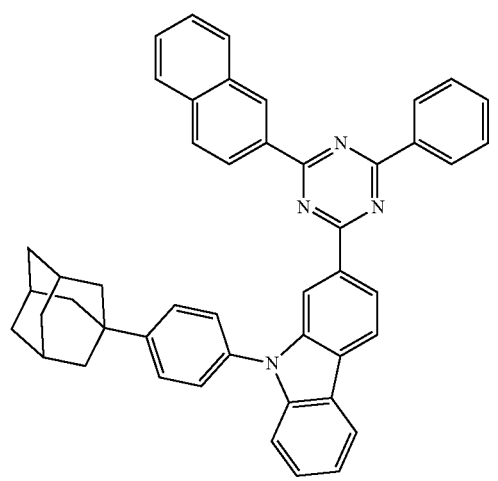
374
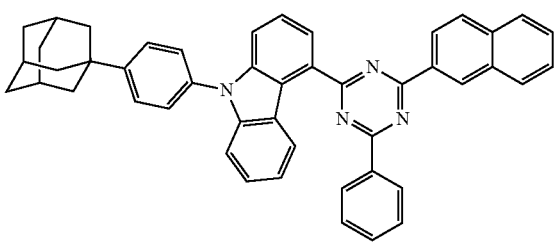

375
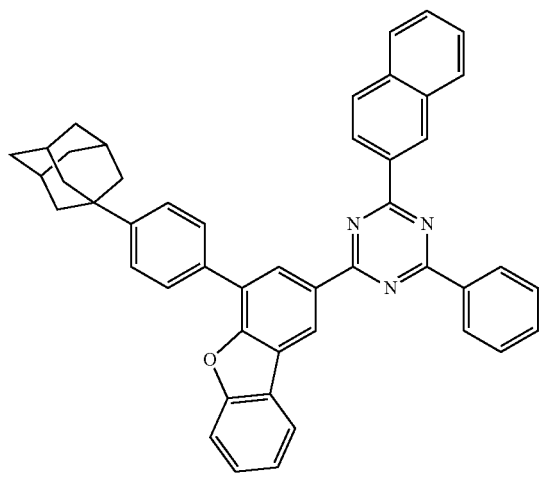
376
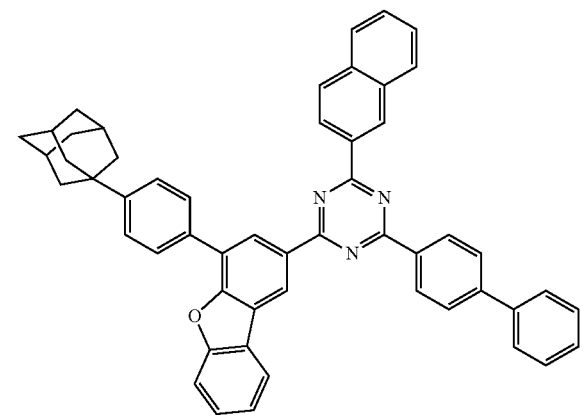
377
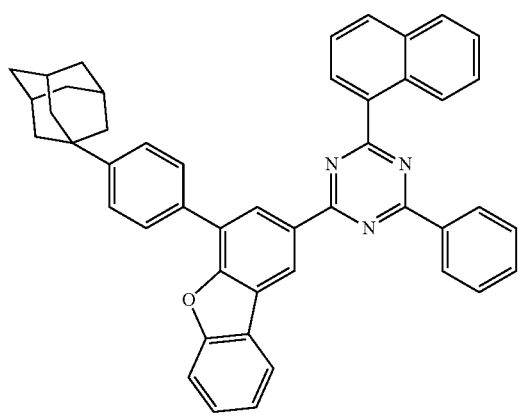
378
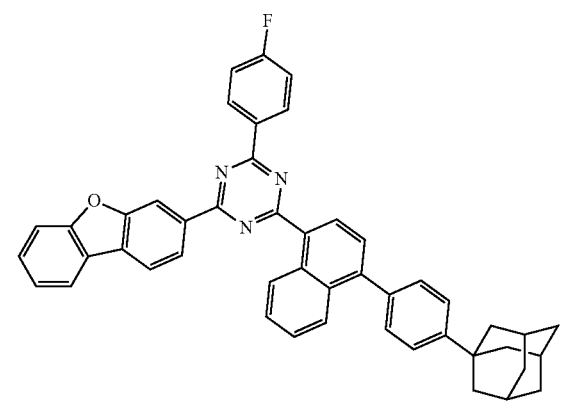
379
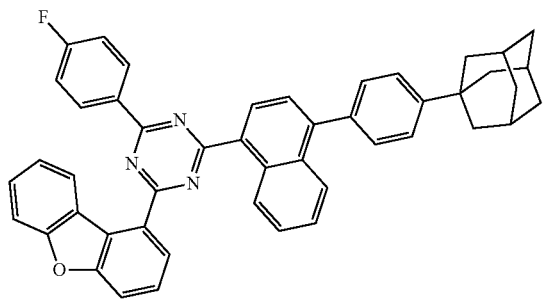
380
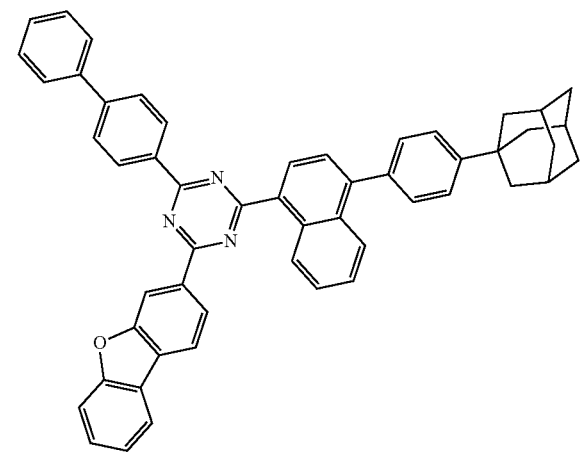

-continued

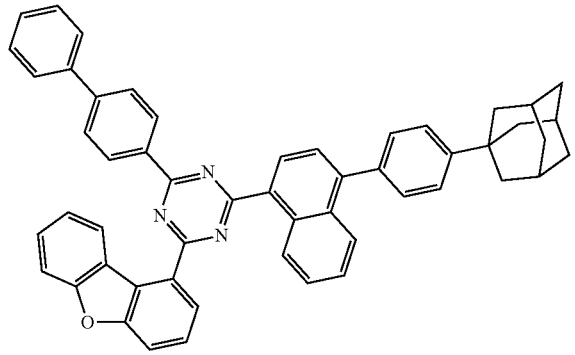
381

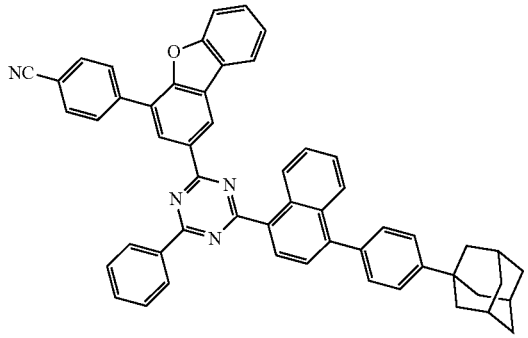
382

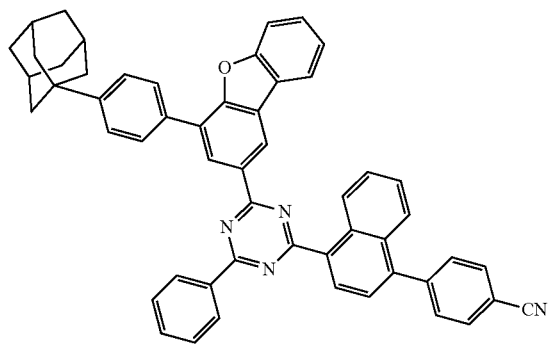
383

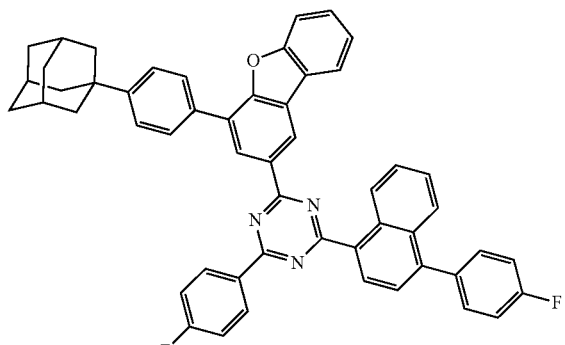
384

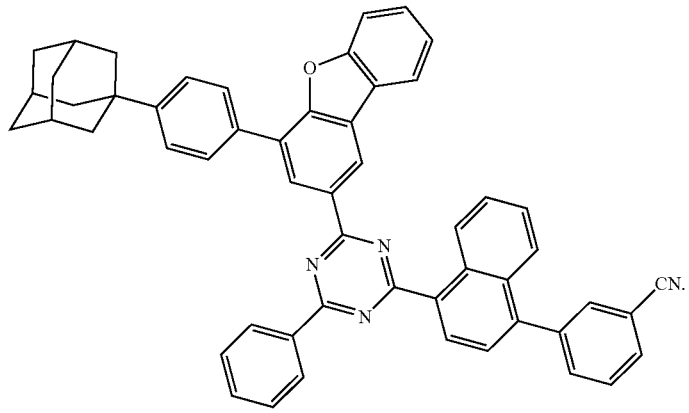
385

The present disclosure does not specifically limit the synthesis method of the organic compound provided, and a person skilled in the art may determine a suitable synthesis method according to the organic compound in conjunction with the preparation methods provided in the synthesis example sections of the present disclosure. In other words, the synthesis example sections of the present disclosure provide example methods for the preparation of organic compounds using raw materials that may be obtained commercially or by methods well known in the art. All organic compounds provided herein may be obtained by those skilled in the art in accordance with these example preparation methods, and all specific preparation methods for preparing the organic compounds will not be described in detail herein, which shall not be construed as limiting this present disclosure by the person skilled in the art.

A second aspect of the present disclosure provides an electronic element, comprising an anode, a cathode which is arranged oppositely to the anode, and a functional layer disposed between the anode and the cathode. The functional layer comprises the organic compound according to the first aspect of the present disclosure.

The organic compounds provided in the present disclosure may be used to form at least one organic film layer in the functional layer, so as to improve the efficiency and lifetime characteristics of the electronic element.

In a specific embodiment, the functional layer comprises an organic light-emitting layer, and the organic light-emitting layer comprises the organic compound. Typically, the organic light-emitting layer may comprise a host material and a guest material, where the host material comprises the organic compound of the present disclosure.

According to an embodiments of the present disclosure, the electronic element is an organic electroluminescent device, for example, a green light device, a blue light device, or a red light device. As shown in FIG. 1, the organic electroluminescent device may comprise an anode 100, a first hole transport layer 321, a second hole transport layer 322, an organic light-emitting layer 330 as an energy conversion layer, an electron transport layer 340, and a cathode 200, which are sequentially stacked.

Optionally, the anode 100 comprises an anode material, which is preferably a material having a large work function that facilitates injection of holes into the functional layer. Specific examples of the anode material contain metals such as nickel, platinum, vanadium, chromium, copper, zinc, and gold or alloys thereof; metal oxides such as zinc oxide, indium oxide, indium tin oxide (ITO), and indium zinc oxide (IZO); combined metals and oxides such as ZnO:Al or SnO$_2$:Sb; or conductive polymers such as poly(3-methylthiophene), poly[3,4-(ethylidene-1,2-dioxy)thiophene] (PEDT), polypyrrole and polyaniline, but are not limited thereto. It is preferable to contain a transparent electrode containing indium tin oxide (ITO) as an anode.

Optionally, the first hole transport layer 321 and the second hole transport layer 322 include one or more hole transport materials, respectively. The hole transport material may be selected from carbazole polymers, carbazole-linked triarylamines, or other types of compounds.

Optionally, the organic light-emitting layer 330 may be composed of a single light-emitting material, or may comprise a host material and a guest material. The host material of the organic light-emitting layer may comprise the organic compound of the present disclosure. Further alternatively, the organic light-emitting layer 330 is composed of a host material and a guest material, and holes injected into the organic light-emitting layer 330 and electrons injected into the organic light-emitting layer 330 may be combined in the organic light-emitting layer 330 to form excitons that transfer energy to the host material, which in turn transfers energy to the guest material, thereby enabling the guest material to emit light.

The guest material of the organic light-emitting layer 330 may be a compound having a condensed aryl ring or a derivative thereof, a compound having a heteroaryl ring or a derivative thereof, an aromatic amine derivative, or other material, but is not particularly limited by the present disclosure. According to a specific embodiment, the organic electroluminescent device is a green light device, in which the organic light-emitting layer comprises a host material and a guest material. The host material is a dual-host light-emitting material, i.e., including a p type host material and a n type host material. The organic compound of the present disclosure may be, for example, a n type host material. According to another specific embodiment, the organic electroluminescent device is a red light device.

The electron transport layer 340 may be a monolayer structure or a multilayer structure, and may comprise one or more electron transport materials. The electron transport material may be selected from, but not limited to, benzimidazole derivatives, oxadiazole derivatives, quinoxaline derivatives, or other electron transport materials. In an embodiment of the present disclosure, the electron transport layer 340 may be composed of ET-1 (with a structure shown in Table 7) and LiQ. In another embodiment of the present disclosure, the electron transport layer 340 may be composed of DBimiBphen and LiQ together.

In the present disclosure, the cathode 200 may comprise a cathode material, which is a material having a small work function that facilitates injection of electrons into the functional layer. Specific examples of the cathode material contain, but are not limited to, metals such as magnesium, calcium, sodium, potassium, titanium, indium, yttrium, lithium, gadolinium, aluminum, silver, tin, and lead, or alloys thereof; or multilayer materials such as LiF/Al, Liq/Al, LiO$_2$/Al, LiF/Ca, LiF/Al and BaF$_2$/Ca. It is preferable to contain a metal electrode containing magnesium and silver as a cathode.

Optionally, a hole injection layer 310 may further be disposed between the anode 100 and the first hole transport layer 321, as shown in FIG. 1, so as to enhance the ability to inject holes into the first hole transport layer 321. The hole injection layer 310 may apply a benzidine derivative, a star-exploded arylamine compound, a phthalocyanine derivative, or other material, and is not particularly limited by the present disclosure. For example, the hole injection layer 310 may be composed of HAT-CN, 1T-NATA, NATA, or NPAPF.

Optionally, an electron injection layer 350 may further be disposed between the cathode 200 and the electron transport layer 340, as shown in FIG. 1, so as to enhance the ability to inject electrons into the electron transport layer 340. The electron injection layer 350 may include an inorganic material such as an alkali metal sulfide, an alkali metal halide, or a complex of alkali metal and organic substance. For example, the electron injection layer 350 may contain LiQ, Yb, or a composition comprising Mg and LiF.

A third aspect of the present disclosure provides an electronic device comprising the electronic element according to the second aspect of the present disclosure.

Figure 2:
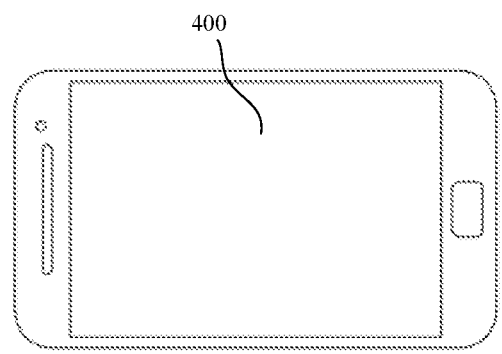
FIG. 2 is a schematic structural view of an electronic device according to an embodiment of the present disclosure.

According to an embodiment, the electronic device is an electronic device 400 comprising the organic electroluminescent device above described, as shown in FIG. 2. The electronic device 400 may be, for example, a display device, a lighting device, an optical communication device, or other type of electronic device, and may comprise, for example, but not limited to, a computer screen, a mobile phone screen, a television, an electronic paper, an emergency light, an optical module, or the like.

The compounds of the present disclosure for which no synthetic method is mentioned are raw products obtained by commercial routes.

The methods for synthesizing the organic compounds according to the present disclosure will now be described in detail with reference to the synthesis examples.

The compounds of the present disclosure were synthesized using the following method.

Preparation Example 1. Preparation of Compound 1

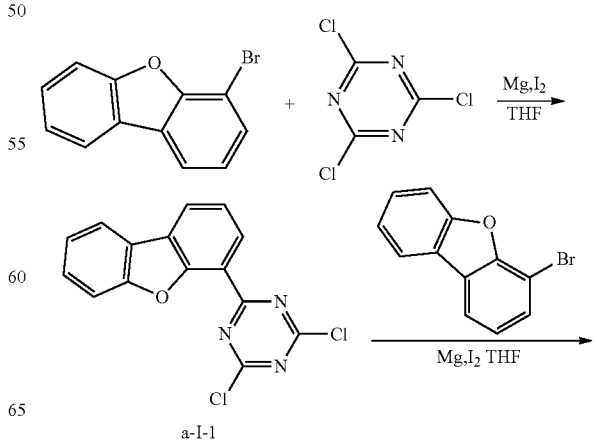

a-I-1

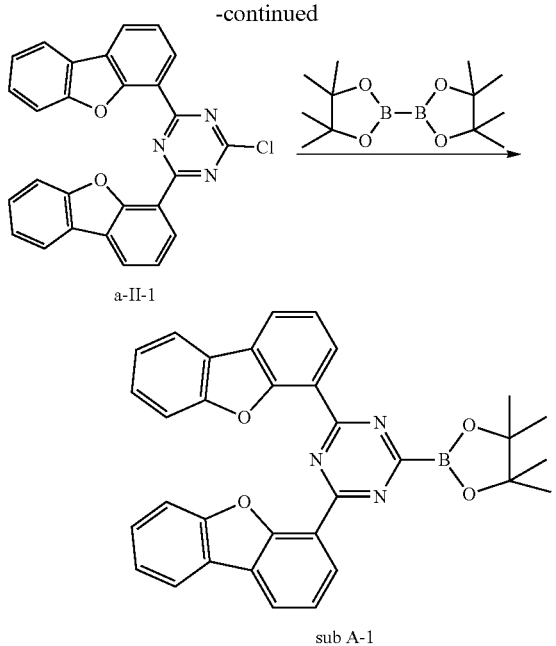

a-II-1 sub A-1

1) Synthesis of Intermediate a-I-1

Magnesium sheets (2.9 g, 120 mmol) and 30 mL of tetrahydrofuran (THF) were added to a three-necked flask under the protection of $N_2$, and the system was raised to a temperature of 80° C. Iodine (0.6 g, 2.4 mmol) and 4-bromodibenzofuran (30.0 g, 120 mmol) were added slowly to the system dropwise within 30 min and dissolved completely in the 30 mL of THF solvent, while controlling the temperature at 80° C. during the addition. After the completion of addition, the reaction was stirred at 80° C. for 2h to obtain a mixed solution. The mixed solution was cooled at room temperature, and then 2,4,6-trichloro-1,3,5-triazine (22.3 g, 120 mmol) dissolved in 80 mL of THF was added dropwise into the mixed solution, and stirred for 3 hours. Then, the reaction was completed to obtain a reaction solution. The reaction solution was extracted with toluene (200 mL). The organic phases were combined, an organic layer was dried with anhydrous magnesium sulfate, filtering was conducted, and distillation under reduced pressure was conducted for concentration. The obtained crude product was purified by silica gel column chromatography, recrystallized with methanol and filtered to obtain the intermediate a-I-1 (24.2 g, yield: 63%) as a solid.

2) Synthesis of Intermediate a-II-1

Magnesium sheets (1.52 g, 63.7 mmol) and 30 mL of THF were added to a three-necked flask under the protection of $N_2$, and the temperature in the system was raised to 80° C. Iodine (0.32 g, 1.26 mmol) was added to the system. Compound 4-bromodibenzofuran (15.73 g, 63.7 mmol) was added slowly to the system dropwise within 30 min and dissolved completely in the 30 mL of THF solvent, while controlling the temperature at 80° C. during the addition. After the completion of addition, the reaction was stirred at 80° C. for 2h to obtain a mixed solution. The mixed solution was cooled at room temperature, added then the intermediate a-I-1 (20.13 g, 63.7 mmol) in 40 mL THF dropwise, and stirred for 3 hours. Then, the reaction was completed to obtain a reaction solution. The reaction solution was extracted with toluene (200 mL). The organic phases were combined, an organic layer was dried with anhydrous magnesium sulfate, filtering was conducted, and distillation under reduced pressure was conducted for concentration. The obtained crude product was purified by silica gel column chromatography, recrystallized with methanol and filtered to obtain the intermediate a-II-1 (22.5 g, yield: 79%) as a solid.

3) Synthesis of Intermediate Sub A-1

Intermediate a-II-1 (12.5 g, 27.9 mmol), bis(pinacolato)diboron (8.5 g, 33.5 mmol), $Pd(dppf)Cl_2$ (0.20 g, 0.27 mmol), and KOAc (6.8 g, 69.7 mmol) were added to 1,4-dioxane (100 mL), and refluxed at a temperature of 80° C. for 12 h. After the reaction was completed, the reaction solution was extracted with $CH_2Cl_2$ and water. The organic layer was dried with $MgSO_4$ and concentrated. The resulting compound was subjected to a silica gel column chromatography and recrystallization to obtain the intermediate sub A-1 (9.2 g, yield: 61%).

4) Synthesis of Sub B-1

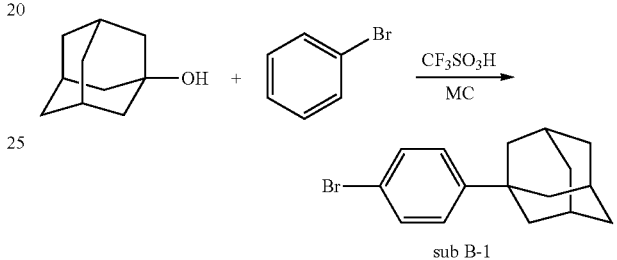

sub B-1

1-adamantanol (50.0 g, 328.4 mmol), bromobenzene (51.6 g, 328.4 mmol) and dichloromethane (500 mL) were added to a round bottom flask, and cooled to −5° C. to 0° C. under nitrogen protection. Trifluoromethanesulfonic acid (73.9 g, 492.6 mmol) was added dropwise under −5° C. to 0° C., and stirred for 3h with maintaining this temperature. The reaction solution was washed with deionized water (300 mL) to pH=7, then extracted by adding dichloromethane (100 mL). The organic phases were combined, dried with anhydrous magnesium sulfate, and filtered, and then a solvent was removed under reduced pressure. The resulting crude product was purified by silica gel column chromatography using n-heptane as a mobile phase to obtain the sub B-1 (53.1 g, yield: 55%) as a white solid.

5) Preparation of Compound 1

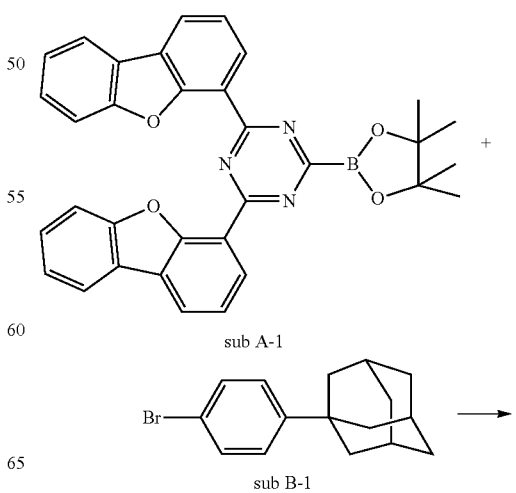

sub A-1 sub B-1

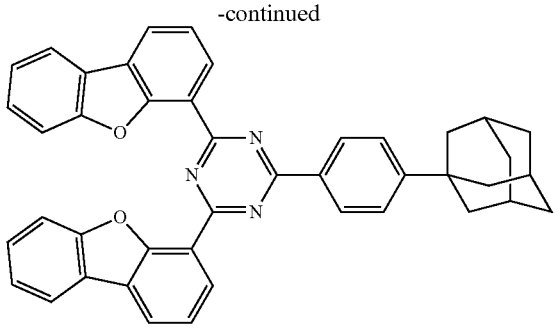

1

Intermediate sub A-1 (9.0 g, 15.8 mmol), sub B-1 (4.6 g, 15.7 mmol), tetrakis(triphenylphosphine)palladium (0.4 g, 0.13 mmol), potassium carbonate (5.5 g, 39.7 mmol), tetrabutylammonium bromide (0.1 g, 0.4 mmol), toluene (48 mL), ethanol (24 mL) and deionized water (12 mL) were added to a three-necked flask, warmed to 75° C. to 80° C. under nitrogen protection, and subjected to heating reflux stirring for 8 h. After completion of the reaction, the resulting reaction solution was cooled to room temperature, and extracted by adding toluene (100 mL). The organic phases were combined, and an organic layer was dried with anhydrous magnesium sulfate, filtered, and concentrated. The crude was purified by silica gel column chromatography to obtain the compound 1 (6.0 g, yield: 61%) as a solid. Mass spectrometry: M/z=624.26[M+H]$^+$.

Synthesis of Intermediate Sub B-I

The intermediate sub B-I listed in Table 1 was prepared with reference to the preparation method of sub B-1 in Preparation Example 1, except that each raw material A was used instead of the raw material bromobenzene in the preparation of the intermediate sub B-1, where the raw material A used, the structure of target intermediate synthesized, and the yield thereof were shown in Table 1.

TABLE 1

| Sub B-1 No. | 1-adamantanol | Raw material A | Structure of sub B-1 | Yield/% |
|---|---|---|---|---|
| sub B-2 | ![adamantanol] | ![4-bromobiphenyl] | ![structure] | 74 |
| sub B-3 | | ![1-bromonaphthalene] | ![structure] | 69 |
| sub B-4 | | ![3-bromotoluene] | ![structure] | 65 |
| sub B-56 | ![adamantanol] | ![structure] | ![structure] | 40 |

Synthesis of Intermediate sub A-I

The intermediate sub A-I listed in Table 2 was prepared with reference to the preparation method (steps 1) to 3)) of the intermediate sub A-1 of Preparation Example 1, except that the raw material 4-bromodibenzofuran in the preparation of intermediate a-I-1 was replaced with each raw material B, the raw material 4-bromodibenzofuran in the preparation of intermediate a-II-1 was replaced with each raw material C, and the major raw materials used, the target intermediate synthesized and the structure thereof, and the yield from the final step were shown in Table 2.

TABLE 2

| Sub A-1 No. | Raw material B | Raw material C |
|---|---|---|
| sub A-2 | 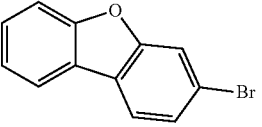 [SMILES: Brc1ccc2c(c1)oc1ccccc12] | 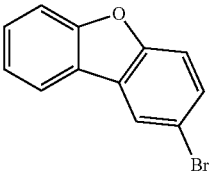 [SMILES: Brc1ccc2oc3ccccc3c2c1] |
| Sub A-3 | 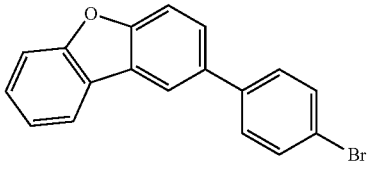 [SMILES: Brc1ccc(-c2ccc3oc4ccccc4c3c2)cc1] | 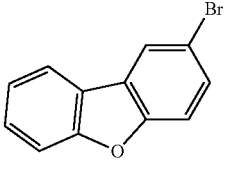 [SMILES: Brc1ccc2oc3ccccc3c2c1] |
| sub A-4 | 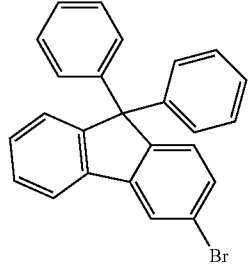 [SMILES: Brc1ccc2c(c1)-c1ccccc1C2(c1ccccc1)c1ccccc1] | 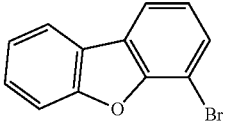 |
| sub A-5 | 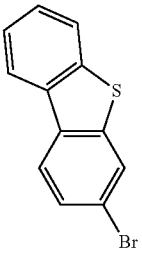 [SMILES: Brc1ccc2c(c1)sc1ccccc12] | 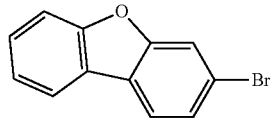 [SMILES: Brc1ccc2c(c1)oc1ccccc12] |
| sub A-6a | 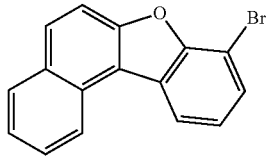 [SMILES: Brc1cccc2c1oc1ccc3ccccc3c12] | 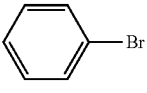 |
| sub A-7a | 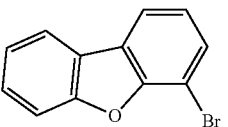 [SMILES: Brc1cccc2c1oc1ccccc12] | 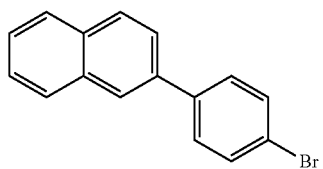 [SMILES: Brc1ccc(-c2ccc3ccccc3c2)cc1] |
| sub A-8a | 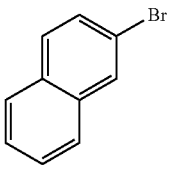 [SMILES: Brc1ccc2ccccc2c1] | 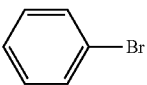 |

TABLE 2-continued
| | | |
|---|---|---|
| sub A-9a | 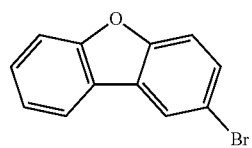 [SMILES: Brc1ccc2oc3ccccc3c2c1] | 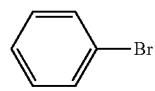 |
| sub A-10a | 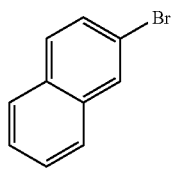 [SMILES: Brc1ccc2ccccc2c1] | 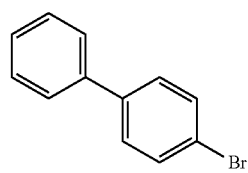 [SMILES: Brc1ccc(-c2ccccc2)cc1] |
| sub A-12a | 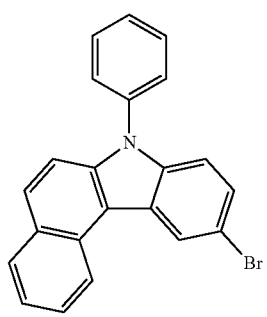 [SMILES: Brc1ccc2c(c1)c1c3ccccc3ccc1n2-c1ccccc1] | 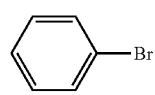 |
| sub A-13a | 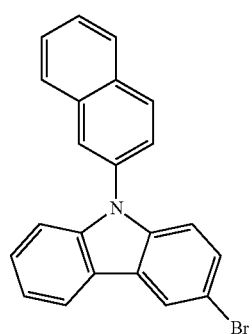 [SMILES: Brc1ccc2c(c1)c1ccccc1n2-c1ccc2ccccc2c1] | 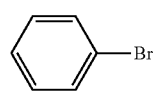 |
| sub A-14a | 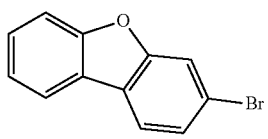 [SMILES: Brc1ccc2c(c1)oc1ccccc12] |  |
| sub A-15a | 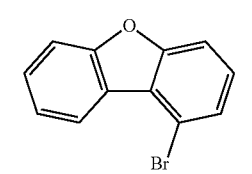 [SMILES: Brc1cccc2oc3ccccc3c12] | 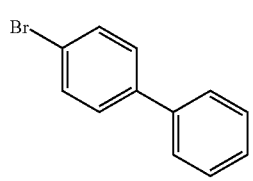 [SMILES: Brc1ccc(-c2ccccc2)cc1] |
| sub A-21 | 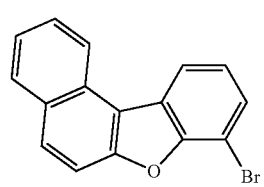 [SMILES: Brc1cccc2c1oc1ccc3ccccc3c12] | 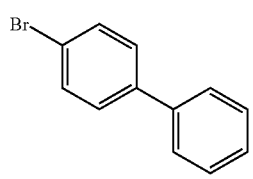 |

TABLE 2-continued
sub A-22
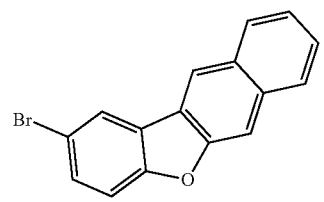 [SMILES: Brc1ccc2oc3cc4ccccc4cc3c2c1]
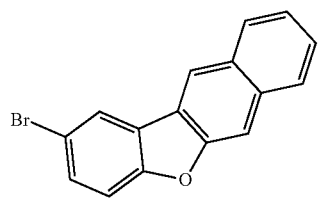 [SMILES: Brc1ccc2oc3cc4ccccc4cc3c2c1]
sub A-23
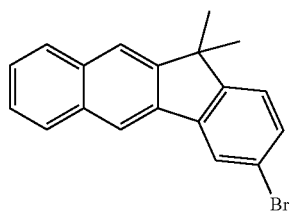 [SMILES: CC1(C)c2ccc(Br)cc2-c2cc3ccccc3cc21]
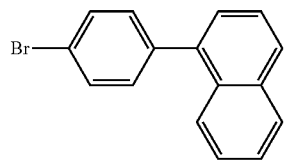 [SMILES: Brc1ccc(-c2cccc3ccccc23)cc1]
sub A-24
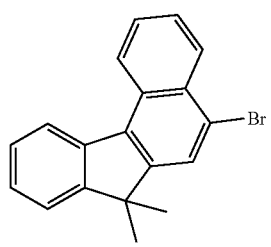 [SMILES: CC1(C)c2ccccc2-c2c1cc(Br)c1ccccc21]
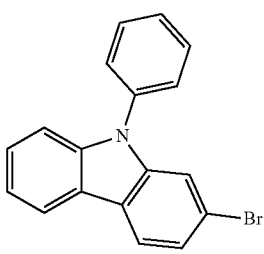 [SMILES: Brc1ccc2c3ccccc3n(-c3ccccc3)c2c1]
| Sub A-1 No. | Structure of sub A-1 | Yield/% |
|---|---|---|
| sub A-2 | 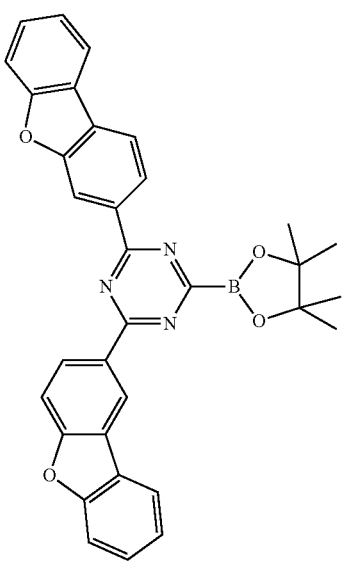 [SMILES: CC1(C)OB(c2nc(-c3ccc4c(c3)oc3ccccc34)nc(-c3ccc4oc5ccccc5c4c3)n2)OC1(C)C] | 54 |

TABLE 2-continued
sub A-3 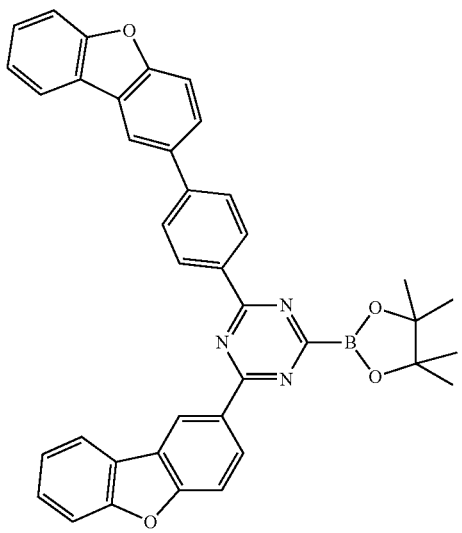 [SMILES: CC1(C)OB(c2nc(-c3ccc(-c4ccc5oc6ccccc6c5c4)cc3)nc(-c3ccc4oc5ccccc5c4c3)n2)OC1(C)C] 53
sub A-4 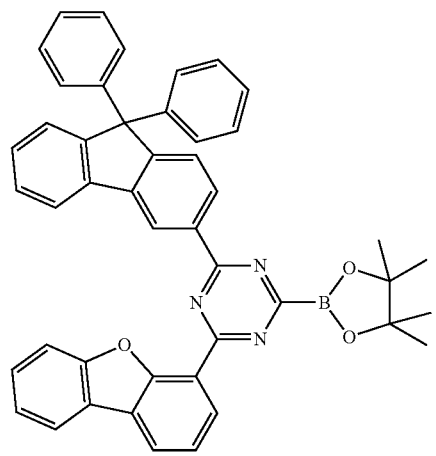 [SMILES: CC1(C)OB(c2nc(-c3ccc4c(c3)-c3ccccc3C4(c3ccccc3)c3ccccc3)nc(-c3cccc4c3oc3ccccc34)n2)OC1(C)C] 62
sub A-5 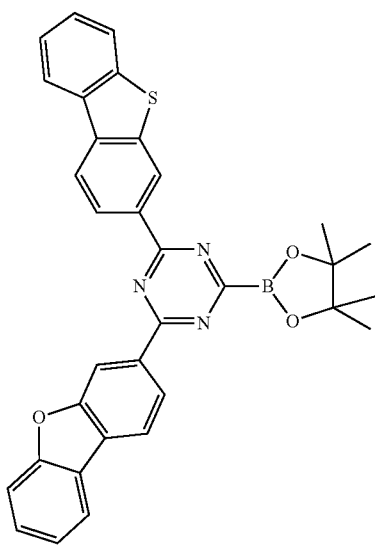 [SMILES: CC1(C)OB(c2nc(-c3ccc4c(c3)oc3ccccc34)nc(-c3ccc4c(c3)sc3ccccc34)n2)OC1(C)C] 57

TABLE 2-continued
| sub A-6a | 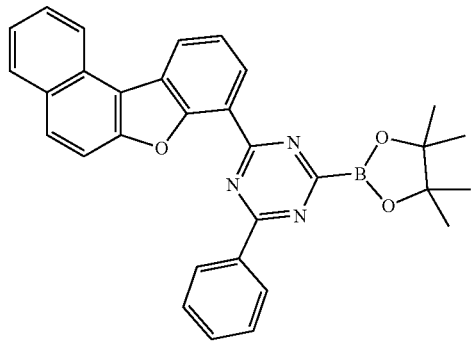 [SMILES: CC1(C)OB(c2nc(-c3ccccc3)nc(-c3cccc4c3oc3ccc5ccccc5c34)n2)OC1(C)C] | 41 |
| sub A-7a | 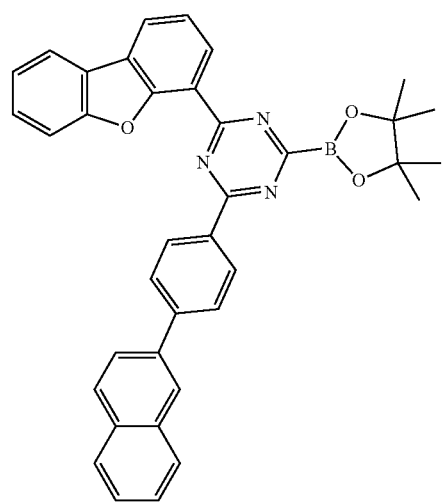 [SMILES: CC1(C)OB(c2nc(-c3ccc(-c4ccc5ccccc5c4)cc3)nc(-c3cccc4c3oc3ccccc34)n2)OC1(C)C] | 45 |
| sub A-8a | 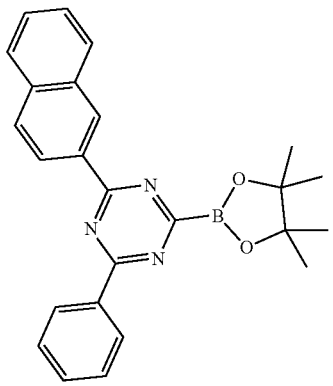 [SMILES: CC1(C)OB(c2nc(-c3ccccc3)nc(-c3ccc4ccccc4c3)n2)OC1(C)C] | 51 |
| sub A-9a | 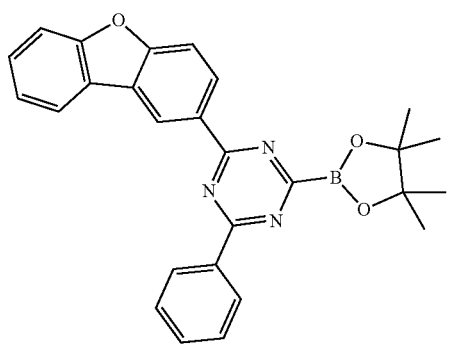 [SMILES: CC1(C)OB(c2nc(-c3ccccc3)nc(-c3ccc4oc5ccccc5c4c3)n2)OC1(C)C] | 53 |

251 252
TABLE 2-continued
| sub A-10a | 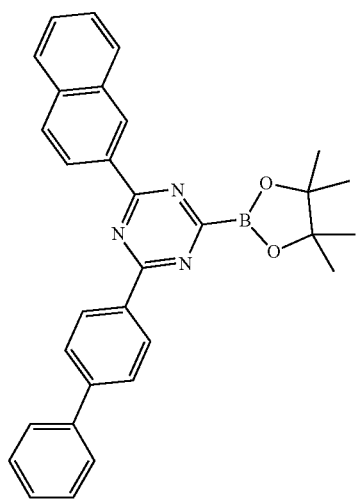 [SMILES: CC1(C)OB(c2nc(-c3ccc(-c4ccccc4)cc3)nc(-c3ccc4ccccc4c3)n2)OC1(C)C] | 40 |
| sub A-12a | 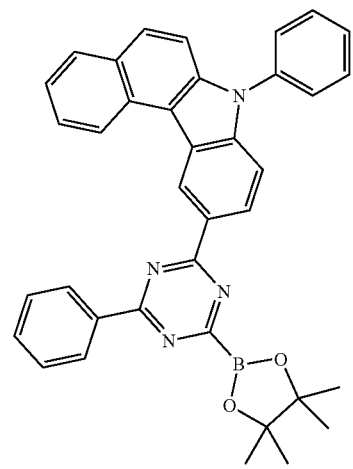 [SMILES: CC1(C)OB(c2nc(-c3ccccc3)nc(-c3ccc4c(c3)c3c5ccccc5ccc3n4-c3ccccc3)n2)OC1(C)C] | 39 |
| sub A-13a | 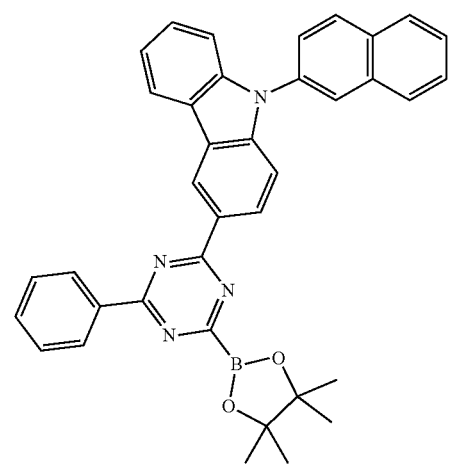 [SMILES: CC1(C)OB(c2nc(-c3ccccc3)nc(-c3ccc4c(c3)c3ccccc3n4-c3ccc4ccccc4c3)n2)OC1(C)C] | 40 |

TABLE 2-continued
sub A-14a 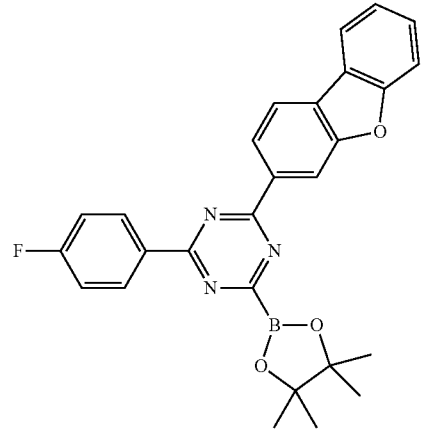 [SMILES: CC1(C)OB(c2nc(-c3ccc(F)cc3)nc(-c3ccc4c(c3)oc3ccccc34)n2)OC1(C)C] 45
sub A-15a 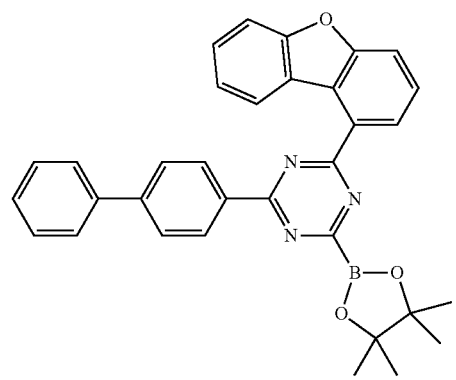 [SMILES: CC1(C)OB(c2nc(-c3ccc(-c4ccccc4)cc3)nc(-c3cccc4oc5ccccc5c34)n2)OC1(C)C] 56
sub A-21 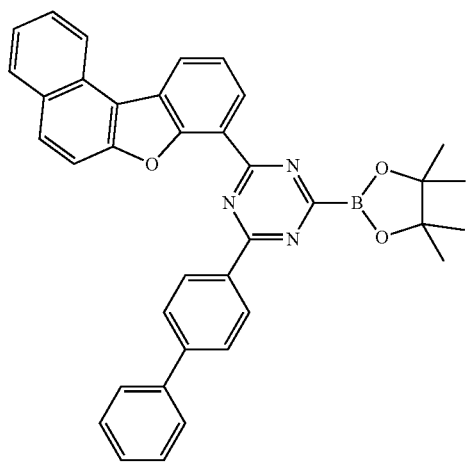 [SMILES: CC1(C)OB(c2nc(-c3ccc(-c4ccccc4)cc3)nc(-c3cccc4c3oc3ccc5ccccc5c34)n2)OC1(C)C] 45

TABLE 2-continued
| sub A-22 | 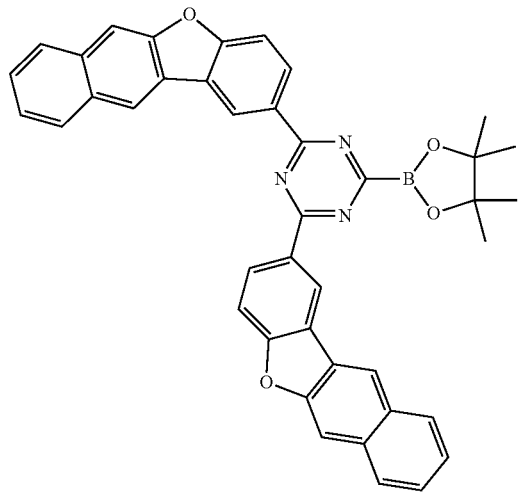 [SMILES: CC1(C)OB(c2nc(-c3ccc4oc5cc6ccccc6cc5c4c3)nc(-c3ccc4oc5cc6ccccc6cc5c4c3)n2)OC1(C)C] | 42 |
| sub A-23 | 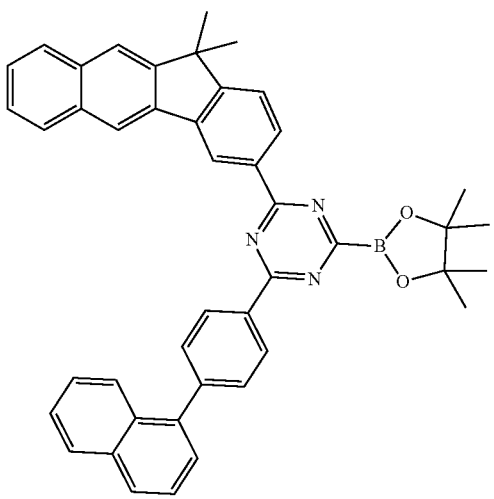 [SMILES: CC1(C)c2ccc(-c3nc(B4OC(C)(C)C(C)(C)O4)nc(-c4ccc(-c5cccc6ccccc56)cc4)n3)cc2-c2cc3ccccc3cc21] | 54 |
| sub A-24 | 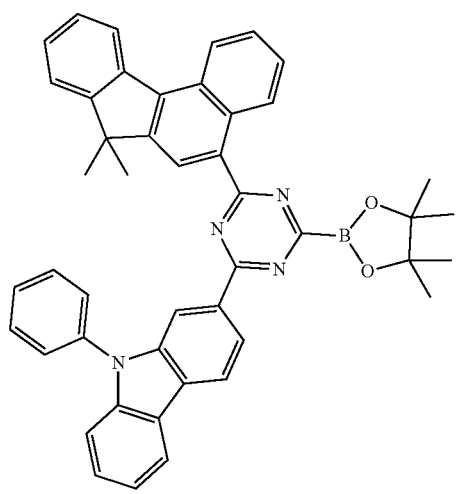 [SMILES: CC1(C)c2ccccc2-c2c1cc(-c1nc(B3OC(C)(C)C(C)(C)O3)nc(-c3ccc4c5ccccc5n(-c5ccccc5)c4c3)n1)c1ccccc21] | 58 |

Preparation Examples 2 to 13

The compounds in Table 3 were synthesized with reference to the method of Preparation Example 1, except that the intermediate sub A-I synthesized as described above was used instead of the intermediate sub A-1, and the intermediate sub B-I was used instead of the intermediate sub B-1. The major raw materials used and the yield, structures and mass spectrum characterization results of compounds were shown in Table 3.

TABLE 3

| Preparation Example | sub A-I | sub B-I |
|---|---|---|
| 2 | 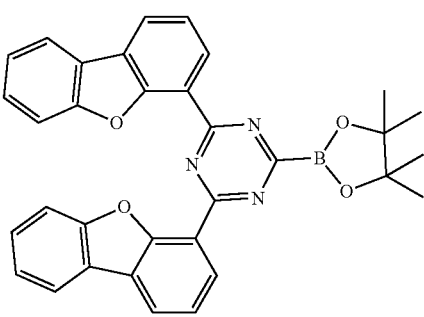<br>sub A-1 | 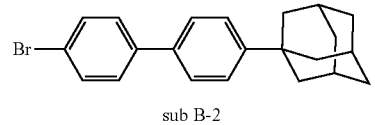 [SMILES: Brc1ccc(-c2ccc(C34CC5CC(CC(C5)C3)C4)cc2)cc1]<br>sub B-2 |
| 3 |  | 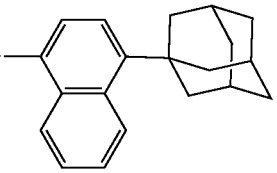<br>sub B-3 |
| 4 | 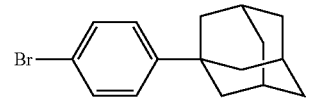<br>sub A-2 | 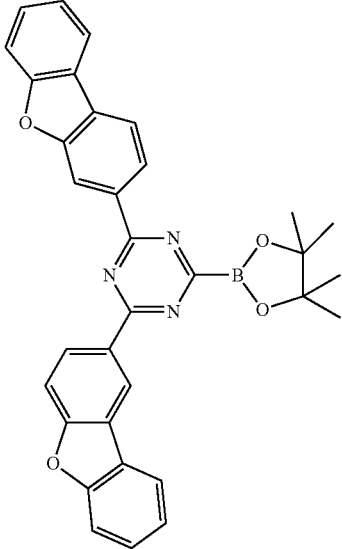<br>sub B-1 |

TABLE 3-continued
5
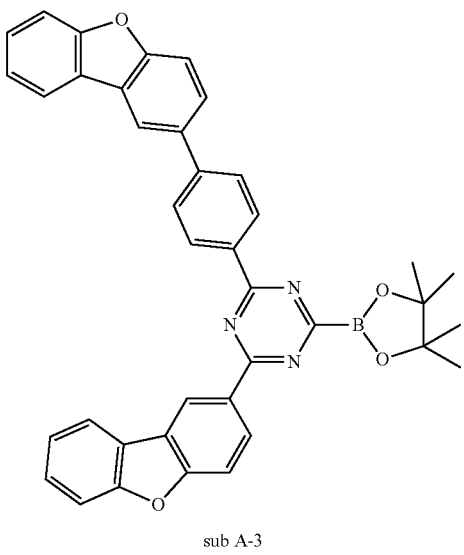 [SMILES: CC1(C)OB(c2nc(-c3ccc(-c4ccc5oc6ccccc6c5c4)cc3)nc(-c3ccc4oc5ccccc5c4c3)n2)OC1(C)C]
sub A-3
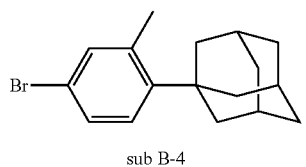 [SMILES: Cc1cc(Br)ccc1C12CC3CC(CC(C3)C1)C2]
sub B-4
6
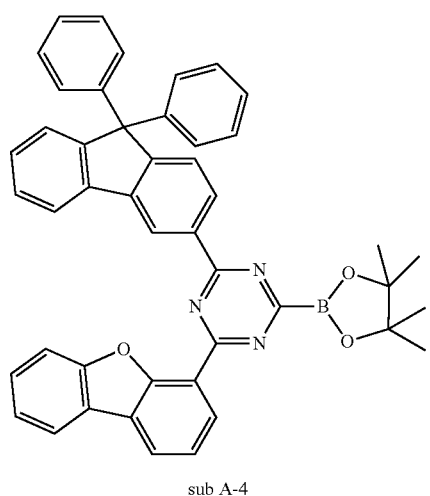 [SMILES: CC1(C)OB(c2nc(-c3ccc4c(c3)-c3ccccc3C4(c3ccccc3)c3ccccc3)nc(-c3cccc4c3oc3ccccc34)n2)OC1(C)C]
sub A-4
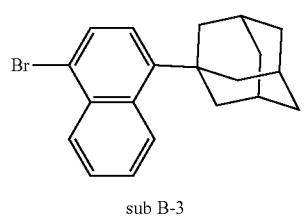 [SMILES: Brc1ccc(C23CC4CC(CC(C4)C2)C3)c2ccccc12]
sub B-3
7
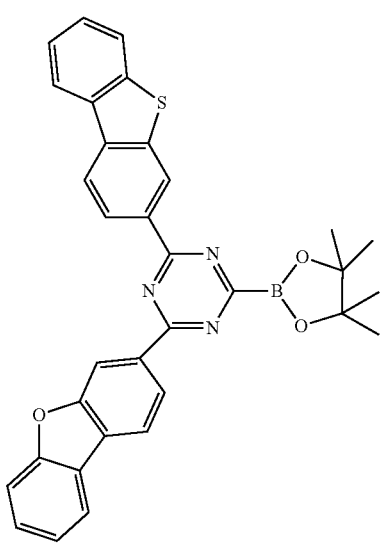
sub A-5
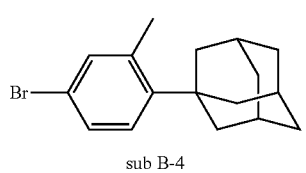 [SMILES: Cc1cc(Br)ccc1C12CC3CC(CC(C3)C1)C2]
sub B-4

TABLE 3-continued
8
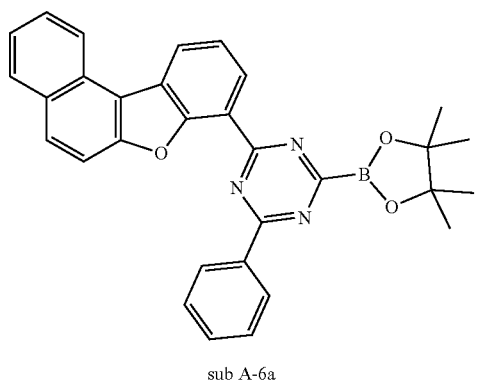 [SMILES: CC1(C)OB(c2nc(-c3ccccc3)nc(-c3cccc4c3oc3ccc5ccccc5c34)n2)OC1(C)C]
sub A-6a
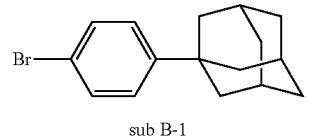 [SMILES: Brc1ccc(C23CC4CC(CC(C4)C2)C3)cc1]
sub B-1
9
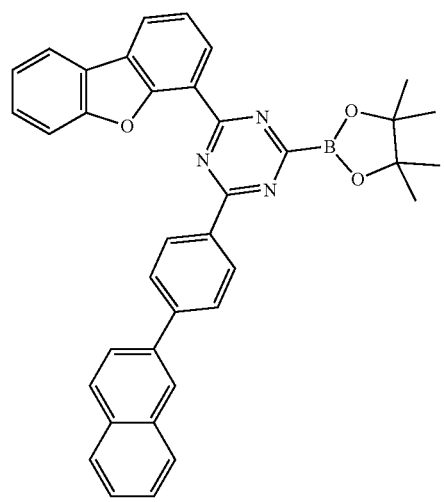
sub A-7a
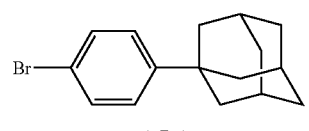
sub B-1
10
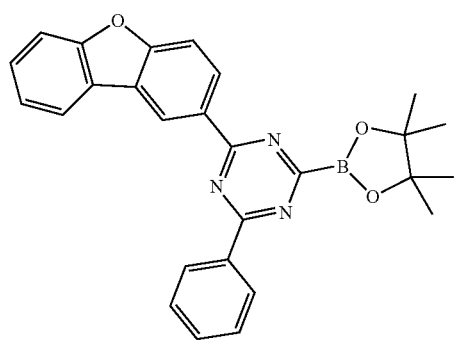
sub A-9a
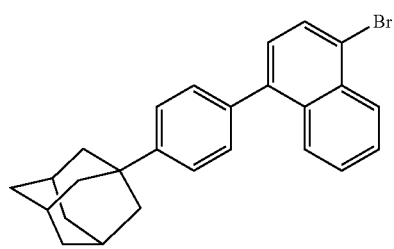
sub B-5b TABLE 3-continued
11 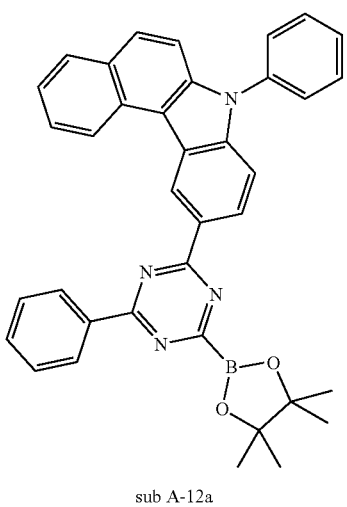 [SMILES: CC1(C)OB(c2nc(-c3ccccc3)nc(-c3ccc4c(c3)c3c5ccccc5ccc3n4-c3ccccc3)n2)OC1(C)C] sub A-12a
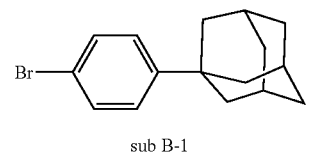 [SMILES: Brc1ccc(C23CC4CC(CC(C4)C2)C3)cc1] sub B-1
12 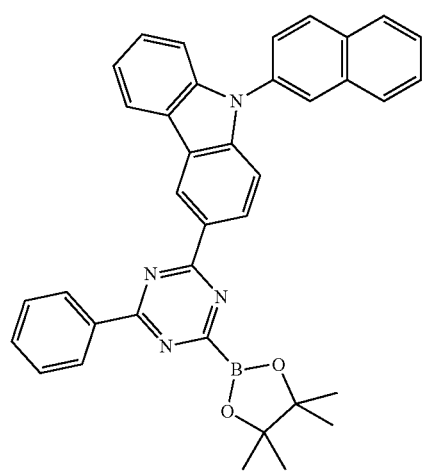 sub A-13a
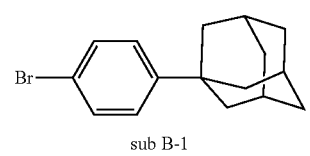 [SMILES: Brc1ccc(C23CC4CC(CC(C4)C2)C3)cc1] sub B-1
13 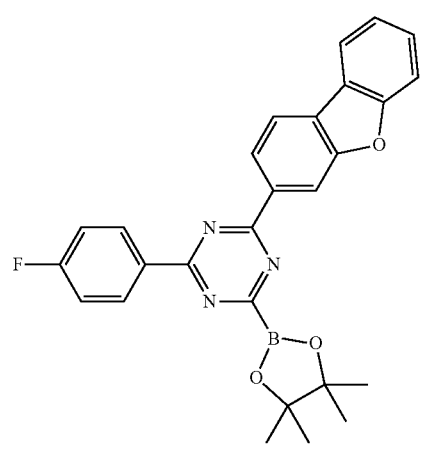 sub A-14a
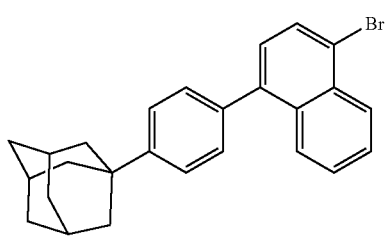 sub B-5b TABLE 3-continued
14
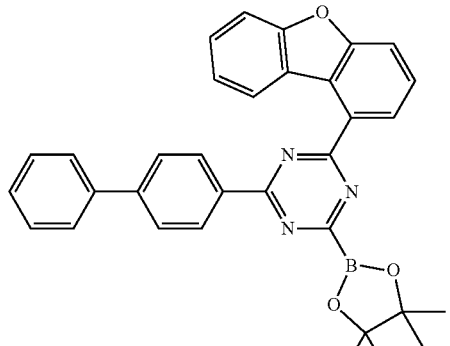
sub A-15a
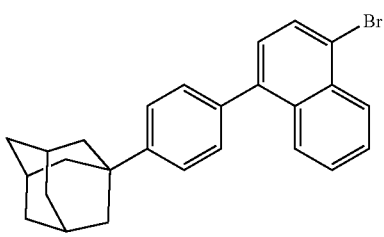
sub B-5b
| Preparation Example | Compound | Yield/% | mass spectrum (m/z), [M + H]+ |
|---|---|---|---|
| 2 | 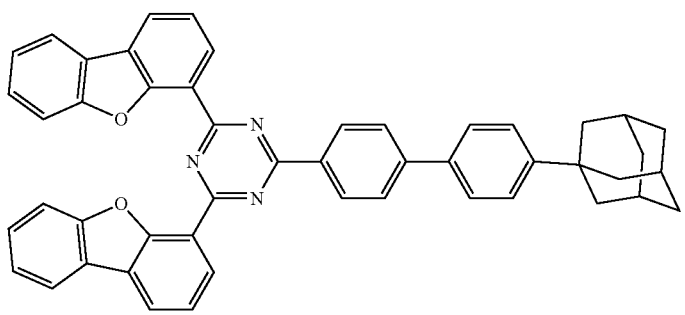<br>34 | 65 | 700.29 |
| 3 | 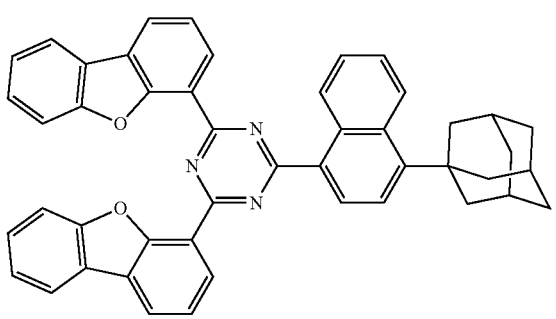<br>43 | 66 | 674.27 |

TABLE 3-continued
| | | | |
|---|---|---|---|
| 4 | 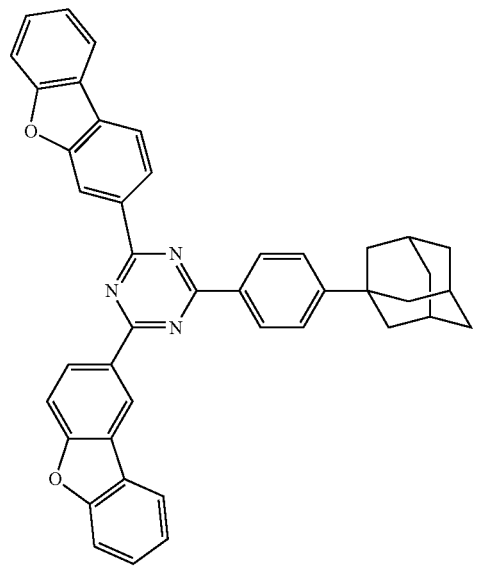 | 65 | 776.32 |
| 5 | 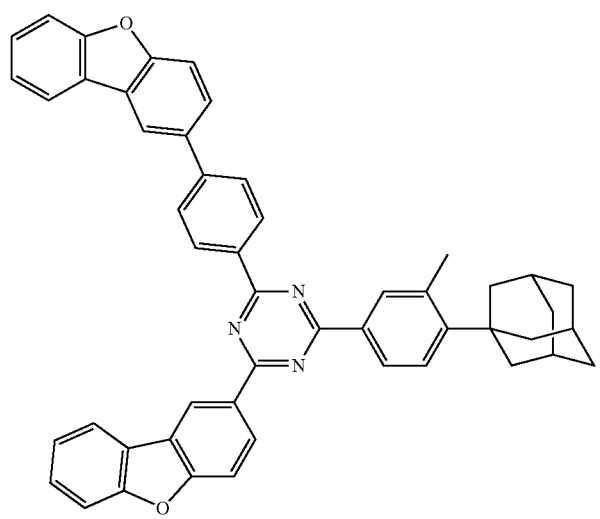 | 63 | 714.30 |
5
6

TABLE 3-continued
| | | | |
|---|---|---|---|
| 6 | 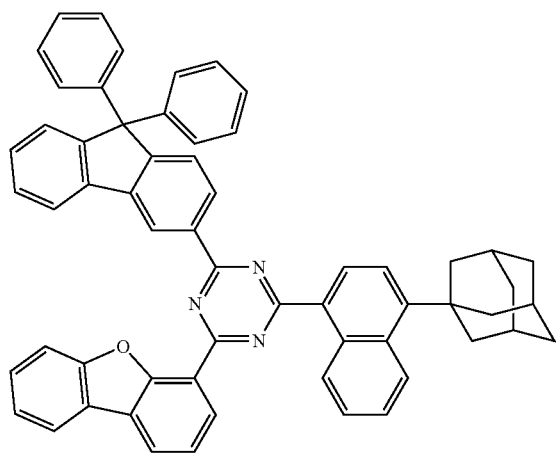<br>16 | 72 | 826.34 |
| 7 | 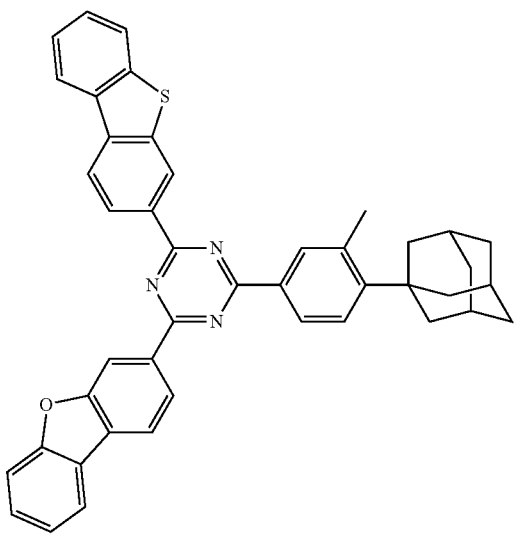<br>352 | 68 | 654.25 |
| 8 | 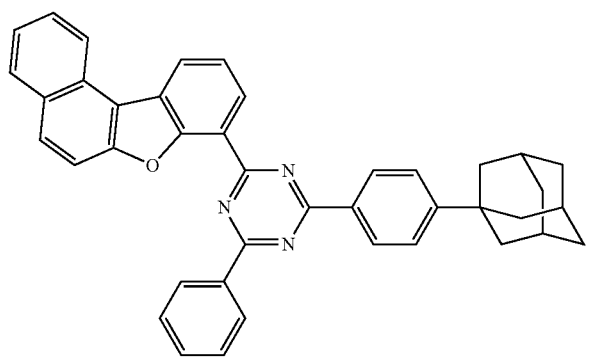<br>362 | 51 | 584.26 |

TABLE 3-continued
| 9 | 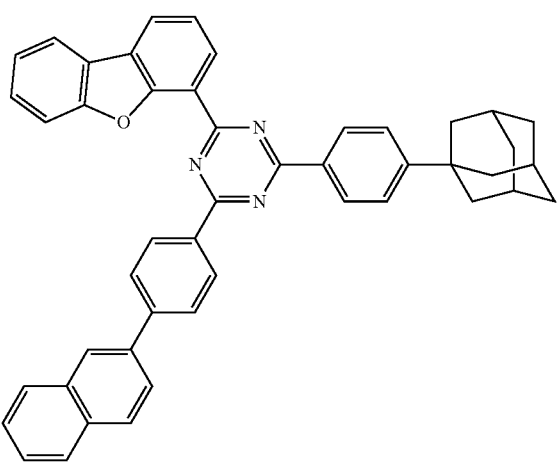 363 | 48 | 660.29 |
| 10 | 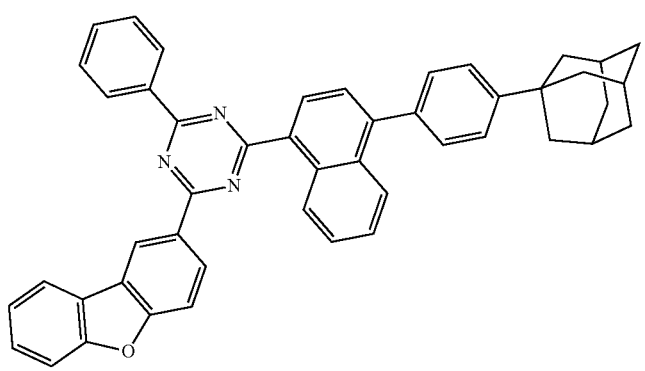 369 | 44 | 660.29 |
| 11 | 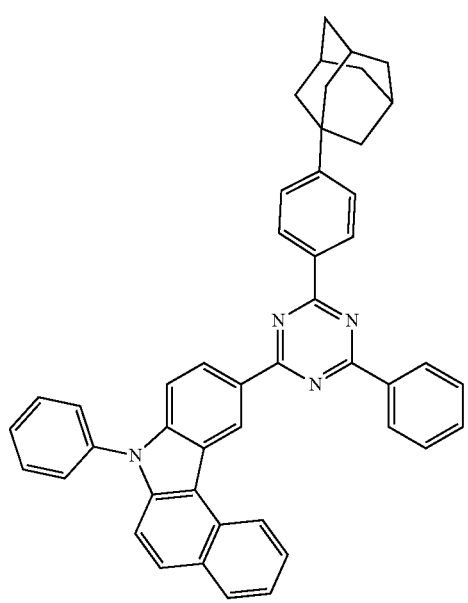 370 | 47 | 659.31 |

TABLE 3-continued
| | | | | |
|---|---|---|---|---|
| 12 | 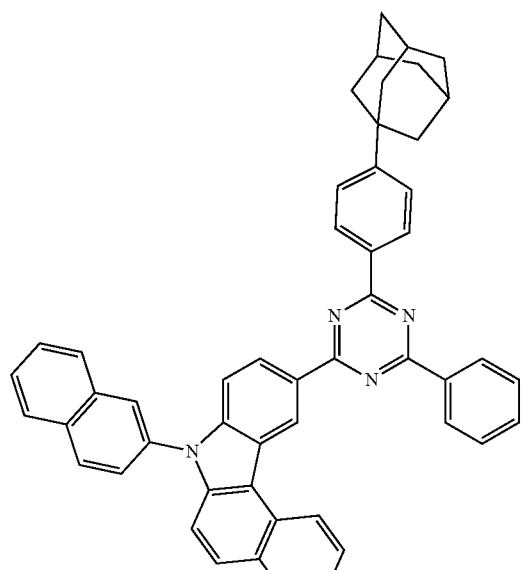 371 | | 43 | 659.31 |
| 13 | 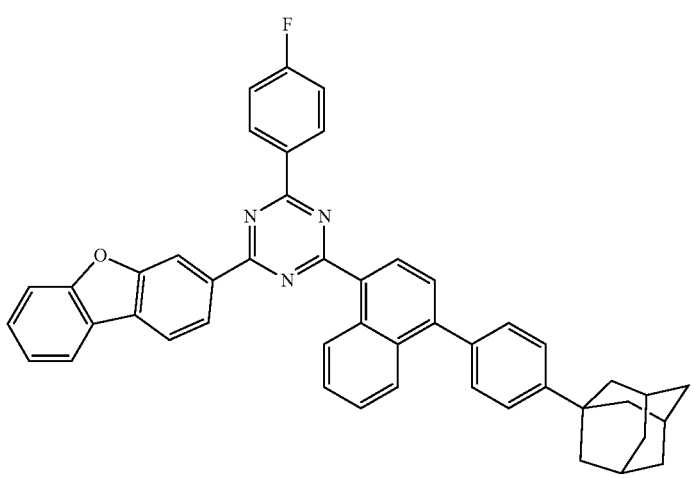 378 | | 42 | 678.28 |
| 14 | 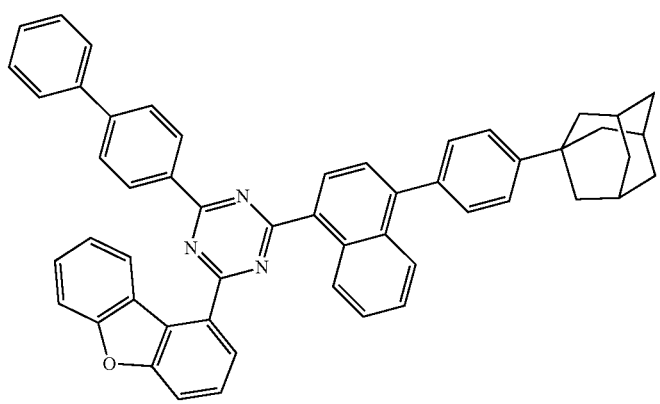 381 | | 42 | 678.28 |

Preparation Example 15. Preparation of Compound 56

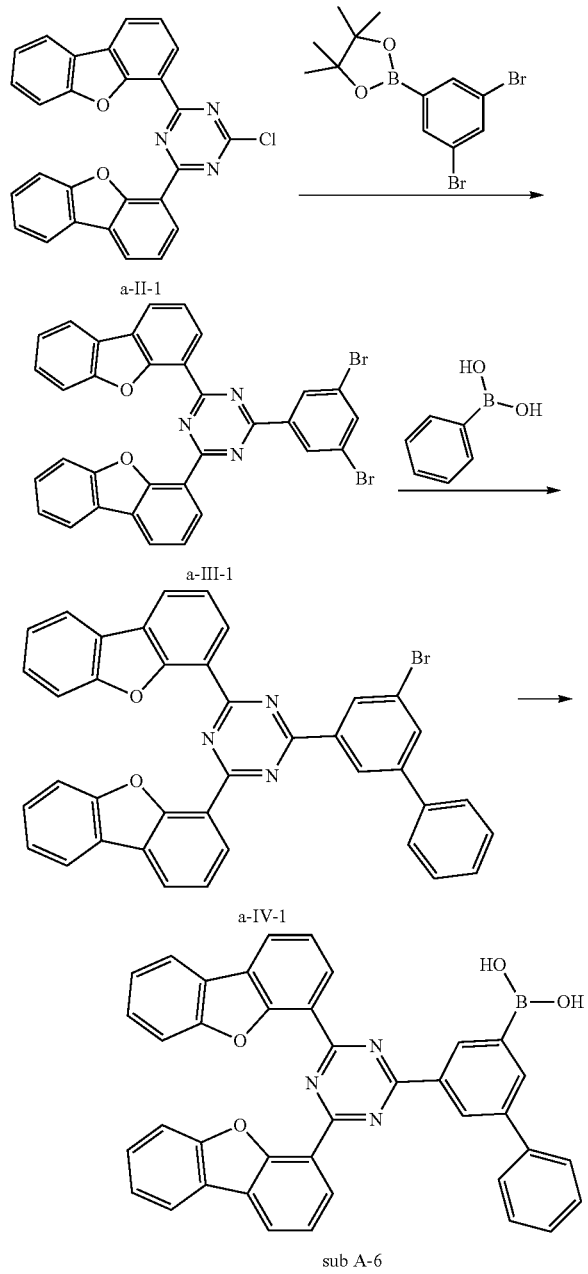

1) Preparation of Intermediate a-III-1

Intermediate a-II-1 (30.0 g, 66.9 mmol), (3,5-dibromophenyl)boronic acid pinacol ester (24.2 g, 66.9 mmol), Pd₂(dba)₃ (0.6 g, 0.6 mmol), x-phos (0.6 g, 1.3 mmol), and KOAc (14.4 g, 147.36 mmol) were added to a three-necked flask. 1,4-dioxane (300 mL) was added, and heated to reflux at a temperature of 80° C. for 8h under nitrogen protection. After the reaction was completed, the reaction solution was extracted with CH₂Cl₂ and water. The organic layer was dried with MgSO₄ and concentrated. The resulting compound was subjected to a silica gel column and recrystallization to obtain the intermediate a-III-1 (26.4 g, yield: 61%).

2) Preparation of Intermediate a-IV-1

Intermediate a-III-1 (26.0 g, 40.1 mmol), phenylboronic acid (4.8 g, 40.1 mmol), tetrakis(triphenylphosphine)palladium (2.3 g, 2.0 mmol), potassium carbonate (12.2 g, 88.3 mmol), tetrabutylammonium bromide (0.1 g, 0.4 mmol), toluene (240 mL), ethanol (120 mL) and deionized water (60 mL) were added to a three-necked flask, warmed up to 75° C.-80° C. under nitrogen protection, and subjected to heating reflux stirring for 15 h. After completion of the reaction, the resulting reaction solution was cooled to room temperature, extracted by adding toluene (200 mL). The organic phases were combined, and an organic layer was dried with anhydrous magnesium sulfate, filtered, and concentrated. The crude product was purified by silica gel column chromatography to obtain the intermediate a-IV-1 (13.5 g, yield: 52%).

3) Preparation of Intermediate Sub A-6

Intermediate a-IV-1 (18.0 g, 27.9 mmol) was added to a round bottom flask, and 180 mL of THF with water removed was added to the flask. The system was cooled to −80° C. to −90° C. with liquid nitrogen, and then n-butyl lithium (1.78 g, 27.9 mmol) was added dropwise, while maintaining the temperature for 1 h after completion of the addition. Trimethyl borate (3.2 g, 30.7 mmol) was added dropwise, and the system was maintained at a temperature of −80° C. to −90° C. After maintaining the temperature for 1 hour from completion of the addition, the system was naturally warmed up to room temperature. After completion of the reaction, 20 mL of aqueous HCl solution (concentration as 2.5 mol/L) was added, and stirred for 0.5 h. The mixture was separated and extracted with dichloromethane and water. The organic phase was washed to neutral (pH=7). The organic phases were combined, dried with anhydrous MgSO₄ for 10 minutes, and filtered, and the filtrate was spin-dried and slurried twice with n-heptane to obtain the intermediate sub A-6 (11.2 g, yield: 66%) as a white solid.

4) Preparation of Compound 56

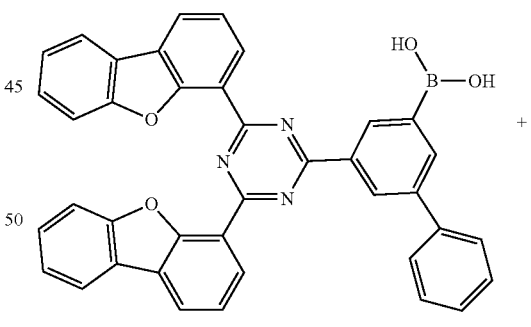

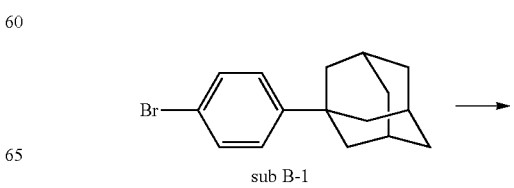

-continued

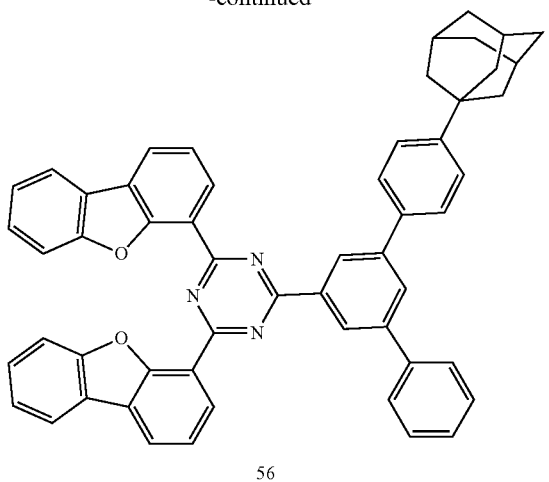

56

Intermediate sub A-6 (10.0 g, 16.4 mmol), sub B-1 (4.7 g, 16.4 mmol), tetrakis(triphenylphosphine)palladium (0.9 g, 0.8 mmol), potassium carbonate (4.9 g, 36.0 mmol), tetra-butylammonium bromide (0.05 g, 0.16 mmol), toluene (80 mL), ethanol (40 mL) and deionized water (20 mL) were added to a three-necked flask, warmed up to 75° C.-80° C. under nitrogen protection, and then subjected to heating reflux stirring for 8 h. After completion of the reaction, the resulting reaction solution was cooled to room temperature, and extracted by adding toluene (100 mL). The organic phases were combined, and an organic layer was dried with anhydrous magnesium sulfate, filtered, and concentrated. The crude product was purified by silica gel column chromatography to obtain the compound 56 (9.16 g, yield:72%) as a solid. Mass spectrometry: m/z=776.32[M+H]$^+$.

Preparation Examples 16 to 20

1) Preparation of Intermediates Sub A-7 to Sub A-11

Intermediates sub A-7 to sub A-11 (hereinafter collectively referred to as intermediate sub A-X) were synthesized according to the synthesis method of intermediate sub A-6 in Preparation Example 15 (steps 2) to 3)), except that the phenylboronic acid in step 2) was replaced with the raw material D. The intermediates obtained and the yield of the final steps were shown in Table 4.

2) Preparation of Compounds

The compounds in Table 4 were prepared according to the synthesis method of Compound 56 (steps 4)) in Preparation Example 15, except that the intermediates sub A-X listed in Table 4 were used instead of the intermediate sub A-6 to prepare the compounds. The synthetized compounds and their yield from the final steps and mass spectrometry characterization results were shown in Table 4.

TABLE 4

| Preparation Example | Raw material D | Intermediate sub A-X | Yield/% of intermediate sub A-X |
|---|---|---|---|
| 16 | (naphthalen-2-ylboronic acid) | sub A-7 | 42 |
| 17 | ([1,1'-biphenyl]-2-ylboronic acid) | sub A-8 | 45 |

TABLE 4-continued
| 18 | 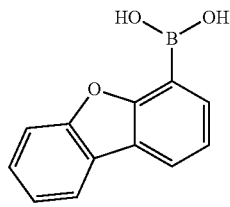 [SMILES: OB(O)c1cccc2c1oc1ccccc12] | 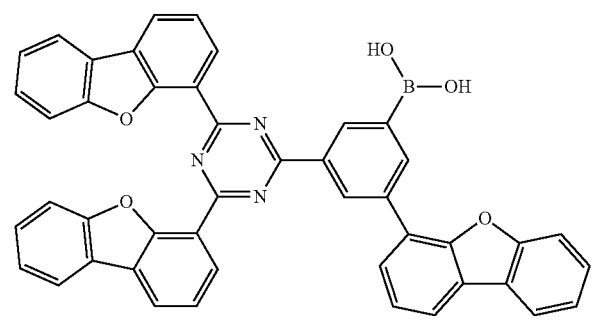 sub A-9 | 51 |
|---|---|---|---|
| 19 | 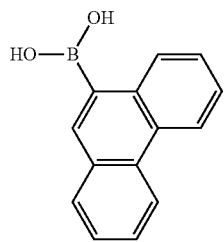 [SMILES: OB(O)c1cc2ccccc2c2ccccc12] | 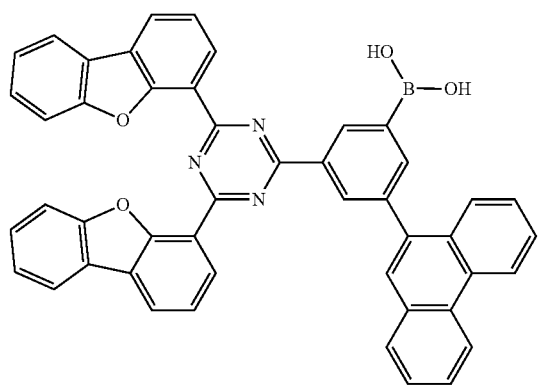 sub A-10 | 47 |
| 20 | 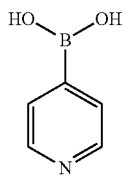 | 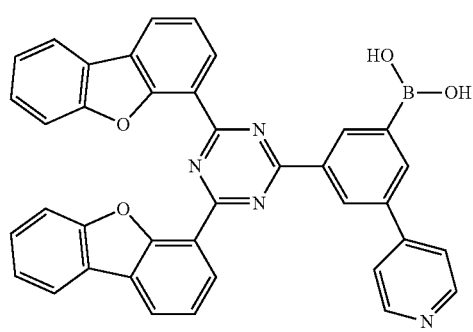 sub A-11 | 55 |

TABLE 4-continued

| Preparation Example | Compound | Yield (%) | Mass spectrum (m/z), [M + H]+ |
|---|---|---|---|
| 16 | 71 | 54 | 826.34 |
| 17 | 67 | 64 | 852.35 |
| 18 | 73 | 53 | 866.33 |

| | | | |
|---|---|---|---|
| 19 | 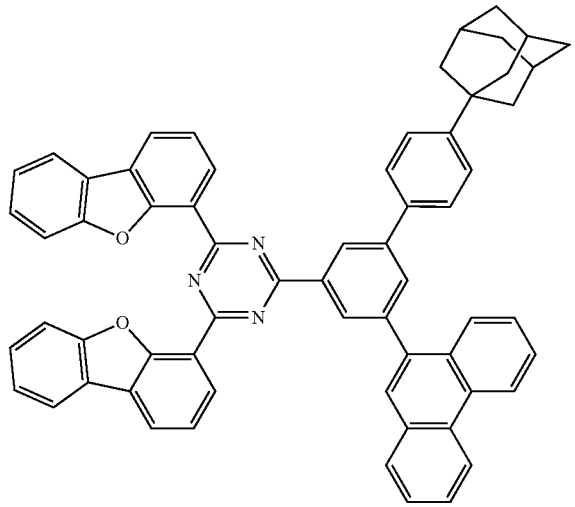 86 | 62 | 876.35 |
| 20 | 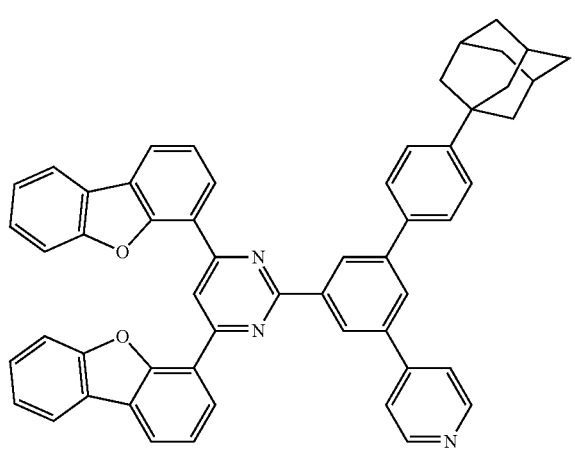 82 | 57 | 776.32 |

Preparation Example 21. Preparation of Compound 100

1) Preparation of Intermediate 1-1

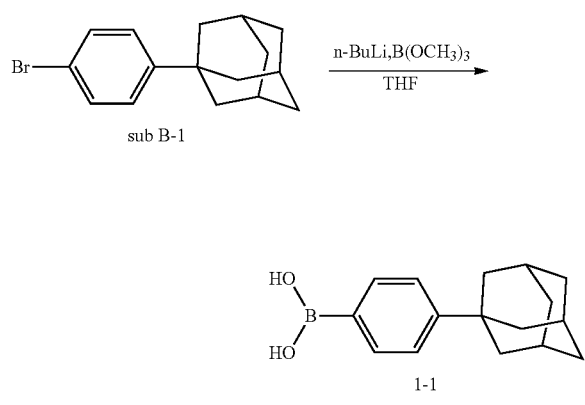

Intermediate sub B-1 (35.0 g, 120.1 mmol) was added to a round bottom flask, and 630 mL of THF that has been removed water was added to the flask. The system was cooled to −80° C. to −90° C. with liquid nitrogen, and then n-butyl lithium (8.46 g, 132.1 mmol) was added dropwise, with maintaining the temperature for 1 hour after completion of the addition. Trimethyl borate (13.7 g, 132.1 mmol) was added dropwise, and the system was maintained at a temperature of −80° C. to −90° C. After maintaining the temperature for 1 hour from completion of the addition, the system was naturally warmed up to room temperature. After completion of the reaction, 100 mL of aqueous HCl solution (the concentration is 2 mol/L) was added, and stirred for 0.5 h. The mixture was separated and extracted with dichloromethane and water. The organic phase was washed to neutral (pH=7). The organic phases were combined, dried with anhydrous $MgSO_4$ for 10 minutes, and filtered. The filtrate was spin-dried, and slurried twice with n-heptane to obtain the intermediate 1-1 (20.9 g, yield: 68%) as a white solid.

2) Preparation of Intermediate a-II-7

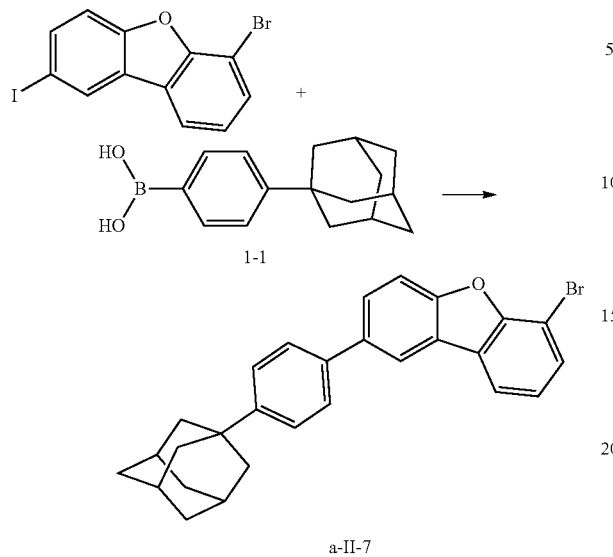

a-II-7

6-Bromo-2-iododibenzofuran (15.0 g, 40.2 mmol), intermediate 1-1 (10.3 g, 40.2 mmol), tetrakis(triphenylphosphine)palladium (2.3 g, 2.0 mmol), potassium carbonate (12.2 g, 88.4 mmol) and tetrabutylammonium bromide (0.13 g, 0.4 mmol) were added to a three-necked flask, and toluene (120 mL), ethanol (60 mL) and deionized water (30 mL) were added to the three-necked flask, warmed up to 76° C. under nitrogen protection, the reaction solution was stirred under heating and refluxing for 18 h. The mixture was cooled to room temperature, and stirring was stopped. The reaction solution was washed with water to separate an organic phase. The organic phase was dried with anhydrous magnesium sulfate, and a solvent was removed under reduced pressure. The obtained crude product was purified by silica gel column chromatography with dichloromethane/n-heptane as a mobile phase, to obtain the white intermediate a-II-7 (11.6 g, yield: 62%).

3) Preparation of Intermediate Sub A-12

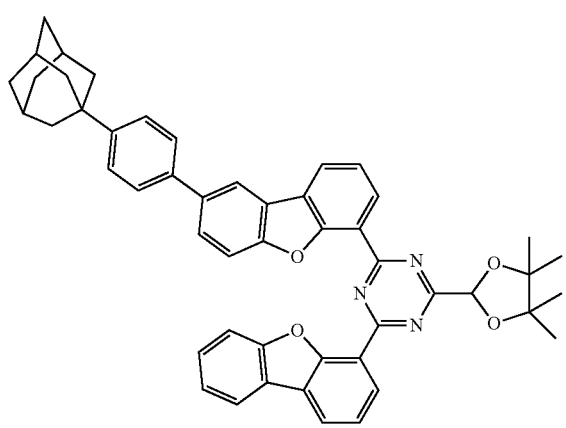

sub A-12

The intermediate sub A-12 was prepared with reference to the preparation method of the intermediate sub A-1 in Preparation Example 1 (step 2) to step 3)), except that the intermediate a-II-7 was used in step 2) instead of the raw material 4-bromodibenzofuran of preparation of intermediate a-II-1, thereby obtaining the intermediate sub A-12 (13.0 g, yield: 55%).

4) Preparation of Compound 100

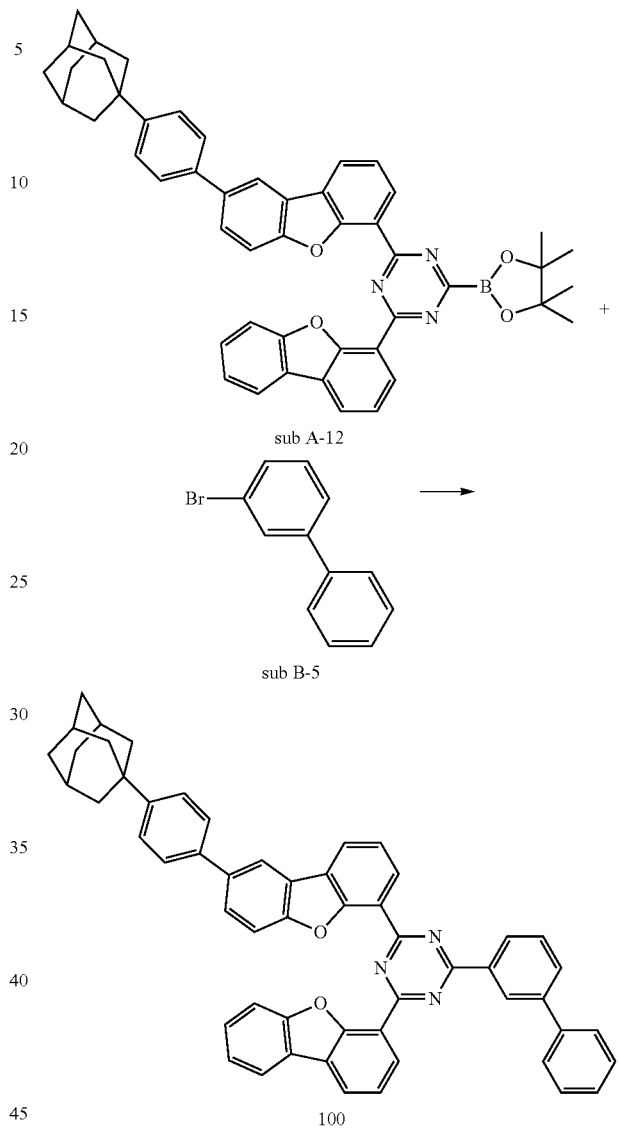

Compound 100 was prepared with reference to step 5) of the Preparation Example 1, except that sub A-12 was used instead of the intermediate sub A-1 in the Preparation Example 1, and raw material sub B-5 was used instead of sub B-1 in the Preparation Example 1, thereby obtaining compound 100 (9.5 g, yield: 57%). Mass spectrometry: m/z=776.32[M+H]$^+$.

Preparation Examples 22 to 29

The compounds shown in the following Table 5 were synthesized with reference to the method of Preparation Example 21 (steps 2) to 4)), except that raw material E was used instead of the raw material 6-bromo-2-iododibenzofuran in step 2), raw material F was used instead of the intermediate 1-1 in step 2), and the intermediate sub B-5 in step 4) was replaced by each intermediate sub B-I. The main raw materials used, the synthesized compounds, and the yield of the final steps and mass spectrum characterization results were shown in Table 5.

TABLE 5
| Preparation Example | Raw material E | Raw material F | Intermediate sub B-1 |
|---|---|---|---|
| 22 | 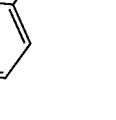 | 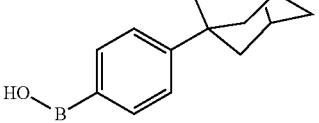 | 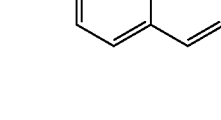 |
| 23 | | | 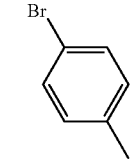 |
| 24 | | | 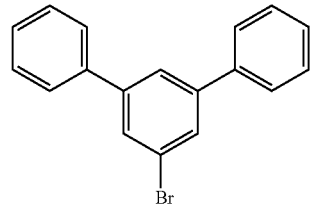 [SMILES: Brc1cc(-c2ccccc2)cc(-c2ccccc2)c1] |
| 25 | | | 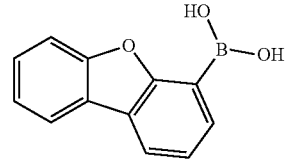 [SMILES: OB(O)c1cccc2c1oc1ccccc12] |
| 26 | 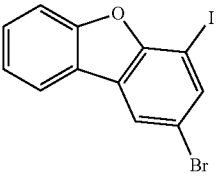 [SMILES: Brc1cc(I)c2oc3ccccc3c2c1] | 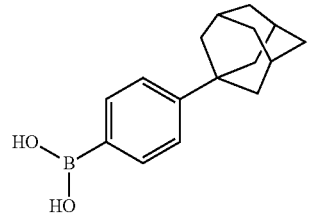 [SMILES: OB(O)c1ccc(C23CC4CC(CC(C4)C2)C3)cc1] | 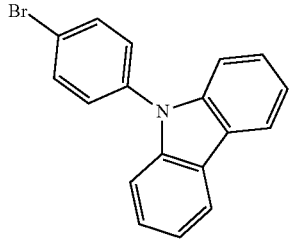 [SMILES: Brc1ccc(-n2c3ccccc3c3ccccc32)cc1] |
| 27 | | | 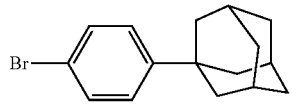 [SMILES: Brc1ccc(C23CC4CC(CC(C4)C2)C3)cc1] |
| 28 | 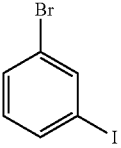 | 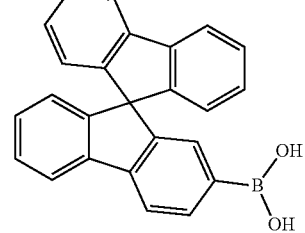 | 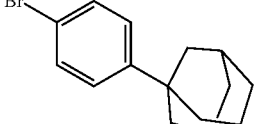 |

TABLE 5-continued
| 29 | 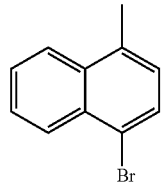 | 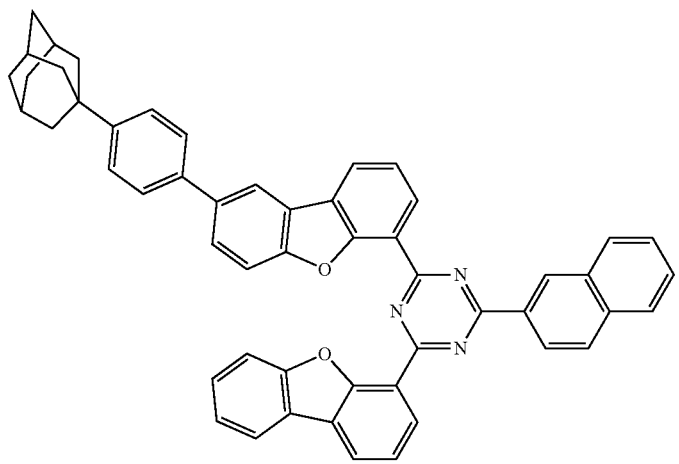 | 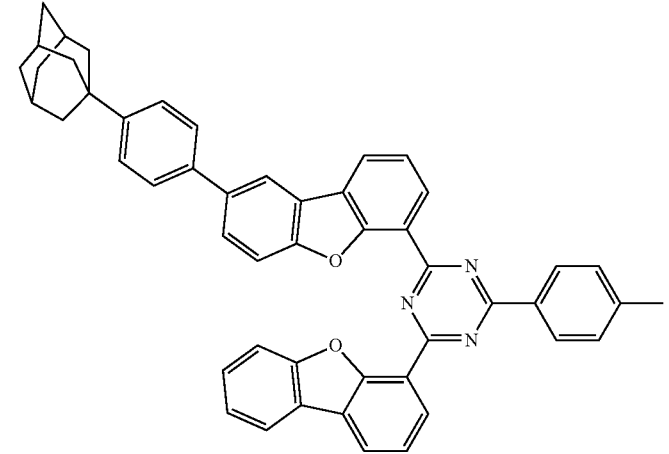 |
|---|---|---|---|
| Preparation Example | Compound | Yield/% | mass spectrum m/z, [M + H]+ |
|---|---|---|---|
| 22 | 114 | 58 | 750.30 |
| 23 | 115 | 64 | 714.31 |

TABLE 5-continued
| 24 | 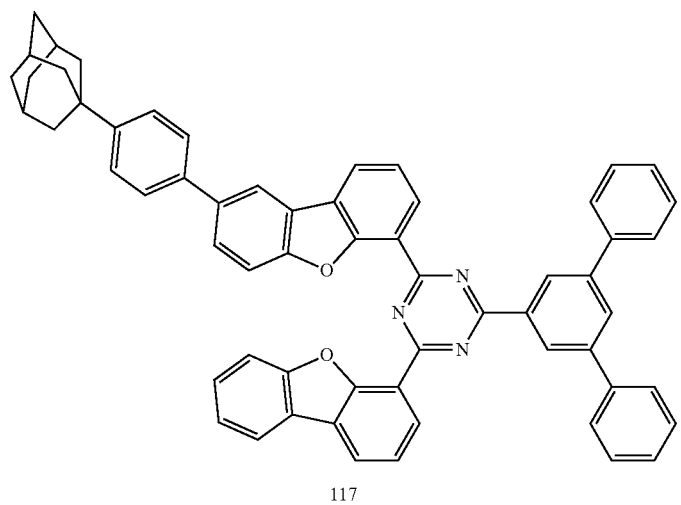 [SMILES: c1ccc(-c2cc(-c3ccccc3)cc(-c3nc(-c4cccc5c4oc4ccccc45)nc(-c4cccc5c4oc4ccc(-c6ccc(C78CC9CC(CC(C9)C7)C8)cc6)cc45)n3)c2)cc1]
117 | 64 | 852.35 |
| 25 | 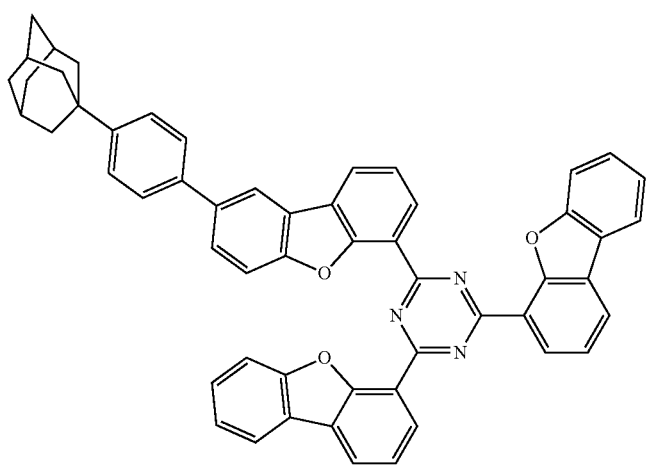
121 | 66 | 790.30 |
| 26 | 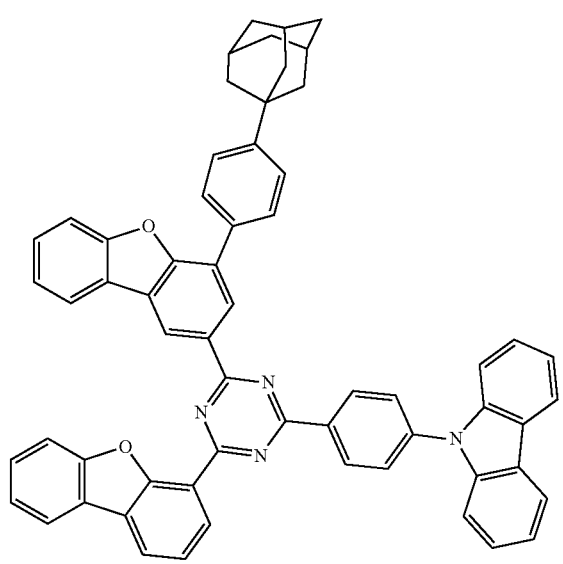
125 | 53 | 865.35 |

TABLE 5-continued
| 27 | 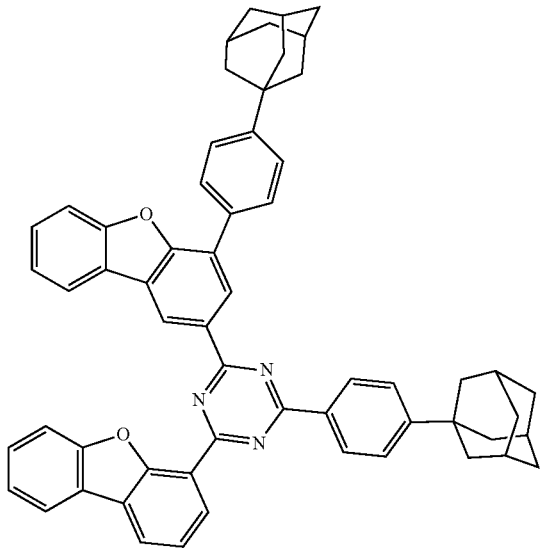 128 | 61 | 834.40 |
| 28 | 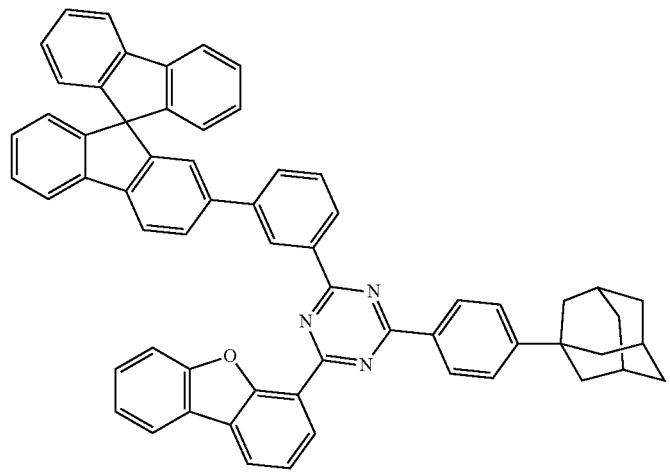 142 | 58 | 848.36 |

TABLE 5-continued

| 29 | | 53 | 776.36 |
|---|---|---|---|
| 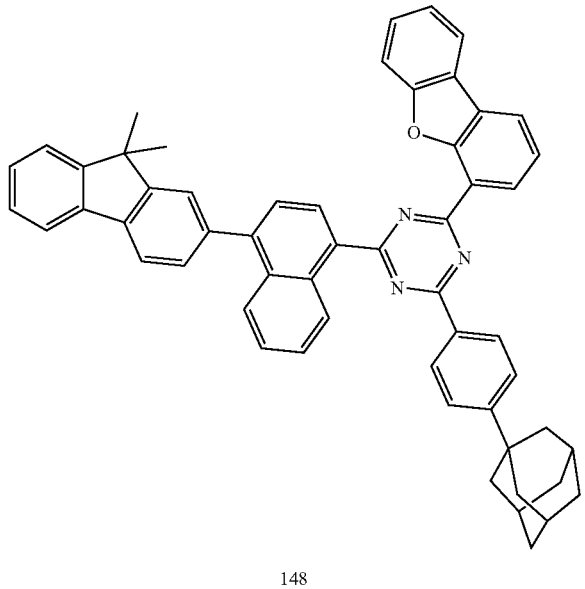 [SMILES: CC1(C)c2ccccc2-c2ccc(-c3ccc(-c4nc(-c5ccc(C67CC8CC(CC(C8)C6)C7)cc5)nc(-c5cccc6c5oc5ccccc56)n4)c4ccccc34)cc21] | | | |
| 148 | | | |

Preparation Examples 30 to 35

1) Preparation of Intermediate a-II-11

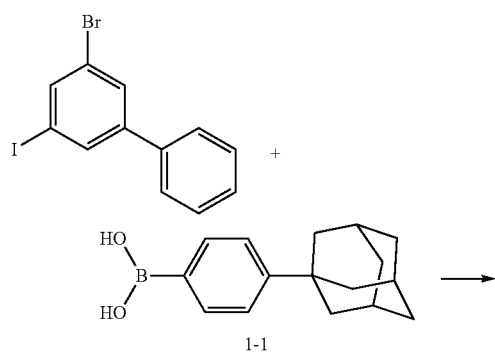

2) Preparation of Intermediate a-II-11

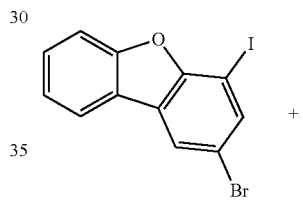

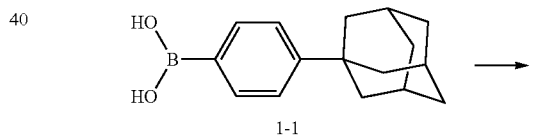

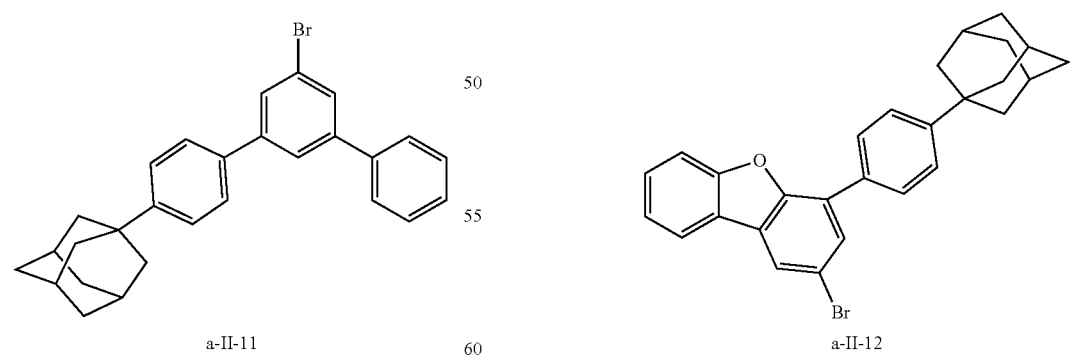

The intermediate a-II-11 was synthesized with reference to step 2) in the Preparation Example 21, except that 3-bromo-5-iodo-1,1'-biphenyl was used instead of 6-bromo-2-iododibenzofuran, to obtain the intermediate a-II-11 (12 g, yield: 54%).

The intermediate a-II-12 was synthesized with reference to step 2) in Preparation Example 21, except that 4-iodo-2-bromo-dibenzofuran was used instead of 6-bromo-2-iododibenzofuran, to obtain the intermediate a-II-12 (10 g, yield: 43%).

3) Preparation of Intermediate a-II-13

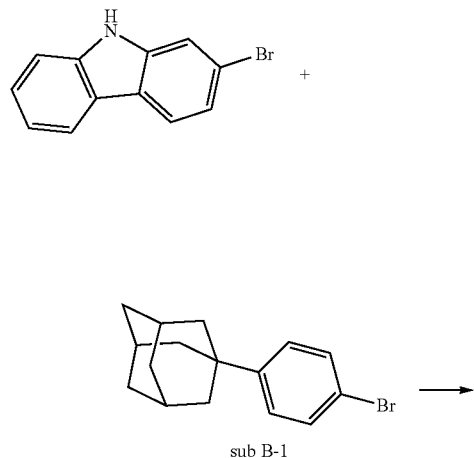

2-Bromocarbazole (15.0 g, 60.9 mmol), sub B-1 (17.5 g, 60.9 mmol), Pd$_2$(dba)$_3$ (0.5 g, mmol), x-phos (0.6 g, 1.2 mmol), sodium tert-butoxide (11.7 g, 121.8 mmol), and xylene (300 mL) were added to a three-necked flask, warmed up to 140° C. under nitrogen protection, the reaction solution was stirred under heating and refluxing for 10 h. After completion of the reaction, the resulting reaction solution was cooled to room temperature, extracted by adding toluene and water. The organic phases were combined, and an organic layer was dried with anhydrous magnesium sulfate, filtered and concentrated. The crude product was purified by silica gel column chromatography (dichloromethane/n-heptane) to obtain the intermediate a-II-13 (12.5 g, yield: 45%).

4) Synthesis of Compounds

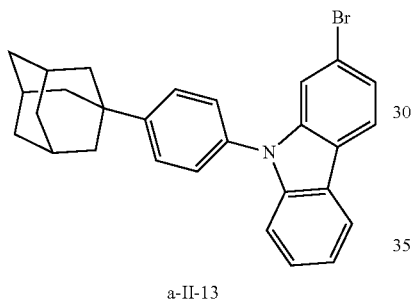

a-II-13

The compounds in Table 6 were synthesized with reference to step 5) in Preparation Example 1, except that intermediates sub A-I synthesized above were used instead of the intermediate sub A-1, and one of intermediates a-II-11 to a-II-13 was used instead of the intermediate sub B-1, thereby the compounds were synthesized. The main raw materials and compounds used and their yield and mass spectrum results were shown in Table 6.

TABLE 6

| Preparation Example | Intermediate sub A-1 | a-II-11/a-II-12/intermediate a-II-13 |
|---|---|---|
| 30 | sub A-21 | a-II-11 |

TABLE 6-continued
| | | |
|---|---|---|
| 31 | 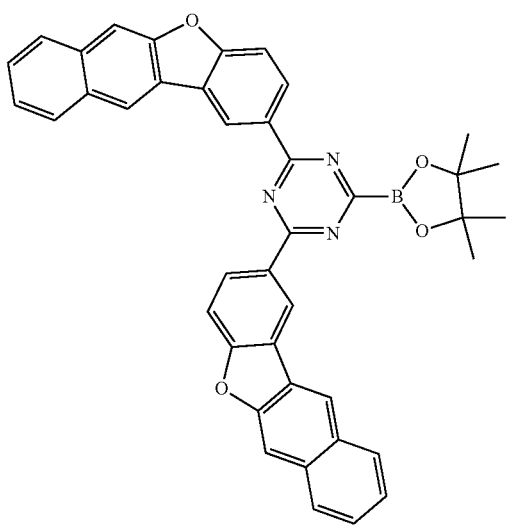<br>sub A-22 | 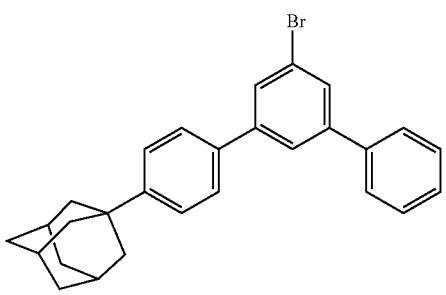<br>a-II-11 |
| 32 | 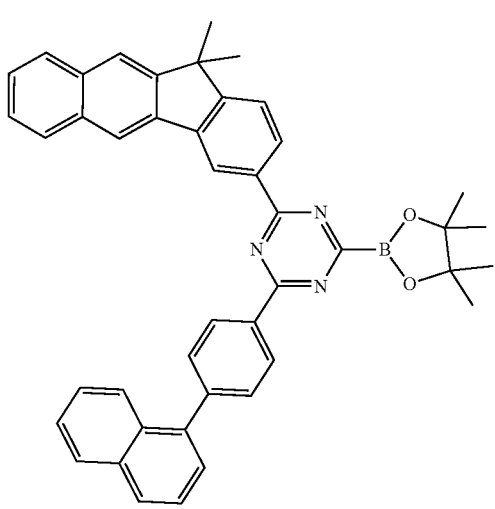<br>sub A-23 | 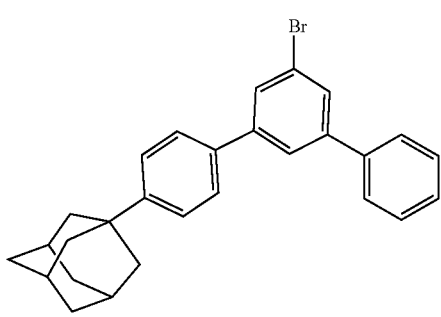<br>a-II-11 |
| 33 | 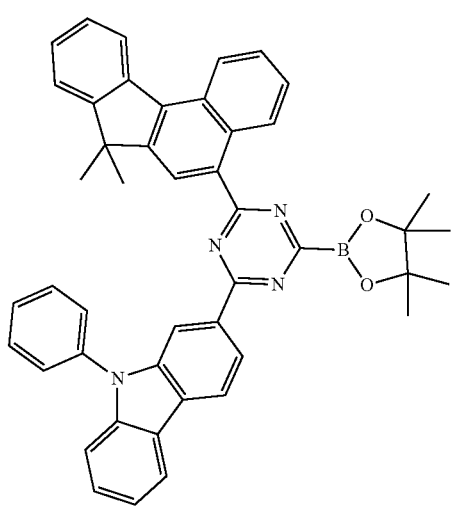<br>sub A-24 | 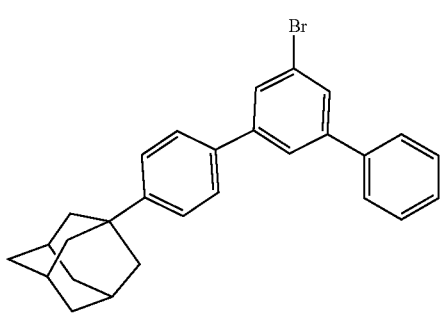<br>a-II-11 |

TABLE 6-continued
34
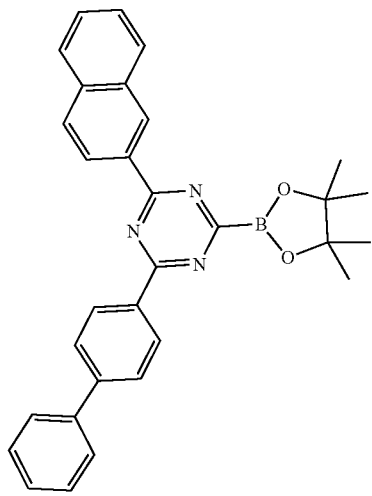
sub A-10a
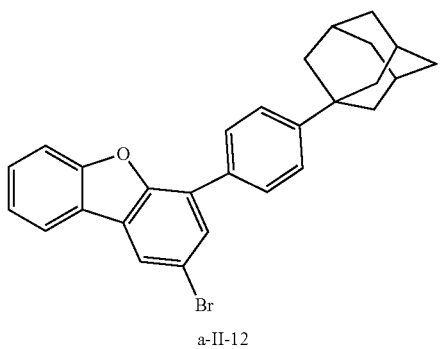 [SMILES: Brc1cc(-c2ccc(C34CC5CC(CC(C5)C3)C4)cc2)c2oc3ccccc3c2c1]
a-II-12
35
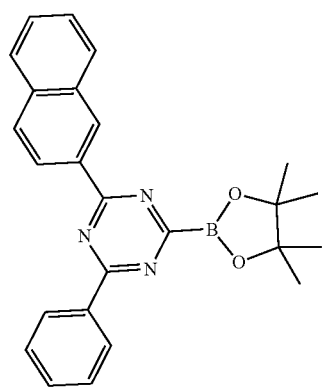
sub A-8a
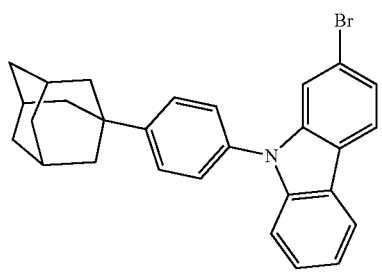
a-II-13

TABLE 6-continued
| Preparation Example | Compound | Yield/% | mass spectrum (m/z), [M + H]+ |
|---|---|---|---|
| 30 | 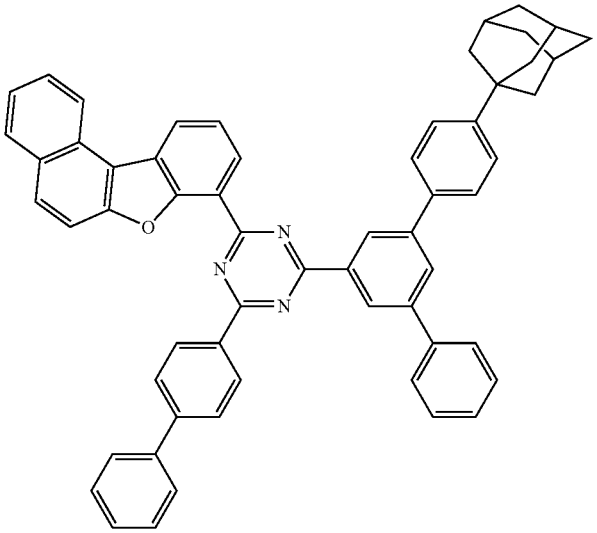 280 | 67 | 812.36 |
| 31 | 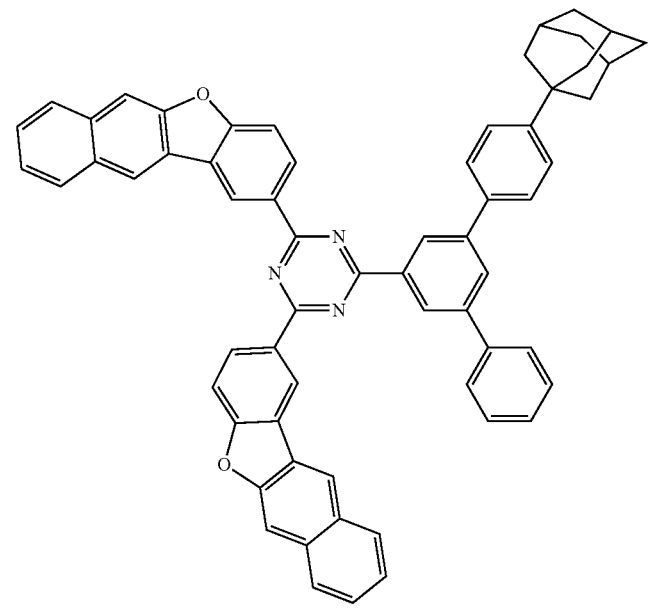 297 | 61 | 876.35 |

TABLE 6-continued
| 32 | | 67 | 888.42 |
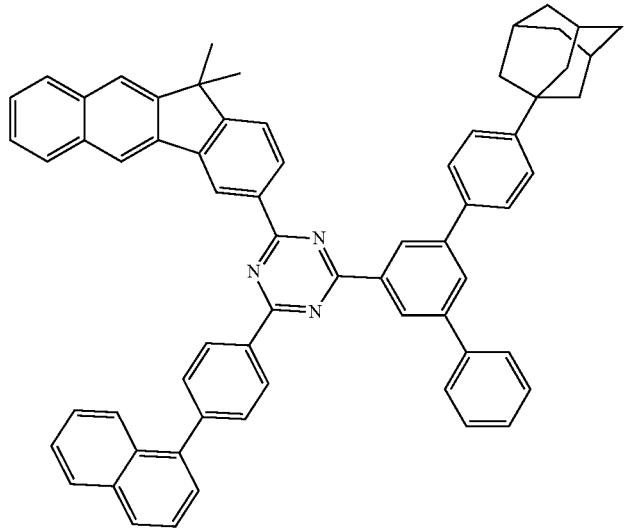
288
| 33 | | 56 | 927.43 |
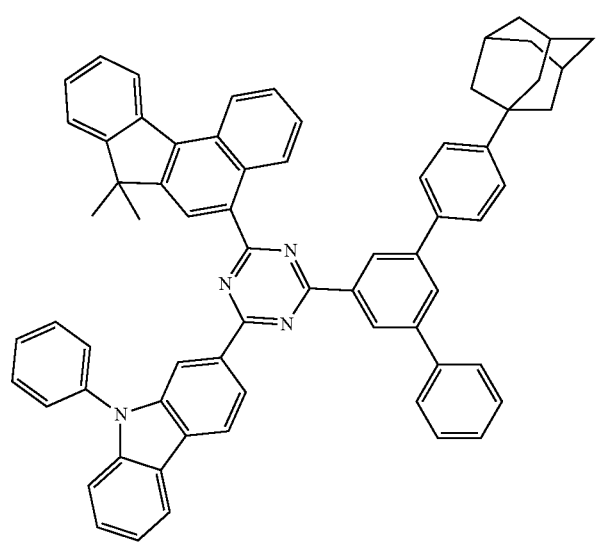
304

TABLE 6-continued
| 34 | 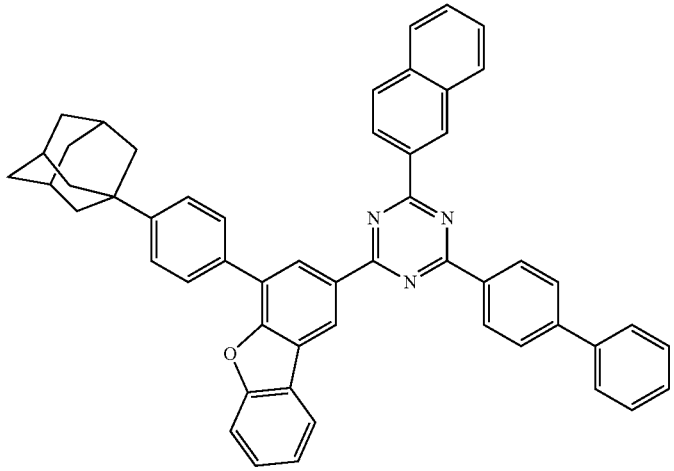 376 | 51 | 756.32 |
| 35 | 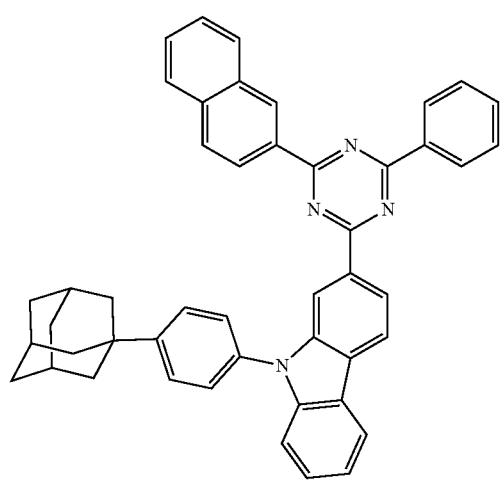 373 | 42 | 659.31 |

Preparation Example 36. Preparation of Compound 358

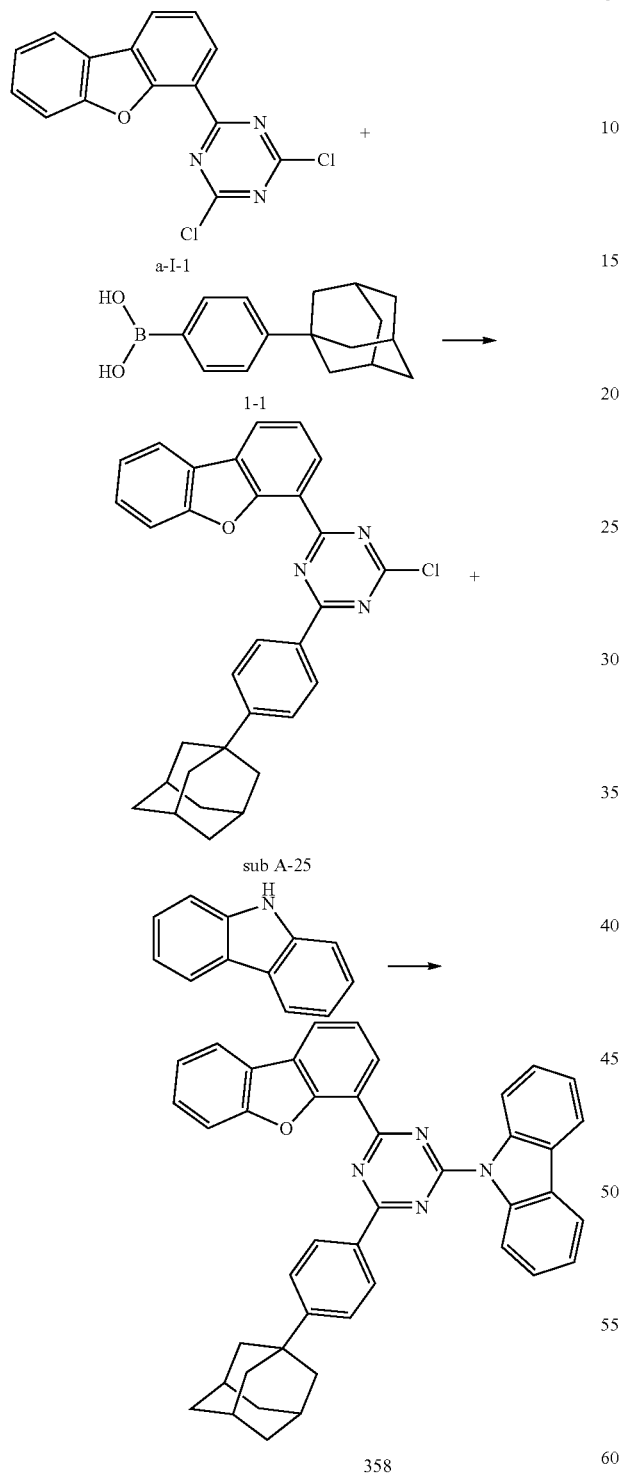

1) Intermediate a-I-1 (30.0 g, 94.9 mmol), intermediate 1-1 (19.4 g, 75.9 mmol), tetrakis(triphenylphosphine) palladium (5.5 g, 4.7 mmol), potassium carbonate (26.2 g, 189.8 mmol), tetrabutylammonium bromide (0.6 g, 1.9 mmol), toluene (240 mL), ethanol (120 mL) and deionized water (60 mL) were added to a three-necked flask, warmed up to 76° C. under nitrogen protection. The reaction solution was stirred under heating and refluxing for 15 h. After completion of the reaction, the resulting reaction solution was cooled to room temperature, and extracted by adding toluene (200 mL). The organic phases were combined, and an organic layer was dried with anhydrous magnesium sulfate, filtered and concentrated. The crude product was purified by silica gel column chromatography (dichloromethane/n-heptane) to obtain the intermediate sub A-25 (23.3 g, yield: 50%).

2) The intermediate sub A-25 (22.0 g, 44.8 mmol), carbazole (5.0 g, 29.9 mmol), and DMF (200 mL) were added to a three-necked flask, and cooled to 0° C. under nitrogen protection. NaH (0.8 g, 32.8 mmol) was added and raised to room temperature naturally. After completion of the reaction, the resulting reaction solution system was added water, and filtered to obtain a solid product. The solid product was rinsed with a small amount of ethanol. The crude product was recrystallized from toluene to obtain the compound 358 (11.4 g, yield: 78%). Mass spectrometry: m/z=623.27 [M+H]$^+$.

Preparation Example 37. Preparation of Compound 33

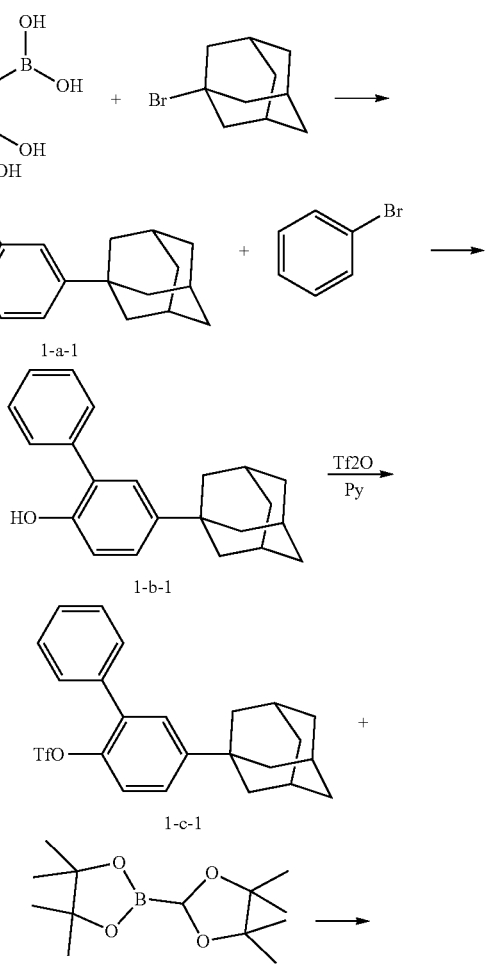

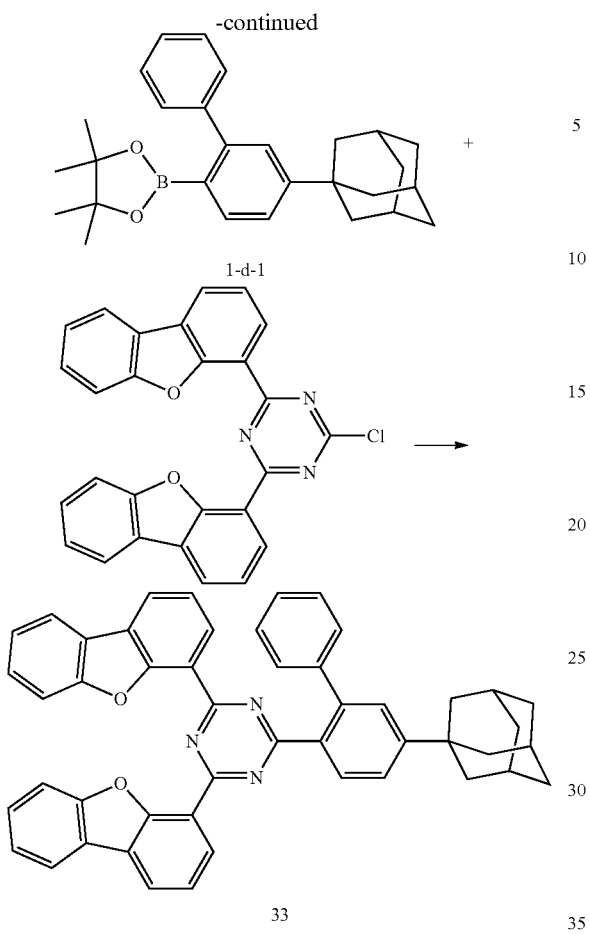

1) 4-hydroxyphenylboronic acid (50.0 g, 362.5 mmol), 1-bromoadamantane (77.9 g, 362.5 mmol) and dichloromethane (500 mL) were added to a round bottom flask, cooled to −5° C. to 0° C. under nitrogen protection. At this temperature, trifluoromethanesulfonic acid (81.6 g, 543.8 mmol) was added dropwise. After maintaining the temperature and stirring for 3 h, the mixture was raised to room temperature naturally. The reaction solution was washed with deionized water (300 mL) to pH=7, and extracted by adding dichloromethane (100 mL). The organic phases were combined, dried with anhydrous magnesium sulfate, and filtered, and a solvent was removed under reduced pressure. The resulting crude product was purified by silica gel column chromatography with n-heptane as a mobile phase to obtain the intermediate 1-a-1 (54.2 g, yield: 55%) as a white solid.

2) Intermediate 1-a-1 (50.0 g, 183.6 mmol), bromobenzene (23.0 g, 146.9 mmol), tetrakis(triphenylphosphine)palladium (4.2 g, 3.6 mmol), potassium carbonate (50.7 g, 367.3 mmol), tetrabutylammonium bromide (1.2 g, 3.6 mmol), toluene (480 mL), ethanol (240 mL) and deionized water (120 mL) were added to a three-necked flask, warmed up to 76° C. under nitrogen protection. The reaction solution was stirred under heating and refluxing for 15 h. After completion of the reaction, the resulting reaction solution was cooled to room temperature, extracted by adding toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-b-1 (34.6 g, yield: 62%).

3) Intermediate 1-b-1 (30.0 g, 98.5 mmol), pyridine (23.4 g, 295.6 mmol), dichloromethane (300 mL) were added to a three-necked flask, cooled to −5° C. under nitrogen protection, and then added trifluoromethanesulfonic anhydride (36.1 g, 128.1 mmol) slowly. After maintaining at a temperature of 0° C. for 2 hours, the mixture was raised to room temperature and stirred naturally. After completion of the reaction, the obtained reaction solution was added to an aqueous hydrochloric acid solution (2 mmol/L), washed to a weakly acidic (ph=5 to 6) system, and separated and extracted with dichloromethane and water. The organic phase in dichloromethane was dried with MgSO₄ to remove water, filtered, and concentrated to obtain a crude product. The resulting crude product was purified by silica gel column chromatography with n-heptane as a mobile phase (dichloromethane/n-heptane) to obtain the intermediate 1-c-1 (34.4 g, yield: 80%).

4) Intermediate 1-c-1 (20.0 g, 45.8 mmol), bis(pinacolato)diboron (17.4 g, 68.7 mmol), Pd(dppf)Cl₂ ([1,1'-bis(diphenylphosphino)ferrocenyl]palladium dichloride, 1.6 g, 2.3 mmol), and KOAc (8.9 g, 91.6 mmol) were added to 1,4-dioxane (200 mL), and refluxed and reacted at 80° C. for 12 h. After the reaction was completed, the mixture was extracted with CH₂Cl₂ and water. The organic phase was dried with MgSO₄ to remove the moisture in it, and an organic layer was concentrated. The resulting compound was subjected to silica gel column chromatography and recrystallization to obtain the intermediate 1-d-1 (11.5 g, yield: 61%).

5) Intermediate 1-d-1 (9.7 g, 23.4 mmol), a-II-1 (10.0 g, 22.3 mmol), tetrakis(triphenylphosphine)palladium (0.5 g, 0.4 mmol), potassium carbonate (6.1 g, 44.6 mmol), tetrabutylammonium bromide (0.07 g, 0.2 mmol), toluene (80 mL), ethanol (40 mL) and deionized water (20 mL) were added to a three-necked flask, warmed up to 76° C. under nitrogen protection. The reaction solution was stirred under heating and refluxing for 12 h. After completion of the reaction, the resulting reaction solution was cooled to room temperature, and extracted by adding toluene and water. The organic phases were combined, and an organic layer was dried with anhydrous magnesium sulfate, filtered and concentrated. The crude product was purified by silica gel column chromatography (dichloromethane/n-heptane) to obtain the compound 33 (10.4 g, yield: 67%). Mass spectrometry: m/z=700.29[M+H]⁺.

Preparation Example 38. Preparation of Compound 354

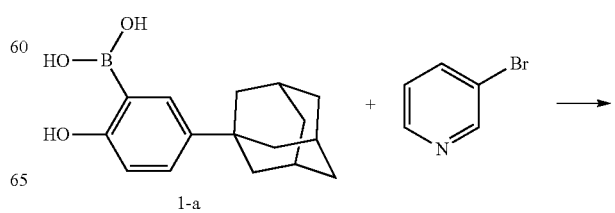

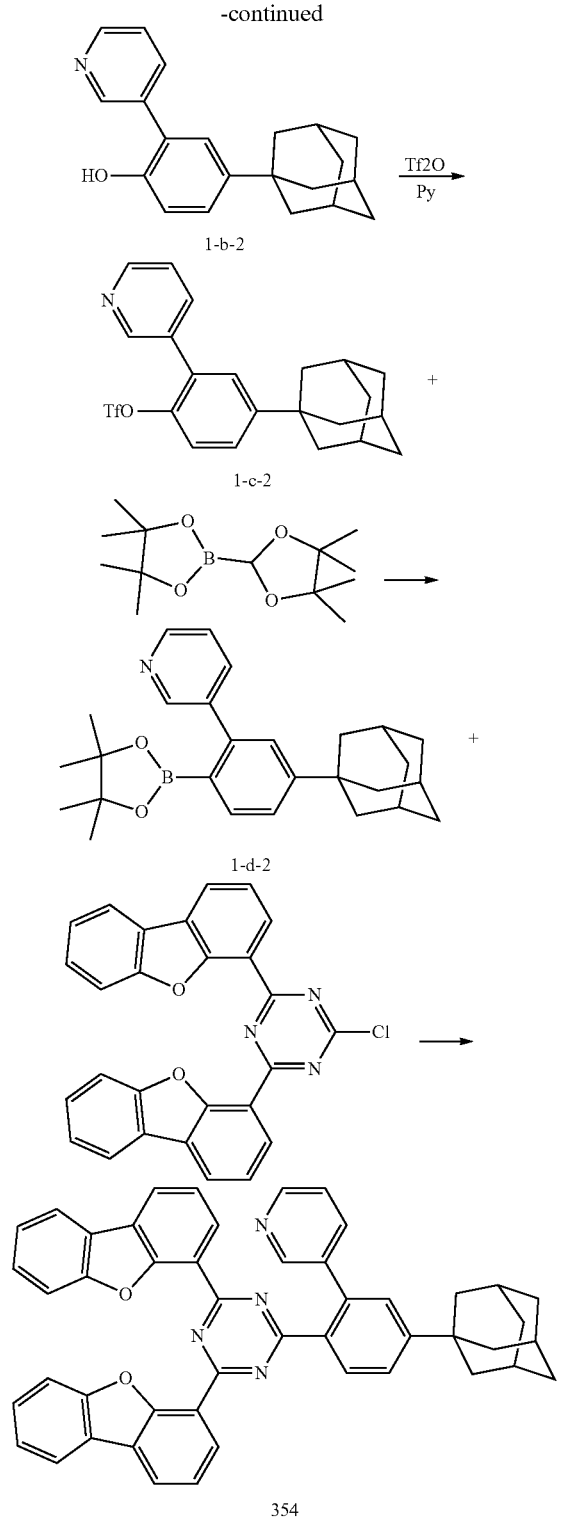

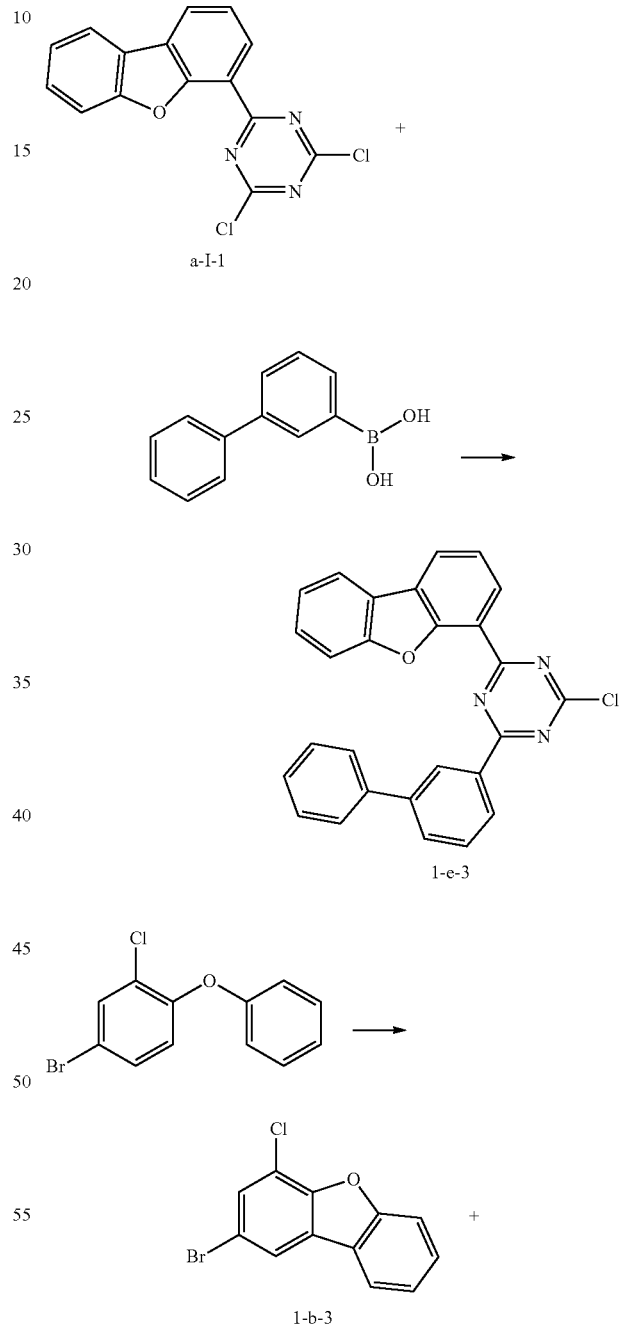

(d, 1H), 7.61-7.51 (m, 7H), 7.45-7.37 (m, 4H), 2.09 (s, 3H), 1.99 (s, 6H), 1.82-1.75 (m, 6H).

Preparation Example 39. Preparation of Compound 87

Compound 354 was synthesized according to the procedure in Preparation Example 37, except that 3-bromopyridine was used instead of the raw material bromobenzene in step 2) to synthesize compound 354 (4.1 g, yield: 47%), Mass spectrometry: m/z=701.28[M+H]$^+$.

The nuclear magnetic data of Compound 354 are $^1$HNMR (400 MHz, CD$_2$Cl$_2$) δ(ppm): 8.87 (d, 1H), 8.80 (d, 1H), 8.62 (s, 1H), 8.23-8.22 (d, 2H), 8.07 (m, 3H), 7.75 (d, 1H), 7.66

-continued

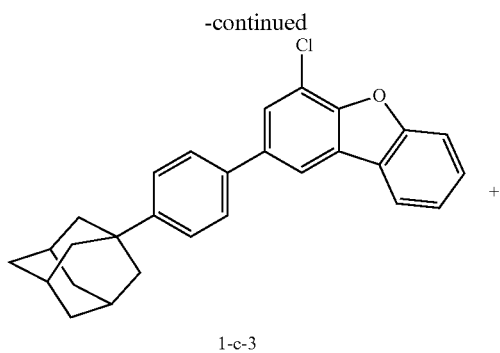
1-c-3

+

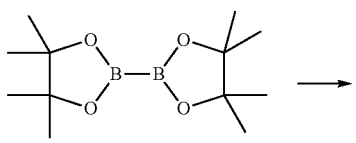

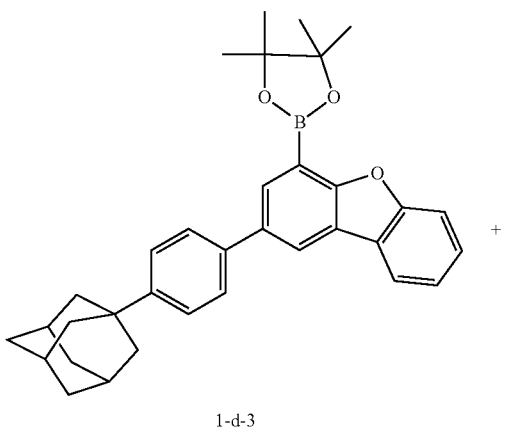
1-d-3

+

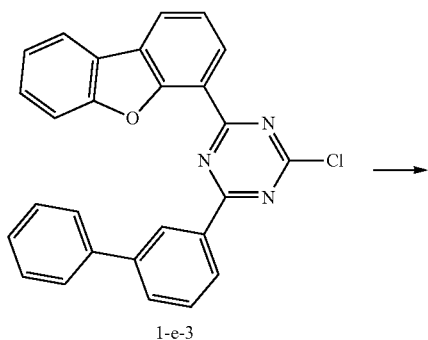
1-e-3

-continued

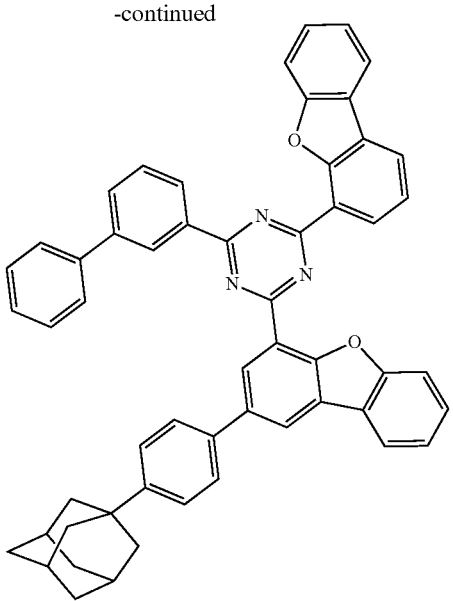
87

1) 4-Bromo-2-chloro-1-phenoxybenzene (50.0 g, 176.3 mmol), $K_2CO_3$ (24.3 g, 176.3 mmol), $PdOAc_2$ (1.97 g, 8.81 mmol) and acetic acid (500 mL) were added to a round bottom flask, heated to 120° C. under nitrogen protection, and reacted at this temperature for 50 h. The reaction solution was washed with deionized water (300 mL) to pH=7, and extracted with dichloromethane (100 mL). The organic phases were combined, dried with anhydrous magnesium sulfate, and filtered, and a solvent was removed under reduced pressure. The obtained crude product was purified by silica gel column chromatography with n-heptane as a mobile phase to obtain the intermediate 1-b-3 (19.8 g, yield: 40%) as a white solid.

2) Intermediate 1-b-3 (19.0 g, 67.5 mmol), 1-1 (18.1 g, 70.8 mmol), tetrakis(triphenylphosphine)palladium (3.8 g, 3.3 mmol), potassium carbonate (18.6 g, 134.9 mmol), tetrabutylammonium bromide (0.2 g, 0.6 mmol), toluene (160 mL), ethanol (40 mL) and deionized water (40 mL) were added to a three-necked flask, warmed up to 76° C. under nitrogen protection. The reaction solution was stirred under heating and refluxing for 12 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-c-3 (18.1 g, yield: 65%) as a solid.

3) Intermediate 1-c-3 (18.0 g, 43.5 mmol), bis(pinacolato)diboron (16.6 g, 65.3 mmol), $Pd(dppf)Cl_2$ (1.5 g, 2.1 mmol), and KOAc (0.6 g, 108.0 mmol) were added 1,4-dioxane (200 mL), and refluxed at 100° C. for 12 hours. After the reaction was completed, the mixture was extracted with $CH_2Cl_2$ and water. The organic phase was dried with $MgSO_4$ to remove the moisture in it, and an organic layer was concentrated. The resulting compound was purified by silica gel column chromatography, and recrystallized to obtain the intermediate 1-d-3 (12.9 g, yield: 59%).

4) a-I-1 (20.0 g, 63.2 mmol), 3-diphenylboronic acid (18.7 g, 94.4 mmol), tetrakis(triphenylphosphine)palladium (3.6 g, 3.1 mmol), potassium carbonate (21.8 g, 158.1 mmol), tetrabutylammonium bromide (0.2 g, 0.6 mmol), toluene (160 mL), ethanol (40 mL) and deionized water (40 mL) were added to a three-necked flask, warmed up to 76° C. under nitrogen protection, and heated with refluxing for 12 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-e-3 (18.3 g, yield: 67%) as a solid.

5) Intermediate 1-e-3 (9.0 g, 20.7 mmol), 1-d-3 (11.5 g, 22.8 mmol), tetrakis(triphenylphosphine)palladium (1.2 g, 1.0 mmol), potassium carbonate (7.1 g, 51.8 mmol), tetrabutylammonium bromide (0.06 g, 0.2 mmol), toluene (80 mL), ethanol (40 mL) and deionized water (20 mL) were added to a three-necked flask, warmed up to 76° C. under nitrogen protection. The reaction solution was stirred under heating and refluxing for 11 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the compound 87 (9.5 g, yield: 59%). Mass spectrometry: m/z=776.32[M+H]$^+$.

Preparation Example 40. Preparation of Compound 365

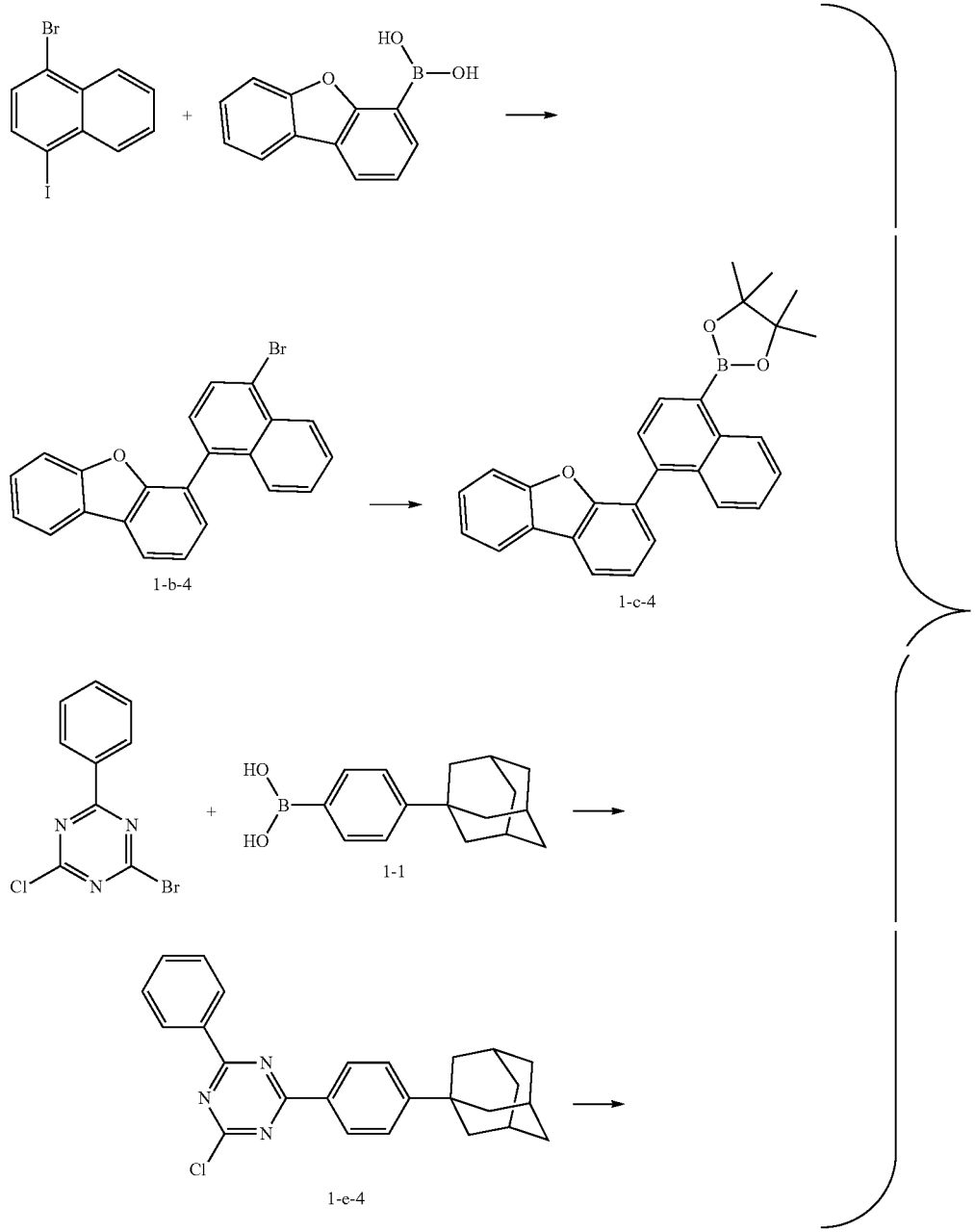

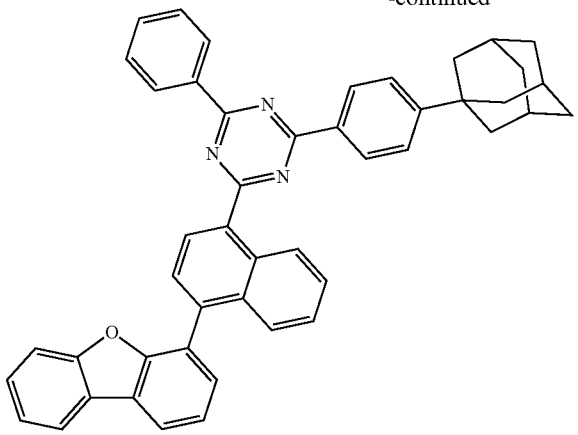

365

1) 1-Bromo-4-iodonaphthalene (50.0 g, 150.1 mmol), 4-dibenzofuran boronic acid (31.8 g, 150.1 mmol), tetrakis(triphenylphosphine)palladium (1.7 g, 1.5 mmol), potassium carbonate (41.5 g, 300.3 mmol) and tetrabutylammonium bromide (0.5 g, 1.5 mmol) were added to a three-necked flask, and toluene (400 mL), ethanol (200 mL) and deionized water (100 mL) were added to the three-necked flask, warmed to 76° C. under nitrogen protection. The reaction solution was stirred under heating and refluxing for 18 h. Then, the mixture was cooled to room temperature, and stirring is stopped. The reaction solution was washed with water, and then the organic phase was separated, and dried with anhydrous magnesium sulfate, and a solvent was removed under reduced pressure to obtain a crude. The crude product was purified by silica gel column chromatography with dichloromethane/n-heptane as a mobile phase to obtain the white intermediate 1-b-4 (37.5 g, yield: 67%).

2) Intermediate 1-b-4 (30.0 g, 80.3 mmol), bis(pinacolato)diboron (30.6 g, 120.5 mmol), Pd(dppf)Cl$_2$ (1.1 g, 1.6 mmol), and KOAc (15.7 g, 160.7 mmol) were added to 1,4-dioxane (300 mL), and refluxed and reacted at 100° C. for 12 hours. After the reaction was completed, the mixture was extracted with CH$_2$Cl$_2$ and water. The organic phase was dried with MgSO$_4$ to remove the moisture in it, and an organic layer was concentrated. The obtained compound was subjected to silica gel column chromatography and recrystallization to obtain the intermediate 1-c-4 (21.9 g, yield: 65%).

3) 2,4-dichloro-6-phenyl-1,3,5-triazine (20.0 g, 88.4 mmol), intermediate 1-1 (18.1 g, 70.7 mmol), tetrakis(triphenylphosphine)palladium (2.0 g, 1.7 mmol), potassium carbonate (24.4 g, 176.9 mmol) were added to a three-necked flask, and THF (80 mL) and deionized water (20 mL) was added to the three-necked flask, warmed up to 66° C. under nitrogen protection. The reaction solution was stirred under heating and refluxing for 18 h. The mixture was cooled to room temperature, and stirring is stopped. The reaction solution was washed with water, and the organic phase was separated, and dried with anhydrous magnesium sulfate, and a solvent was removed under reduced pressure to obtain a crude product. The crude product was purified by silica gel column chromatography with dichloromethane/n-heptane as a mobile phase to obtain the white intermediate 1-e-4 (20.2 g, yield: 71%).

4) Intermediate 1-e-4 (15.0 g, 37.3 mmol), (16.5 g, 39.1 mmol), tetrakis(triphenylphosphine)palladium (0.8 g, 0.7 mmol), potassium carbonate (10.3 g, 74.6 mmol), tetrabutylammonium bromide (0.1 g, 0.37 mmol), toluene (120 mL), ethanol (60 mL) and deionized water (30 mL) were added to a three-necked flask, warmed up to 76° C. under nitrogen protection. The reaction solution was stirred under heating and refluxing for 10 h. After completion of the reaction, the obtained reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the compound 365 (14.7 g, yield: 60%). Mass spectrometry: m/z=660.29[M+H]$^+$. Nuclear magnetic data of compound 365: $^1$H NMR (400 MHz, CD$_2$Cl$_2$) δ(ppm): 8.86-8.82 (d, 2H), 8.78-8.76 (d, 1H), 8.50-8.47 (d, 1H), 8.40-8.38 (d, 1H), 8.30-8.27 (m, 3H), 8.05-8.03 (d, 1H), 7.98-7.96 (d, 1H), 7.77-7.75 (d, 1H), 7.68-7.52 (m, 8H), 7.49-7.46 (d, 2H), 7.3-7.30 (m, 1H), 2.13 (s, 3H), 1.95 (s, 6H), 1.82-1.75 (m, 6H).

Preparation Example 41. Preparation of Compound 367

Compound 367 was synthesized according to the procedure of Preparation Example 40, except that dibenzofuran-2-boronic acid was used instead of the raw material 4-dibenzofuranboronic acid in the synthesis of intermediate 1-b-4, thereby synthesizing compound 367 (11.2 g, yield: 55%). Mass spectrometry: m/z=660.28[M+H]$^+$.

Preparation Example 42. Preparation of Compound 384
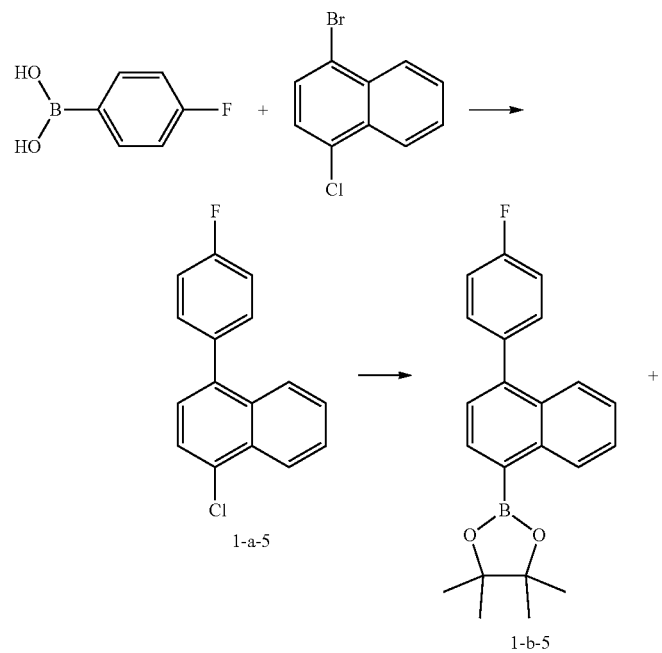
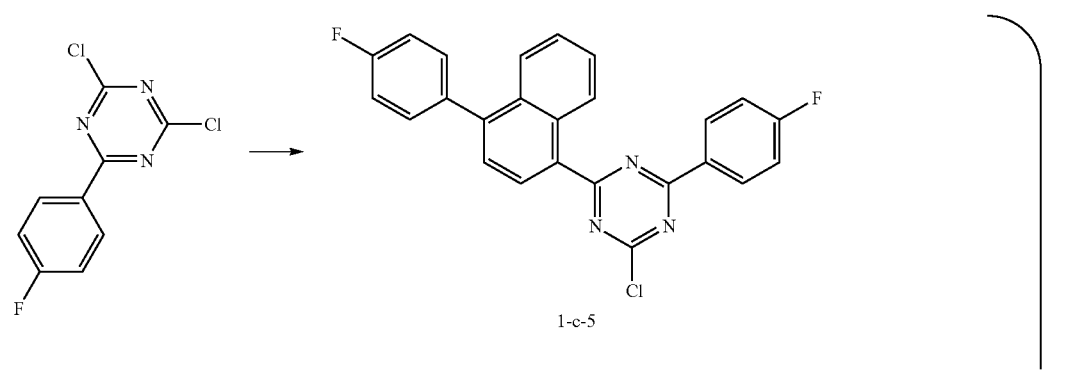
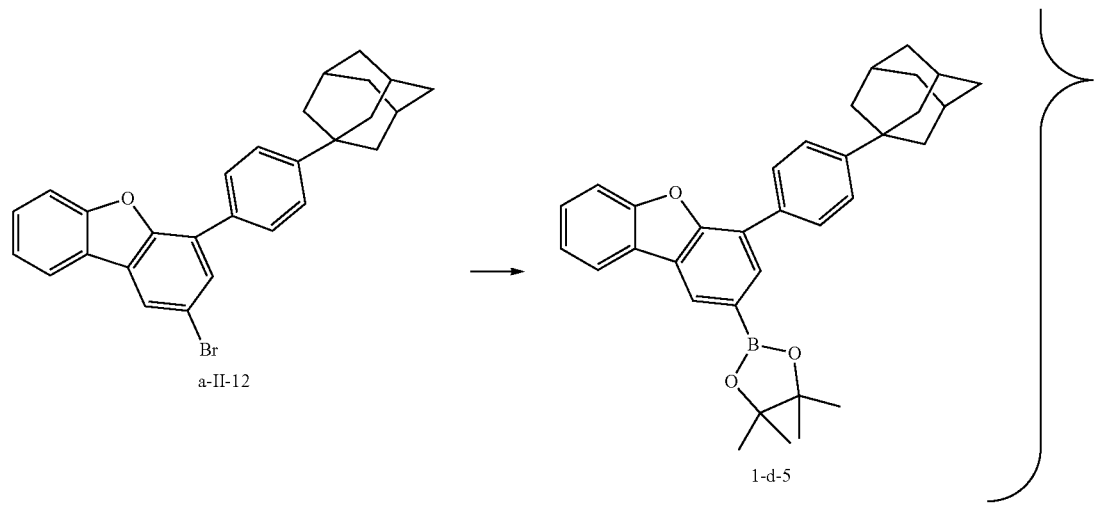

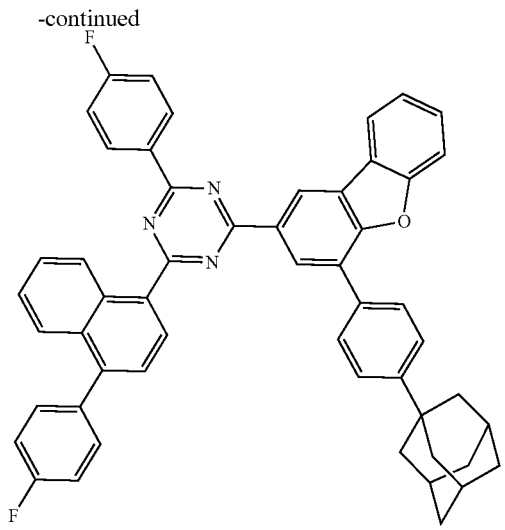

384

1) 1-Bromo-4-chloronaphthalene (49.3 g, 204.4 mmol), p-fluorophenylboronic acid (26.0 g, 185.8 mmol), tetrakis(triphenylphosphine)palladium (2.1 g, 1.8 mmol), potassium carbonate (51.3 g, 371.6 mmol), tetrabutylammonium bromide (0.6 g, 1.8 mmol), toluene (400 mL), ethanol (200 mL) and deionized water (100 mL) were added to a three-necked flask, warmed up to 76° C. under nitrogen protection. The reaction solution was stirred under heating and refluxing for 15 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate I-a-5 (31.0 g, yield: 65%).

2) Intermediate I-a-5 (30.0 g, 116.8 mmol), bis(pinacolato)diboron (35.6 g, 140.2 mmol, Pd(dppf)Cl₂ ([1,1'-bis(diphenylphosphino)ferrocenyl]-palladium dichloride) (0.8 g, 1.2 mmol), and KOAc (22.9 g, 233.7 mmol) were added to 1,4-dioxane (300 mL), and refluxed and reacted at 100° C. for 10 hours. After the reaction was completed, the mixture was extracted with CH₂Cl₂ and water. The organic phase was dried with MgSO₄ to remove the moisture in it, and an organic layer was concentrated. The resulting compound was subjected to silica gel column chromatography and recrystallization to obtain the intermediate 1-b-5 (23.6 g, yield: 58%).

3) Intermediate 1-b-5 (20.0 g, 57.4 mmol), 2,4-dichloro-6-(4-fluorophenyl)-1,3,5-triazine (15.4 g, 63.1 mmol), tetrakis(triphenylphosphine)palladium (0.6 g, 0.5 mmol), potassium carbonate (15.8 g, 114.8 mmol), tetrabutylammonium bromide (0.2 g, 0.5 mmol), toluene (200 mL), ethanol (100 mL) and deionized water (50 mL) were added to a three-necked flask, warmed up to 76° C. under nitrogen protection. The reaction solution was stirred under heating and refluxing for 8 h. After completion of the reaction, the obtained reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-c-5 (15.7 g, yield: 64%).

4) Intermediate a-II-12 (25.0 g, 54.6 mmol), bis(pinacolato)diboron (16.6 g, 65.5 mmol), Pd(dppf)Cl₂ ([1,1'-bis(diphenylphosphino)ferrocenyl]palladium dichloride) (0.4 g, 0.5 mmol), and KOAc (10.7 g, 109.3 mmol) were added to 1,4-dioxane (250 mL), and refluxed and reacted at 100° C. for 14 h. After the reaction was completed, the mixture was extracted with CH₂Cl₂ and water. The organic phase was dried with MgSO₄ to remove the moisture in it, and an organic layer was concentrated. The obtained compound was subjected to silica gel column chromatography and recrystallization to obtain the intermediate 1-d-5, (17.9 g, yield: 65%).

5) Intermediate 1-c-5 (12.0 g, 27.9 mmol), 1-d-5 (15.5 g, 30.7 mmol), tetrakis(triphenylphosphine)palladium (0.3 g, 0.3 mmol), potassium carbonate (7.7 g, 55.8 mmol), tetrabutylammonium bromide (0.17 g, 0.5 mmol), toluene (96 mL), ethanol (48 mL) and deionized water (24 mL) were added to a three-necked flask, warmed up to 76° C. under nitrogen protection. The reaction solution was stirred under heating and refluxing for 12 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the compound 384 (11.8 g, yield: 55%). Mass spectrometry: m/z=772.31[M+H]⁺. Nuclear magnetic data of compound 384: ¹HNMR (400 MHz, CD₂Cl₂) δ(ppm): 8.87 (s, 1H), 8.79 (s, 1H), 8.77-8.75 (d, 1H), 8.60-8.57 (m, 2H), 8.35-8.33 (d, 1H), 8.25-8.21 (d, 1H), 8.05-8.03 (d, 1H), 7.86-7.83 (d, 1H), 7.60-7.56 (m, 4H), 7.50-7.41 (m, 9H), 7.10-7.06 (m, 2H), 2.12 (s, 3H), 1.96 (s, 6H), 1.82-1.76 (m, 6H).

Preparation Example 43. Preparation of Compound 385

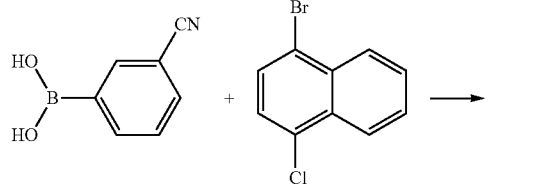

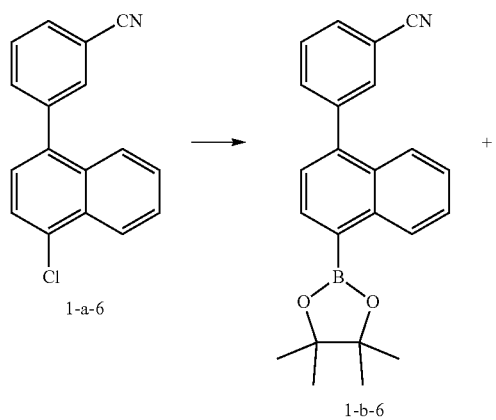

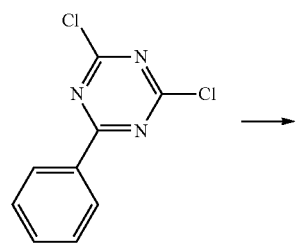

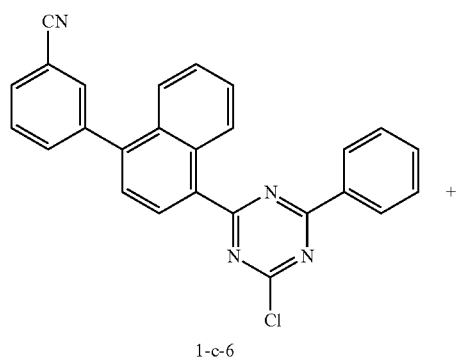

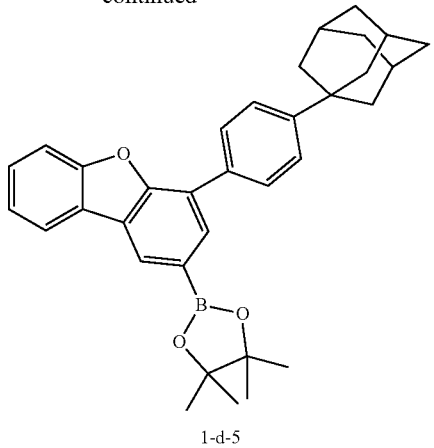

1-d-5

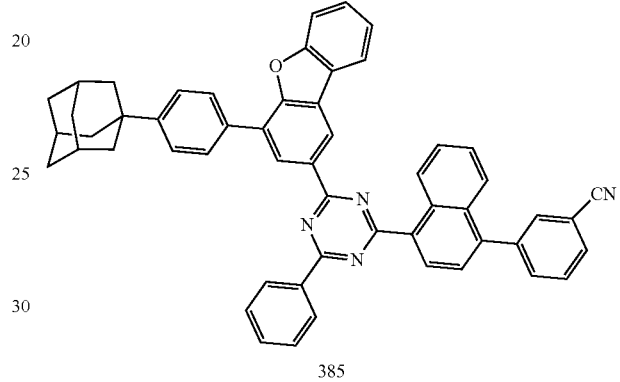

385

1) 1-Bromo-4-chloronaphthalene (49.3 g, 204.3 mmol), 3-cyanophenylboronic acid (27.3 g, 185.8 mmol), tetrakis(triphenylphosphine)palladium (2.1 g, 1.8 mmol), potassium carbonate (51.3 g, 371.5 mmol), tetrabutylammonium bromide (0.6 g, 1.8 mmol), toluene (400 mL), ethanol (200 mL) and deionized water (100 mL) were added to a three-necked flask, warmed up to 76° C. under nitrogen protection. The reaction solution was stirred under heating and refluxing for 15 h. After completion of the reaction, the obtained reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-a-6 (32.8 g, yield: 67%).

2) Intermediate 1-a-6 (30.0 g, 113.8 mmol, bis(pinacolato)diboron (34.6 g, 136.5 mmol), Pd(dppf)Cl$_2$ ([1,1'-bis(diphenylphosphino)ferrocenyl]palladium dichloride) (0.8 g, 1.2 mmol), and KOAc (22.3 g, 227.5 mmol) were added to 1,4-dioxane (300 mL), and refluxed and reacted at 100° C. for 10 h. After the reaction was completed, the mixture was extracted with CH$_2$Cl$_2$ and water. The organic phase was dried with MgSO$_4$ to remove the moisture in it, and an organic layer was concentrated. The resulting compound was subjected to silica gel column chromatography and recrystallization to obtain the intermediate 1-b-6 (24.2 g, yield: 60%).

3) Intermediate 1-b-6 (15.0 g, 42.2 mmol), 2,4-dichloro-6-phenyl-1,3,5-triazine (10.0 g, 44.3 mmol), tetrakis(triphenylphosphine)palladium (0.5 g, 0.4 mmol), potassium carbonate (11.6 g, 84.4 mmol), tetrabutylammonium bromide (0.1 g, 0.4 mmol), toluene (200 mL), ethanol (100 mL) and deionized water (50 mL) were added to a three-necked flask, warmed up to 76° C. under nitrogen protection. The reaction solution was stirred under heating and refluxing for 8 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtain the intermediate 1-c-6 (10.7 g, yield: 61%).

5) Intermediate 1-c-6 (10.0 g, 23.8 mmol), 1-d-5 (13.2 g, 26.2 mmol), tetrakis(triphenylphosphine)palladium (0.3 g, 0.2 mmol), potassium carbonate (6.6 g, 47.7 mmol), tetrabutylammonium bromide (0.07 g, 0.2 mmol), toluene (80 mL), ethanol (40 mL) and deionized water (20 mL) were added to a three-necked flask, warmed up to 76° C. under nitrogen protection. The reaction solution was stirred under heating and refluxing for 12 h. After completion of the reaction, the resulting reaction solution was cooled to room temperature, and extracted with toluene and water. The organic phases were combined, and an organic layer was dried with anhydrous magnesium sulfate, filtered and concentrated. The crude product was purified by silica gel column chromatography (dichloromethane/n-heptane) to obtained the compound 385 (9.0 g, yield: 50%). Mass spectrometry: m/z=761.32[M+H]$^+$.

Preparation and Evaluation of Organic Electroluminescent Devices

Example 1

An anode was produced by the following process: the ITO substrate with a thickness of 1300 Å was cutted into a size of 40 mm (length)×40 mm (width)×0.7 mm (thickness), then the substrate was processed through photolithography into an experimental substrate with a cathode overlaping area, an anode, and insulating layer patterns, and the experimental substrate was subjected to a surface treatment by ultraviolet ozone and $O_2$:$N_2$ plasma to increase work function of the anode, and cleaning the surface of the ITO substrate with an organic solvent to remove impurities and oil stains from the surface of the ITO substrate.

1T-NATA was vacuum deposited on the experimental substrate (anode) to form a hole injection layer (HIL) with a thickness of 100 Å, and NPB was vacuum deposited on the hole injection layer to form the first hole transport layer (HTL1) with a thickness of 1080 Å.

HT-02 was vacuum evaporated on the first hole transport layer to form the second hole transport layer (HTL2) with a thickness of 300 Å.

Next, a green light-emitting layer (EML) with a thickness of 350 Å was formed by co-evaporation of GHp1:compound 82:fac-Ir(ppy)$_3$ at a film thickness ratio of 45%:45%:10% on the second hole transport layer.

An electron transport layer (ETL) with a thickness of 300 Å was formed by mixing ET-1 with LiQ at a weight ratio of 1:1 and evaporating, and an electron injection layer (EIL) with a thickness of 15 Å was formed by evaporation of Yb on the electron transport layer. Then, magnesium (Mg) and argentum (Ag) were mixed at an evaporation rate of 1:9, and the mixture was vacuum deposited on the electron injection layer to form a cathode with a thickness of 120 Å.

Furthermore, CP-1 with a thickness of 700 Å was vacuum evaporated on the cathode to complete the manufacturing of the organic electroluminescent device.

Examples 2 to 14

Organic electroluminescent devices were manufactured in the same manner as in Example 1, except that compounds shown in Table 8 were used in place of compound 82 in Example 1, respectively, when the light-emitting layer was formed.

Comparative Examples 1 to 4

Organic electroluminescent devices were manufactured in the same manner as in Example 1, except that Compounds C to F shown in Table 7 were used in place of compound 82 in Example 1, respectively, when forming the light-emitting layer.

In the preparation of the organic electroluminescent devices, the structural formulae of partial materials used in the above comparative examples and examples were shown in Table 7.

TABLE 7

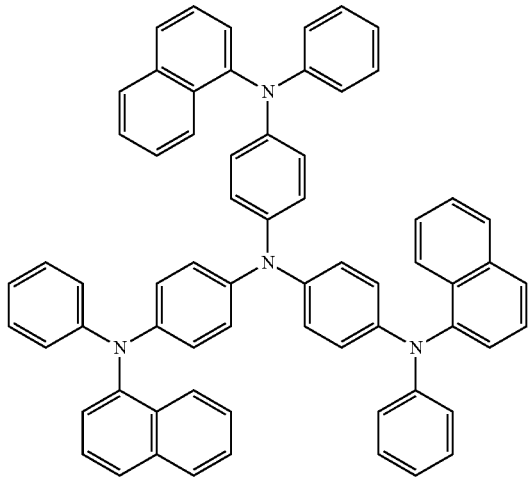

1T-NATA

TABLE 7-continued
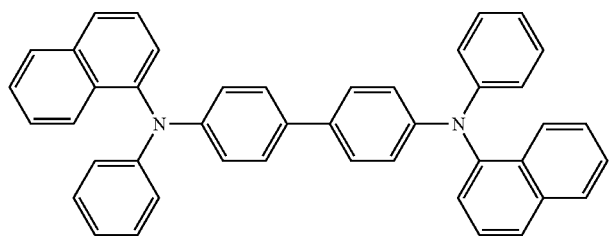
NPB
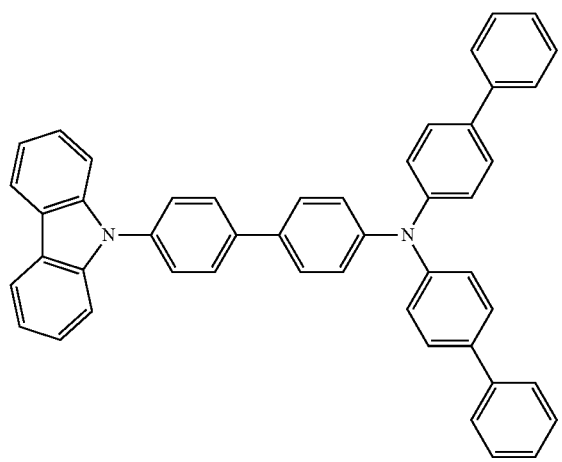
HT-02
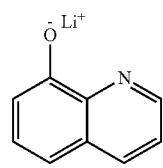
LiQ
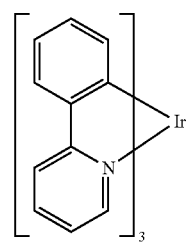
fac-Ir(ppy)$_3$ TABLE 7-continued
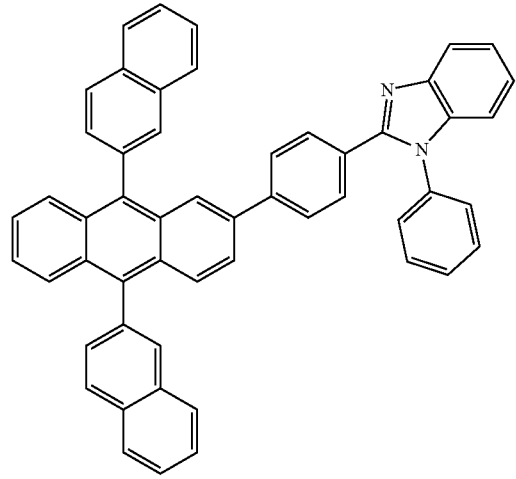
ET-1
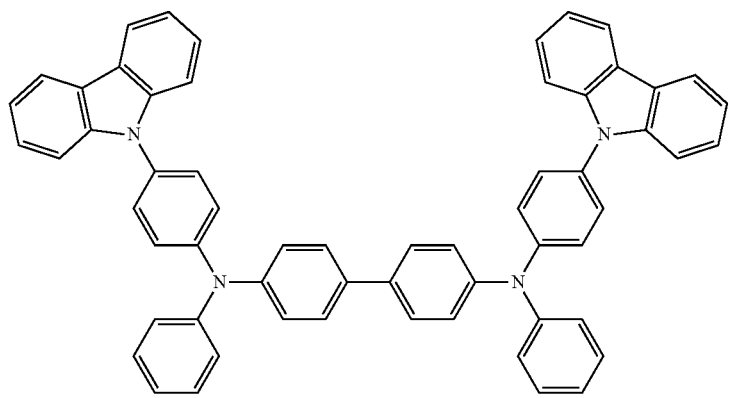
CP-1
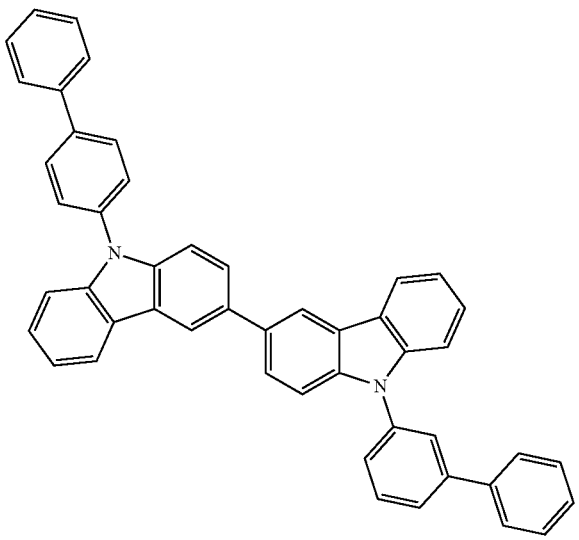
GHp1

TABLE 7-continued
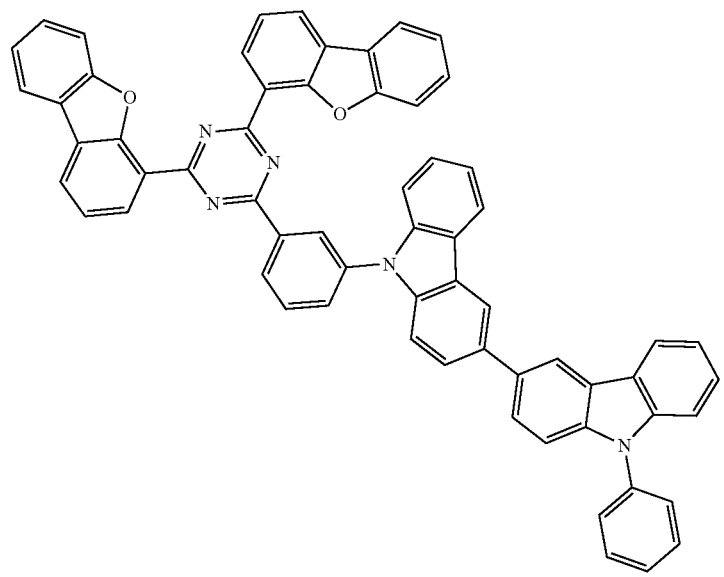
Compound C
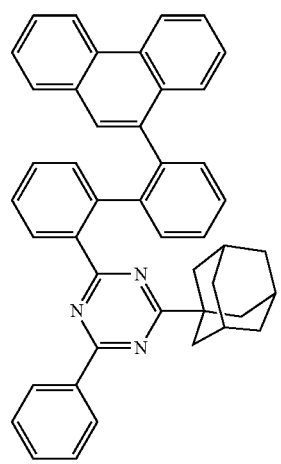
Compound D

TABLE 7-continued

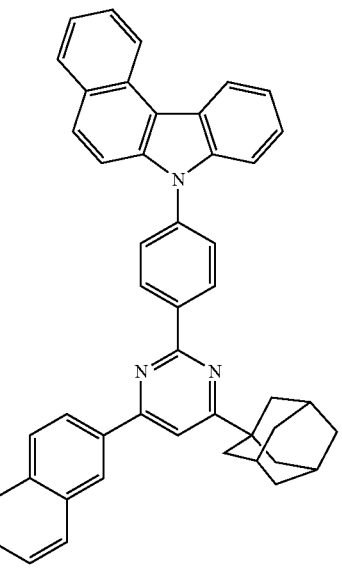

Compound E

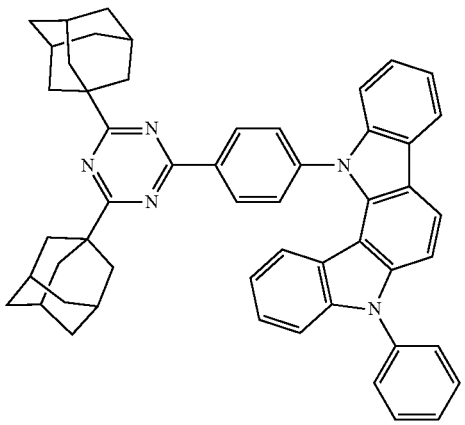

Compound F

The green organic electroluminescent devices prepared in Examples 1 to 14 and Comparative Examples 1 to 4 were subjected to performance tests. Specifically, the IVL performance of devices was tested under the condition of 10 mA/cm$^2$, and the T95 device lifetime was tested under the condition of 20 mA/cm$^2$. The test results were shown in Table 8.

TABLE 8

| Examples | Light-emitting layer: a ratio of three materials = 45%:45%:10% | Drive voltage (V) | Current efficiency (Cd/A) | Color coordinates CIEx, CIEy | External quantum efficiency EQE (%) | T95 lifetime (h) |
| --- | --- | --- | --- | --- | --- | --- |
| Example 1 | GHp1: compound 82:fac-Ir(ppy)$_3$ | 3.92 | 93.5 | 0.262,0.702 | 28.3 | 173 |
| Example 2 | GHp1: compound 100:fac-Ir(ppy)$_3$ | 3.87 | 93.0 | 0.261,0.703 | 28.1 | 174 |
| Example 3 | GHp1: compound 114:fac-Ir(ppy)$_3$ | 3.85 | 93.3 | 0.262,0.702 | 27.4 | 172 |
| Example 4 | GHp1: compound 115:fac-Ir(ppy)$_3$ | 3.88 | 91.7 | 0.261,0.704 | 27.8 | 177 |

TABLE 8-continued

| Examples | Light-emitting layer: a ratio of three materials = 45%:45%:10% | Drive voltage (V) | Current efficiency (Cd/A) | Color coordinates CIEx, CIEy | External quantum efficiency EQE (%) | T95 lifetime (h) |
|---|---|---|---|---|---|---|
| Example 5 | GHp1: compound 117:fac-Ir(ppy)$_3$ | 3.85 | 93.5 | 0.266,0.700 | 27.3 | 172 |
| Example 6 | GHp1: compound 121:fac-Ir(ppy)$_3$ | 3.87 | 92.1 | 0.266,0.700 | 28.0 | 178 |
| Example 7 | GHp1: compound 125:fac-Ir(ppy)$_3$ | 3.89 | 94.1 | 0.266,0.701 | 27.5 | 170 |
| Example 8 | GHp1: compound 128:fac-Ir(ppy)$_3$ | 3.88 | 92.5 | 0.265,0.700 | 27.7 | 173 |
| Example 9 | GHp1: compound 142:fac-Ir(ppy)$_3$ | 3.90 | 92.5 | 0.262,0.702 | 27.2 | 178 |
| Example 10 | GHp1: compound 148:fac-Ir(ppy)$_3$ | 3.89 | 90.9 | 0.262,0.702 | 27.2 | 174 |
| Example 11 | GHp1: compound 280:fac-Ir(ppy)$_3$ | 3.88 | 94.9 | 0.261,0.704 | 27.6 | 172 |
| Example 12 | GHp1: compound 297:fac-Ir(ppy)$_3$ | 3.90 | 92.9 | 0.266,0.700 | 27.2 | 173 |
| Example 13 | GHp1: compound 288:fac-Ir(ppy)$_3$ | 3.87 | 91.3 | 0.261,0.704 | 28.0 | 170 |
| Example 14 | GHp1: compound 304:fac-Ir(ppy)$_3$ | 3.89 | 93.6 | 0.266,0.700 | 27.8 | 178 |
| Comparative Example 1 | GHp1: compound C:fac-Ir(ppy)$_3$ | 3.89 | 77.6 | 0.266,0.700 | 19.6 | 150 |
| Comparative Example 2 | GHp1: compound D:fac-Ir(ppy)$_3$ | 3.91 | 70.6 | 0.267,0.700 | 16.9 | 155 |
| Comparative Example 3 | GHp1: compound E:fac-Ir(ppy)$_3$ | 3.82 | 69.6 | 0.266,0.700 | 16.1 | 157 |
| Comparative Example 4 | GHp1: compound F:fac-Ir(ppy)$_3$ | 3.94 | 80.5 | 0.266,0.700 | 20.1 | 143 |

According to the performance test results of devices in Table 8, it can be seen that the compounds of the present disclosure used as host materials of the green light-emitting layer in Examples 1 to 14 have an effect of improving the device efficiency and lifetime compared with Comparative Examples 1 to 4. Specifically, in the case that the compounds of the present disclosure were used as n type light-emitting materials in Examples 1 to 14, the device efficiency and T95 lifetime of Examples 1 to 14 were increased by at least 12.9% and 8.3%, respectively, compared to Comparative Examples 1 to 4, while ensuring a lower drive voltage.

Example 15. Green Organic Electroluminescent Device

An anode was produced by the following process: the ITO with thickness of 1200 Å was cutted into a size of 40 mm (length)×40 mm (width)×0.7 mm (T), then the substrate was processed through photolithography into an experimental substrate with an anode, a cathode overlaping area, and insulating layer patterns, and the experimental substrate was subjected to a surface treatment by ultraviolet ozone and O$_2$:N$_2$ plasma to increase work function of the anode, and cleaning the surface of the ITO substrate with an organic solvent to remove impurities and oil stains from the surface of the ITO substrate.

1T-NATA was vacuum evaporated on the experimental substrate (anode) to form a hole injection layer (HIL) with a thickness of 100 Å, and NPAPF was vacuum evaporated on the hole injection layer to form the first hole transport layer (HTL1) with a thickness of 1050 Å.

HT-02 was vacuum evaporated on the first hole transport layer to form the second hole transport layer (HTL2) with a thickness of 400 Å.

Next, a green light-emitting layer (EML) with a thickness of 380 Å was formed by co-evaporation of GHp1:compound 1:fac-Ir(ppy)$_3$ at a film thickness ratio of 45%:45%:10% on the second hole transport layer.

An electron transport layer (ETL) with a thickness of 300 Å was formed by mixing ET-1 with LiQ at a weight ratio of 1:1 and evaporating. Then, an electron injection layer (EIL) with a thickness of 30 Å was formed by co-evaporation of Mg:LiF at a film thickness ratio of 1:1. Then, Then, magnesium (Mg) and argentum (Ag) were mixed at an evaporation rate of 1:9, and the mixture was vacuum evaporated on the electron injection layer to form a cathode with a thickness of 120 Å.

Furthermore, CP-1 with a thickness of 700 Å was vacuum-evaporated on the cathode to complete the manufacturing of the organic electroluminescent device.

Examples 16 to 20

Organic electroluminescent devices were manufactured in the same manner as in Example 15, except that compounds shown in Table 10 were used in place of compound 1 in Example 15, respectively, when the light-emitting layer was formed.

Example 21

An organic electroluminescent device was manufactured in the same manner as in Example 15, except that a green light-emitting layer with a thickness of 380 Å was formed by co-evaporation of GhP2:compound 352:fac-Ir(ppy)$_3$ at a film thickness ratio of 45%:45%:10%, when the light-emitting layer was formed.

Examples 22 to 30

Organic electroluminescent devices were manufactured in the same manner as in Example 21, except that the compounds shown in Table 10 were used in place of Compound 352 in Example 21, respectively, when the light-emitting layer was formed.

Comparative Examples 5 to 6

Organic electroluminescent devices were manufactured in the same manner as in Example 15, except that Compound A and Compound B shown in Table 9 were used in place of Compound 1 in Example 15, respectively, when the light-emitting layer was formed.

Comparative Examples 7 to 9

Organic electroluminescent devices were manufactured in the same manner as in Example 21, except that Compound C, Compound D, and Compound E shown in Table 9 were used in place of Compound 352 in Example 21, when the light-emitting layer was formed.

The structural formulae of some of the materials used in Comparative Examples 5 to 9 and Examples 15 to 30 in the preparation of organic electroluminescent devices are shown in Table 9.

TABLE 9

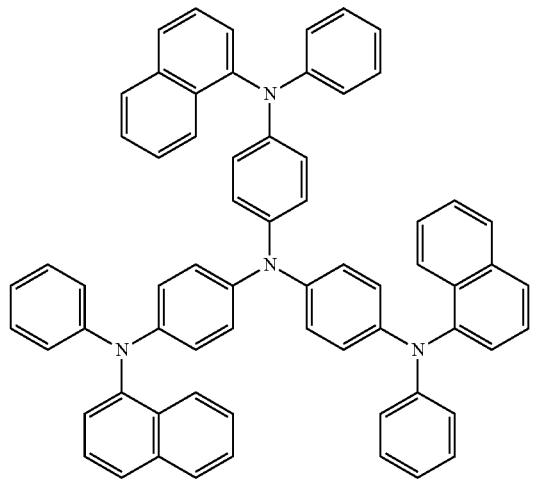

1T-NATA

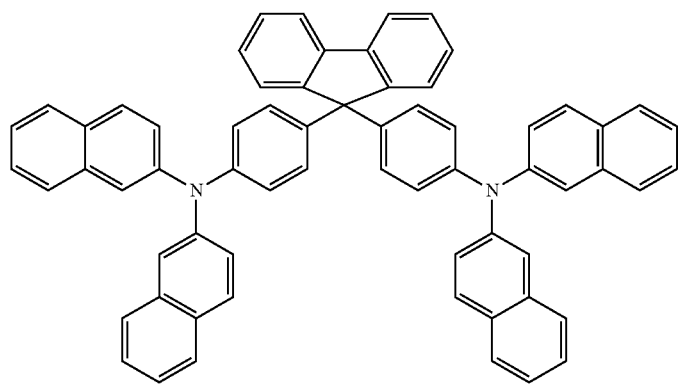

NPAPF

TABLE 9-continued
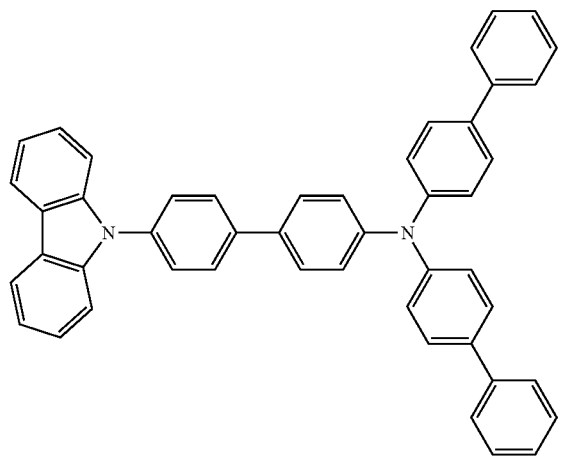
HT-02
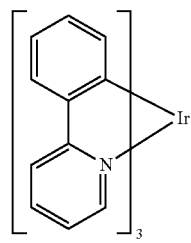
fac-Ir(ppy)3
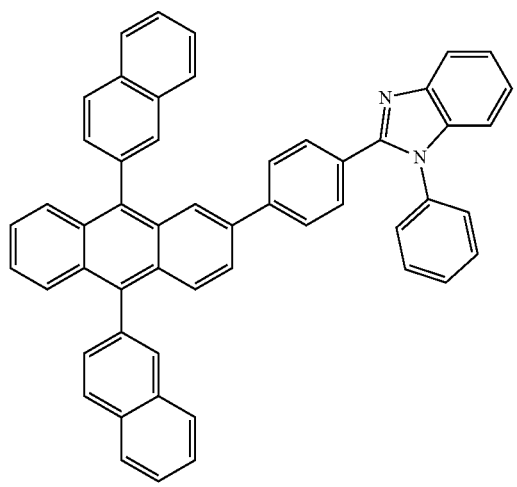
ET-1
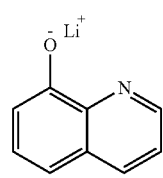
LiQ TABLE 9-continued
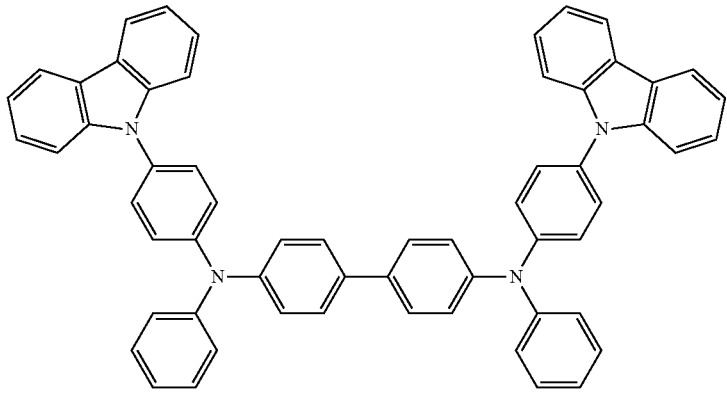
CP-1
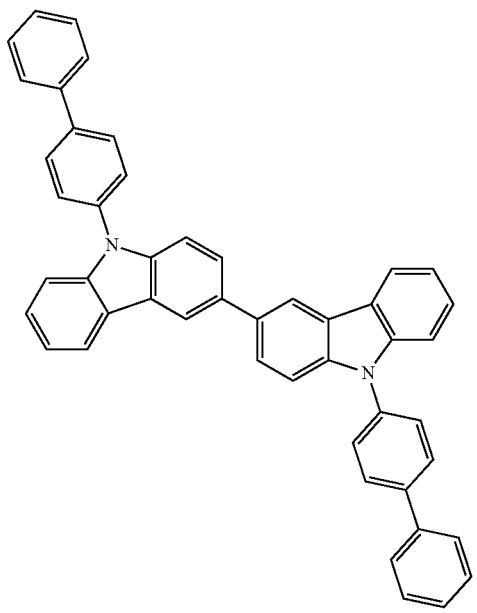
GhP1
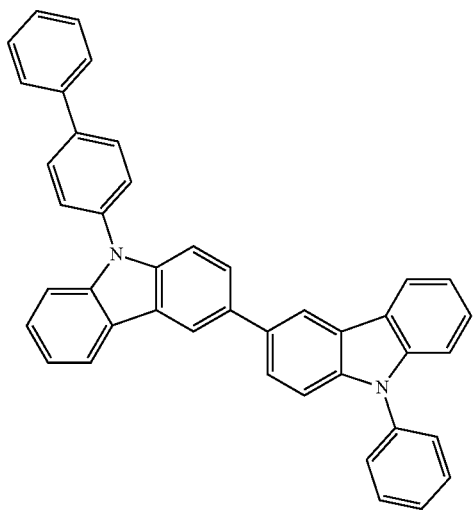
GhP2

TABLE 9-continued
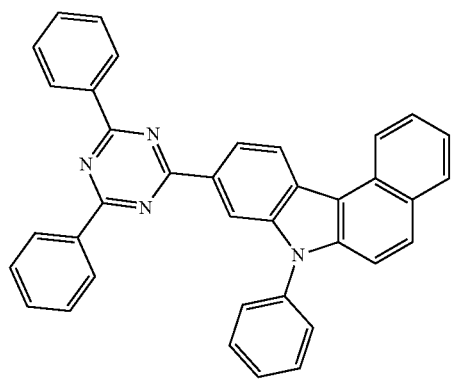
Compound A
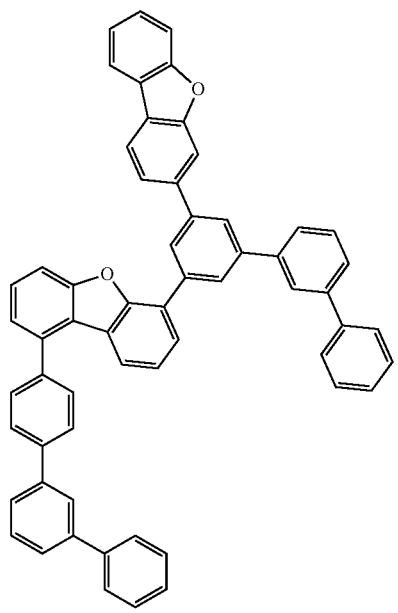
Compound B

TABLE 9-continued
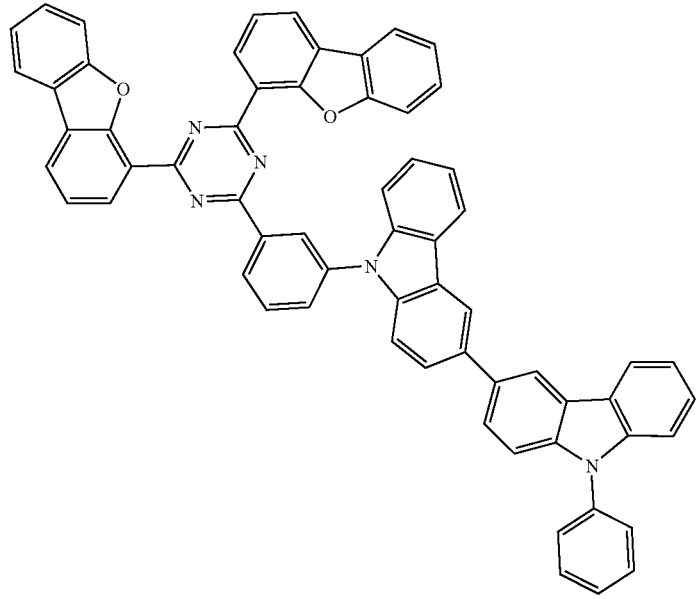
Compound C
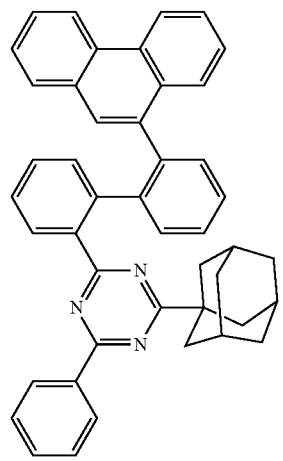
Compound D

TABLE 9-continued

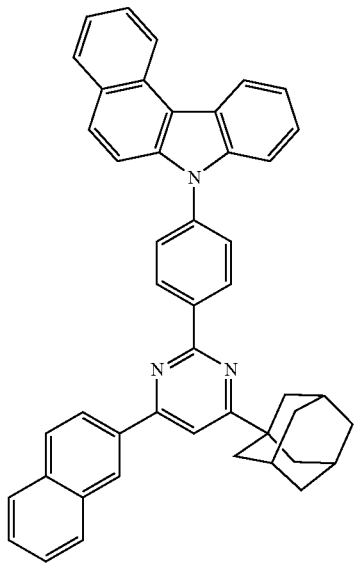

Compound E

The green organic electroluminescent devices prepared in Examples 15 to 30 and Comparative Examples 5 to 9 were subjected to performance tests. Specifically, the IVL performance of the devices was tested under the condition of 10 mA/cm², and the T95 device lifetime was tested under the condition of 20 mA/cm 2. The test results were shown in Table 10.

TABLE 10

Performance Test Results of Green Organic Light-Emitting Devices

| Examples | Light-emitting layer: a ration of three materials = 45%:45%:10% | Drive voltage (V) | Current efficiency (Cd/A) | Color coordinates CIEx, CIEy | External quantum efficiency EQE (%) | T95 lifetime (H) |
|---|---|---|---|---|---|---|
| Example 15 | GhP1: Compound 1:fac-Ir(ppy)$_3$ | 3.89 | 97.0 | 0.266,0.700 | 28.7 | 189 |
| Example 16 | GhP1: Compound 34:fac-Ir(ppy)$_3$ | 3.93 | 94.8 | 0.262,0.704 | 26.9 | 183 |
| Example 17 | GhP1: compound 43:fac-Ir(ppy)$_3$ | 3.98 | 95.0 | 0.262,0.704 | 27.1 | 181 |
| Example 18 | GhP1: Compound No.5:fac-Ir(ppy)$_3$ | 3.91 | 95.7 | 0.264,0.702 | 27.5 | 179 |
| Example 19 | GhP1: compound 6: fac-Ir(ppy)$_3$ | 3.90 | 95.0 | 0.261,0.704 | 27.0 | 180 |
| Example 20 | GhP1: compound 16:fac-Ir(ppy)$_3$ | 3.98 | 95.7 | 0.262,0.704 | 27.4 | 179 |
| Example 21 | GhP2: compound 352 :fac-Ir(ppy)$_3$ | 3.95 | 95.9 | 0.263,0.704 | 27.9 | 182 |
| Example 22 | GhP2: Compound 56:fac-Ir(ppy)$_3$ | 3.89 | 96.9 | 0.265,0.701 | 28.5 | 188 |
| Example 23 | GhP2: Compound 71-fac-Ir(ppy)$_3$ | 3.92 | 95.0 | 0.265,0.701 | 27.1 | 182 |
| Example 24 | GhP2: compound 67:fac-Ir(ppy)$_3$ | 3.90 | 95.8 | 0.263,0.703 | 27.7 | 180 |
| Example 25 | GhP2: compound 73:fac-Ir(ppy)$_3$ | 3.94 | 95.9 | 0.266,0.701 | 27.8 | 181 |
| Example 26 | GhP2: compound 86:fac-Ir(ppy)$_3$ | 3.98 | 95.5 | 0.263,0.704 | 27.3 | 180 |
| Example 27 | GhP2: compound 358:fac-Ir(ppy)$_3$ | 3.90 | 96.5 | 0.265,0.701 | 28.4 | 187 |
| Example 28 | GhP2: compound 33:fac-Ir(ppy)$_3$ | 3.88 | 96.8 | 0.266,0.700 | 28.8 | 187 |

TABLE 10-continued

Performance Test Results of Green Organic Light-Emitting Devices

| Examples | Light-emitting layer: a ration of three materials = 45%:45%:10% | Drive voltage (V) | Current efficiency (Cd/A) | Color coordinates CIEx, CIEy | External quantum efficiency EQE (%) | T95 lifetime (H) |
|---|---|---|---|---|---|---|
| Example 29 | GhP2: compound 354:fac-Ir(ppy)$_3$ | 3.91 | 96.0 | 0.264, 0.703 | 28.6 | 186 |
| Example 30 | GhP2: compound 87:fac-Ir(ppy)$_3$ | 3.89 | 96.9 | 0.265, 0.701 | 28.9 | 185 |
| Comparative Example 5 | GhP1: compound A:fac-Ir(ppy)$_3$ | 3.88 | 72.2 | 0.266, 0.700 | 18.9 | 150 |
| Comparative Example 6 | GhP1: compound B:fac-Ir(ppy)$_3$ | 3.94 | 77.9 | 0.262, 0.704 | 19.5 | 140 |
| Comparative Example 7 | GhP2: compound C:fac-Ir(ppy)$_3$ | 4.01 | 70.9 | 0.266, 0.700 | 18.1 | 149 |
| Comparative Example 8 | GhP2: compound D:fac-Ir(ppy)$_3$ | 4.11 | 83.7 | 0.267, 0.700 | 24.9 | 154 |
| Comparative Example 9 | GhP2: compound E:fac-Ir(ppy)$_3$ | 3.99 | 67.8 | 0.266, 0.700 | 15.6 | 162 |

According to the performance test results of devices in Table 10, it can be seen that the compounds of the present disclosure used as n type host materials of the green light-emitting layer in Examples 15 to 30 have an effect of improving the device efficiency and lifetime compared with Comparative Examples 5 to 9. Among them, the drive voltage is almost equivalent, the device efficiency is improved by at least 13.3%, and the T95 lifetime is improved by at least 10.5%. In conclusion, the organic compounds of the present disclosure may effectively prolong the lifetime and greatly improve the luminous efficiency of the organic electroluminescent device, when being used to prepare the green organic electroluminescent devices.

Preparation of Red Organic Electroluminescent Devices

Example 31

An anode was produced by the following process: the ITO substrate (manufactured by Corning) with a thickness of 1300 Å was cutted into a size of 40 mm (length)×40 mm (width)×0.7 mm (thickness), then the substrate was processed through photolithography into an experimental substrate with an anode, a cathode overlap region, and insulating layer patterns, and the experimental substrate was subjected to a surface treatment by ultraviolet ozone and $O_2:N_2$ plasma to increase work function of the anode (experimental substrate) and remove dross.

NATA was vacuum evaporated on the experimental substrate (anode) to form a hole injection layer (HIL) with a thickness of 100 Å, and NPAPF was vacuum evaporated on the hole injection layer to form the first hole transport layer (HTL1) with a thickness of 1200 Å.

Next, PAPB was vacuum evaporated on the first hole transport layer to form the second hole transport layer (HTL2) with a thickness of 300 Å.r.

Then, an organic light-emitting layer (EML) with a thickness of 370 Å was formed by co-evaporation of compound 362:RH-P:Ir(MDQ)$_2$(acac) at a ratio (evaporation rate) of 45%:45%:3% on the second hole transport layer.

An electron transport layer (ETL) with a thickness of 300 Å was formed by mixing DbimiBphen with LiQ at a weight ratio of 1:1 and evaporating. Then, an electron injection layer (EIL) with a thickness of 15 Å was formed by vacuum evaporation of Yb on the electron transport layer.

Then, magnesium (Mg) and argentum (Ag) were mixed at an evaporation rate of 1:9, and the mixture was vacuum evaporated on the electron injection layer to form a cathode with a thickness of 120 Å.

Furthermore, CP-1 with a thickness of 630 Å was vacuum evaporated on the cathode to form a capping layer (CPL), thereby completing the manufacture of the organic light-emitting device.

Examples 32 to 43

Organic electroluminescent devices were manufactured in the same manner as in Example 31, except that compounds shown in Table 11 were used in place of compound 362 in Example 31, respectively, when the light-emitting layer was formed.

Comparative Examples 10 to 11

Organic electroluminescent devices were manufactured in the same manner as in Example 31, except that compounds G and H were used in place of compound 362 in Example 31, when the light-emitting layer was formed.

In Examples 31 to 43 and Comparative Examples 10 to 11, the structures of the main materials used were as follows:

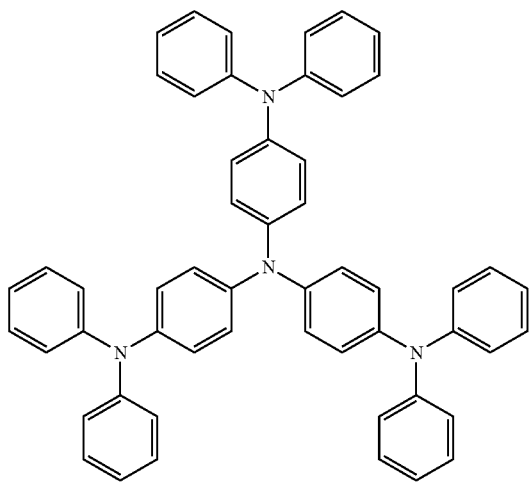
NATA
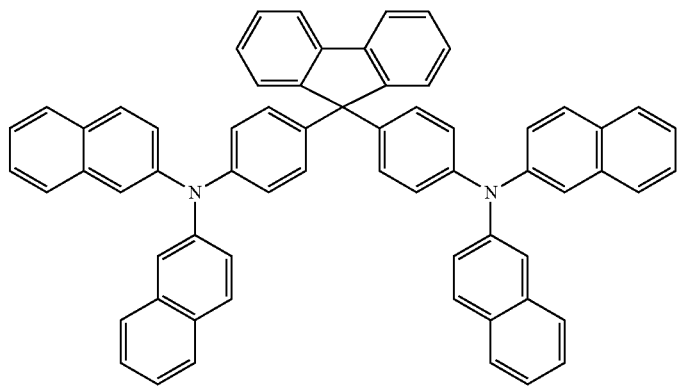
NPAPF
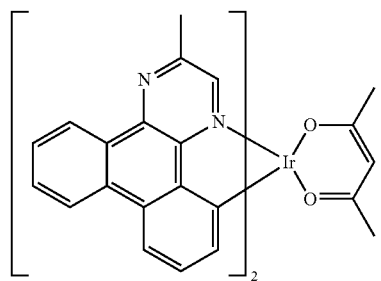
Ir (MDQ)$_2$(acac)

-continued
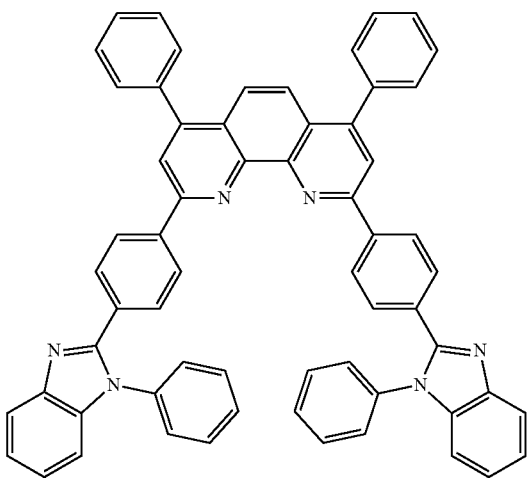
DBimiBphen
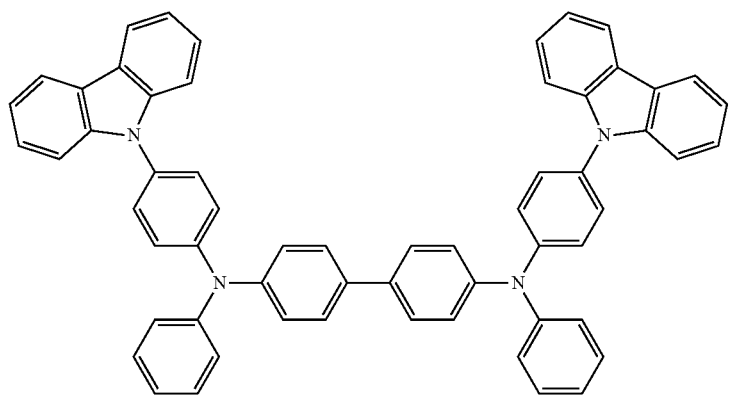
CP-1
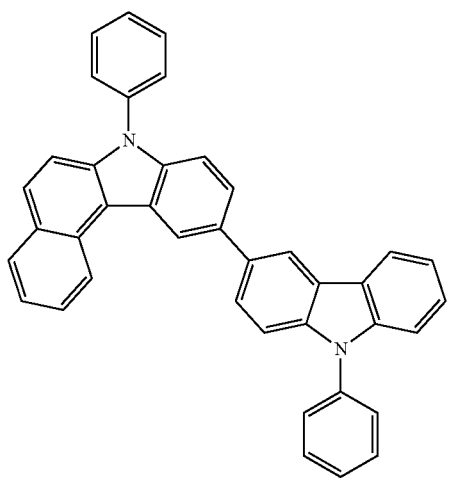
RH-P

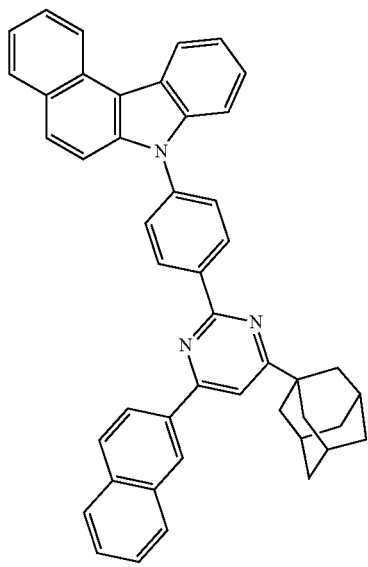

Compound G

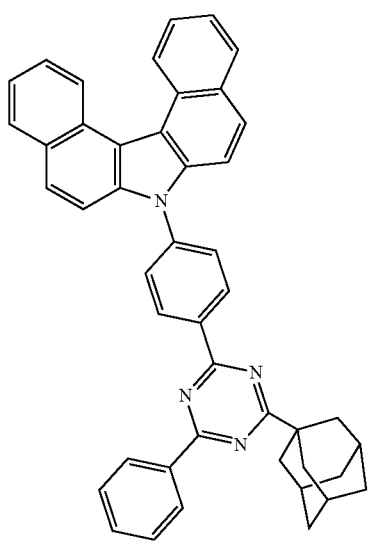

Compound H

The performance (IVL and lifetime) of the organic electroluminescent devices of Examples 31 to 43 and Comparative Examples 10 to 11 described above were analyzed, and the results are shown in the following table. The drive voltage, luminous efficiency, external quantum efficiency, and color coordinates were measured at a constant current density 10 mA/cm 2, and the T95 device lifetime was measured at a constant current density 20 mA/cm 2.

TABLE 11

Performance of Red Organic Luminescence Devices

| Example | host material of Light-emitting layer | Operating voltage Volt (V) | Luminous efficiency (Cd/A) | External quantum efficiency EQE (%) | T95 device lifetime (H) | Color coordinate CIEx |
|---|---|---|---|---|---|---|
| Example 31 | Compound 362 | 3.77 | 33.9 | 23.1 | 537 | 0.679 |
| Example 32 | Compound 363 | 3.76 | 34.3 | 23.9 | 539 | 0.678 |
| Example 33 | Compound 365 | 3.77 | 34.0 | 23.7 | 560 | 0.680 |
| Example 34 | Compound 367 | 3.74 | 35.1 | 24.2 | 555 | 0.678 |
| Example 35 | Compound 369 | 3.76 | 34.4 | 23.9 | 558 | 0.678 |
| Example 36 | Compound 370 | 3.78 | 34.0 | 23.6 | 540 | 0.677 |
| Example 37 | Compound 371 | 3.76 | 34.1 | 23.7 | 536 | 0.680 |
| Example 38 | Compound 373 | 3.77 | 34.6 | 24.1 | 541 | 0.680 |
| Example 39 | Compound 376 | 3.78 | 34.1 | 23.7 | 553 | 0.679 |
| Example 40 | Compound 378 | 3.74 | 33.8 | 23.1 | 556 | 0.679 |
| Example 41 | Compound 381 | 3.75 | 34.1 | 23.6 | 559 | 0.680 |
| Example 42 | Compound 384 | 3.76 | 35.4 | 24.5 | 552 | 0.680 |
| Example 43 | Compound 385 | 3.75 | 35.5 | 24.5 | 558 | 0.679 |
| Comparative Example 10 | Compound G | 4.02 | 28.6 | 19.9 | 469 | 0.678 |
| Comparative Example 11 | Compound H | 3.97 | 29.8 | 20.6 | 487 | 0.679 |

According to the performance test results of devices in Table 11, it can be seen that the compounds of the present disclosure used as n type host materials of the red light-emitting layer in Examples 31 to 43 have an effect of improving the device efficiency and lifetime compared with Comparative Examples 10 to 11. Among them, the drive voltage is equivalent, the device efficiency is improved by at least 13.4%, and the T95 lifetime is improved by at least 10.1%.

In conclusion, the organic compounds of the present disclosure may effectively prolong the lifetime and improve the luminous efficiency of the organic electroluminescent device, when being used in the organic electroluminescent devices.

Preferred embodiments of the present disclosure have been described above in detail with reference to the accompanying drawings, but the present disclosure is not limited to the specific details in the above-described examples, and various simple variations of the technical solutions of the present disclosure may be made within the scope of the technical concept of the present disclosure, all of which fall within the scope of the present disclosure.

It should also be noted that each of the specific technical features described in the above-described specific embodiments can be combined in any suitable manner without contradiction, and in order to avoid unnecessary repetition, the present disclosure does not explain the various possible ways of combination separately.

In addition, any combination of various embodiments of the present disclosure may be made, as long as it does not contradict the idea of the present disclosure, which should also be considered as disclosed in the present disclosure.

What is claimed is:

1. An organic compound, having a structure represented by the following formula 3-1, formula 3-2 or formula 3-4:

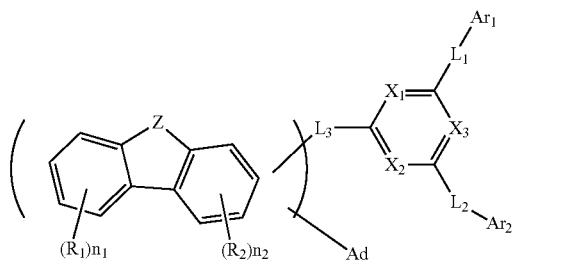

3-1

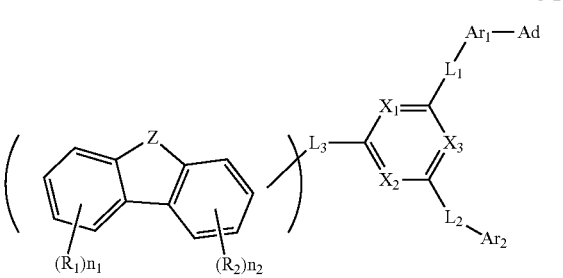

3-2

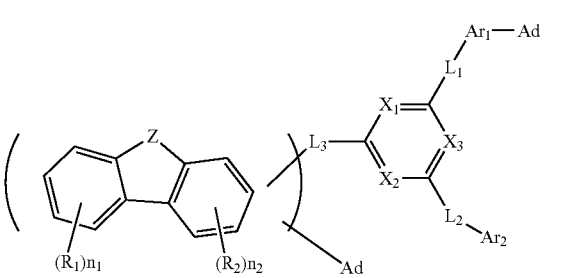

3-4 wherein Z is selected from O, S, C($R_3R_4$), and N($R_5$);
$R_3$ and $R_4$ are the same or different, and are each independently selected from alkyl with 1 to 4 carbon atoms, aryl with 6 to 12 carbon atoms, or heteroaryl with 3 to 12 carbon atoms;

R₅ is selected from substituted or unsubstituted aryl with 6 to 20 carbon atoms, and substituted or unsubstituted heteroaryl with 3 to 20 carbon atoms, and substituents in R₅ are each independently selected from deuterium, fluorine, alkyl with 1 to 4 carbon atoms, cycloalkyl with 5 to 10 carbon atoms, and trialkylsilyl with 3 to 7 carbon atoms;

$X_1$, $X_2$ and $X_3$ are the same or different, and are each independently selected from C(H) or N, and at least one of $X_1$, $X_2$ and $X_3$ is N;

$R_1$ and $R_2$ are the same or different, and are each independently selected from deuterium, fluorine, alkyl with 1 to 4 carbon atoms, cycloalkyl with 5 to 10 carbon atoms, alkoxy with 1 to 4 carbon atoms, alkylthio with 1 to 4 carbon atoms, trialkylsilyl with 3 to 7 carbon atoms, and a group D; wherein the group D is selected from substituted or unsubstituted aryl with 6 to 20 carbon atoms, and substituted or unsubstituted heteroaryl with 3 to 20 carbon atoms, and substituents in the group D are each selected from deuterium, fluorine, alkyl with 1 to 4 carbon atoms, cycloalkyl with 5 to 10 carbon atoms, and trialkylsilyl with 3 to 7 carbon atoms; $n_1$ represents the number of $R_1$, and $n_2$ represents the number of $R_2$; $R_1$ and $R_2$ are represented by $R_i$, and $n_1$ to $n_2$ are represented by $n_i$, i is a variable representing 1 or 2; $n_i$ is each independently selected from 0, 1, 2, 3 or 4; and any two $n_i$s are the same or different when $n_i$ is greater than one; optionally, any two adjacent $R_i$s form a ring;

$Ar_i$ is selected from the group consisting of the following groups:

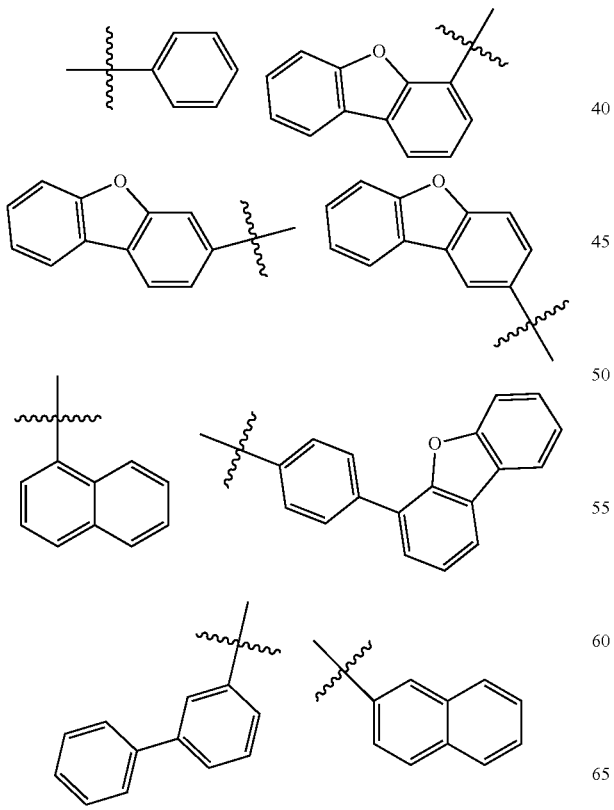

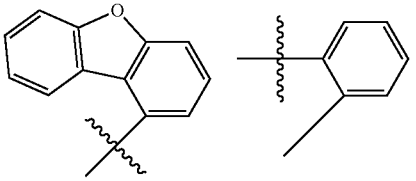

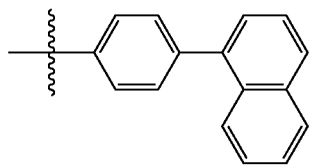

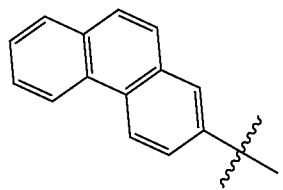

-continued

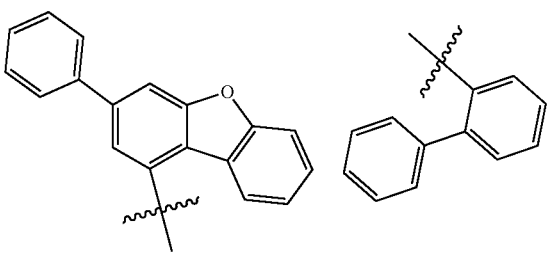

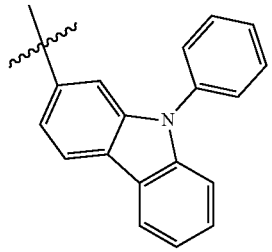

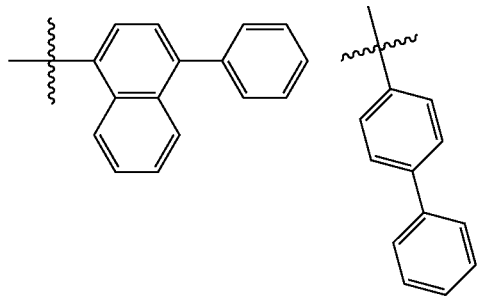

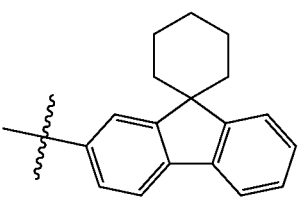

363
-continued
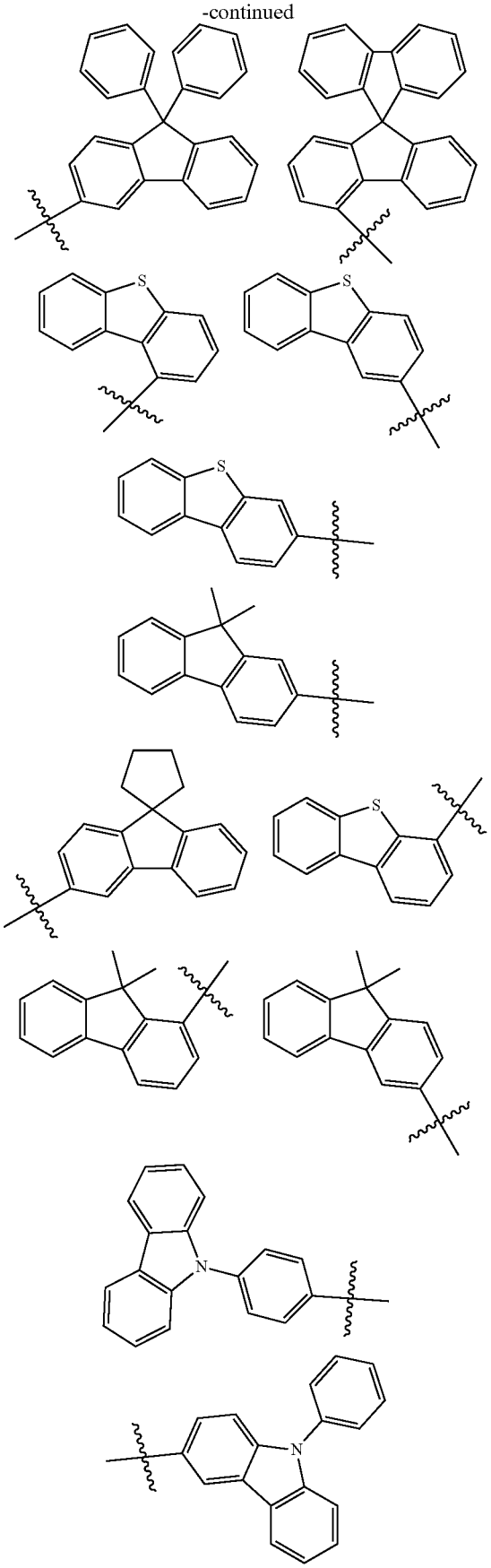
364
-continued
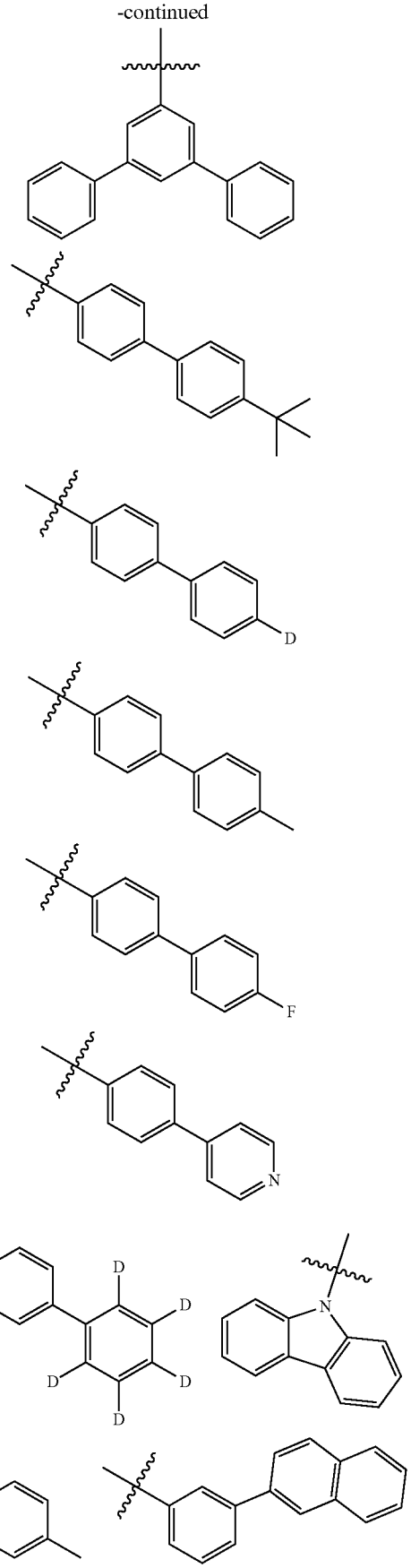

365
-continued
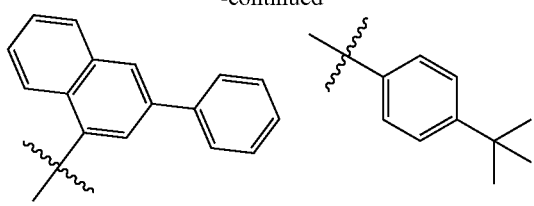
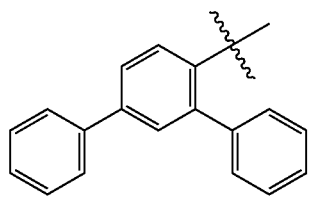
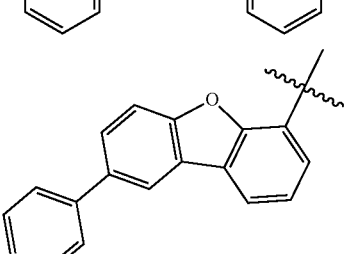
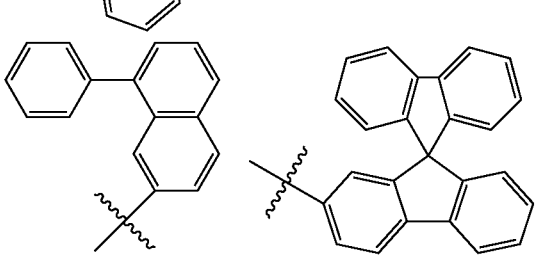
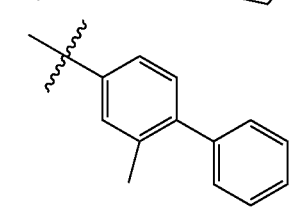
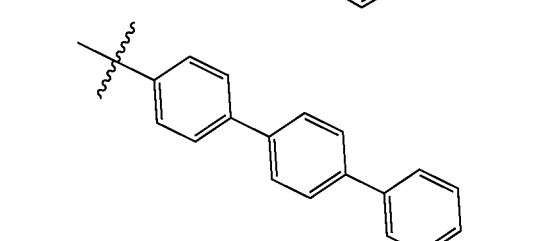
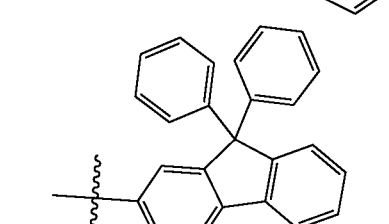
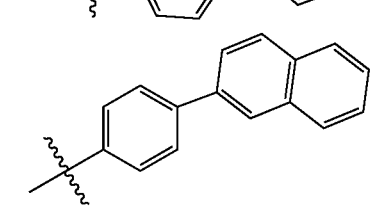
366
-continued
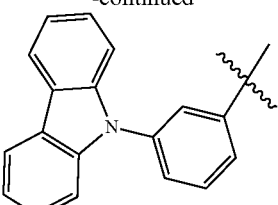
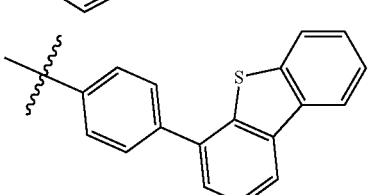
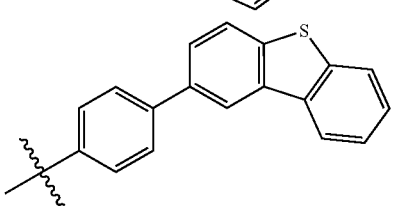
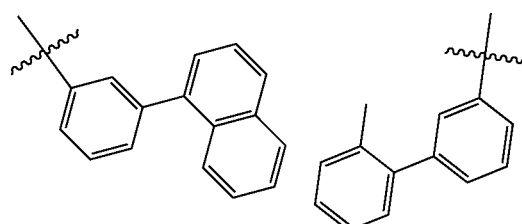
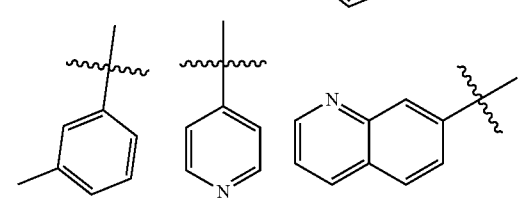
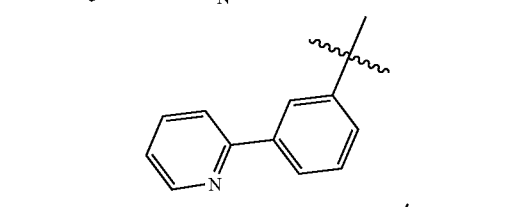
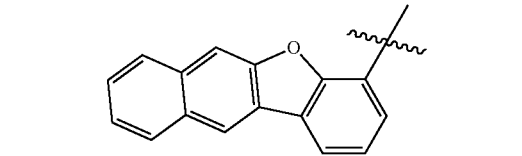
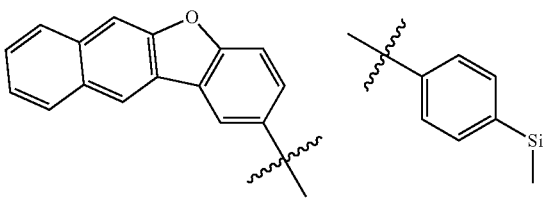
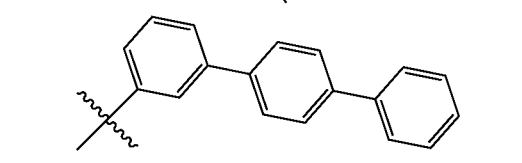

-continued

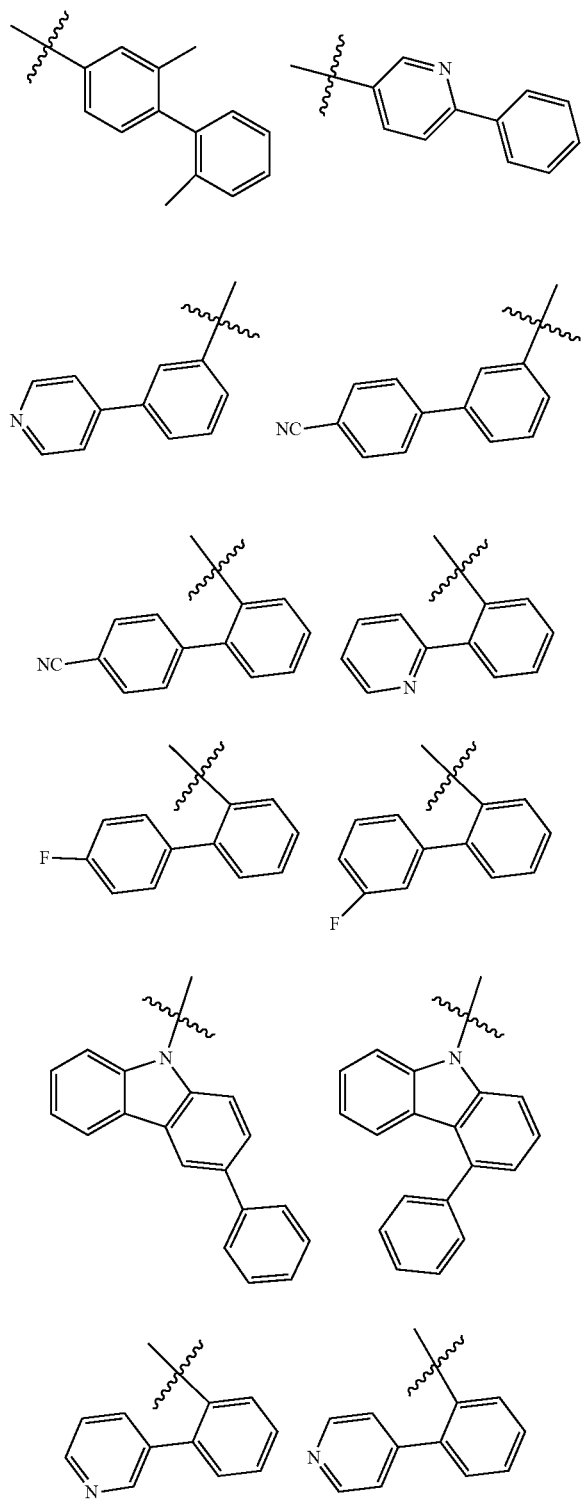

wherein, in formula 3-2 and formula 3-4, one hydrogen of Ar₁ is replaced by an Ad;

$L_1$, $L_2$ and $L_3$ are the same or different, and are each independently selected from a single bond, substituted or unsubstituted arylene with 6 to 35 carbon atoms, and substituted or unsubstituted heteroarylene with 3 to 30 carbon atoms;

$Ar_2$ is selected from a substituted or unsubstituted group $V_1$, and the unsubstituted group $V_1$ is selected from the group consisting of the following groups:

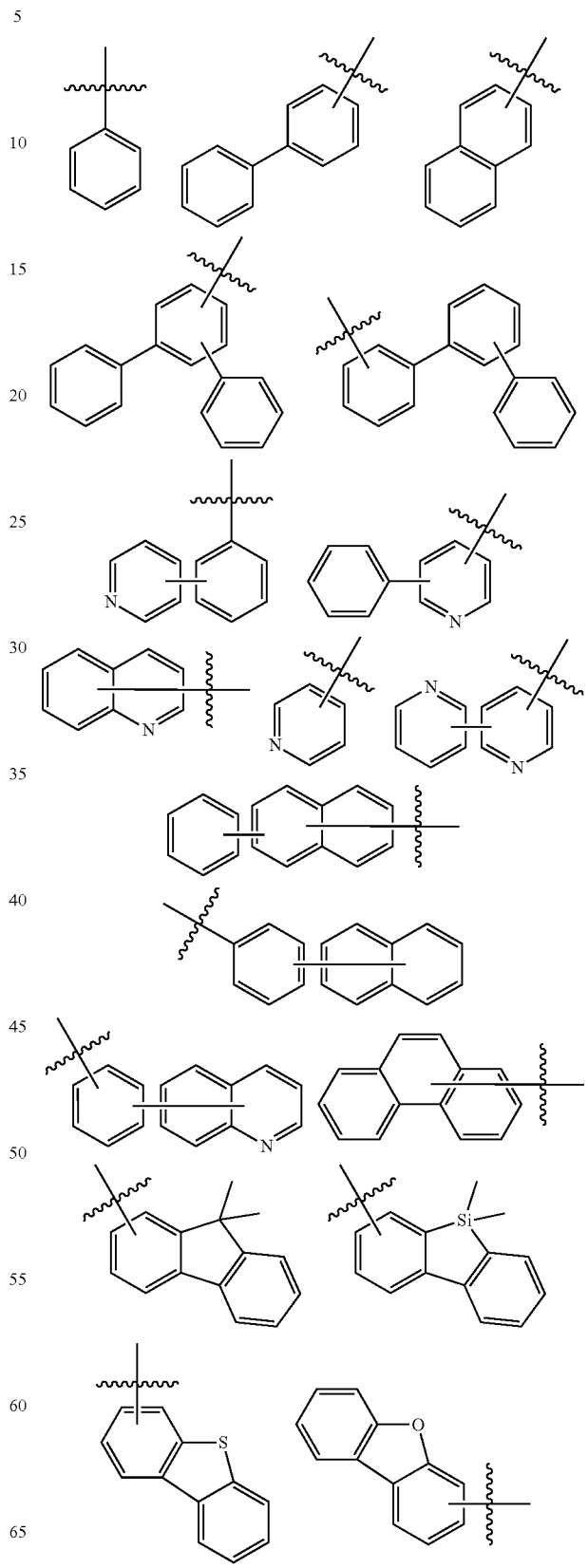

-continued

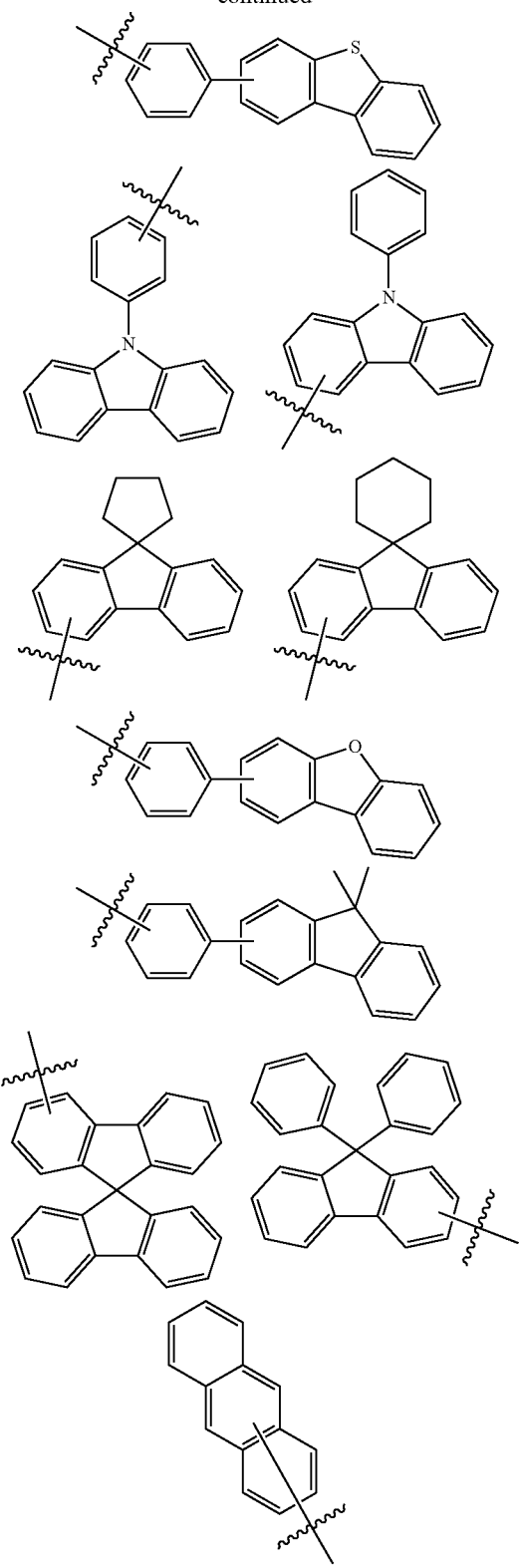

the substituted group V₁ has one or more substituents, wherein the substituents are each independently selected from deuterium, fluorine, alkyl with 1 to 4 carbon atoms, fluoroalkyl with 1 to 4 carbon atoms, trialkylsilyl with 3 to 7 carbon atoms, alkoxy with 1 to 4 carbon atoms, alkylthio with 1 to 4 carbon atoms, cyclopentyl, cyclohexyl, pyridyl, and phenyl;

substituents in L₁ to L₃ are the same or different, and are each independently selected from deuterium, halogen group, a group A, trialkylsilyl with 3 to 12 carbon atoms, triarylsilyl with 18 to 24 carbon atoms, alkyl with 1 to 10 carbon atoms, haloalkyl with 1 to 10 carbon atoms, alkenyl with 2 to 6 carbon atoms, cycloalkyl with 3 to 10 carbon atoms, alkoxy with 1 to 10 carbon atoms, alkylthio with 1 to 10 carbon atoms; the group A is selected from substituted or unsubstituted heteroaryl with 3 to 20 carbon atoms or substituted or unsubstituted aryl with 6 to 20 carbon atoms, and substituents in the group A are selected from deuterium, halogen group, and alkyl with 1 to 4 carbon atoms; optionally, any two adjacent substituents form a ring; and Ad represents adamantyl, in formula 3-1 and formula 3-2, just only one Ad is present; in formula 3-4, just only two Ads are present.

2. The organic compound of claim 1, wherein L₁ is selected from a single bond, substituted or unsubstituted arylene with 6 to 30 carbon atoms, and substituted or unsubstituted heteroarylene with 5 to 30 carbon atoms; and
L₂ and L₃ are the same or different, and are each independently selected from a single bond, substituted or unsubstituted arylene with 6 to 25 carbon atoms, or substituted or unsubstituted heteroarylene with 3 to 20 carbon atoms.

3. The organic compound of claim 1, wherein L₁ is selected from a single bond, substituted or unsubstituted phenylene, substituted or unsubstituted naphthylene, substituted or unsubstituted biphenylene, substituted or unsubstituted terphenylene, substituted or unsubstituted fluorenylene, substituted or unsubstituted anthrylene, substituted or unsubstituted phenanthrylene, substituted or unsubstituted carbazolylene, substituted or unsubstituted dibenzofuranylene, substituted or unsubstituted dibenzothenylene, and substituted or unsubstituted pyridylene; substituents in the L₁ are each independently selected from a group C, deuterium, fluorine, alkyl with 1 to 4 carbon atoms, trialkylsilyl with 3 to 7 carbon atoms, and cycloalkyl with 5 to 10 carbon atoms; the group C is selected from substituted or unsubstituted aryl with 6 to 15 carbon atoms, and substituted or unsubstituted heteroaryl with 5 to 15 carbon atoms, and substituents in the group C are each selected from deuterium, fluorine, and alkyl with 1 to 4 carbon atoms; and
L₂ and L₃ are the same or different, and are each independently selected from a single bond, substituted or unsubstituted phenylene, substituted or unsubstituted naphthylene, substituted or unsubstituted biphenyl ene, substituted or unsubstituted fluorenylene, substituted or unsubstituted anthrylene, substituted or unsubstituted phenanthrylene, substituted or unsubstituted carbazolylene, substituted or unsubstituted dibenzofuranylene, substituted or unsubstituted dibenzothenylene, and substituted or unsubstituted pyridylene; substituents in the L₂ and L₃ are each independently selected from deuterium, fluorine, alkyl with 1 to 4 carbon atoms, trialkylsilyl with 3 to 7 carbon atoms, cycloalkyl with 5 to 10 carbon atoms, aryl with 6 to 12 carbon atoms, and heteroaryl with 5 to 12 carbon atoms.

4. The organic compound of claim 1, wherein L₁ is a single bond, or a substituted or unsubstituted group T₁, and the unsubstituted group T₁ is selected from the group consisting of the following groups:

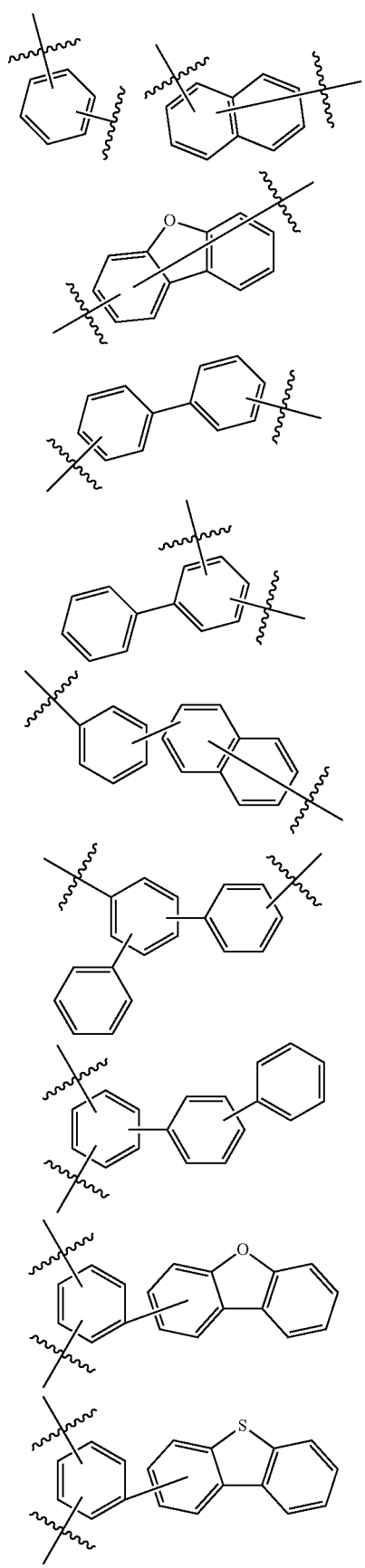
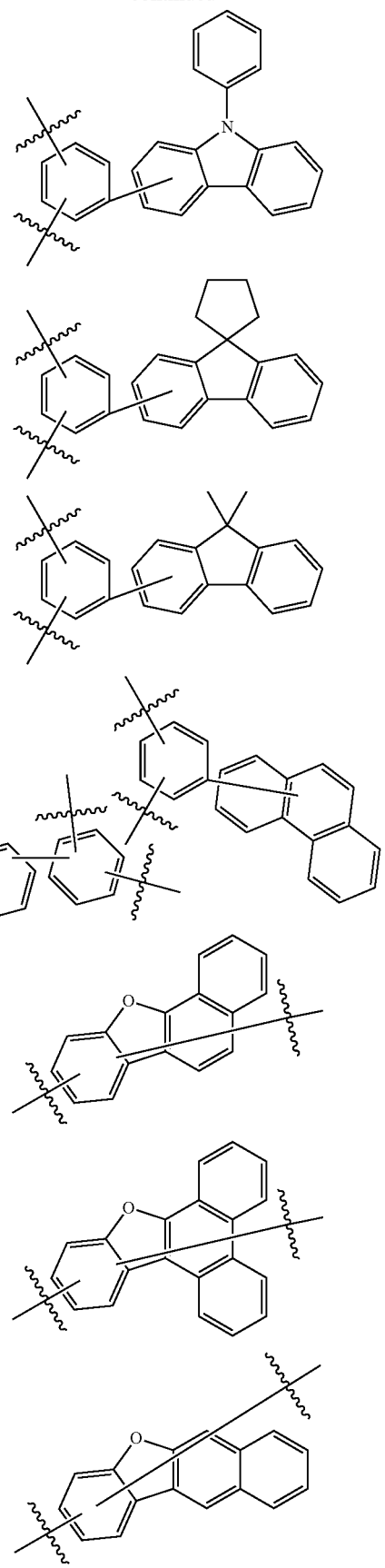

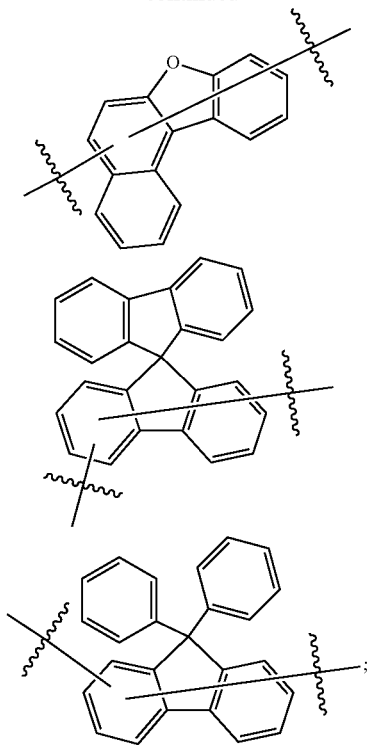

wherein the substituted group $T_1$ has one or more substituents, and the substituents in the substituted group $T_1$ are independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, trialkylsilyl with 3 to 7 carbon atoms, and naphthyl.

5. The organic compound of claim 1, wherein $L_2$ is selected from a single bond, and a substituted or unsubstituted group $T_2$, and the unsubstituted group $T_2$ is selected from the group consisting of the following groups:

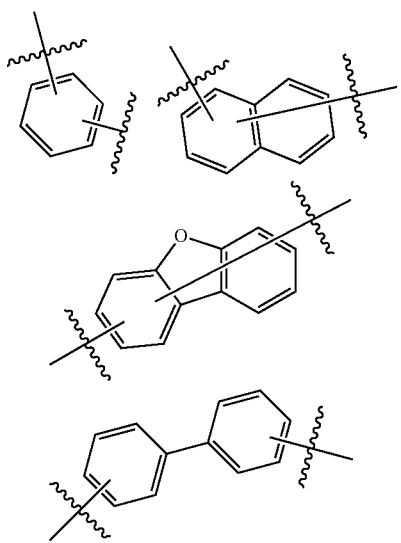
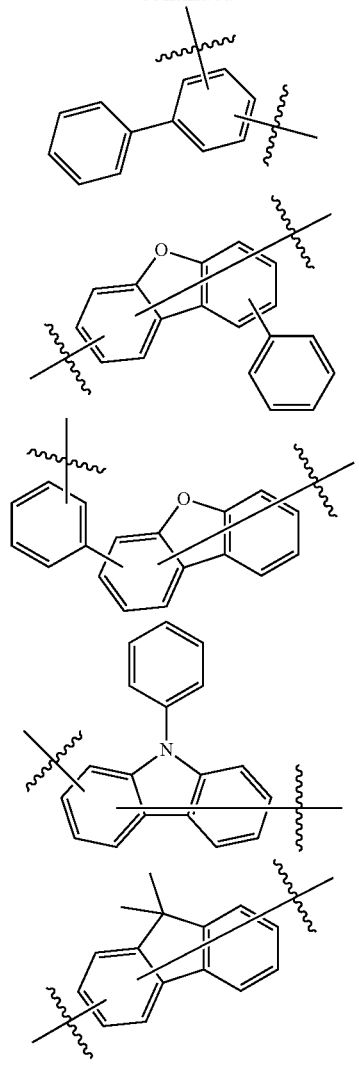
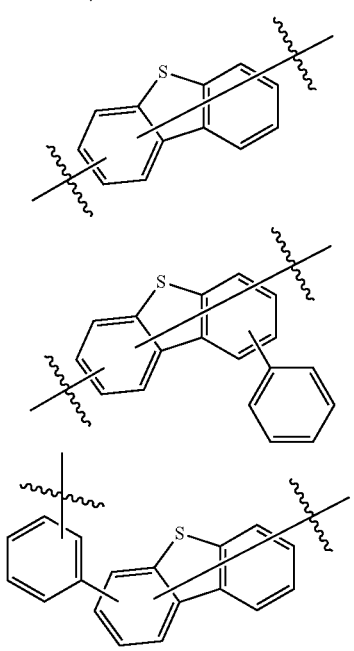

wherein the substituted group T₂ has one or more substituents, and the substituents in the substituted group T₂ are independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, trialkylsilyl with 3 to 7 carbon atoms, and phenyl.

6. The organic compound of claim 1, wherein L₃ is a single bond, or a substituted or unsubstituted group T₃, and the unsubstituted group T₃ is selected from the group consisting of the following groups:

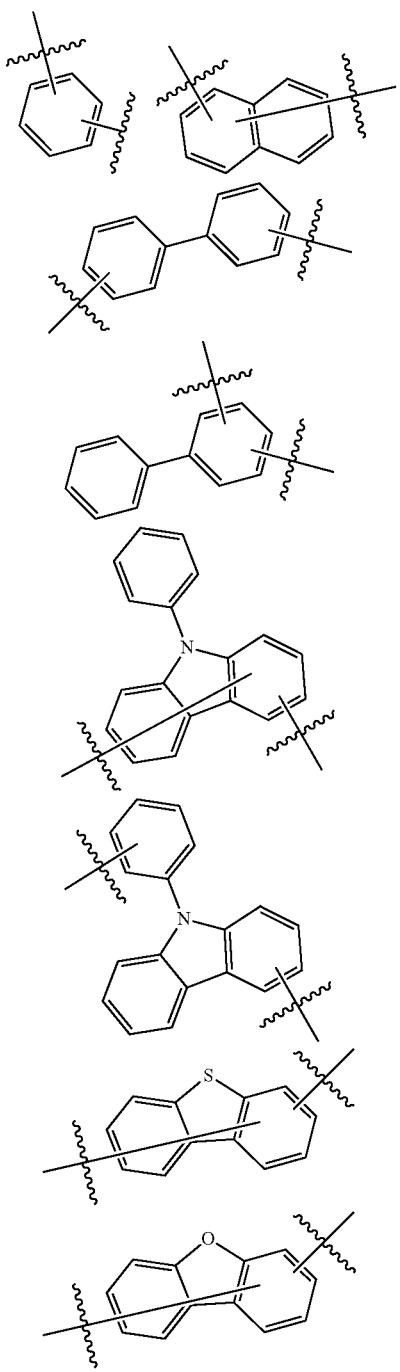

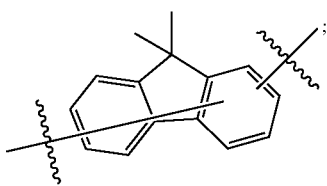

wherein the substituted group T₃ has one or more substituents, and the substituents in the substituted group T₃ are independently selected from deuterium, fluorine, alkyl with 1 to 4 carbon atoms, alkoxy with 1 to 4 carbon atoms, alkylthio with 1 to 4 carbon atoms, fluoroalkyl with 1 to 4 carbon atoms, cycloalkyl with 5 to 10 carbon atoms, and trialkylsilyl with 3 to 7 carbon atoms.

7. The organic compound of claim 1, ⸹-L₁-Ar₁-Ad is selected from the group consisting of the following structures:

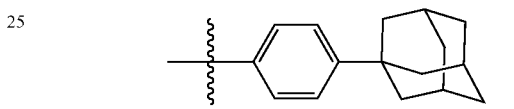

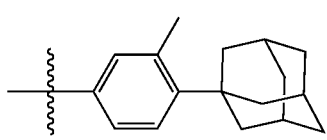

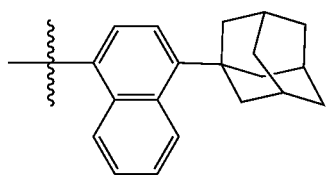

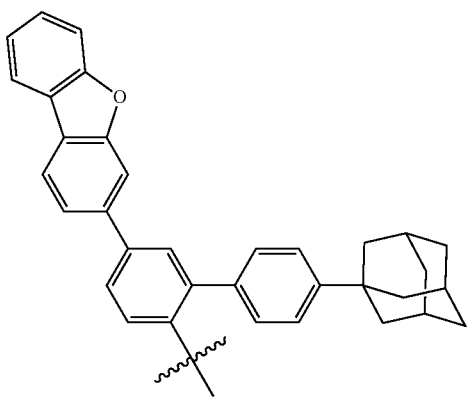

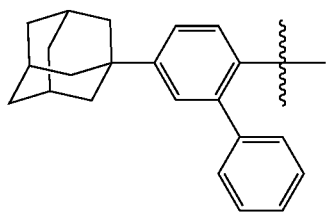

377
-continued
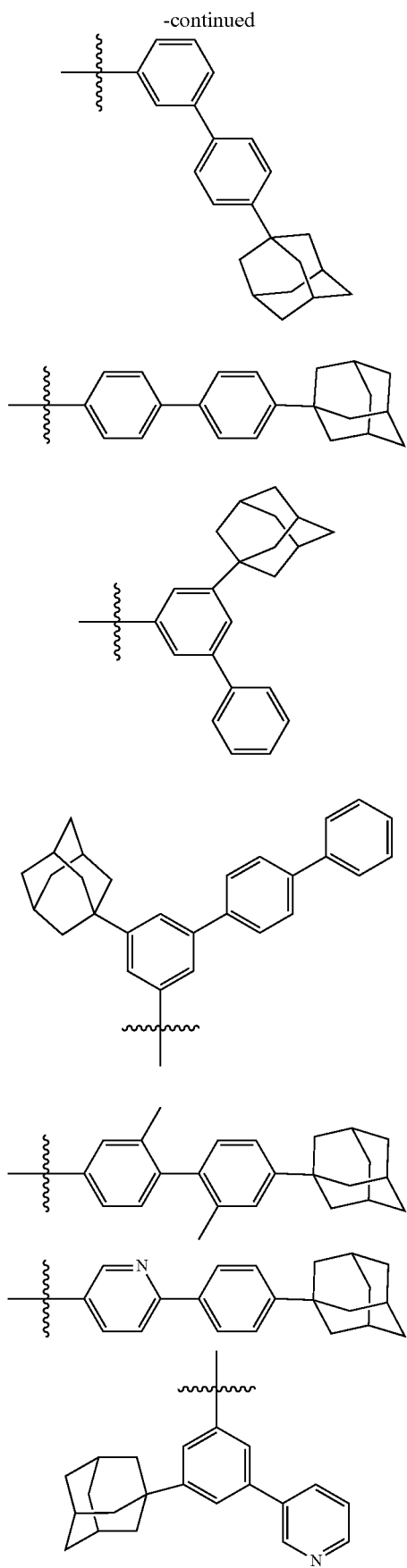
378
-continued
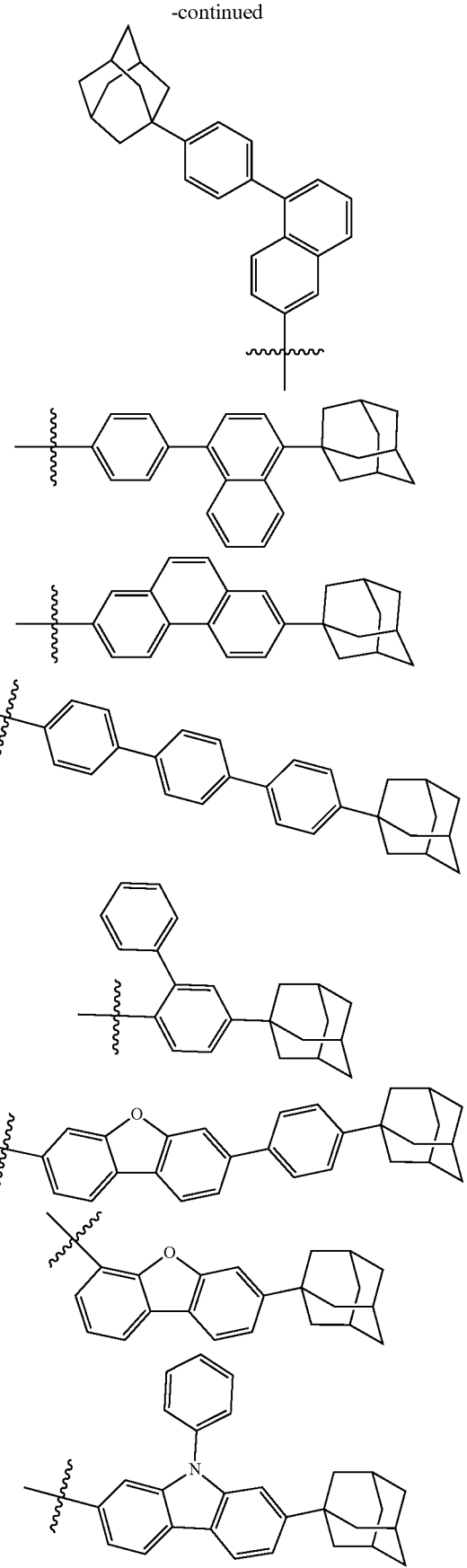

379
-continued
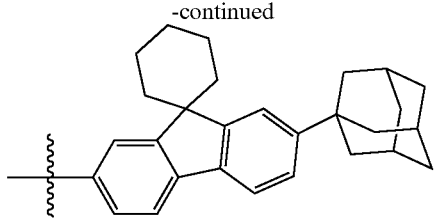
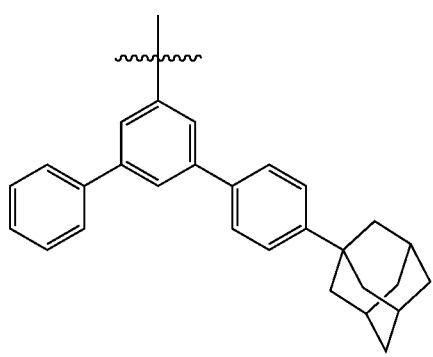
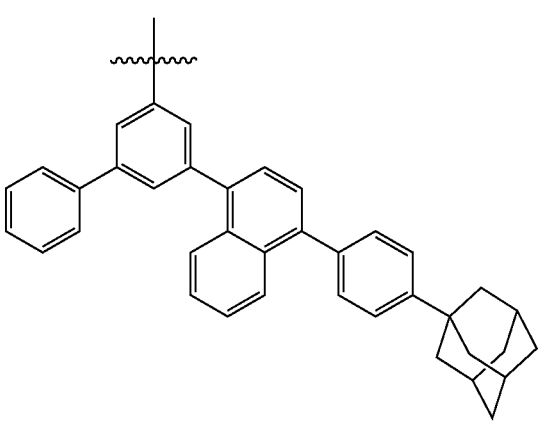
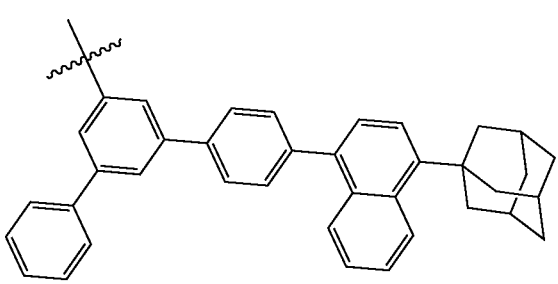
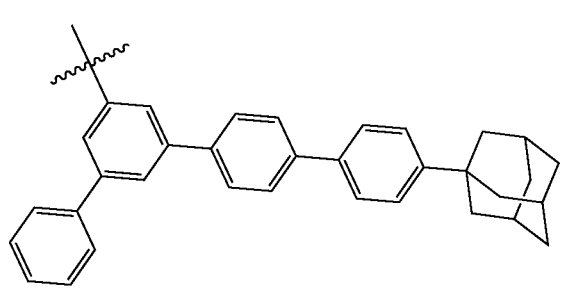
380
-continued
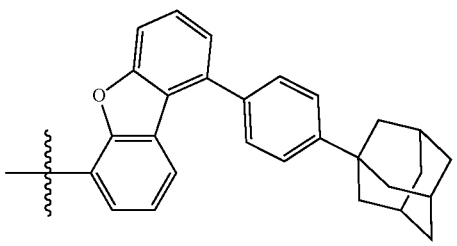
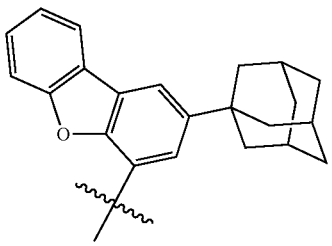
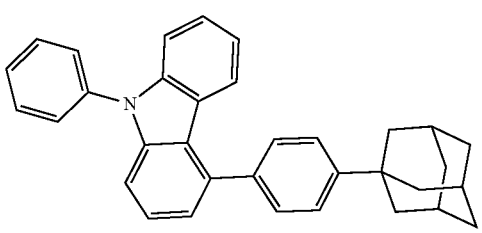
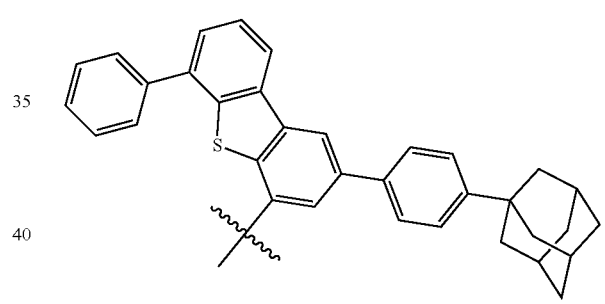
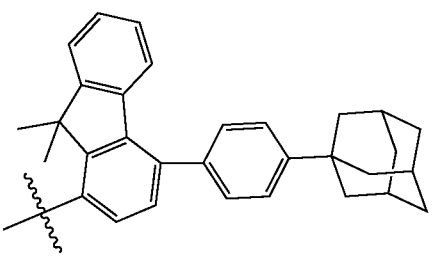
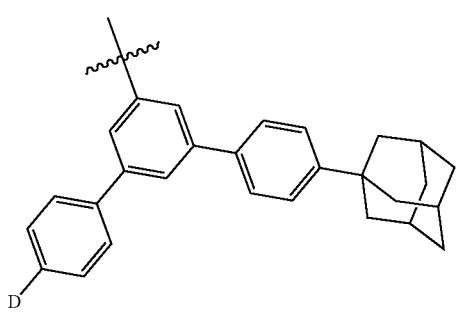

381
-continued
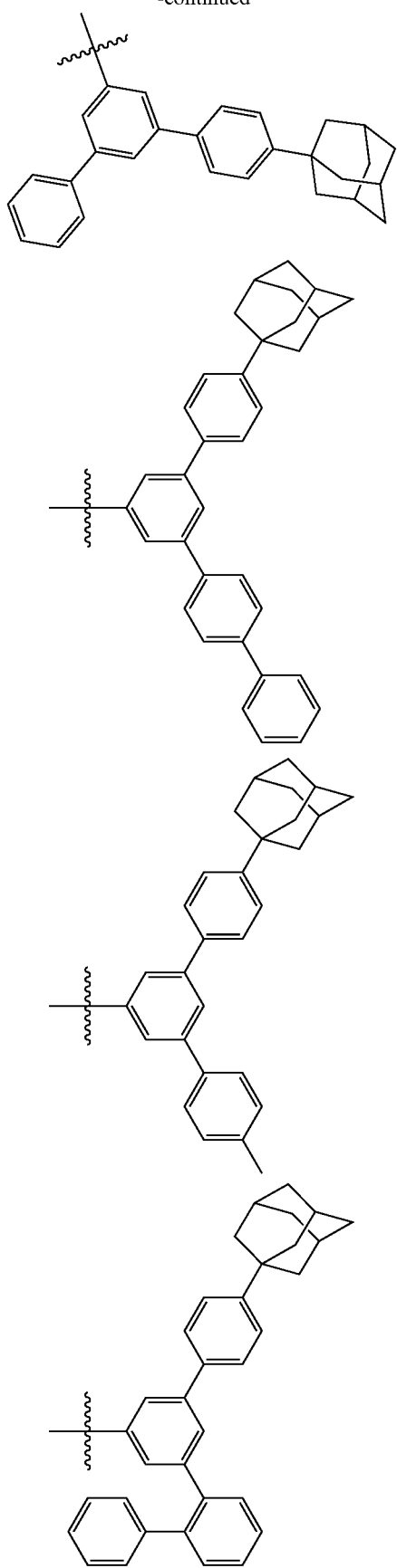
382
-continued
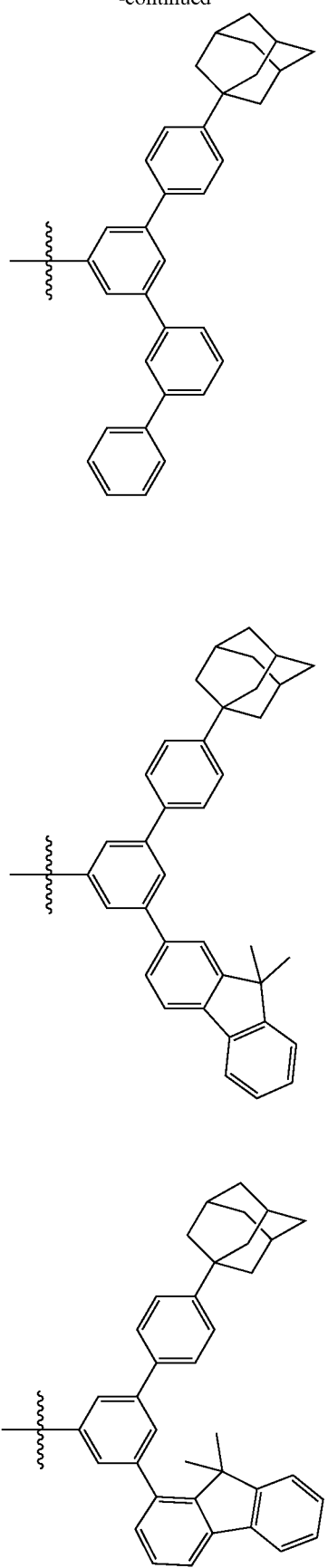

383
-continued
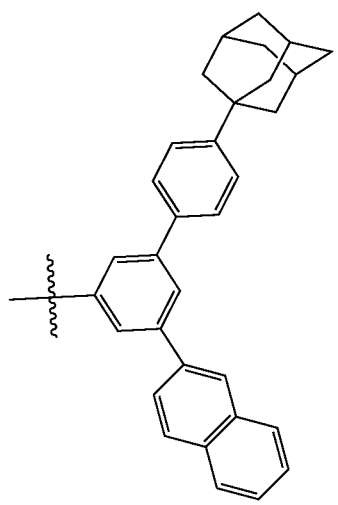
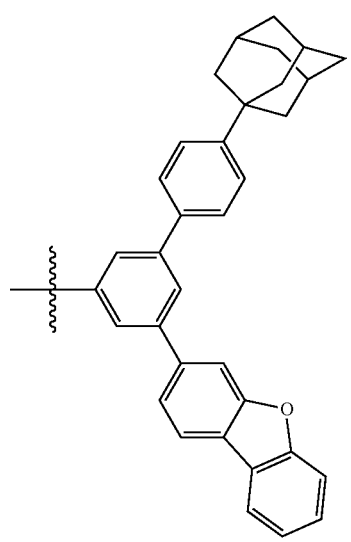
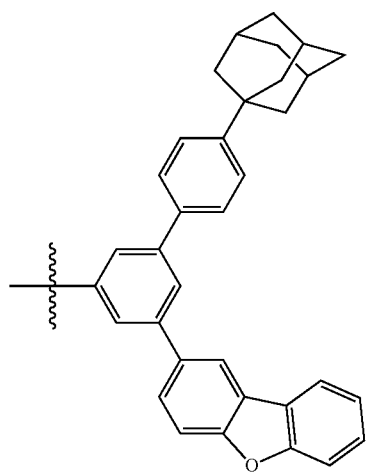
384
-continued
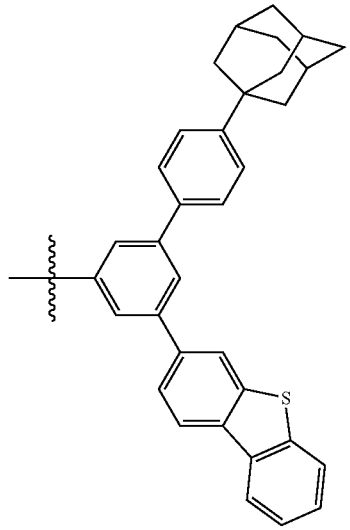
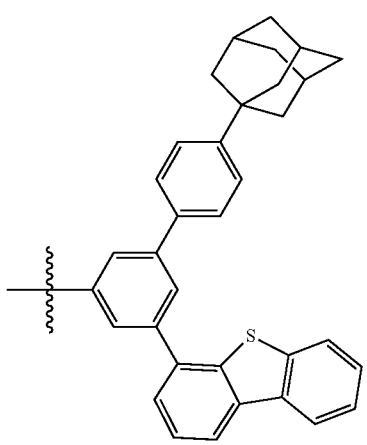
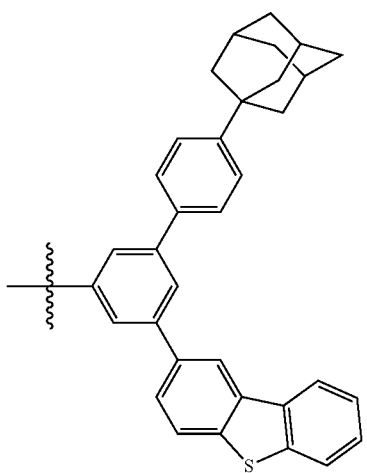

385
-continued
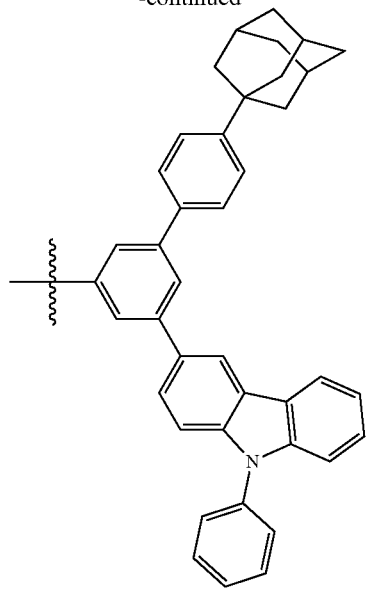
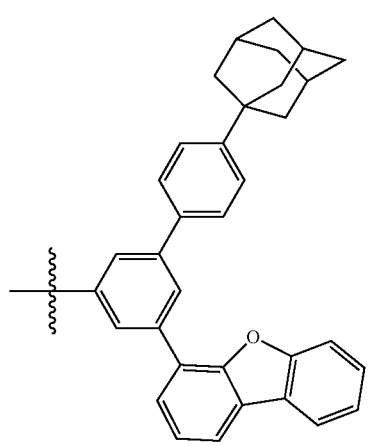
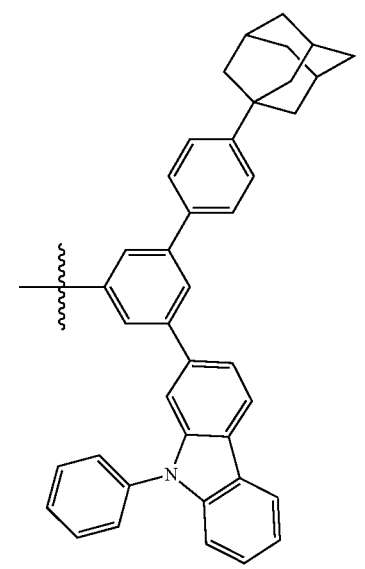
386
-continued
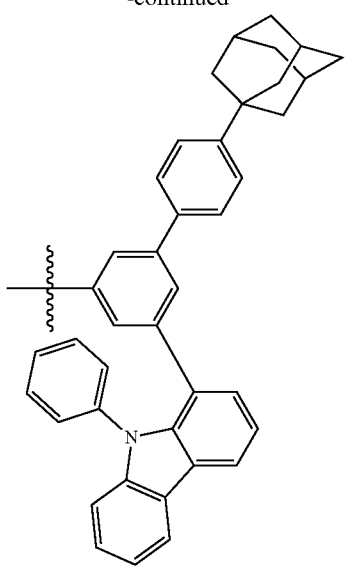
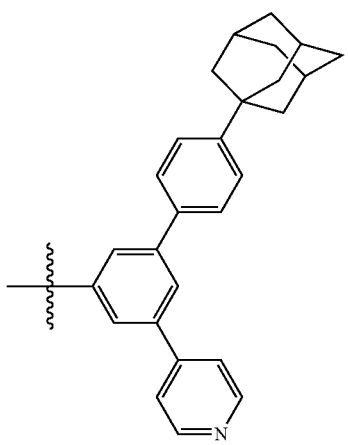
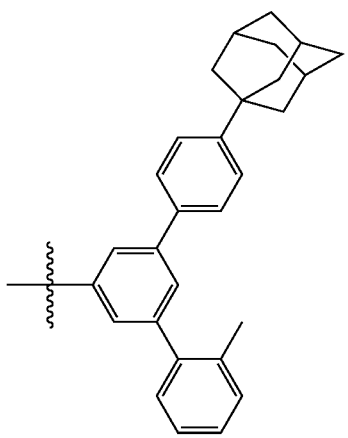

387
-continued
388
-continued
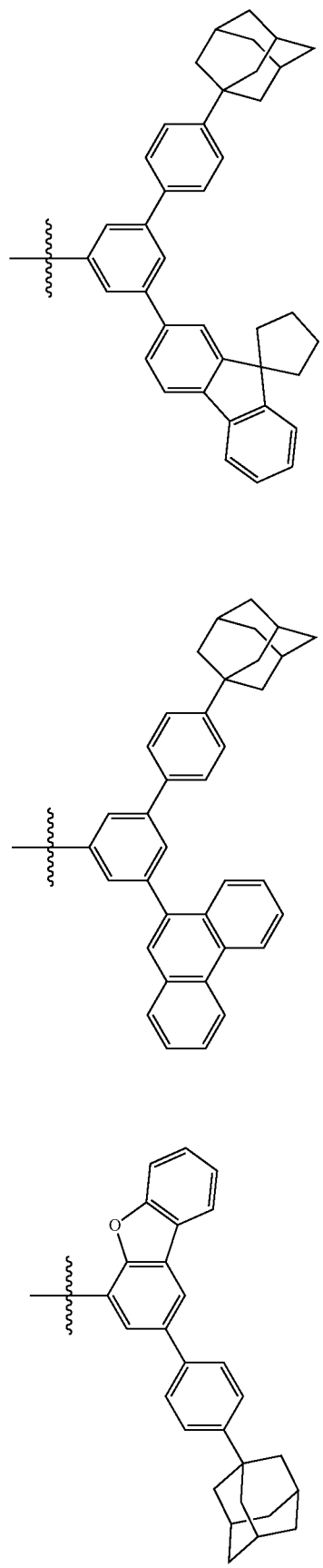
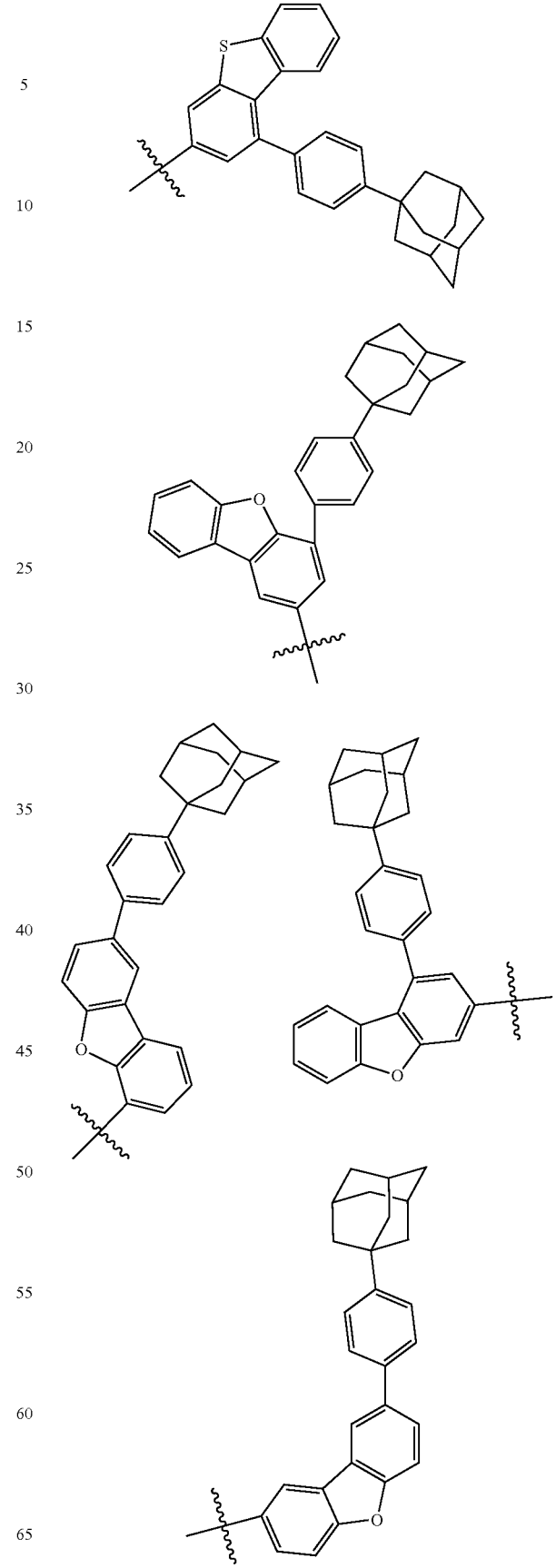

389
-continued
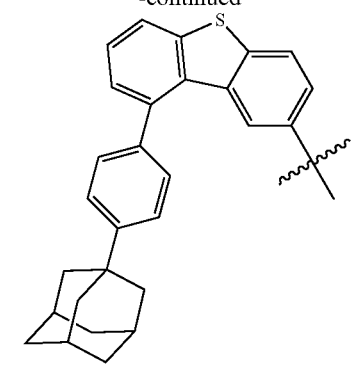
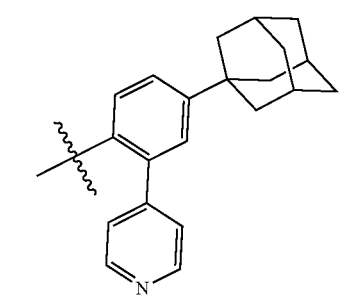
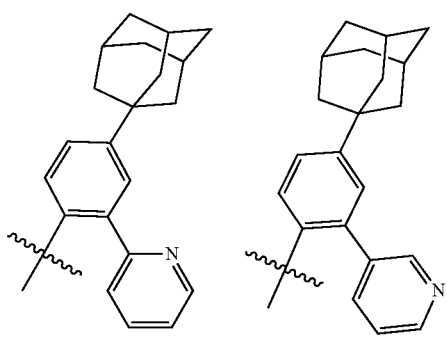
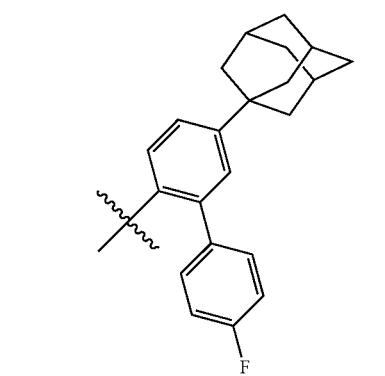
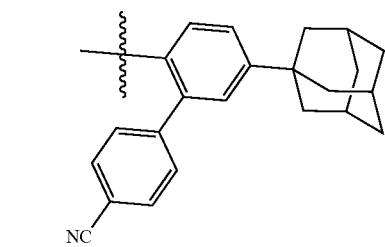
390
-continued
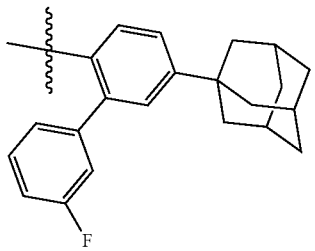
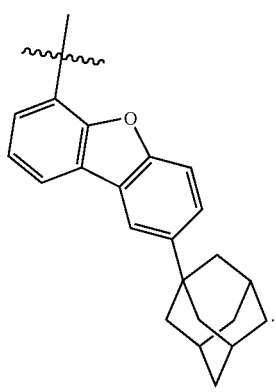
8. The organic compound of claim 1, wherein in formula 3-1 and formula 3-4,
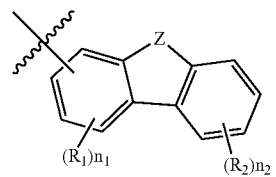
connected with one Ad is selected from the group consisting of the following groups:
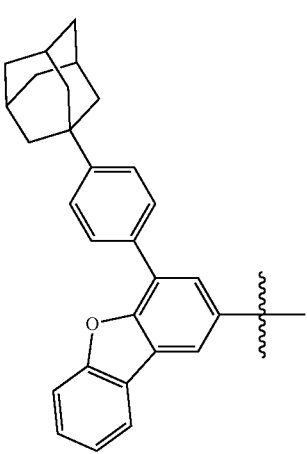

391
-continued
392
-continued
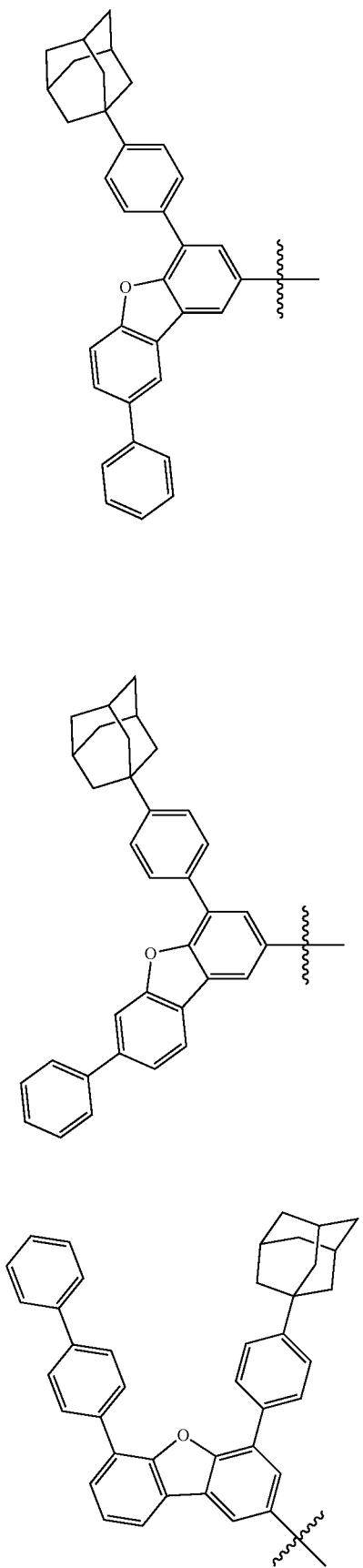
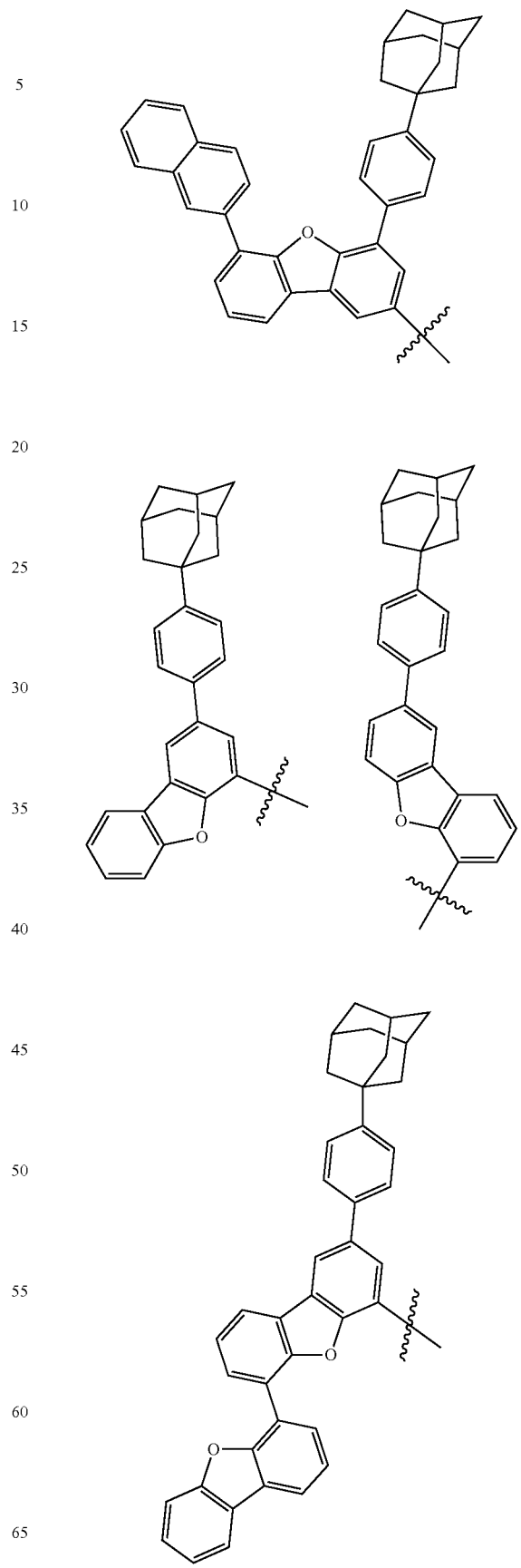

393
-continued
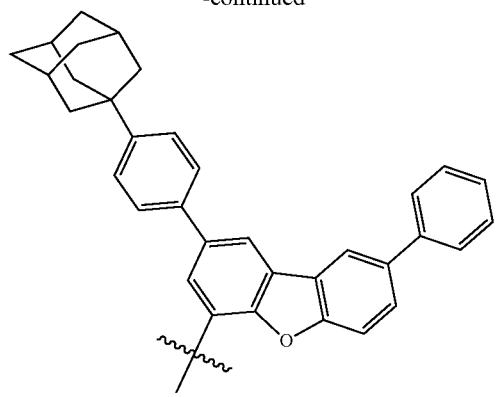
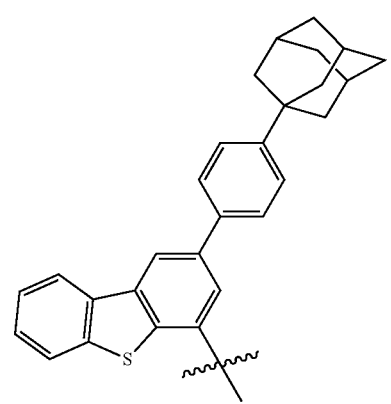
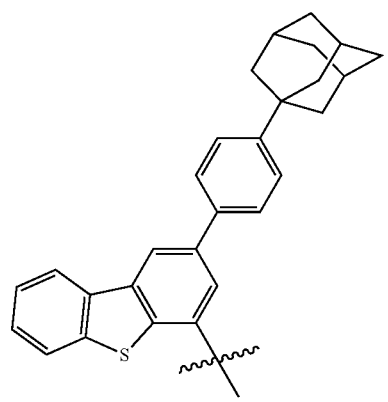
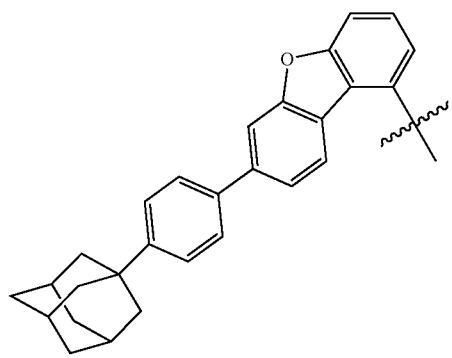
394
-continued
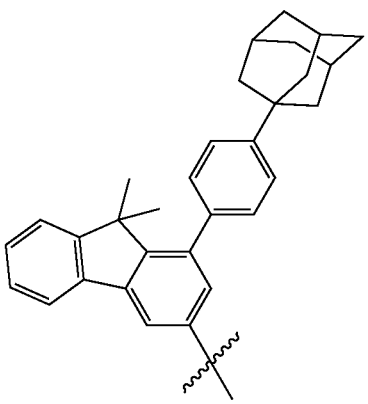
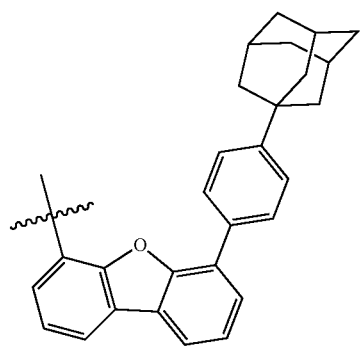
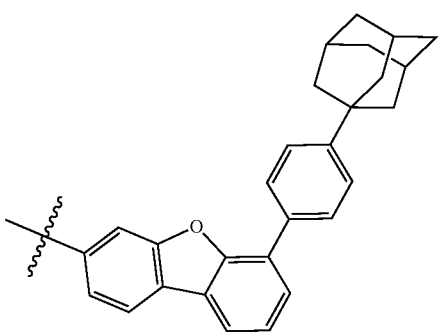
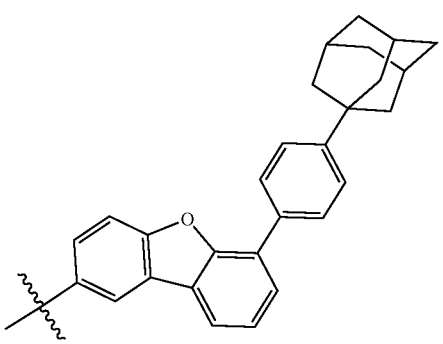

395
-continued
396
-continued
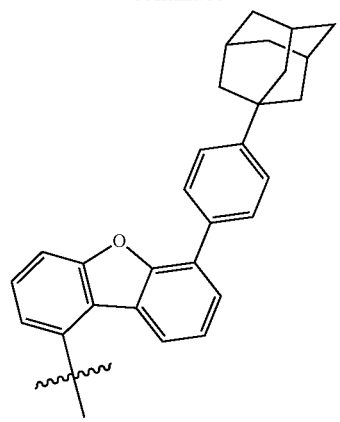
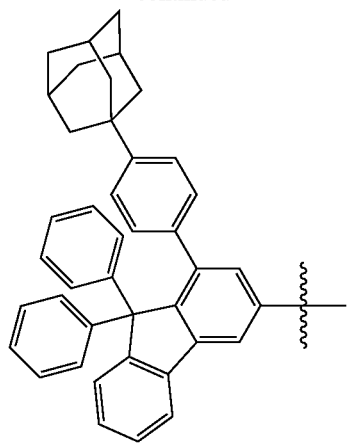
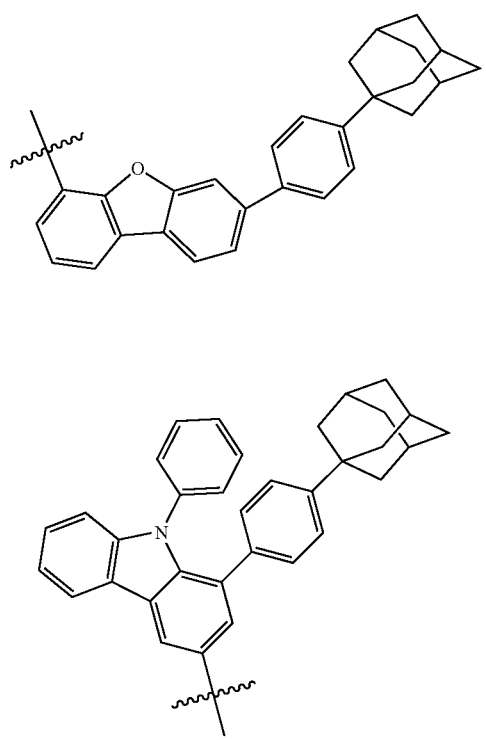
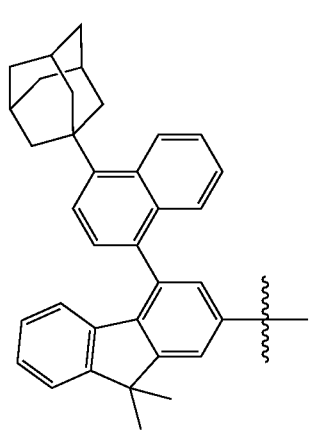
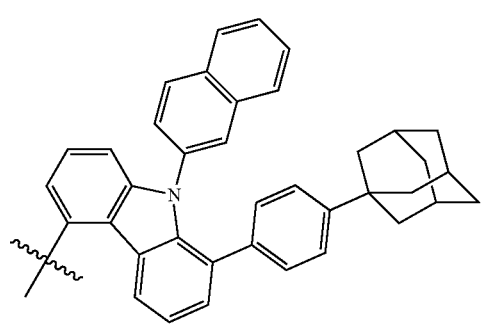
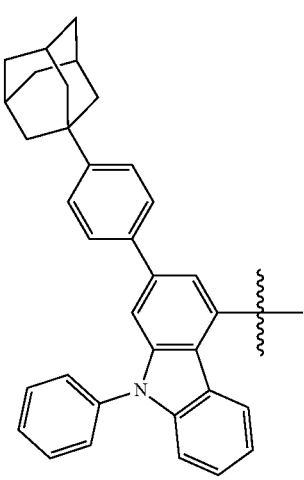

397
-continued
398
-continued
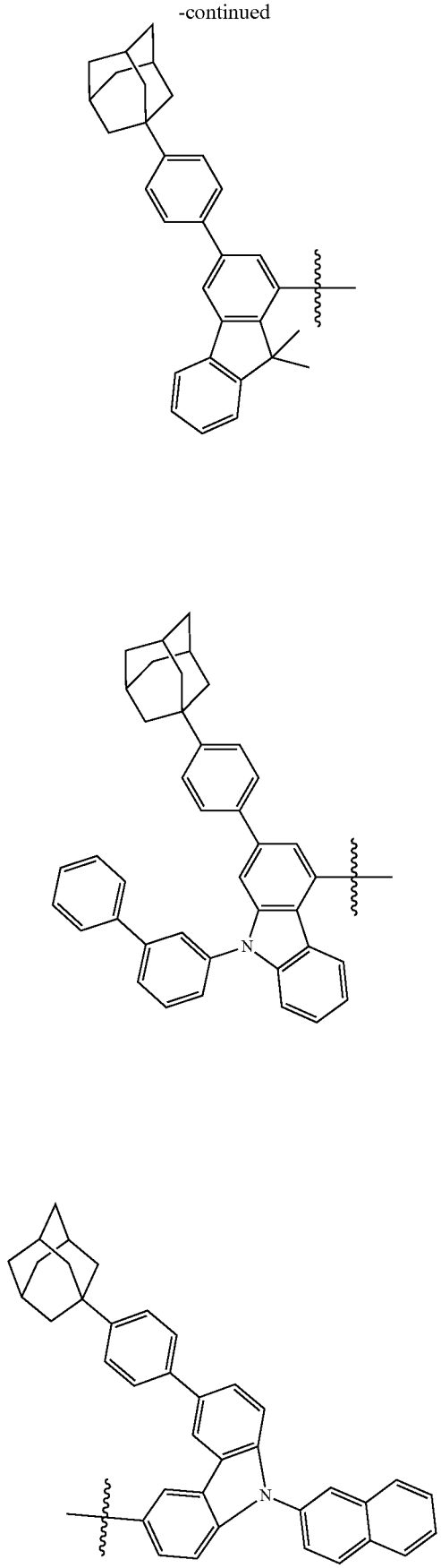
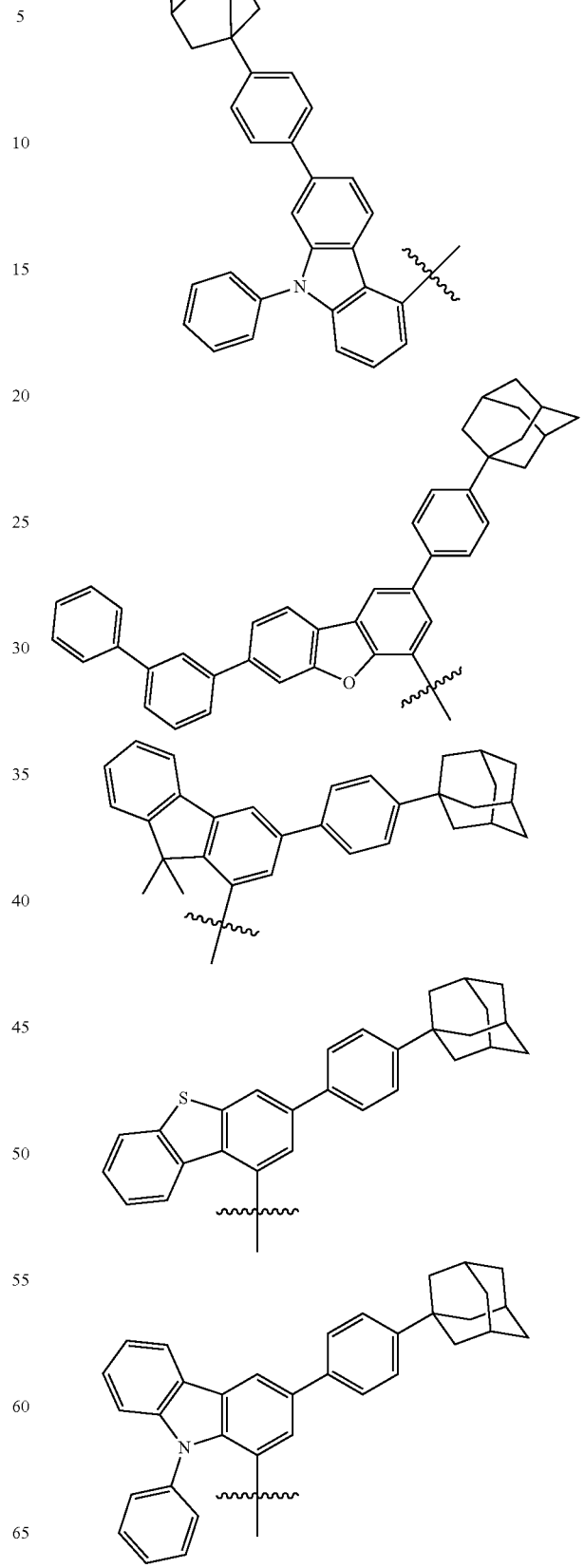

399 400
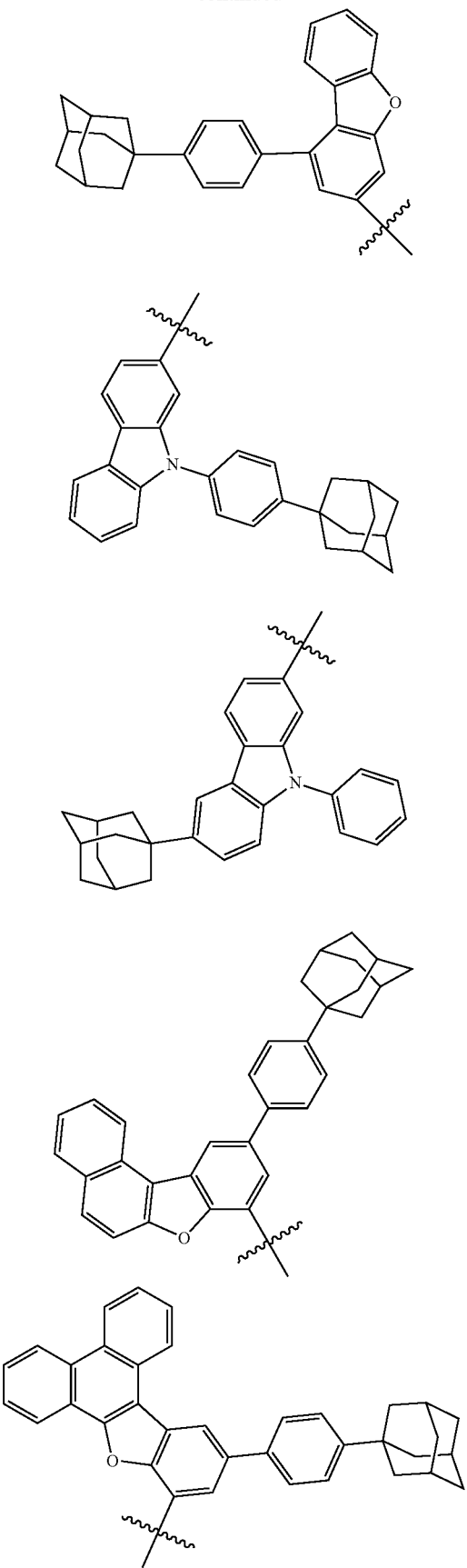

401
-continued
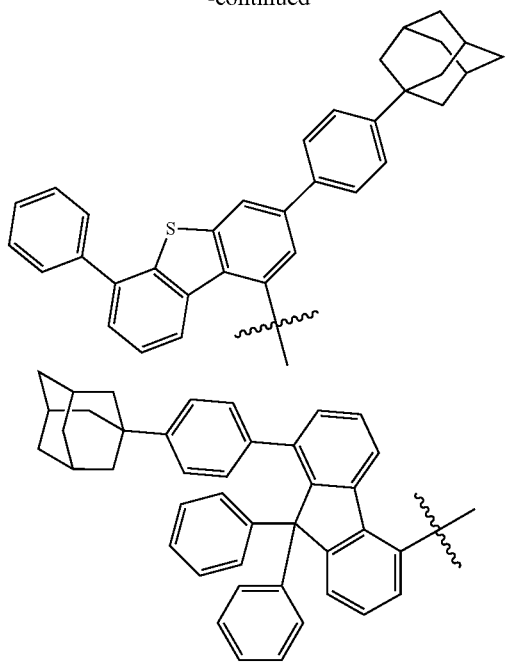
402
-continued
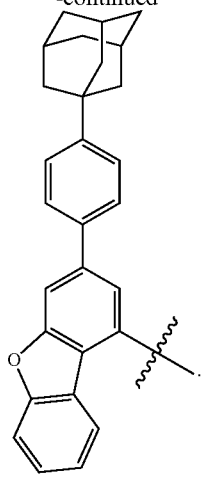
9. The organic compound of claim 1, wherein the organic compound is selected from the group consisting of the following compounds:
1
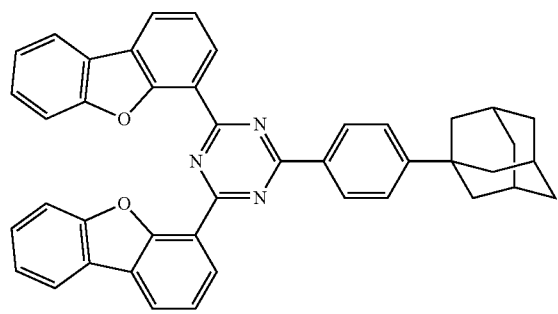
2
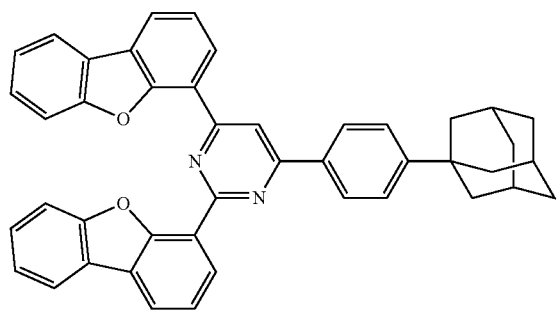
3
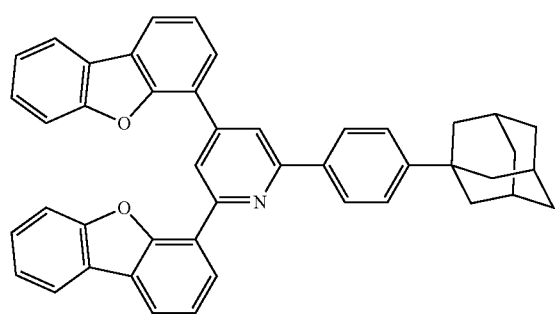
4
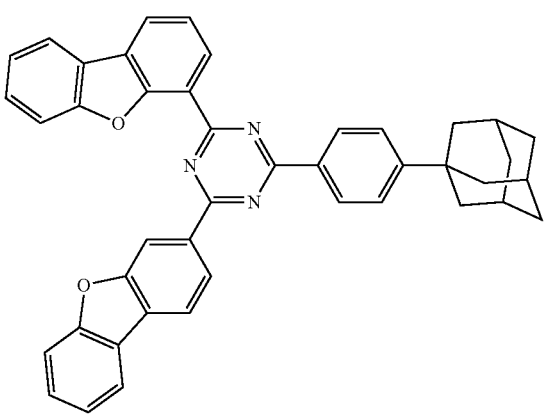

403
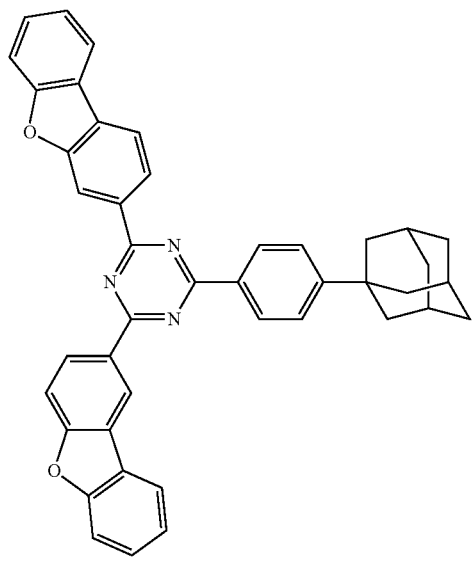
404
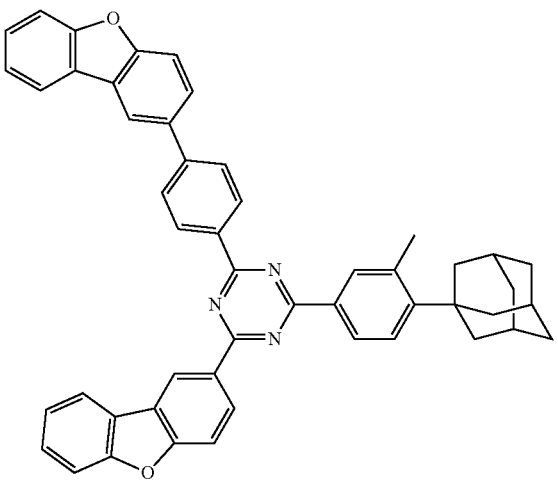
-continued
5
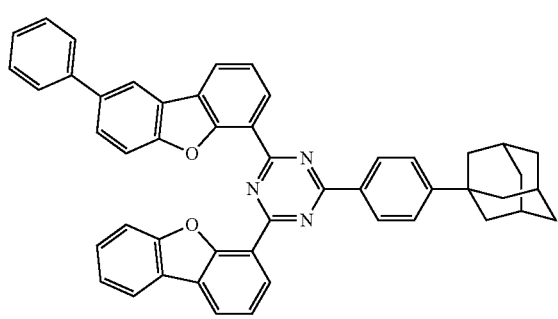
6
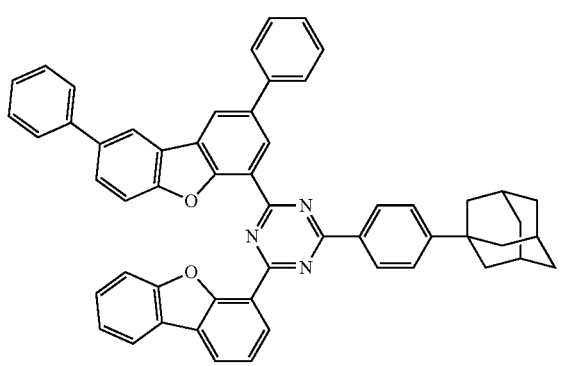
7
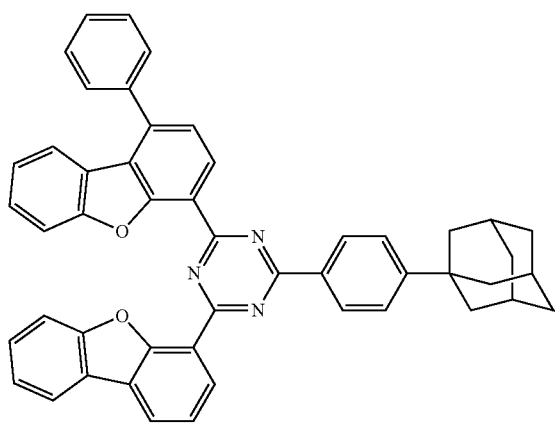
8
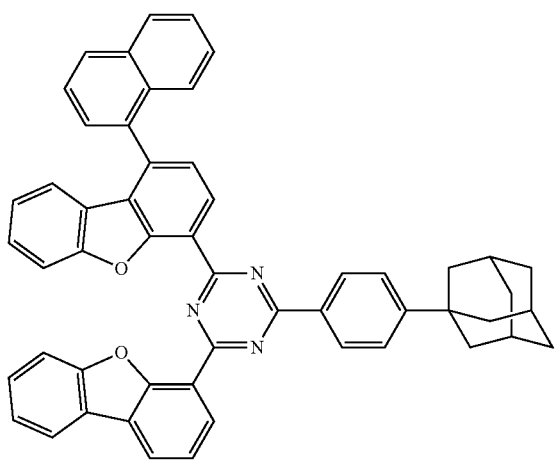
9
10

| 11 | 12 |
|---|---|
| 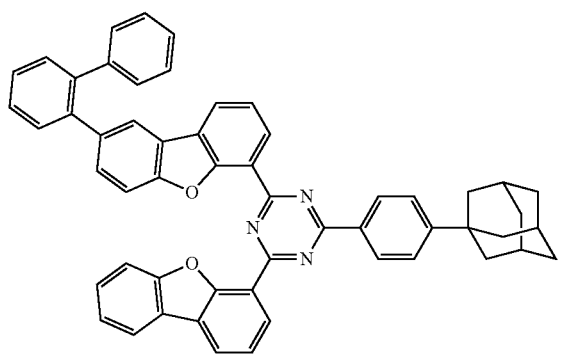 | 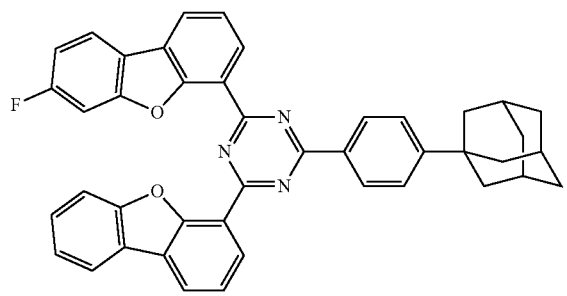 |
| 13 | 14 |
| 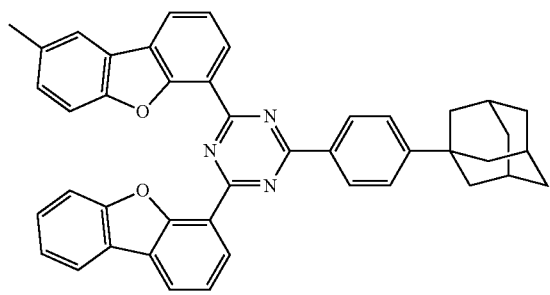 | 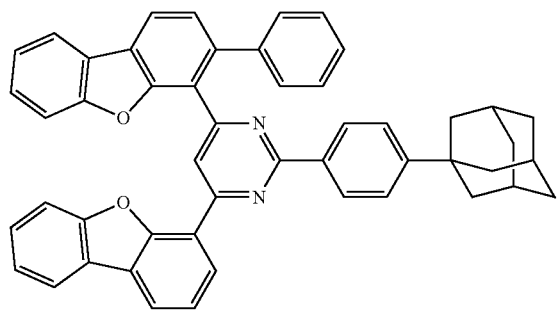 |
| 15 | 16 |
| 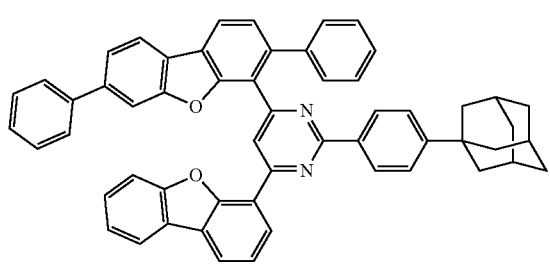 | 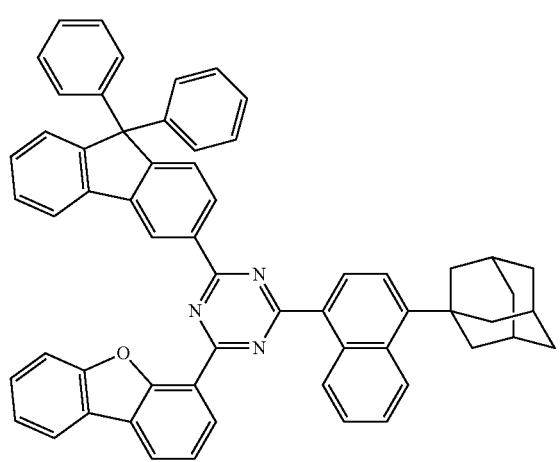 |

407 408
-continued
17
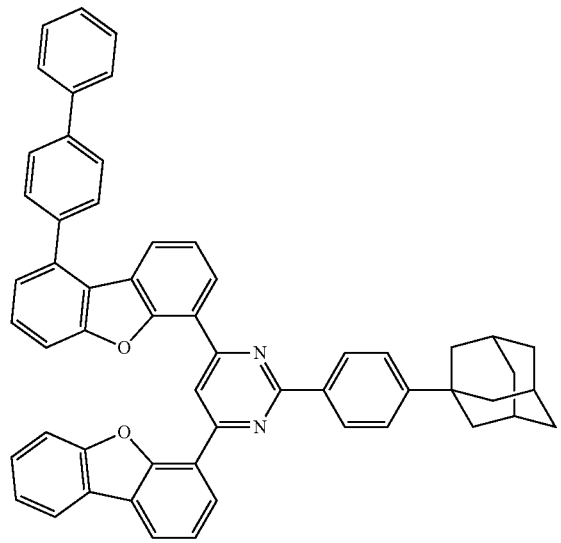
18
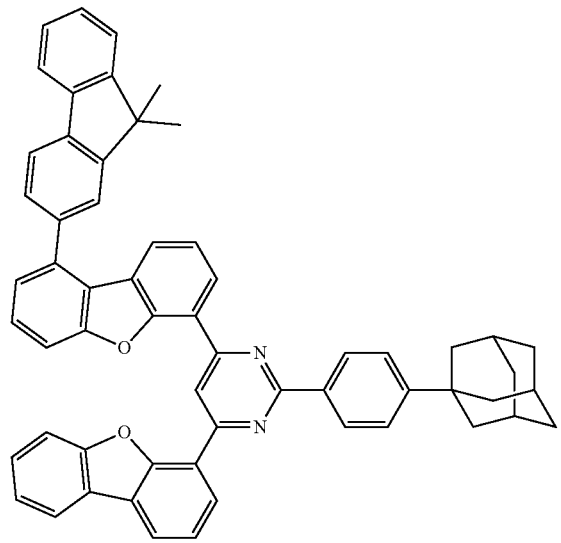
19
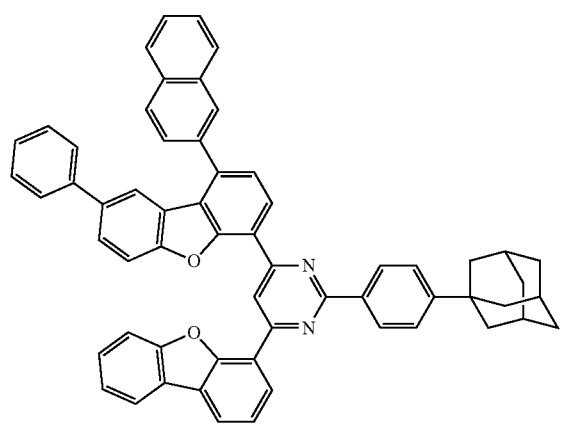
20
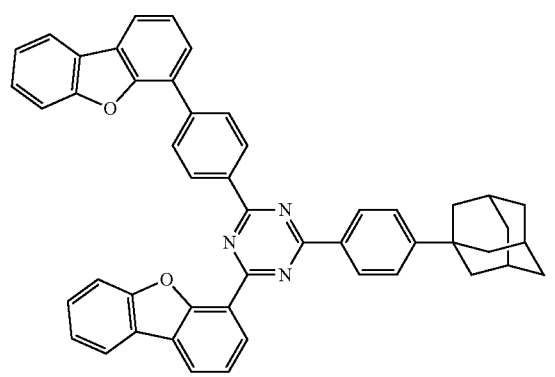
21
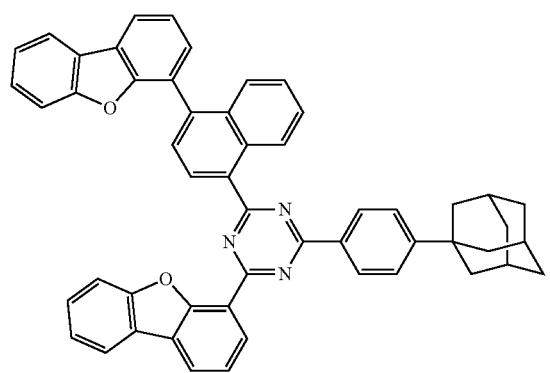
22
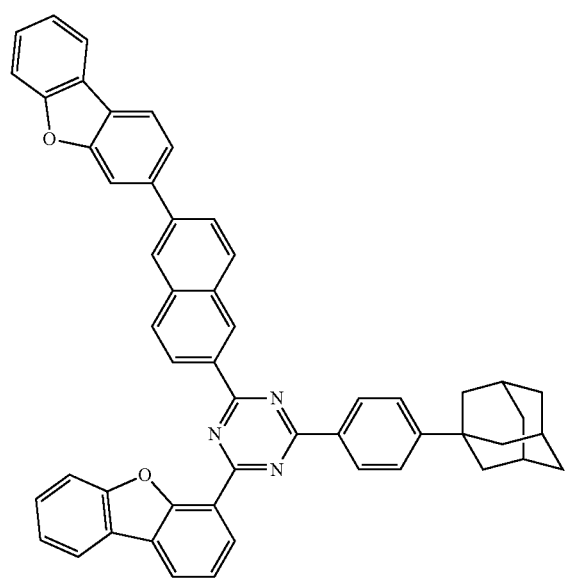

-continued
23
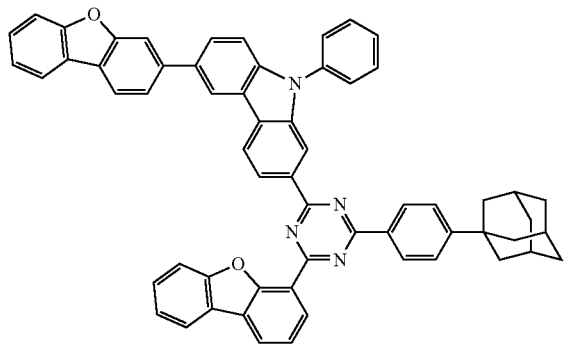
24
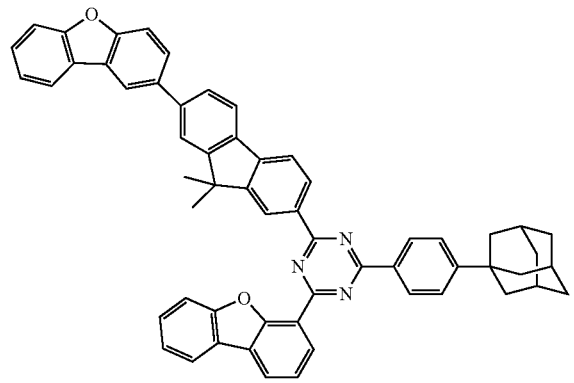
25
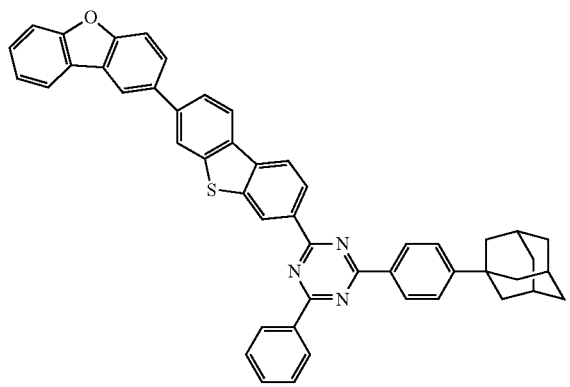
26
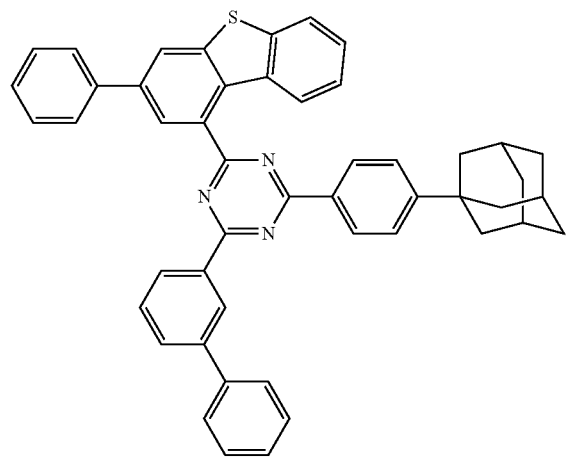
27
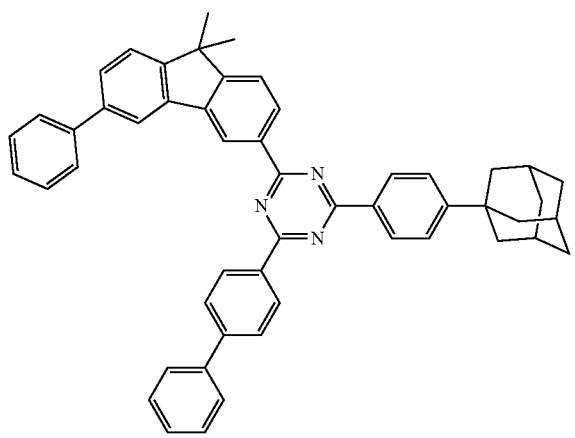
28
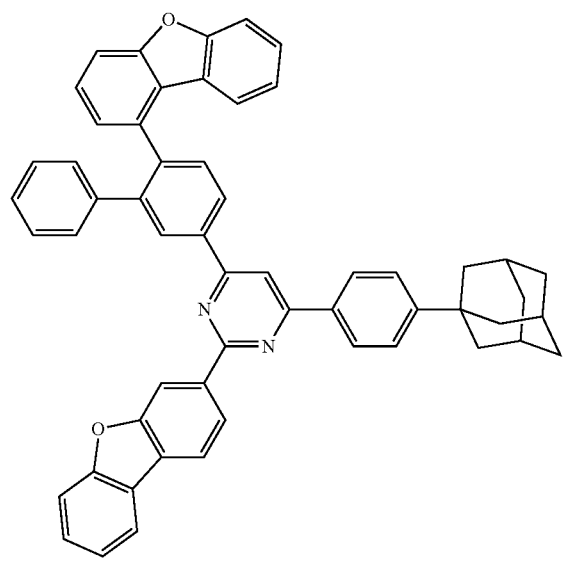

30
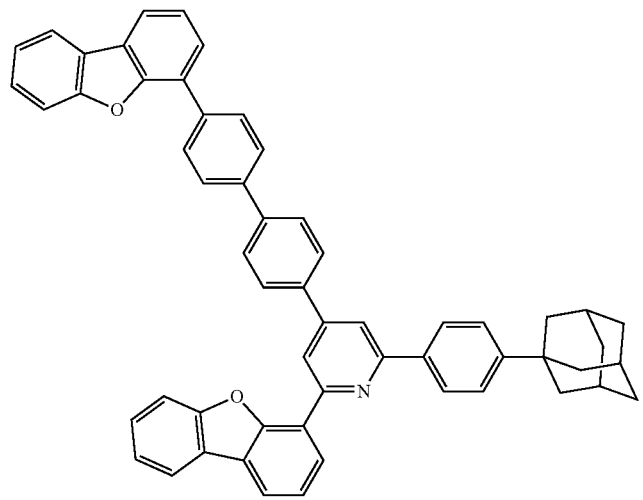
33
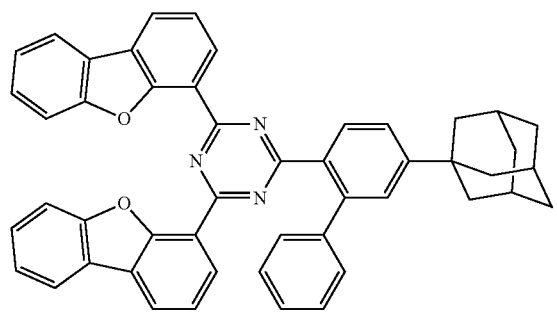
34
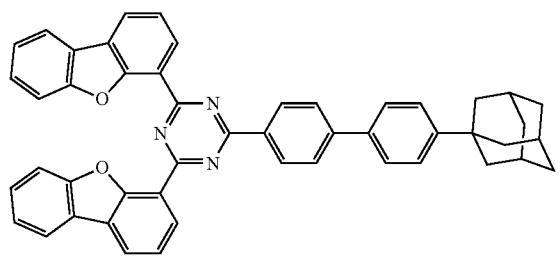
35
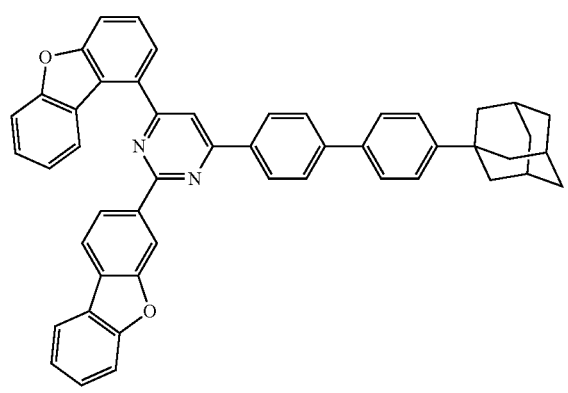
36
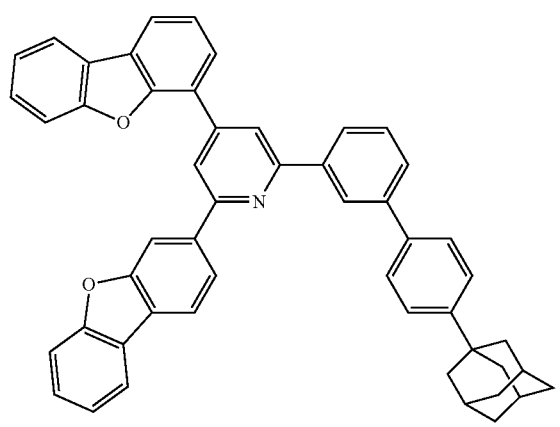

-continued
413
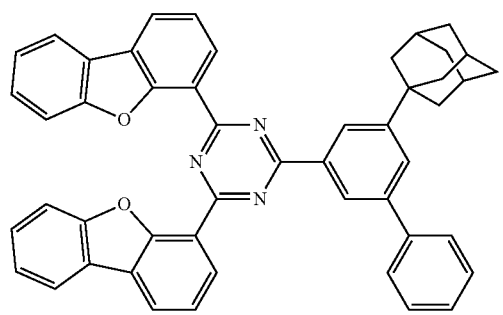
37
414
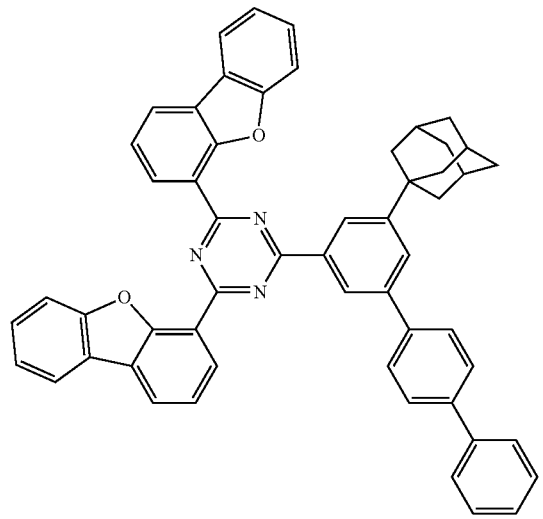
38
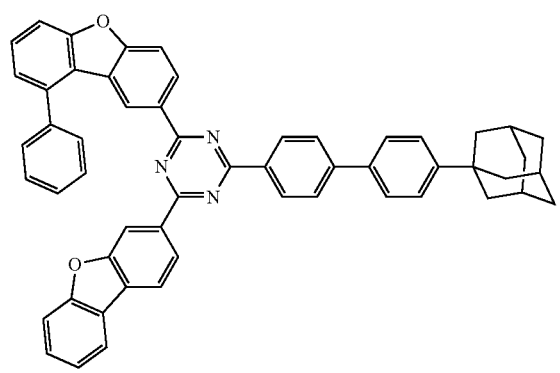
39
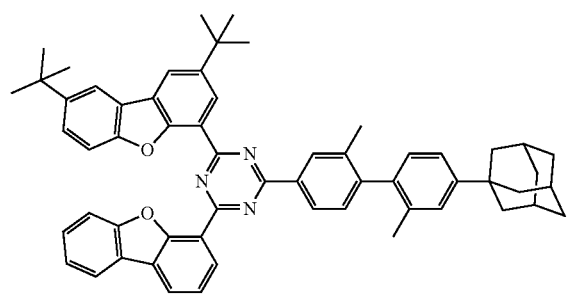
40
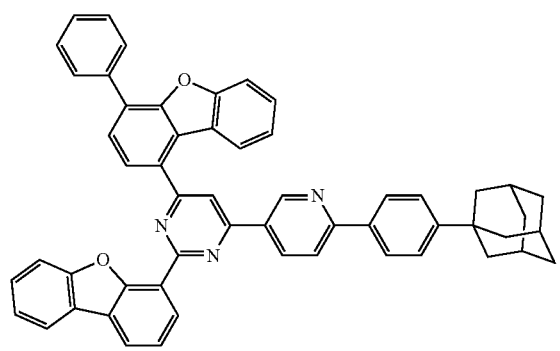
41
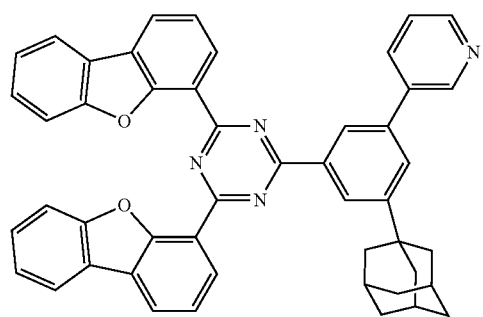
42

-continued
415
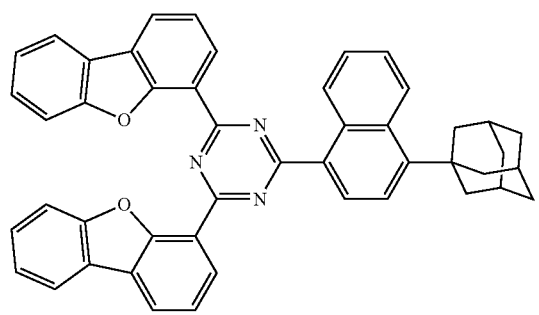
416
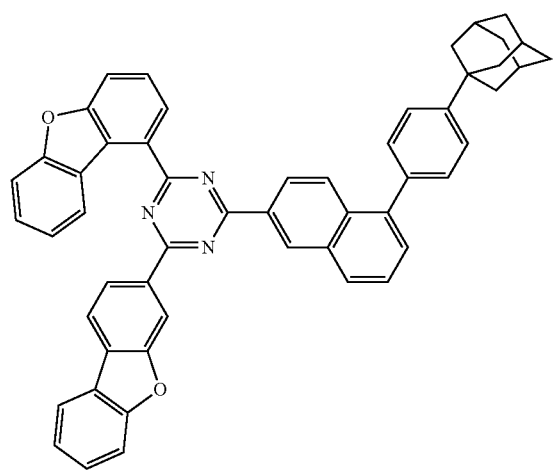
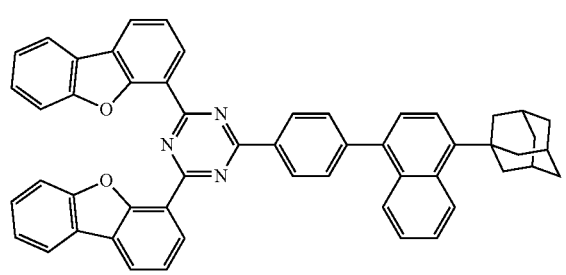
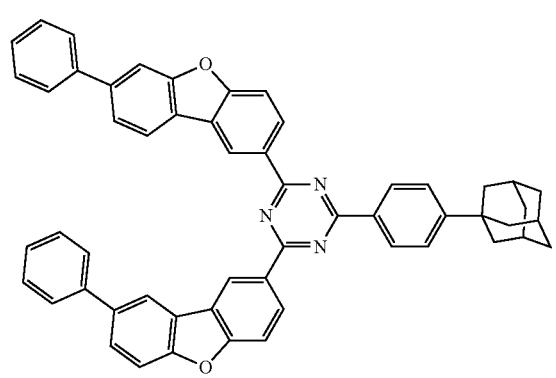
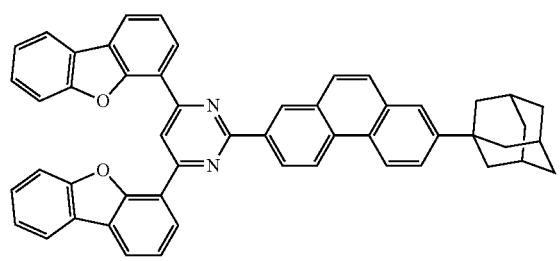
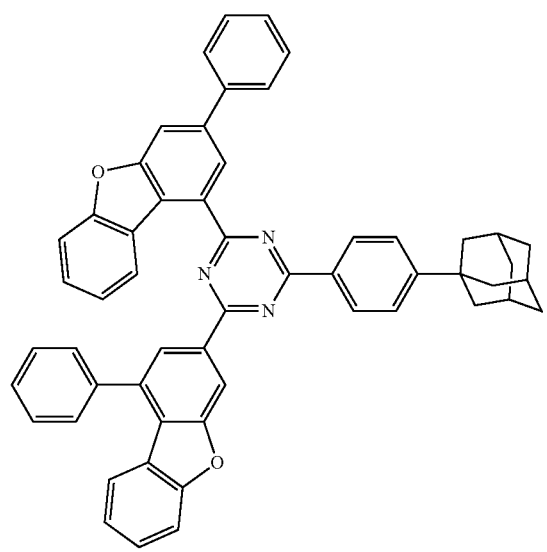

49
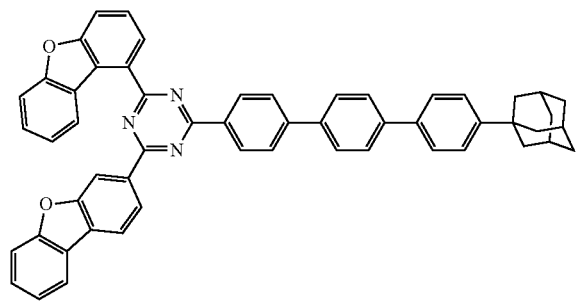
50
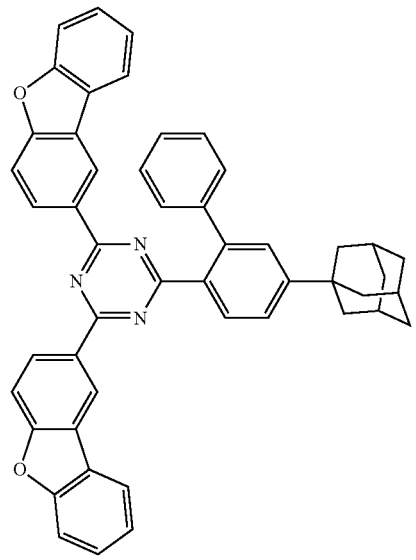
51
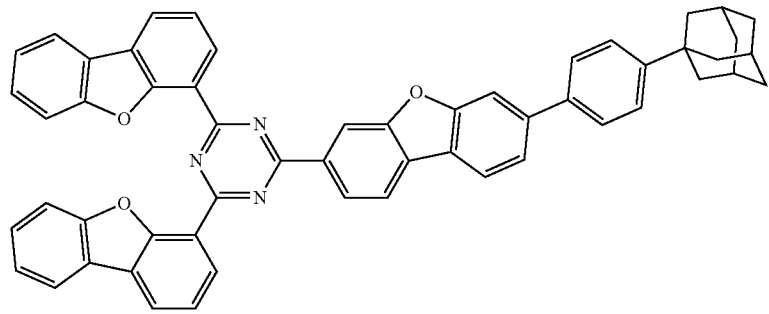
52
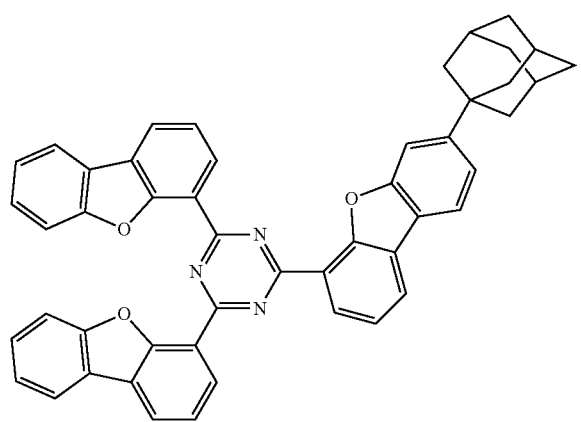
53
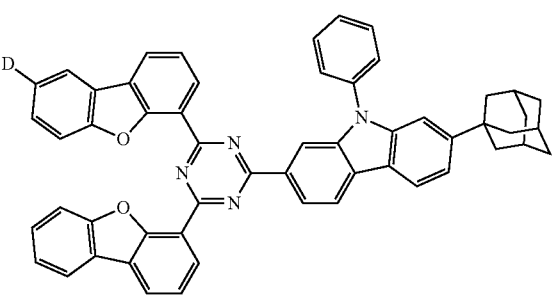

-continued
54
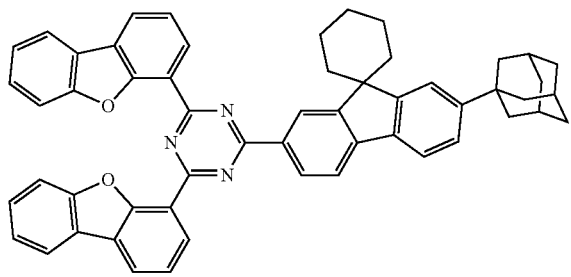
55
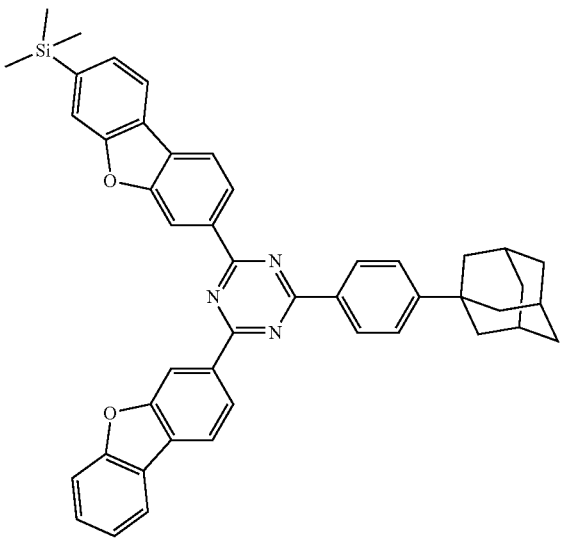
56
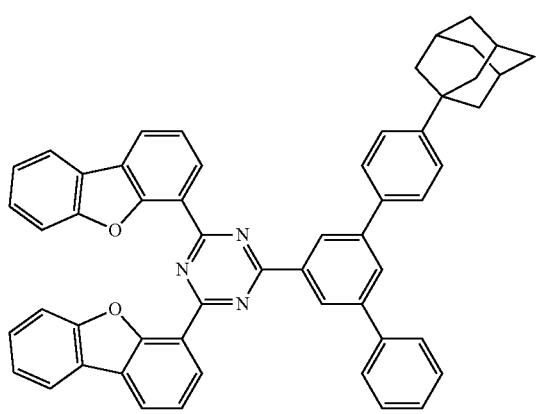
57
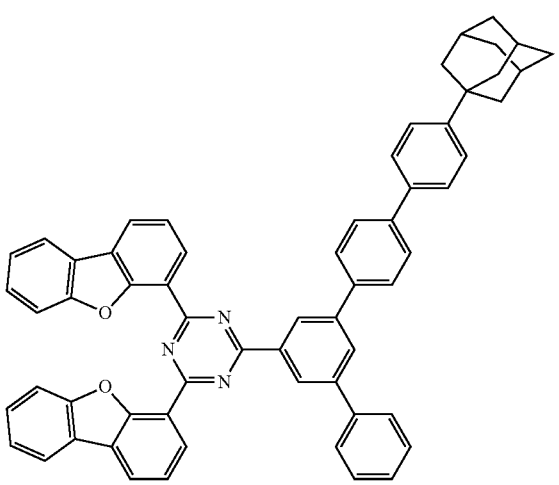
58
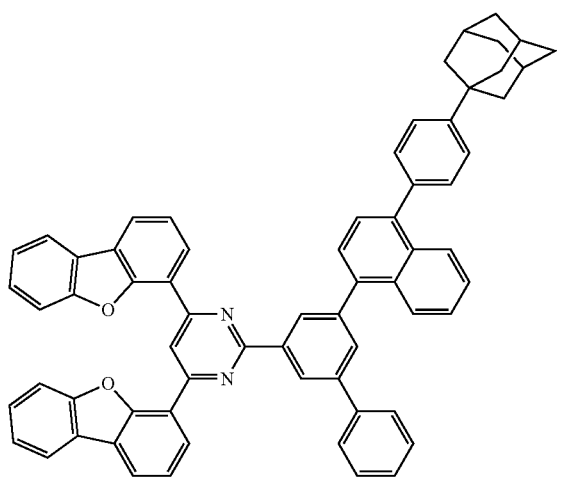
59
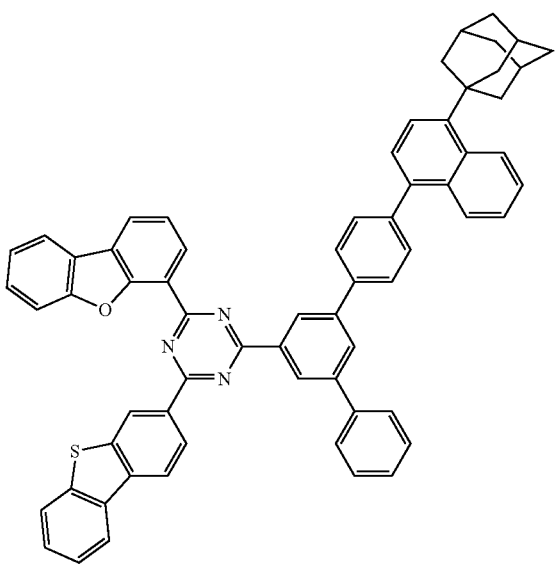

-continued
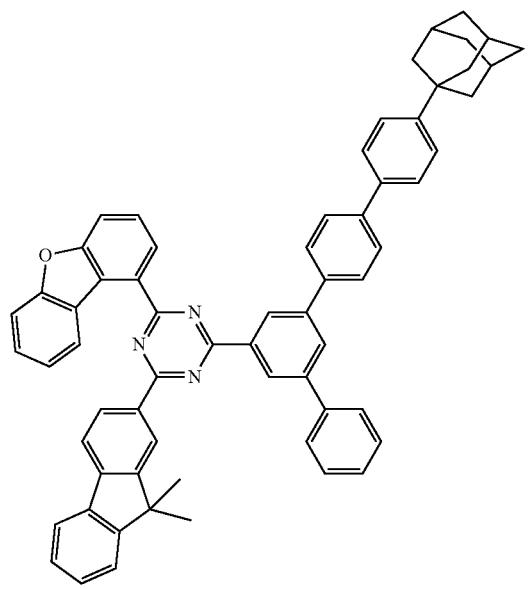
60
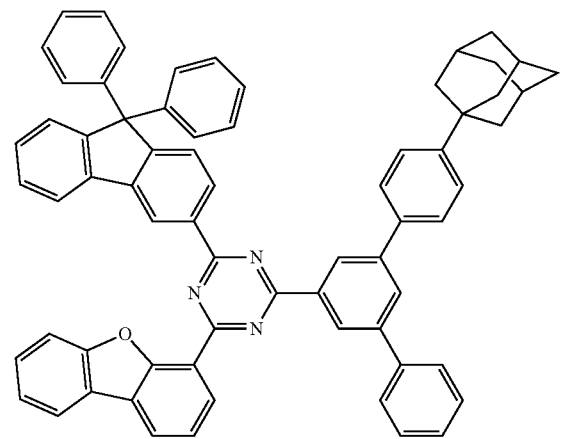
61
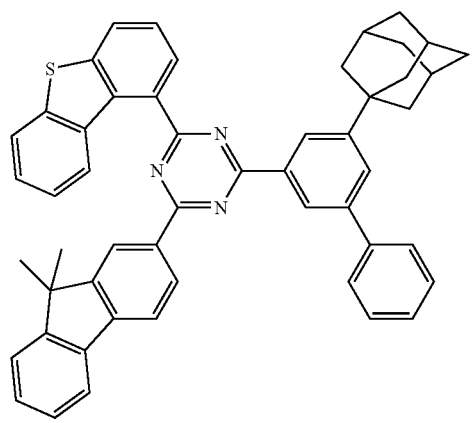
62
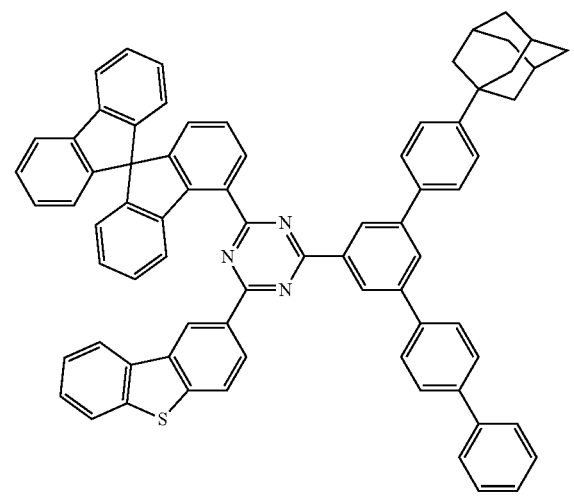
63
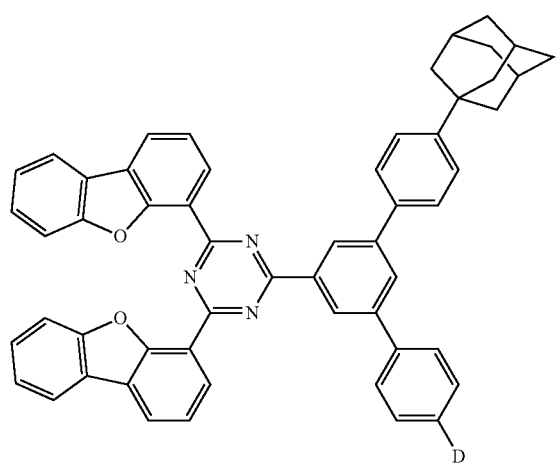
64
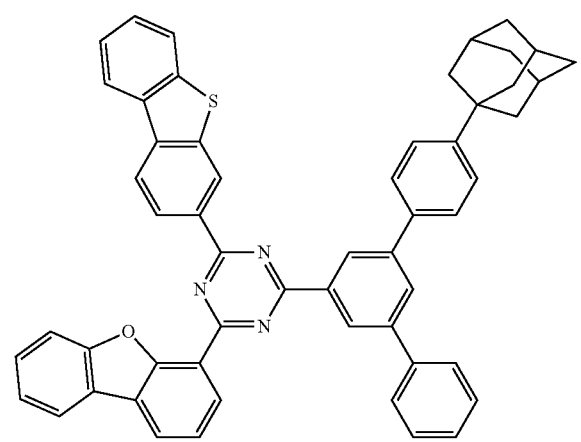
65

-continued
66
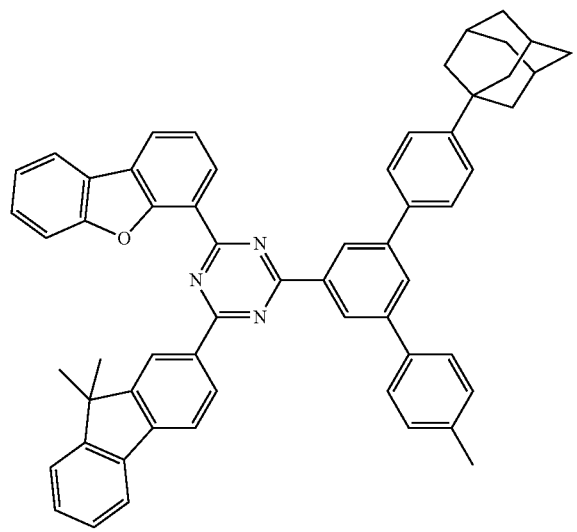
67
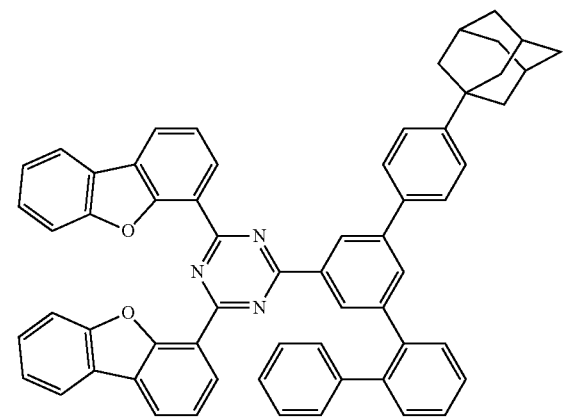
68
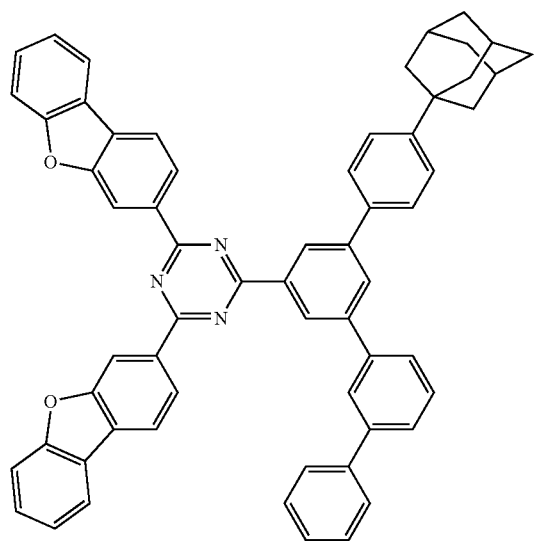
69
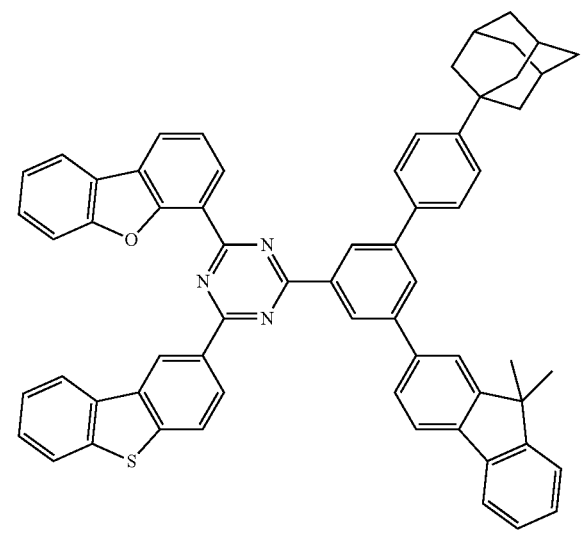
70
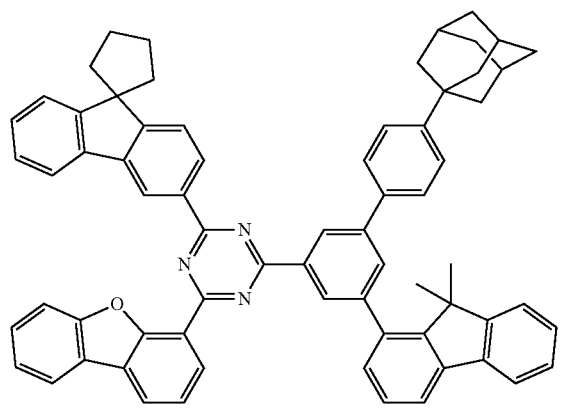
71
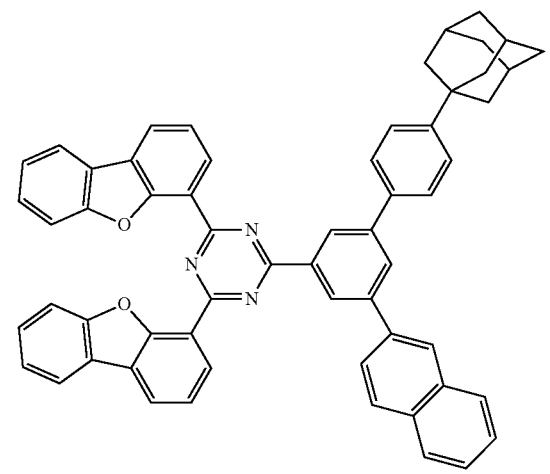

-continued
72
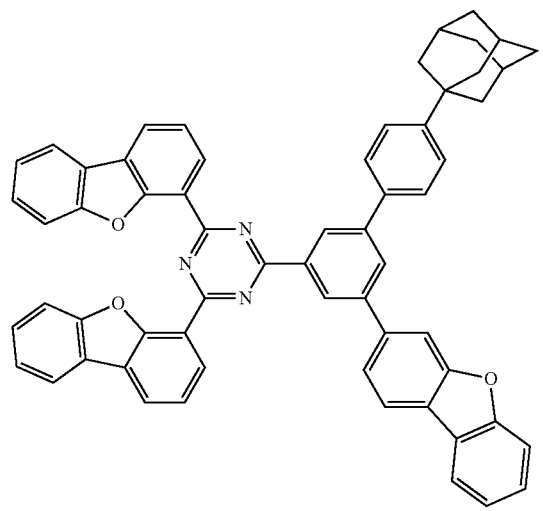
73
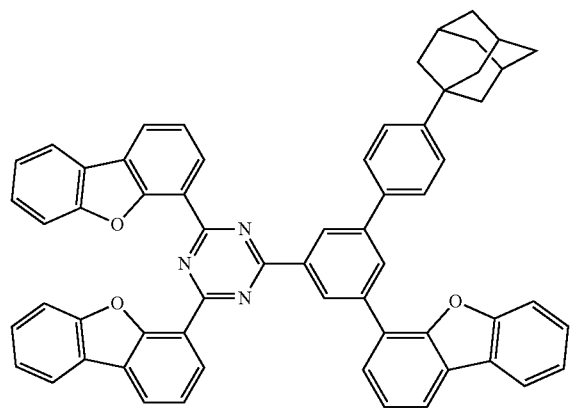
74
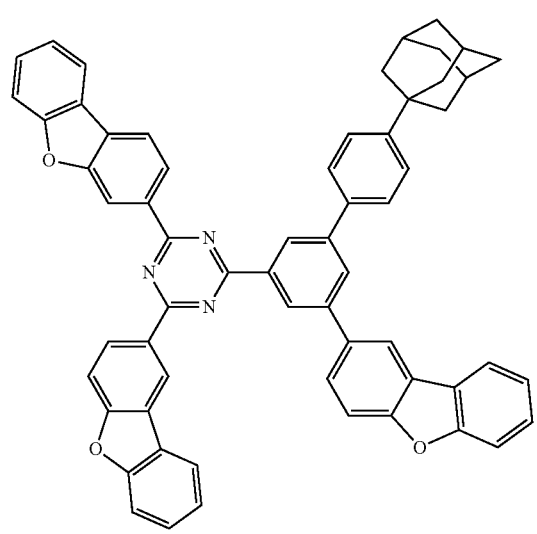
75
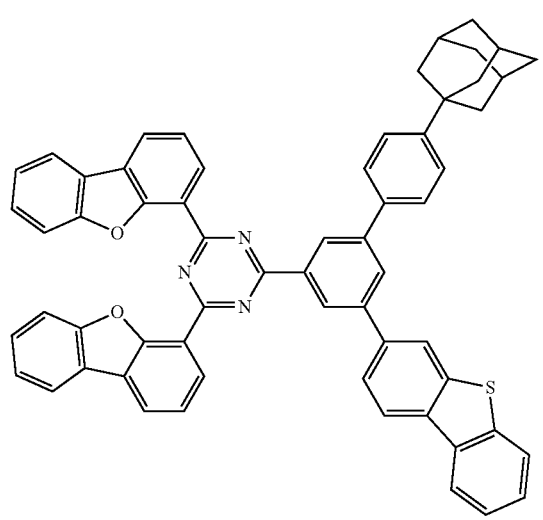
76
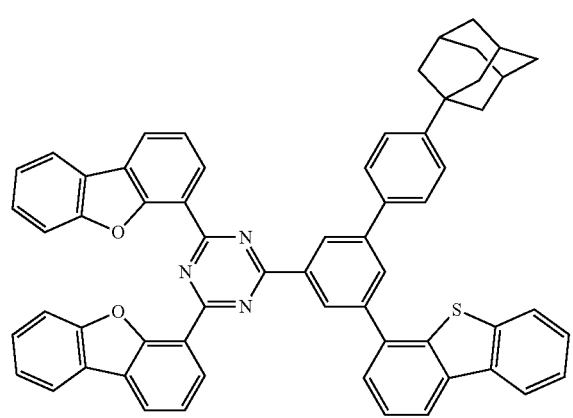
77
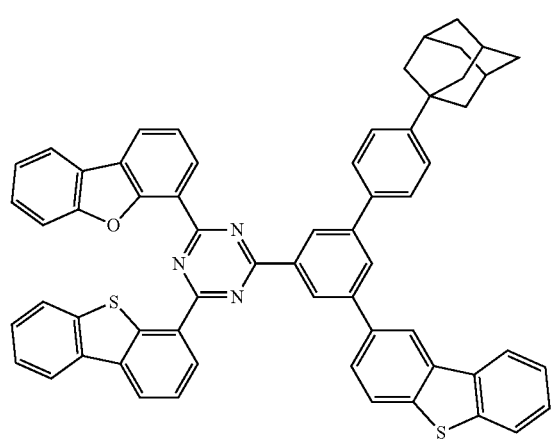

427
428
-continued
78
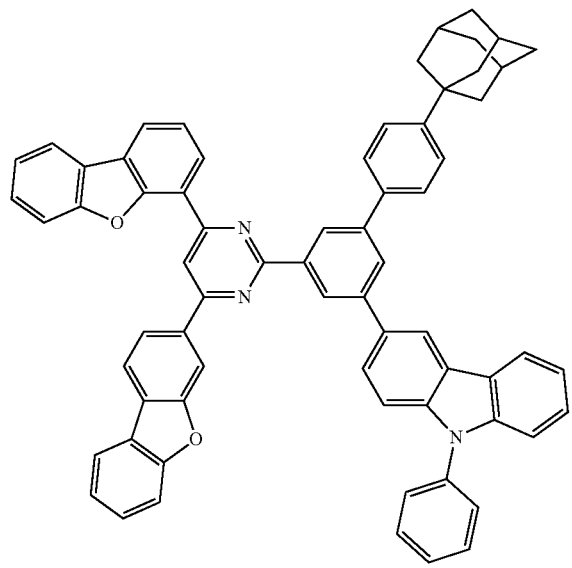
79
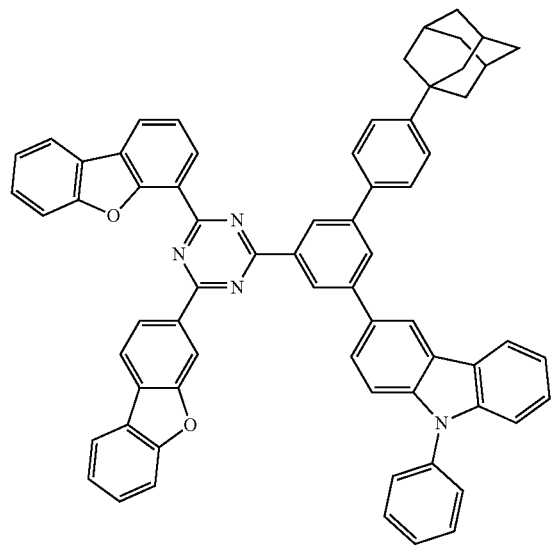
80
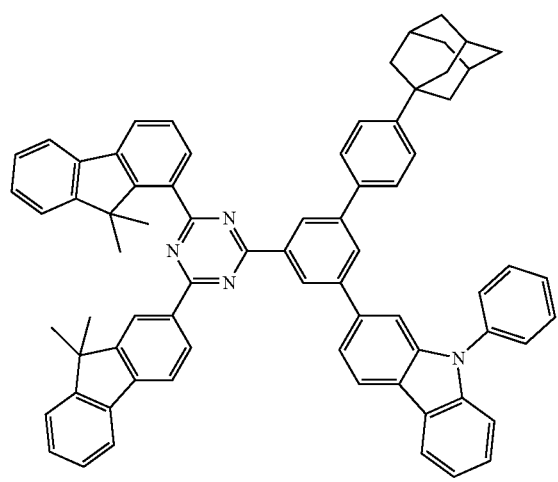
81
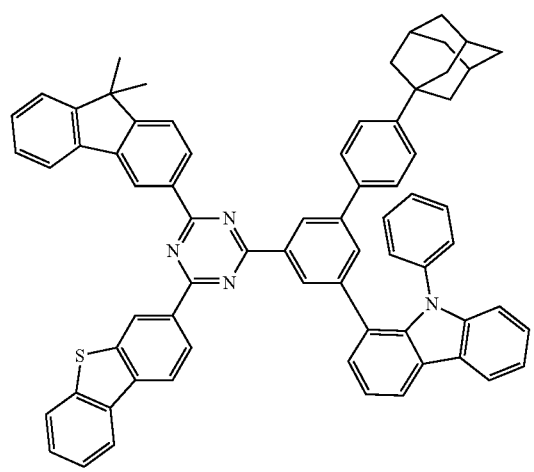
82
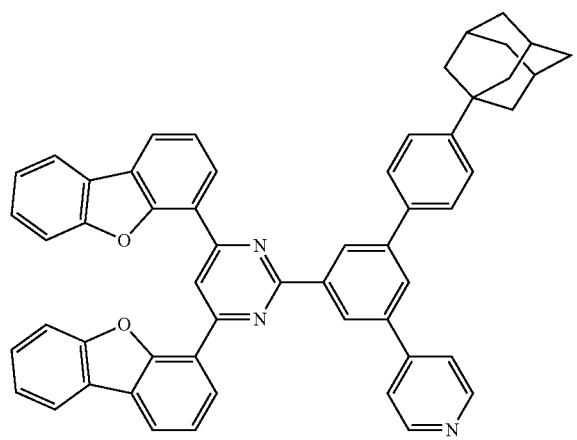
83
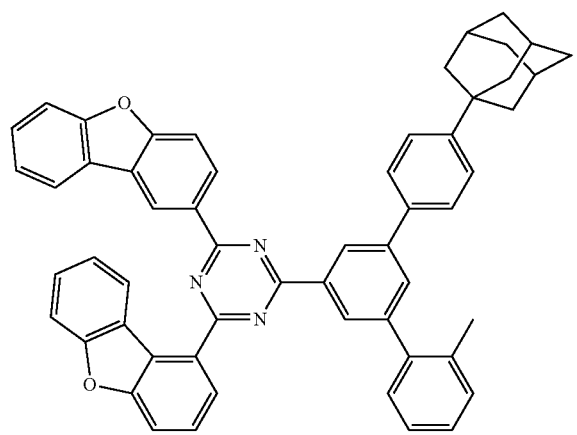

-continued
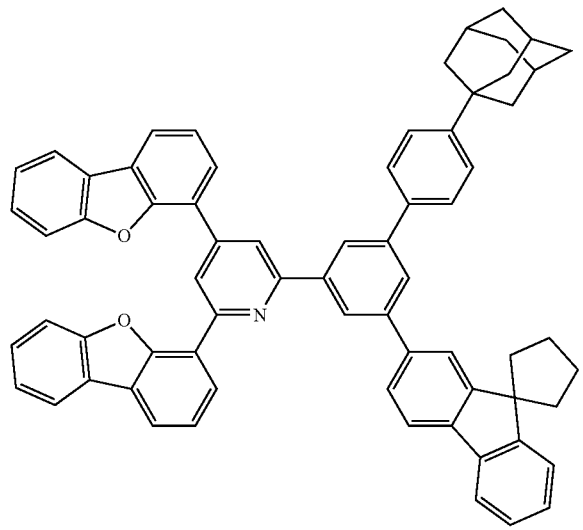
84
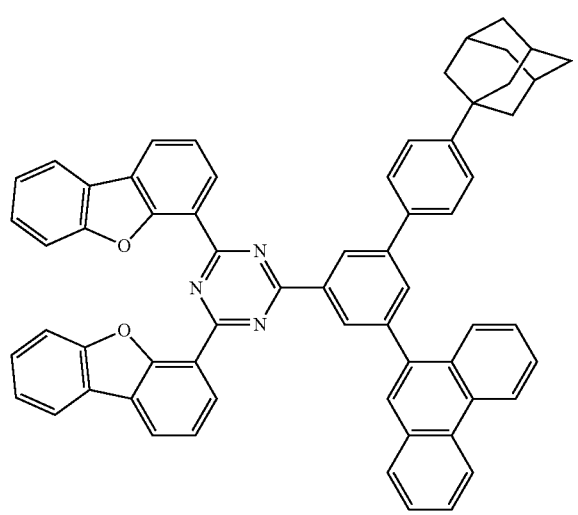
86
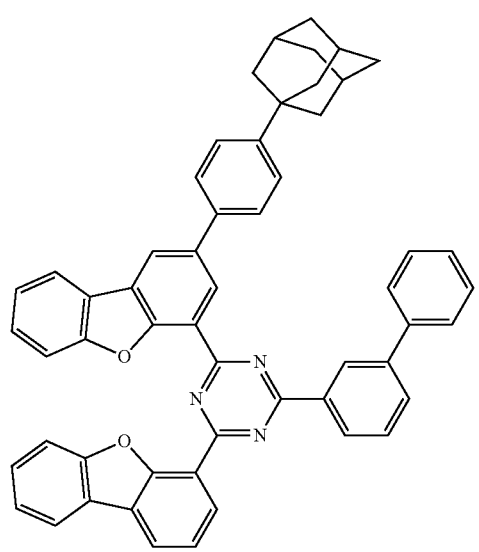
87
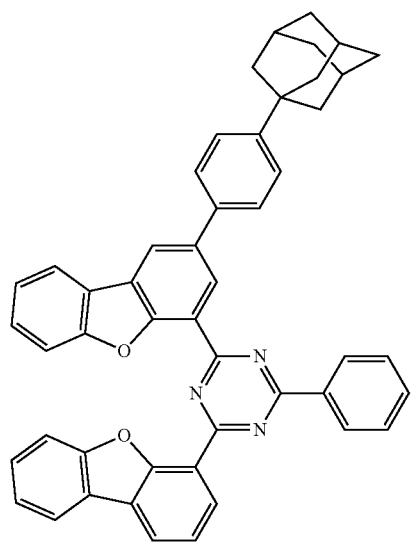
88
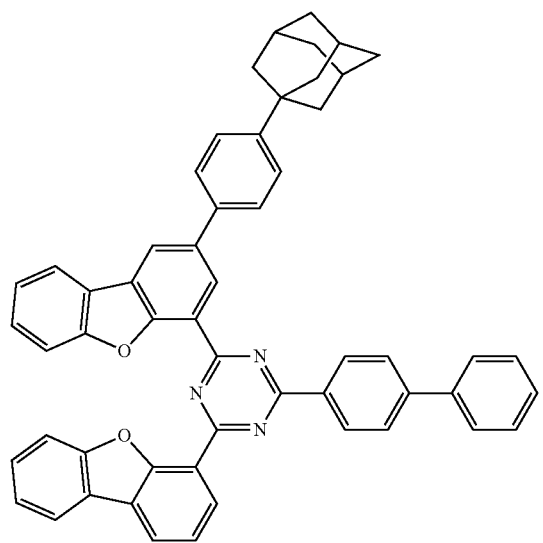
89

-continued
431
90
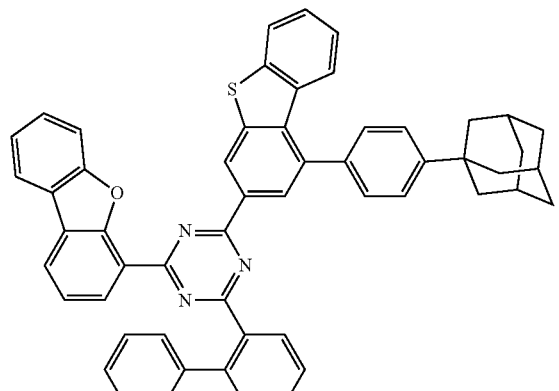
432
91
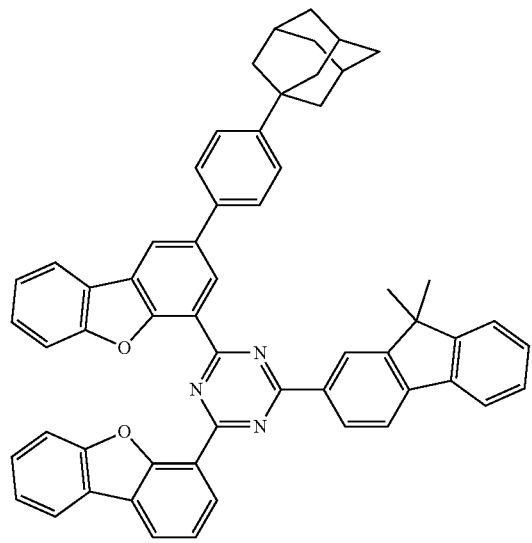
92
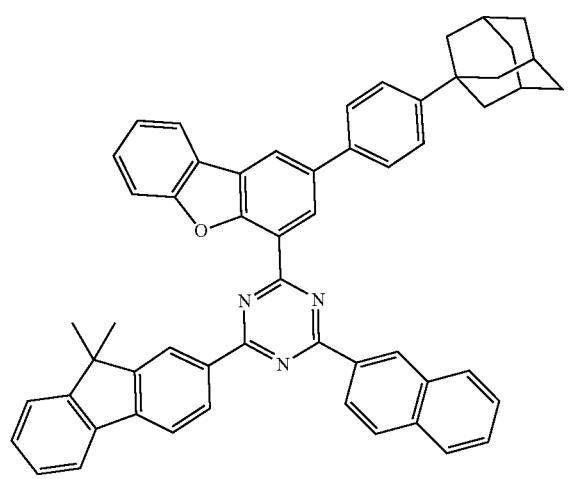
93
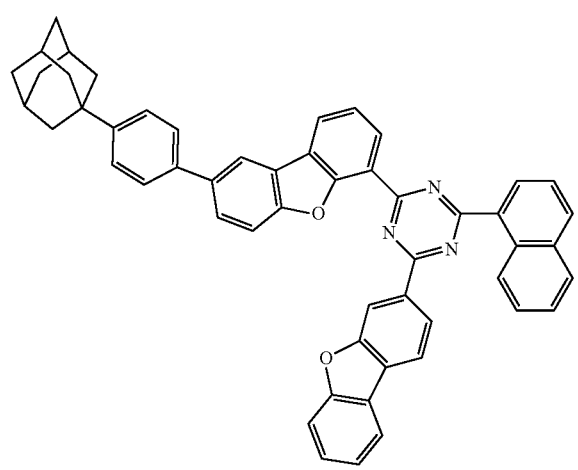
94
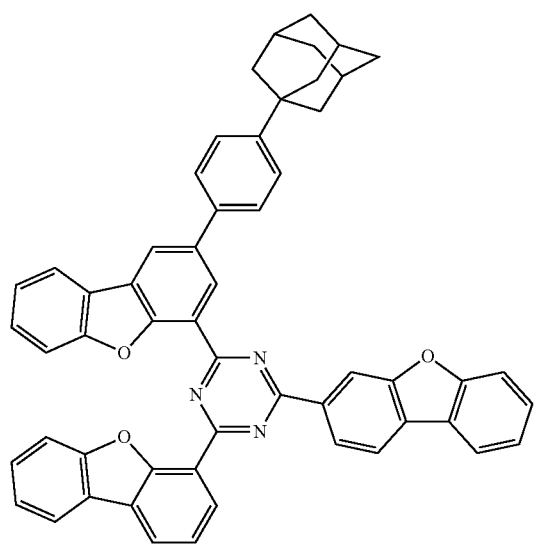
95
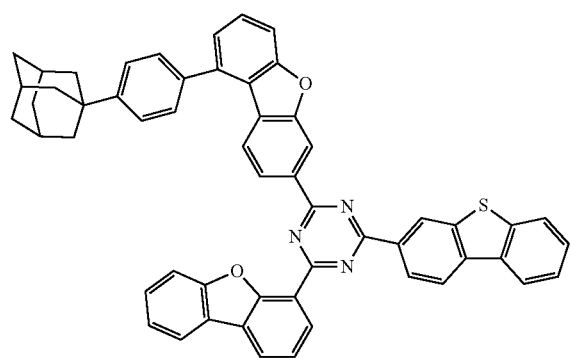

96
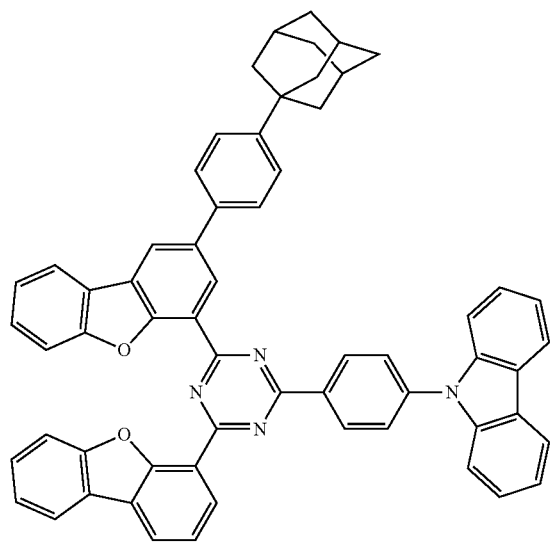
97
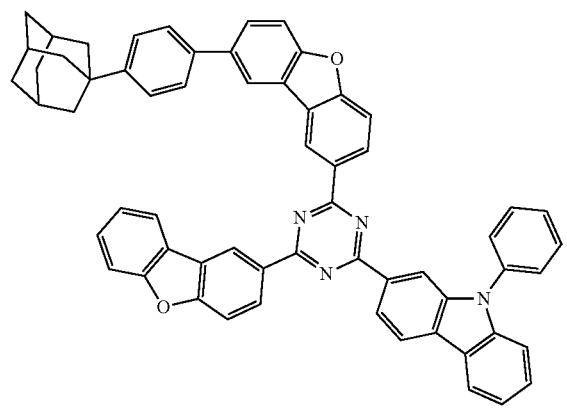
98
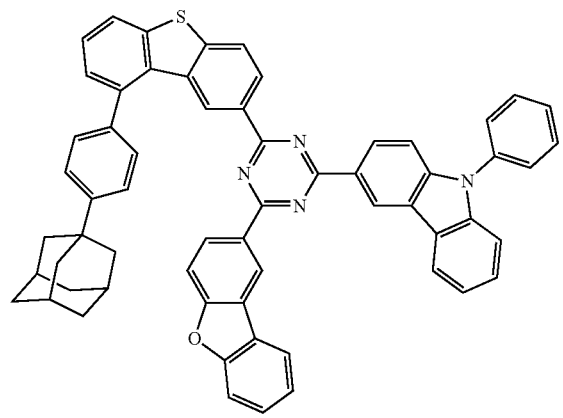
99
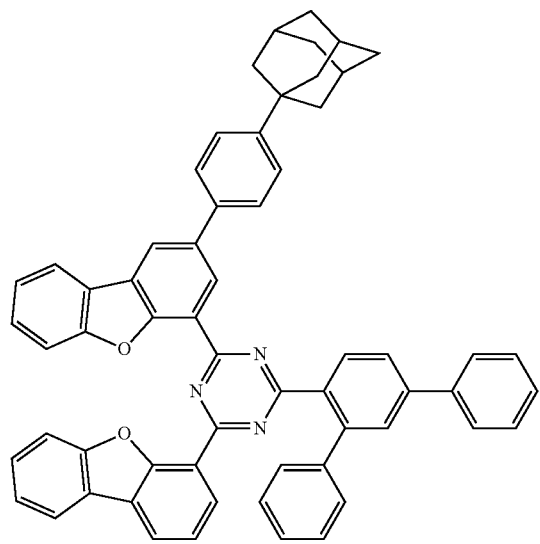
100
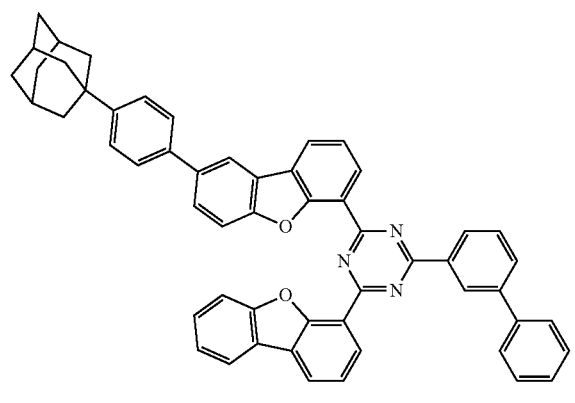
101
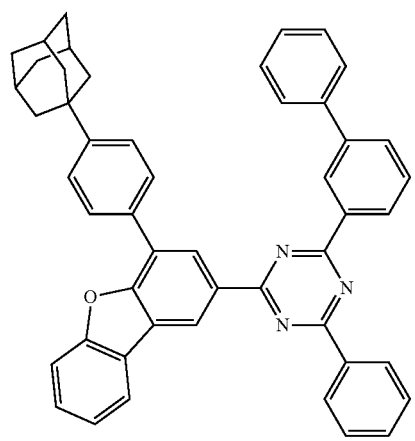

-continued
102
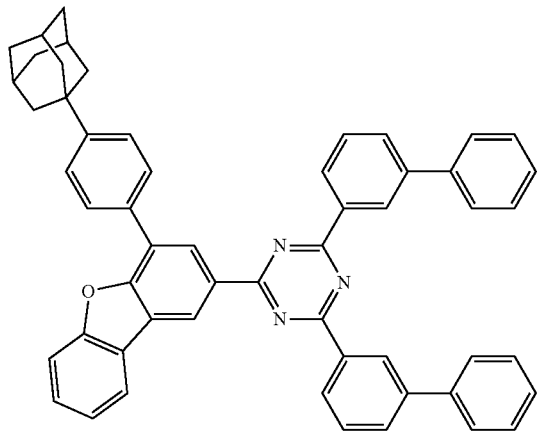
103
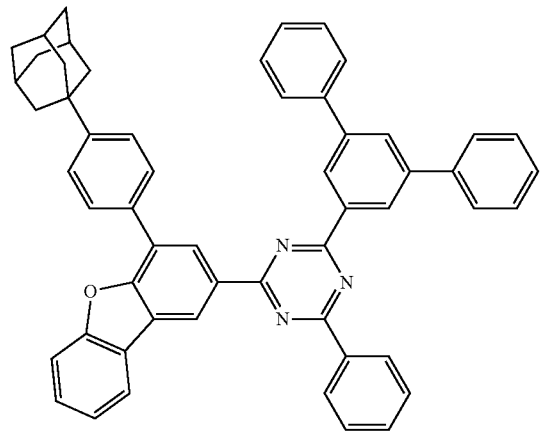
104
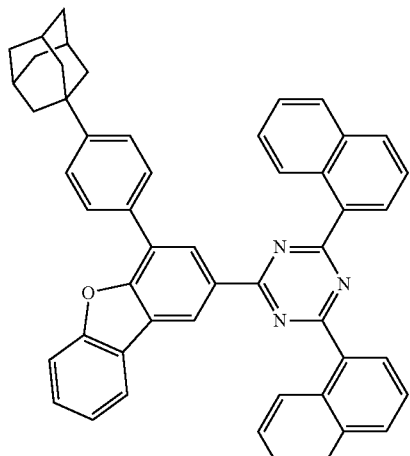
105
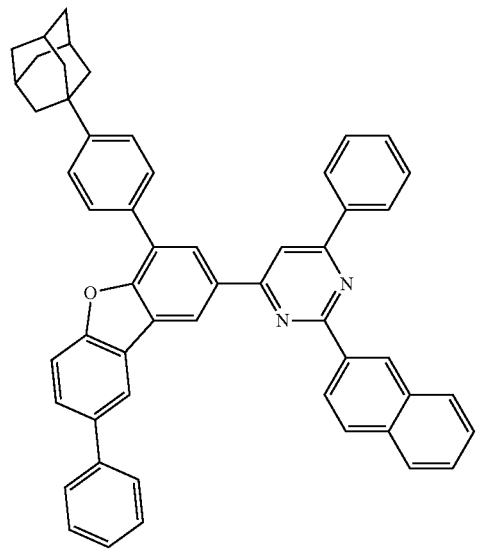
106
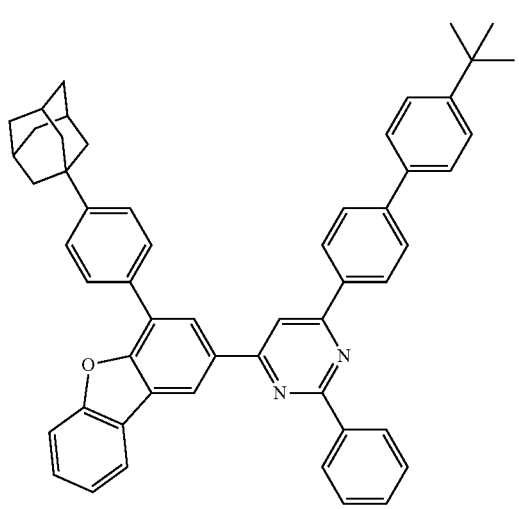
107
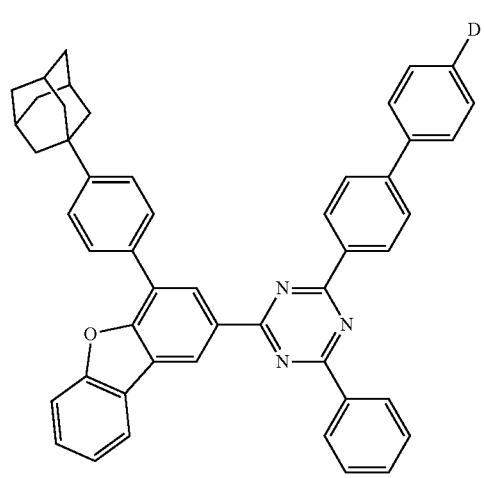

-continued
108
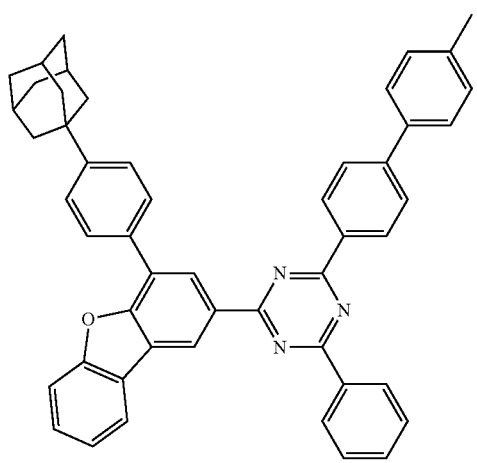
109
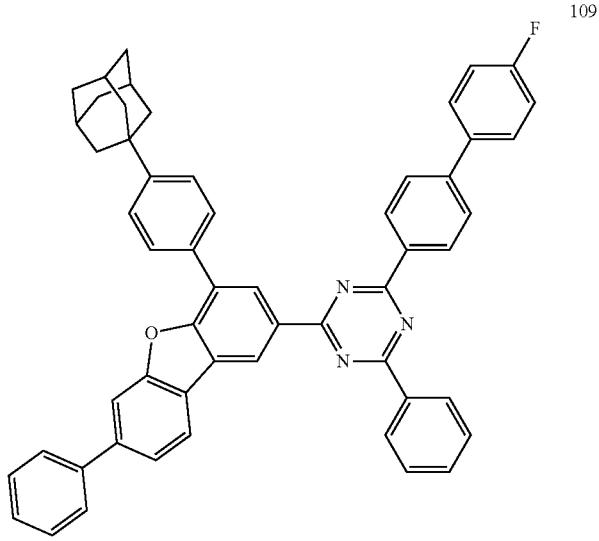
110
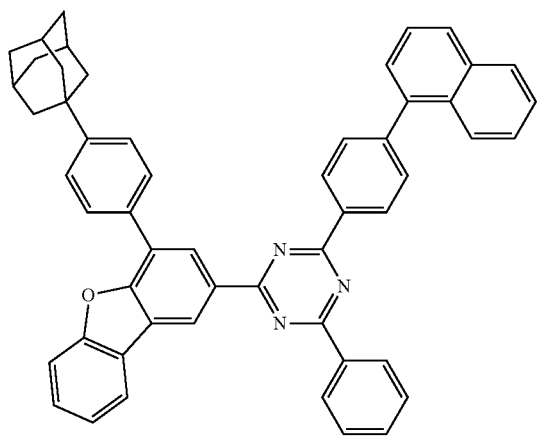
111
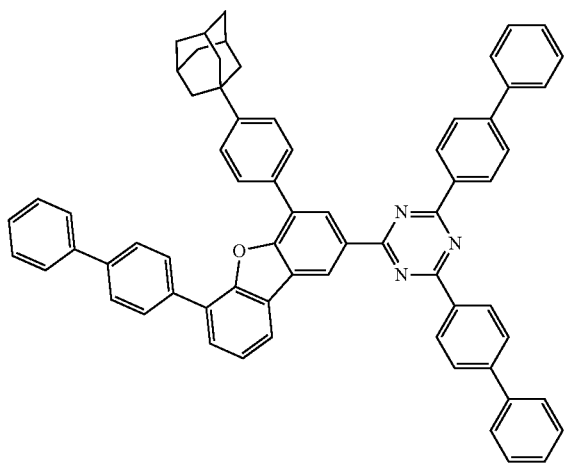
112
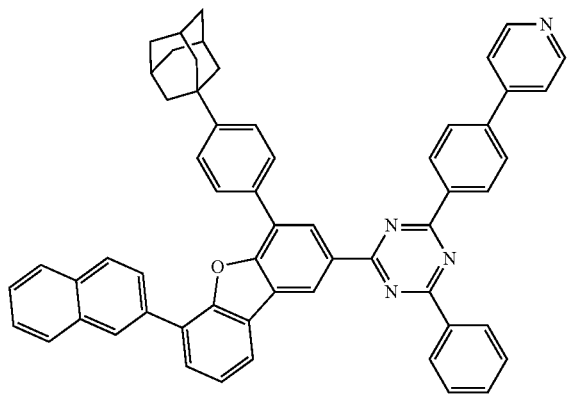
113
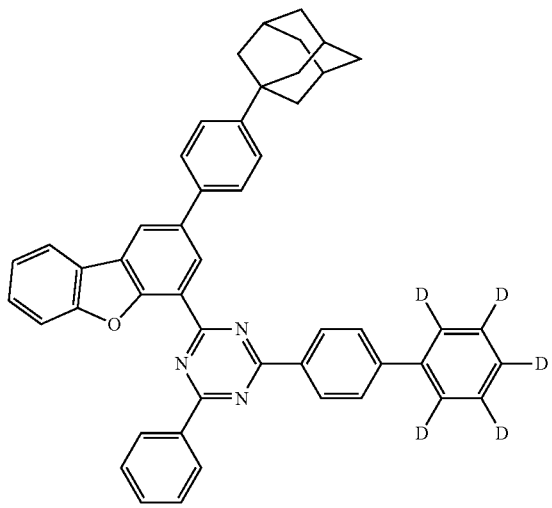

-continued
114
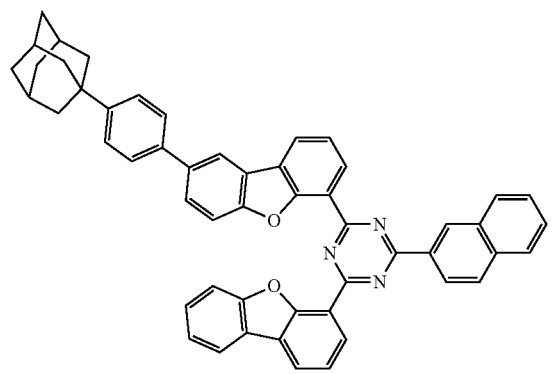
115
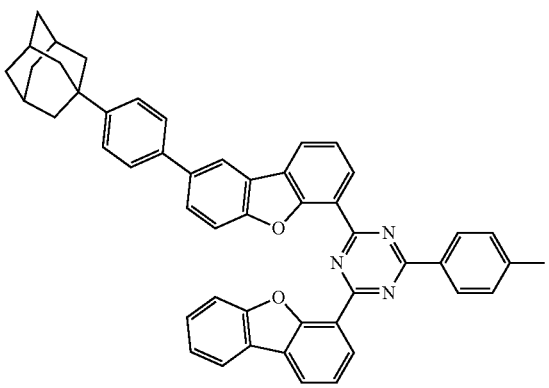
116
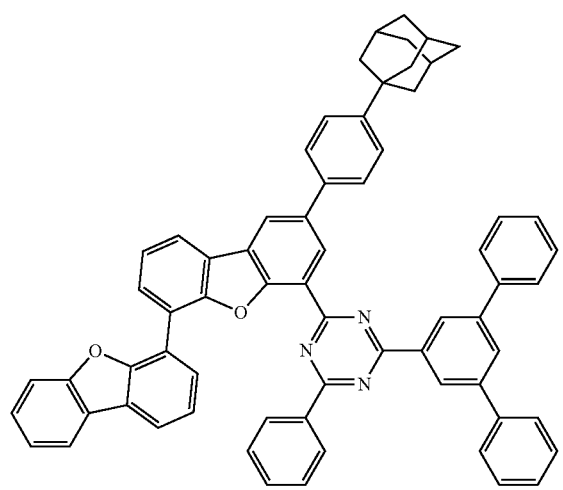
117
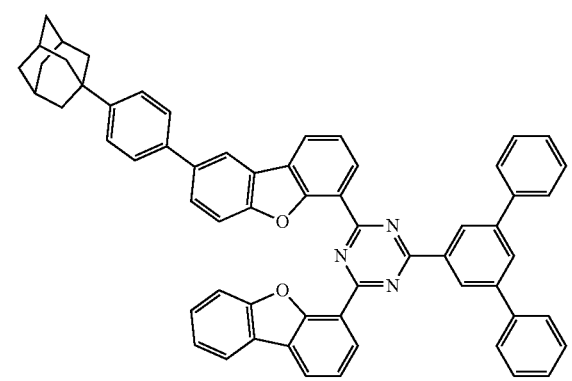
118
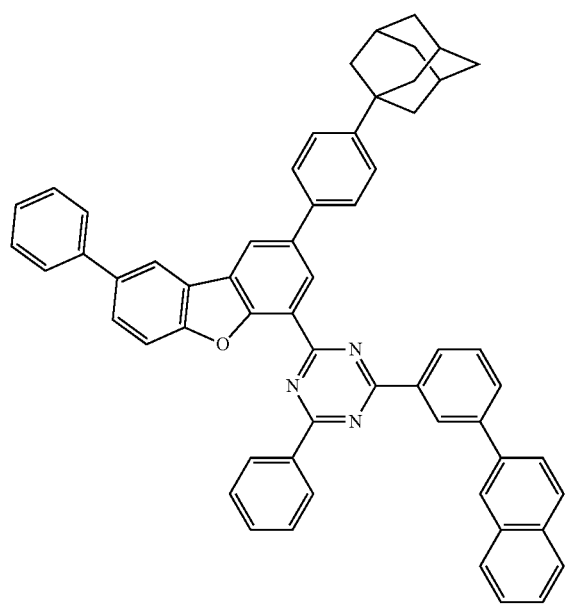
119
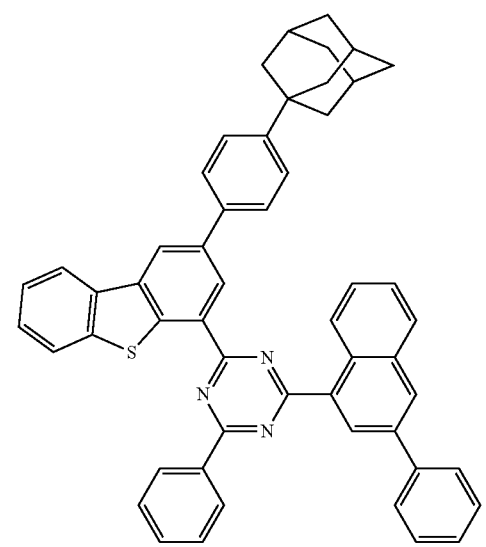

441 442
-continued
120 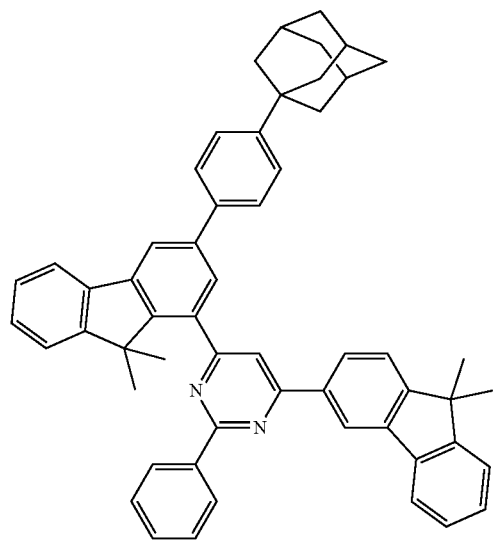 121 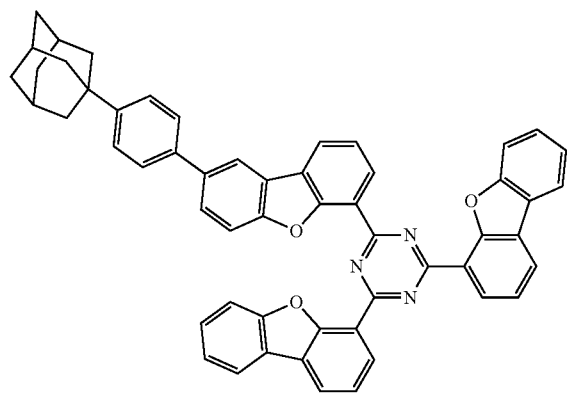
122 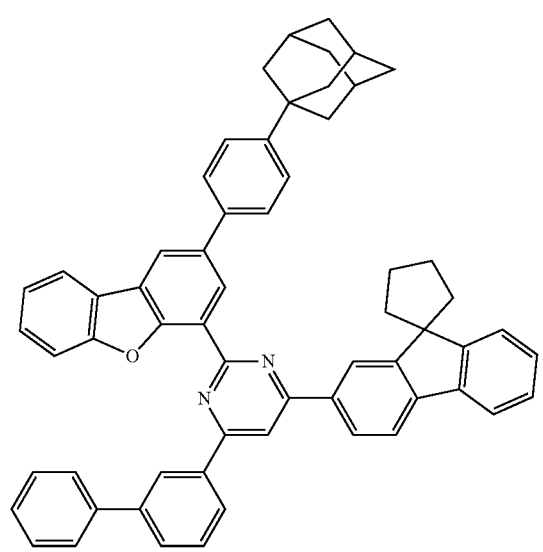 123 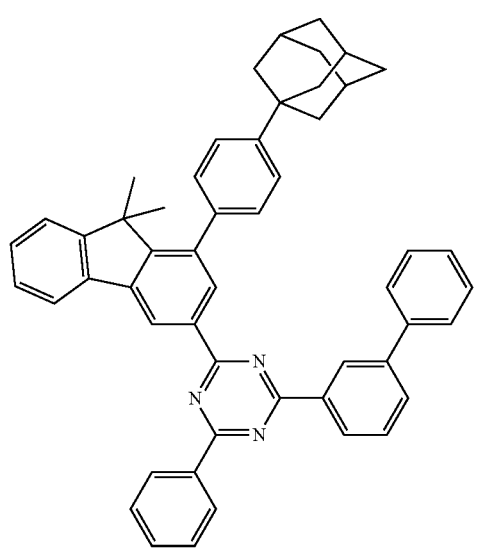
124 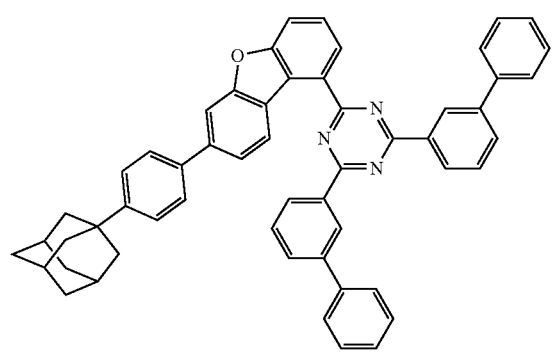 125 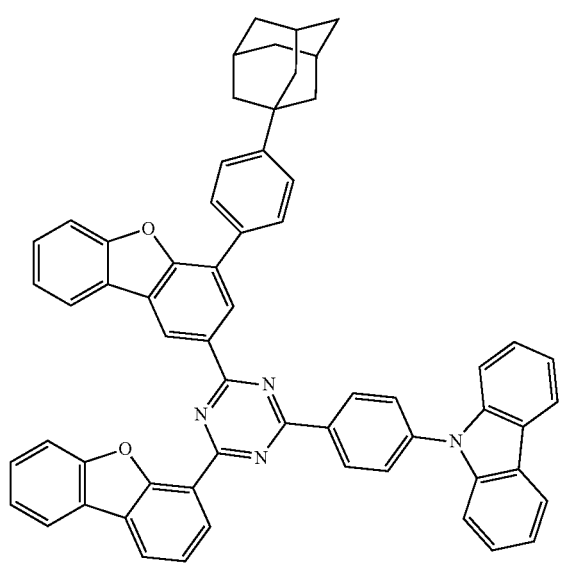

126
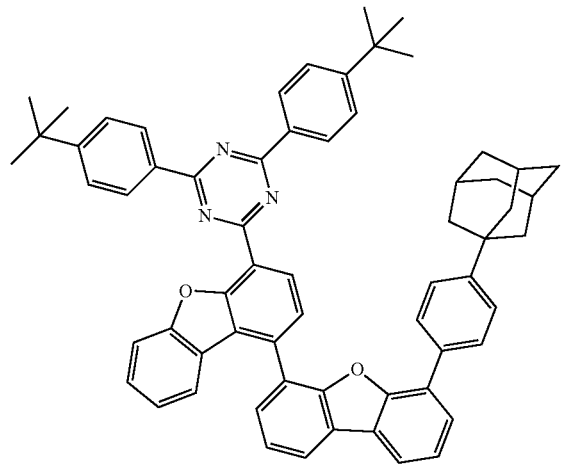
127
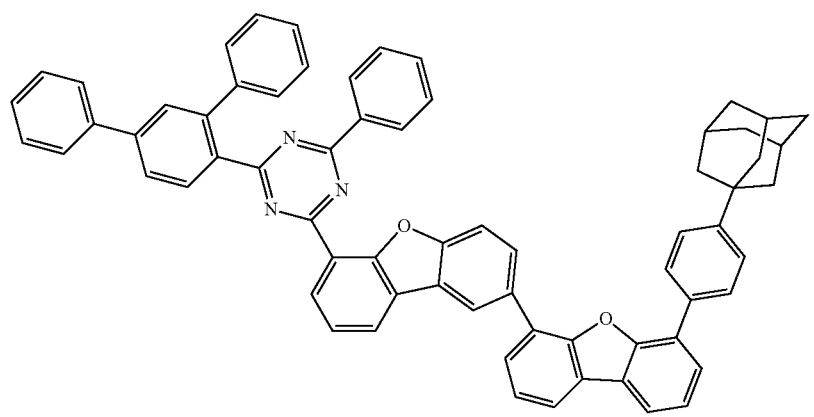
128
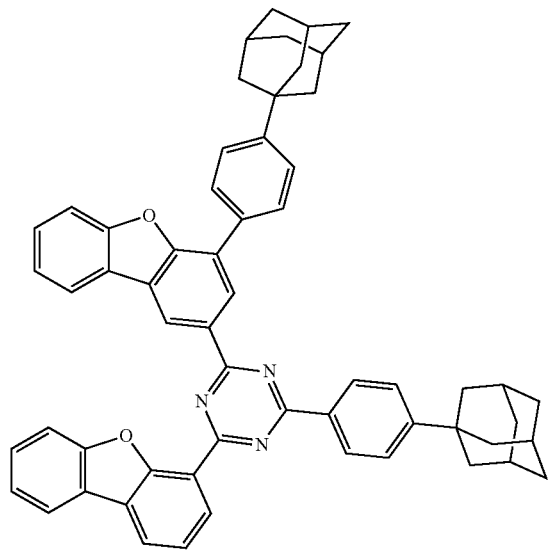
129
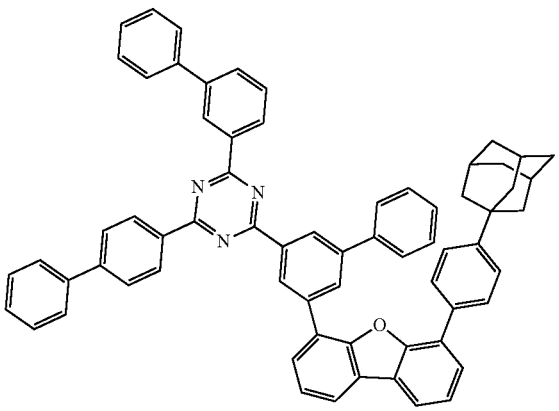

-continued
130
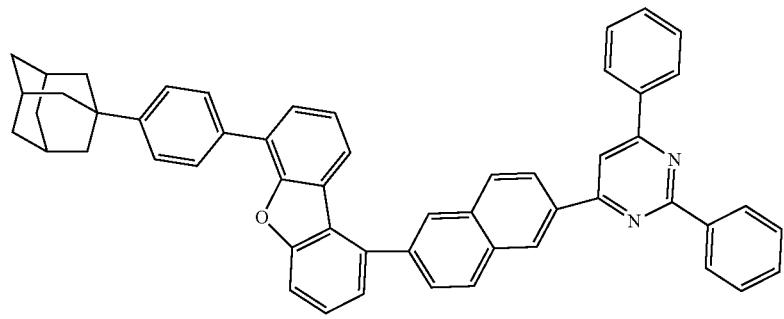
131
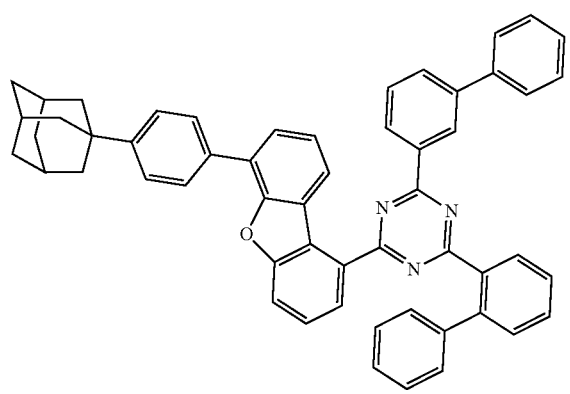
132
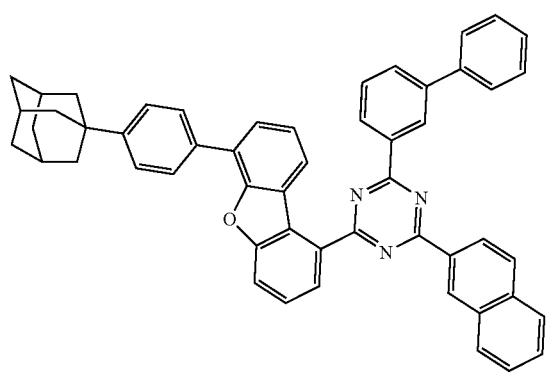
133
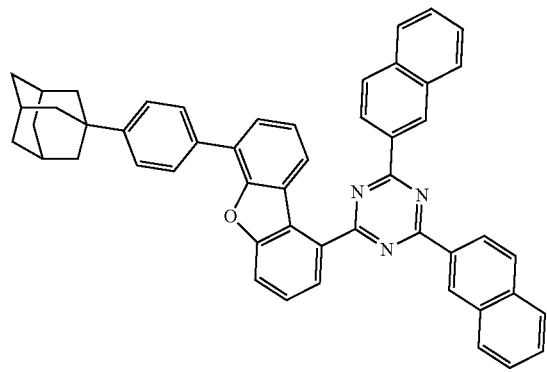
134
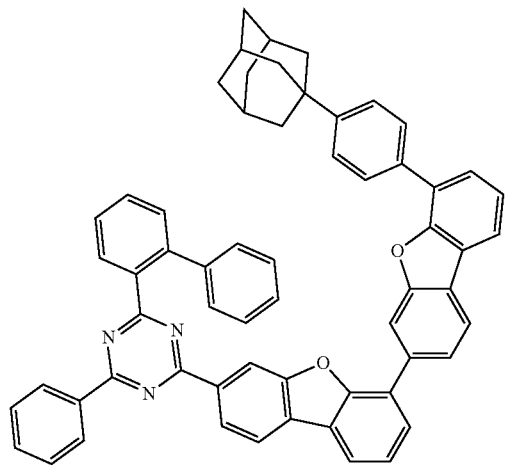
135
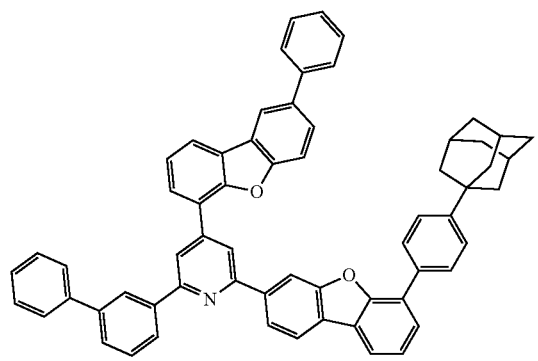
136
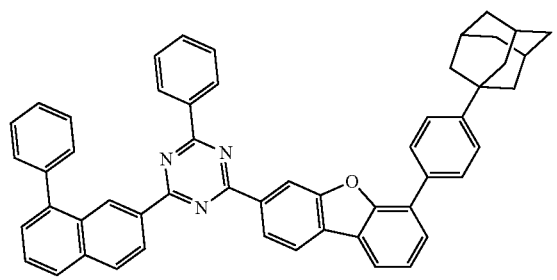

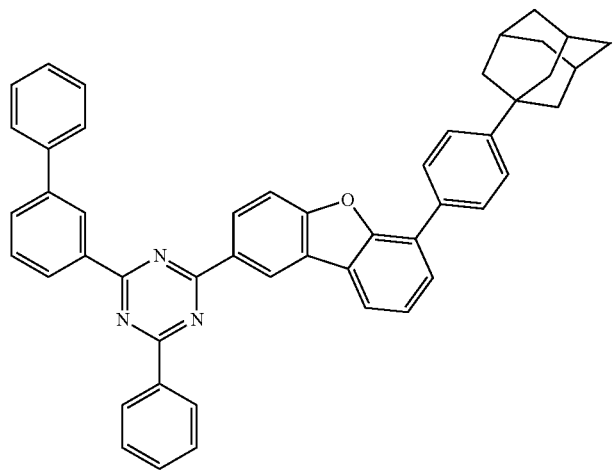
137
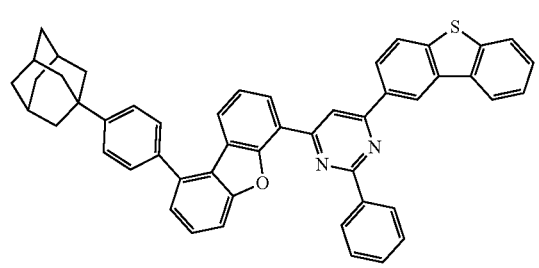
139
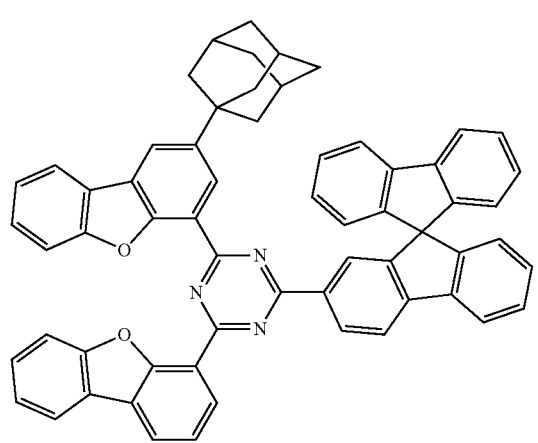
140
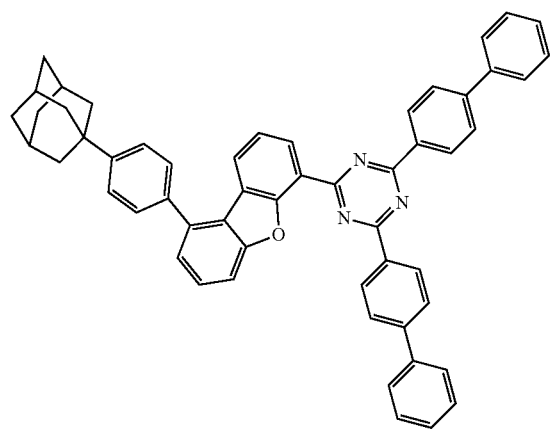
141
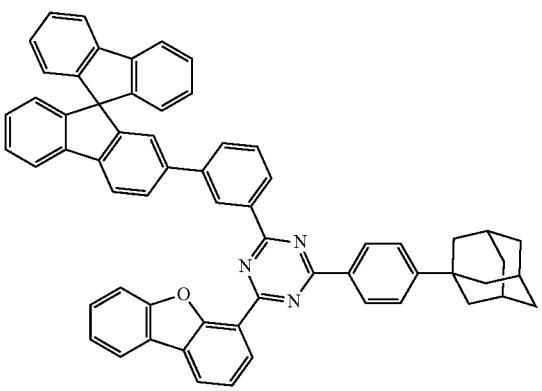
142

-continued
143
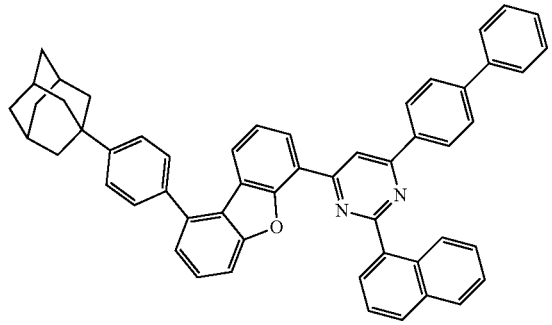
144
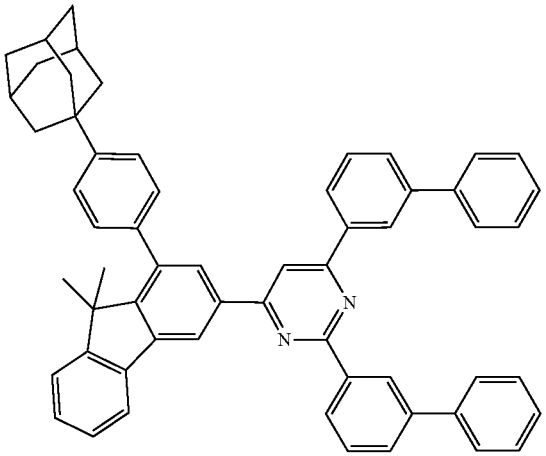
145
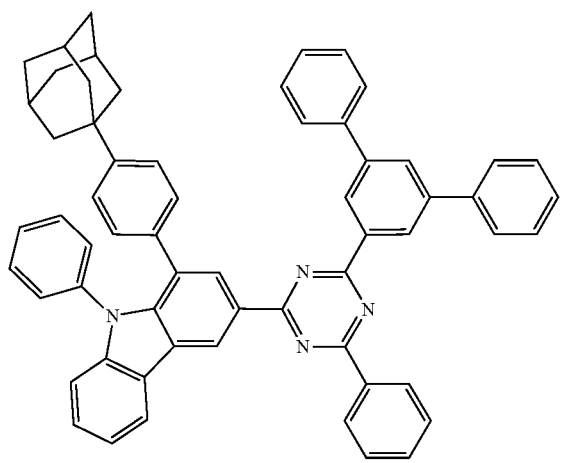
146
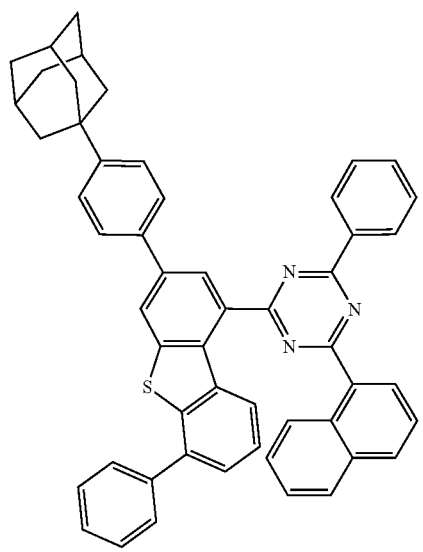
147
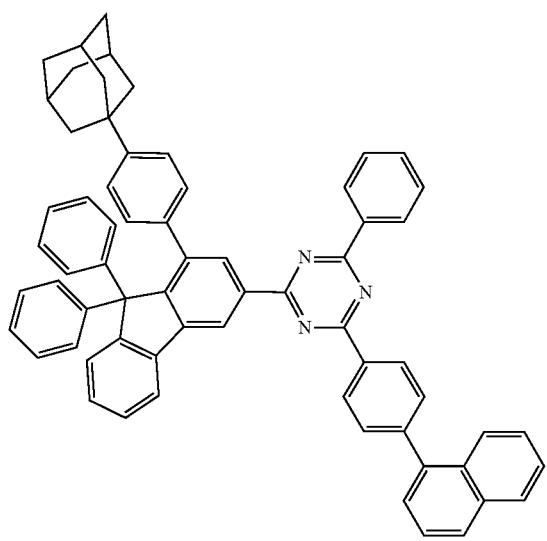
148
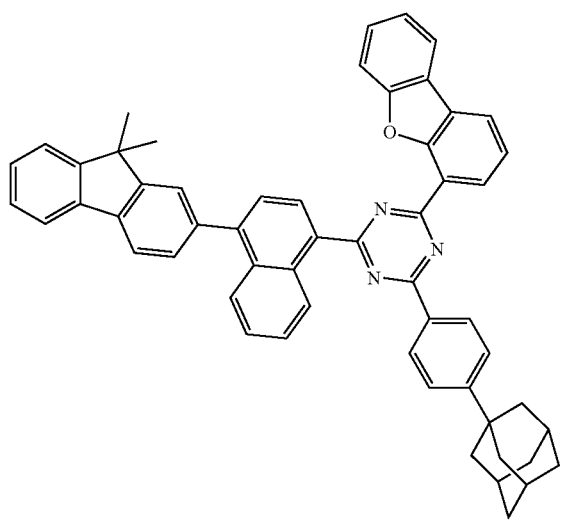

-continued
149
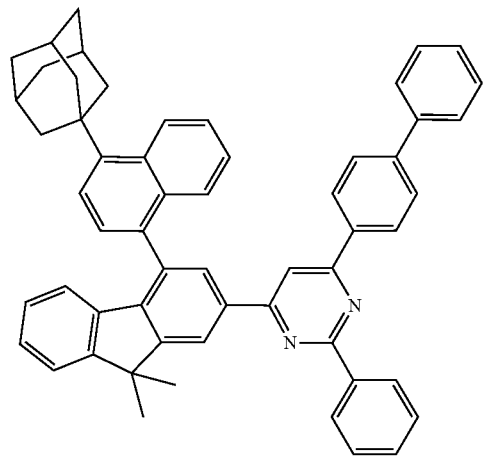
151
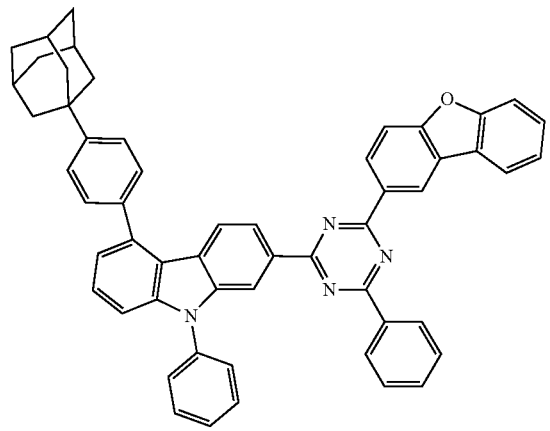
152
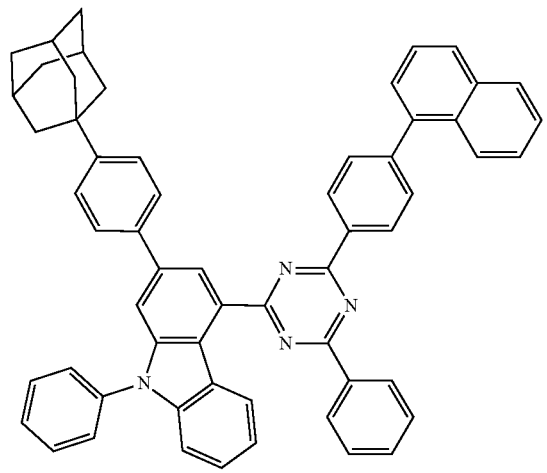
153
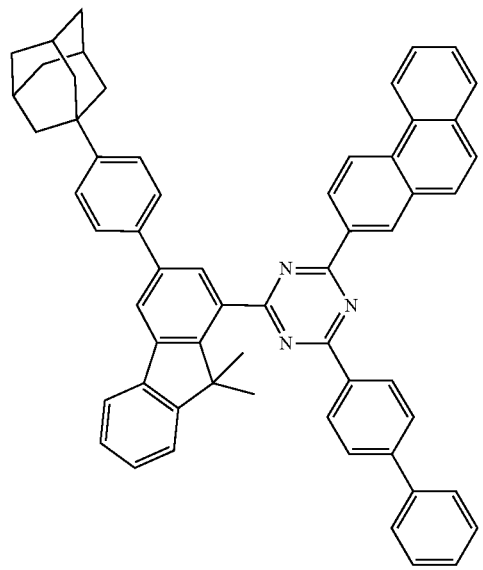
154
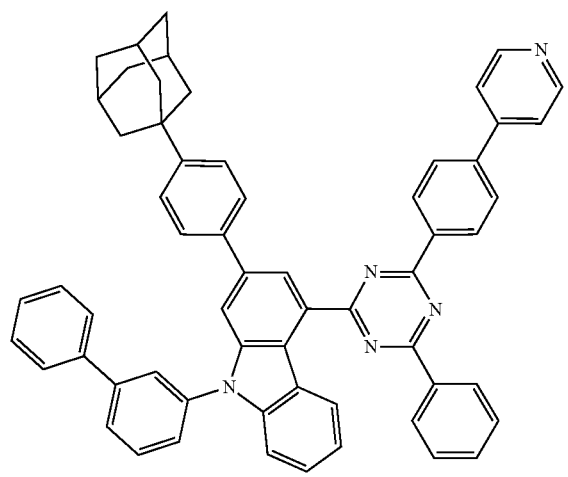
155
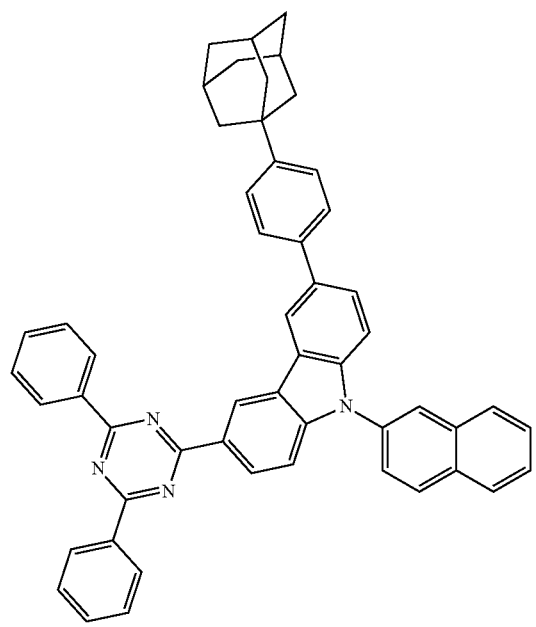

156
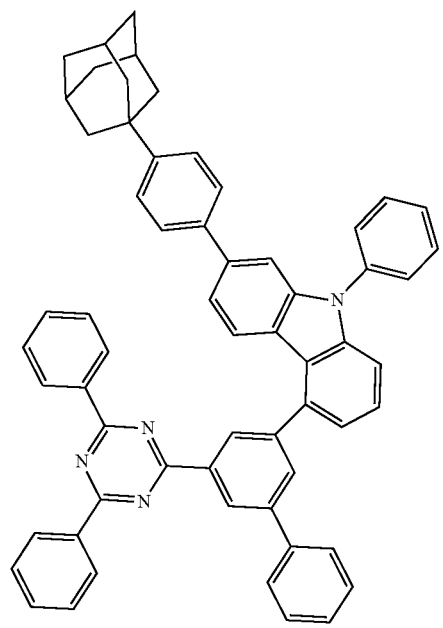
157
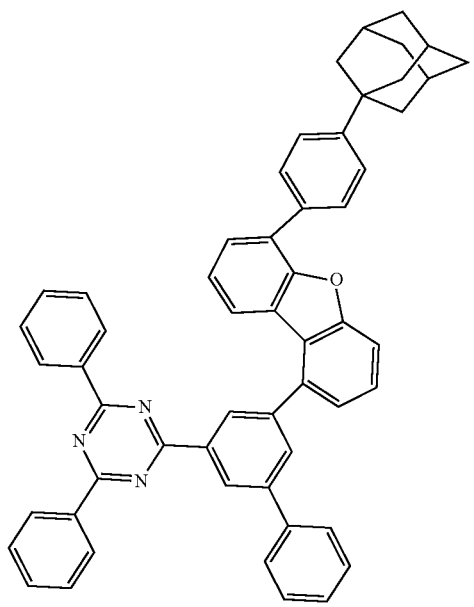
158
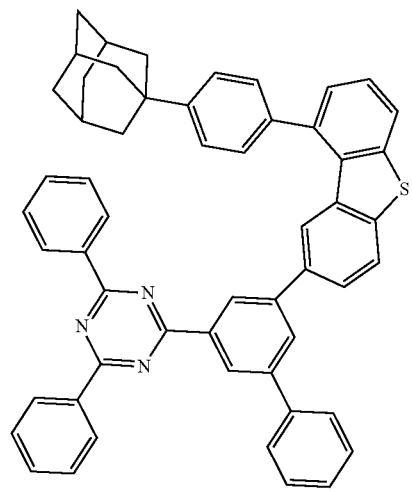
159
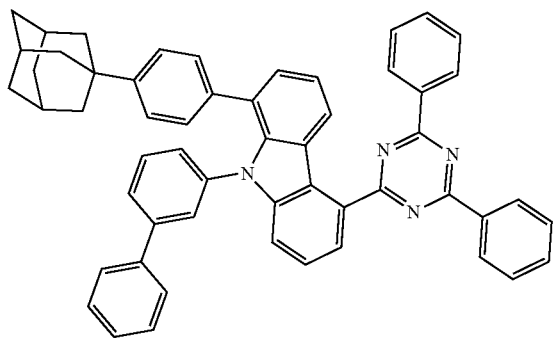
160
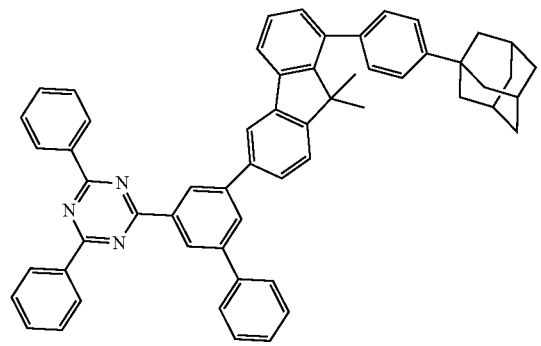
161
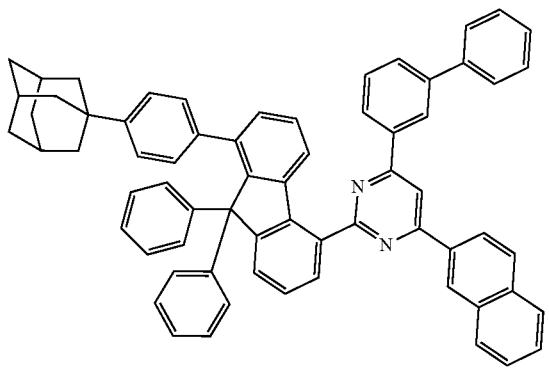

-continued
162
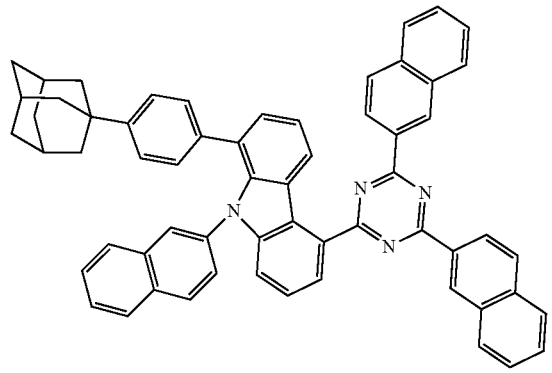
163
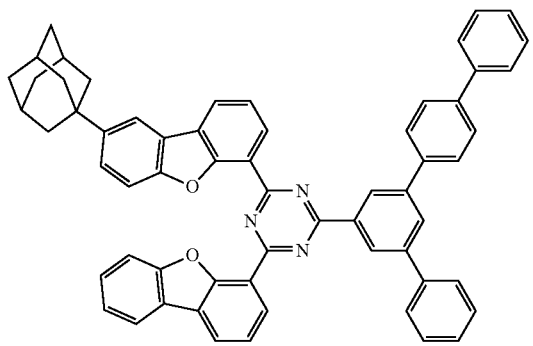
164
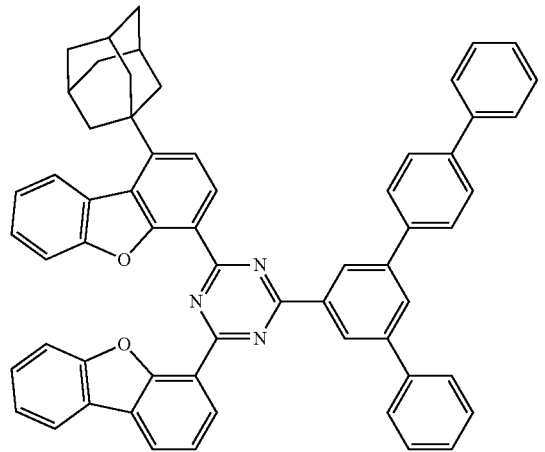
165
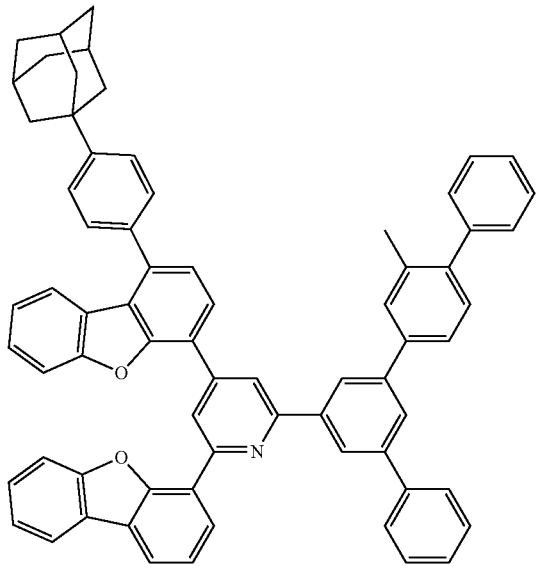
166
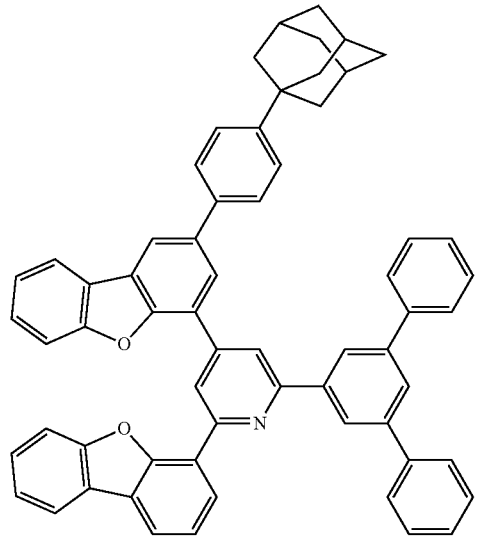
167
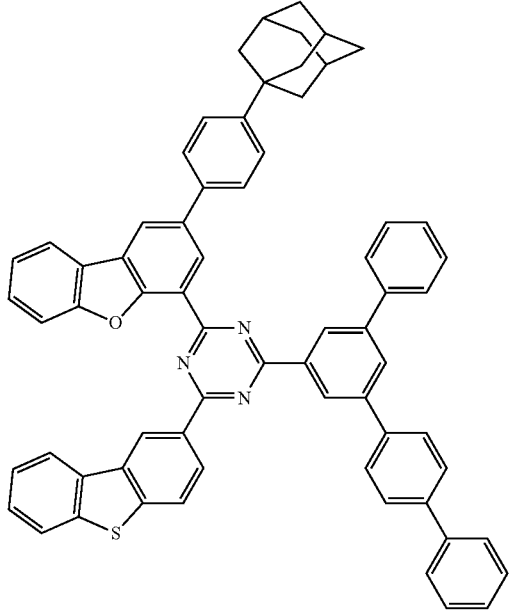

457
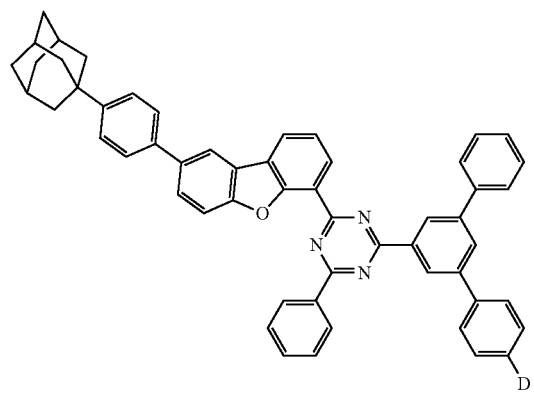
458
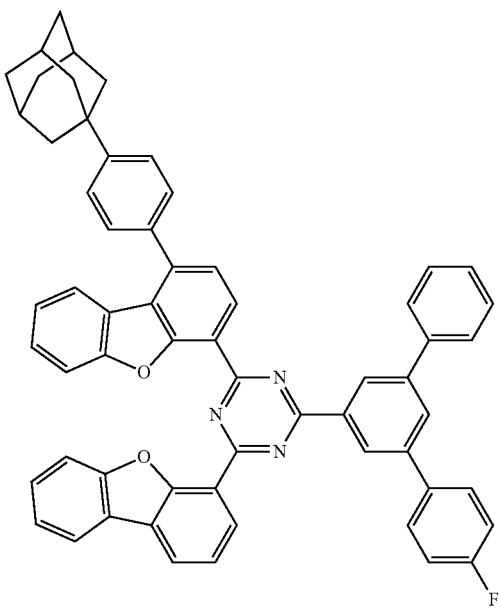
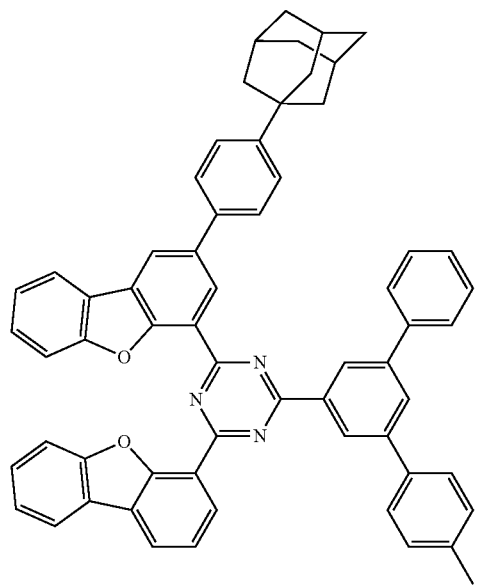
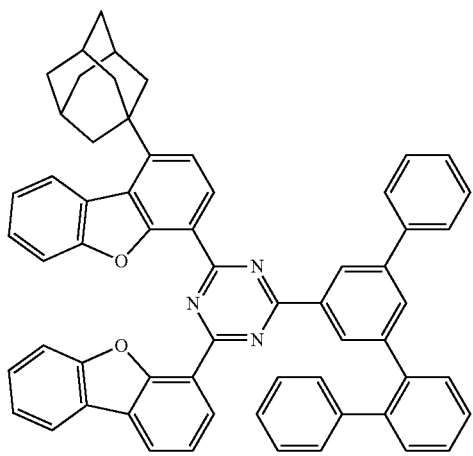

-continued
172
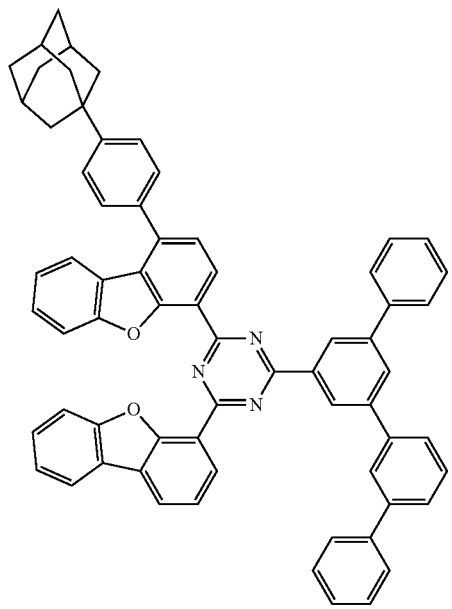
173
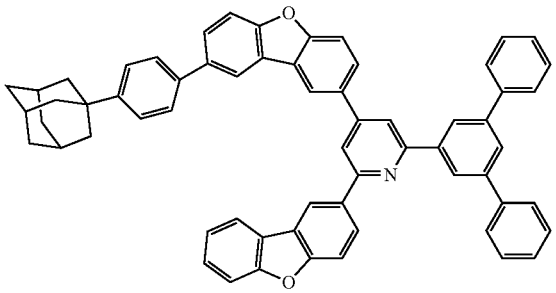
174
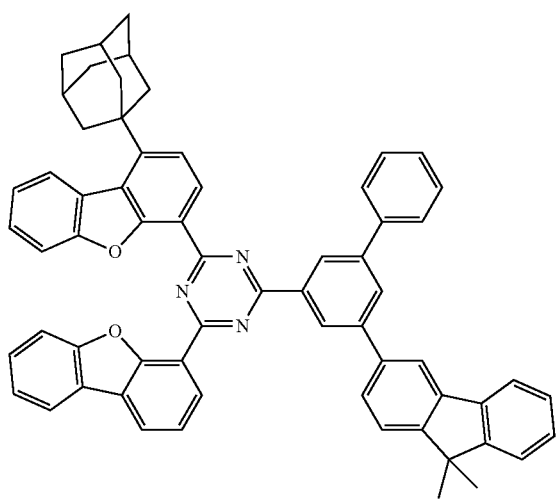
175
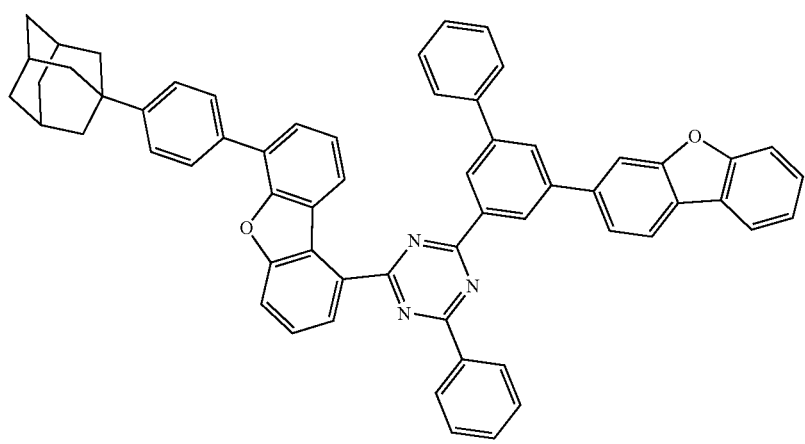

176
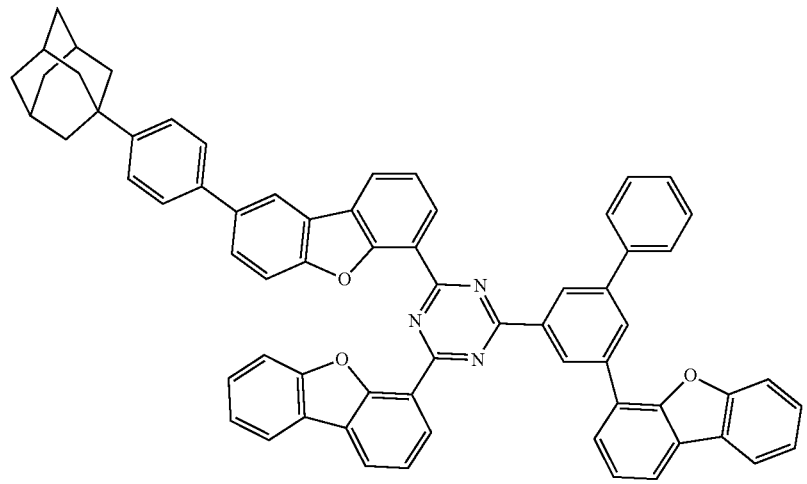
177
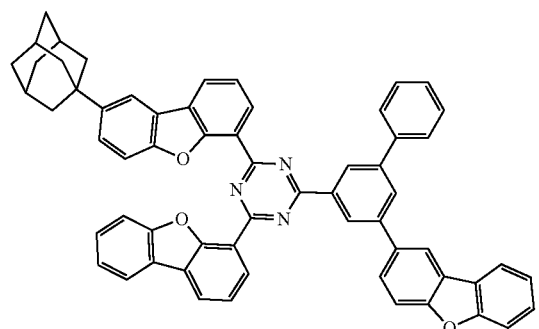
178
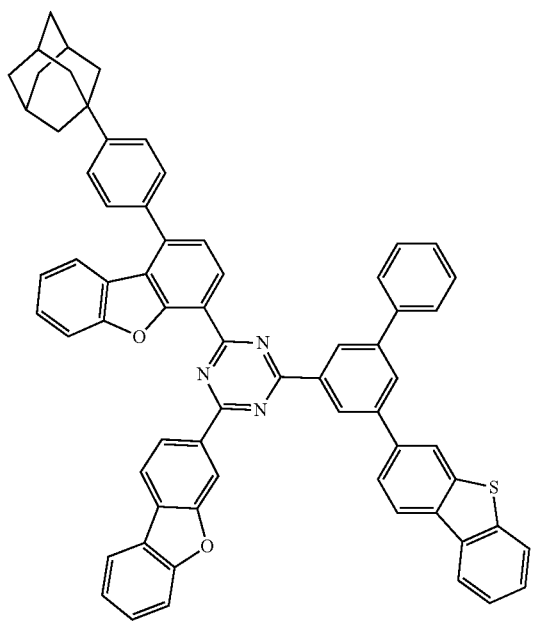

-continued
179
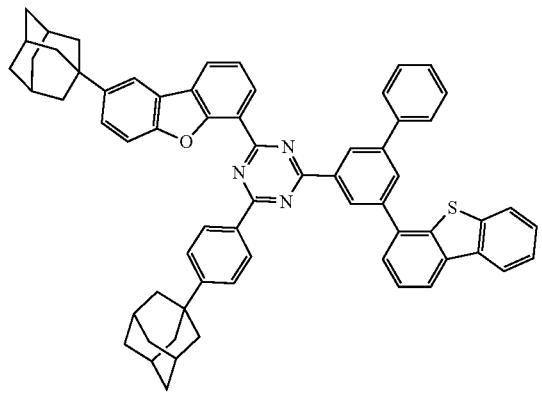
180
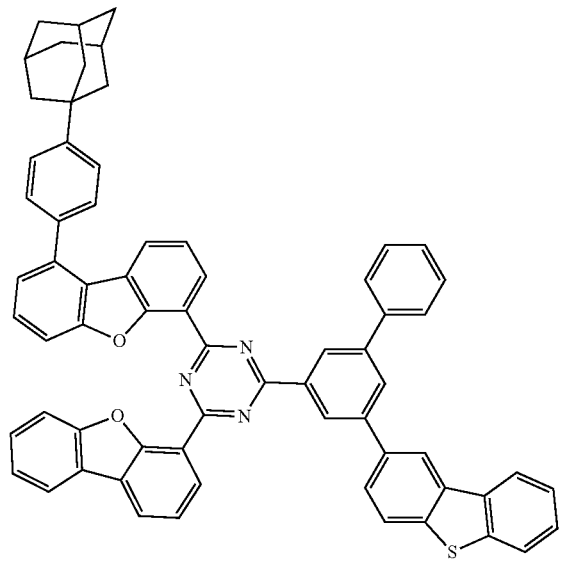
181
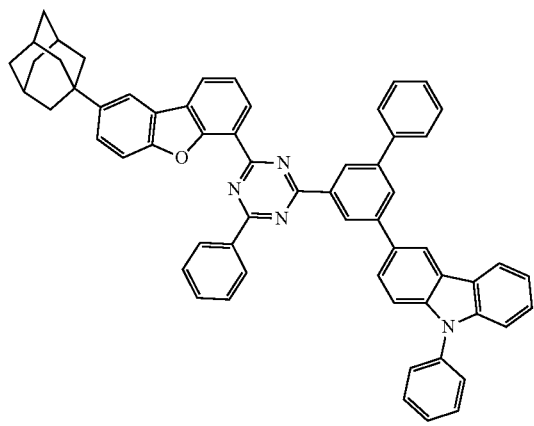
184
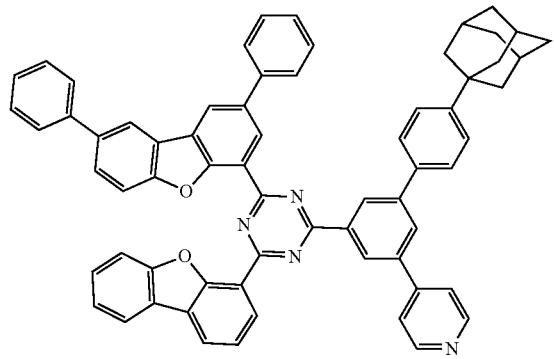
187
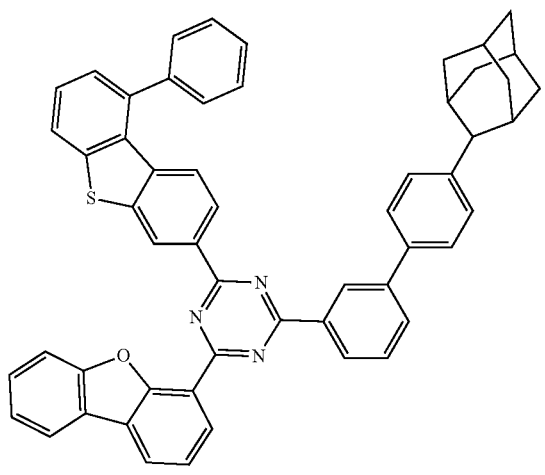
188
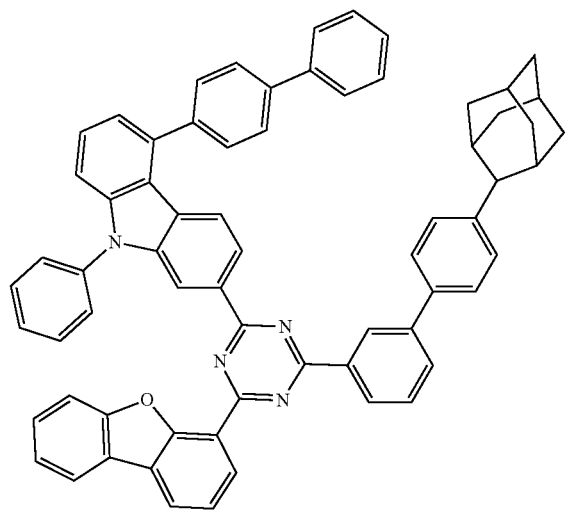

-continued
189
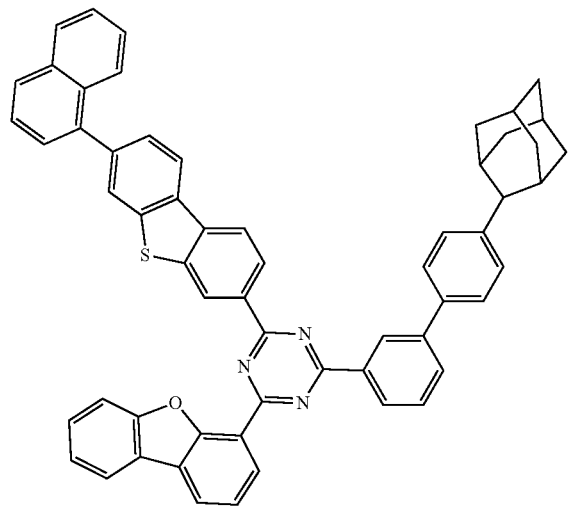
190
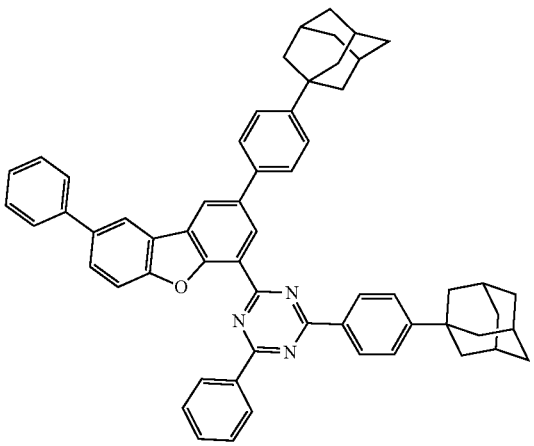
191
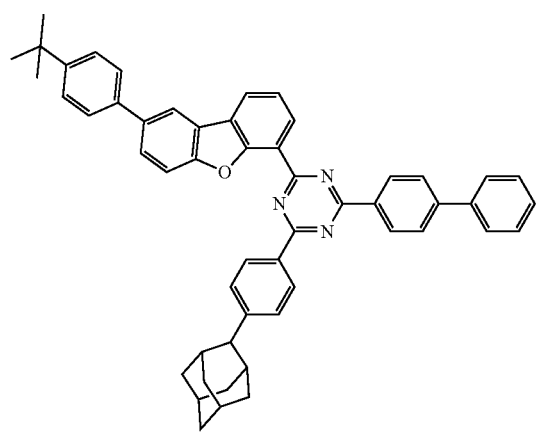
192
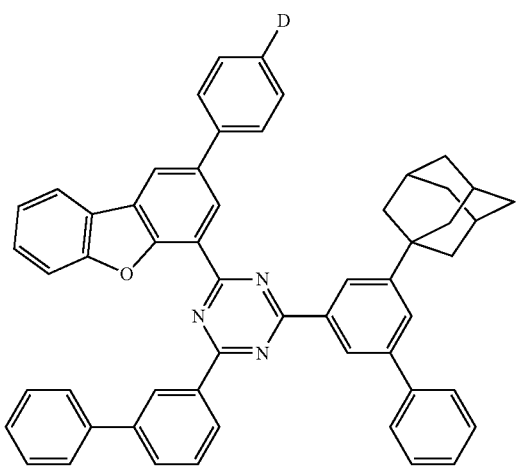
193
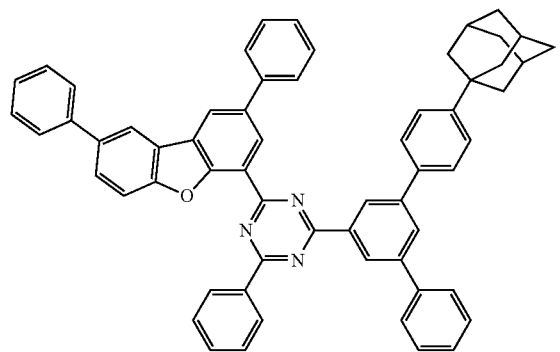
194
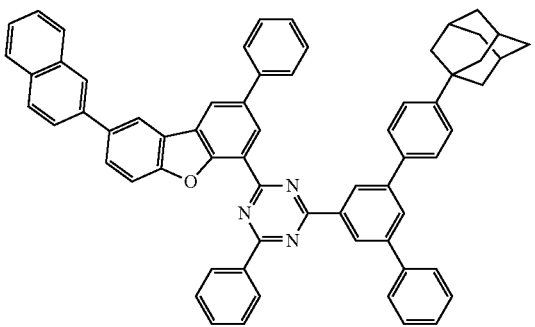

-continued
195
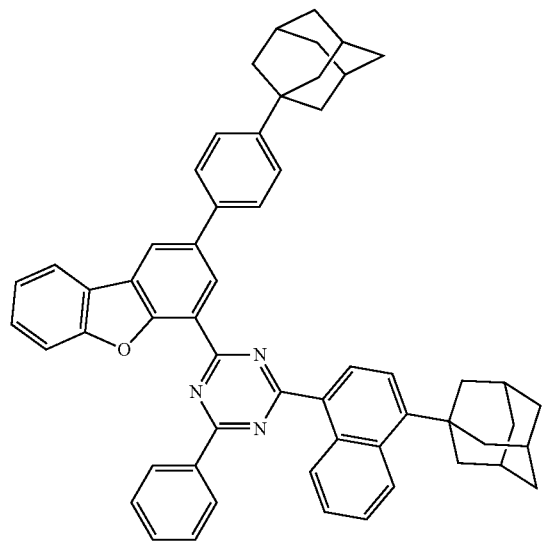
196
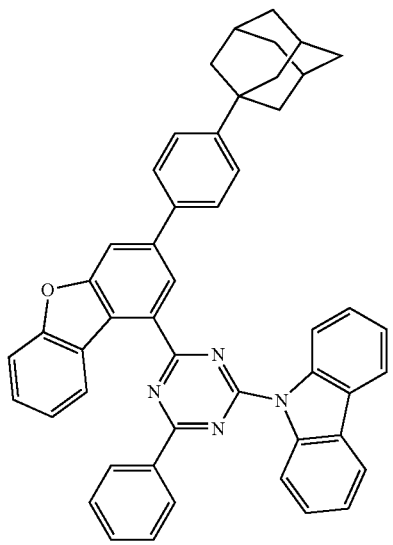
197
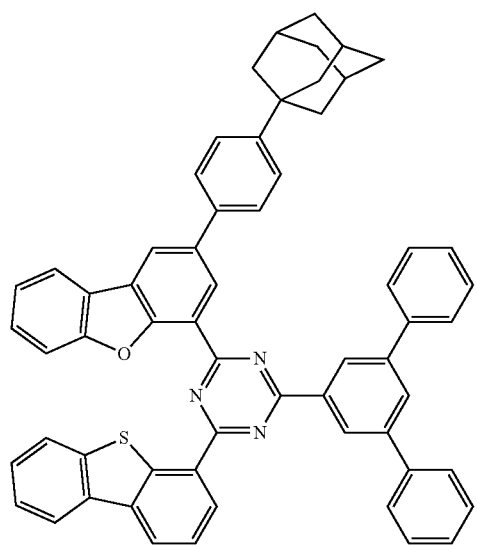
198
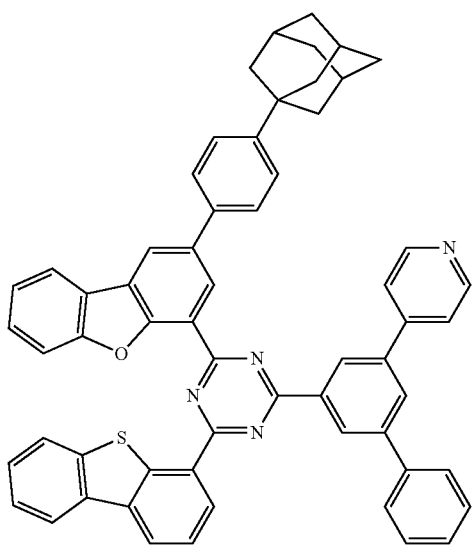
199
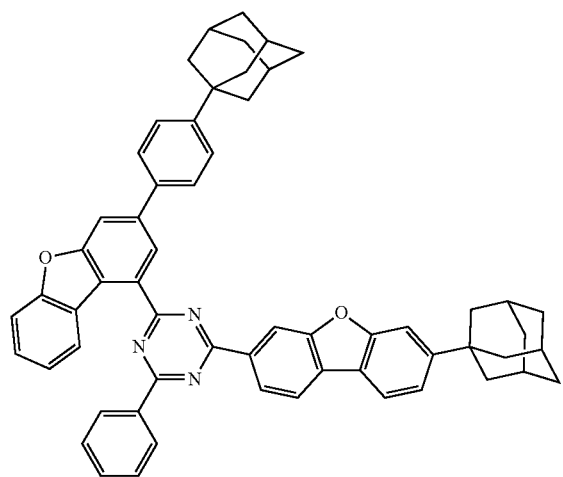
248
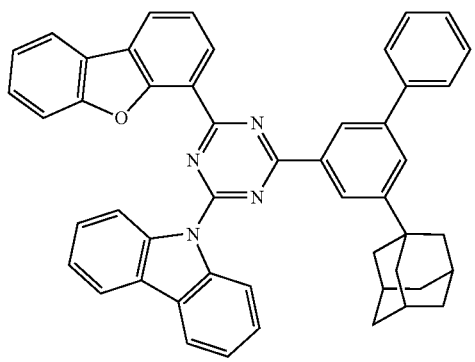

-continued
200
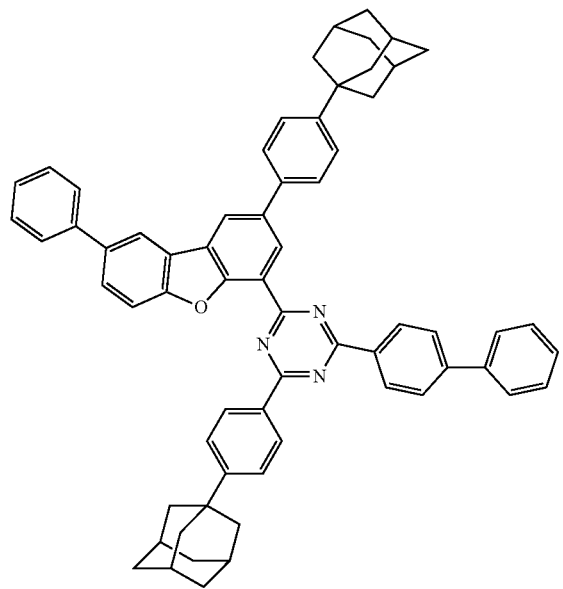
201
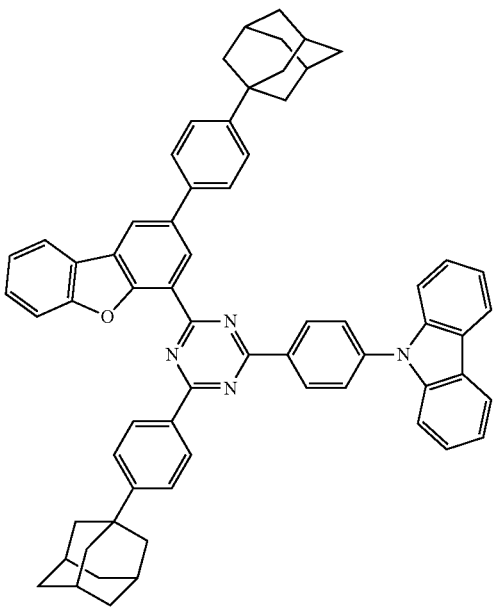
202
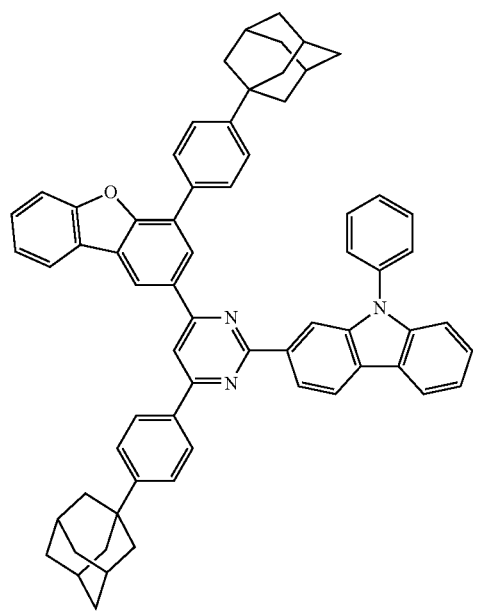
203
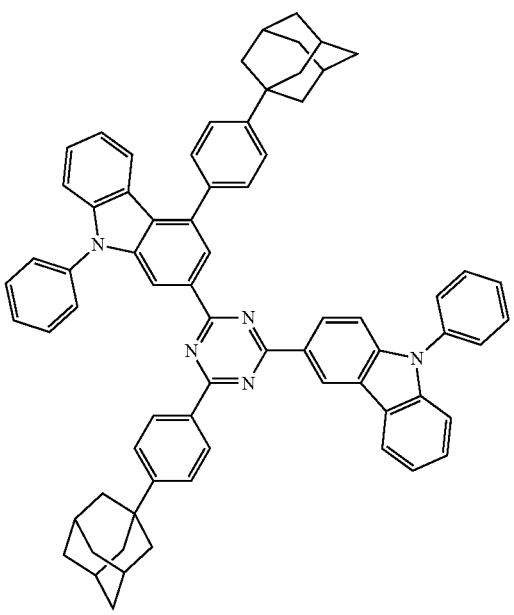

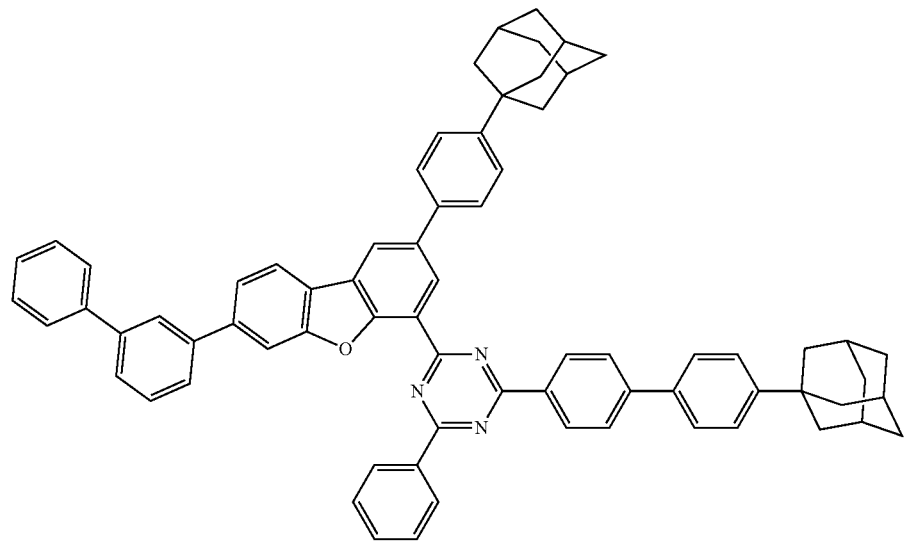
204
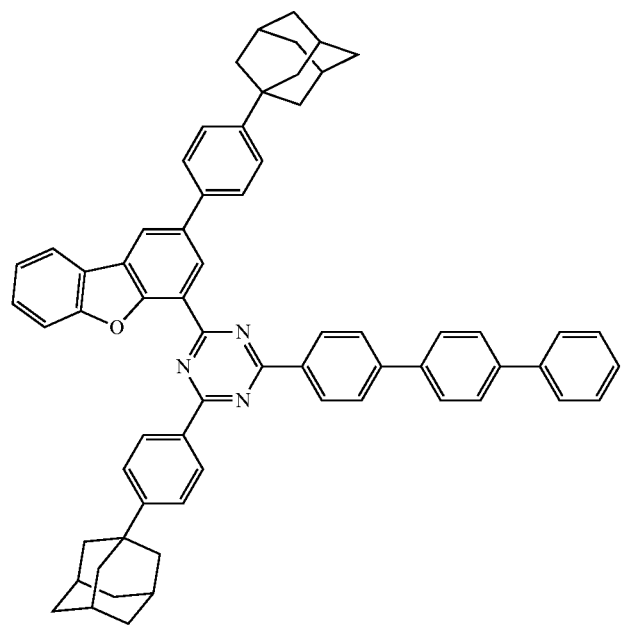
206

-continued
207
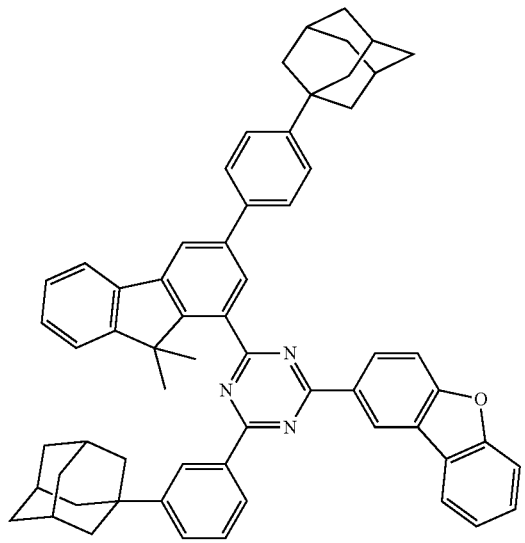
208
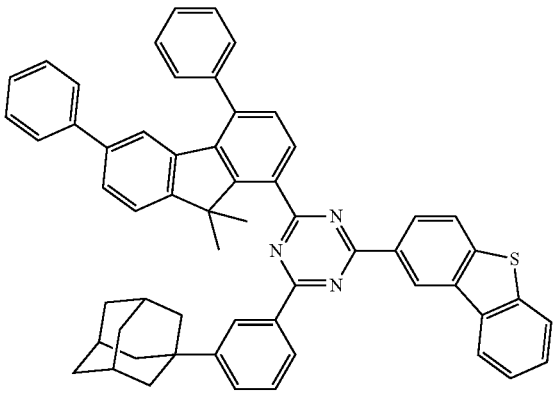
209
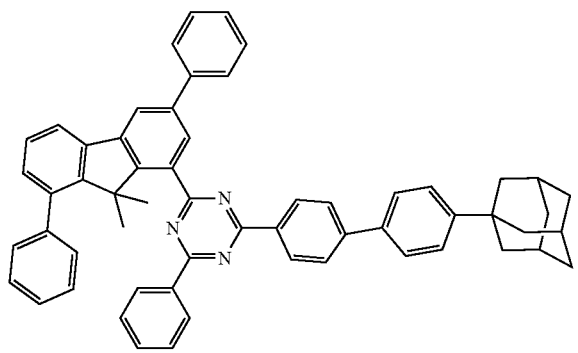
210
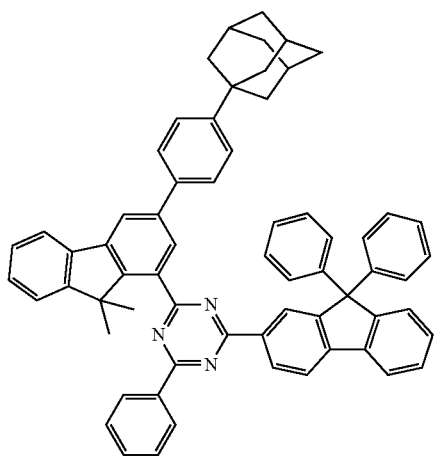
211
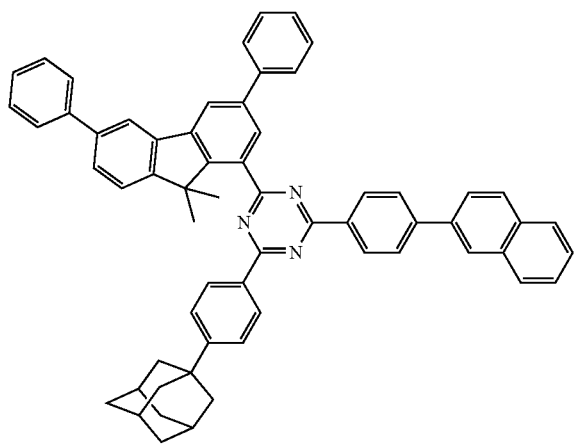
212
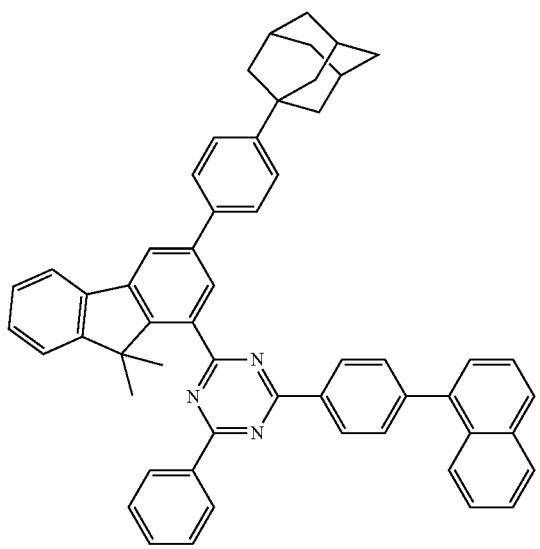

475
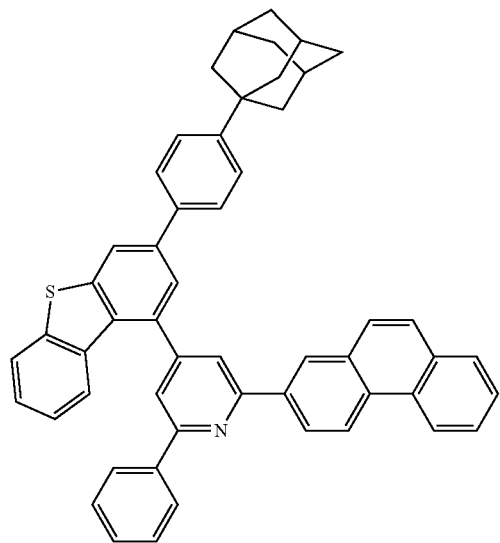
476
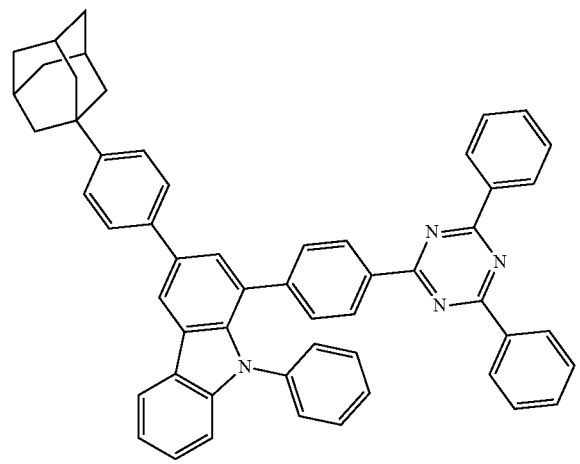
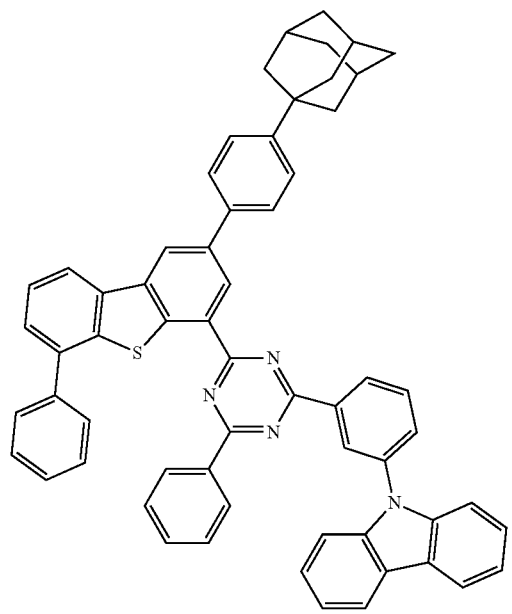
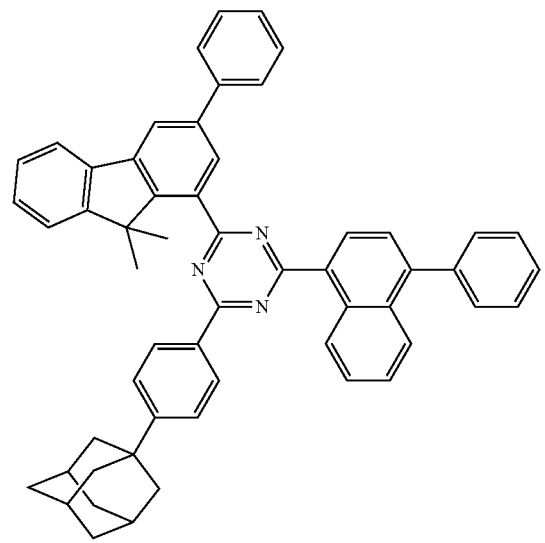

-continued
217
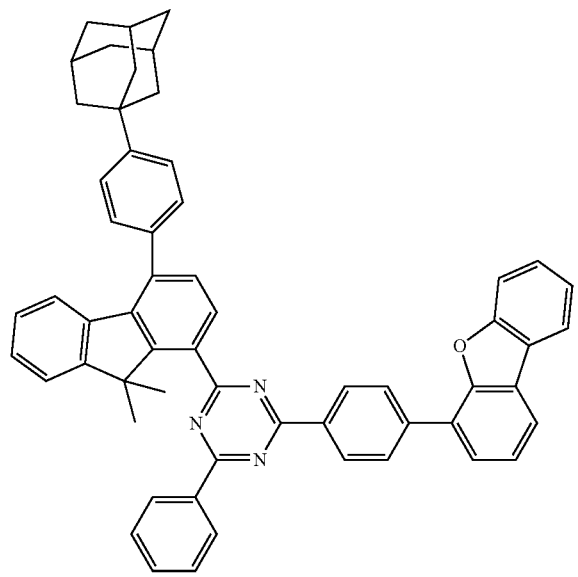
218
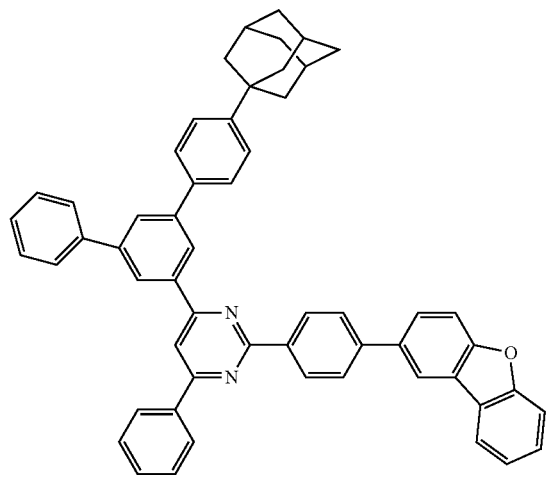
219
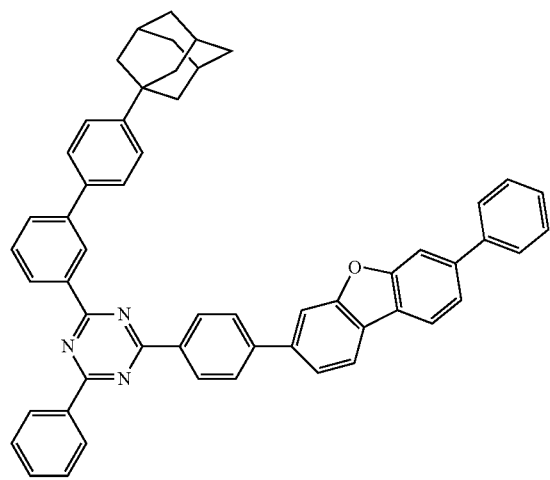
221
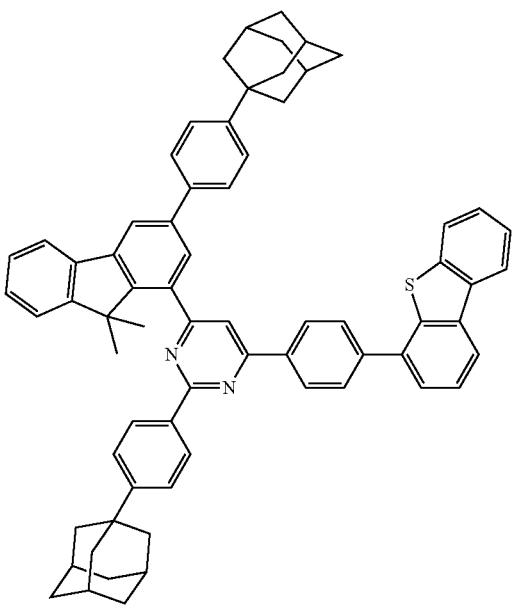

-continued
479
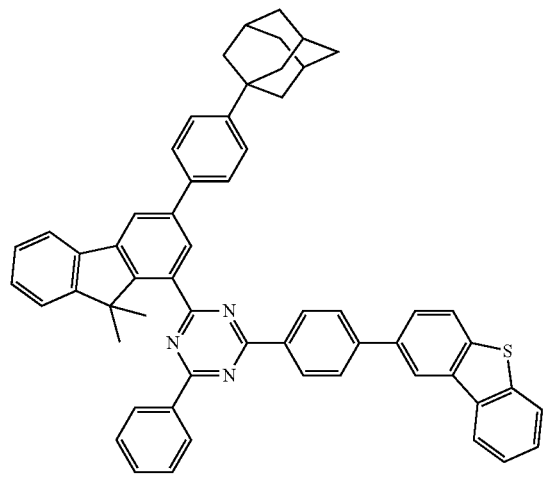
222
480
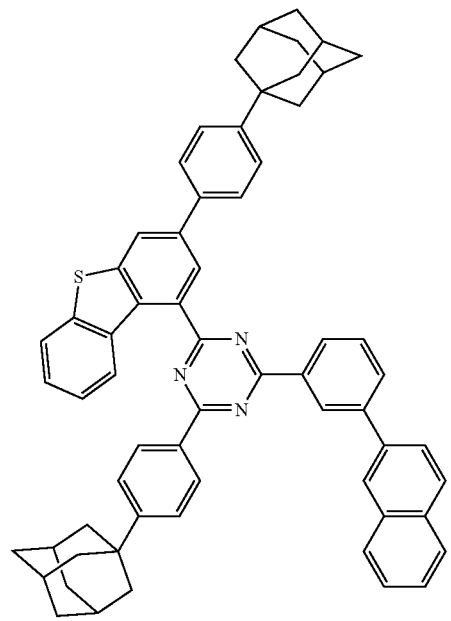
223
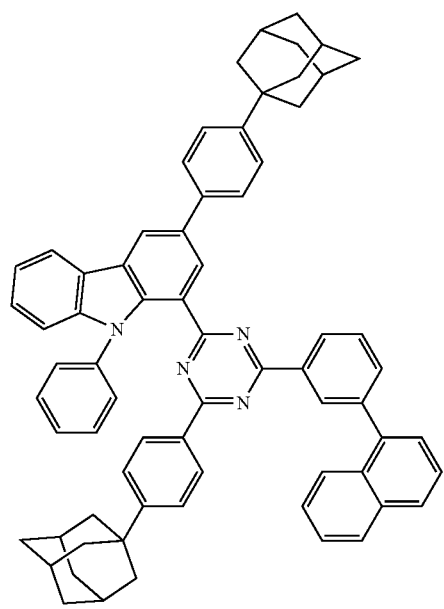
224
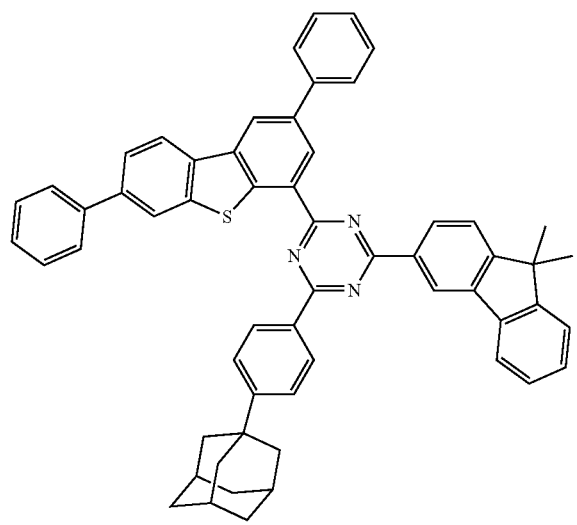
225

481
482
-continued
229
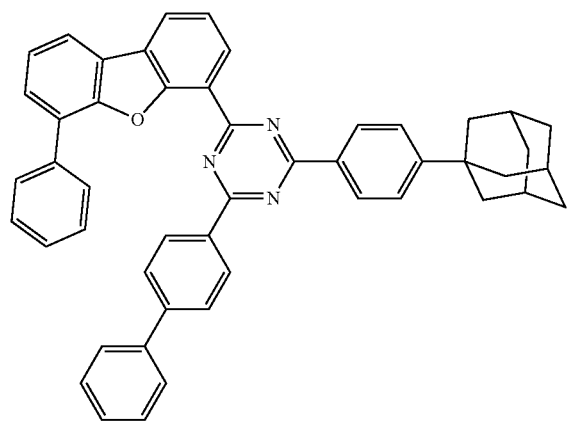
230
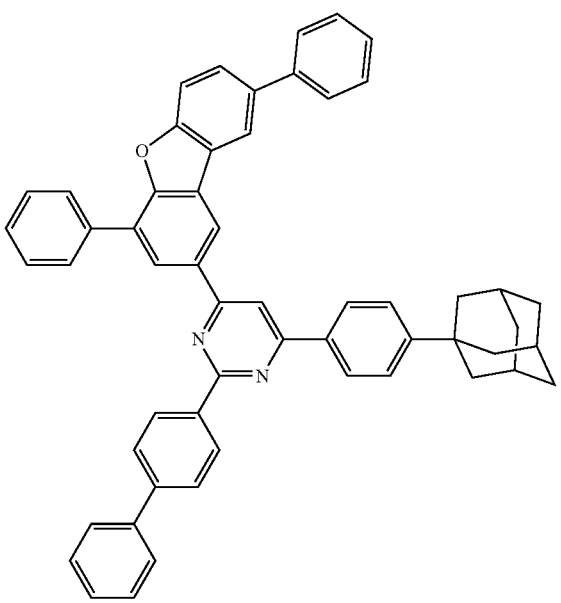
231
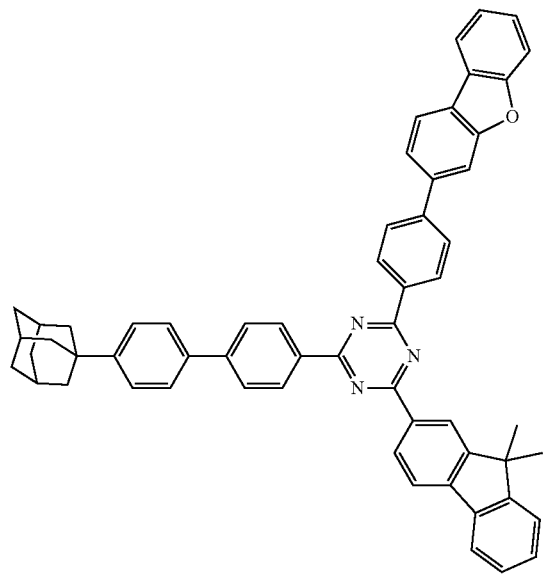
232
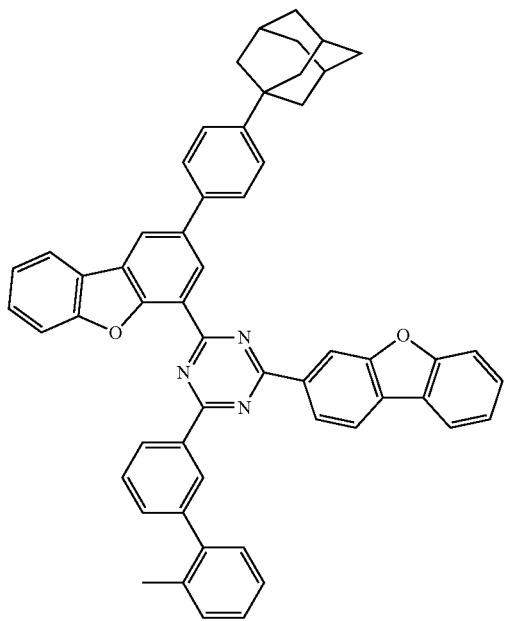

483
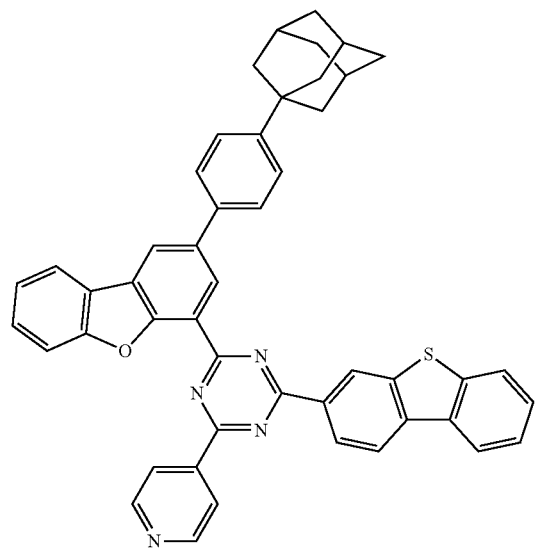
484
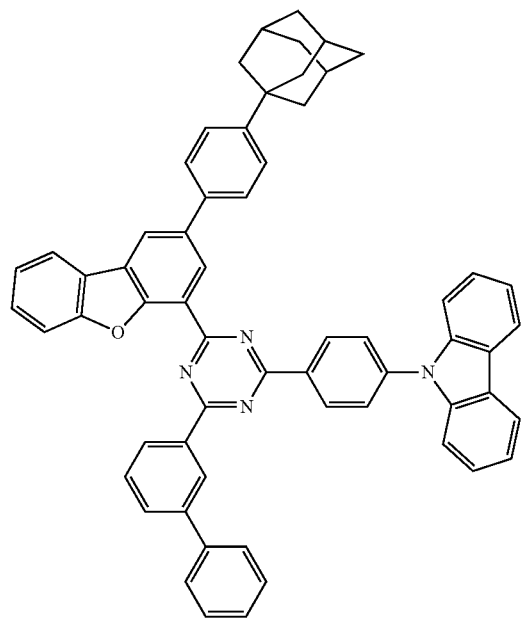
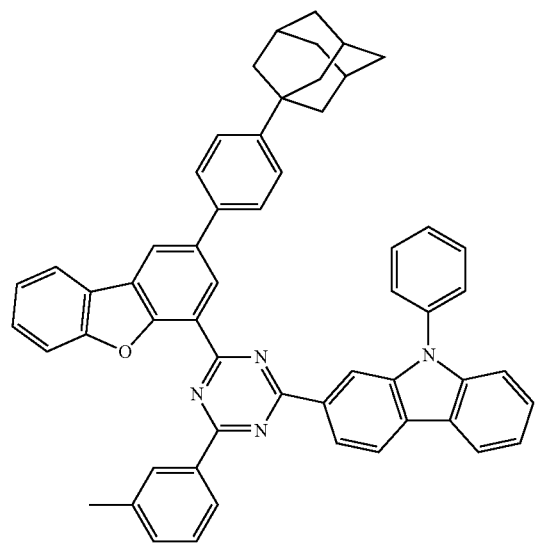
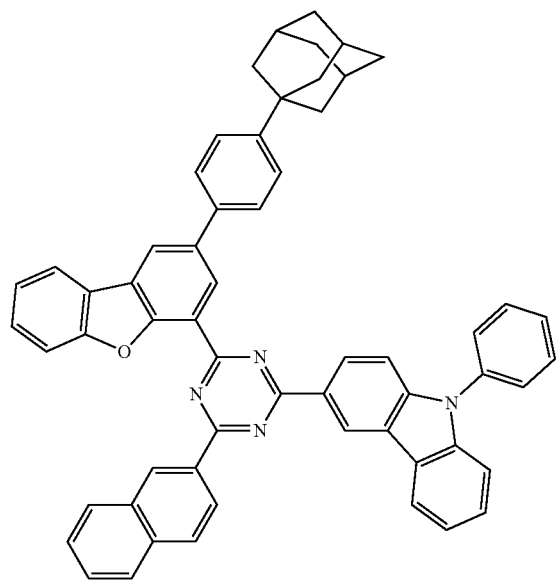

485
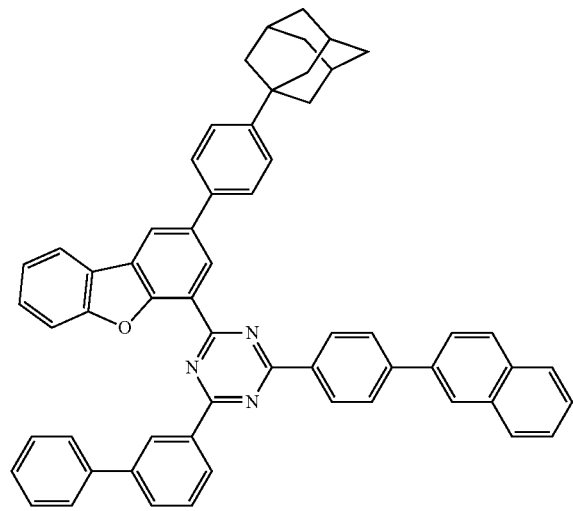
486
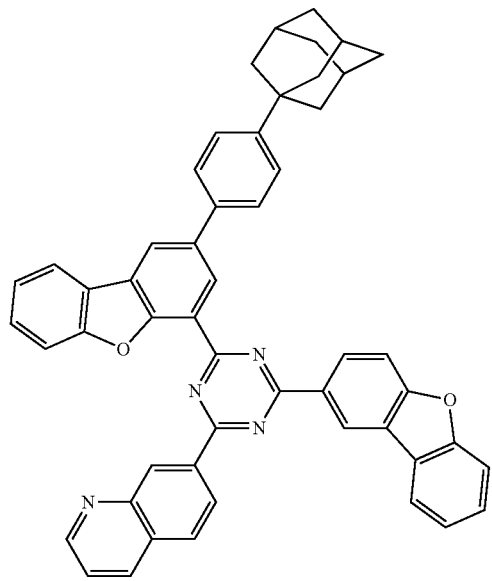
239
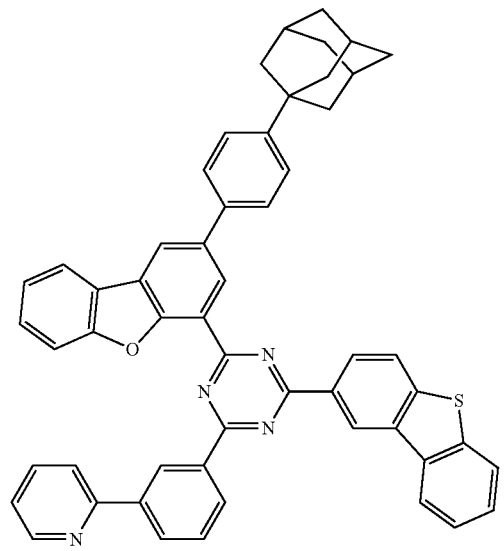
240
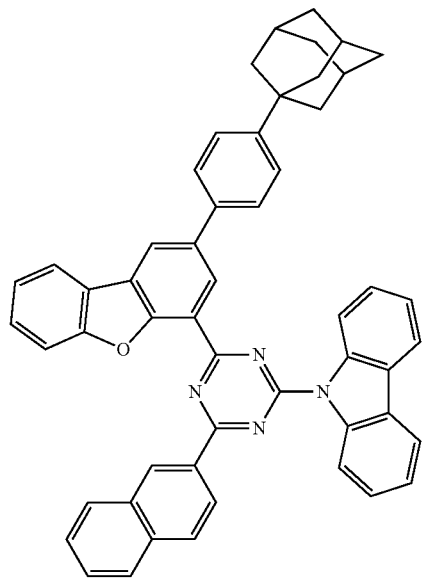

-continued
487
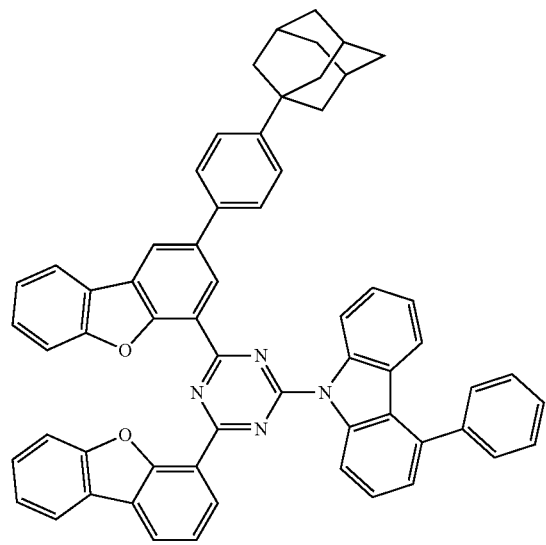
488
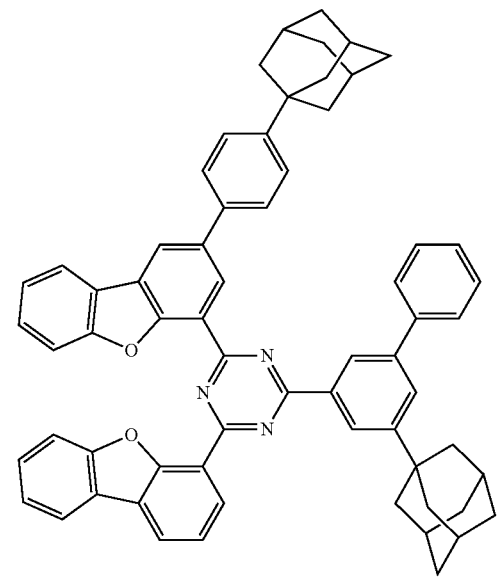
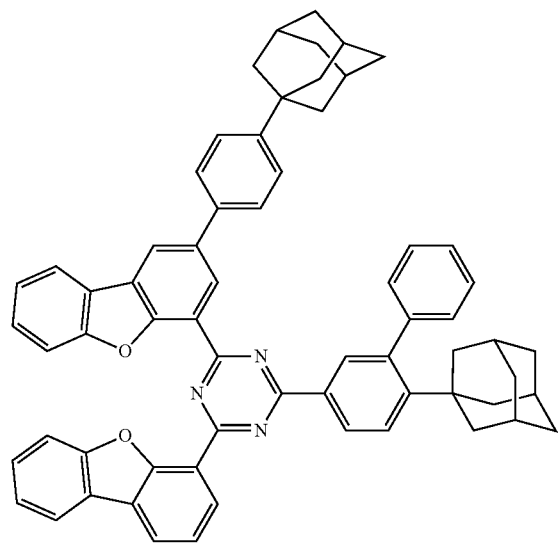
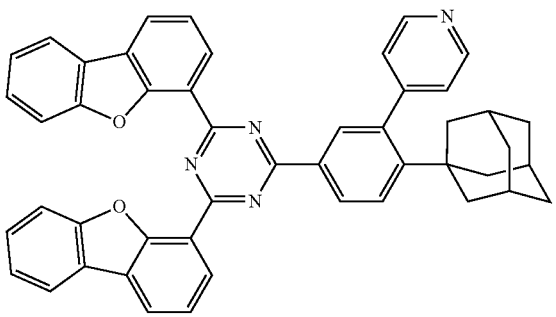

-continued
245
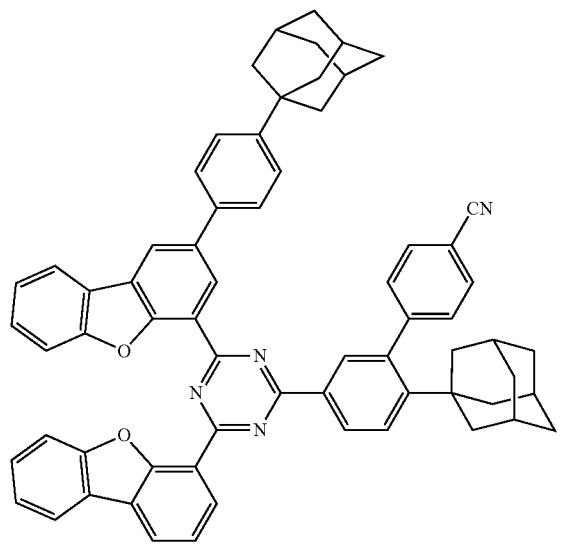
246
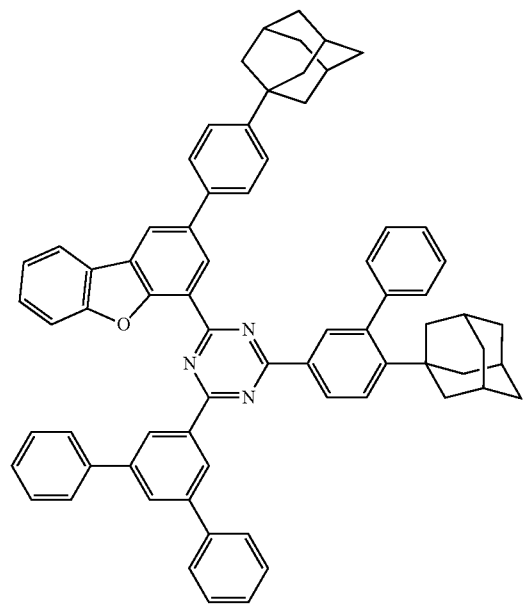
247
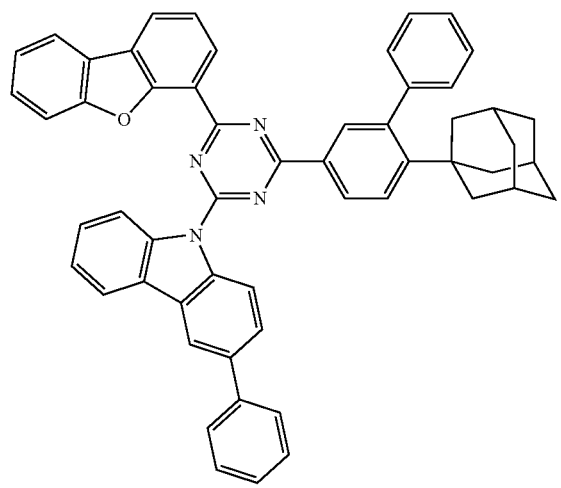
249
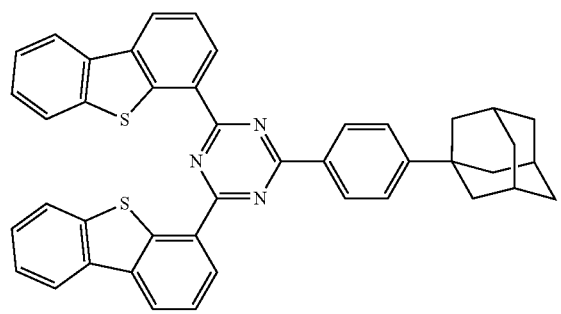
250
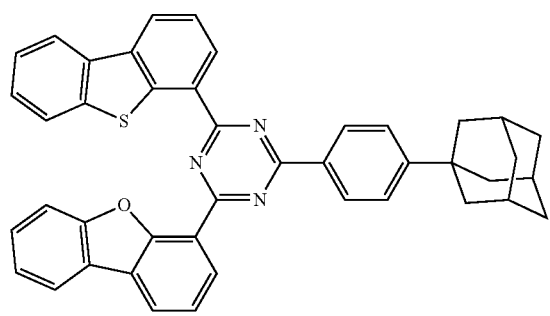
251
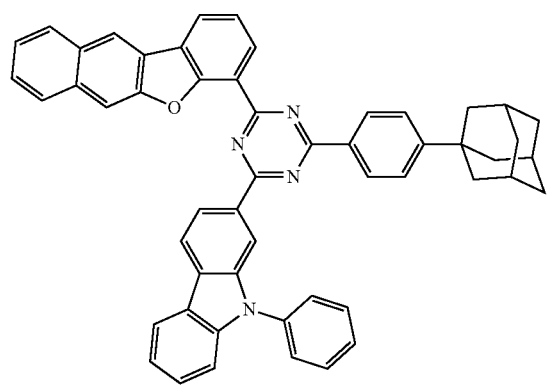

491
252
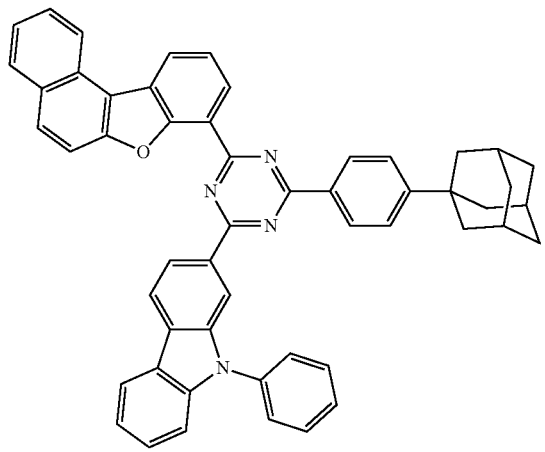
253
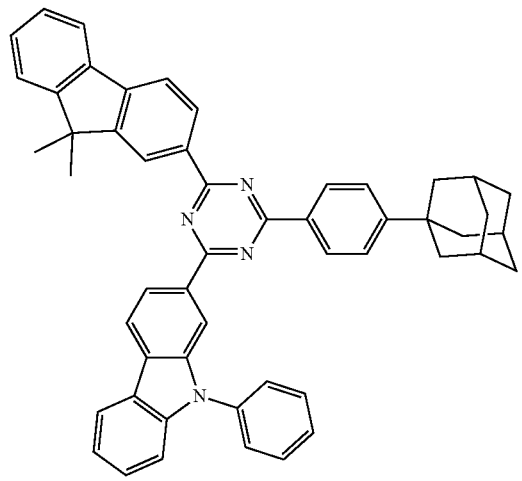
254
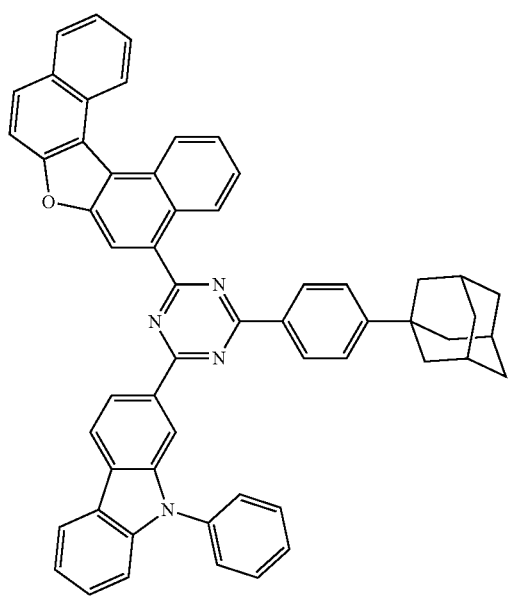
255
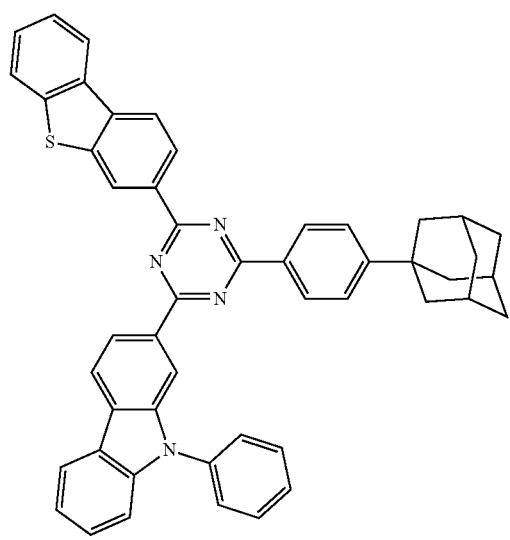
256
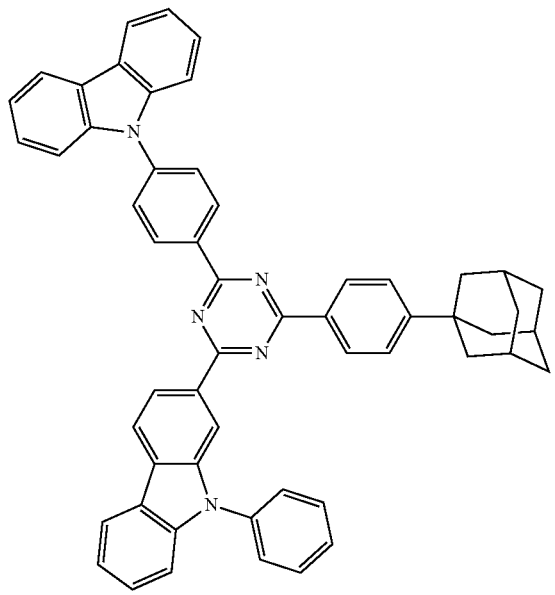
257
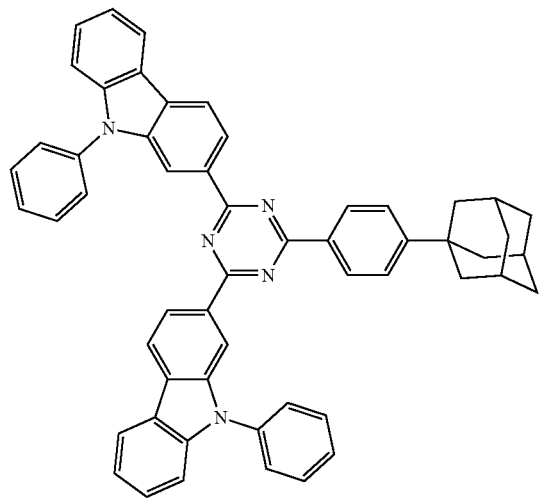

-continued
258
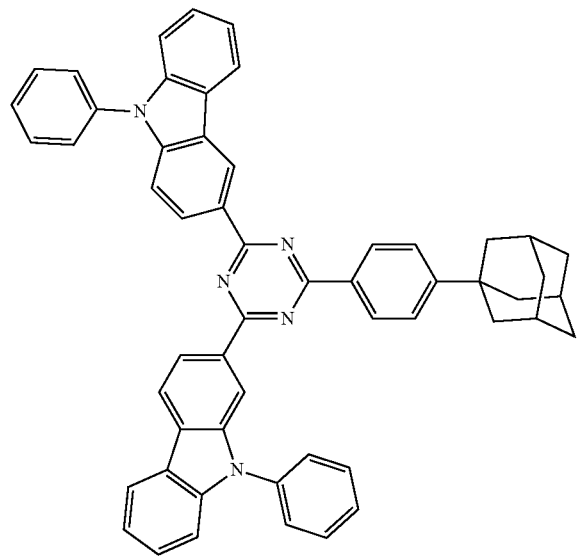
259
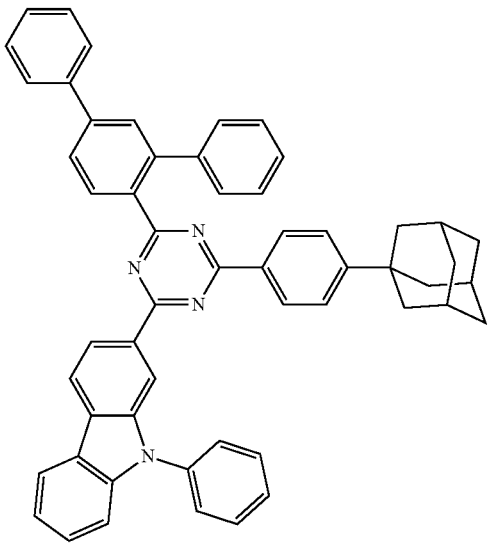
260
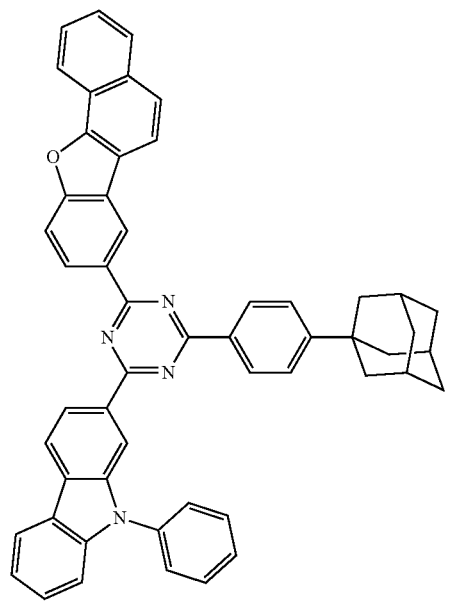
261
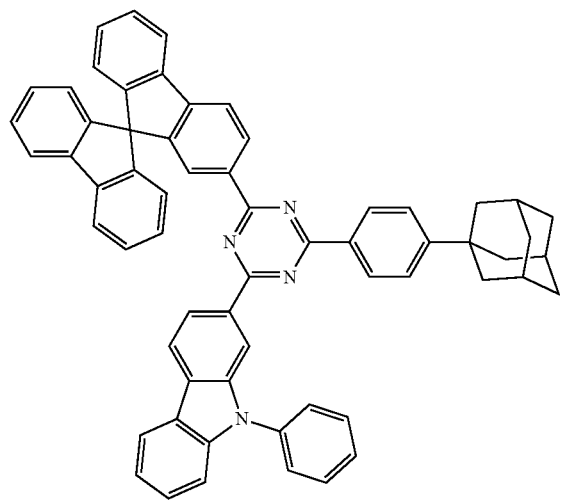
262
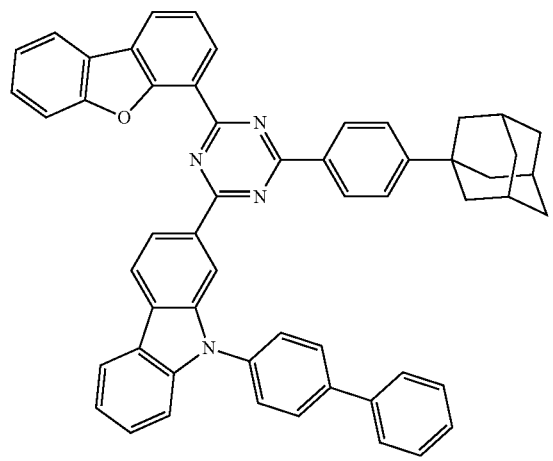
263
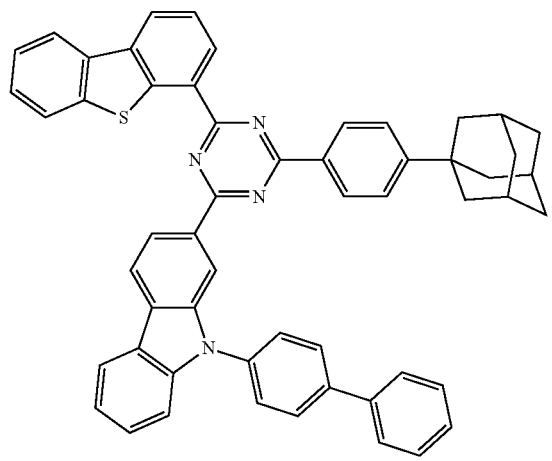

-continued
264
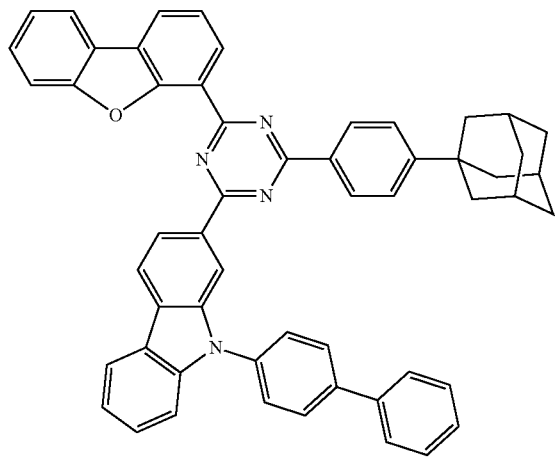
265
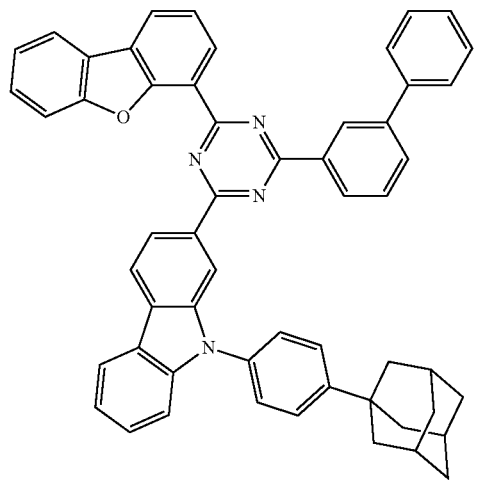
266
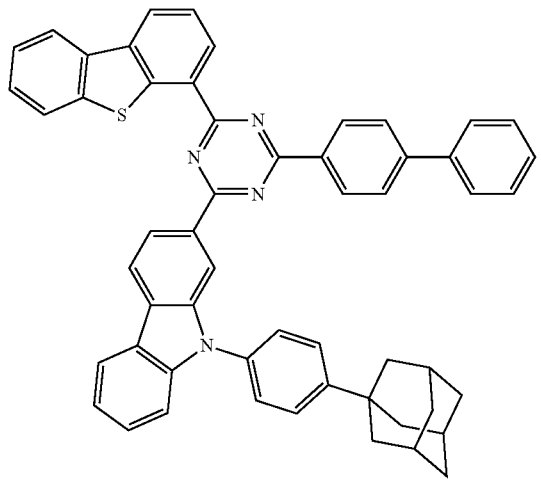
267
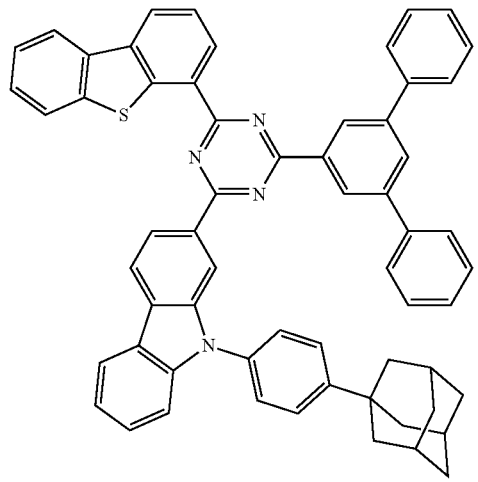
268
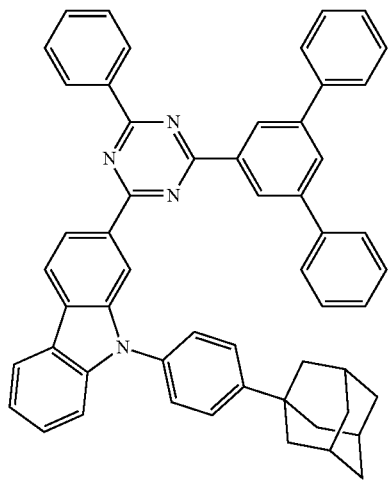
269
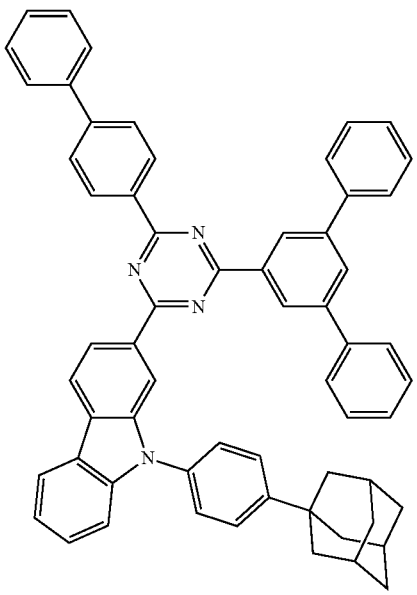

-continued
497
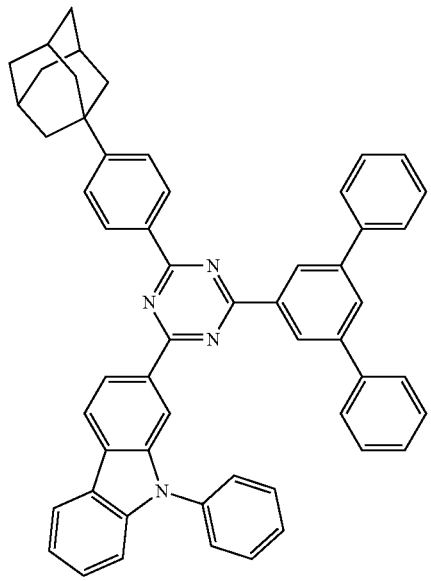
270
498
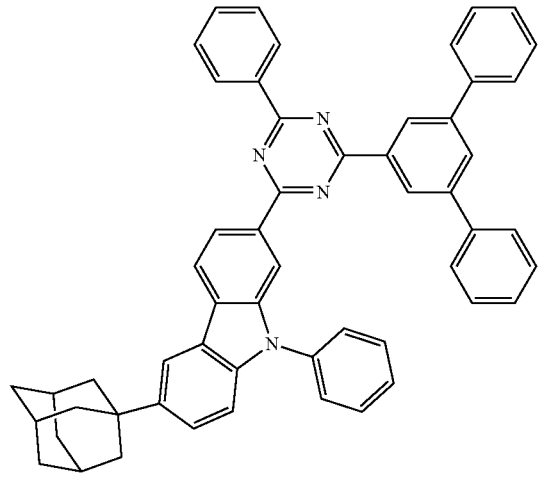
271
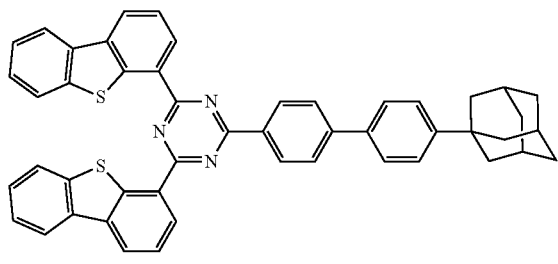
272
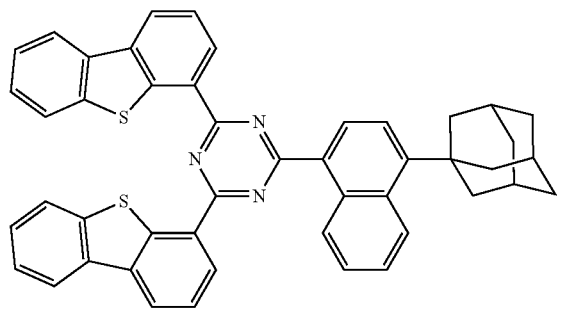
273
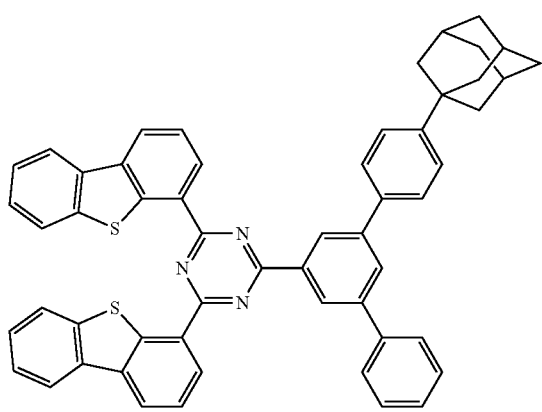
274
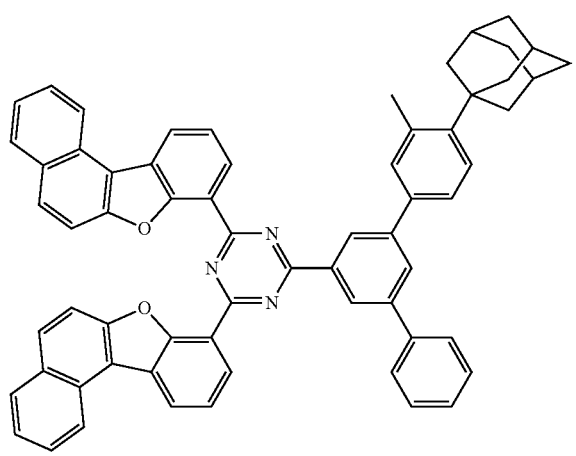
275

-continued
276
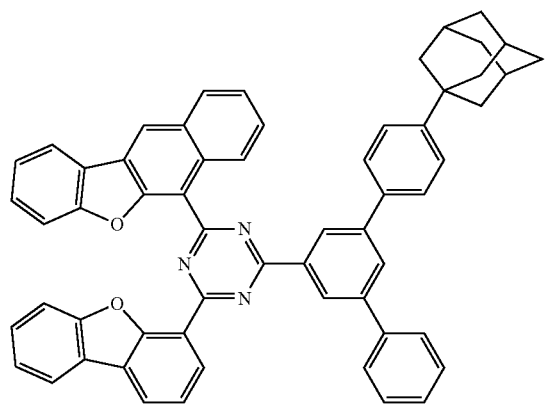
277
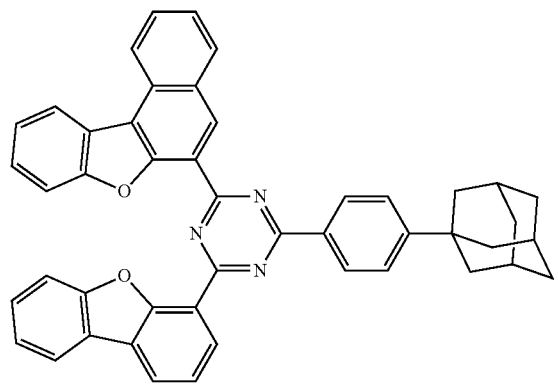
278
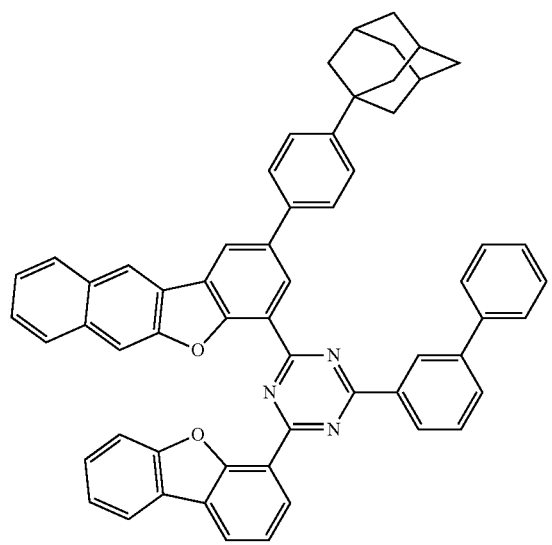
279
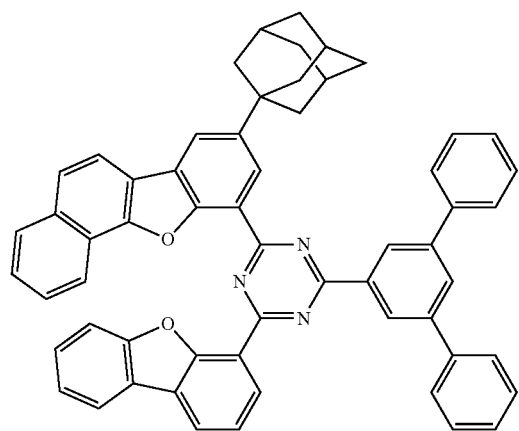
280
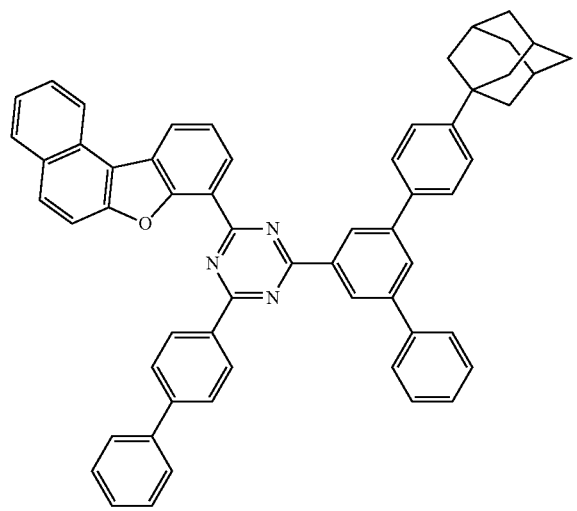

-continued
285
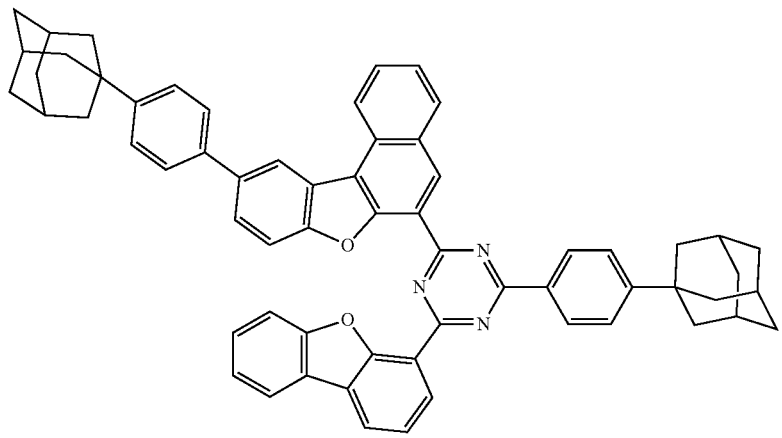
286
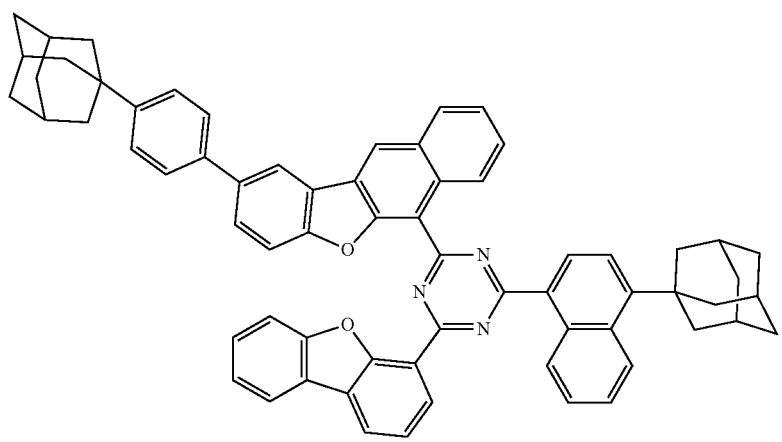
287
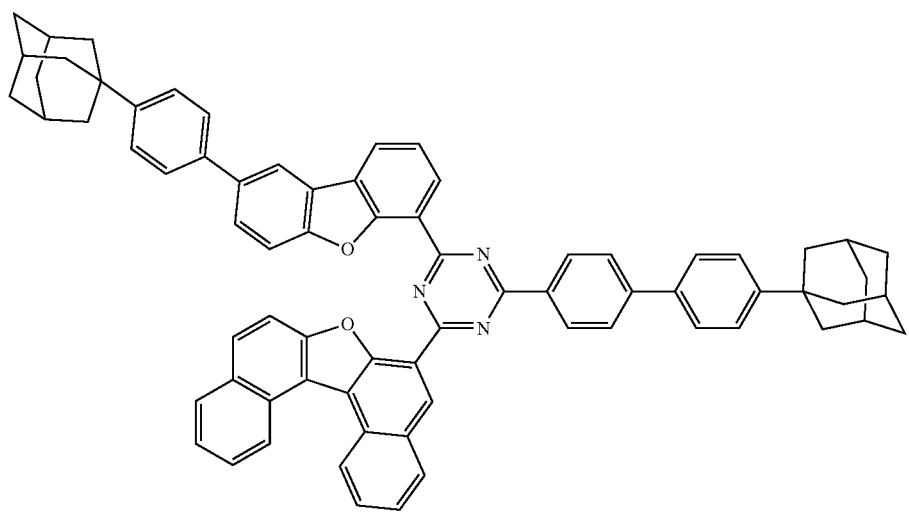

288
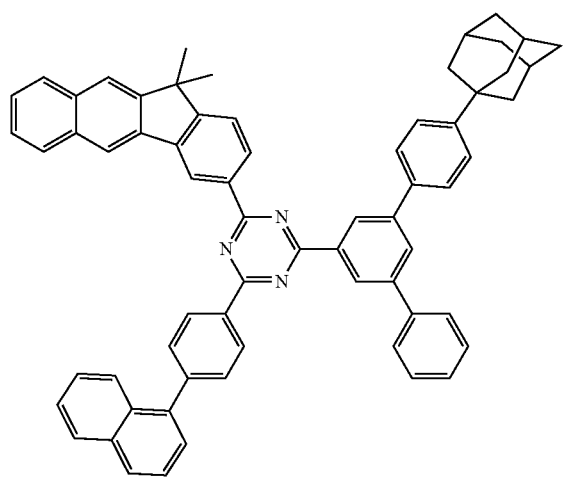
290
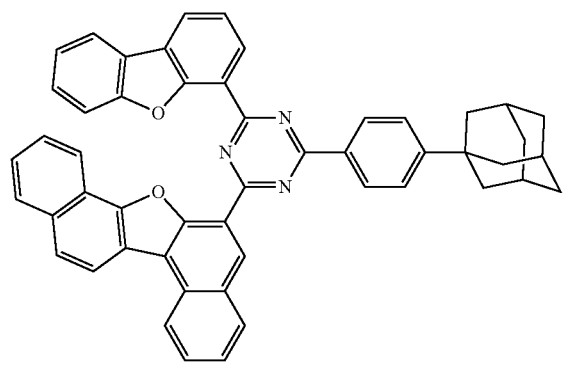
291
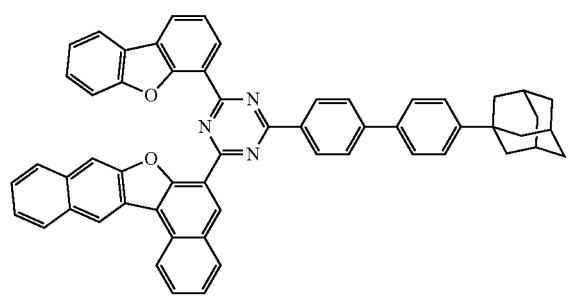
292
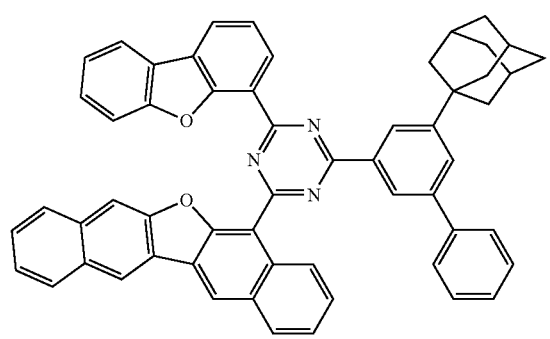
293
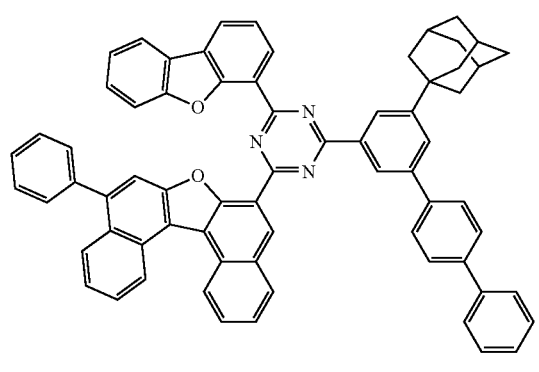
294
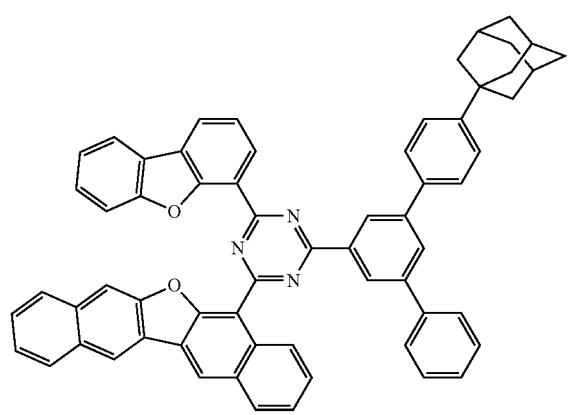

-continued
295
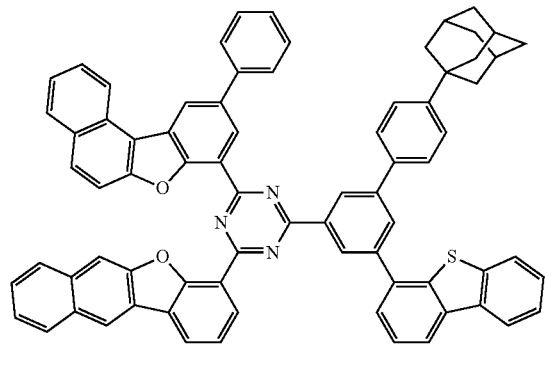
296
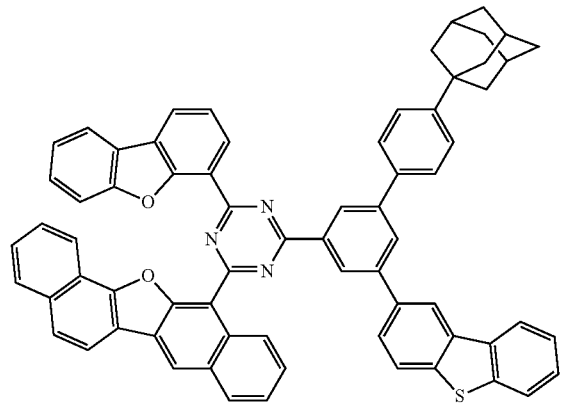
297
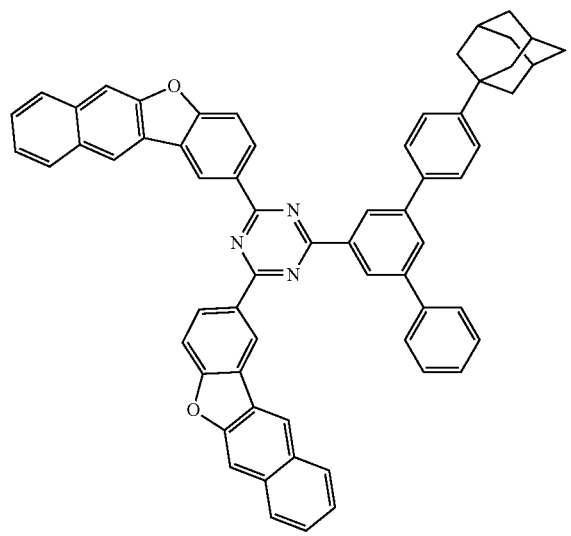
298
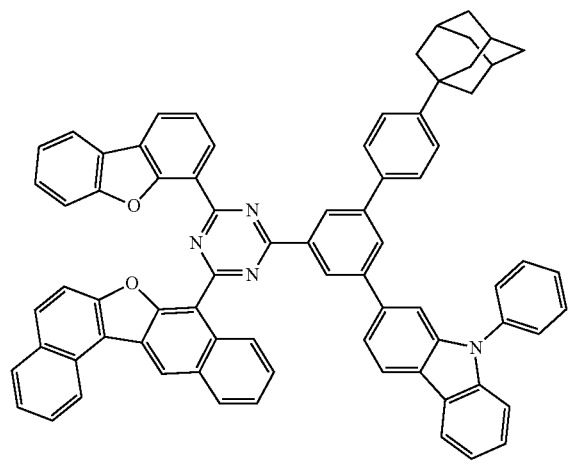
299
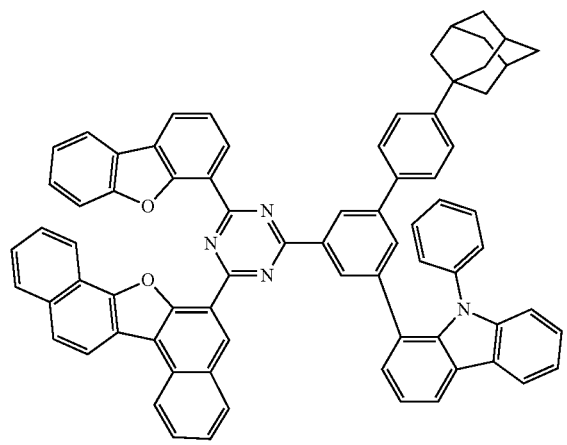
300
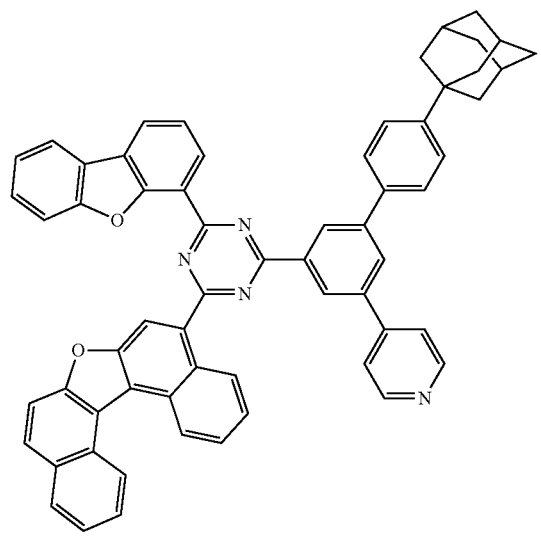

507 508
-continued
301 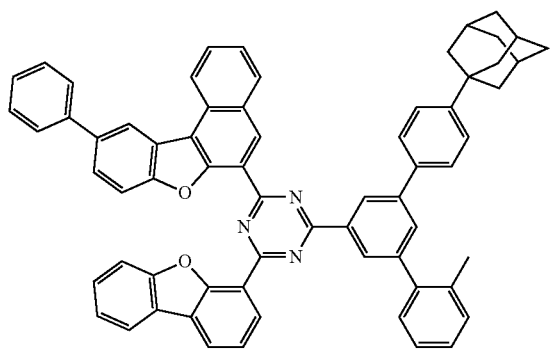 302 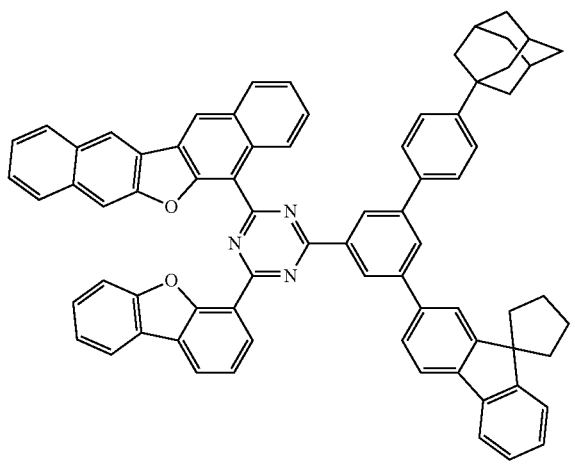
304 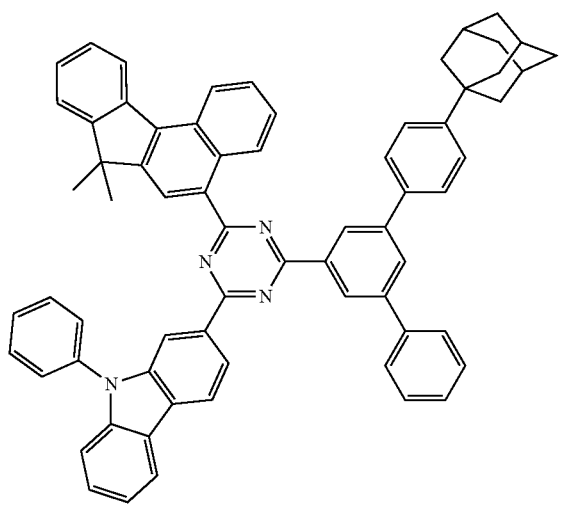 305 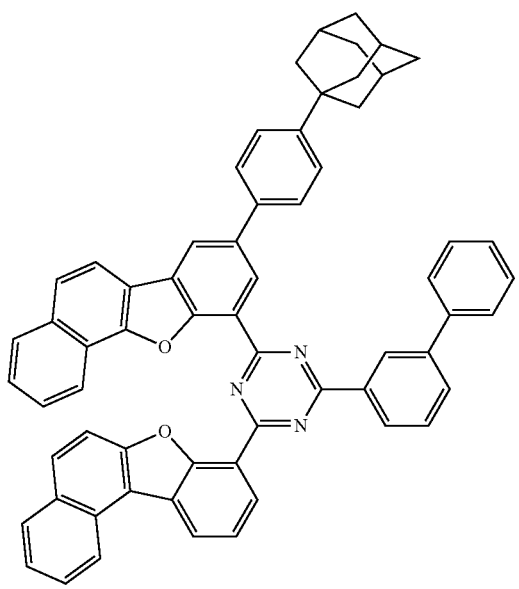

-continued
306 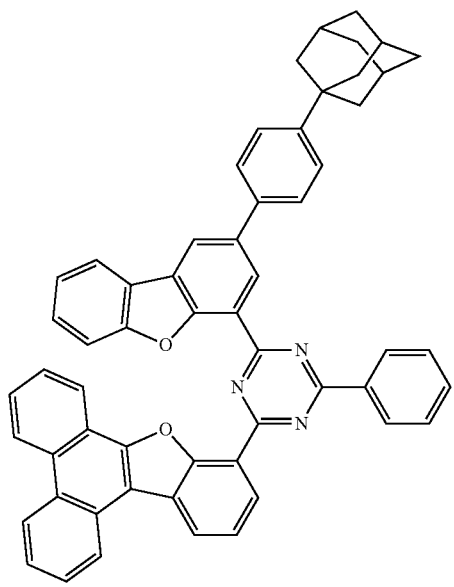
307 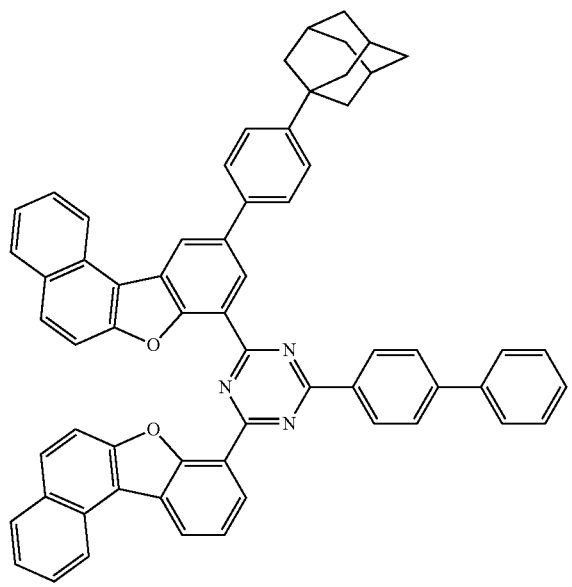
308 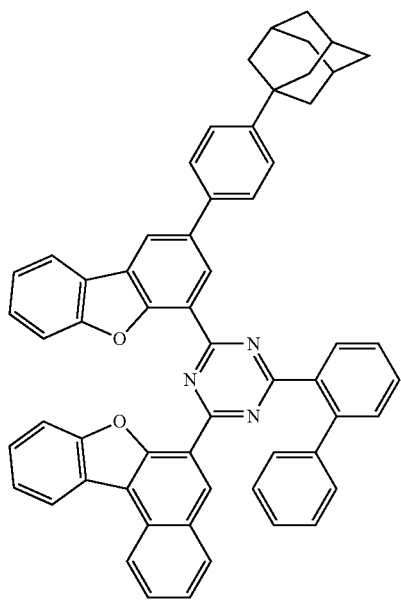
309 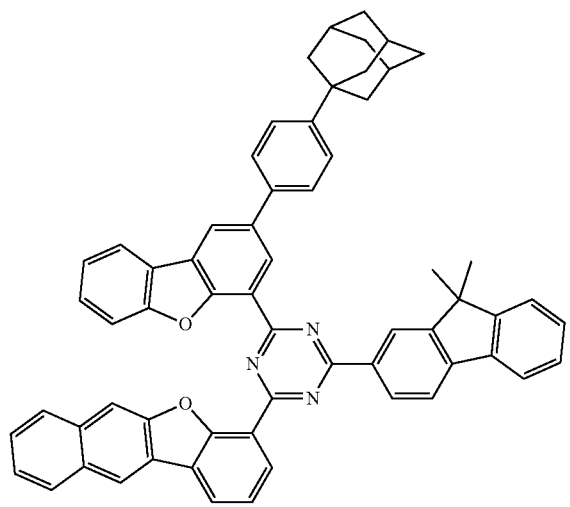

-continued
511
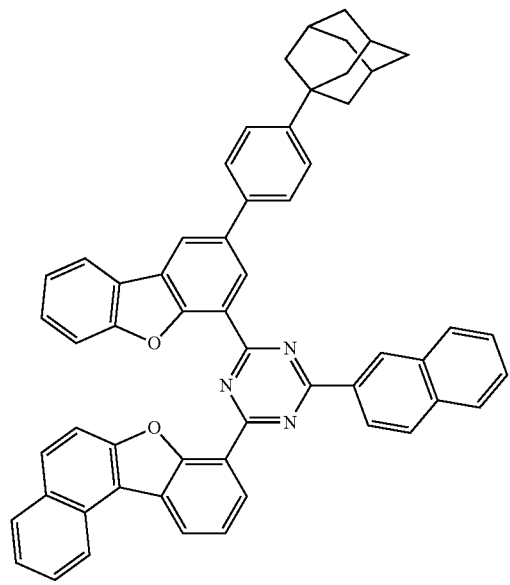
310
512
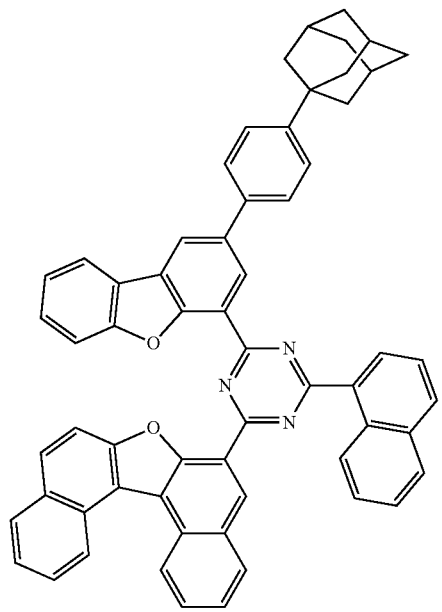
311
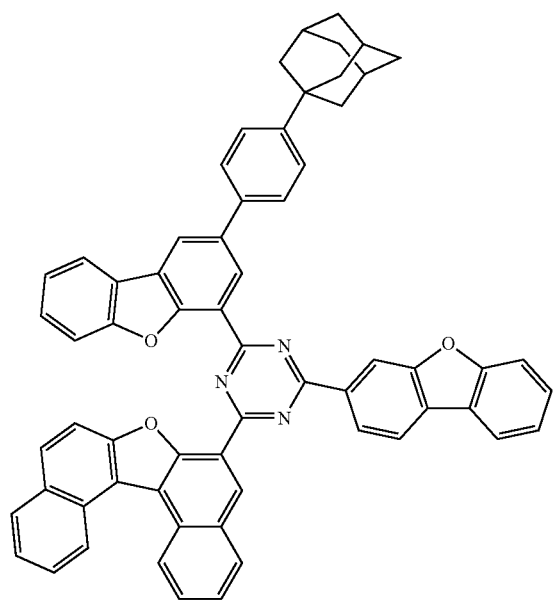
312
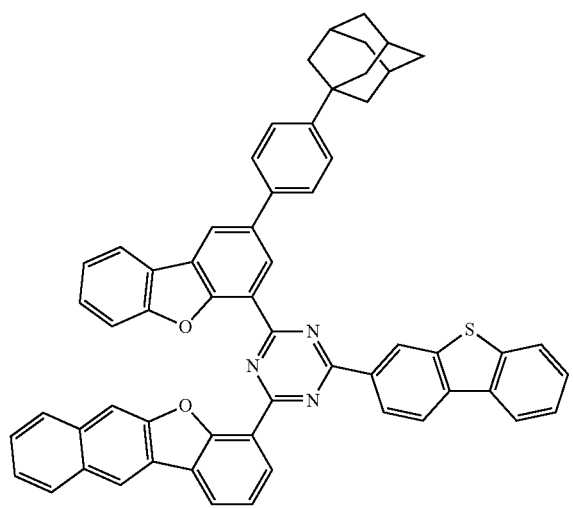
313

313
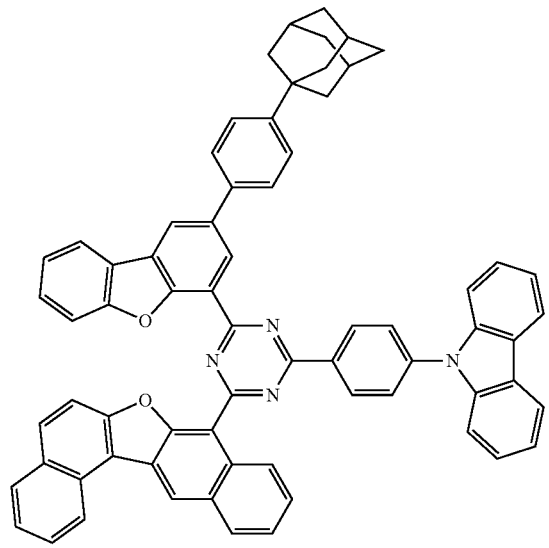
514
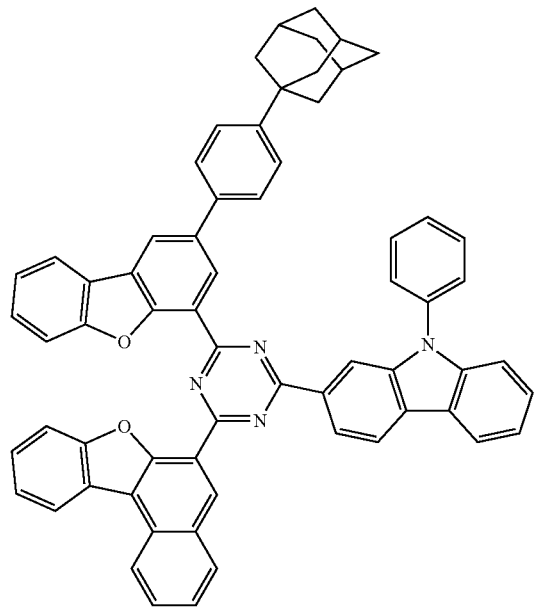
316
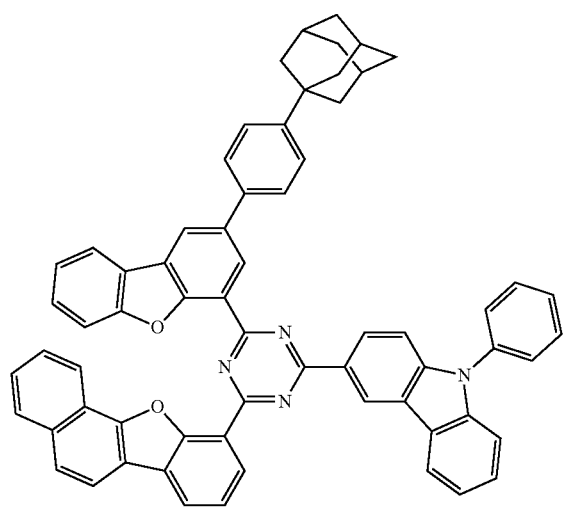
317
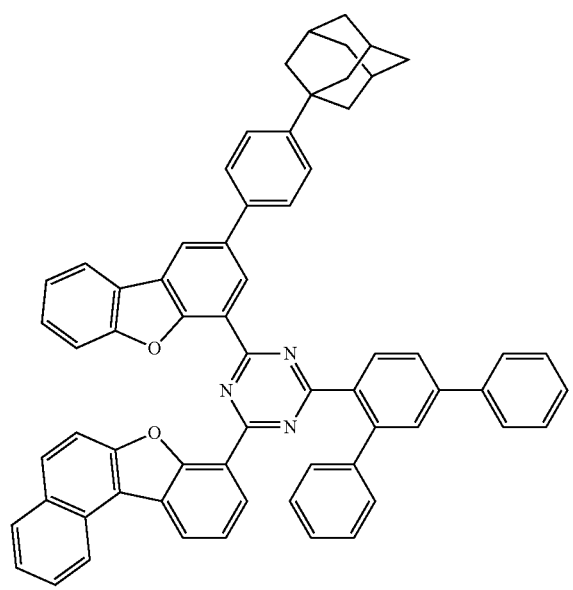

-continued
318
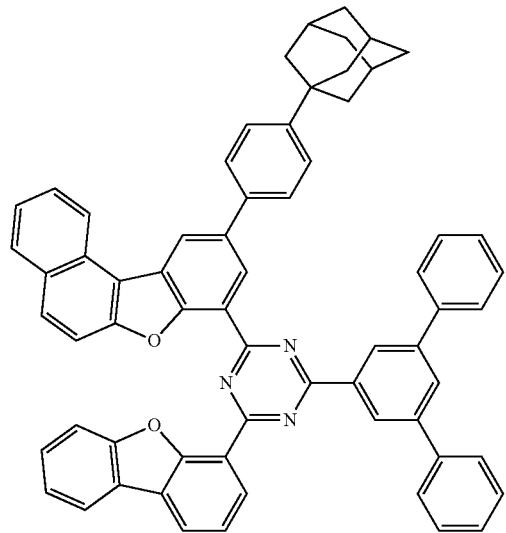
319
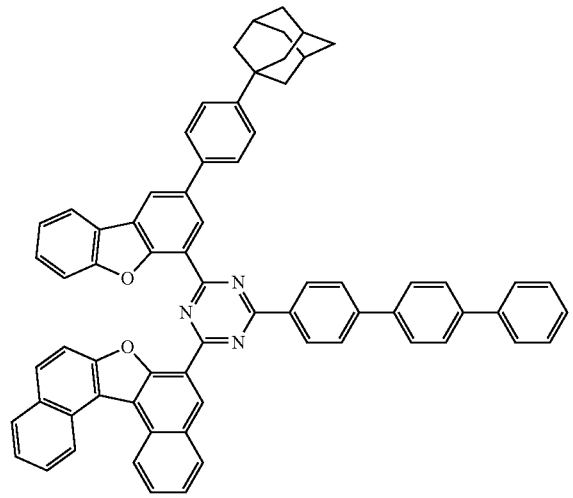
320
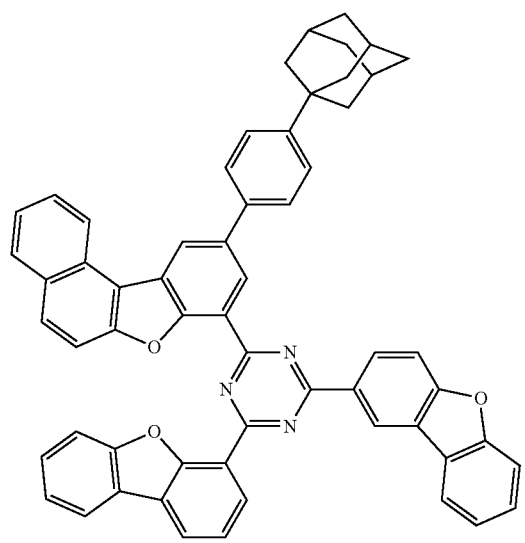
321
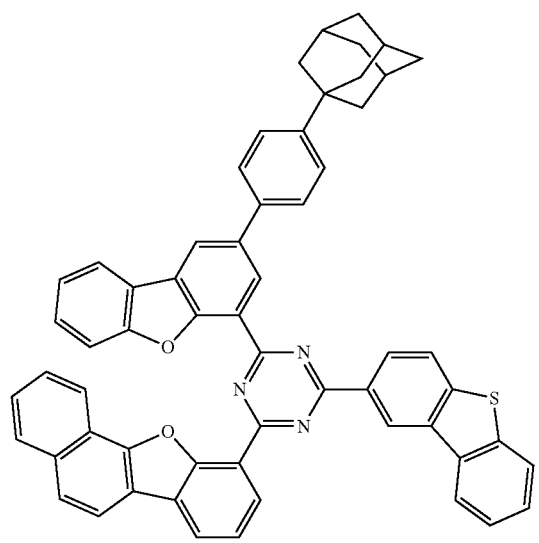

-continued
322
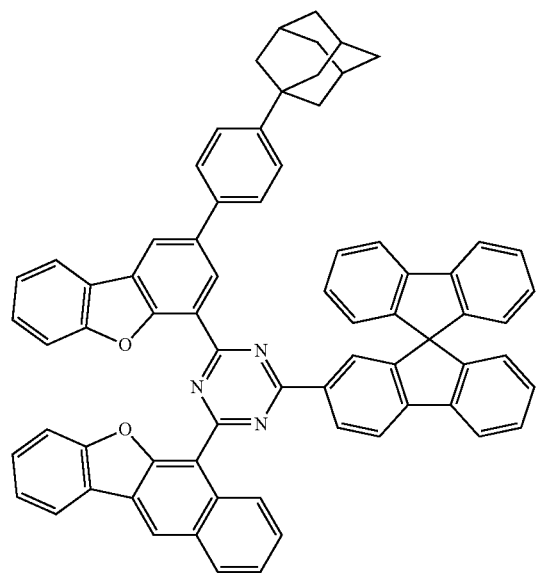
323
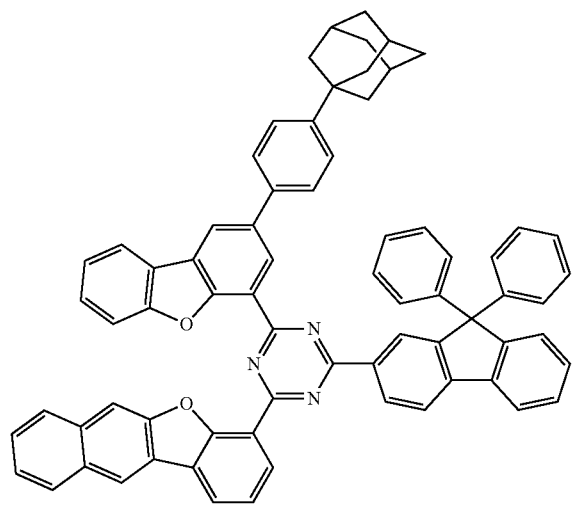
324
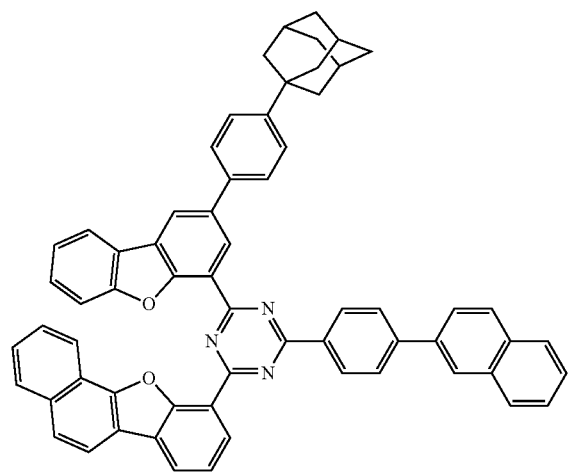
325
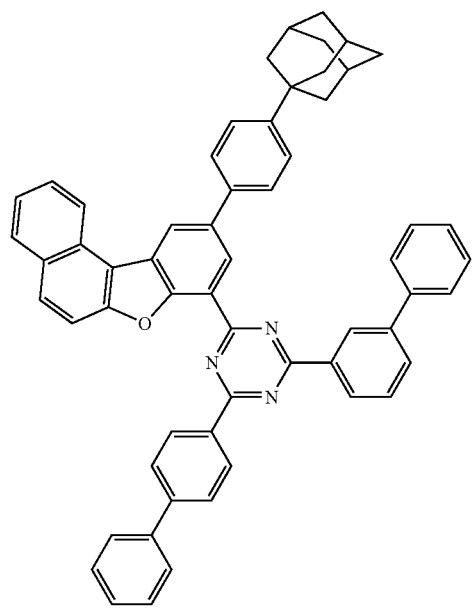

-continued
326
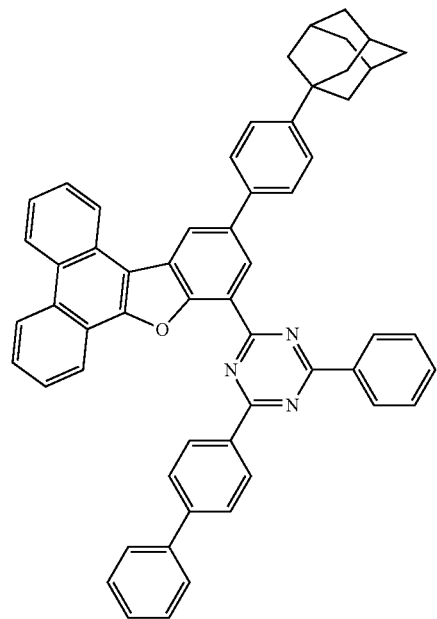
327
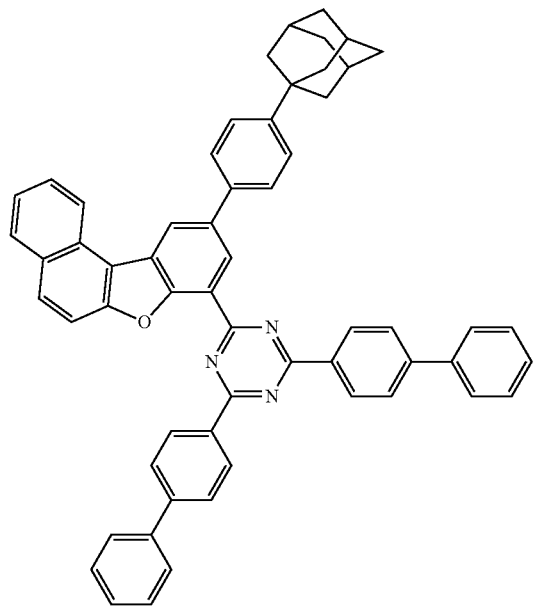
328
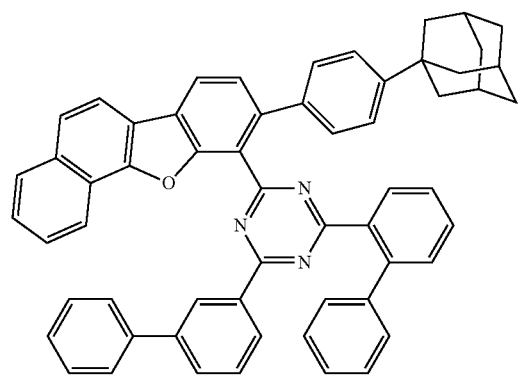
329
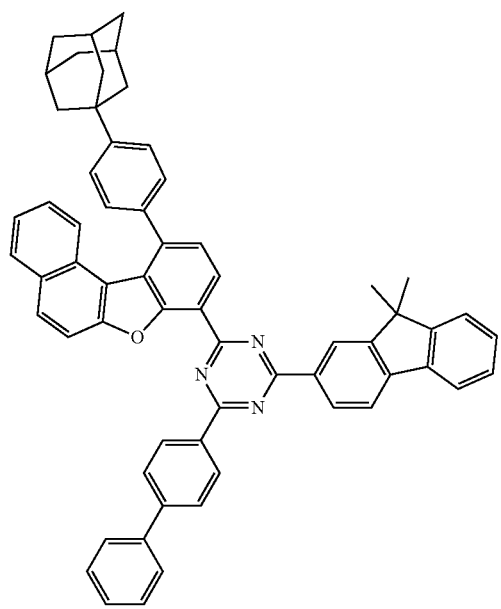

-continued
521
330
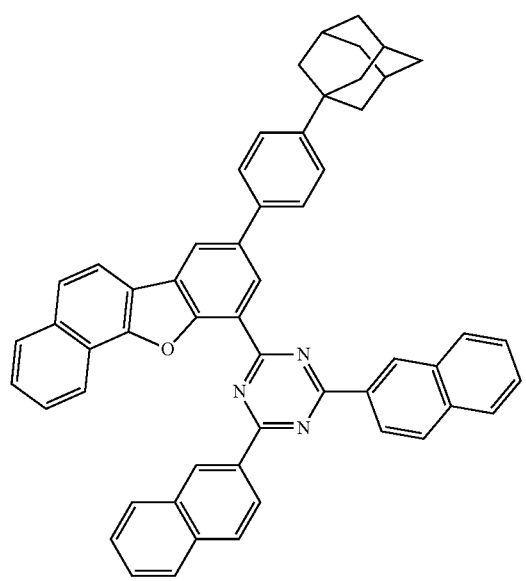
522
331
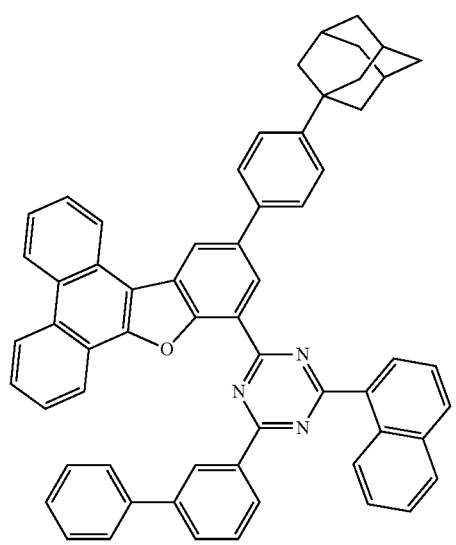
332
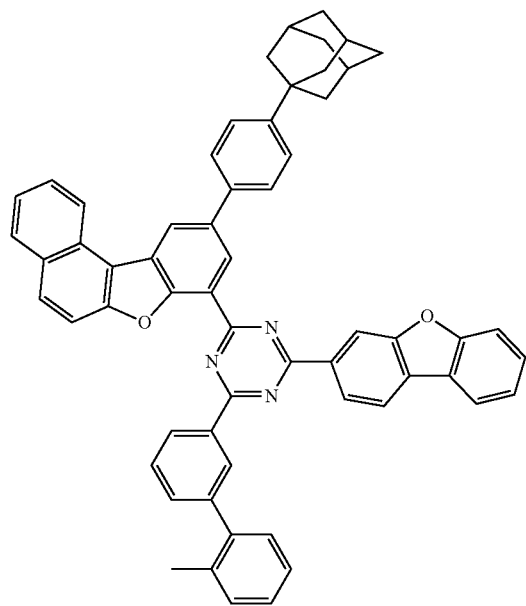
333
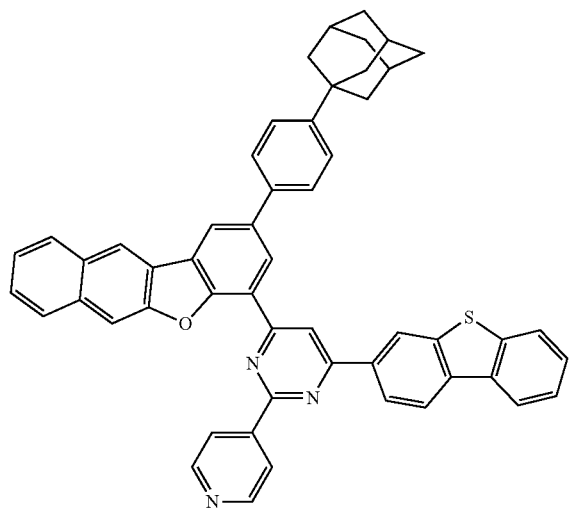

334
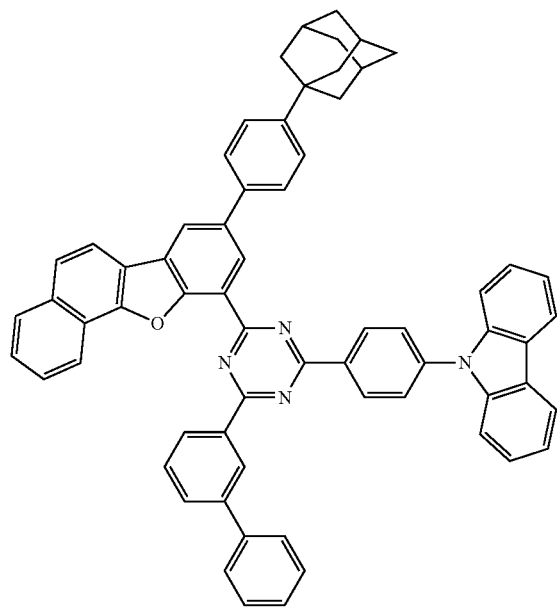
335
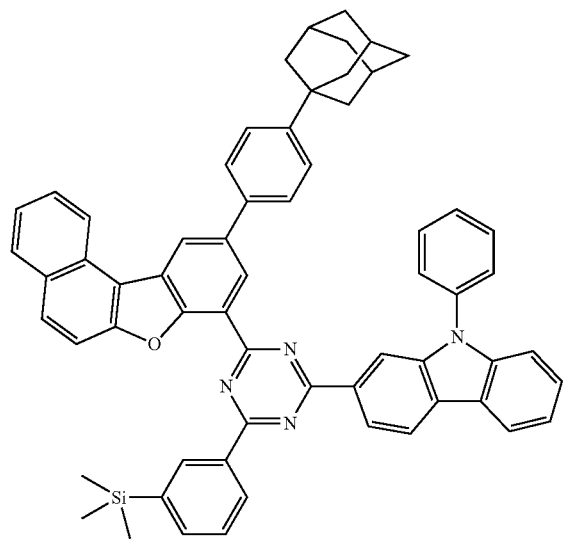
336
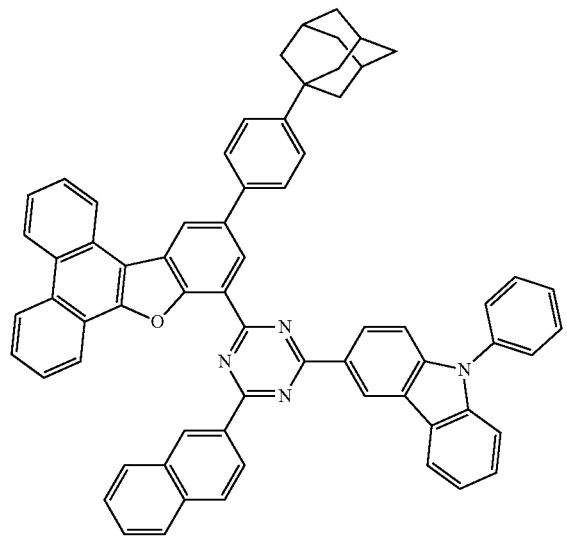
337
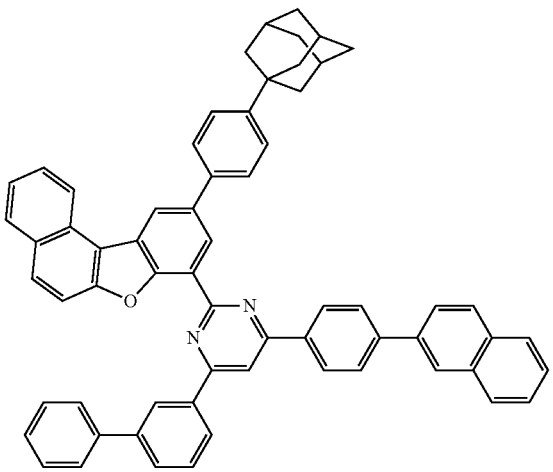

-continued
338
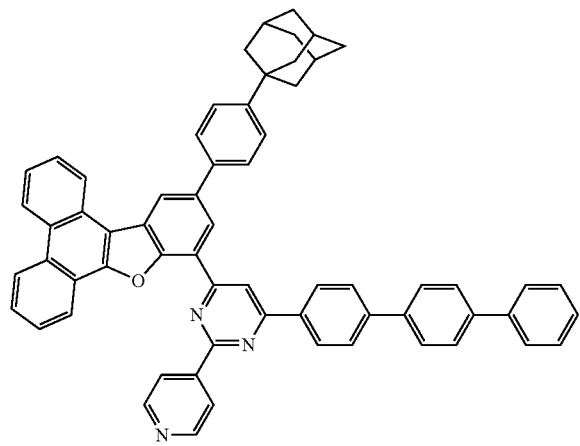
339
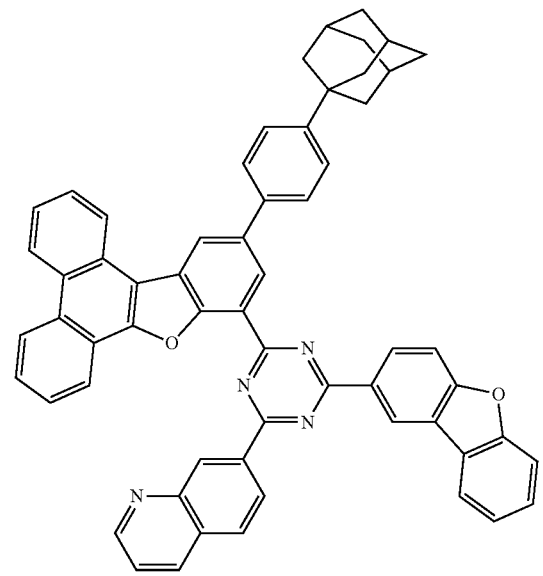
340
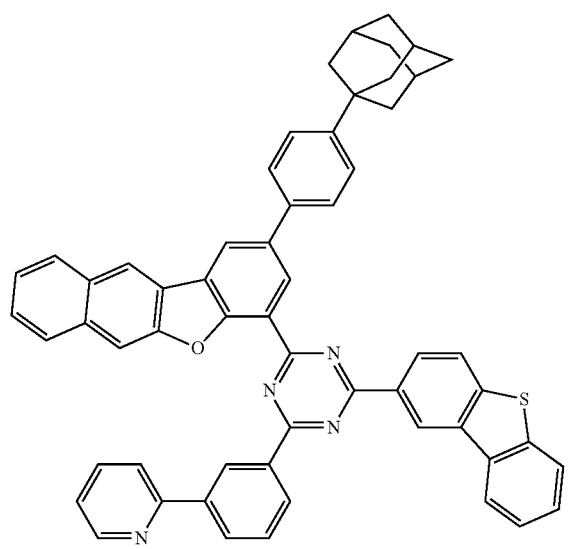
341
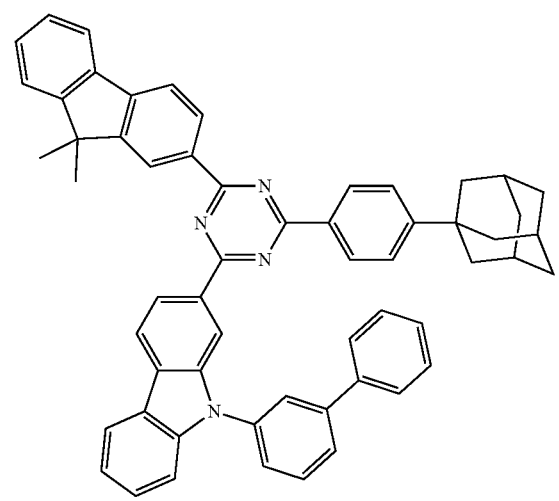
342
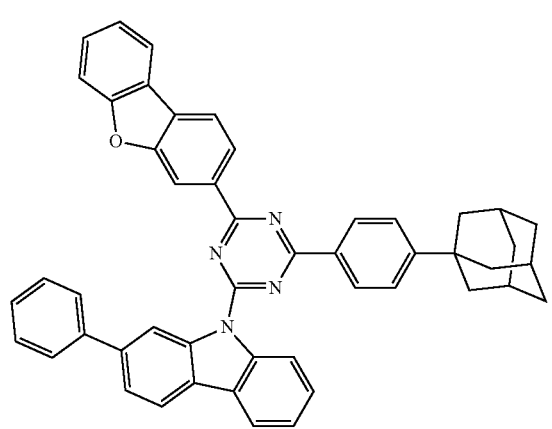
343
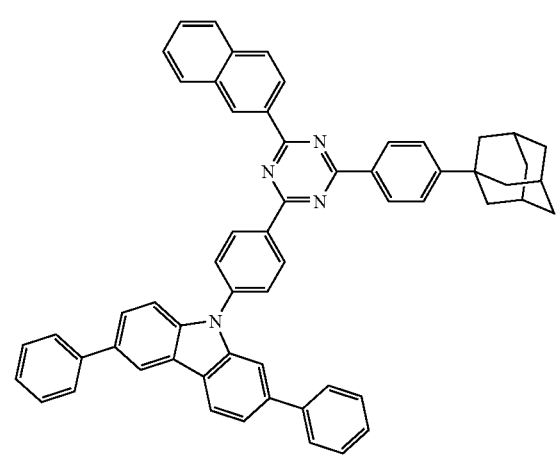

344
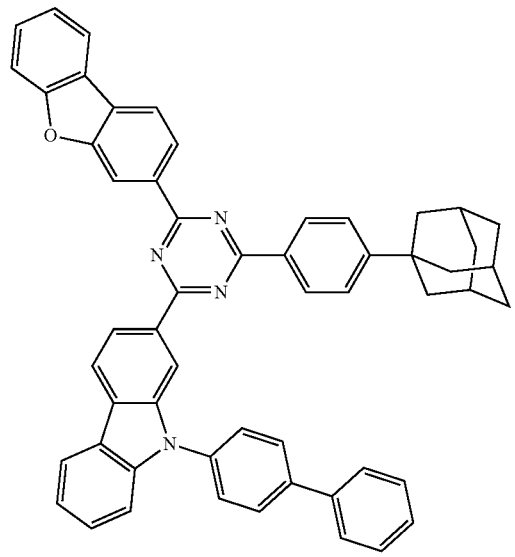
345
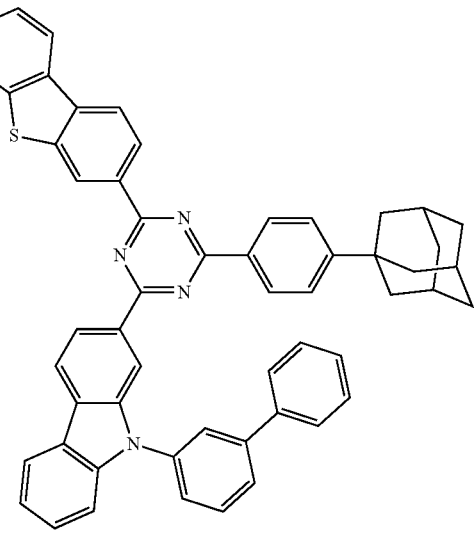
346
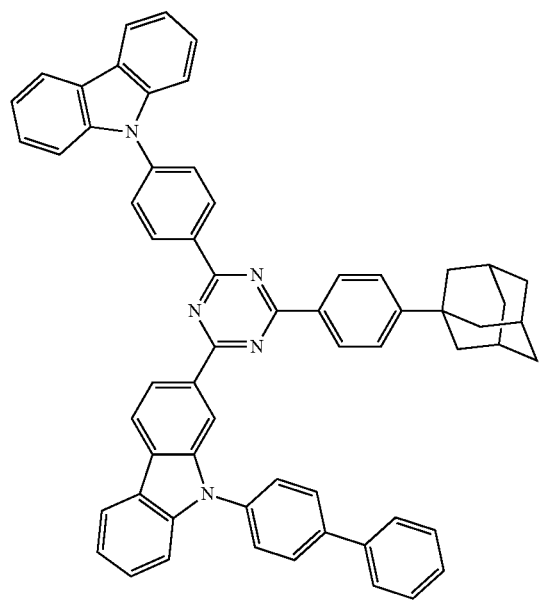
347
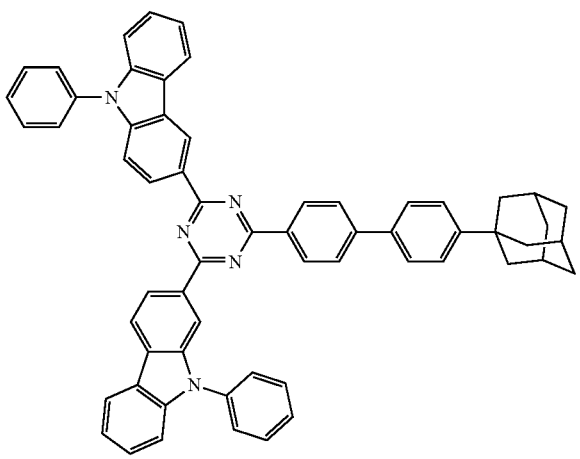

-continued
348
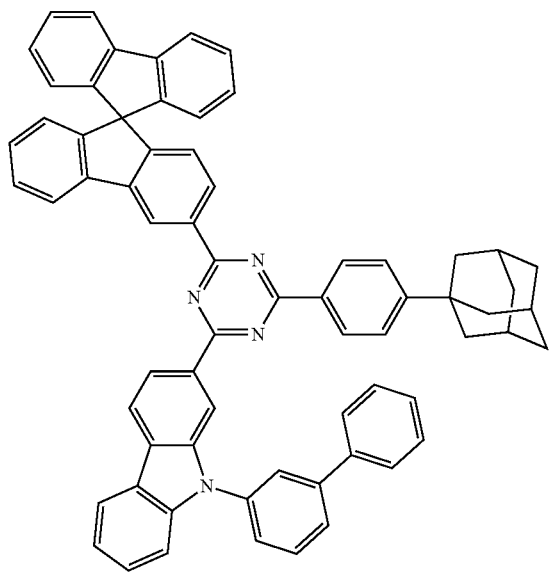
349
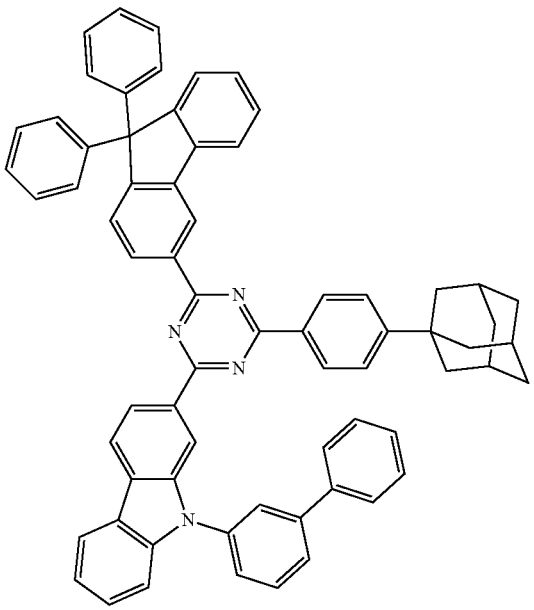
350
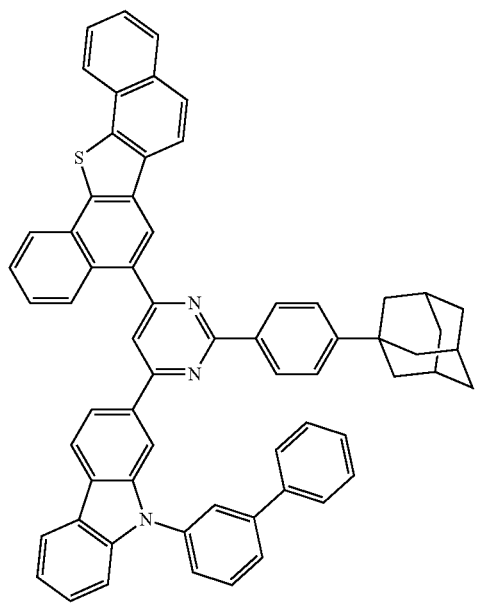
351
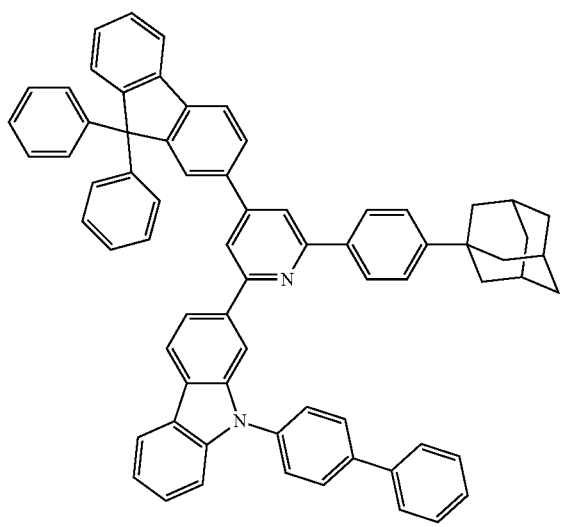

531 532
-continued
351 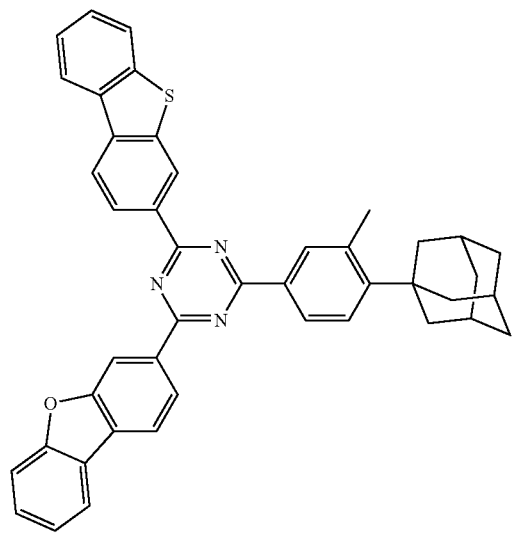 353 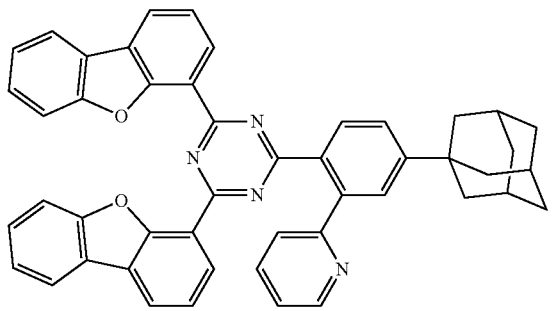
354 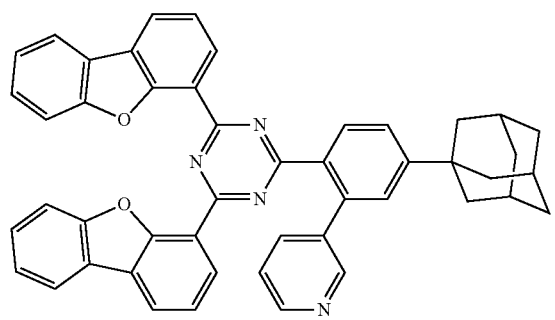 355 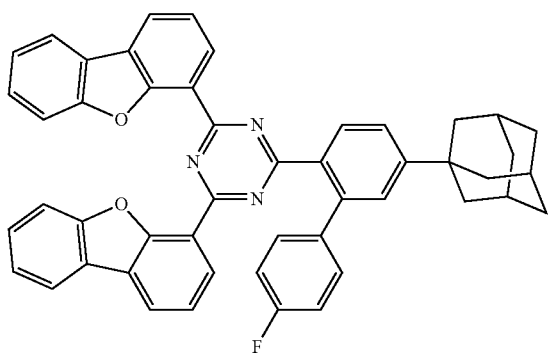
356 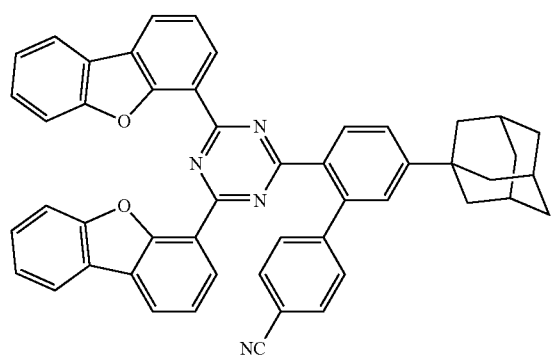 357 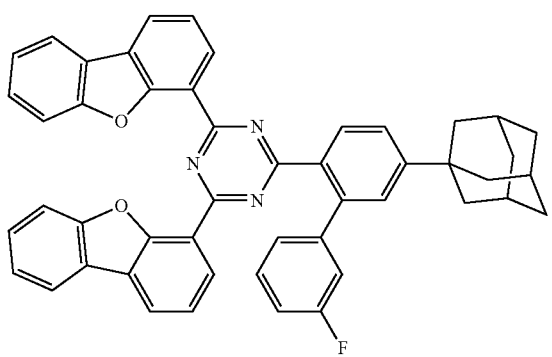

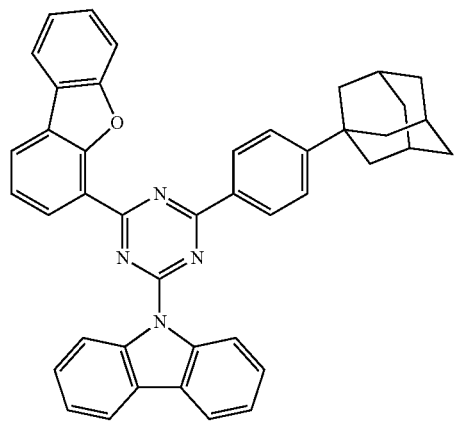
358

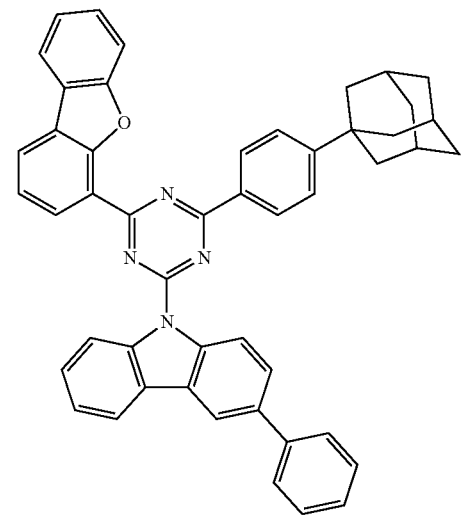
359

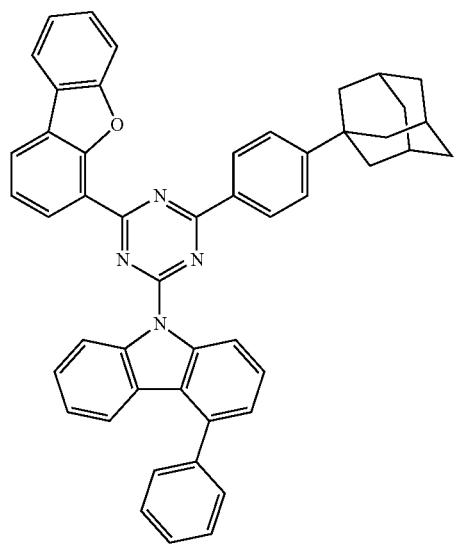
360

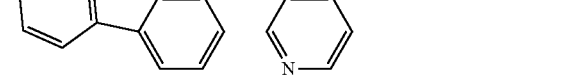
361

10. An electronic element, comprising an anode, a cathode which is arranged oppositely to the anode, and a functional layer disposed between the anode and the cathode, wherein the functional layer comprises the organic compound of claim 1.

11. The electronic element of claim 10, wherein the functional layer comprises an organic light-emitting layer comprising the organic compound.

12. The electronic element of claim 10, wherein the electronic element is an organic electroluminescent device or photoelectric conversion device.

13. An electronic device, comprising the electronic element of claim 10.

14. The electronic element of claim 12, wherein the electronic element is an organic electroluminescent device.

15. The electronic element of claim 14, wherein the organic electroluminescent device is a green organic electroluminescent device.

* * * * *